(12) United States Patent
Balestra et al.

(10) Patent No.: US 9,181,272 B2
(45) Date of Patent: Nov. 10, 2015

(54) ALDOSTERONE SYNTHASE INHIBITORS

(71) Applicants: Michael Balestra, New Fairfield, CT (US); Jennifer Burke, Newtown, CT (US); Zhidong Chen, New Milford, CT (US); Derek Cogan, Sandy Hook, CT (US); Lee Fader, New Milford, CT (US); Xin Guo, Danbury, CT (US); Bryan McKibben, New Milford, CT (US); Daniel Richard Marshall, Norwalk, CT (US); Peter Allen Nemoto, Southbury, CT (US); Hui Yu, New Milford, CT (US)

(72) Inventors: Michael Balestra, New Fairfield, CT (US); Jennifer Burke, Newtown, CT (US); Zhidong Chen, New Milford, CT (US); Derek Cogan, Sandy Hook, CT (US); Lee Fader, New Milford, CT (US); Xin Guo, Danbury, CT (US); Bryan McKibben, New Milford, CT (US); Daniel Richard Marshall, Norwalk, CT (US); Peter Allen Nemoto, Southbury, CT (US); Hui Yu, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/262,828

(22) Filed: Apr. 28, 2014

(65) Prior Publication Data

US 2014/0323468 A1  Oct. 30, 2014

Related U.S. Application Data

(60) Provisional application No. 61/912,571, filed on Dec. 6, 2013, provisional application No. 61/817,564, filed on Apr. 30, 2013.

(51) Int. Cl.
*C07D 471/02* (2006.01)
*C07D 498/04* (2006.01)
*C07D 471/04* (2006.01)

(52) U.S. Cl.
CPC ............ *C07D 498/04* (2013.01); *C07D 471/04* (2013.01)

(58) Field of Classification Search
CPC ...................................................... C07D 471/04
USPC ........................................................... 546/113
See application file for complete search history.

(56) References Cited

U.S. PATENT DOCUMENTS

| 2011/0112067 A1 | 5/2011 | Hartmann et al. |
| 2011/0118241 A1 | 5/2011 | Hartmann |
| 2011/0172217 A1 | 7/2011 | Fujioka et al. |

FOREIGN PATENT DOCUMENTS

| EP | 2341052 A1 | 7/2011 |
| WO | 2009135651 | 11/2009 |
| WO | 2009135651 A1 | 11/2009 |
| WO | 2014055595 | 4/2010 |
| WO | 2010107765 A1 | 9/2010 |
| WO | 2010129467 | 11/2010 |
| WO | 2013037779 | 3/2013 |

OTHER PUBLICATIONS

International Search Report, PCT/ISA/210, mailed Aug. 8, 2014, for PCT/US2014/035596.

*Primary Examiner* — Nizal Chandrakumar
(74) *Attorney, Agent, or Firm* — Michael P. Morris; Edward S. Lazer

(57) ABSTRACT

The present invention relates to compounds of formula (I):

and pharmaceutically acceptable salts thereof, wherein $R^1$, $R^2$, $R^3$, $R^4$, $R^5$, $R^6$, $R^7$, W, Y, m and n are as defined herein. The invention also relates to pharmaceutical compositions comprising these compounds, methods of using these compounds in the treatment of various diseases and disorders, processes for preparing these compounds and intermediates useful in these processes.

16 Claims, No Drawings

ALDOSTERONE SYNTHASE INHIBITORS

FIELD OF THE INVENTION

This invention relates to heteroaryl compounds that are useful as inhibitors of aldosterone synthase and are thus useful for treating a variety of diseases that are mediated or sustained by aldosterone activity, including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

BACKGROUND

Aldosterone is a steroid hormone having mineralcorticoid activity. It is produced primarily by the adrenal glomerulosa in response to angiotensin II, adrenocorticotropic hormone and increased serum potassium levels. A primary physiological role of aldosterone in the kidney is to maintain sodium and potassium balance by regulating cation exchange ($Na^+$ reabsorption and $K^+$ secretion) in the distal nephron. However, aldosterone has also been shown to be a pro-inflammatory and profibrotic hormone in blood vessels, heart and kidneys. The effects of aldosterone on gene expression are mediated via binding to the mineralocorticoid receptor (MR) and a canonical nuclear hormone receptor pathway. However, the hormone also elicits rapid, non-genomic responses, including acute regulation of the activity of tubular ion transporters, for example $Na^+/H^+$ exchangers (NHEs), $H^+$-ATPase, ENaC, and $Na^+/K^+$ ATPase (D. W. Good, 2007, Hypertension, 49, 728-739). It is likely that some of these effects are mediated by MR-independent pathways. Conversely, the MR can bind alternative ligands, including deoxycorticosterone, corticosterone, cortisol and progesterone. Thus, inhibition of aldosterone synthesis is predicted to have a pharmacodynamic profile distinct from what is observed with MR antagonists.

Aldosterone is synthesized in the zona glomerulosa of the adrenal glands, where a single enzyme, CYP11B2 (aldosterone synthase), catalyses the 3-step conversion of 11-deoxycorticosterone (11-DOC) to aldosterone, via corticosterone and 18-hydroxycorticosterone. Adrenal aldosterone synthase activity is regulated by Angiotensin II and K+ levels and unidentified adipocyte-derived mediators. Low levels of aldosterone synthase have also been detected in the heart and CNS, though the physiological relevance is uncertain, perhaps relating to paracrine effects. Systemic aldosterone is believed to derive essentially entirely from the adrenals.

Beyond its role in regulating sodium and potassium balance, aldosterone has been shown to have pro-inflammatory and pro-fibrotic actions in multiple tissues including the kidney, blood vessels and the heart. The harmful effects of inappropriate aldosterone levels on blood pressure and cardiac, renal, cerebral and vascular function and structure, have been widely reported in the literature, including: i) increase in sodium retention through $Na^+/K^+$ ATPase pump induction in distal tubules resulting in volume expansion and high blood pressure, ii) endothelial dysfunction, iii) oxidative stress, iv) renal and cardiac hypertrophy, v) fibroblast proliferation, and, vi) excessive synthesis of extracellular matrix resulting in renal, cardiac and vascular fibrosis.

Benefits of aldosterone blockade/inhibition include reduction of kidney fibrosis and improvement of glomerular filtration rate and albuminuria in models of chronic kidney disease (CKD) and diabetic nephropathy. This is supported by preclinical data (for example, Fiebler et al., 2005, Circulation, 111, 3087-3094; Lea et al., 2009, Kidney International, 75, 936-945). Other benefits reported in the literature include decreased blood pressure and end-organ damage (heart, kidney, vessels) in both renin-dependent and salt-sensitive hypertension.

Although many of aldosterone's known effects are mediated through mineralcorticoid receptor (MR) activation, and much of the evidence favoring targeting this pathway comes from experiments with MR antagonists, non MR-mediated effects are reported and knockout mice for MR and aldosterone synthase exhibit different phenotypes (Makhanova et al. 2006, Berger et al. 1998, Funder 2007). These observations further suggest that aldosterone synthase inhibitors may have a different profile and offer advantages compared to MR antagonists.

For example, several aldosterone actions are not inhibited by MR antagonists, including the including potentially deleterious effects on the vasculature (increased peripheral vascular resistance), the heart (effects on myocardial re-polarization) and the endocrine system (decreased insulin secretion). Furthermore, MR antagonism leads to an increase in circulating aldosterone, predicted to increase aldosterone signaling via non-MR pathways and, potentially, partially overcoming the MR blockade itself.

Current therapeutic strategies focus on slowing progression and treating conditions underlying diabetic nephropathy: control of blood glucose and control of high blood pressure. Angiotensin converting enzyme (ACE) inhibitors and angiotensin receptor blockers (ARB) have shown renal benefit in diabetic patients. To date, representatives of the ACE inhibitor class and from the ARB class have been approved for the treatment of diabetic nephropathy. These therapies represent limited benefit for the diabetic nephropathy patients.

Although the use of ACE inhibitors and ARBs represents the current standard of care for patients with diabetic nephropathy, patients progressively lose kidney function while on these medications, as seen in the IDNT (E. J. Lewis et al., 2001, N. Engl. J. Med., 345, 851-860) and RENAAL (B. M. Brenner et al., 2001, N. Engl. J. Med., 345, 861-869) studies, which reported a decrease over time in estimated glomerular filtration rate, which is an accurate measure of chronic kidney disease progression in patients treated by these conventional methods. At stage 5 chronic kidney disease, renal replacement therapy is required, in the form of either dialysis or transplant.

Aldosterone synthase inhibition may also be predicted to offer advantages as add-on therapy with ACE inhibitors and ARBs. Notably, 25-50% of patients receiving these agents experience "aldosterone breakthrough" in which aldosterone levels initially lowered by these treatments eventually return to pretreatment levels. This phenomenon would not occur with direct aldosterone synthase inhibition and could enhance efficacy in combination therapy.

There remains a high unmet medical need to treat diabetic nephropathy, to halt or regress disease progression by specifically targeting the underlying pathophysiological mechanisms associated with chronic inflammation and fibrosis, irrespective of the original cause of the disease and when co-administered with current therapies. The studies described above and in the literature provide evidence that inhibitors of aldosterone synthesis will be useful for the treatment of diabetic kidney disease including diabetic nephropathy; non-diabetic kidney disease including glomerulosclerosis, glomerulonephritis, IGA nephropathy, nephritic syndrome and focal segmental glomerulosclerosis (FSGS); cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism; adrenal hyperplasia and primary and secondary hyperaldosteronism.

BRIEF SUMMARY OF THE INVENTION

The present invention provides novel compounds that inhibit aldosterone synthase and thus useful for treating a variety of diseases and disorders that can be alleviated by lowering levels of aldosterone including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In an embodiment, there are provided compounds of the formula I

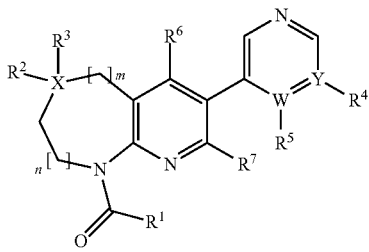

wherein:
$R^1$ is selected from —$NH_2$, —$NHCH_3$ and —$CH_3$;
X is selected from C and O;
Y and W are selected from C and N, wherein if Y is N, then W is C and $R^4$ is an electron pair and if W is N, then Y is C and $R^5$ is an electron pair;
$R^2$ and $R^3$ are independently selected from —H, —F, —OH and $C_{1-4}$ alkyl, when X is C; $R^2$ and $R^3$ is an electron pair when X is O;
$R^4$ is the group of —$(CR^aR^b)_p(A)_{0-1}(CR^aR^b)_qB$, wherein:
p and q are independently selected from integers between 0 and 5, but p+q is always equal or less than 6;
A is selected from O, S and $NR^e$;
B is selected from:
—H;
—OH;
—CN;
halogen;
—$SO_2R^c$;
—$C(O)R^c$;
—$CO_2R^c$;
—$NR^cSO_2R^d$;
—$SO_2NR^cR^d$;
—$CONR^cR^d$;
—$NR^cCOR^d$;

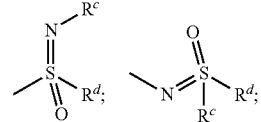

—$NR^cR^d$;
-Phenyl, optionally substituted with 1 to 3 groups selected from halogen, —CN, —$CH_2CN$, —$NR^cC(O)R^d$, —$SO_2C_{1-3}$alkyl, —$C(O)NR^cR^d$, $C_{1-4}$alkoxy, —$SO_2NR^cR^d$, —$CO_2R^c$, —$NR^cSO_2R^d$, —$(CH_2)_{0-3}SO_2C_{1-3}$alkyl and $C_{1-3}$alkyl, wherein said $C_{1-3}$alkyl is optionally substituted with —OH, halogen or —$OCH_3$;
-heteroaryl optionally substituted with 1 to 2 groups independently selected from, —OH, $C_{1-3}$alkoxy, —$(CH_2)_{0-2}$morpholin-4-yl and $C_{1-6}$alkyl wherein said $C_{1-6}$alkyl is optionally substituted with —OH, —CN, $C_{1-3}$alkoxy-$N(R^e)_2$, —$CON(R^e)_2$, —$SO_2C_{1-3}$alkyl, —$SO_2N(R^e)_2$ or halogen; and
—$C_{3-7}$ cycloalkyl, optionally partially unsaturated, wherein up to 3 ring constituting carbons of the cycloalkyl can be optionally replaced with a group selected from O, S, N, $NR^e$, SO, $SO_2$ and CO; and wherein the resulting cycloalkyl or heterocyclyl is optionally substituted with 1 to 3 groups selected from —OH, oxo, —CN, $C_{1-3}$alkoxy, —$N(R^e)_2$, —$CON(R^e)_2$, —$CO_2C_{1-4}$alkyl, —$C(O)C_{1-3}$alkyl, —$SO_2C_{1-3}$alkyl, —$SO_2N(R^e)_2$, halogen and $C_{1-6}$alkyl, wherein the $C_{1-6}$alkyl is optionally substituted with —OH;
$R^5$ is selected from
—H;
—$C_{1-6}$alkyl optionally substituted with —OH, oxo, —$OC_{1-6}$alkyl or —$OCH_2$phenyl;
—$C_{3-6}$ cycloalkyl, wherein up to 3 ring constituting carbons can be optionally replaced with a group selected from O, S, N, $NR^e$, SO, $SO_2$ or CO and wherein the resulting cycloalkyl or heterocyclyl is optionally substituted with —OH, —CN, halogen or $C_{1-3}$alkyl, wherein the $C_{1-3}$alkyl is optionally substituted with —OH;
—$CO_2R^c$;
—CN;
—$CF_3$;
-halogen;
—$(CR^aR^b)_{0-2}OC_{1-3}$alkyl;
—$C(O)NR^cR^d$;
—$CH_2O$phenyl, wherein the phenyl is optionally substituted with halogen;
-Phenyl, optionally substituted with halogen or $SO_2C_{1-3}$alkyl;
—$CR^aR^bNHR^e$; and
-heteroaryl, optionally substituted with $C_{1-3}$alkyl;
$R^6$ and $R^7$ are independently selected from H, —Cl, —F, —CN and —$CH_3$;
wherein at least one of $R^6$ or $R^7$ is H;
$R^a$ and $R^b$ are independently selected from
—H;
—$C_{1-6}$alkyl;
—$C_{3-7}$cycloalkyl wherein up to 3 ring constituting carbons can be optionally replaced with a group selected from O, S, $NR^e$, SO, $SO_2$ and CO;
—OH;
—CN;

-halogen; and
—OC$_{1-3}$alkyl; or

R$^a$ and R$^b$, attached to the same or different atom, along with the atoms that they are attached to can form a C$_{3-7}$cycloalkyl ring in which up to 3 ring constituting carbon atoms can be optionally replaced with a group selected from O, S, NR$^e$, SO, SO$_2$ and CO;

R$^c$ and R$^d$ are independently selected from:
- —H;
- —C$_{1-6}$alkyl optionally substituted with —OH, oxo, —CN, C$_{1-3}$alkoxyl, —N(R$^e$)$_2$, —CON(R$^e$)$_2$, —SO$_2$C$_{1-3}$alkyl, —SO$_2$N(R$^e$)$_2$, halogen, heterocyclyl or heteroaryl;
- —C$_{3-7}$cycloalkyl optionally substituted with —OH, —CN, C$_{1-6}$alkyl, C$_{1-3}$alkoxyl, —N(R$^e$)$_2$, —CON(R$^e$)$_2$, —SO$_2$C$_{1-3}$alkyl, —SO$_2$N(R$^e$)$_2$ or halogen; wherein up to 3 ring constituting carbon atoms of the ring can be optionally replaced with a group selected from O, S, NR$^e$, SO, SO$_2$ and CO;
- —(CH$_2$)$_{0-1}$phenyl, optionally substituted with 1 to 3 groups selected from —OH, —CN, C$_{1-6}$alkyl, C$_{1-3}$alkoxyl, —N(R$^e$)$_2$, —CON(R$^e$)$_2$, —SO$_2$C$_{1-3}$alkyl, —SO$_2$N(R$^e$)$_2$ and halogen;
- -heteroaryl optionally substituted with 1 to 2 groups independently selected from —OH, —CN, C$_{1-6}$alkyl, C$_{1-3}$alkoxyl, —N(R$^e$)$_2$, —CON(R$^e$)$_2$, —SO$_2$C$_{1-3}$alkyl, —SO$_2$N(R$^e$)$_2$ and halogen;
- —SO$_2$C$_{1-3}$alkyl; and
- —CO$_2$C$_{1-3}$alkyl; or R$^c$ and R$^d$ along with the atoms that they are attached to can form a C$_{3-7}$cycloalkyl ring in which up to 3 ring constituting carbon atoms can be optionally replaced by O, S, N, NR$^e$, SO, SO$_2$ or CO, wherein the cycloalkyl or heterocyclyl ring formed can be optionally substituted with one to three groups selected from —OH, —CN, C$_{1-6}$alkyl, C$_{1-3}$alkoxyl, —N(R$^e$)$_2$, —CON(R$^e$)$_2$, —SO$_2$C$_{1-3}$alkyl, —SO$_2$N(R$^e$)$_2$ and halogen, wherein if the ring is substituted with two groups on the same carbon, the groups may join to form a spiro ring;

each R$^e$ is independently selected from:
- —H;
- —C$_{1-6}$alkyl optionally substituted with —OH, —CN or halogen;
- —COC$_{1-3}$alkyl;
- —CO$_2$C$_{1-4}$alkyl; and
- —SO$_2$C$_{1-3}$alkyl;

m is 0 or 1; and
n is 0 or 1;
wherein if m is 1, then n is 1 and X is O;
or a salt thereof.

In another embodiment there are provided compounds of the formula I as described according to the embodiment above and wherein R$^1$ is selected from —NH$_2$, —NHCH$_3$ and —CH$_3$;
X is selected from C and O;
Y and W are selected from C and N, wherein if Y is N, then W is C and R$^4$ is an electron pair and if W is N, then Y is C and R$^5$ is an electron pair;
R$^2$ and R$^3$ are independently selected from —H, —F, —OH and C$_{1-4}$ alkyl, when X is C; R$^2$ and R$^3$ is an electron pair when X is O;
R$^4$ is the group of —(CR$^a$R$^b$)$_p$(A)$_{0-1}$(CR$^a$R$^b$)$_q$B, wherein:
p and q are independently selected from integers between 0 and 5, but p+q is always equal or less than 6;
A is selected from O, S and NR$^e$;
B is selected from:
- —H;
- —OH;
- —CN;
- halogen;
- —SO$_2$R$^c$;
- —C(O)R$^c$;
- —CO$_2$R$^c$;
- —NR$^c$SO$_2$R$^d$;
- —SO$_2$NR$^c$R$^d$;
- —CONR$^c$R$^d$;
- —NR$^c$COR$^d$;

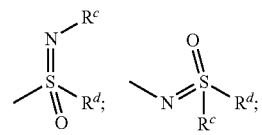

- —NR$^c$R$^d$;
- -Phenyl, optionally substituted with 1 to 3 groups selected from halogen, —CN, —CH$_2$CN, —NR$^c$C(O)R$^d$, —SO$_2$C$_{1-3}$alkyl, —C(O)NR$^c$R$^d$, C$_{1-4}$alkoxy, —SO$_2$NR$^c$R$^d$, —CO$_2$R$^c$, —NR$^c$SO$_2$R$^d$— (CH$_2$)$_{0-3}$SO$_2$C$_{1-3}$alkyl and C$_{1-3}$alkyl, wherein said C$_{1-3}$alkyl is optionally substituted with —OH, halogen or —OCH$_3$;
- -heteroaryl optionally substituted with 1 to 2 groups independently selected from, —OH, C$_{1-3}$alkoxy, —(CH$_2$)$_{0-2}$morpholin-4-yl and C$_{1-6}$alkyl wherein said C$_{1-6}$alkyl is optionally substituted with —OH, —CN, C$_{1-3}$alkoxy-N(R$^e$)$_2$, —CON(R$^e$)$_2$, —SO$_2$C$_{1-3}$alkyl, —SO$_2$N(R$^e$)$_2$ or halogen; and
- —C$_{3-7}$ cycloalkyl, optionally partially unsaturated, wherein up to 3 ring constituting carbons of the cycloalkyl can be optionally replaced with a group selected from O, S, NR$^e$, SO, SO$_2$ or CO; and wherein the resulting cycloalkyl or heterocyclyl is optionally substituted with 1 to 3 groups selected from —OH, oxo, —CN, C$_{1-3}$alkoxy, —N(R$^e$)$_2$, —CON(R$^e$)$_2$, —CO$_2$C$_{1-4}$alkyl, —C(O)C$_{1-3}$alkyl, —SO$_2$C$_{1-3}$alkyl, —SO$_2$N(R$^e$)$_2$, halogen and C$_{1-6}$alkyl, wherein the C$_{1-6}$alkyl is optionally substituted with —OH;

R$^5$ is selected from
- —H;
- —C$_{1-6}$alkyl optionally substituted with —OH;
- —C$_{3-6}$ cycloalkyl, wherein up to 3 ring constituting carbons can be optionally replaced with a group selected from O, S, NR$^e$, SO, SO$_2$ and CO and wherein the resulting cycloalkyl or heterocyclyl is optionally substituted with —OH, —CN, halogen or C$_{1-3}$alkyl, wherein the C$_{1-3}$alkyl is optionally substituted with —OH;
- —CO$_2$R$^c$;
- —CN;
- —CF$_3$;
- -halogen;
- —(CR$^a$R$^b$)$_{0-2}$OC$_{1-3}$alkyl;
- —C(O)NR$^c$R$^d$;
- —CH$_2$Ophenyl, wherein the phenyl is optionally substituted with halogen;
- -Phenyl, optionally substituted with halogen or SO$_2$C$_{1-3}$alkyl;
- —CR$^a$R$^b$NHR$^e$; and
- -heteroaryl, optionally substituted with C$_{1-3}$alkyl;

R$^6$ is H;
R$^7$ is H;
R$^a$ and R$^b$ are independently selected from
- —H;
- —C$_{1-6}$alkyl;

—$C_{3-7}$cycloalkyl wherein up to 3 ring constituting carbons can be optionally replaced with a group selected from O, S, NR$^e$, SO, SO$_2$ and CO;
—OH;
—CN;
-halogen; and
—OC$_{1-3}$alkyl; or R$^a$ and R$^b$, attached to the same or different atom, along with the atoms that they are attached to can form a $C_{3-7}$cycloalkyl ring in which up to 3 ring constituting carbon atoms can be optionally replaced with a group selected from O, S, NR$^e$, SO, SO$_2$ and CO;

R$^c$ and R$^d$ are independently selected from:
—H;
—$C_{1-6}$alkyl optionally substituted with —OH, oxo, —CN, $C_{1-3}$alkoxyl, —N(R$^e$)$_2$, —CON(R$^e$)$_2$, —SO$_2$C$_{1-3}$alkyl, —SO$_2$N(R$^e$)$_2$ or halogen;
—$C_{3-7}$cycloalkyl optionally substituted with —OH, —CN, $C_{1-6}$alkyl, $C_{1-3}$alkoxyl, —N(R$^e$)$_2$, —CON(R$^e$)$_2$, —SO$_2$C$_{1-3}$alkyl, —SO$_2$N(R$^e$)$_2$ or halogen; wherein up to 3 ring constituting carbon atoms of the ring can be optionally replaced with a group selected from O, S, NR$^e$, SO, SO$_2$ and CO;
—(CH$_2$)$_{0-1}$phenyl, optionally substituted with 1 to 3 groups selected from —OH, —CN, $C_{1-6}$alkyl, $C_{1-3}$alkoxyl, —N(R$^e$)$_2$, —CON(R$^e$)$_2$, —SO$_2$C$_{1-3}$alkyl, —SO$_2$N(R$^e$)$_2$ and halogen;
-heteroaryl optionally substituted with 1 to 2 groups independently selected from —OH, —CN, $C_{1-6}$alkyl, $C_{1-3}$alkoxyl, —N(R$^e$)$_2$, —CON(R$^e$)$_2$, —SO$_2$C$_{1-3}$alkyl, —SO$_2$N(R$^e$)$_2$ and halogen;
—SO$_2$C$_{1-3}$alkyl; and
—CO$_2$C$_{1-3}$alkyl; or R$^c$ and R$^d$ along with the atoms that they are attached to can form a $C_{3-7}$cycloalkyl ring in which up to 3 ring constituting carbon atoms can be optionally replaced by O, S, NR$^e$, SO, SO$_2$ or CO, wherein the cycloalkyl or heterocyclyl ring formed can be optionally substituted with —OH, —CN, $C_{1-6}$alkyl, $C_{1-3}$alkoxyl, —N(R$^e$)$_2$, —CON(R$^e$)$_2$, —SO$_2$C$_{1-3}$alkyl, —SO$_2$N(R$^e$)$_2$ or halogen;

each R$^e$ is independently selected from:
—H;
—$C_{1-6}$alkyl optionally substituted with —OH, —CN or halogen;
—COC$_{1-3}$alkyl;
—CO$_2$C$_{1-4}$alkyl; and
—SO$_2$C$_{1-3}$alkyl;

m is 0 or 1; and
n is 0 or 1;
wherein if m is 1, then n is 1 and X is O;
or a salt thereof.

In another embodiment there are provided compounds of the formula I as described according to any of the embodiments herein and wherein:

R$^1$ is selected from —NH$_2$ and —CH$_3$;
R$^2$ and R$^3$ are independently selected from —H, —F and —OH, when X is C; R$^2$ and R$^3$ is an electron pair when X is O;
R$^4$ is selected from
—H;
—OH;
—(CH$_2$)$_{0-1}$CN;
—$C_{1-6}$alkyl, optionally substituted with one to seven groups independently selected from halogen, —OH or —OCH$_3$;
—OC$_{1-4}$alkyl, optionally substituted with —OH;
-halogen;
—CF$_3$;
—(CH$_2$)$_{0-1}$(O)$_{0-1}$(CH$_2$)$_{0-3}$SO$_2$C$_{1-3}$alkyl;
—C(O)C$_{1-3}$alkyl;
—CO$_2$R$^c$;
—C$_{0-2}$alkyl-NHSO$_2$C$_{1-3}$alkyl;
—C$_{0-2}$alkyl-NHC(O)NHC$_{1-3}$alkyl;
—(O)$_{0-1}$(CH$_2$)$_{0-1}$(O)$_{0-1}$C(O)NR$^c$R$^d$;
—(CH$_2$)$_{0-1}$NR$^c$R$^d$;
—(O)$_{0-1}$(CH$_2$)$_{0-1}$(O)$_{0-1}$phenyl, optionally substituted with 1 to 3 groups selected from halogen, —CN, —CH$_2$CN, —NHC(O)C$_{1-3}$alkyl, —SO$_2$C$_{1-3}$alkyl, —C(O)NR$^c$R$^d$, hydroxyC$_{2-4}$alkoxy, C$_{1-3}$alkoxy, C(O)morphilin-4-yl, —SO$_2$NH(CH$_2$)$_{2-3}$OH, —SO$_2$NR$^c$R$^d$ and C$_{1-3}$alkyl optionally substituted with —OH or —OCH$_3$;
—(O)$_{0-1}$(CH$_2$)$_{0-2}$heteroaryl selected from indolyl, pyridinyl, pyrazolyl, pyrazinyl, and pyrimidinyl, wherein said heteroaryl is optionally substituted with one to two groups independently selected from C$_{1-3}$alkyl, —OH, C$_{1-3}$alkoxy, hydroxymethyl, —CO$_2$C$_{1-4}$alkyl, —C(O)C$_{1-3}$alkyl and —(CH$_2$)$_{0-2}$morpholin-4-yl;
—O$_{0-1}$(CH$_2$)$_{0-2}$(O)$_{0-1}$heterocyclyl, wherein the heterocyclyl is selected from 3,6-dihydro-2H-thiopyranyl, 3,6-dihydro-2H-pyranyl, oxetanyl, tetrahydrofuranyl, tetrahydropyranyl, 1,2,3,6-tetrahydropyridinyl, 3,6-dihydro-2H-thiopyranyl-1,1-dioxide, tetrahydrothiopyranyl-1,1-dioxide, piperidinyl, morpholinyl, piperazinyl and pyrrolidinyl;
wherein said heterocyclyl is optionally substituted with a group selected from —C(O)C$_{1-3}$alkyl, —OH, oxo, —(CH$_2$)$_{1-2}$morpholin-4-yl, —CO$_2$C$_{1-4}$alkyl and C$_{1-3}$alkyl optionally substituted with —OH or —OCH$_3$;
—C(O)heterocyclyl, wherein the heterocyclyl is selected from morpholin-4-yl, pyrrolidinyl and piperidin-1-yl; and
—(CH$_2$)$_{0-1}$O(CH$_2$)$_{1-2}$heterocyclyl, wherein the heterocyclyl is selected from morpholin-4-yl, pyrrolidinyl and piperidin-1-yl; and
—$C_{3-6}$cycloalkyl, optionally substituted 1 to 3 groups selected from OH—CN, C$_{1-6}$alkyl, C$_{1-3}$alkoxyl, and halogen;

R$^5$ is selected from
—H;
—C$_{1-3}$alkyl;
—CO$_2$C$_{1-3}$alkyl;
—CN;
—CF$_3$;
-halogen;
—OC$_{1-3}$alkyl;
—CH$_2$OC$_{1-3}$alkyl;
—C(O)NH$_2$;
—C$_{1-2}$alkyl-OH;
—CH(OH)C$_{1-3}$alkyl;
—CH$_2$Ophenyl, wherein the phenyl is optionally substituted with halogen;
-Phenyl, optionally substituted with halogen or SO$_2$C$_{1-3}$alkyl;
—CH$_2$NHR$^c$; and
-pyrazolyl, optionally substituted with C$_{1-3}$alkyl;
R$^6$ is H;
R$^7$ is H; and
R$^c$ and R$^d$ are independently selected from
H, C$_{1-6}$alkyl, —C(O)C$_{1-3}$alkyl, —(CH$_2$)$_{1-3}$OH, —(CH$_2$)$_{2-3}$NHC(O)C$_{1-3}$alkyl, —CH$_2$phenyl, and —SO$_2$C$_{1-2}$alkyl;
or a salt thereof.

In another embodiment there are provided compounds of the formula I as described according to any of the embodiments herein and wherein:

R$^1$ is —NH$_2$;
X is C;
Y and W are C;

$R^2$ and $R^3$ are H;
$R^4$ is selected from
—H;
—OH;
—$(CH_2)_{0-1}CN$;
—$C_{1-6}$alkyl, optionally substituted with one to four groups independently selected from —F, —OH or —$OCH_3$;
-halogen selected from —F and —Cl;
—$CF_3$;
—$C(O)C_{1-3}$alkyl;
—$C_{0-2}$alkyl-$NHSO_2C_{1-3}$alkyl;
—$(O)_{0-1}(CH_2)_{0-1}(O)_{0-1}C(O)NR^cR^d$;
—$O_{0-1}(CH_2)_{0-2}(O)_{0-1}$heterocyclyl, wherein the heterocyclyl is selected from 3,6-dihydro-2H-thiopyranyl, 3,6-dihydro-2H-pyranyl, oxetanyl, tetrahydrofuranyl, tetrahydropyranyl, 1,2,3,6-tetrahydropyridinyl, 3,6-dihydro-2H-thiopyranyl-1,1-dioxide, tetrahydrothiopyranyl-1,1-dioxide, piperidinyl, morpholinyl, piperazinyl and pyrrolidinyl;
wherein said heterocyclyl is optionally substituted with a group selected from —$C(O)C_{1-3}$alkyl, —OH, oxo, —$(CH_2)_{1-2}$morpholin-4-yl, —$CO_2C_{1-4}$alkyl and $C_{1-3}$alkyl optionally substituted with —OH or —$OCH_3$; and
—$(CH_2)_{0-1}C(O)$heterocyclyl, wherein the heterocyclyl is selected from morpholin-4-yl, pyrrolidinyl and piperidin-1-yl; and
$R^5$ is selected from
—H;
—$C_{1-3}$alkyl;
—CN;
—$CF_3$;
-halogen;
—$CH(OH)C_{1-3}$alkyl;
-Phenyl, optionally substituted with halogen or $SO_2C_{1-3}$alkyl; and
—$CH_2NHR^c$;
$R^6$ is H;
$R^7$ is selected from —H and —$CH_3$; and
$R^c$ and $R^d$ are independently selected from
H, $C_{1-6}$alkyl, —$C(O)C_{1-3}$alkyl, —$(CH_2)_{1-3}OH$, —$(CH_2)_{2-3}NHC(O)C_{1-3}$alkyl, —$CH_2$phenyl, and —$SO_2C_{1-2}$alkyl;
m is 0; and
n is 1;
or a salt thereof.

In another embodiment there are provided compounds of the formula I as described according to any of the embodiments herein and wherein:
$R^4$ is H;
$R^6$ is H; and
$R^7$ is H;
or a salt thereof.

In another embodiment there are provided compounds of the formula I as described according to any of the embodiments herein and wherein:
$R^5$ is H;
$R^6$ is H; and
$R^7$ is H;
or a salt thereof.

In another embodiment there are provided compounds of the formula I as described according to any of the embodiments herein and wherein:
n is 1;
$R^6$ is H; and
$R^7$ is H;
or a salt thereof.

In another embodiment there are provided compounds of the formula I as described according to any of the embodiments herein and wherein:
m=0;
$R^6$ is H; and
$R^7$ is H;
or a salt thereof.

In another embodiment there are provided compounds of the formula I as described according to any of the embodiments herein and wherein:
W and Y are C;
$R^6$ is H; and
$R^7$ is H;
or a salt thereof.

In another embodiment there are provided compounds of the formula I as described according to any of the embodiments herein and wherein:
X is C;
$R^6$ is H;
$R^7$ is H; and
or a salt thereof.

In another embodiment there are provided compounds of the formula I as described according to any of the embodiments herein and wherein:
$R^1$ is —$NH_2$;
$R^6$ is H;
$R^7$ is H; and
or a salt thereof.

In another embodiment there are provided compounds of the formula I as described according to any of the embodiments herein and wherein:
$R^6$ is selected from H, —Cl, —F, and —$CH_3$; and
$R^7$ is selected from H, —$CH_3$ and —CN,
wherein at least one of $R^6$ or $R^7$ is H;
or a salt thereof.

In another aspect of the invention, there is provided a compound of the general formula I or a pharmaceutically acceptable salt thereof for use in a therapeutic method as described hereinbefore and hereinafter The following are representative compounds of the invention which can be made by the general synthetic schemes, the examples, and known methods in the art.

TABLE 1

| Cpd No | STRUCTURE | Name |
|---|---|---|
| 1 | 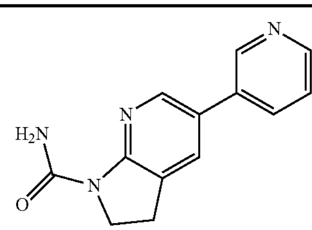 | 5-Pyridin-3-yl-2,3-dihydro-pyrrolo[2,3-b]pyridine-1-carboxylic acid amide |

TABLE 1-continued

| Cpd No | STRUCTURE | Name |
|---|---|---|
| 2 | 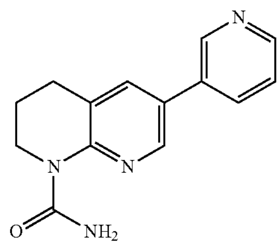 [SMILES: NC(=O)N1CCCc2cc(-c3cccnc3)cnc21] | 6-Pyridin-3-yl-3,4-dihydro-2H-[1,8]napthyridine-1-carboxylic acid amide |
| 3 | 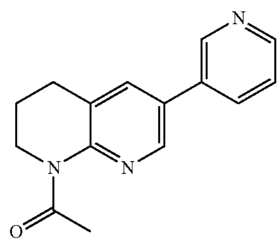 [SMILES: CC(=O)N1CCCc2cc(-c3cccnc3)cnc21] | 1-(6-Pyridine-3-yl-3,4-dihydro-2H-[1,8]naphthyridin-1-yl)-ethanone |
| 4 | 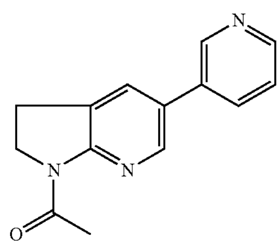 [SMILES: CC(=O)N1CCc2cc(-c3cccnc3)cnc21] | 1-(5-Pyridin-3-yl-2,3-dihydro-pyrrolo[2,3-b]pyridin-1-yl)-ethanone |
| 5 | 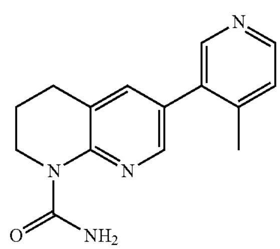 [SMILES: Cc1ccncc1-c1cnc2c(c1)CCCN2C(N)=O] | 6-(4-Methyl-pyridin-3-yl)-3,4-dihydro-2H-[1,8]naphthyridine-1-carboxylic acid amide |
| 6 | 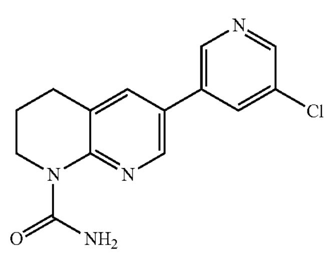 [SMILES: NC(=O)N1CCCc2cc(-c3cncc(Cl)c3)cnc21] | 6-(5-Chloro-pyridin-3-yl)-3,4-dihydro-2H-[1,8]naphthyridine-1-carboxylic acid amide |
| 7 | 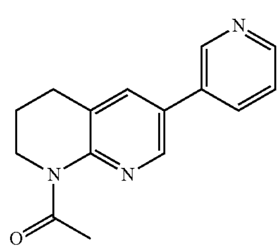 [SMILES: CC(=O)N1CCCc2cc(-c3cccnc3)cnc21] | 1-(7-Pyridin-3-yl-2,3-dihydro-pyrido[3,2-b][1,4]oxazin-4-yl)-ethanone |

TABLE 1-continued

| Cpd No | STRUCTURE | Name |
|---|---|---|
| 8 | 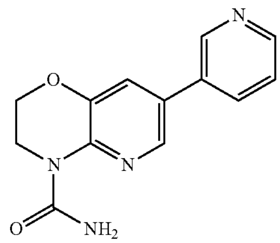 | 7-Pyridin-3-yl-2,3-dihydro-pyrido[3,2-b][1,4]oxazin-4-carboxylic acid amide |
| 9 | 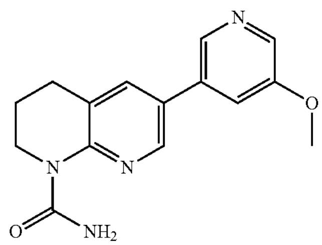 | 6-(5-Methoxy-pyridin-3-yl)-3,4-dihydro-2H-[1,8]naphthyridine-1-carboxylic acid amide |
| 10 | 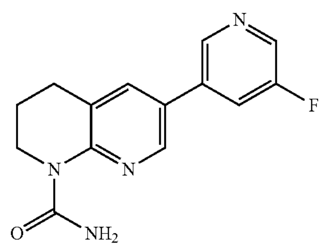 | 6-(5-Fluoro-pyridin-3-yl)-3,4-dihydro-2H-[1,8]naphthyridine-1-carboxylic acid amide |
| 11 | 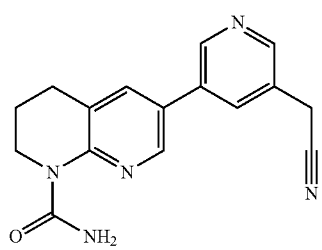 [SMILES: N#CCc1cncc(-c2cnc3c(c2)CCCN3C(N)=O)c1] | 6-(5-Cyanomethyl-pyridin-3-yl)-3,4-dihydro-2H-[1,8]naphthyridine-1-carboxylic acid amide |
| 12 | 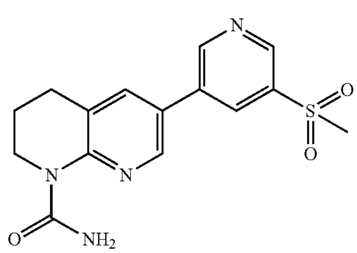 [SMILES: CS(=O)(=O)c1cncc(-c2cnc3c(c2)CCCN3C(N)=O)c1] | 6-(5-Methanesulfonyl-pyridin-3-yl)-3,4-dihydro-2H-[1,8]naphthyridine-1-carboxylic acid amide |
| 13 | 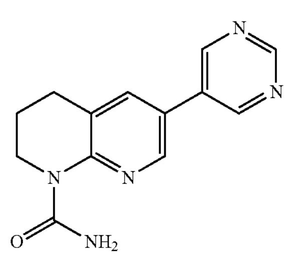 [SMILES: NC(=O)N1CCCc2cc(-c3cncnc3)cnc21] | 6-Pyrimidin-5-yl-3,4-dihydro-2H-[1,8]naphthyridine-1-carboxylic acid amide |

TABLE 1-continued

| Cpd No | STRUCTURE | Name |
|---|---|---|
| 14 | 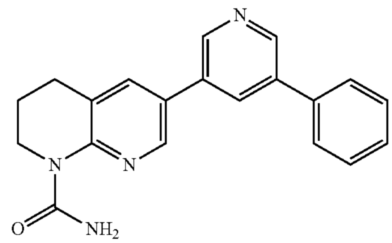 [SMILES: NC(=O)N1CCCc2cc(-c3cncc(-c4ccccc4)c3)cnc21] | 6-(5-Phenyl-pyridin-3-yl)-3,4-dihydro-2H-[1,8]naphthyridine-1-carboxylic acid amide |
| 15 | 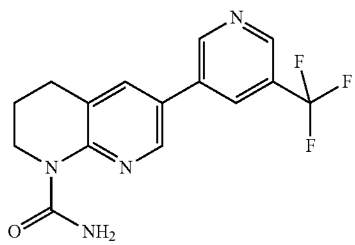 | 6-(5-Trifluoromethyl-pyridin-3-yl)-3,4-dihydro-2H-[1,8]naphthyridine-1-carboxylic acid amide |
| 16 | 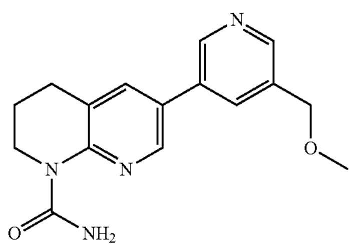 [SMILES: COCc1cncc(-c2cnc3c(c2)CCCN3C(N)=O)c1] | 6-(5-Methoxymethyl-pyridin-3-yl)-3,4-dihydro-2H-[1,8]naphthyridine-1-carboxylic acid amide |
| 17 | 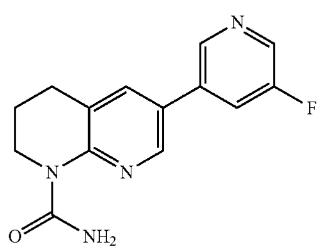 | 1-[6-(5-Fluoro-pyridin-3-yl)-3,4-dihydro-2H-[1,8]naphthyridin-1-yl]-ethanone |
| 18 | 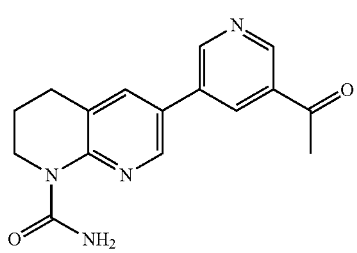 [SMILES: CC(=O)c1cncc(-c2cnc3c(c2)CCCN3C(N)=O)c1] | 6-(5-Acetyl-pyridin-3-yl)-3,4-dihydro-2H-[1,8]naphthyridine-1-carboxylic acid amide |
| 19 | 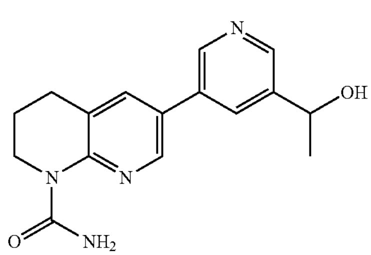 | 6-[5-(1-Hydroxy-ethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 20 | 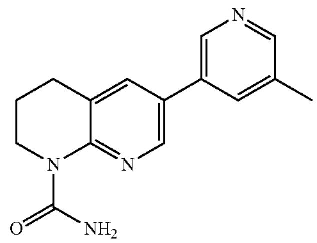 [SMILES: Cc1cncc(-c2cnc3c(c2)CCCN3C(N)=O)c1] | 6-(5-Methyl-pyridin-3-yl)-3,4-dihydro-2H-[1,8]naphthyridine-1-carboxylic acid amide |
| 21 | 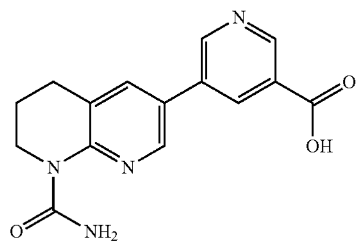 | 5-(8-Carbamoyl-5,6,7,8-tetrahydro-[1,8]naphthyridin-3-yl)-nicotinic acid |
| 22 | 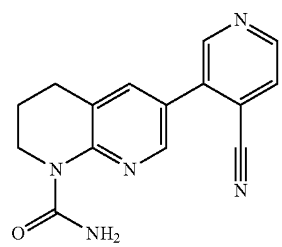 [SMILES: N#Cc1ccncc1-c1cnc2c(c1)CCCN2C(N)=O] | 6-(4-Cyano-pyridin-3-yl)-3,4-dihydro-2H-[1,8]naphthyridine-1-carboxylic acid amide |
| 23 | 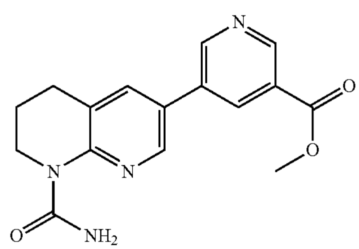 | 5-(8-Carbamoyl-5,6,7,8-tetrahydro-[1,8]naphthyridin-3-yl)-nicotinic acid methyl ester |
| 24 | 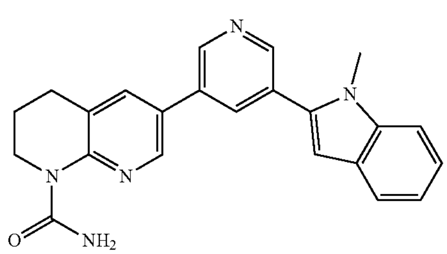 [SMILES: Cn1c(-c2cncc(-c3cnc4c(c3)CCCN4C(N)=O)c2)cc2ccccc21] | 6-[5-(1-Methyl-1H-indol-2-yl)-pyridin-3-yl]-3,4-dihydro-2H-[1,8]naphthyridine-1-carboxylic acid amide |
| 25 | 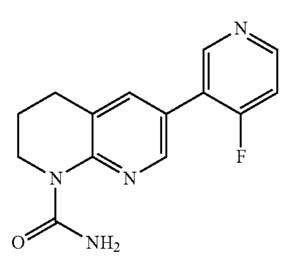 | 6-(4-Fluoro-pyridin-3-yl)-3,4-dihydro-2H-[1,8]naphthyridine-1-carboxylic acid amide |

TABLE 1-continued

| Cpd No | Name |
|---|---|
| 26 | 6-(5-Cyano-pyridin-3-yl)-3,4-dihydro-2H-[1,8]naphthyridine-1-carboxylic acid amide |
| 27 | 7-(5-Fluoro-pyridin-3-yl)-2,3-dihydro-pyrido[3,2-b][1,4]oxazine-4-carboxylic acid amide |
| 28 | 1-[7-(5-Fluoro-pyridin-3-yl)-2,3-dihydro-pyrido[3,2-b][1,4]oxazin-4-yl]-ethanone |
| 29 | 6-(4-Chloro-pyridin-3-yl)-3,4-dihydro-2H-[1,8]naphthyridine-1-carboxylic acid amide |
| 30 | 6-Pyrazin-2-yl-3,4-dihydro-2H-[1,8]naphthyridine-1-carboxylic acid amide |
| 31 | 6-[5-(4-Fluoro-phenyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 32 | 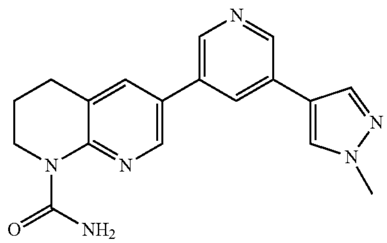 [SMILES: Cn1cc(-c2cncc(-c3cnc4c(c3)CCCN4C(N)=O)c2)cn1] | 6-[5-(1-Methyl-1H-pyrazol-4-yl)-pyridin-3-yl]-3,4-dihydro-2H-[1,8]naphthyridine-1-carboxylic acid amide |
| 33 | 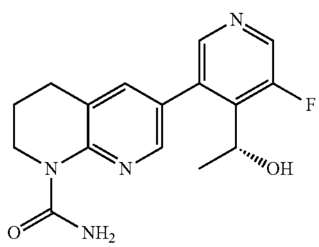 | 6-[5-fluoro-4-((R)-1-hydroxy-ethyl)-pyridin-3-yl]-3,4-dihydro-2H-[1,8]naphthyridine-1-carboxylic acid amide |
| 34 | 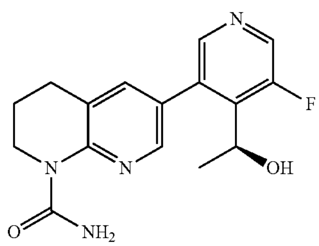 [SMILES: C[C@H](O)c1c(F)cncc1-c1cnc2c(c1)CCCN2C(N)=O] | 6-[5-fluoro-4-((S)-1-hydroxy-ethyl)-pyridin-3-yl]-3,4-dihydro-2H-[1,8]naphthyridine-1-carboxylic acid amide |
| 35 | 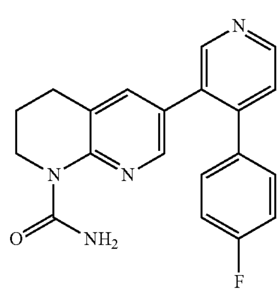 [SMILES: NC(=O)N1CCCc2cc(-c3cnccc3-c3ccc(F)cc3)cnc21] | 6-[4-(4-fluoro-phenyl)-pyridin-3-yl]-3,4-dihydro-2H-[1,8]naphthyridine-1-carboxylic acid amide |
| 36 | 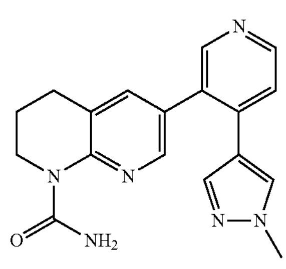 [SMILES: Cn1cc(-c2ccncc2-c2cnc3c(c2)CCCN3C(N)=O)cn1] | 6-[4-(1-Methyl-1H-pyrazol-4-yl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 37 | 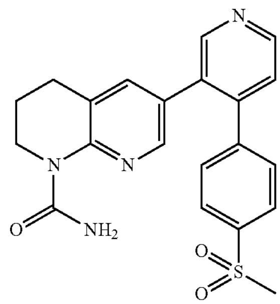 [SMILES: CS(=O)(=O)c1ccc(-c2ccncc2-c2cnc3c(c2)CCCN3C(N)=O)cc1] | 6-[4-(4-Methanesulfonyl-phenyl)-pyridin-3-yl]-3,4-dihydro-2H-[1,8]naphthyridine-1-carboxylic acid amide |
| 38 | 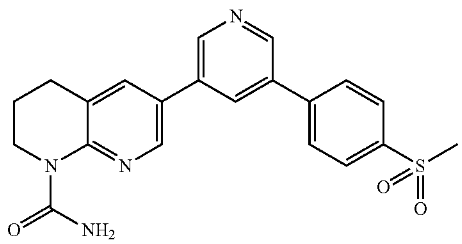 [SMILES: CS(=O)(=O)c1ccc(-c2cncc(-c3cnc4c(c3)CCCN4C(N)=O)c2)cc1] | 6-[5-(4-Methanesulfonyl-phenyl)-pyridin-3-yl]-3,4-dihydro-2H-[1,8]naphthyridine-1-carboxylic acid amide |
| 39 | 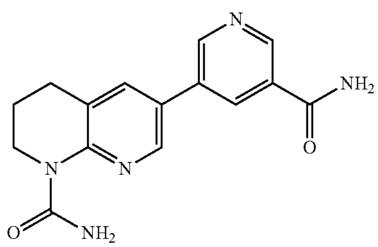 [SMILES: NC(=O)c1cncc(-c2cnc3c(c2)CCCN3C(N)=O)c1] | 6-(5-Carbamoyl-pyridin-3-yl)-3,4-dihydro-2H-[1,8]naphthyridine-1-carboxylic acid amide |
| 40 | 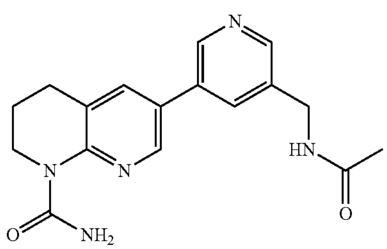 [SMILES: CC(=O)NCc1cncc(-c2cnc3c(c2)CCCN3C(N)=O)c1] | 6-[5-(acetylamino-methyl)-pyridin-3-yl]-3,4-dihydro-2H-[1,8]naphthyridine-1-carboxylic acid amide |
| 41 | 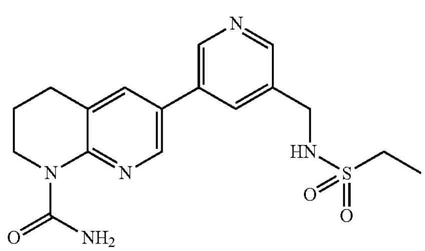 [SMILES: CCS(=O)(=O)NCc1cncc(-c2cnc3c(c2)CCCN3C(N)=O)c1] | 6-[5-(ethanesulfonylamino-methyl)-pyridin-3-yl]-3,4-dihydro-2H-[1,8]naphthyridine-1-carboxylic acid amide |
| 42 | 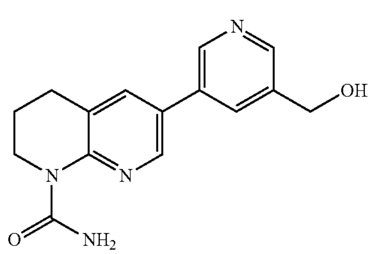 [SMILES: NC(=O)N1CCCc2cc(-c3cncc(CO)c3)cnc21] | 6-(5-hydroxymethyl-pyridin-3-yl)-3,4-dihydro-2H-[1,8]naphthyridine-1-carboxylic acid amide |

TABLE 1-continued

| Cpd No | STRUCTURE | Name |
|---|---|---|
| 43 | 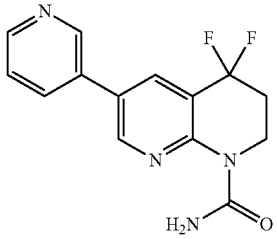 | 4,4-Difluoro-6-pyridin-3-yl-3,4-dihydro-2H-[1,8]naphthyridine-1-carboxylic acid amide |
| 44 | 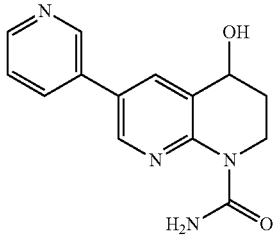 | 4-Hydroxy-6-pyridin-3-yl-3,4-dihydro-2H-[1,8]naphthyridine-1-carboxylic acid amide |
| 45 | 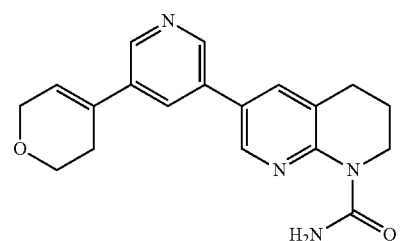 | 6-[5-(3,6-Dihydro-2H-pyran-4-yl)-pyridin-3-yl]-3,4-dihydro-2H-[1,8]naphthyridine-1-carboxylic acid amide |
| 46 | 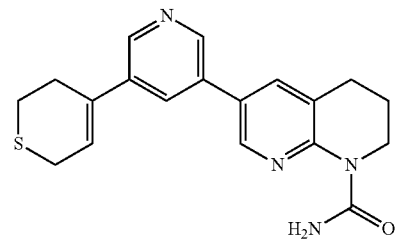 [SMILES: NC(=O)N1CCCc2cc(-c3cncc(C4=CCSCC4)c3)cnc21] | 6-[5-(3,6-Dihydro-2H-thiopyran-4-yl)-pyridin-3-yl]-3,4-dihydro-2H-[1,8]naphthyridine-1-carboxylic acid amide |
| 47 | 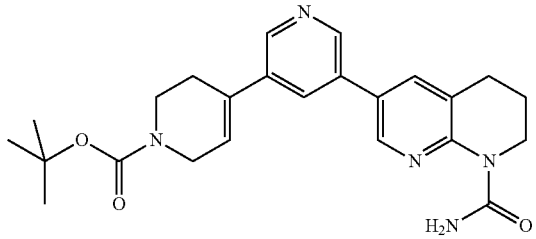 [SMILES: CC(C)(C)OC(=O)N1CC=C(c2cncc(-c3cnc4c(c3)CCCN4C(N)=O)c2)CC1] | 5-(8-Carbamoyl-5,6,7,8-tetrahydro-[1,8]naphthyridin-3-yl)-3',6'-dihydro-2'H-[3,4']bipyridinyl-1'-carboxylic acid tert-butyl ester |
| 48 | 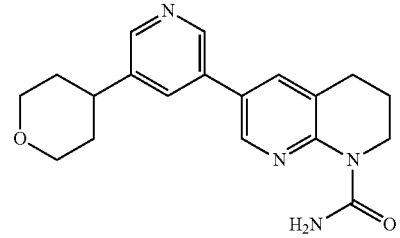 [SMILES: NC(=O)N1CCCc2cc(-c3cncc(C4CCOCC4)c3)cnc21] | 6-[5-(Tetrahydro-pyran-4-yl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 49 | 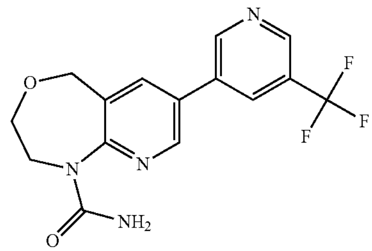 [SMILES: NC(=O)N1CCOCc2cc(-c3cncc(C(F)(F)F)c3)cnc21] | 3-(5-trifluoromethyl-pyridin-3-yl)-7,8-dihydro-5H-6-oxa-1,9-diaza-benzocycloheptene-9-carboxylic acid amide |
| 50 | 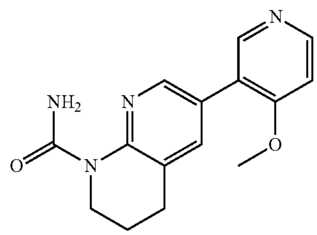 [SMILES: COc1ccncc1-c1cnc2c(c1)CCCN2C(N)=O] | 6-(4-Methoxy-pyridin-3-yl)-3,4-dihydro-2H-[1,8]naphthyridine-1-carboxylic acid amide |
| 51 | 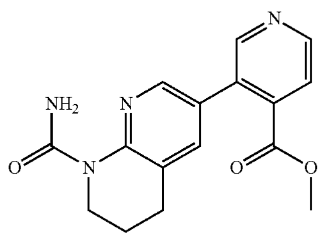 [SMILES: COC(=O)c1ccncc1-c1cnc2c(c1)CCCN2C(N)=O] | 3-(8-Carbamoyl-5,6,7,8-tetrahydro-[1,8]naphthyridin-3-yl)-isonicotinic acid methyl ester |
| 52 | 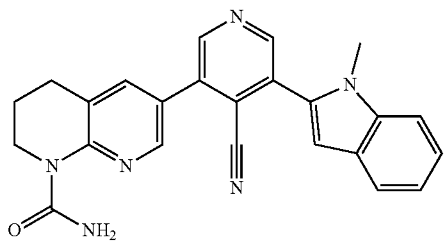 [SMILES: Cn1c(-c2cncc(-c3cnc4c(c3)CCCN4C(N)=O)c2C#N)cc2ccccc21] | 6-[4-Cyano-5-(1-methyl-1H-indol-2-yl)-pyridin-3-yl]-3,4-dihydro-2H-[1,8]naphthyridine-1-carboxylic acid amide |
| 53 | 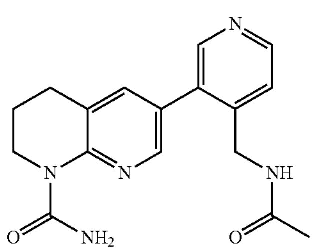 [SMILES: CC(=O)NCc1ccncc1-c1cnc2c(c1)CCCN2C(N)=O] | 6-[4-(Acetylamino-methyl)-pyridin-3-yl]-3,4-dihydro-2H-[1,8]naphthyridine-1-carboxylic acid amide |
| 54 | 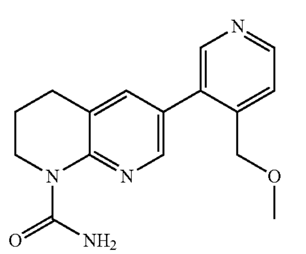 [SMILES: COCc1ccncc1-c1cnc2c(c1)CCCN2C(N)=O] | 6-(4-Methoxymethyl-pyridin-3-yl)-3,4-dihydro-2H-[1,8]naphthyridine-1-carboxylic acid amide |

TABLE 1-continued

| Cpd No | STRUCTURE | Name |
|---|---|---|
| 55 | 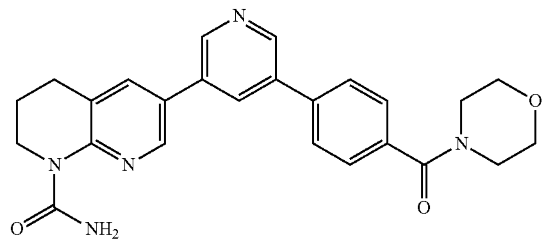 [SMILES: NC(=O)N1CCCc2cc(-c3cncc(-c4ccc(C(=O)N5CCOCC5)cc4)c3)cnc21] | 6-{5-[4-(Morpholine-4-carbonyl)-phenyl]-pyridin-3-yl}-3,4-dihydro-2H-[1,8]naphthyridine-1-carboxylic acid amide |
| 56 | 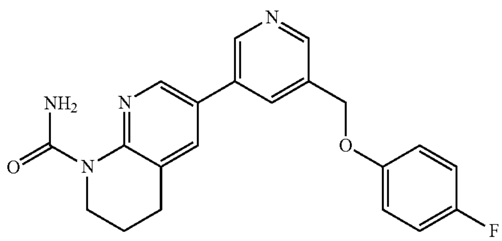 [SMILES: NC(=O)N1CCCc2cc(-c3cncc(COc4ccc(F)cc4)c3)cnc21] | 6-[5-(4-Fluoro-phenoxymethyl)-pyridin-3-yl]-3,4-dihydro-2H-[1,8]naphthyridine-1-carboxylic acid amide |
| 57 | 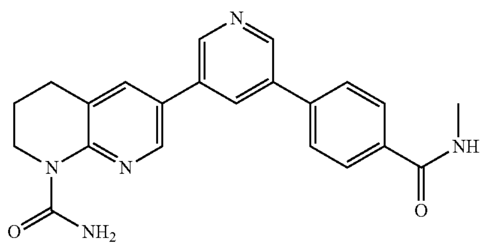 [SMILES: CNC(=O)c1ccc(-c2cncc(-c3cnc4c(c3)CCCN4C(N)=O)c2)cc1] | 6-[5-(4-Methylcarbamoyl-phenyl)-pyridin-3-yl]-3,4-dihydro-2H-[1,8]naphthyridine-1-carboxylic acid amide |
| 58 | 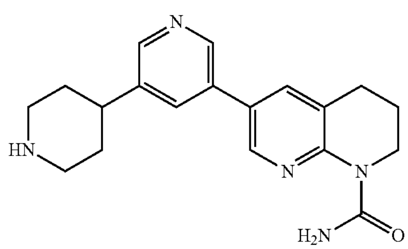 [SMILES: NC(=O)N1CCCc2cc(-c3cncc(C4CCNCC4)c3)cnc21] | 6-(1',2',3',4',5',6'-Hexahydro-[3,4']bipyridinyl-5-yl)-3,4-dihydro-2H-[1,8]naphthyridine-1-carboxylic acid amide |
| 59 | 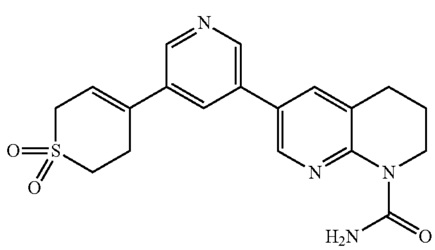 [SMILES: NC(=O)N1CCCc2cc(-c3cncc(C4=CCS(=O)(=O)CC4)c3)cnc21] | 6-[5-(1,1-Dioxo-1,2,3,6-tetrahydro-1lambda6-thiopyran-4-yl)-pyridin-3-yl]-3,4-dihydro-2H-[1,8]naphthyridine-1-carboxylic acid amide |
| 60 | 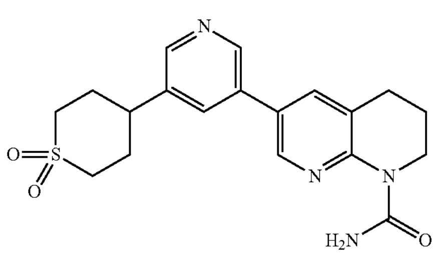 | 6-[5-(1,1-Dioxo-hexahydro-1lambda6-thiopyran-4-yl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 61 | 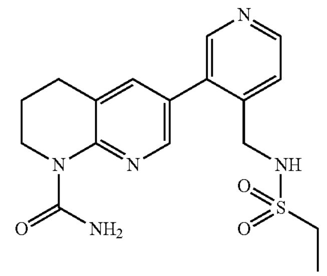 [SMILES: CCS(=O)(=O)NCc1ccncc1-c1cnc2c(c1)CCCN2C(N)=O] | 6-[4-(Ethanesulfonylamino-methyl)-pyridin-3-yl]-3,4-dihydro-2H-[1,8]naphthyridine-1-carboxylic acid amide |
| 62 | 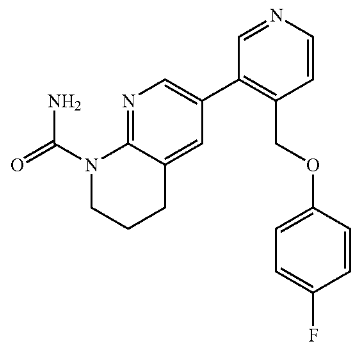 [SMILES: NC(=O)N1CCCc2cc(-c3cnccc3COc3ccc(F)cc3)cnc21] | 6-[4-(4-Fluoro-phenoxymethyl)-pyridin-3-yl]-3,4-dihydro-2H-[1,8]naphthyridine-1-carboxylic acid amide |
| 63 | 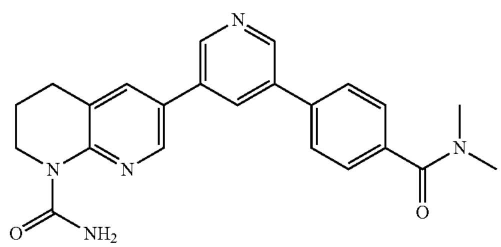 [SMILES: CN(C)C(=O)c1ccc(-c2cncc(-c3cnc4c(c3)CCCN4C(N)=O)c2)cc1] | 6-[5-(4-Dimethylcarbamoyl-phenyl)-pyridin-3-yl]-3,4-dihydro-2H-[1,8]naphthyridine-1-carboxylic acid amide |
| 64 | 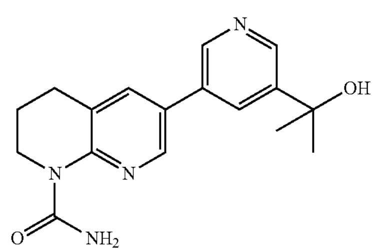 [SMILES: CC(C)(O)c1cncc(-c2cnc3c(c2)CCCN3C(N)=O)c1] | 6-[5-(1-Hydroxy-1-methyl-ethyl)-pyridin-3-yl]-3,4-dihydro-2H-[1,8]naphthyridine-1-carboxylic acid amide |
| 65 | 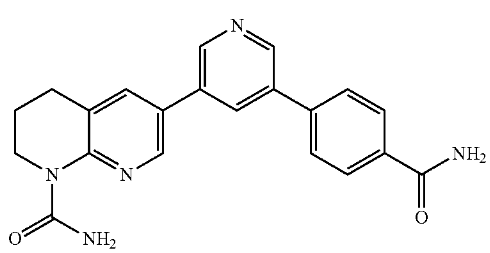 [SMILES: NC(=O)c1ccc(-c2cncc(-c3cnc4c(c3)CCCN4C(N)=O)c2)cc1] | 6-[5-(4-Carbamoyl-phenyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 66 | 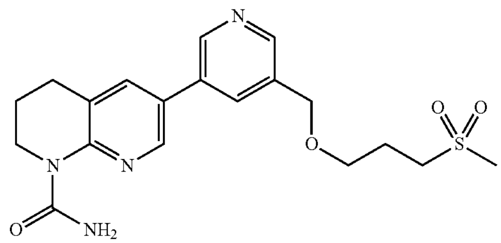 [SMILES: CS(=O)(=O)CCCOCc1cncc(-c2cnc3c(c2)CCCN3C(N)=O)c1] | 6-[5-(3-Methanesulfonyl-propoxymethyl)-pyridin-3-yl]-3,4-dihydro-2H-[1,8]naphthyridine-1-carboxylic acid amide |
| 67 | 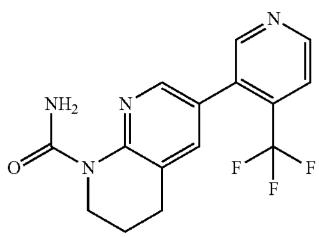 [SMILES: NC(=O)N1CCCc2cc(-c3cnccc3C(F)(F)F)cnc21] | 6-(4-Trifluoromethyl-pyridin-3-yl)-3,4-dihydro-2H-[1,8]naphthyridine-1-carboxylic acid amide |
| 68 | 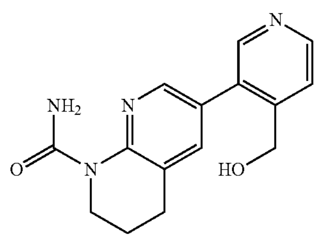 [SMILES: NC(=O)N1CCCc2cc(-c3cnccc3CO)cnc21] | 6-(4-Hydroxymethyl-pyridin-3-yl)-3,4-dihydro-2H-[1,8]naphthyridine-1-carboxylic acid amide |
| 69 | 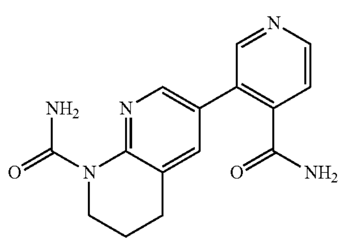 [SMILES: NC(=O)c1ccncc1-c1cnc2c(c1)CCCN2C(N)=O] | 6-(4-Carbamoyl-pyridin-3-yl)-3,4-dihydro-2H-[1,8]naphthyridine-1-carboxylic acid amide |
| 70 | 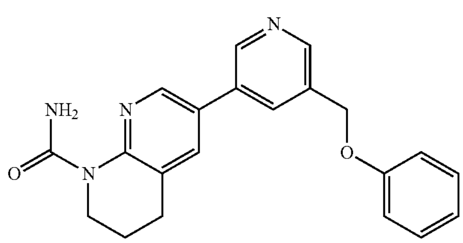 [SMILES: NC(=O)N1CCCc2cc(-c3cncc(COc4ccccc4)c3)cnc21] | 6-(5-Benzyloxy-pyridin-3-yl)-3,4-dihydro-2H-[1,8]naphthyridine-1-carboxylic acid amide |
| 71 | 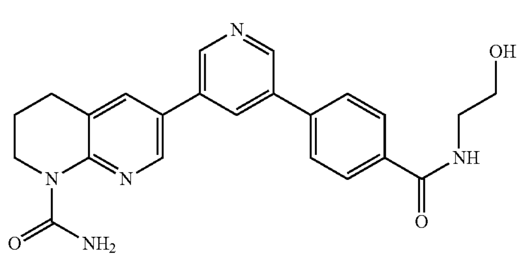 [SMILES: NC(=O)N1CCCc2cc(-c3cncc(-c4ccc(C(=O)NCCO)cc4)c3)cnc21] | 6-{5-[4-(2-Hydroxy-ethylcarbamoyl)-phenyl]-pyridin-3-yl}-3,4-dihydro-2H-[1,8]naphthyridine-1-carboxylic acid amide |

TABLE 1-continued

| Cpd No | STRUCTURE | Name |
|---|---|---|
| 72 | 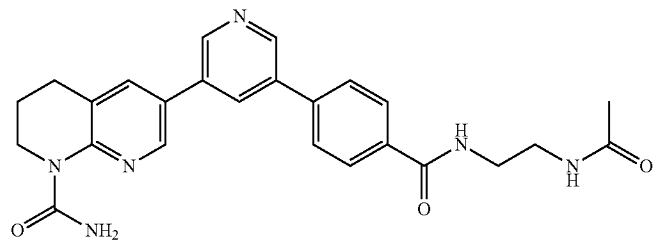 [SMILES: CC(=O)NCCNC(=O)c1ccc(-c2cncc(-c3cnc4c(c3)CCCN4C(N)=O)c2)cc1] | 6-{5-[4-(2-Acetylamino-ethylcarbamoyl)-phenyl]-pyridin-3-yl}-3,4-dihydro-2H-[1,8]naphthyridine-1-carboxylic acid amide |
| 73 | 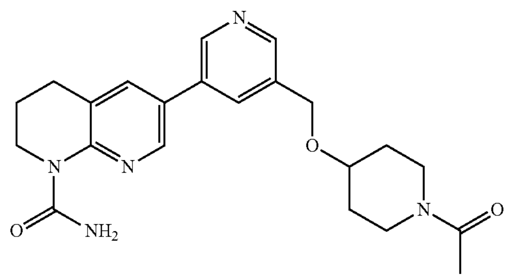 [SMILES: CC(=O)N1CCC(OCc2cncc(-c3cnc4c(c3)CCCN4C(N)=O)c2)CC1] | 6-[5-(1-Acetyl-piperidin-4-yloxymethyl)-pyridin-3-yl]-3,4-dihydro-2H-[1,8]naphthyridine-1-carboxylic acid amide |
| 74 | 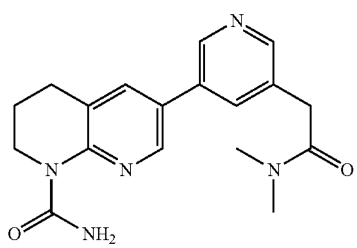 [SMILES: CN(C)C(=O)Cc1cncc(-c2cnc3c(c2)CCCN3C(N)=O)c1] | 6-(5-Dimethylcarbamoylmethyl-pyridin-3-yl)-3,4-dihydro-2H-[1,8]naphthyridine-1-carboxylic acid amide |
| 75 | 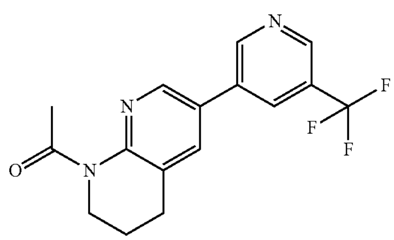 [SMILES: CC(=O)N1CCCc2cc(-c3cncc(C(F)(F)F)c3)cnc21] | 1-[6-(5-Trifluoromethyl-pyridin-3-yl)-3,4-dihydro-2H-[1,8]naphthyridin-1-yl]-ethanone |
| 76 | 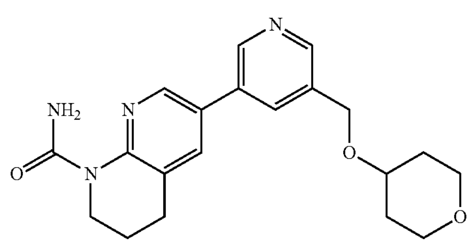 [SMILES: NC(=O)N1CCCc2cc(-c3cncc(COC4CCOCC4)c3)cnc21] | 6-[5-(Tetrahydro-pyran-4-yloxymethyl)-pyridin-3-yl]-3,4-dihydo-2H-[1,8]naphthyridine-1-carboxylic acid amide |
| 77 | 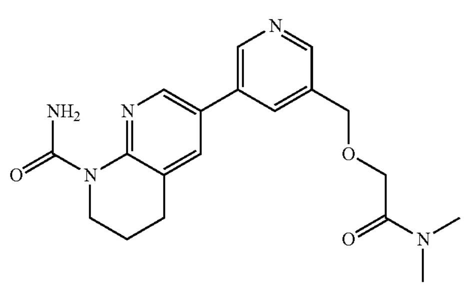 [SMILES: CN(C)C(=O)COCc1cncc(-c2cnc3c(c2)CCCN3C(N)=O)c1] | 6-(5-Dimethylcarbamoylmethoxymethyl-pyridin-3-yl)-3,4-dihydro-2H-[1,8]naphthyridine-1-carboxylic acid amide |

TABLE 1-continued

| Cpd No | STRUCTURE | Name |
|---|---|---|
| 78 | 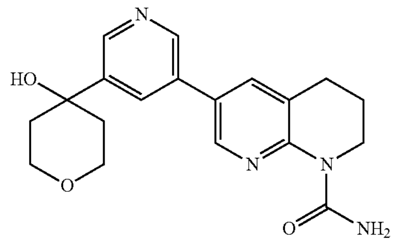 [SMILES: NC(=O)N1CCCc2cc(-c3cncc(C4(O)CCOCC4)c3)cnc21] | 6-[5-(4-Hydroxy-tetrahydro-pyran-4-yl)-pyridin-3-yl]-3,4-dihydro-2H-[1,8]naphthyridine-1-carboxylic acid amide |
| 79 | 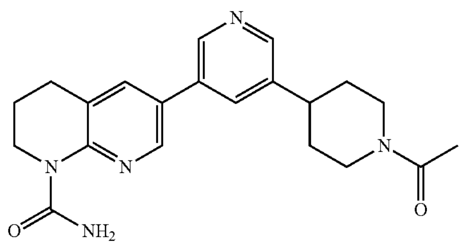 [SMILES: CC(=O)N1CCC(c2cncc(-c3cnc4c(c3)CCCN4C(N)=O)c2)CC1] | 6-(1'-Acetyl-1',2',3',4',5',6'-hexahydro-[3,4']bipyridinyl-5-yl)-3,4-dihydro-2H-[1,8]naphthyridine-1-carboxylic acid amide |
| 80 | 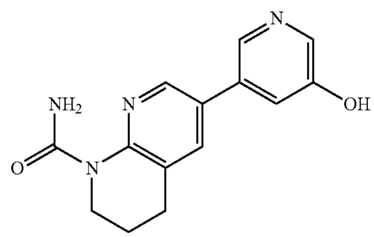 [SMILES: NC(=O)N1CCCc2cc(-c3cncc(O)c3)cnc21] | 6-(5-Hydroxy-pyridin-3-yl)-3,4-dihydro-2H-[1,8]naphthyridine-1-carboxylic acid amide |
| 81 | 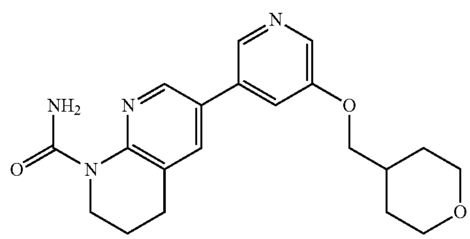 [SMILES: NC(=O)N1CCCc2cc(-c3cncc(OCC4CCOCC4)c3)cnc21] | 6-[5-(Tetrahydro-pyran-4-ylmethoxy)-pyridin-3-yl]-3,4-dihydro-2H-[1,8]naphthyridine-1-carboxylic acid amide |
| 82 | 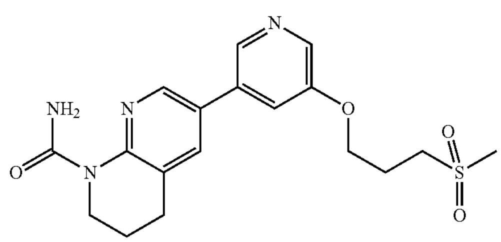 [SMILES: CS(=O)(=O)CCCOc1cncc(-c2cnc3c(c2)CCCN3C(N)=O)c1] | 6-[5-(3-Methanesulfonyl-propoxy)-pyridin-3-yl]-3,4-dihydro-2H-[1,8]naphthyridine-1-carboxylic acid amide |
| 83 | 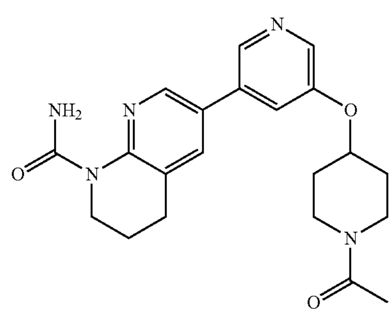 [SMILES: CC(=O)N1CCC(Oc2cncc(-c3cnc4c(c3)CCCN4C(N)=O)c2)CC1] | 6-[5-(1-Acetyl-piperidin-4-yloxy)-pyridin-3-yl]-3,4-dihydro-2H-[1,8]naphthyridine-1-carboxylic acid amide |

TABLE 1-continued

| Cpd No | STRUCTURE | Name |
|---|---|---|
| 84 | 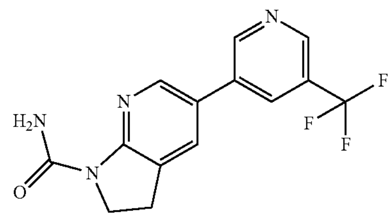 [SMILES: NC(=O)N1CCc2cc(-c3cncc(C(F)(F)F)c3)cnc21] | 5-(5-Trifluoromethyl-pyridin-3-yl)-2,3-dihydro-pyrrolo[2,3-b]pyridine-1-carboxylic acid amide |
| 85 | 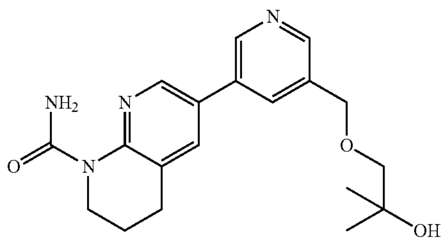 [SMILES: CC(C)(O)COCc1cncc(-c2cnc3c(c2)CCCN3C(N)=O)c1] | 6-[5-(2-Hydroxy-2-methyl-propoxymethyl)-pyridin-3-yl]-3,4-dihydro-2H-[1,8]naphthyridine-1-carboxylic acid amide |
| 86 | 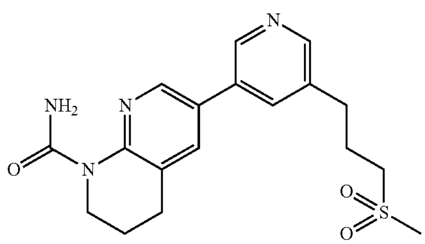 [SMILES: CS(=O)(=O)CCCc1cncc(-c2cnc3c(c2)CCCN3C(N)=O)c1] | 6-[5-(3-Methanesulfonyl-propyl)-pyridin-3-yl]-3,4-dihydro-2H-[1,8]naphthyridine-1-carboxylic acid amide |
| 87 | 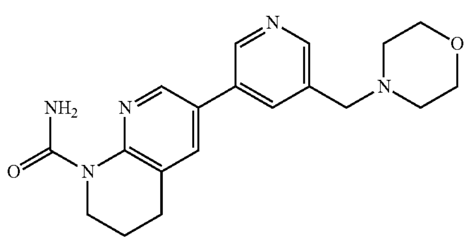 [SMILES: NC(=O)N1CCCc2cc(-c3cncc(CN4CCOCC4)c3)cnc21] | 6-(5-Morpholin-4-ylmethyl-pyridin-3-yl)-3,4-dihydro-2H-[1,8]naphthyridine-1-carboxylic acid amide |
| 88 | 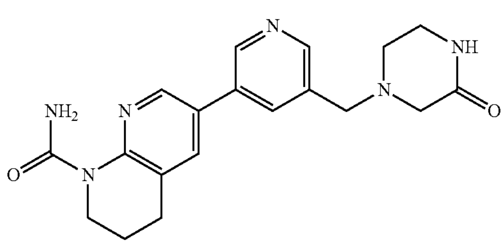 [SMILES: NC(=O)N1CCCc2cc(-c3cncc(CN4CCNC(=O)C4)c3)cnc21] | 6-[5-(3-Oxo-piperazin-1-ylmethyl)-pyridin-3-yl]-3,4-dihydro-2H-[1,8]naphthyridine-1-carboxylic acid amide |
| 89 | 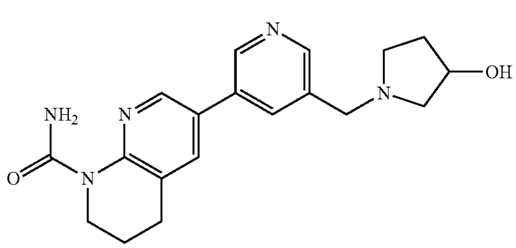 [SMILES: NC(=O)N1CCCc2cc(-c3cncc(CN4CCC(O)C4)c3)cnc21] | 6-[5-(3-Hydroxy-pyrrolidin-1-ylmethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 90 | 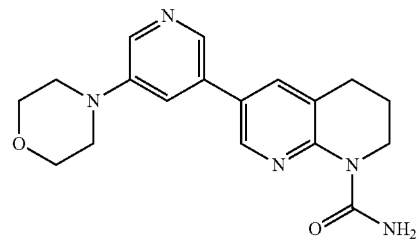 [SMILES: NC(=O)N1CCCc2cc(-c3cncc(N4CCOCC4)c3)cnc21] | 6-(5-Morpholin-4-yl-pyridin-3-yl)-3,4-dihydro-2H-[1,8]naphthyridine-1-carboxylic acid amide |
| 91 | 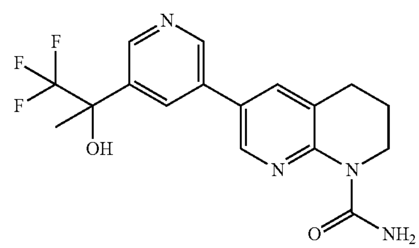 [SMILES: CC(O)(c1cncc(-c2cnc3c(c2)CCCN3C(N)=O)c1)C(F)(F)F] | 6-[5-(2,2,2-Trifluoro-1-hydroxy-1-methyl-ethyl)-pyridin-3-yl]-3,4-dihydro-2H-[1,8]naphthyridine-1-carboxylic acid amide |
| 92 | 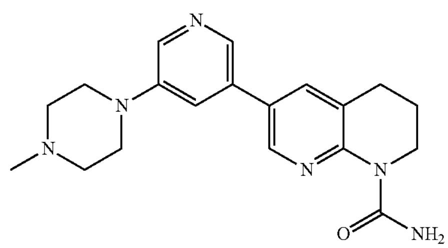 [SMILES: CN1CCN(c2cncc(-c3cnc4c(c3)CCCN4C(N)=O)c2)CC1] | 6-[5-(4-Methyl-piperazin-1-yl)-pyridin-3-yl]-3,4-dihydro-2H-[1,8]naphthyridine-1-carboxylic acid amide |
| 93 | 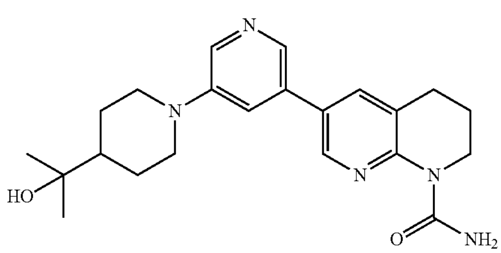 [SMILES: CC(C)(O)C1CCN(c2cncc(-c3cnc4c(c3)CCCN4C(N)=O)c2)CC1] | 6-[4-(1-Hydroxy-1-methyl-ethyl)-3,4,5,6-tetrahydro-2H-[1,3']bipyridinyl-5'-yl]-3,4-dihydro-2H-[1,8]naphthyridine-1-carboxylic acid amide |
| 94 | 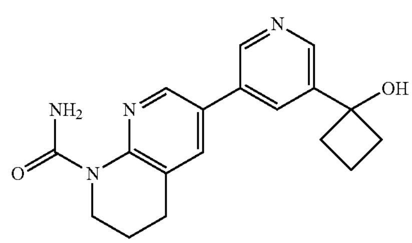 [SMILES: NC(=O)N1CCCc2cc(-c3cncc(C4(O)CCC4)c3)cnc21] | 6-[5-(1-Hydroxy-cyclobutyl)-pyridin-3-yl]-3,4-dihydro-2H-[1,8]naphthyridine-1-carboxylic acid amide |
| 95 | 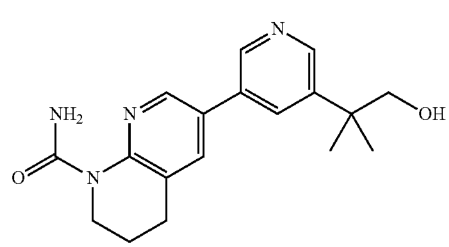 [SMILES: CC(C)(CO)c1cncc(-c2cnc3c(c2)CCCN3C(N)=O)c1] | 6-[5-(2-Hydroxy-1,1-dimethyl-ethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 96 | 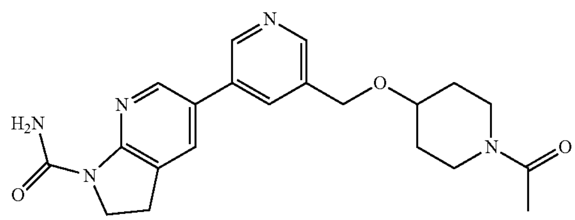 [SMILES: CC(=O)N1CCC(OCc2cncc(-c3cnc4c(c3)CCN4C(N)=O)c2)CC1] | 5-[5-(1-Acetyl-piperidin-4-yloxymethyl)-pyridin-3-yl]-2,3-dihydro-pyrrolo[2,3-b]pyridine-1-carboxylic acid amide |
| 97 | 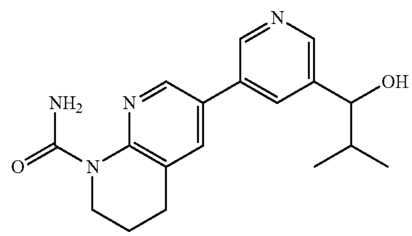 [SMILES: CC(C)C(O)c1cncc(-c2cnc3c(c2)CCCN3C(N)=O)c1] | 6-[5-(1-Hydroxy-2-methyl-propyl)-pyridin-3-yl]-3,4-dihydro-2H-[1,8]naphthyridine-1-carboxylic acid amide |
| 98 | 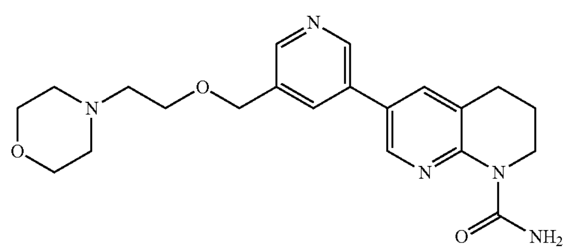 [SMILES: NC(=O)N1CCCc2cc(-c3cncc(COCCN4CCOCC4)c3)cnc21] | 6-[5-(2-Morpholin-4-yl-ethoxymethyl)-pyridin-3-yl]-3,4-dihydro-2H-[1,8]naphthyridine-1-carboxylic acid amide |
| 99 | 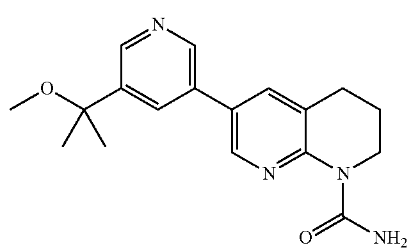 [SMILES: COC(C)(C)c1cncc(-c2cnc3c(c2)CCCN3C(N)=O)c1] | 6-[5-(1-Methoxy-1-methyl-ethyl)-pyridin-3-yl]-3,4-dihydro-2H-[1,8]naphthyridine-1-carboxylic acid amide |
| 100 | 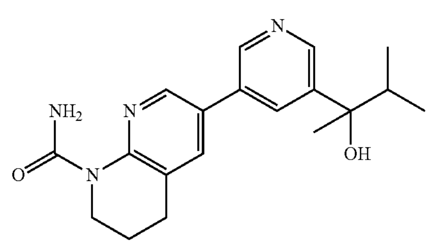 [SMILES: CC(C)C(C)(O)c1cncc(-c2cnc3c(c2)CCCN3C(N)=O)c1] | 6-[5-(1-Hydroxy-1,2-dimethyl-propyl)-pyridin-3-yl]-3,4-dihydro-2H-[1,8]naphthyridine-1-carboxylic acid amide |
| 101 | 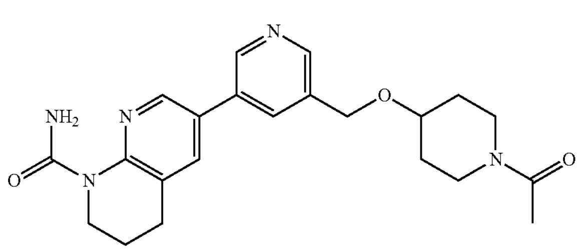 [SMILES: CC(=O)N1CCC(OCc2cncc(-c3cnc4c(c3)CCCN4C(N)=O)c2)CC1] | 1-{4-[5-(8-Acetyl-5,6,7,8-tetrahydro-[1,8]naphthyridin-3-yl)-pyridin-3-ylmethoxy]-piperidin-1-yl}-ethanone |

TABLE 1-continued

| Cpd No | STRUCTURE | Name |
|---|---|---|
| 102 | 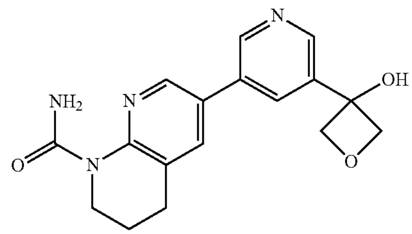 | 6-[5-(3-Hydroxy-oxetan-3-yl)-pyridin-3-yl]-3,4-dihydro-2H-[1,8]naphthyridine-1-carboxylic acid amide |
| 103 | 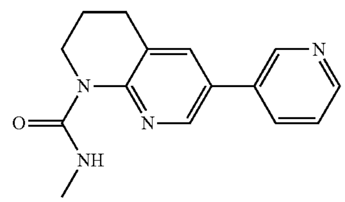 [SMILES: CNC(=O)N1CCCc2cc(-c3cccnc3)cnc21] | 6-Pyridin-3-yl-3,4-dihydro-2H-[1,8]naphthyridine-1-carboxylic acid methylamide |
| 104 | 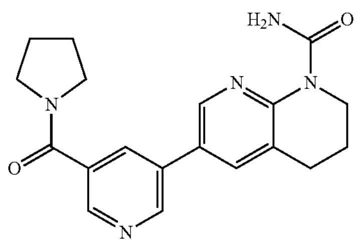 [SMILES: NC(=O)N1CCCc2cc(-c3cncc(C(=O)N4CCCC4)c3)cnc21] | 6-[5-(Pyrrolidine-1-carbonyl)-pyridin-3-yl]-3,4-dihydro-2H-[1,8]naphthyridine-1-carboxylic acid amide |
| 105 | 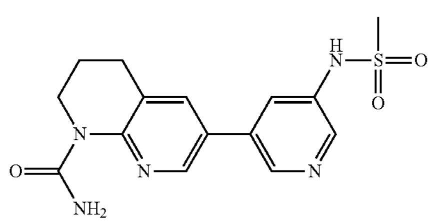 [SMILES: CS(=O)(=O)Nc1cncc(-c2cnc3c(c2)CCCN3C(N)=O)c1] | 6-(5-Methanesulfonylamino-pyridin-3-yl)-3,4-dihydro-2H-[1,8]naphthyridine-1-carboxylic acid amide |
| 106 | 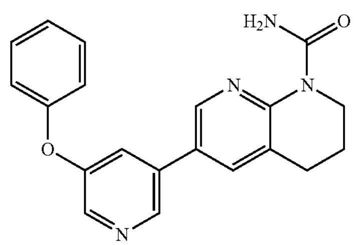 [SMILES: NC(=O)N1CCCc2cc(-c3cncc(Oc4ccccc4)c3)cnc21] | 6-(5-Phenoxy-pyridin-3-yl)-3,4-dihydro-2H-[1,8]naphthyridine-1-carboxylic acid amide |
| 107 | 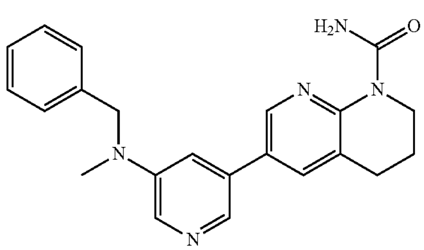 [SMILES: CN(Cc1ccccc1)c1cncc(-c2cnc3c(c2)CCCN3C(N)=O)c1] | 6-[5-(Benzyl-methyl-amino)-pyridin-3-yl]-3,4-dihydro-2H-[1,8]naphthyridine-1-carboxylic acid amide |

TABLE 1-continued

| Cpd No | STRUCTURE | Name |
|---|---|---|
| 108 | 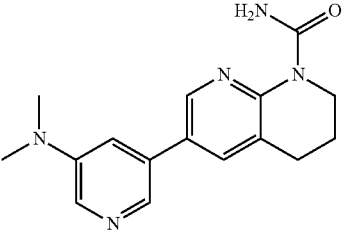 [SMILES: CN(C)c1cncc(-c2cnc3c(c2)CCCN3C(N)=O)c1] | 6-(5-Dimethylamino-pyridin-3-yl)-3,4-dihydro-2H-[1,8]naphthyridine-1-carboxylic acid amide |
| 109 | 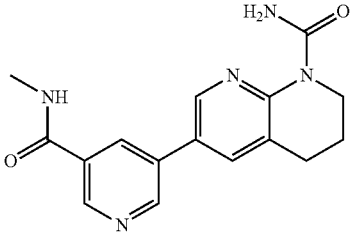 [SMILES: CNC(=O)c1cncc(-c2cnc3c(c2)CCCN3C(N)=O)c1] | 6-(5-Methylcarbamoyl-pyridin-3-yl)-3,4-dihydro-2H-[1,8]naphthyridine-1-carboxylic acid amide |
| 110 | 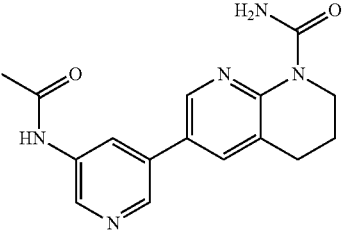 [SMILES: CC(=O)Nc1cncc(-c2cnc3c(c2)CCCN3C(N)=O)c1] | 6-(5-Acetylamino-pyridin-3-yl)-3,4-dihydro-2H-[1,8]naphthyridine-1-carboxylic acid amide |
| 111 | 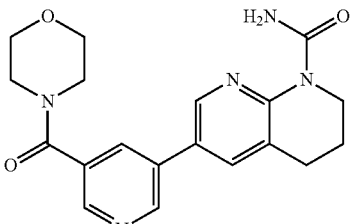 | 6-[5-(Morpholine-4-carbonyl)-pyridin-3-yl]-3,4-dihydro-2H-[1,8]naphthyridine-1-carboxylic acid amide |
| 112 | 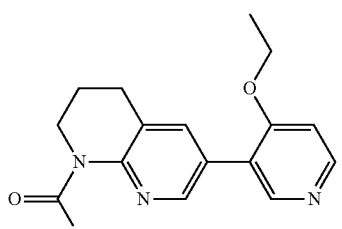 | 6-(4-Ethoxy-pyridin-3-yl)-3,4-dihydro-2H-[1,8]naphthyridine-1-carboxylic acid amide |
| 113 | 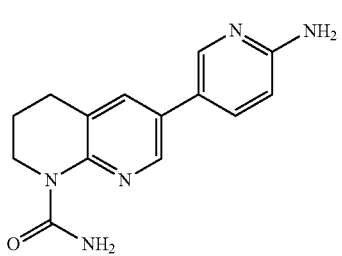 [SMILES: NC(=O)N1CCCc2cc(-c3ccc(N)nc3)cnc21] | 6-(6-Amino-pyridin-3-yl)-3,4-dihydro-2H-[1,8]naphthyridine-1-carboxylic acid amide |

TABLE 1-continued

| Cpd No | STRUCTURE | Name |
|---|---|---|
| 114 | 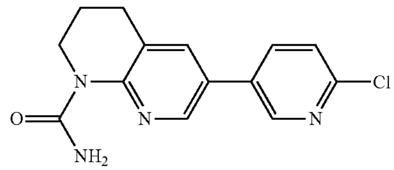 [SMILES: NC(=O)N1CCCc2cc(-c3ccc(Cl)nc3)cnc21] | 6-(6-Chloro-pyridin-3-yl)-3,4-dihydro-2H-[1,8]naphthyridine-1-carboxylic acid amide |
| 115 | 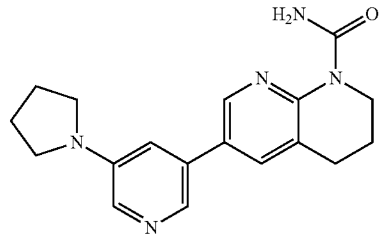 [SMILES: NC(=O)N1CCCc2cc(-c3cncc(N4CCCC4)c3)cnc21] | 6-(5-Pyrrolidine-1-yl-pyridin-3-yl)-3,4-dihydro-2H-[1,8]naphthyridine-1-carboxylic acid amide |
| 116 | 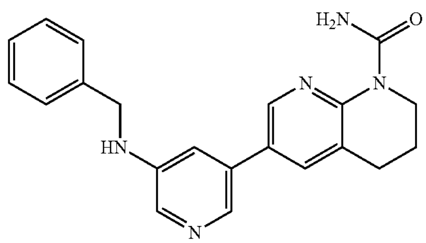 [SMILES: NC(=O)N1CCCc2cc(-c3cncc(NCc4ccccc4)c3)cnc21] | 6-(5-Benzylamino-pyridin-3-yl)-3,4-dihydro-2H-[1,8]naphthyridine-1-carboxylic acid amide |
| 117 | 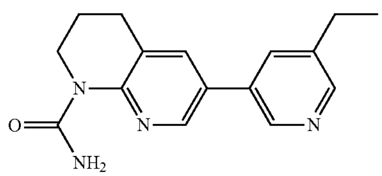 | 6-(5-Ethyl-pyridin-3-yl)-3,4-dihydro-2H-[1,8]naphthyridine-1-carboxylic acid amide |
| 118 | 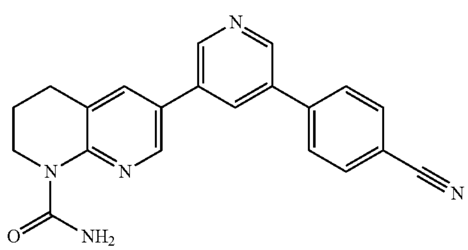 [SMILES: N#Cc1ccc(-c2cncc(-c3cnc4c(c3)CCCN4C(N)=O)c2)cc1] | 6-[5-(4-Cyano-phenyl)-pyridin-3-yl]-3,4-dihydro-2H-[1,8]naphthyridine-1-carboxylic acid amide |
| 119 | 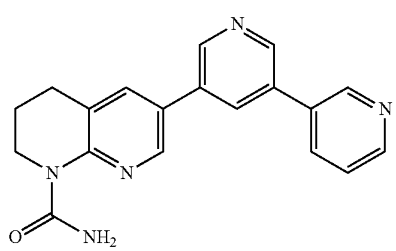 [SMILES: NC(=O)N1CCCc2cc(-c3cncc(-c4cccnc4)c3)cnc21] | 6-[3,3']Bipyridinyl-5-yl-3,4-dihydro-2H-[1,8]naphthyridine-1-carboxylic acid amide |
| 120 | 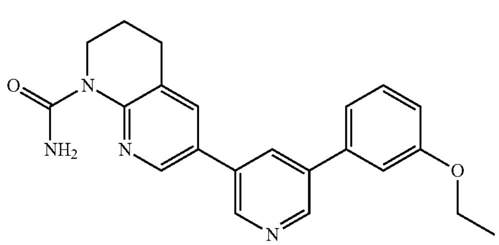 [SMILES: CCOc1cccc(-c2cncc(-c3cnc4c(c3)CCCN4C(N)=O)c2)c1] | 6-[5-(3-Ethoxy-phenyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 121 | 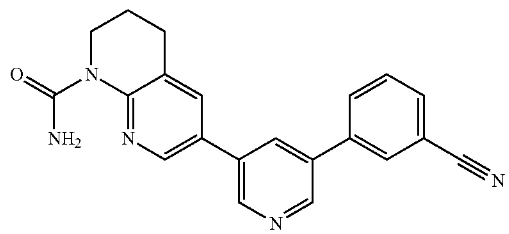 [SMILES: N#Cc1cccc(-c2cncc(-c3cnc4c(c3)CCCN4C(N)=O)c2)c1] | 6-[5-(3-Cyano-phenyl)-pyridin-3-yl]-3,4-dihydro-2H-[1,8]naphthyridine-1-carboxylic acid amide |
| 122 | 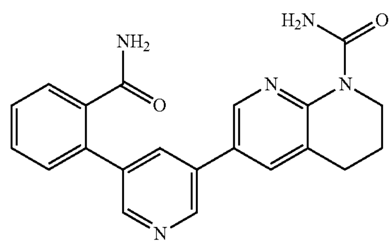 [SMILES: NC(=O)c1ccccc1-c1cncc(-c2cnc3c(c2)CCCN3C(N)=O)c1] | 6-[5-(2-Carbamoyl-phenyl)-pyridin-3-yl]-3,4-dihydro-2H-[1,8]naphthyridine-1-carboxylic acid amide |
| 123 | 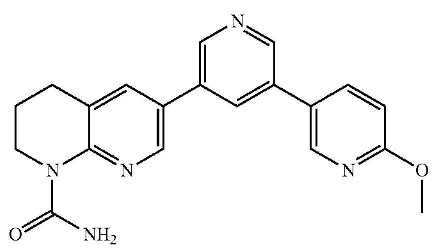 [SMILES: COc1ccc(-c2cncc(-c3cnc4c(c3)CCCN4C(N)=O)c2)cn1] | 6-(6'-Methoxy-[3,3']bipyridinyl-5-yl)-3,4-dihydro-2H-[1,8]naphthyridine-1-carboxylic acid amide |
| 124 | 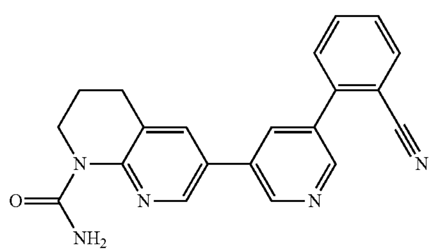 [SMILES: N#Cc1ccccc1-c1cncc(-c2cnc3c(c2)CCCN3C(N)=O)c1] | 6-[5-(2-Cyano-phenyl)-pyridin-3-yl]-3,4-dihydro-2H-[1,8]naphthyridine-1-carboxylic acid amide |
| 125 | 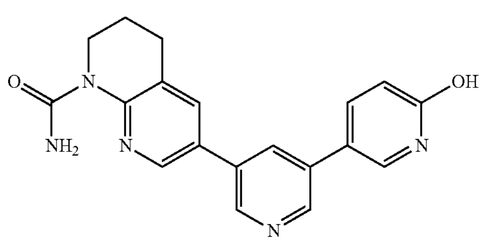 [SMILES: NC(=O)N1CCCc2cc(-c3cncc(-c4ccc(O)nc4)c3)cnc21] | 6-(6'-Hydroxy-[3,3']bipyridinyl-5-yl)-3,4-dihydro-2H-[1,8]naphthyridine-1-carboxylic acid amide |
| 126 | 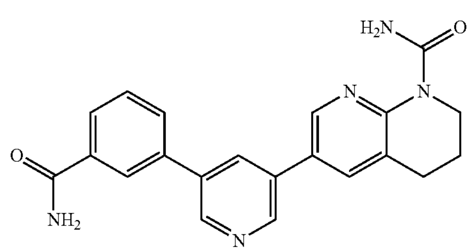 [SMILES: NC(=O)c1cccc(-c2cncc(-c3cnc4c(c3)CCCN4C(N)=O)c2)c1] | 6-[5-(3-Carbamoyl-phenyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 127 | 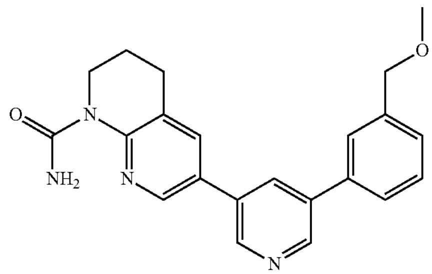 [SMILES: COCc1cccc(-c2cncc(-c3cnc4c(c3)CCCN4C(N)=O)c2)c1] | 6-[5-(3-Methoxymethyl-phenyl)-pyridin-3-yl]-3,4-dihydro-2H-[1,8]naphthyridine-1-carboxylic acid amide |
| 128 | 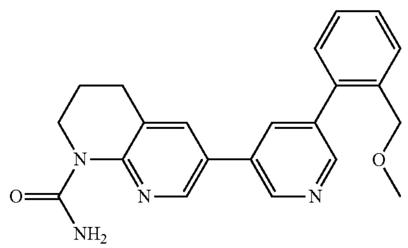 [SMILES: COCc1ccccc1-c1cncc(-c2cnc3c(c2)CCCN3C(N)=O)c1] | 6-[5-(2-Methoxymethyl-phenyl)-pyridin-3-yl]-3,4-dihydro-2H-[1,8]naphthyridine-1-carboxylic acid amide |
| 129 | 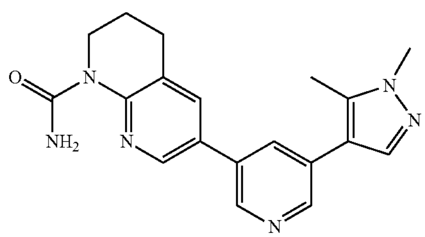 [SMILES: Cc1c(-c2cncc(-c3cnc4c(c3)CCCN4C(N)=O)c2)cnn1C] | 6-[5-(1,5-Dimethyl-1H-pyrazol-4-yl)-pyridin-3-yl]-3,4-dihydro-2H-[1,8]naphthyridine-1-carboxylic acid amide |
| 130 | 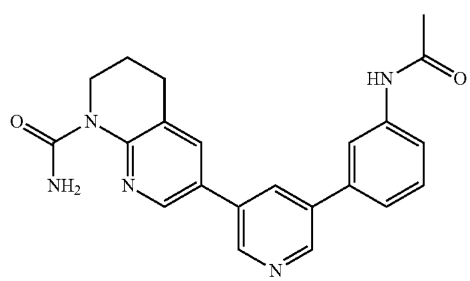 [SMILES: CC(=O)Nc1cccc(-c2cncc(-c3cnc4c(c3)CCCN4C(N)=O)c2)c1] | 6-[5-(3-Acetylamino-phenyl)-pyridin-3-yl]-3,4-dihydro-2H-[1,8]naphthyridine-1-carboxylic acid amide |
| 131 | 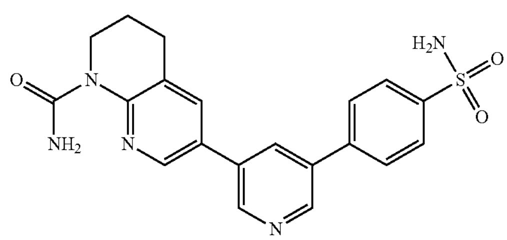 [SMILES: NC(=O)N1CCCc2cc(-c3cncc(-c4ccc(S(N)(=O)=O)cc4)c3)cnc21] | 6-[5-(4-Sulfamoyl-phenyl)-pyridin-3-yl]-3,4-dihydro-2H-[1,8]naphthyridine-1-carboxylic acid amide |
| 132 | 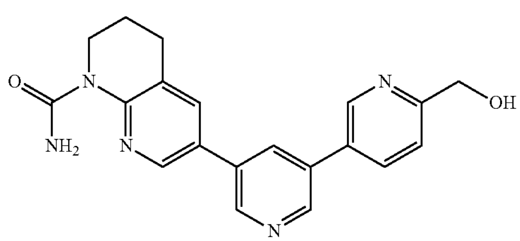 [SMILES: NC(=O)N1CCCc2cc(-c3cncc(-c4ccc(CO)nc4)c3)cnc21] | 6-(6'-Hydroxymethyl-[3,3']bipyridinyl-5-yl)-3,4-dihydro-2H-[1,8]naphthyridine-1-carboxylic acid amide |

TABLE 1-continued

| Cpd No | STRUCTURE | Name |
|---|---|---|
| 133 | 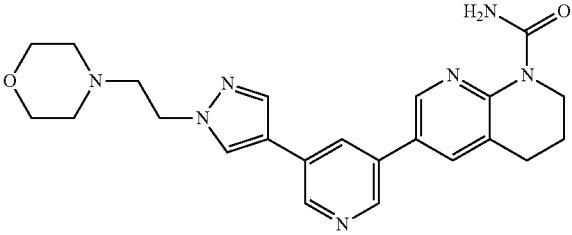 [SMILES: NC(=O)N1CCCc2cc(-c3cncc(-c4cnn(CCN5CCOCC5)c4)c3)cnc21] | 6-{5-[1-(2-Morpholin-4-yl-ethyl)-1H-pyrazol-4-yl]-pyridin-3-yl}-3,4-dihydro-2H-[1,8]naphthyridine-1-carboxylic acid amide |
| 134 | 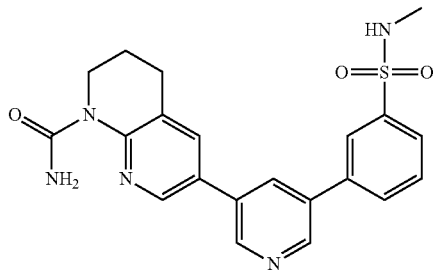 [SMILES: CNS(=O)(=O)c1cccc(-c2cncc(-c3cnc4c(c3)CCCN4C(N)=O)c2)c1] | 6-[5-(3-Methylsulfamoyl-phenyl)-pyridin-3-yl]-3,4-dihydro-2H-[1,8]naphthyridine-1-carboxylic acid amide |
| 135 | 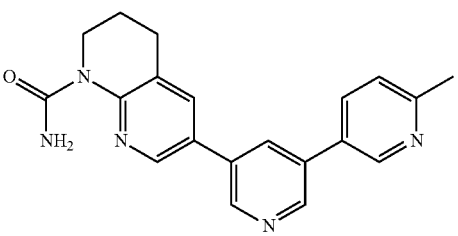 [SMILES: Cc1ccc(-c2cncc(-c3cnc4c(c3)CCCN4C(N)=O)c2)cn1] | 6-(6'-Methyl-[3,3']bipyridinyl-5-yl)-3,4-dihydro-2H-[1,8]naphthyridine-1-carboxylic acid amide |
| 136 | 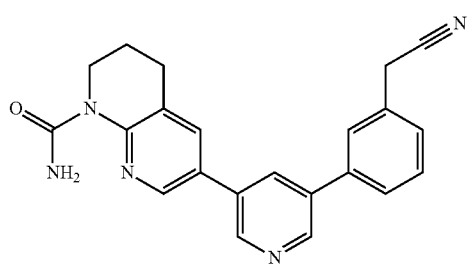 [SMILES: N#CCc1cccc(-c2cncc(-c3cnc4c(c3)CCCN4C(N)=O)c2)c1] | 6-[5-(3-Cyanomethyl-phenyl)-pyridin-3-yl]-3,4-dihydro-2H-[1,8]naphthyridine-1-carboxylic acid amide |
| 137 | 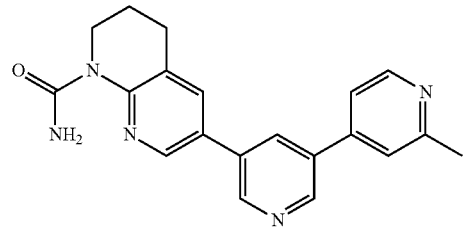 [SMILES: Cc1cc(-c2cncc(-c3cnc4c(c3)CCCN4C(N)=O)c2)ccn1] | 6-(2'-Methyl-[3,4']bipyridinyl-5-yl)-3,4-dihydro-2H-[1,8]naphthyridine-1-carboxylic acid amide |
| 138 | 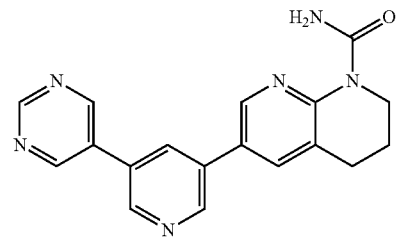 [SMILES: NC(=O)N1CCCc2cc(-c3cncc(-c4cncnc4)c3)cnc21] | 6-(5-Pyrimidin-5-yl-pyridin-3-yl)-3,4-dihydro-2H-[1,8]naphthyridine-1-carboxylic acid amide |

TABLE 1-continued

| Cpd No | STRUCTURE | Name |
|---|---|---|
| 139 | 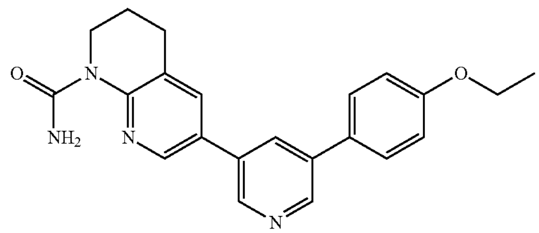 [SMILES: CCOc1ccc(-c2cncc(-c3cnc4c(c3)CCCN4C(N)=O)c2)cc1] | 6-[5-(4-Ethoxy-phenyl)-pyridin-3-yl]-3,4-dihydro-2H-[1,8]naphthyridine-1-carboxylic acid amide |
| 140 | 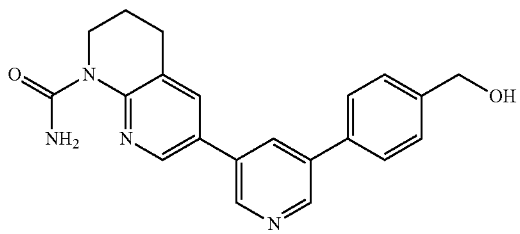 [SMILES: NC(=O)N1CCCc2cc(-c3cncc(-c4ccc(CO)cc4)c3)cnc21] | 6-[5-(4-Hydroxymethyl-phenyl)-pyridin-3-yl]-3,4-dihydro-2H-[1,8]naphthyridine-1-carboxylic acid amide |
| 141 | 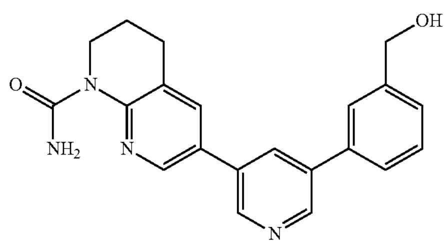 [SMILES: NC(=O)N1CCCc2cc(-c3cncc(-c4cccc(CO)c4)c3)cnc21] | 6-[5-(3-Hydroxymethyl-phenyl)-pyridin-3-yl]-3,4-dihydro-2H-[1,8]naphthyridine-1-carboxylic acid amide |
| 142 | 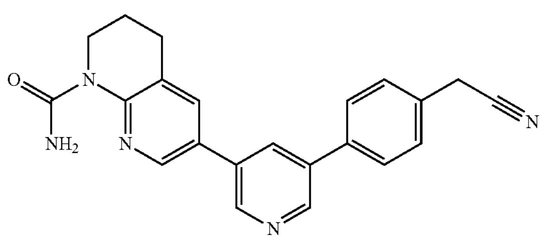 [SMILES: N#CCc1ccc(-c2cncc(-c3cnc4c(c3)CCCN4C(N)=O)c2)cc1] | 6-[5-(4-Cyanomethyl-phenyl)-pyridin-3-yl]-3,4-dihydro-2H-[1,8]naphthyridine-1-carboxylic acid amide |
| 143 | 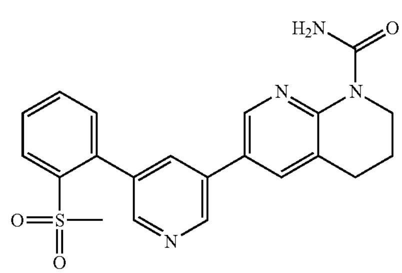 [SMILES: CS(=O)(=O)c1ccccc1-c1cncc(-c2cnc3c(c2)CCCN3C(N)=O)c1] | 6-[5-(2-Methanesulfonyl-phenyl)-pyridin-3-yl]-3,4-dihydro-2H-[1,8]naphthyridine-1-carboxylic acid amide |
| 144 | 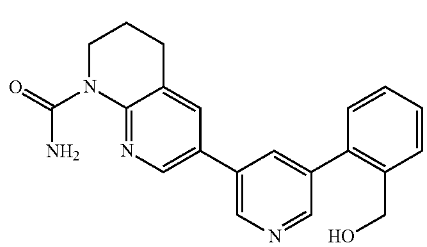 [SMILES: NC(=O)N1CCCc2cc(-c3cncc(-c4ccccc4CO)c3)cnc21] | 6-[5-(2-Hydroxymethyl-phenyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 145 | 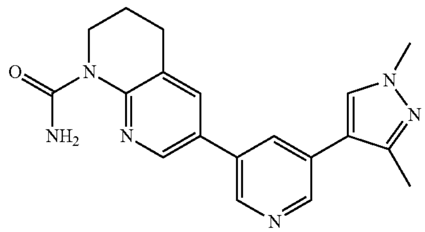 [SMILES: Cc1nn(C)cc1-c1cncc(-c2cnc3c(c2)CCCN3C(N)=O)c1] | 6-[5-(1,3-Dimethyl-1H-pyrazol-4-yl)-pyridin-3-yl]-3,4-dihydro-2H-[1,8]naphthyridine-1-carboxylic acid amide |
| 146 | 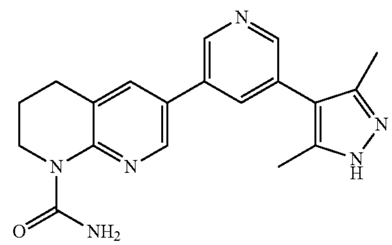 [SMILES: Cc1n[nH]c(C)c1-c1cncc(-c2cnc3c(c2)CCCN3C(N)=O)c1] | 6-[5-(3,5-Dimethyl-1H-pyrazol-4-yl)-pyridin-3-yl]-3,4-dihydro-2H-[1,8]naphthyridine-1-carboxylic acid amide |
| 147 | 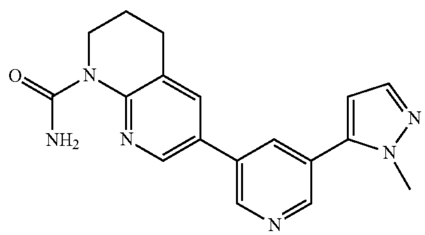 [SMILES: Cn1nccc1-c1cncc(-c2cnc3c(c2)CCCN3C(N)=O)c1] | 6-[5-(2-Methyl-2H-pyrazol-3-yl)-pyridin-3-yl]-3,4-dihydro-2H-[1,8]naphthyridine-1-carboxylic acid amide |
| 148 | 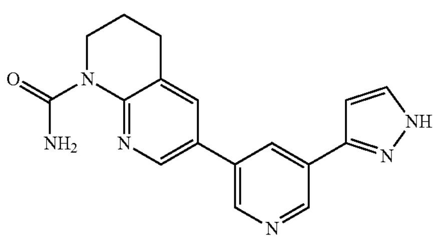 [SMILES: NC(=O)N1CCCc2cc(-c3cncc(-c4cc[nH]n4)c3)cnc21] | 6-[5-(1H-Pyrazol-3-yl)-pyridin-3-yl]-3,4-dihydro-2H-[1,8]naphthyridine-1-carboxylic acid amide |
| 149 | 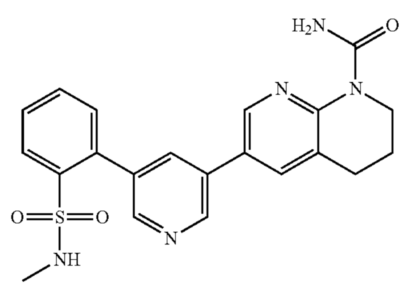 [SMILES: CNS(=O)(=O)c1ccccc1-c1cncc(-c2cnc3c(c2)CCCN3C(N)=O)c1] | 6-[5-(2-Methylsulfamoyl-phenyl)-pyridin-3-yl]-3,4-dihydro-2H-[1,8]naphthyridine-1-carboxylic acid amide |
| 150 | 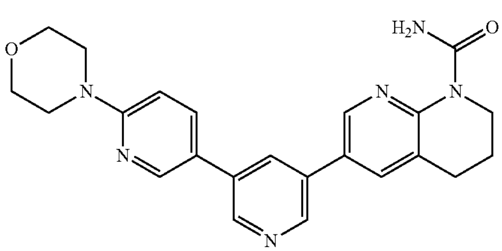 [SMILES: NC(=O)N1CCCc2cc(-c3cncc(-c4ccc(N5CCOCC5)nc4)c3)cnc21] | 6-(6'-Morpholin-4-yl-[3,3']bipyridinyl-5-yl)-3,4-dihydro-2H-[1,8]naphthyridine-1-carboxylic acid amide |

TABLE 1-continued

| Cpd No | STRUCTURE | Name |
|---|---|---|
| 151 | 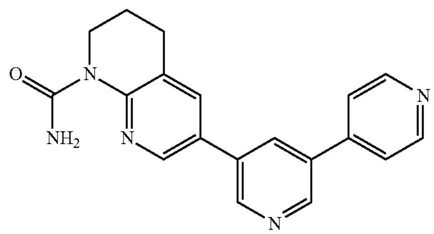 [SMILES: NC(=O)N1CCCc2cc(-c3cncc(-c4ccncc4)c3)cnc21] | 6-[3,4']Bipyridinyl-5-yl-3,4-dihydro-2H-[1,8]naphthyridine-1-carboxylic acid amide |
| 152 | 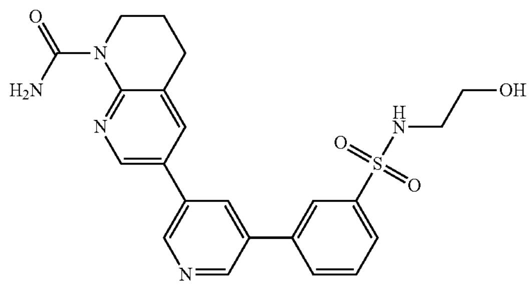 [SMILES: NC(=O)N1CCCc2cc(-c3cncc(-c4cccc(S(=O)(=O)NCCO)c4)c3)cnc21] | 6-{5-[3-(2-Hydroxy-ethylsulfamoyl)-phenyl]-pyridin-3-yl}-3,4-dihydro-2H-[1,8]naphthyridine-1-carboxylic acid amide |
| 153 | 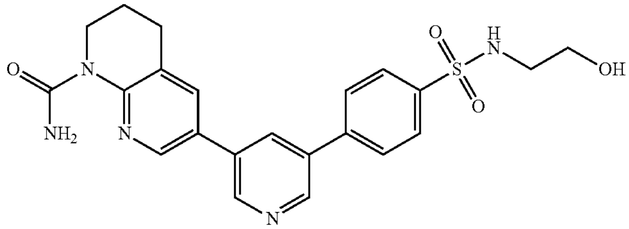 [SMILES: NC(=O)N1CCCc2cc(-c3cncc(-c4ccc(S(=O)(=O)NCCO)cc4)c3)cnc21] | 6-{5-[4-(2-Hydroxy-ethylsulfamoyl)-phenyl]-pyridin-3-yl}-3,4-dihydro-2H-[1,8]naphthyridine-1-carboxylic acid amide |
| 154 | 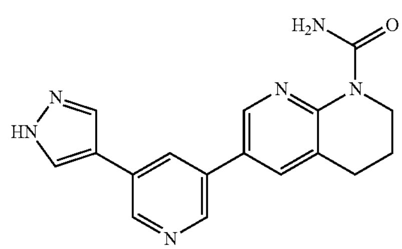 [SMILES: NC(=O)N1CCCc2cc(-c3cncc(-c4cn[nH]c4)c3)cnc21] | 6-[5-(1H-Pyrazol-4-yl)-pyridin-3-yl]-3,4-dihydro-2H-[1,8]naphthyridine-1-carboxylic acid amide |
| 155 | 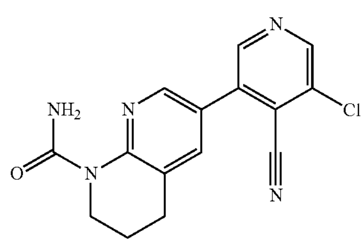 [SMILES: N#Cc1c(Cl)cncc1-c1cnc2c(c1)CCCN2C(N)=O] | 6-(5-Chloro-4-cyano-pyridin-3-yl)-3,4-dihydro-2H-[1,8]naphthyridine-1-carboxylic acid amide |
| 156 | 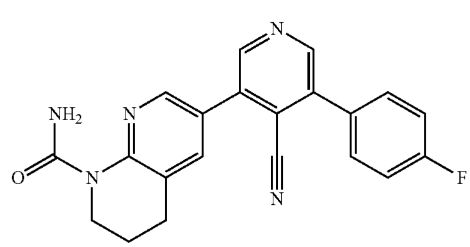 [SMILES: N#Cc1c(-c2ccc(F)cc2)cncc1-c1cnc2c(c1)CCCN2C(N)=O] | 6-[4-Cyano-5-(4-fluoro-phenyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 157 | 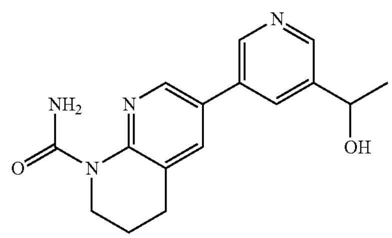 [SMILES: CC(O)c1cncc(-c2cnc3c(c2)CCCN3C(N)=O)c1] | 6-[5-(1-Hydroxy-ethyl)-pyridin-3-yl]-3,4-dihydro-2H-[1,8]naphthyridine-1-carboxylic acid amide Enantiomer A |
| 158 | 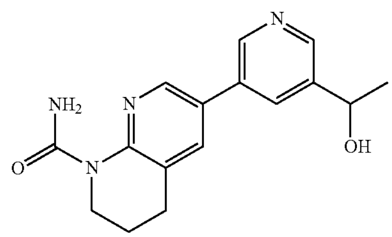 [SMILES: CC(O)c1cncc(-c2cnc3c(c2)CCCN3C(N)=O)c1] | 6-[5-(1-Hydroxy-ethyl)-pyridin-3-yl]-3,4-dihydro-2H-[1,8]naphthyridine-1-carboxylic acid amide Enantiomer B |
| 159 | 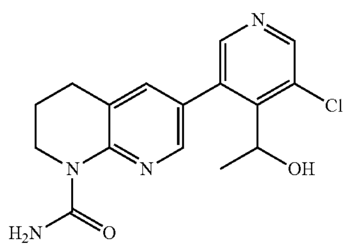 [SMILES: CC(O)c1c(Cl)cncc1-c1cnc2c(c1)CCCN2C(N)=O] | 6-[5-Chloro-4-(1-hydroxy-ethyl)-pyridin-3-yl]-3,4-dihydro-2H-[1,8]naphthyridine-1-carboxylic acid amide |
| 160 | 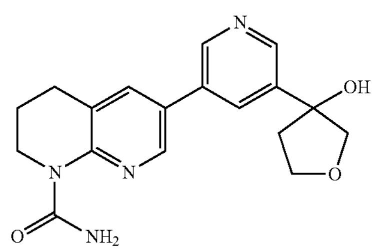 | 6-[5-(3-Hydroxy-tetrahydro-furan-3-yl)-pyridin-3-yl]-3,4-dihydro-2H-[1,8]naphthyridine-1-carboxylic acid amide |
| 161 | 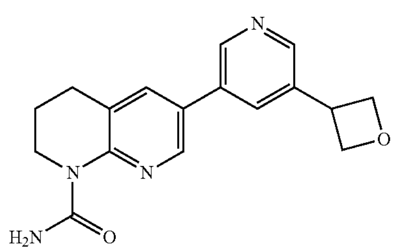 [SMILES: NC(=O)N1CCCc2cc(-c3cncc(C4COC4)c3)cnc21] | 6-(5-Oxetan-3-yl-pyridin-3-yl)-3,4-dihydro-2H-[1,8]naphthyridine-1-carboxylic acid amide |
| 162 | 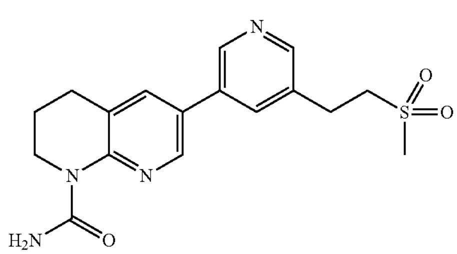 [SMILES: CS(=O)(=O)CCc1cncc(-c2cnc3c(c2)CCCN3C(N)=O)c1] | 6-[5-(2-Methanesulfonyl-ethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 163 | 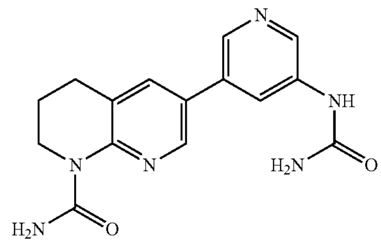 [SMILES: NC(=O)Nc1cncc(-c2cnc3c(c2)CCCN3C(N)=O)c1] | 6-(5-Ureido-pyridin-3-yl)-3,4-dihydro-2H-[1,8]naphthyridine-1-carboxylic acid amide |
| 164 | 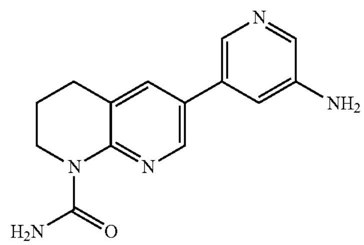 [SMILES: NC(=O)N1CCCc2cc(-c3cncc(N)c3)cnc21] | 6-(5-Amino-pyridin-3-yl)-3,4-dihydro-2H-[1,8]naphthyridine-1-carboxylic acid amide |
| 165 | 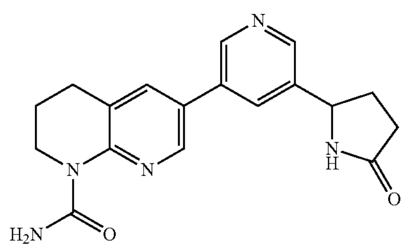 [SMILES: NC(=O)N1CCCc2cc(-c3cncc(C4CCC(=O)N4)c3)cnc21] | 6-[5-(5-Oxo-pyrrolidin-2-yl)-pyridin-3-yl]-3,4-dihydro-2H-[1,8]naphthyridine-1-carboxylic acid amide |
| 166 | 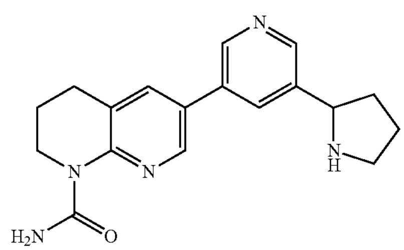 [SMILES: NC(=O)N1CCCc2cc(-c3cncc(C4CCCN4)c3)cnc21] | 6-(5-Pyrrolidin-2-yl-pyridin-3-yl)-3,4-dihydro-2H-[1,8]naphthyridine-1-carboxylic acid amide |
| 167 | 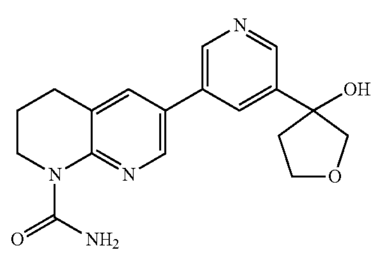 [SMILES: NC(=O)N1CCCc2cc(-c3cncc(C4(O)CCOC4)c3)cnc21] | 6-[5-(3-Hydroxy-tetrahydro-furan-3-yl)-pyridin-3-yl]-3,4-dihydro-2H-[1,8]naphthyridine-1-carboxylic acid amide Enantiomer A |
| 168 | 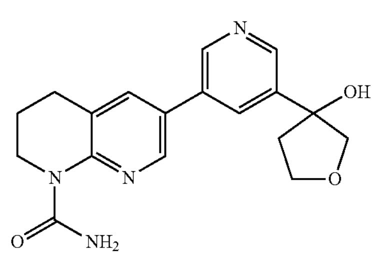 | 6-[5-(3-Hydroxy-tetrahydro-furan-3-yl)-pyridin-3-yl]-3,4-dihydro-2H-[1,8]naphthyridine-1-carboxylic acid amide Enantiomer B |

| Cpd No | STRUCTURE | Name |
|---|---|---|
| 169 | 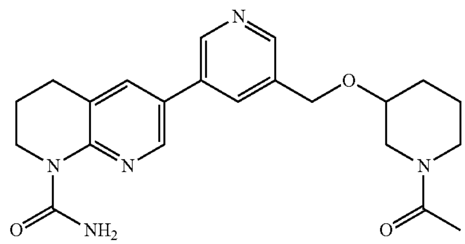 [SMILES: CC(=O)N1CCCC(OCc2cncc(-c3cnc4c(c3)CCCN4C(N)=O)c2)C1] | 6-[5-(1-Acetyl-piperidin-3-yloxymethyl)-pyridin-3-yl]-3,4-dihydro-2H-[1,8]naphthyridine-1-carboxylic acid amide Enantiomer A |
| 170 | 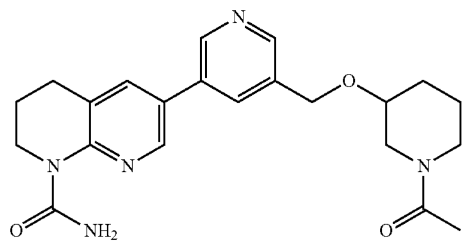 [SMILES: CC(=O)N1CCCC(OCc2cncc(-c3cnc4c(c3)CCCN4C(N)=O)c2)C1] | 6-[5-(1-Acetyl-piperidin-3-yloxymethyl)-pyridin-3-yl]-3,4-dihydro-2H-[1,8]naphthyridine-1-carboxylic acid amide Enantiomer B |
| 171 | 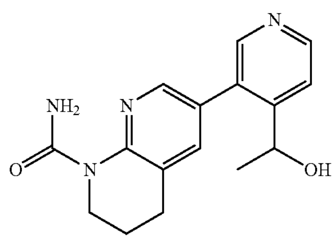 [SMILES: CC(O)c1ccncc1-c1cnc2c(c1)CCCN2C(N)=O] | 6-[4-(1-Hydroxy-ethyl)-pyridin-3-yl]-3,4-dihydro-2H-[1,8]naphthyridine-1-carboxylic acid amide |
| 172 | 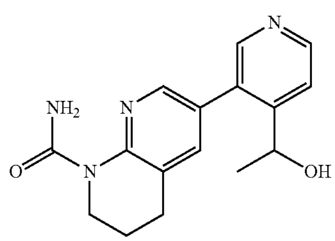 [SMILES: CC(O)c1ccncc1-c1cnc2c(c1)CCCN2C(N)=O] | 6-[4-(1-Hydroxy-ethyl)-pyridin-3-yl]-3,4-dihydro-2H-[1,8]naphthyridine-1-carboxylic acid amide Enantiomer A |
| 173 | 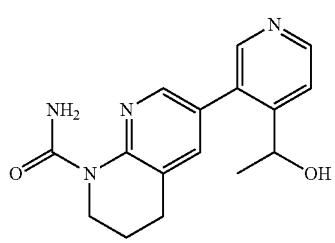 [SMILES: CC(O)c1ccncc1-c1cnc2c(c1)CCCN2C(N)=O] | 6-[4-(1-Hydroxy-ethyl)-pyridin-3-yl]-3,4-dihydro-2H-[1,8]naphthyridine-1-carboxylic acid amide Enantiomer B |
| 174 | 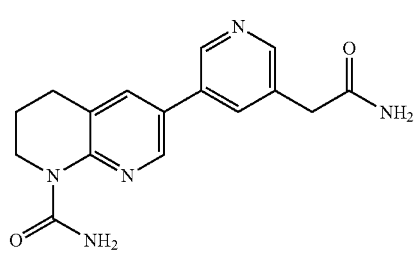 [SMILES: NC(=O)Cc1cncc(-c2cnc3c(c2)CCCN3C(N)=O)c1] | 6-(5-Carbamoylmethyl-pyridin-3-yl)-3,4-dihydro-2H-[1,8]naphthyridine-1-carboxylic acid amide |

TABLE 1-continued

| Cpd No | STRUCTURE | Name |
|---|---|---|
| 175 | 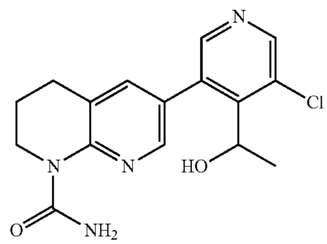 [SMILES: CC(O)c1c(Cl)cncc1-c1cnc2c(c1)CCCN2C(N)=O] | 6-[5-Chloro-4-(1-hydroxy-ethyl)-pyridin-3-yl]-3,4-dihydro-2H-[1,8]naphthyridine-1-carboxylic acid amide<br>Enantiomer A |
| 176 | 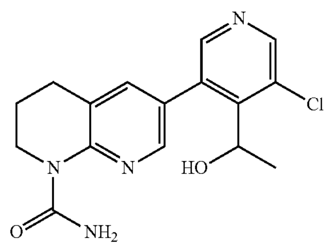 [SMILES: CC(O)c1c(Cl)cncc1-c1cnc2c(c1)CCCN2C(N)=O] | 6-[5-Chloro-4-(1-hydroxy-ethyl)-pyridin-3-yl]-3,4-dihydro-2H-[1,8]naphthyridine-1-carboxylic acid amide<br>Enantiomer B |
| 177 | 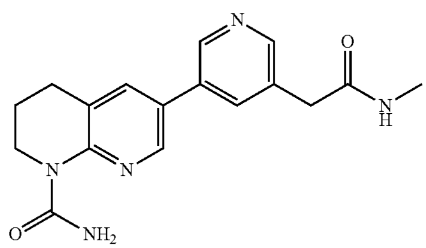 [SMILES: CNC(=O)Cc1cncc(-c2cnc3c(c2)CCCN3C(N)=O)c1] | 6-(5-Methylcarbamoylmethyl-pyridin-3-yl)-3,4-dihydro-2H-[1,8]naphthyridine-1-carboxylic acid amide |
| 178 | 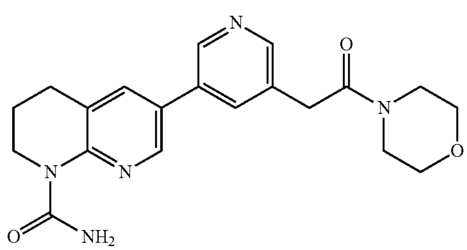 [SMILES: NC(=O)N1CCCc2cc(-c3cncc(CC(=O)N4CCOCC4)c3)cnc21] | 6-[5-(2-Morpholin-4-yl-2-oxo-ethyl)-pyridin-3-yl]-3,4-dihydro-2H-[1,8]naphthyridine-1-carboxylic acid amide |
| 179 | 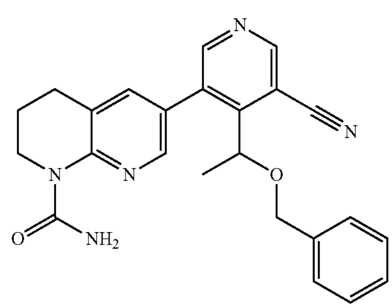 [SMILES: CC(OCc1ccccc1)c1c(C#N)cncc1-c1cnc2c(c1)CCCN2C(N)=O] | 6-[4-(1-Benzyloxy-ethyl)-5-cyano-pyridin-3-yl]-3,4-dihydro-2H-[1,8]naphthyridine-1-carboxylic acid amide |
| 180 | 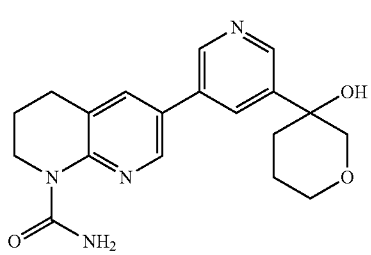 | 6-[5-(3-Hydroxy-tetrahydro-pyran-3-yl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 181 | 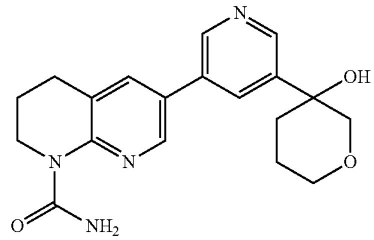 [SMILES: NC(=O)N1CCCc2cc(-c3cncc(C4(O)CCCOC4)c3)cnc21] | 6-[5-(3-Hydroxy-tetrahydro-pyran-3-yl)-pyridin-3-yl]-3,4-dihydro-2H-[1,8]naphthyridine-1-carboxylic acid amide Enantiomer A |
| 182 | 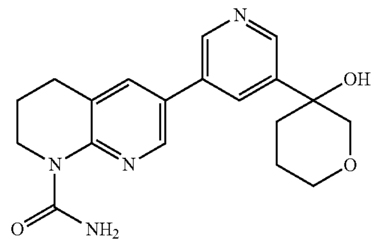 [SMILES: NC(=O)N1CCCc2cc(-c3cncc(C4(O)CCCOC4)c3)cnc21] | 6-[5-(3-Hydroxy-tetrahydro-pyran-3-yl)-pyridin-3-yl]-3,4-dihydro-2H-[1,8]naphthyridine-1-carboxylic acid amide Enantiomer B |
| 183 | 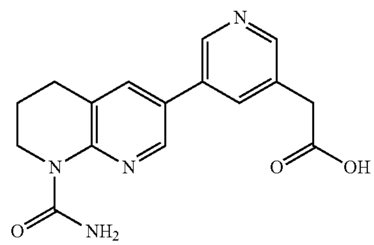 [SMILES: NC(=O)N1CCCc2cc(-c3cncc(CC(=O)O)c3)cnc21] | [5-(8-Carbamoyl-5,6,7,8-tetrahydro-[1,8]naphthyridin-3-yl)-pyridin-3-yl]-acetic acid |
| 184 | 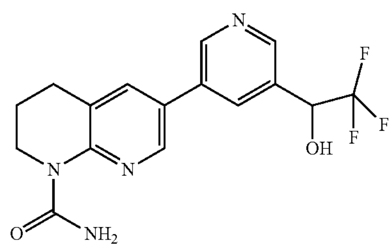 [SMILES: NC(=O)N1CCCc2cc(-c3cncc(C(O)C(F)(F)F)c3)cnc21] | 6-[5-(2,2,2-Trifluoro-1-hydroxy-ethyl)-pyridin-3-yl]-3,4-dihydro-2H-[1,8]naphthyridine-1-carboxylic acid amide |
| 185 | 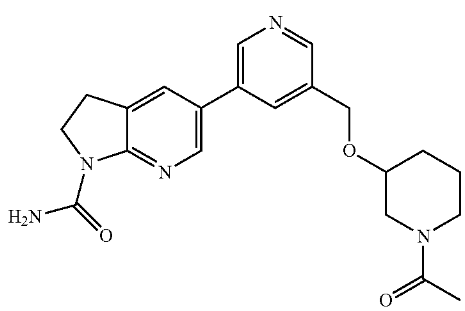 [SMILES: CC(=O)N1CCCC(OCc2cncc(-c3cnc4c(c3)CCN4C(N)=O)c2)C1] | 5-[5-(1-Acetyl-piperidin-3-yloxymethyl)-pyridin-3-yl]-2,3-dihydro-pyrrolo[2,3-b]pyridine-1-carboxylic acid amide |
| 186 | 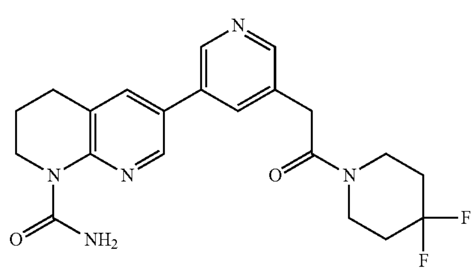 [SMILES: NC(=O)N1CCCc2cc(-c3cncc(CC(=O)N4CCC(F)(F)CC4)c3)cnc21] | 6-{5-[2-(4,4-Difluoro-piperidin-1-yl)-2-oxo-ethyl]-pyridin-3-yl}-3,4-dihydro-2H-[1,8]naphthyridine-1-carboxylic acid amide |

TABLE 1-continued

| Cpd No | STRUCTURE | Name |
|---|---|---|
| 187 | 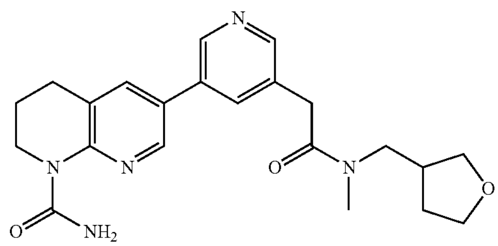 [SMILES: CN(CC1CCOC1)C(=O)Cc1cncc(-c2cnc3c(c2)CCCN3C(N)=O)c1] | 6-(5-{[Methyl-(tetrahydro-furan-3-ylmethyl)-carbamoyl]-methyl}-pyridin-3-yl)-3,4-dihydro-2H-[1,8]naphthyridine-1-carboxylic acid amide |
| 188 | 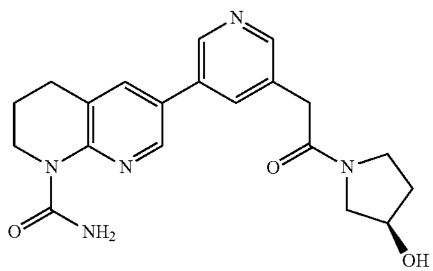 [SMILES: NC(=O)N1CCCc2cc(-c3cncc(CC(=O)N4CC[C@@H](O)C4)c3)cnc21] | 6-{5-[2-((R)-3-Hydroxy-pyrrolidin-1-yl)-2-oxo-ethyl]-pyridin-3-yl}-3,4-dihydro-2H-[1,8]naphthyridine-1-carboxylic acid amide |
| 189 | 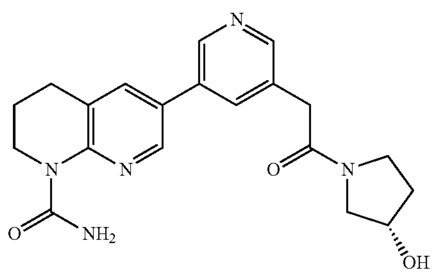 [SMILES: NC(=O)N1CCCc2cc(-c3cncc(CC(=O)N4CC[C@H](O)C4)c3)cnc21] | 6-{5-[2-((S)-3-Hydroxy-pyrrolidin-1-yl)-2-oxo-ethyl]-pyridin-3-yl}-3,4-dihydro-2H-[1,8]naphthyridine-1-carboxylic acid amide |
| 190 | 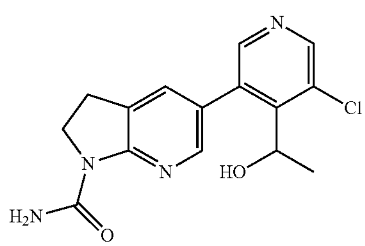 [SMILES: CC(O)c1c(Cl)cncc1-c1cnc2c(c1)CCN2C(N)=O] | 5-[5-Chloro-4-(1-hydroxy-ethyl)-pyridin-3-yl]-2,3-dihydro-pyrrolo[2,3-b]pyridine-1-carboxylic acid amide Enantiomer A |
| 191 | 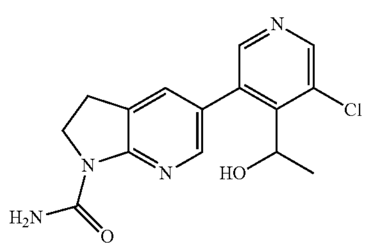 [SMILES: CC(O)c1c(Cl)cncc1-c1cnc2c(c1)CCN2C(N)=O] | 5-[5-Chloro-4-(1-hydroxy-ethyl)-pyridin-3-yl]-2,3-dihydro-pyrrolo[2,3-b]pyridine-1-carboxylic acid amide Enantiomer B |
| 192 | 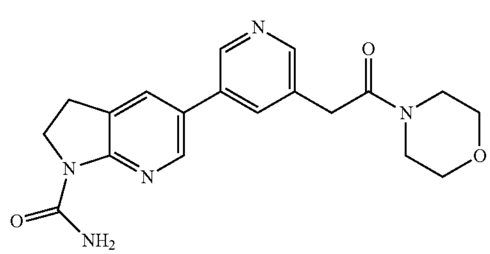 [SMILES: NC(=O)N1CCc2cc(-c3cncc(CC(=O)N4CCOCC4)c3)cnc21] | 5-[5-(2-Morpholine-4-yl-2-oxo-ethyl)-pyridin-3-yl]-2,3-dihydro-pyrrolo[2,3-b]pyridine-1-carboxylic acid amide |

TABLE 1-continued

| Cpd No | STRUCTURE | Name |
|---|---|---|
| 193 | 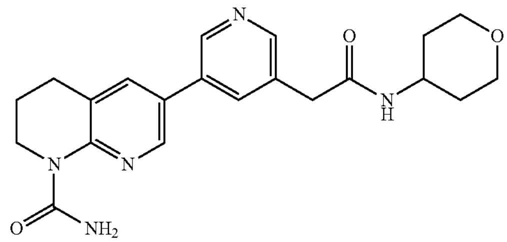 [SMILES: NC(=O)N1CCCc2cc(-c3cncc(CC(=O)NC4CCOCC4)c3)cnc21] | 6-{5-[(Tetrahydro-pyran-4-ylcarbamoyl)-methyl]-pyridin-3-yl}-3,4-dihydro-2H-[1,8]naphthyridine-1-carboxylic acid amide |
| 194 | 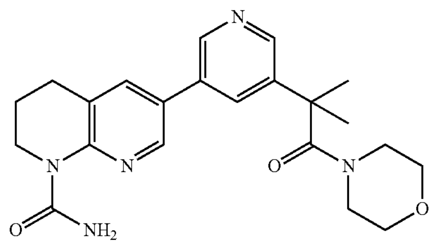 [SMILES: CC(C)(C(=O)N1CCOCC1)c1cncc(-c2cnc3c(c2)CCCN3C(N)=O)c1] | 6-[5-(1,1-Dimethyl-2-morpholin-4-yl-2-oxo-ethyl)-pyridin-3-yl]-3,4-dihydro-2H-[1,8]naphthyridine-1-carboxylic acid amide |
| 195 | 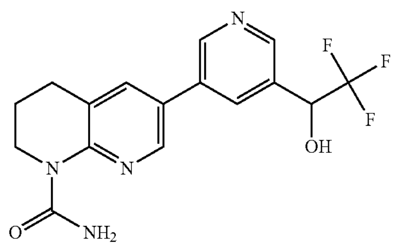 [SMILES: NC(=O)N1CCCc2cc(-c3cncc(C(O)C(F)(F)F)c3)cnc21] | 6-[5-(2,2,2-Trifluoro-1-hydroxy-ethyl)-pyridin-3-yl]-3,4-dihydro-2H-[1,8]naphthyridine-1-carboxylic acid amide Enantiomer A |
| 196 | 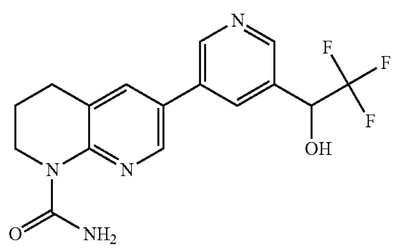 [SMILES: NC(=O)N1CCCc2cc(-c3cncc(C(O)C(F)(F)F)c3)cnc21] | 6-[5-(2,2,2-Trifluoro-1-hydroxy-ethyl)-pyridin-3-yl]-3,4-dihydro-2H-[1,8]naphthyridine-1-carboxylic acid amide Enantiomer B |
| 197 | 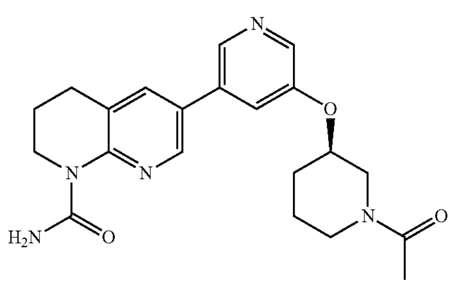 [SMILES: CC(=O)N1CCC[C@@H](Oc2cncc(-c3cnc4c(c3)CCCN4C(N)=O)c2)C1] | 6-[5-((R)-1-Acetyl-piperidin-3-yloxy)-pyridin-3-yl]-3,4-dihydro-2H-[1,8]naphthyridine-1-carboxylic acid amide |
| 198 | 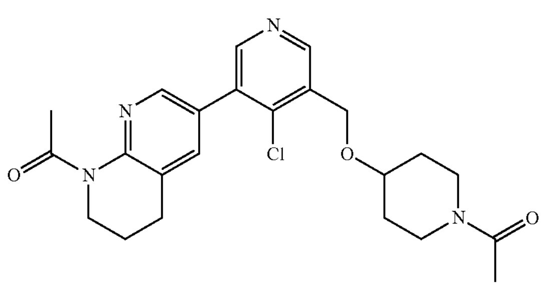 [SMILES: CC(=O)N1CCC(OCc2cncc(-c3cnc4c(c3)CCCN4C(C)=O)c2Cl)CC1] | 1-{4-[5-(8-Acetyl-5,6,7,8-tetrahydro-[1,8]naphthyridin-3-yl)-4-chloro-pyridin-3-ylmethoxy]-piperidin-1-yl}-ethanone |

TABLE 1-continued

| Cpd No | STRUCTURE | Name |
|---|---|---|
| 199 | 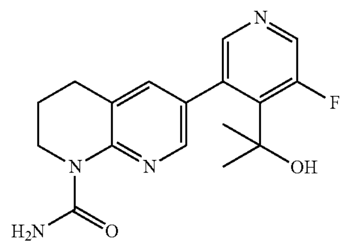 [SMILES: CC(C)(O)c1c(F)cncc1-c1cnc2c(c1)CCCN2C(N)=O] | 6-[5-Fluoro-4-(1-hydroxy-1-methyl-ethyl)-pyridin-3-yl]-3,4-dihydro-2H-[1,8]naphthyridine-1-carboxylic acid amide |
| 200 | 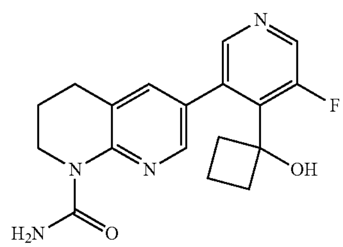 | 6-[5-Fluoro-4-(1-hydroxy-cyclobutyl)-pyridin-3-yl]-3,4-dihydro-2H-[1,8]naphthyridine-1-carboxylic acid amide |
| 201 | 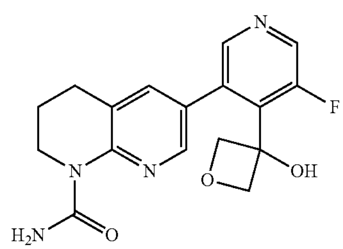 [SMILES: NC(=O)N1CCCc2cc(-c3cncc(F)c3C3(O)COC3)cnc21] | 6-[5-Fluoro-4-(3-hydroxy-oxetan-3-yl)-pyridin-3-yl]-3,4-dihydro-2H-[1,8]naphthyridine-1-carboxylic acid amide |
| 202 | 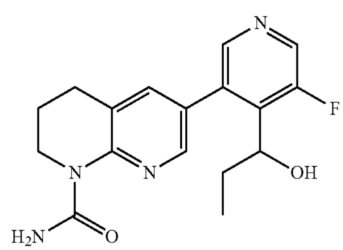 | 6-[5-Fluoro-4-(1-hydroxy-propyl)-pyridin-3-yl]-3,4-dihydro-2H-[1,8]naphthyridine-1-carboxylic acid amide |
| 203 | 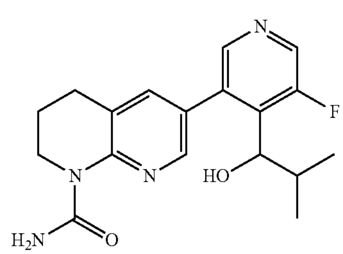 [SMILES: CC(C)C(O)c1c(F)cncc1-c1cnc2c(c1)CCCN2C(N)=O] | 6-[5-Fluoro-4-(1-hydroxy-2-methyl-propyl)-pyridin-3-yl]-3,4-dihydro-2H-[1,8]naphthyridine-1-carboxylic acid amide |
| 204 | 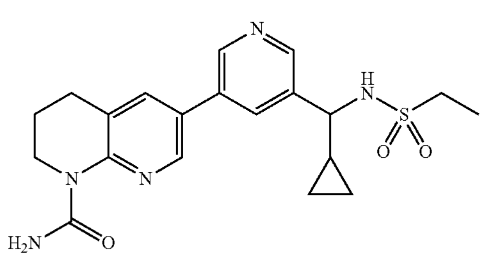 [SMILES: CCS(=O)(=O)NC(c1cncc(-c2cnc3c(c2)CCCN3C(N)=O)c1)C1CC1] | 6-[5-(Cyclopropyl-ethanesulfonylamino-methyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 205 | 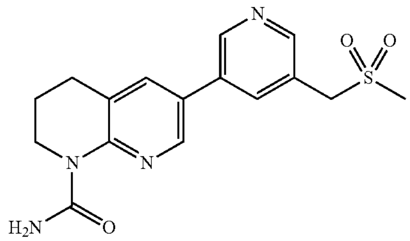 [SMILES: CS(=O)(=O)Cc1cncc(-c2cnc3c(c2)CCCN3C(N)=O)c1] | 6-(5-Methanesulfonylmethyl-pyridin-3-yl)-3,4-dihydro-2H-[1,8]naphthyridine-1-carboxylic acid amide |
| 206 | 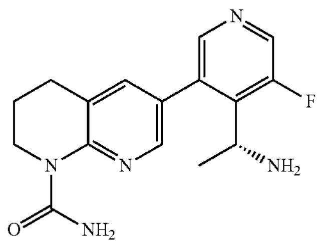 [SMILES: C[C@@H](N)c1c(F)cncc1-c1cnc2c(c1)CCCN2C(N)=O] | 6-[4-((R)-1-Amino-ethyl)-5-fluoro-pyridin-3-yl]-3,4-dihydro-2H-[1,8]naphthyridine-1-carboxylic acid amide |
| 207 | 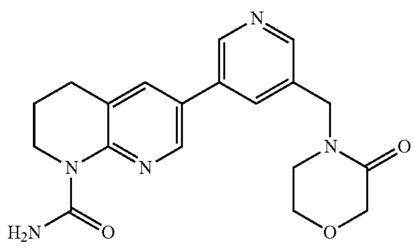 | 6-[5-(3-Oxo-morpholin-4-ylmethyl)-pyridin-3-yl]-3,4-dihydro-2H-[1,8]naphthyridine-1-carboxylic acid amide |
| 208 | 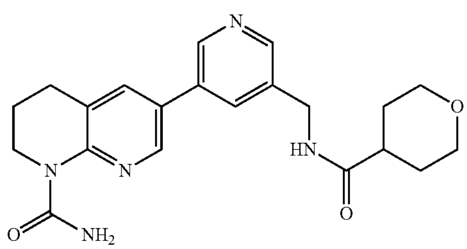 [SMILES: NC(=O)N1CCCc2cc(-c3cncc(CNC(=O)C4CCOCC4)c3)cnc21] | 6-(5-{[(Tetrahydro-pyran-4-carbonyl)-amino]-methyl}-pyridin-3-yl)-3,4-dihydro-2H-[1,8]naphthyridine-1-carboxylic acid amide |
| 209 | 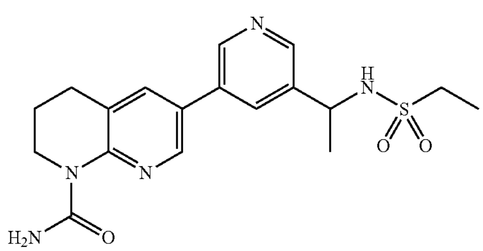 [SMILES: CCS(=O)(=O)NC(C)c1cncc(-c2cnc3c(c2)CCCN3C(N)=O)c1] | 6-[5-(1-Ethanesulfonylamino-ethyl)-pyridin-3-yl]-3,4-dihydro-2H-[1,8]naphthyridine-1-carboxylic acid amide |
| 210 | 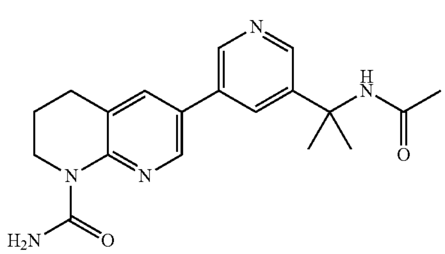 [SMILES: CC(=O)NC(C)(C)c1cncc(-c2cnc3c(c2)CCCN3C(N)=O)c1] | 6-[5-(1-Acetylamino-1-methyl-ethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 211 | 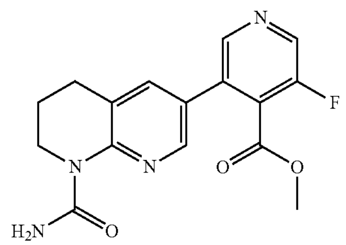 [SMILES: COC(=O)c1c(F)cncc1-c1cnc2c(c1)CCCN2C(N)=O] | 3-(8-Carbamoyl-5,6,7,8-tetrahydro-[1,8]naphthyridin-3-yl)-5-fluoro-isonicotinic acid methyl ester |
| 212 | 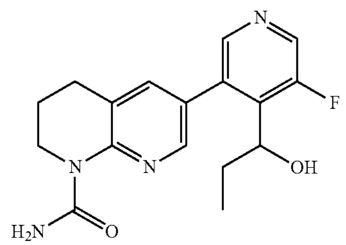 [SMILES: CCC(O)c1c(F)cncc1-c1cnc2c(c1)CCCN2C(N)=O] | 6-[5-Fluoro-4-(1-hydroxy-propyl)-pyridin-3-yl]-3,4-dihydro-2H-[1,8]naphthyridine-1-carboxylic acid amide Enantiomer A |
| 213 | 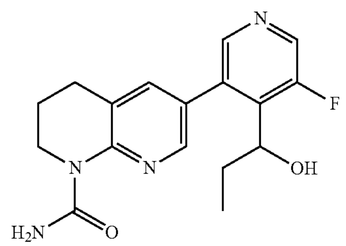 [SMILES: CCC(O)c1c(F)cncc1-c1cnc2c(c1)CCCN2C(N)=O] | 6-[5-Fluoro-4-(1-hydroxy-propyl)-pyridin-3-yl]-3,4-dihydro-2H-[1,8]naphthyridine-1-carboxylic acid amide |
| 214 | 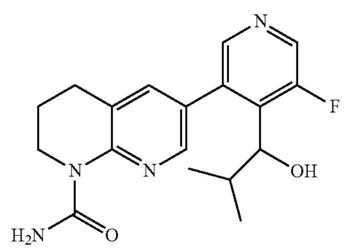 [SMILES: CC(C)C(O)c1c(F)cncc1-c1cnc2c(c1)CCCN2C(N)=O] | 6-[5-Fluoro-4-(1-hydroxy-2-methyl-propyl)-pyridin-3-yl]-3,4-dihydro-2H-[1,8]naphthyridine-1-carboxylic acid amide Enantiomer A |
| 215 | 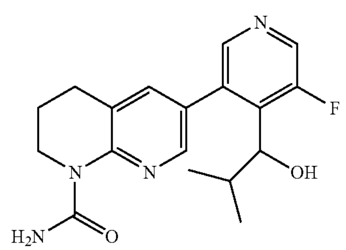 [SMILES: CC(C)C(O)c1c(F)cncc1-c1cnc2c(c1)CCCN2C(N)=O] | 6-[5-Fluoro-4-(1-hydroxy-2-methyl-propyl)-pyridin-3-yl]-3,4-dihydro-2H-[1,8]naphthyridine-1-carboxylic acid amide Enantiomer B |
| 216 | 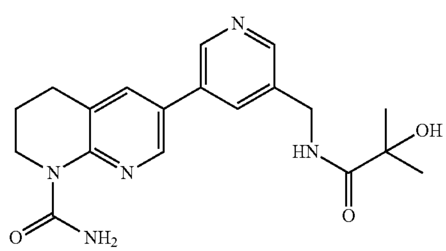 [SMILES: CC(C)(O)C(=O)NCc1cncc(-c2cnc3c(c2)CCCN3C(N)=O)c1] | 6-{5-[(2-Hydroxy-2-methyl-propionylamino)-methyl]-pyridin-3-yl}-3,4-dihydro-2H-[1,8]naphthyridine-1-carboxylic acid amide |

| Cpd No | STRUCTURE | Name |
|---|---|---|
| 217 | 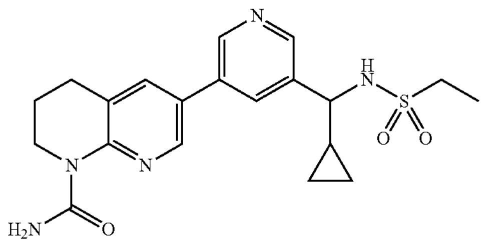 [SMILES: CCS(=O)(=O)NC(c1cncc(-c2cnc3c(c2)CCCN3C(N)=O)c1)C1CC1] | 6-[5-(Cyclopropyl-ethanesulfonylamino-methyl)-pyridin-3-yl]-3,4-dihydro-2H-[1,8]naphthyridine-1-carboxylic acid amide Enantiomer A |
| 218 | 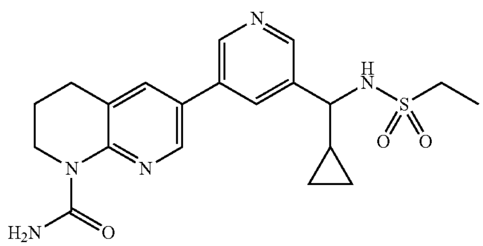 [SMILES: CCS(=O)(=O)NC(c1cncc(-c2cnc3c(c2)CCCN3C(N)=O)c1)C1CC1] | 6-[5-(Cyclopropyl-ethanesulfonylamino-methyl)-pyridin-3-yl]-3,4-dihydro-2H-[1,8]naphthyridine-1-carboxylic acid amide Enantiomer B |
| 219 | 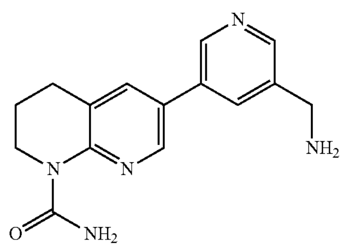 [SMILES: NCc1cncc(-c2cnc3c(c2)CCCN3C(N)=O)c1] | 6-(5-Aminomethyl-pyridin-3-yl)-3,4-dihydro-2H-[1,8]naphthyridine-1-carboxylic acid amide |
| 220 | 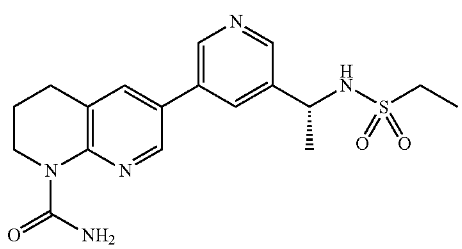 [SMILES: CCS(=O)(=O)N[C@H](C)c1cncc(-c2cnc3c(c2)CCCN3C(N)=O)c1] | 6-[5-((R)-1-Ethanesulfonylamino-ethyl)-pyridin-3-yl]-3,4-dihydro-2H-[1,8]naphthyridine-1-carboxylic acid amide |
| 221 | 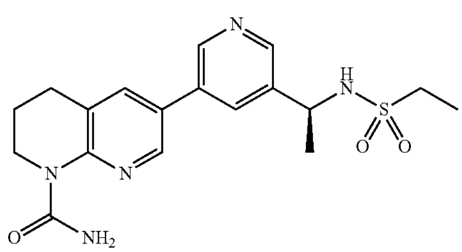 [SMILES: CCS(=O)(=O)N[C@@H](C)c1cncc(-c2cnc3c(c2)CCCN3C(N)=O)c1] | 6-[5-((S)-1-Ethanesulfonylamino-ethyl)-pyridin-3-yl]-3,4-dihydro-2H-[1,8]naphthyridine-1-carboxylic acid amide |
| 222 | 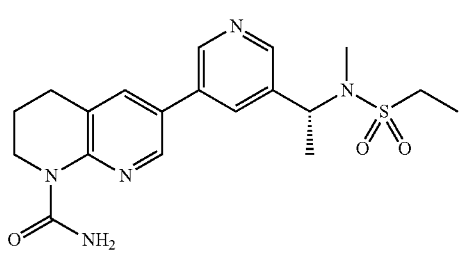 [SMILES: CCS(=O)(=O)N(C)[C@H](C)c1cncc(-c2cnc3c(c2)CCCN3C(N)=O)c1] | 6-{5-[(R)-1-(Ethanesulfonyl-methyl-amino)-ethyl]-pyridin-3-yl}-3,4-dihydro-2H-[1,8]naphthyridine-1-carboxylic acid amide |

TABLE 1-continued

| Cpd No | STRUCTURE | Name |
|---|---|---|
| 223 | 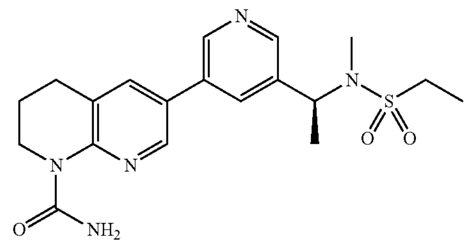 [SMILES: CCS(=O)(=O)N(C)[C@@H](C)c1cncc(-c2cnc3c(c2)CCCN3C(N)=O)c1] | 6-{5-[(S)-1-(Ethanesulfonyl-methyl-amino)-ethyl]-pyridin-3-yl}-3,4-dihydro-2H-[1,8]naphthyridine-1-carboxylic acid amide |
| 224 | 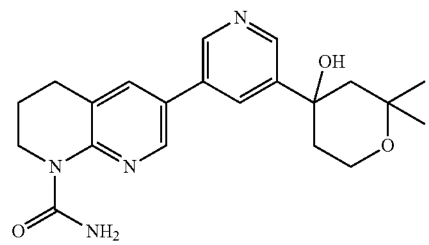 [SMILES: CC1(C)CC(O)(c2cncc(-c3cnc4c(c3)CCCN4C(N)=O)c2)CCO1] | 6-{5-(4-Hydroxy-2,2-dimethyl-tetrahydro-pyran-4-yl)-pyridin-3-yl]-3,4-dihydro-2H-[1,8]naphthyridine-1-carboxylic acid amide |
| 225 | 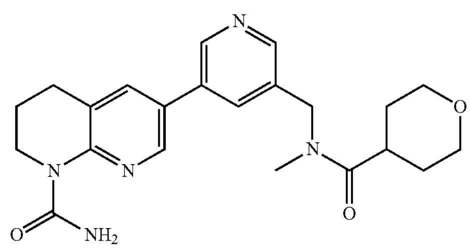 | 6-(5-{[Methyl-(tetrahydro-pyran-4-carbonyl)-amino]-methyl}-pyridin-3-yl)-3,4-dihydro-2H-[1,8]naphthyridine-1-carboxylic acid amide |
| 226 | 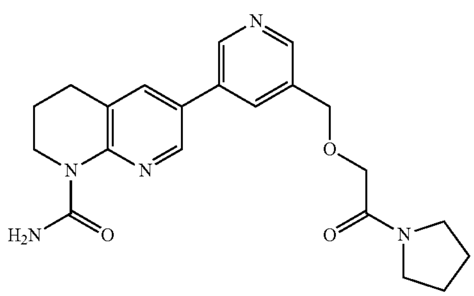 [SMILES: NC(=O)N1CCCc2cc(-c3cncc(COCC(=O)N4CCCC4)c3)cnc21] | 6-[5-(2-Oxo-2-pyrrolidin-1-yl-ethoxymethyl)-pyridin-3-yl]-3,4-dihydro-2H-[1,8]naphthyridine-1-carboxylic acid amide |
| 227 | 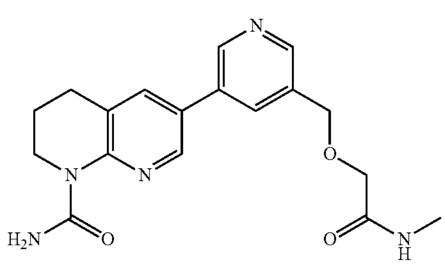 [SMILES: CNC(=O)COCc1cncc(-c2cnc3c(c2)CCCN3C(N)=O)c1] | 6-(5-Methylcarbamoylmethoxymethyl-pyridin-3-yl)-3,4-dihydro-2H-[1,8]naphthyridine-1-carboxylic acid amide |
| 228 | 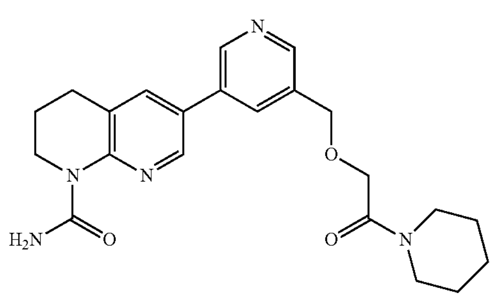 [SMILES: NC(=O)N1CCCc2cc(-c3cncc(COCC(=O)N4CCCCC4)c3)cnc21] | 6-[5-(2-Oxo-2-piperidin-1-yl-ethoxymethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 229 | 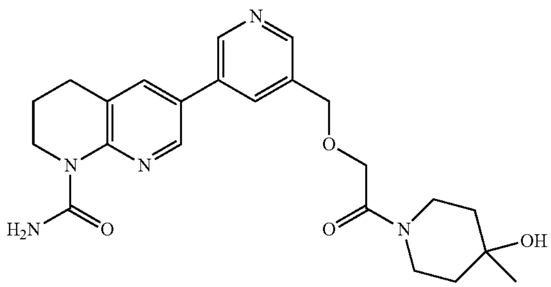 [SMILES: CC1(O)CCN(C(=O)COCc2cncc(-c3cnc4c(c3)CCCN4C(N)=O)c2)CC1] | 6-{5-[2-(4-Hydroxy-4-methyl-piperidin-1-yl)-2-oxo-ethoxymethyl]-pyridin-3-yl}-3,4-dihydro-2H-[1,8]naphthyridine-1-carboxylic acid amide |
| 230 | 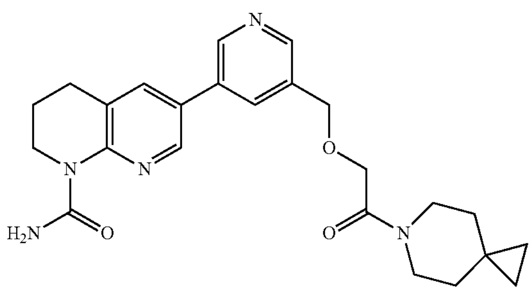 [SMILES: NC(=O)N1CCCc2cc(-c3cncc(COCC(=O)N4CCC5(CC4)CC5)c3)cnc21] | 6-{5-[2-(6-Aza-spiro[2.5]oct-6-yl)-2-oxo-ethoxymethyl]-pyridin-3-yl}-3,4-dihydro-2H-[1,8]naphthyridine-1-carboxylic acid amide |
| 231 | 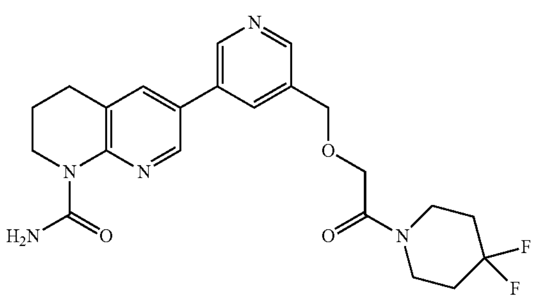 [SMILES: NC(=O)N1CCCc2cc(-c3cncc(COCC(=O)N4CCC(F)(F)CC4)c3)cnc21] | 6-{5-[2-(4,4-Difluoro-piperidin-1-yl)-2-oxo-ethoxymethyl]-pyridin-3-yl}-3,4-dihydro-2H-[1,8]naphthyridine-1-carboxylic acid amide |
| 232 | 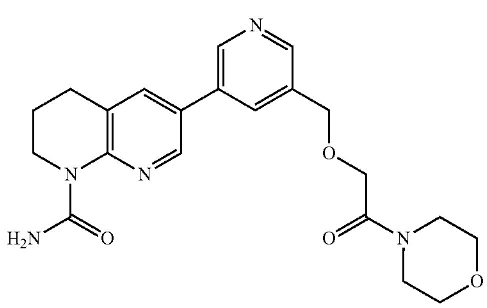 [SMILES: NC(=O)N1CCCc2cc(-c3cncc(COCC(=O)N4CCOCC4)c3)cnc21] | 6-[5-(2-Morpholin-4-yl-2-oxo-ethoxymethyl)-pyridin-3-yl]-3,4-dihydro-2H-[1,8]naphthyridine-1-carboxylic acid amide |
| 233 | 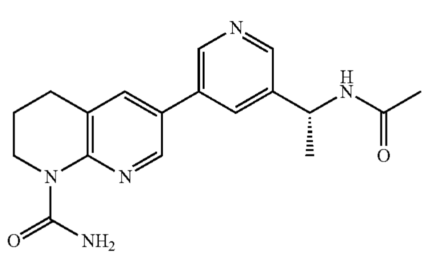 [SMILES: CC(=O)N[C@H](C)c1cncc(-c2cnc3c(c2)CCCN3C(N)=O)c1] | 6-[5-((R)-1-Acetylamino-ethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 234 | 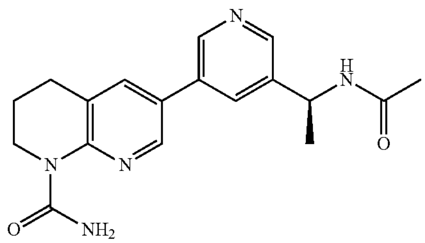 [SMILES: CC(=O)N[C@@H](C)c1cncc(-c2cnc3c(c2)CCCN3C(N)=O)c1] | 6-[5-((S)-1-Acetylamino-ethyl)-pyridin-3-yl]-3,4-dihydro-2H-[1,8]naphthyridine-1-carboxylic acid amide |
| 235 | 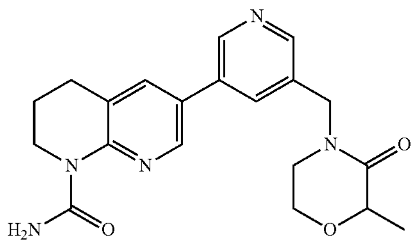 [SMILES: CC1OCCN(Cc2cncc(-c3cnc4c(c3)CCCN4C(N)=O)c2)C1=O] | 6-[5-(2-Methyl-3-oxo-morpholin-4-ylmethyl)-pyridin-3-yl]-3,4-dihydro-2H-[1,8]naphthyridine-1-carboxylic acid amide |
| 236 | 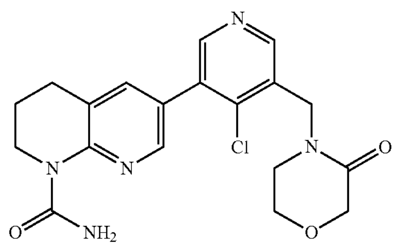 [SMILES: NC(=O)N1CCCc2cc(-c3cncc(CN4CCOCC4=O)c3Cl)cnc21] | 6-[4-Chloro-5-(3-oxo-morpholin-4-ylmethyl)-pyridin-3-yl]-3,4-dihydro-2H-[1,8]naphthyridine-1-carboxylic acid amide |
| 237 | 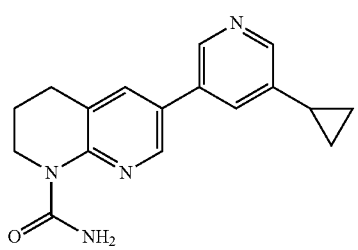 [SMILES: NC(=O)N1CCCc2cc(-c3cncc(C4CC4)c3)cnc21] | 6-(5-Cyclopropyl-pyridin-3-yl)-3,4-dihydro-2H-[1,8]naphthyridine-1-carboxylic acid amide |
| 238 | 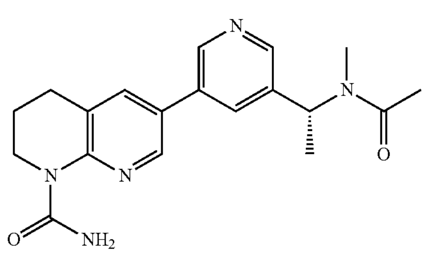 | 6-{5-[(R)-1-(Acetyl-methyl-amino)-ethyl]-pyridin-3-yl}-3,4-dihydro-2H-[1,8]naphthyridine-1-carboxylic acid amide |
| 239 | 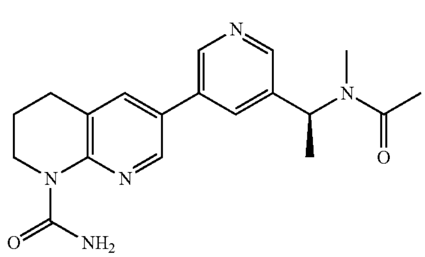 | 6-{5-[(S)-1-(Acetyl-methyl-amino)-ethyl]-pyridin-3-yl}-3,4-dihydro-2H-[1,8]naphthyridine-1-carboxylic acid amide |

| Cpd No | STRUCTURE | Name |
|---|---|---|
| 240 | 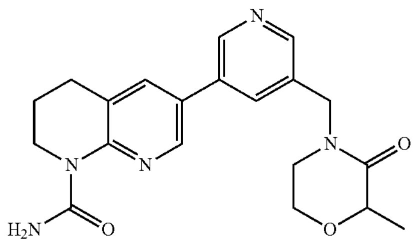 [SMILES: CC1OCCN(Cc2cncc(-c3cnc4c(c3)CCCN4C(N)=O)c2)C1=O] | 6-[5-(2-Methyl-3-oxo-morpholin-4-ylmethyl)-pyridin-3-yl]-3,4-dihydro-2H-[1,8]naphthyridine-1-carboxylic acid amide Enantiomer A |
| 241 | 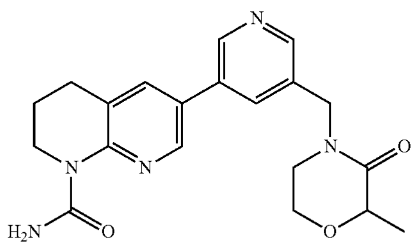 [SMILES: CC1OCCN(Cc2cncc(-c3cnc4c(c3)CCCN4C(N)=O)c2)C1=O] | 6-[5-(2-Methyl-3-oxo-morpholin-4-ylmethyl)-pyridin-3-yl]-3,4-dihydro-2H-[1,8]naphthyridine-1-carboxylic acid amide Enantiomer B |
| 242 | 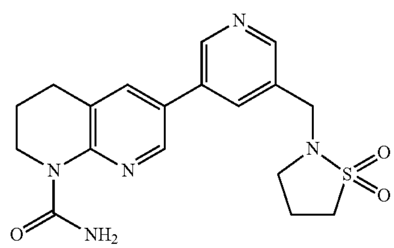 [SMILES: NC(=O)N1CCCc2cc(-c3cncc(CN4CCCS4(=O)=O)c3)cnc21] | 6-[5-(1,1-Dioxo-1lambda6-isothiazolidin-2-ylmethyl)-pyridin-3-yl]-3,4-dihydro-2H-[1,8]naphthyridine-1-carboxylic acid amide |
| 243 | 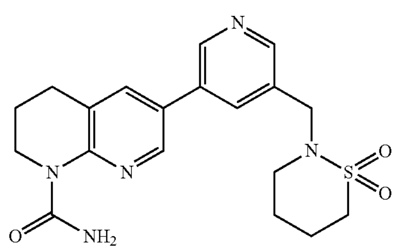 [SMILES: NC(=O)N1CCCc2cc(-c3cncc(CN4CCCCS4(=O)=O)c3)cnc21] | 6-[5-(1,1-Dioxo-1lambda6-[1,2]thiazinan-2-ylmethyl)-pyridin-3-yl]-3,4-dihydro-2H-[1,8]naphthyridine-1-carboxylic acid amide |
| 244 | 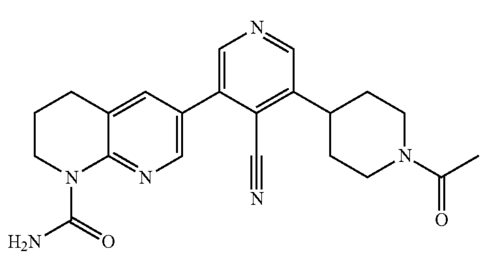 [SMILES: CC(=O)N1CCC(c2cncc(-c3cnc4c(c3)CCCN4C(N)=O)c2C#N)CC1] | 6-(1'-Acetyl-4-cyano-1',2',3',4',5',6'-hexahydro-[3,4']bipyridinyl-5-yl)-3,4-dihydro-2H-[1,8]naphthyridine-1-carboxylic acid amide |
| 245 | 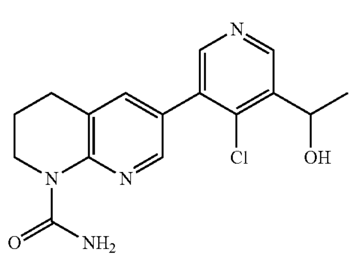 [SMILES: CC(O)c1cncc(-c2cnc3c(c2)CCCN3C(N)=O)c1Cl] | 6-[4-Chloro-5-(1-hydroxy-ethyl)-pyridin-3-yl]-3,4-dihydro-2H-[1,8]naphthyridine-1-carboxylic acid amide |

… TABLE 1-continued

| Cpd No | STRUCTURE | Name |
|---|---|---|
| 246 | 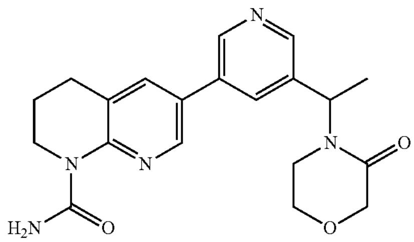 [SMILES: CC(c1cncc(-c2cnc3c(c2)CCCN3C(N)=O)c1)N1CCOCC1=O] | 6-{5-[1-(3-Oxo-morpholin-4-yl)-ethyl]-pyridin-3-yl}-3,4-dihydro-2H-[1,8]naphthyridine-1-carboxylic acid amide Enantiomer A |
| 247 | 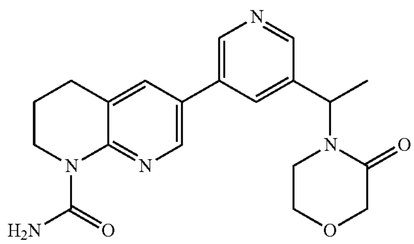 [SMILES: CC(c1cncc(-c2cnc3c(c2)CCCN3C(N)=O)c1)N1CCOCC1=O] | 6-{5-[1-(3-Oxo-morpholin-4-yl)-ethyl]-pyridin-3-yl}-3,4-dihydro-2H-[1,8]naphthyridine-1-carboxylic acid amide Enantiomer B |
| 248 | 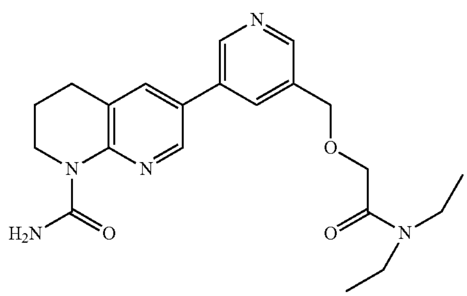 [SMILES: CCN(CC)C(=O)COCc1cncc(-c2cnc3c(c2)CCCN3C(N)=O)c1] | 6-(5-Diethylcarbamoylmethoxymethyl-pyridin-3-yl)-3,4-dihydro-2H-[1,8]naphthyridine-1-carboxylic acid amide |
| 249 | 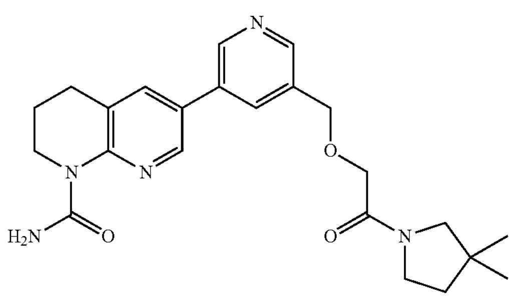 [SMILES: CC1(C)CCN(C(=O)COCc2cncc(-c3cnc4c(c3)CCCN4C(N)=O)c2)C1] | 6-{5-[2-(3,3-Dimethyl-pyrrolidin-1-yl)-2-oxo-ethoxymethyl]-pyridin-3-yl}-3,4-dihydro-2H-[1,8]naphthyridine-1-carboxylic acid amide |
| 250 | 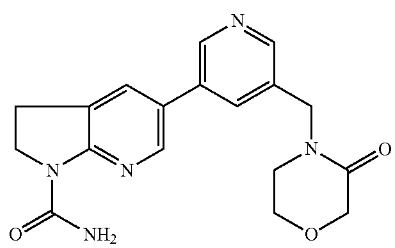 [SMILES: NC(=O)N1CCc2cc(-c3cncc(CN4CCOCC4=O)c3)cnc21] | 5-[5-(3-Oxo-morpholin-4-ylmethyl)-pyridin-3-yl]-2,3-dihydro-pyrrolo[2,3-b]pyridine-1-carboxylic acid amide |
| 251 | 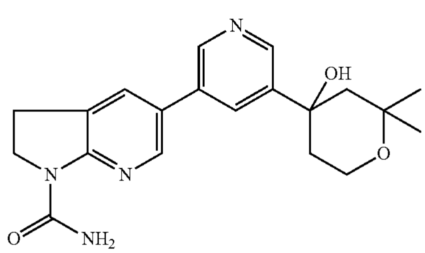 [SMILES: CC1(C)CC(O)(c2cncc(-c3cnc4c(c3)CCN4C(N)=O)c2)CCO1] | 5-[5-(4-Hydroxy-2,2-dimethyl-tetrahydro-pyran-4-yl)-pyridin-3-yl]-2,3-dihydro-pyrrolo[2,3-b]pyridine-1-carboxylic acid amide |

TABLE 1-continued

| Cpd No | STRUCTURE | Name |
|---|---|---|
| 252 | 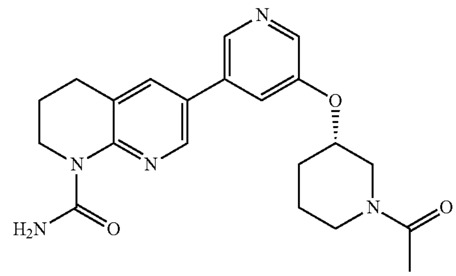 [SMILES: CC(=O)N1CCC[C@H](Oc2cncc(-c3cnc4c(c3)CCCN4C(N)=O)c2)C1] | 6-[5-((S)-1-Acetyl-piperidin-3-yloxy)-pyridin-3-yl]-3,4-dihydro-2H-[1,8]naphthyridine-1-carboxylic acid amide |
| 253 | 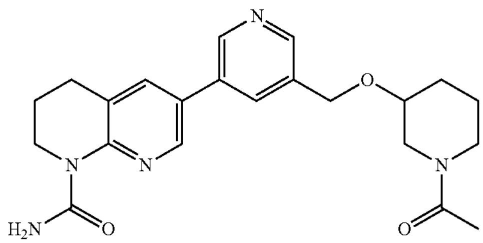 [SMILES: CC(=O)N1CCCC(OCc2cncc(-c3cnc4c(c3)CCCN4C(N)=O)c2)C1] | 6-[5-(1-Acetyl-piperidin-3-yloxymethyl)-pyridin-3-yl]-3,4-dihydro-2H-[1,8]naphthyridine-1-carboxylic acid amide |
| 254 | 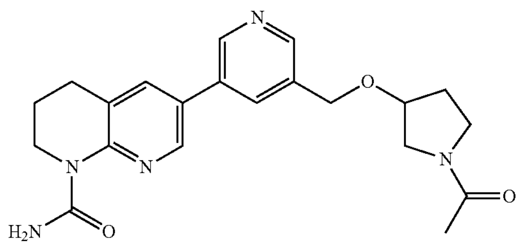 [SMILES: CC(=O)N1CCC(OCc2cncc(-c3cnc4c(c3)CCCN4C(N)=O)c2)C1] | 6-[5-(1-Acetyl-pyrrolidin-3-yloxymethyl)-pyridin-3-yl]-3,4-dihydro-2H-[1,8]naphthyridine-1-carboxylic acid amide |
| 255 | 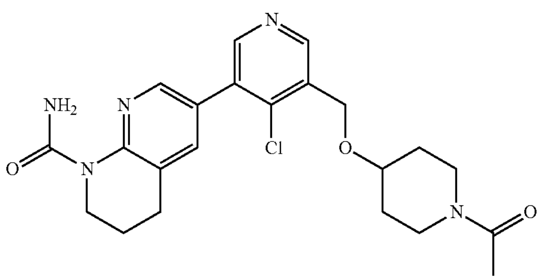 [SMILES: CC(=O)N1CCC(OCc2cncc(-c3cnc4c(c3)CCCN4C(N)=O)c2Cl)CC1] | 6-[5-(1-Acetyl-piperidin-4-yloxymethyl)-4-chloro-pyridin-3-yl]-3,4-dihydro-2H-[1,8]naphthyridine-1-carboxylic acid amide |
| 256 | 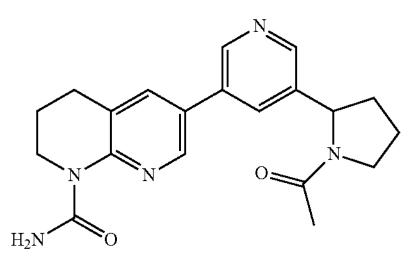 | 6-[5-(1-Acetyl-pyrrolidin-2-yl)-pyridin-3-yl]-3,4-dihydro-2H-[1,8]naphthyridine-1-carboxylic acid amide |
| 257 | 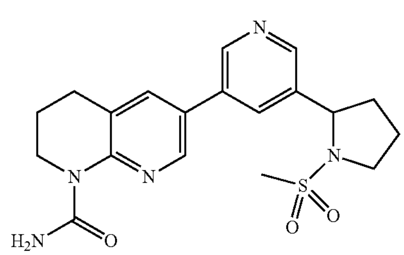 [SMILES: CS(=O)(=O)N1CCCC1c1cncc(-c2cnc3c(c2)CCCN3C(N)=O)c1] | 6-[5-(1-Methanesulfonyl-pyrrolidin-2-yl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 258 | 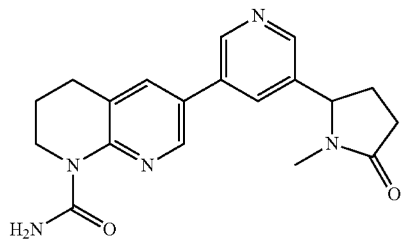 | 6-[5-(1-Methyl-5-oxo-pyrrolidin-2-yl)-pyridin-3-yl]-3,4-dihydro-2H-[1,8]naphthyridine-1-carboxylic acid amide |
| 259 | 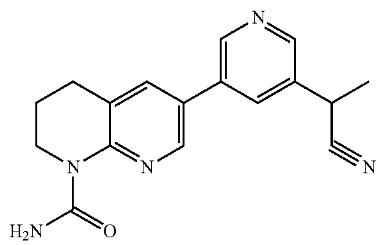 [SMILES: CC(C#N)c1cncc(-c2cnc3c(c2)CCCN3C(N)=O)c1] | 6-[5-(Cyano-methyl-methyl)-pyridin-3-yl]-3,4-dihydro-2H-[1,8]naphthyridine-1-carboxylic acid amide |
| 260 | 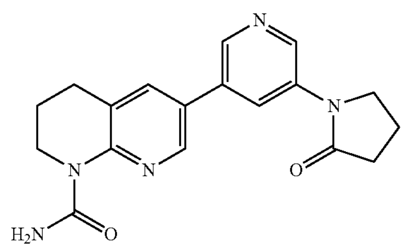 | 6-[5-(2-Oxo-pyrrolidin-1-yl)-pyridin-3-yl]-3,4-dihydro-2H-[1,8]naphthyridine-1-carboxylic acid amide |
| 261 | 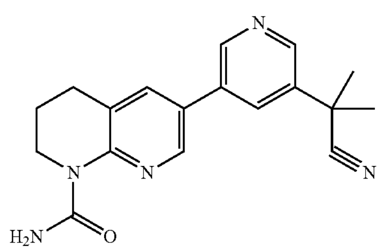 | 6-[5-(Cyano-dimethyl-methyl)-pyridin-3-yl]-3,4-dihydro-2H-[1,8]naphthyridine-1-carboxylic acid amide |
| 262 | 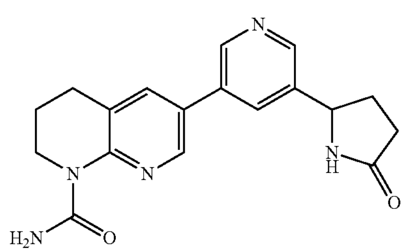 [SMILES: NC(=O)N1CCCc2cc(-c3cncc(C4CCC(=O)N4)c3)cnc21] | 6-[5-(5-Oxo-pyrrolidin-2-yl)-pyridin-3-yl]-3,4-dihydro-2H-[1,8]naphthyridine-1-carboxylic acid amide Enantiomer A |
| 263 | 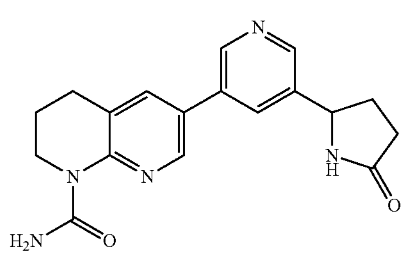 [SMILES: NC(=O)N1CCCc2cc(-c3cncc(C4CCC(=O)N4)c3)cnc21] | 6-[5-(5-Oxo-pyrrolidin-2-yl)-pyridin-3-yl]-3,4-dihydro-2H-[1,8]naphthyridine-1-carboxylic acid amide Enantiomer B |

TABLE 1-continued

| Cpd No | STRUCTURE | Name |
|---|---|---|
| 264 | 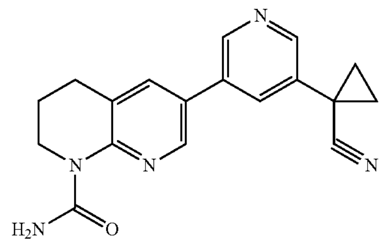 | 6-[5-(1-Cyano-cyclopropyl)-pyridin-3-yl]-3,4-dihydro-2H-[1,8]naphthyridine-1-carboxylic acid amide |
| 265 | 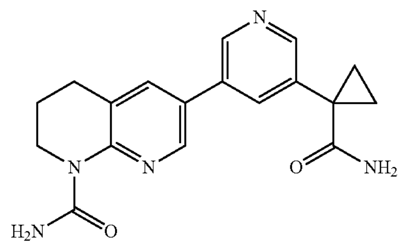 [SMILES: NC(=O)N1CCCc2cc(-c3cncc(C4(C(N)=O)CC4)c3)cnc21] | 6-[5-(1-Carbamoyl-cyclopropyl)-pyridin-3-yl]-3,4-dihydro-2H-[1,8]naphthyridine-1-carboxylic acid amide |
| 266 | 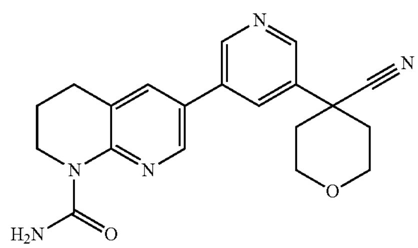 | 6-[5-(4-Cyano-tetrahydro-pyran-4-yl)-pyridin-3-yl]-3,4-dihydro-2H-[1,8]naphthyridine-1-carboxylic acid amide |
| 267 | 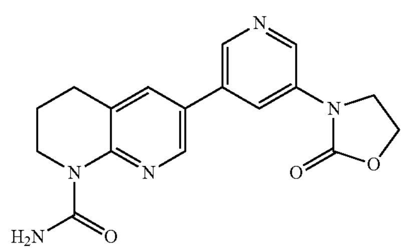 | 6-[5-(2-Oxo-oxazolidin-3-yl)-pyridin-3-yl]-3,4-dihydro-2H-[1,8]naphthyridine-1-carboxylic acid amide |
| 268 | 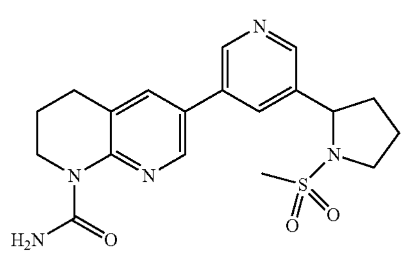 [SMILES: CS(=O)(=O)N1CCCC1c1cncc(-c2cnc3c(c2)CCCN3C(N)=O)c1] | 6-[5-(1-Methanesulfonyl-pyrrolidin-2-yl)-pyridin-3-yl]-3,4-dihydro-2H-[1,8]naphthyridine-1-carboxylic acid amide Enantiomer A |
| 269 | 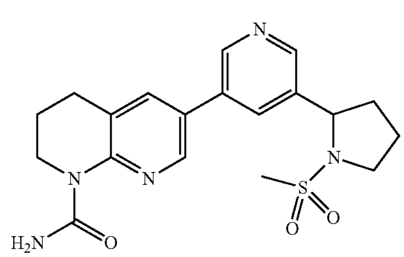 [SMILES: CS(=O)(=O)N1CCCC1c1cncc(-c2cnc3c(c2)CCCN3C(N)=O)c1] | 6-[5-(1-Methanesulfonyl-pyrrolidin-2-yl)-pyridin-3-yl]-3,4-dihydro-2H-[1,8]naphthyridine-1-carboxylic acid amide Enantiomer B |

TABLE 1-continued

| Cpd No | STRUCTURE | Name |
|---|---|---|
| 270 | 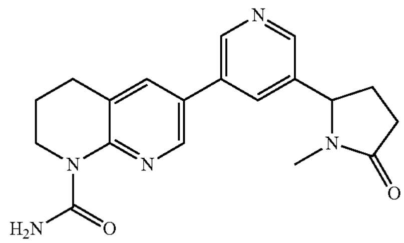 [SMILES: CN1C(=O)CCC1c1cncc(-c2cnc3c(c2)CCCN3C(N)=O)c1] | 6-[5-(1-Methyl-5-oxo-pyrrolidin-2-yl)-pyridin-3-yl]-3,4-dihydro-2H-[1,8]naphthyridine-1-carboxylic acid amide Enantiomer A |
| 271 | 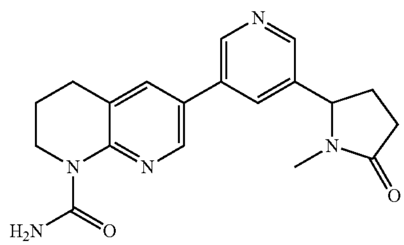 [SMILES: CN1C(=O)CCC1c1cncc(-c2cnc3c(c2)CCCN3C(N)=O)c1] | 6-[5-(1-Methyl-5-oxo-pyrrolidin-2-yl)-pyridin-3-yl]-3,4-dihydro-2H-[1,8]naphthyridine-1-carboxylic acid amide Enantiomer B |
| 272 | 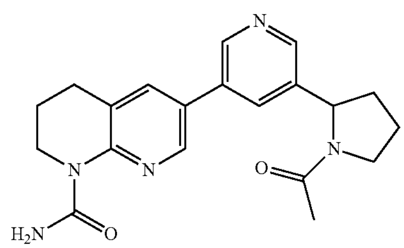 [SMILES: CC(=O)N1CCCC1c1cncc(-c2cnc3c(c2)CCCN3C(N)=O)c1] | 6-[5-(1-Acetyl-pyrrolidin-2-yl)-pyridin-3-yl]-3,4-dihydro-2H-[1,8]naphthyridine-1-carboxylic acid amide Enantiomer A |
| 273 | 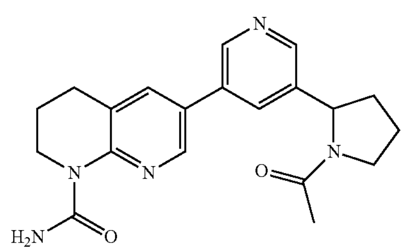 [SMILES: CC(=O)N1CCCC1c1cncc(-c2cnc3c(c2)CCCN3C(N)=O)c1] | 6-[5-(1-Acetyl-pyrrolidin-2-yl)-pyridin-3-yl]-3,4-dihydro-2H-[1,8]naphthyridine-1-carboxylic acid amide Enantiomer B |
| 274 | 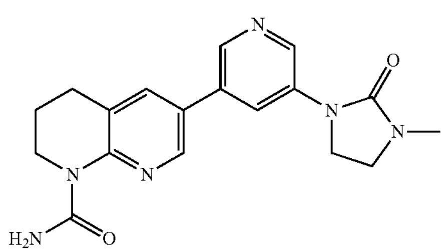 | 6-[5-(3-Methyl-2-oxo-imidazolidin-1-yl)-pyridin-3-yl]-3,4-dihydro-2H-[1,8]naphthyridine-1-carboxylic acid amide |
| 275 | 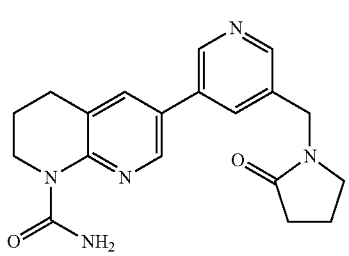 | 6-[5-(2-Oxo-pyrrolidin-1-ylmethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 276 | 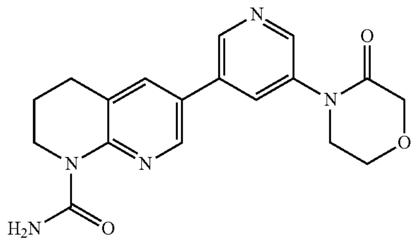 [SMILES: NC(=O)N1CCCc2cc(-c3cncc(N4CCOCC4=O)c3)cnc21] | 6-[5-(3-Oxo-morpholin-4-yl)-pyridin-3-yl]-3,4-dihydro-2H-[1,8]naphthyridine-1-carboxylic acid amide |
| 277 | 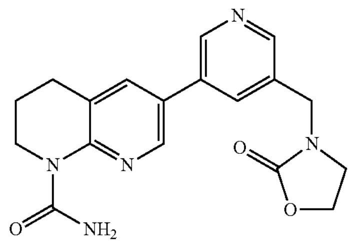 | 6-[5-(2-Oxo-oxazolidin-3-ylmethyl)-pyridin-3-yl]-3,4-dihydro-2H-[1,8]naphthyridine-1-carboxylic acid amide |
| 278 | 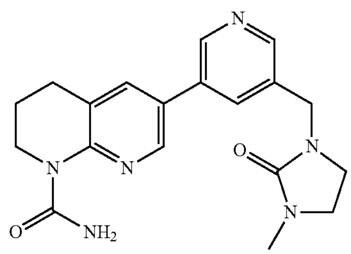 [SMILES: CN1CCN(Cc2cncc(-c3cnc4c(c3)CCCN4C(N)=O)c2)C1=O] | 6-[5-(3-Methyl-2-oxo-imidazolidin-1-ylmethyl)-pyridin-3-yl]-3,4-dihydro-2H-[1,8]naphthyridine-1-carboxylic acid amide |
| 279 | 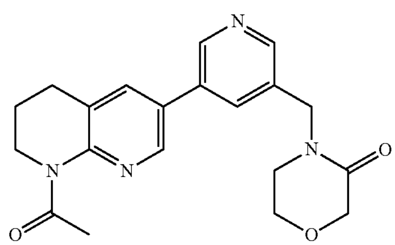 [SMILES: CC(=O)N1CCCc2cc(-c3cncc(CN4CCOCC4=O)c3)cnc21] | 4-[5-(8-Acetyl-5,6,7,8-tetrahydro-[1,8]naphthyridin-3-yl)-pyridin-3-ylmethyl]-morpholin-3-one |
| 280 | 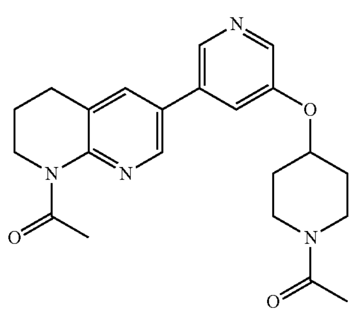 [SMILES: CC(=O)N1CCC(Oc2cncc(-c3cnc4c(c3)CCCN4C(C)=O)c2)CC1] | 1-{4-[5-(8-Acetyl-5,6,7,8-tetrahydro-[1,8]naphthyridin-3-yl)-pyridin-3-yloxy]-piperidin-1-yl}-ethanone |
| 281 | 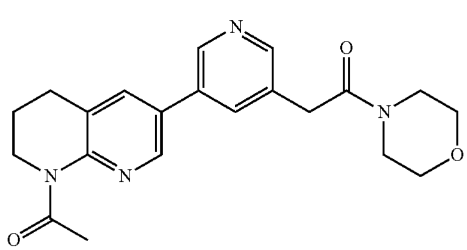 [SMILES: CC(=O)N1CCCc2cc(-c3cncc(CC(=O)N4CCOCC4)c3)cnc21] | 2-[5-(8-Acetyl-5,6,7,8-tetrahydro-[1,8]naphthyridin-3-yl)-pyridin-3-yl]-1-morpholin-4-yl-ethanone |

| Cpd No | STRUCTURE | Name |
|---|---|---|
| 282 | 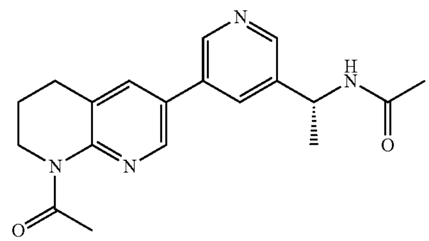 [SMILES: CC(=O)N[C@H](C)c1cncc(-c2cnc3c(c2)CCCN3C(C)=O)c1] | N-{(R)-1-[5-(8-Acetyl-5,6,7,8-tetrahydro-[1,8]naphthyridin-3-yl)-pyridin-3-yl]-ethyl}-acetamide |
| 283 | 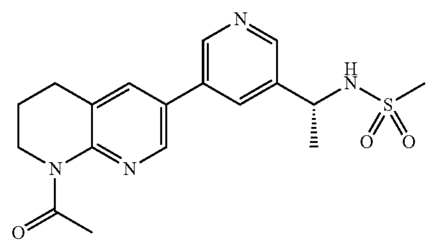 [SMILES: CC(=O)N1CCCc2cc(-c3cncc([C@@H](C)NS(C)(=O)=O)c3)cnc21] | Ethanesulfonic acid {(R)-1-[5-(8-acetyl-5,6,7,8-tetrahydro-[1,8]naphthyridin-3-yl)-pyridin-3-yl]-ethyl}-amide |
| 284 | 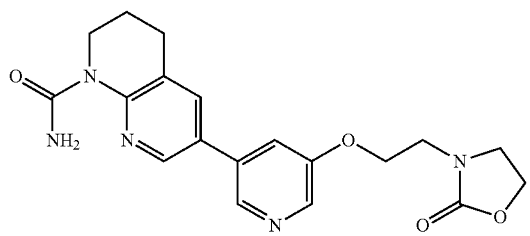 [SMILES: NC(=O)N1CCCc2cc(-c3cncc(OCCN4CCOC4=O)c3)cnc21] | 6-{5-[2-(2-Oxo-oxazolidin-3-yl)-ethoxy]-pyridin-3-yl}-3,4-dihydro-2H-[1,8]naphthyridine-1-carboxylic acid amide |
| 285 | 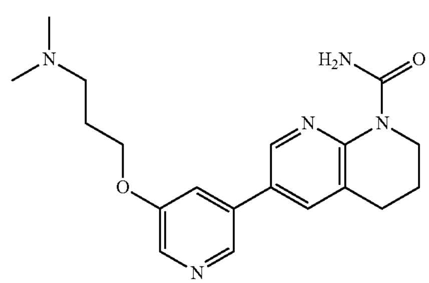 [SMILES: CN(C)CCCOc1cncc(-c2cnc3c(c2)CCCN3C(N)=O)c1] | 6-[5-(3-Dimethylamino-propoxy)-pyridin-3-yl]-3,4-dihydro-2H-[1,8]naphthyridine-1-carboxylic acid amide |
| 286 | 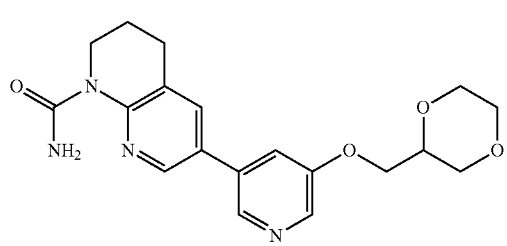 [SMILES: NC(=O)N1CCCc2cc(-c3cncc(OCC4COCCO4)c3)cnc21] | 6-[5-([1,4]Dioxan-2-ylmethoxy)-pyridin-3-yl]-3,4-dihydro-2H-[1,8]naphthyridine-1-carboxylic acid amide |
| 287 | 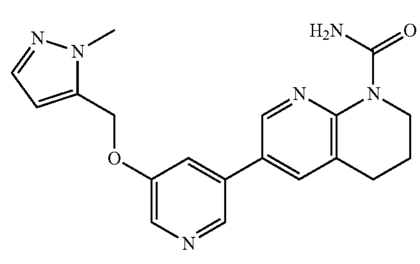 [SMILES: Cn1nccc1COc1cncc(-c2cnc3c(c2)CCCN3C(N)=O)c1] | 6-[5-(2-Methyl-2H-pyrazol-3-ylmethoxy)-pyridin-3-yl]-3,4-dihydro-2H-[1,8]naphthyridine-1-carboxylic acid amide |

TABLE 1-continued

| Cpd No | STRUCTURE | Name |
|---|---|---|
| 288 | 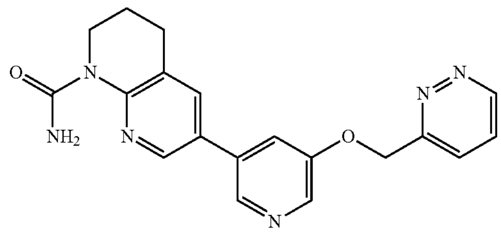 [SMILES: NC(=O)N1CCCc2cc(-c3cncc(OCc4cccnn4)c3)cnc21] | 6-[5-(Pyridazin-3-ylmethoxy)-pyridin-3-yl]-3,4-dihydro-2H-[1,8]naphthyridine-1-carboxylic acid amide |
| 289 | 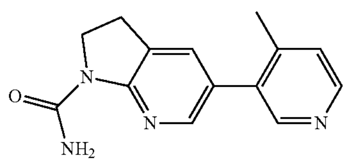 [SMILES: Cc1ccncc1-c1cnc2c(c1)CCN2C(N)=O] | 5-(4-Methyl-pyridin-3-yl)-2,3-dihydro-pyrrolo[2,3-b]pyridine-1-carboxylic acid amide |
| 290 | 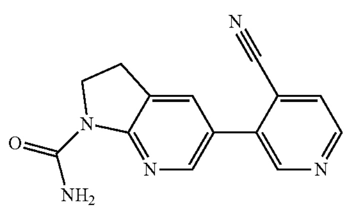 [SMILES: N#Cc1ccncc1-c1cnc2c(c1)CCN2C(N)=O] | 5-(4-Cyano-pyridin-3-yl)-2,3-dihydro-pyrrolo[2,3-b]pyridine-1-carboxylic acid amide |
| 291 | 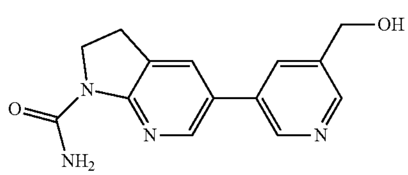 [SMILES: NC(=O)N1CCc2cc(-c3cncc(CO)c3)cnc21] | 5-(5-Hydroxymethyl-pyridin-3-yl)-2,3-dihydro-pyrrolo[2,3-b]pyridine-1-carboxylic acid amide |
| 292 | 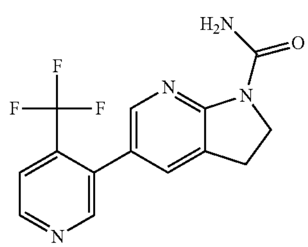 [SMILES: NC(=O)N1CCc2cc(-c3cnccc3C(F)(F)F)cnc21] | 5-(4-Trifluoromethyl-pyridin-3-yl)-2,3-dihydro-pyrrolo[2,3-b]pyridine-1-carboxylic acid amide |
| 293 | 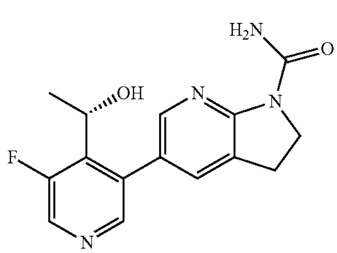 [SMILES: C[C@H](O)c1c(F)cncc1-c1cnc2c(c1)CCN2C(N)=O] | 5-[5-Fluoro-4-((S)-1-hydroxy-ethyl)-pyridin-3-yl]-2,3-dihydro-pyrrolo[2,3-b]pyridine-1-carboxylic acid amide |
| 294 | 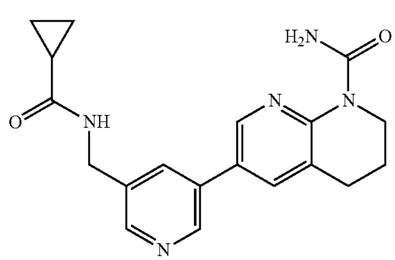 [SMILES: NC(=O)N1CCCc2cc(-c3cncc(CNC(=O)C4CC4)c3)cnc21] | 6-{5-[(Cyclopropanecarbonyl-amino)-methyl]-pyridin-3-yl}-3,4-dihydro-2H-[1,8]naphthyridine-1-carboxylic acid amide |

TABLE 1-continued

| Cpd No | STRUCTURE | Name |
|---|---|---|
| 295 | 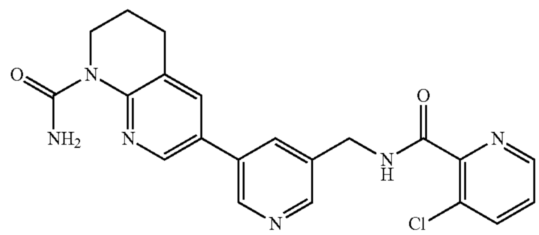 [SMILES: NC(=O)N1CCCc2cc(-c3cncc(CNC(=O)c4ncccc4Cl)c3)cnc21] | 6-(5-{[(3-Chloro-pyridine-2-carbonyl)-amino]-methyl}-pyridin-3-yl)-3,4-dihydro-2H-[1,8]naphthyridine-1-carboxylic acid amide |
| 296 | 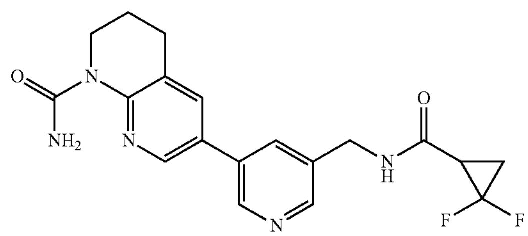 | 6-(5-{[(2,2-Difluoro-cyclopropane-carbonyl)-amino]-methyl}-pyridin-3-yl)-3,4-dihydro-2H-[1,8]naphthyridine-1-carboxylic acid amide |
| 297 | 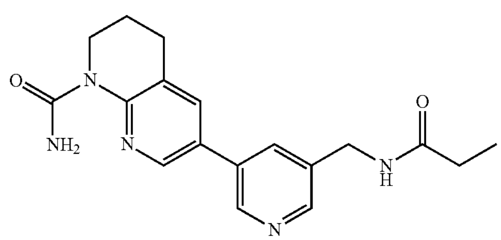 | 6-[5-(Propionylamino-methyl)-pyridin-3-yl]-3,4-dihydro-2H-[1,8]naphthyridine-1-carboxylic acid amide |
| 298 | 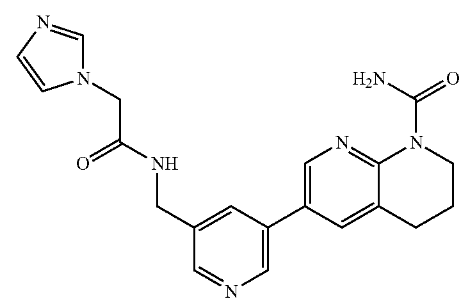 [SMILES: NC(=O)N1CCCc2cc(-c3cncc(CNC(=O)Cn4ccnc4)c3)cnc21] | 6-{5-[(2-Imidazol-1-yl-acetylamino)-methyl]-pyridin-3-yl}-3,4-dihydro-2H-[1,8]naphthyridine-1-carboxylic acid amide |
| 299 | 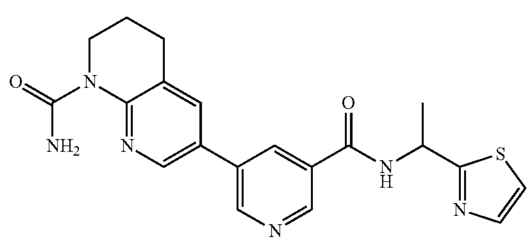 [SMILES: CC(NC(=O)c1cncc(-c2cnc3c(c2)CCCN3C(N)=O)c1)c1nccs1] | 6-[5-(1-Thiazol-2-yl-ethylcarbamoyl)-pyridin-3-yl]-3,4-dihydro-2H-[1,8]naphthyridine-1-carboxylic acid amide |
| 300 | 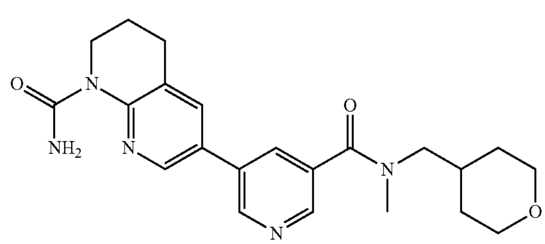 [SMILES: CN(CC1CCOCC1)C(=O)c1cncc(-c2cnc3c(c2)CCCN3C(N)=O)c1] | 6-{5-[Methyl-(tetrahydro-pyran-4-ylmethyl)-carbamoyl]-pyridin-3-yl}-3,4-dihydro-2H-[1,8]naphthyridine-1-carboxylic acid amide |

TABLE 1-continued

| Cpd No | STRUCTURE | Name |
|---|---|---|
| 301 | 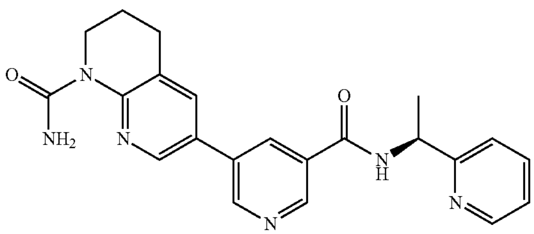 [SMILES: C[C@H](NC(=O)c1cncc(-c2cnc3c(c2)CCCN3C(N)=O)c1)c1ccccn1] | 6-[5-((S)-1-Pyridin-2-yl-ethylcarbamoyl)-pyridin-3-yl]-3,4-dihydro-2H-[1,8]naphthyridine-1-carboxylic acid amide |
| 302 | 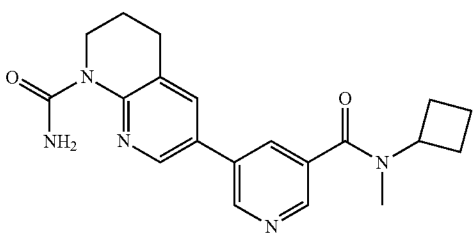 [SMILES: CN(C(=O)c1cncc(-c2cnc3c(c2)CCCN3C(N)=O)c1)C1CCC1] | 6-[5-(Cyclobutyl-methyl-carbamoyl)-pyridin-3-yl]-3,4-dihydro-2H-[1,8]naphthyridine-1-carboxylic acid amide |
| 303 | 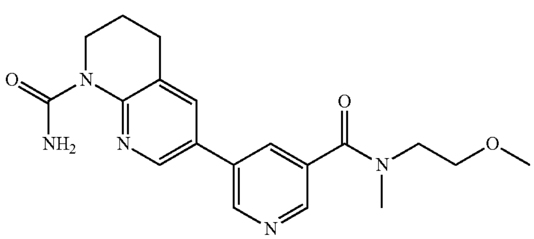 [SMILES: COCCN(C)C(=O)c1cncc(-c2cnc3c(c2)CCCN3C(N)=O)c1] | 6-{5-[(2-Methoxy-ethyl)-methyl-carbamoyl]-pyridin-3-yl}-3,4-dihydro-2H-[1,8]naphthyridine-1-carboxylic acid amide |
| 304 | 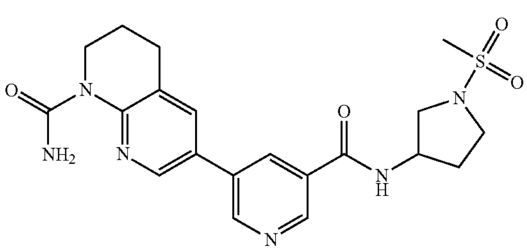 [SMILES: CS(=O)(=O)N1CCC(NC(=O)c2cncc(-c3cnc4c(c3)CCCN4C(N)=O)c2)C1] | 6-[5-(1-Methanesulfonyl-pyrrolidin-3-ylcarbamoyl)-pyridin-3-yl]-3,4-dihydro-2H-[1,8]naphthyridine-1-carboxylic acid amide |
| 305 | 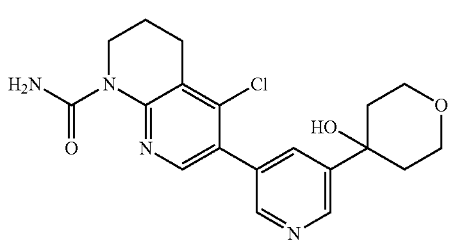 | 5-Chloro-6-[5-(4-hyroxy-tetrahydro-pyran-4-yl)-pyridin-3-yl]-3,4-dihydro-2H-[1,8]naphthyridine-1-carboxylic acid amide |
| 306 | 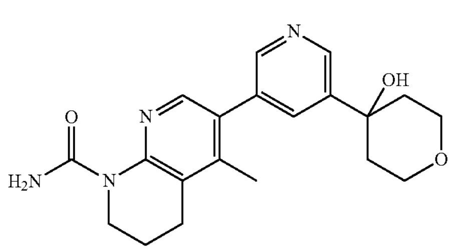 [SMILES: Cc1c(-c2cncc(C3(O)CCOCC3)c2)cnc2c1CCCN2C(N)=O] | 6-[5-(4-Hydroxy-tetrahydro-pyran-4-yl)-pyridin-3-yl]-5-methyl-3,4-dihydro-2H-[1,8]naphthyridine-1-carboxylic acid amide |

| Cpd No | STRUCTURE | Name |
|---|---|---|
| 307 | 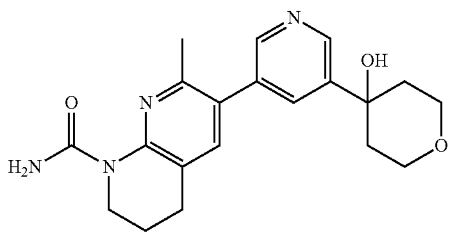 [SMILES: Cc1nc2c(cc1-c1cncc(C3(O)CCOCC3)c1)CCCN2C(N)=O] | 6-[5-(4-Hydroxy-tetrahydro-pyran-4-yl)-pyridin-3-yl]-7-methyl-3,4-dihydro-2H-[1,8]naphthyridine-1-carboxylic acid amide |
| 308 | 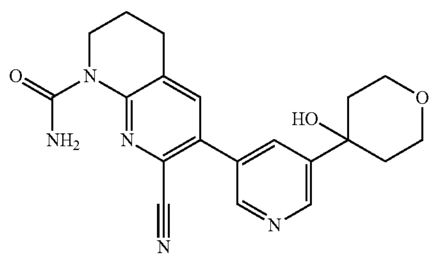 [SMILES: N#Cc1nc2c(cc1-c1cncc(C3(O)CCOCC3)c1)CCCN2C(N)=O] | 7-Cyano-6-[5-(4-hydroxy-tetrahydro-pyran-4-yl)-pyridin-3-yl]-3,4-dihydro-2H-[1,8]naphthyridine-1-carboxylic acid amide |
| 309 | 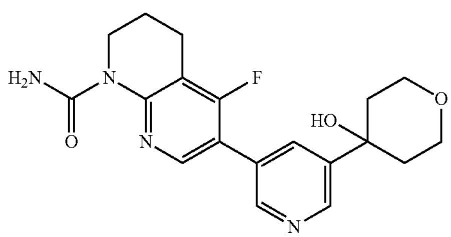 [SMILES: NC(=O)N1CCCc2c1ncc(-c1cncc(C3(O)CCOCC3)c1)c2F] | 5-Fluoro-6-[5-(4-hydroxy-tetrahydro-pyran-4-yl)-pyridin-3-yl]-3,4-dihydro-2H-[1,8]naphthyridine-1-carboxylic acid amide |
| 310 | 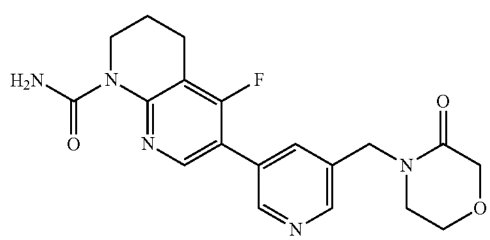 | 5-Fluoro-6-[5-(3-oxo-morpholin-4-ylmethyl)-pyridin-3-yl]-3,4-dihydro-2H-[1,8]naphthyridine-1-carboxylic acid amide |
| 311 | 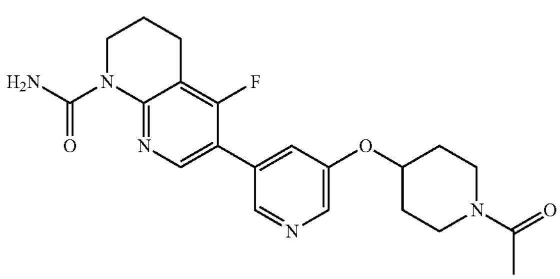 [SMILES: CC(=O)N1CCC(Oc2cncc(-c3cnc4c(c3F)CCCN4C(N)=O)c2)CC1] | 6-[5-(1-Acetyl-piperidin-4-yloxy)-pyridin-3-yl]-5-fluoro-3,4-dihydro-2H-[1,8]naphthyridine-1-carboxylic acid amide |
| 312 | 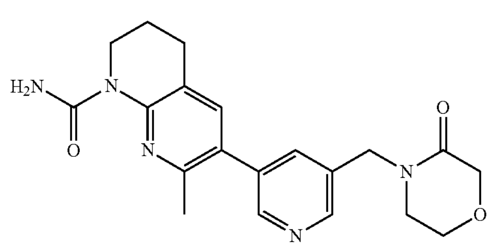 | 7-Methyl-6-[5-(3-oxo-morpholin-4-ylmethyl)-pyridin-3-yl]-3,4-dihydro-2H-[1,8]naphthyridine-1-carboxylic acid amide |

TABLE 1-continued

| Cpd No | STRUCTURE | Name |
|---|---|---|
| 313 | 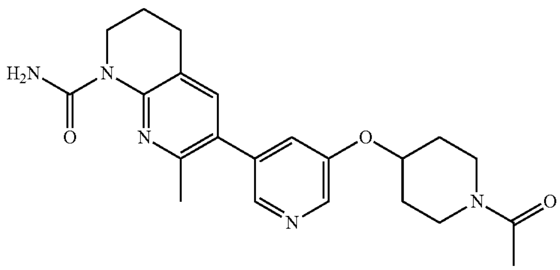 [SMILES: CC(=O)N1CCC(Oc2cncc(-c3cc4c(nc3C)N(C(N)=O)CCC4)c2)CC1] | 6-[5-(1-Acetyl-piperidin-4-yloxy)-pyridin-3-yl]-7-methyl-3,4-dihydro-2H-[1,8]naphthyridine-1-carboxylic acid amide |
| 314 | 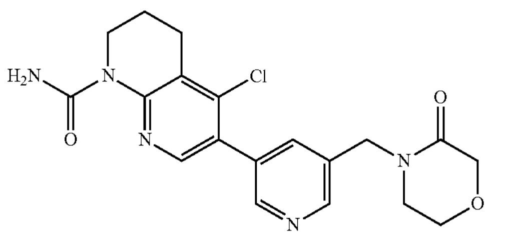 | 5-Chloro-6-[5-(3-oxo-morpholin-4-ylmethyl)-pyridin-3-yl]-3,4-dihydro-2H-[1,8]naphthyridine-1-carboxylic acid amide |
| 315 | 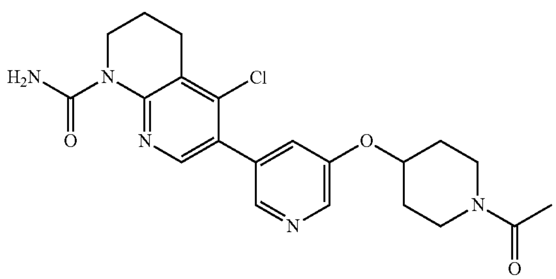 [SMILES: CC(=O)N1CCC(Oc2cncc(-c3cnc4c(c3Cl)CCCN4C(N)=O)c2)CC1] | 6-[5-(1-Acetyl-piperidin-4-yloxy)-pyridin-3-yl]-5-chloro-3,4-dihydro-2H-[1,8]naphthyridine-1-carboxylic acid amide |
| 316 | 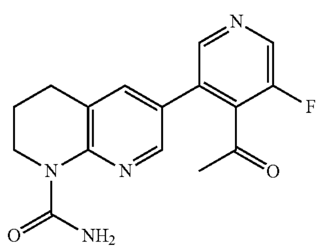 [SMILES: CC(=O)c1c(F)cncc1-c1cnc2c(c1)CCCN2C(N)=O] | 6-(4-Acetyl-5-fluoro-pyridin-3-yl)-3,4-dihydro-2H-[1,8]naphthyridine-1-carboxylic acid amide |
| 317 | 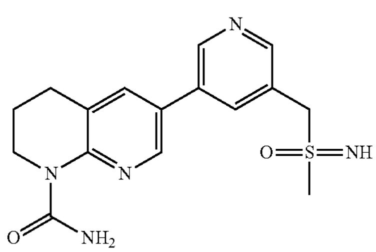 [SMILES: CS(=N)(=O)Cc1cncc(-c2cnc3c(c2)CCCN3C(N)=O)c1] | 6-(5-{[Imino(methyl)oxo-$\lambda^6$-sulfanyl]methyl}pyridin-3-yl)-1,2,3,4-tetahydro-1,8-naphthyridine-1-carboxamide |
| 318 | 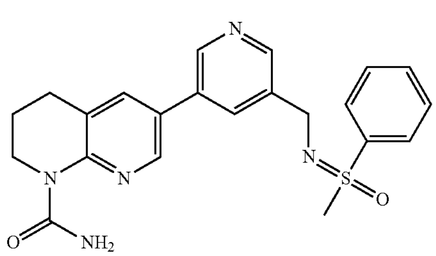 [SMILES: CS(=O)(=NCc1cncc(-c2cnc3c(c2)CCCN3C(N)=O)c1)c1ccccc1] | 6-[5-({[Methyl(oxo)phenyl-$\lambda^6$-sulfanylidene]amino}methyl)pyridine-3-yl]-1,2,3,4-tetrahydro-1,8-naphthyridine-1-carboxamide |

In one embodiment, the invention relates to compounds 1-112 and 115-154 depicted in Table 1 above and the pharmaceutically acceptable salts thereof.

In another embodiment, the invention relates to compounds 1-20, 22-35, 38-107, 109-112, 116, 117, 121, 122, 126-131, 133-137, 141-144 and 147-153 depicted in Table 1 above and the pharmaceutically acceptable salts thereof.

In another embodiment, the invention relates to compounds 1-3, 5-11, 14-20, 22-25, 27-29, 31-35, 38, 40-43, 45, 46, 48, 50-57, 59, 60, 62-68, 70-88, 90-102, 105-107, 109, 110, 112, 116, 117, 121, 126-131, 133-137, 141-144, 147-153, 155-162, 164, 165, 167-182, 184-193, 195-199, 202, 204, 205, 207-213, 216-218, 220-243, 245-250, 252-255, 257-262, 264-270, 272, 274-298, 300, 302, 304-307 and 309-316 depicted in Table 1 above and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C (CH₃)₂—CH₂)—, —(CH(CH₃)—CH(CH₃))—, —(CH₂—CH(CH₂CH₃))—, —(CH(CH₂CH₃)—CH₂)—, —(CH(CH₂CH₂CH₃))—, —(CHCH(CH₃)₂)— and —C(CH₃)(CH₂CH₃)—.

The term "C$_{3-n}$-cycloalkyl", wherein n is an integer 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1λ⁶-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3.3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH₂CHF₂, —CF₃ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—C$_{1-6}$ alkyl radical, unless otherwise specified, this shall be understood to include —S(O)—C$_{1-6}$ alkyl and —S(O)₂—C$_{1-6}$ alkyl, likewise, —S—R$_a$ may be represented as phenyl-S(O)$_m$— when R$_a$ is phenyl and where m is 0, 1 or 2.

GENERAL SYNTHETIC METHODS AND SYNTHESIS OF INTERMEDIATES

The compounds of the invention may be prepared by the methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

Intermediate A

Synthesis of 6-Bromo-1,2,3,4-tetrahydro-[1,8]naphthyridine

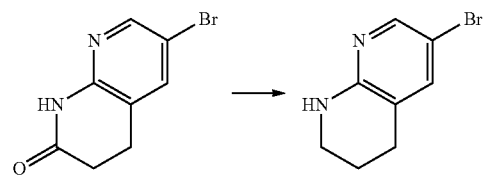 [SMILES: O=C1CCc2cc(Br)cnc2N1 ; Brc1cnc2c(c1)CCCN2]

To a cooled (0° C.) solution of 6-bromo-3,4-dihydro-1H-[1,8]naphthyridin-2-one (10.0 g, 44.0 mmol) in THF (500 mL) is added sodium borohydride (8.3 g, 220 mmol) followed by boron trifluoride diethyl ether complex (38.7 mL, 308 mmol), dropwise. The resulting mixture is allowed to warm and stir at room temperature for 16 h. The reaction is carefully quenched with the dropwise addition of 1N HCl (15 mL). Once quenched, additional 1N HCl (85 mL) is added and the mixture is stirred at room temperature for 16 h. The mixture is concentrated, diluted with water and made basic (pH 8) with the addition of powdered sodium bicarbonate. The mixture is extracted with EtOAc and the combined organic layers are washed with brine, dried (Na₂SO₄) and concentrated to obtain the title compound (9.3 g).

Intermediate B

Synthesis of 6-Bromo-3,4-dihydro-2H-[1,8]naphthyridine-1-carboxylic acid tert-butyl ester

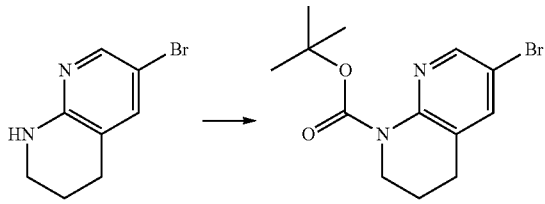 [SMILES: Brc1cnc2c(c1)CCCN2 ; CC(C)(C)OC(=O)N1CCCc2cc(Br)cnc21]

To a cooled (0° C.) suspension of sodium hydride (60% dispersion in mineral oil, 2.8 g, 70.4 mmol) in THF (800 mL) is added a solution of 6-bromo-1,2,3,4-tetrahydro-[1,8]naphthyridine (10.0 g, 46.9 mmol) in THF (300 mL), dropwise. After stifling for 30 min at 0° C., a solution of di-tert-butyl dicarbonate (21.6 mL, 93.9 mnmol) in THF (200 mL) is added dropwise. The resulting mixture is allowed to warm to room temperature then stir at reflux for 16 h. The reaction is cooled to room temperature and quenched with the addition saturated aqueous ammonium chloride solution. The mixture is extracted with EtOAc and the combined organic layers are washed with brine, dried (MgSO$_4$) and concentrated. The crude product is purified by silica gel column (5-40% EtOAc in heptane) to afford the title compound (13.5 g).

Intermediate C

Synthesis of 6-Bromo-3,4-dihydro-2H-[1,8]naphthyridine-1-carboxylic acid amide

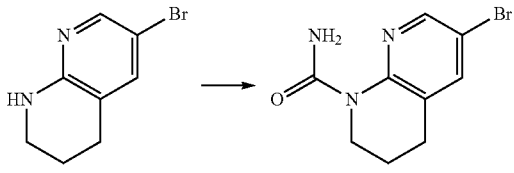 [SMILES: Brc1cnc2c(c1)CCCN2 ; NC(=O)N1CCCc2cc(Br)cnc21]

To a cooled (0° C.) solution of 6-bromo-1,2,3,4-tetrahydro-[1,8]naphthyridine (6.4 g, 30.0 mmol) in DCM (75 mL) is added a trichloroacetyl isocyanate (3.8 mL, 31.5 mmol). After stirring for 1 h at 0° C., a solution of methanolic KOH (1M, 10 mL) is added. The resulting mixture is allowed to warm and stir at room temperature for 16 h. The reaction is concentrated and purified by silica gel column (0-100% EtOAc in heptane) to afford the title compound (7.4 g).

Intermediate D

Synthesis of 5-Bromo-2,3-dihydro-pyrrolo[2,3-b]pyridine-1-carboxylic acid amide

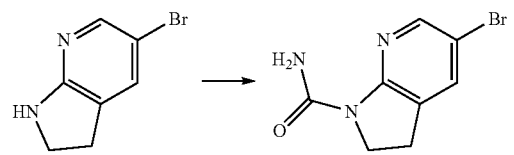 [SMILES: Brc1cnc2c(c1)CCN2 ; NC(=O)N1CCc2cc(Br)cnc21]

To a cooled (0° C.) solution of 5-bromo-2,3-dihydro-1H-pyrrolo[2,3-b]pyridine (2.5 g, 12.6 mmol) in DCM (30 mL) is added a trichloroacetyl isocyanate (1.6 mL, 13.2 mmol). After stirring for 1 h at 0° C., a solution of methanolic KOH (1M, 10 mL) is added. The resulting mixture is allowed to warm and stir at room temperature for 16 h. The reaction is concentrated and purified by silica gel column (0-100% EtOAc in heptane) to afford the title compound (2.6 g).

Intermediate E

Synthesis of 3-Bromo-5-bromomethyl-pyridine

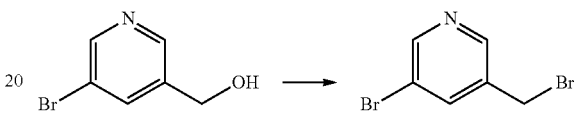

To a cooled (0° C.) solution of (5-bromo-pyridin-3-yl)-methanol (5.0 g, 26.6 mmol) and triphenylphosphine (8.4 g, 31.9 mmol) in DCM (130 mL) is added carbon tetrabromide (13.2 g, 39.9 mmol). The resulting mixture is stirred at 0° C. for 10 min. The mixture is concentrated and purified by silica gel column (0-40% EtOAc in heptane) to afford the title compound (6.1 g).

Intermediate F

Synthesis of 1-[4-(5-Bromo-pyridin-3-ylmethoxy)-piperidin-1-yl]-ethanone

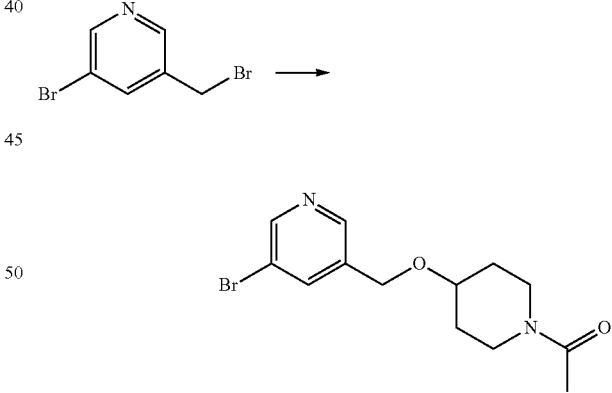

To a cooled (0° C.) solution of 1-acetylpiperidin-4-ol (2.0 g, 14.2 mmol) in DMF (25 mL) is added sodium hydride (60% dispersion in mineral oil, 567 mg, 14.2 mmol). After stifling at 0° C. for 15 min, 3-bromo-5-bromomethyl-pyridine (2.4 g, 9.45 mmol) is added. The reaction is allowed to warm and stir at room temperature for 1 h. The reaction is quenched with the addition of saturated aqueous ammonium chloride and water and is extracted with EtOAc. The combined organic layers are dried (Na$_2$SO$_4$) and concentrated. The crude product is purified by silica gel column (0-10% MeOH in DCM) to provide the title compound (2.1 g).

Intermediate G

Synthesis of 6-(4,4,5,5-Tetramethyl-[1,3,2]dioxaborolan-2-yl)-3,4-dihydro-2H-[1,8]naphthyridine-1-carboxylic acid tert-butyl ester

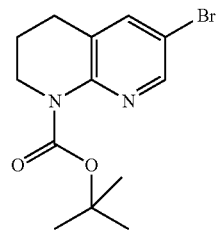
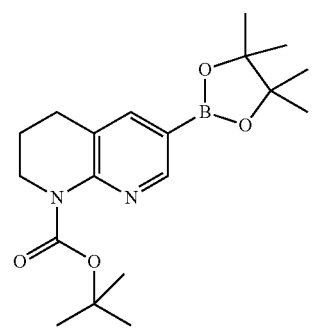

6-Bromo-3,4-dihydro-2H-[1,8]naphthyridine-1-carboxylic acid tert-butyl ester, Intermediate B (200 mg, 0.64 mmol), 4,4,5,5,4',4',5',5'-Octamethyl-[2,2']bi[[1,3,2]dioxaborolanyl] (240 mg, 0.94 mmol) and KOAc (310 mg, 3.2 mmol) are mixed in 1,4-dioxane (4.0 mL). The reaction mixture is purged with Argon stream for 5 min. Then PdCl$_2$(dppf) (47 mg, 0.064 mmol) is added. The reaction mixture is purged again with Argon stream for 5 min. The reaction mixture is heated at 100° C. in for 5 hrs. After cooling down to room temperature, the crude reaction mixture containing the titled product is either used in the next step directly or the solid is filtered and the filtrate is concentrated to give the solid crude which is then used in the next step without purification.

Intermediate H

Synthesis of 6-(4,4,5,5-Tetramethyl-[1,3,2]dioxaborolan-2-yl)-3,4-dihydro-2H-[1,8]naphthyridine-1-carboxylic acid amide

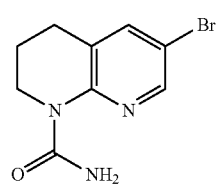
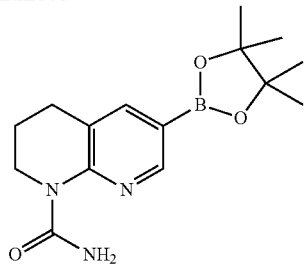

6-Bromo-3,4-dihydro-2H-[1,8]naphthyridine-1-carboxylic acid amide, Intermediate C (600 mg, 2.34 mmol), bis (pinacolato)diboron (773 mg, 3.05 mmol) and KOAc (1.03 g, 10.5 mmol) are mixed in 1,4-dioxane (20 mL). The reaction mixture is purged with Argon stream for 5 min. Then PdCl$_2$(dppf) (171 mg, 0.234 mmol) is added. The reaction mixture is purged again with Argon stream for 5 min. The reaction mixture is heated at 90° C. in for 16 hrs. After cooling down to room temperature, the crude reaction mixture containing the titled product is either used in the next step directly or the solid is filtered and the filtrate is concentrated to give the solid crude which is then used in the next step without purification.

Suzuki Coupling Method I:

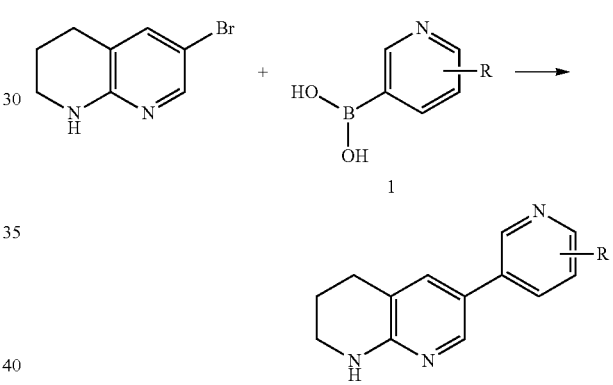

Nitrogen gas is bubbled through toluene (12 mL) for 30 min. Then 6-bromo-1,2,3,4-tetrahydro-[1,8]naphthyridine (200 mg, 0.94 mmol) and bis(di-tert-butyl(4-dimethylaminophenyl)phosphine)dichloropalladium (II) (66 mg, 0.094 mmol) are added. The mixture is degassed and filled with N$_2$ for three times. After stirring at room temperature for 1 hr, boric acid or ester 1 (1.5 eq.), 2.0 M aqueous K$_2$CO$_3$ solution (4.0 mL, 8.0 mmol) and EtOH (12 mL) are added and the mixture is heated to reflux. The progress of the reaction is monitored and after the reaction is completed, the mixture is cooled down to room temperature. The solid is filtered off and the filtrate is concentrated. The residue is partitioned between DCM and water. The organic layer is separated and washed with water and brine, dried over Na$_2$SO$_4$ and concentrated to give the crude product. Purification by various chromatography methods affords the desired product.

Suzuki Coupling Method II:

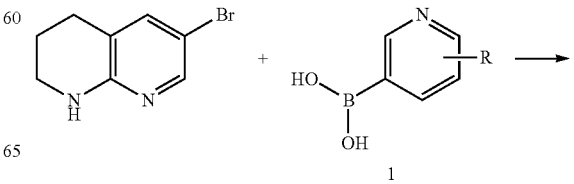

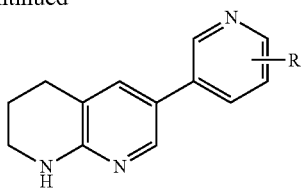

To the solution of 6-bromo-1,2,3,4-tetrahydro-[1,8]naphthyridine (100 mg, 0.47 mmol) in MeCN (2.0 mL) is added boronic acid or boronic ester 1 (1.2 eq.) and saturated aqueous $Na_2CO_3$ solution (1.0 mL). Then $Pd(dppf)Cl_2$ (34 mg, 0.047 mmol) is added under $N_2$ atmosphere and the mixture is microwaved at 120° C. The progress of the reaction is monitored and after the reaction is completed, the solid is filtered and the filtrate is concentrated. The residue is partitioned between DCM and water. The organic layer is separated and washed with water and brine, dried over $Na_2SO_4$ and concentrated to give the crude product. Purification by column chromatography affords the desired product.

Suzuki Coupling Method III:

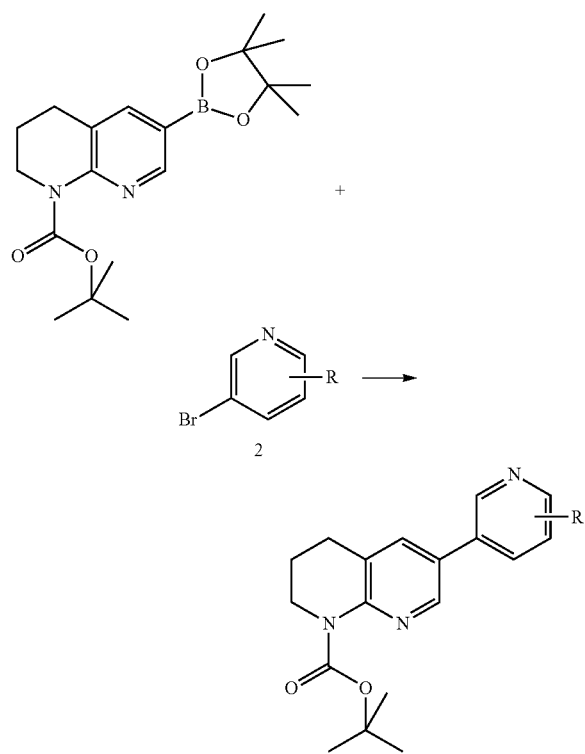

To a solution of crude 6-(4,4,5,5-tetramethyl-[1,3,2]dioxaborolan-2-yl)-3,4-dihydro-2H-[1,8]naphthyridine-1-carboxylic acid tert-butyl ester (175 mg, 0.63 mmol) in MeCN (9.0 mL) is added bromide 2 (1.0 eq.) and saturated aqueous $Na_2CO_3$ solution (4.0 mL). Then $Pd(dppf)Cl_2$ (23 mg, 0.031 mmol) is added under $N_2$ atmosphere and the mixture is microwaved at 120° C. The progress of the reaction is monitored and after the reaction is completed, the solid is filtered and the filtrate is concentrated. The residue is partitioned between DCM and water. The organic layer is separated and washed with water and brine, dried over $Na_2SO_4$ and concentrated to give the crude product. Purification by column chromatography affords the desired product.

Suzuki Coupling Method IV:

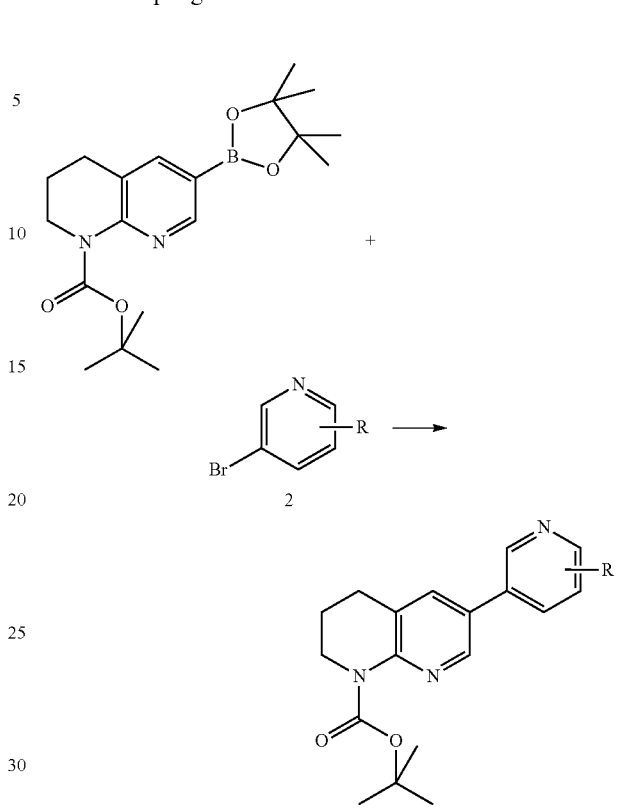

To a solution of crude 6-(4,4,5,5-tetramethyl-[1,3,2]dioxaborolan-2-yl)-3,4-dihydro-2H-[1,8]naphthyridine-1-carboxylic acid tert-butyl ester (480 mg, 1.7 mmol) in 1,4-dioxane (60 mL) are added bromide 2 (1 eq.) and $Na_2CO_3$ (550 mg, 5.2 mmol). Then $Pd(dppf)Cl_2$ (63 mg, 0.086 mmol) is added under $N_2$ atmosphere. The mixture is heated to reflux for 16 hrs. After cooling down to room temperature, the solid in the mixture is filtered and the filtrate is concentrated. The residue is partitioned between DCM and water. The organic layer is separated and washed with water and brine, dried over $Na_2SO_4$ and concentrated to give the crude product. Purification by column chromatography affords the desired product.

Suzuki Coupling Method V:

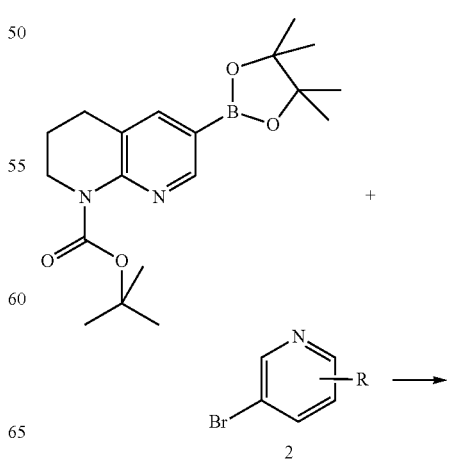

-continued

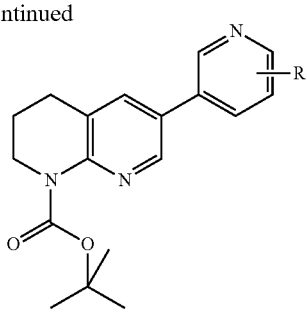

To a solution of crude 6-(4,4,5,5-tetramethyl-[1,3,2]dioxaborolan-2-yl)-3,4-dihydro-2H-[1,8]naphthyridine-1-carboxylic acid tert-butyl ester (260 mg, 0.94 mmol) in 1,4-dioxane (30 mL) are added bromide 2 (1 eq.) and $Cs_2CO_3$ (910 mg, 2.8 mmol). Then $Pd(dppf)Cl_2$ (34 mg, 0.047 mmol) is added under $N_2$ atmosphere. The mixture is heated to reflux for 16 hrs. After cooling down to room temperature, the solid in the mixture is filtered and the filtrate is concentrated. The residue is partitioned between DCM and water. The organic layer is separated and washed with water and brine, dried over $Na_2SO_4$ and concentrated to give the crude product. Purification by column chromatography affords the desired product.

Suzuki Coupling Method VI:

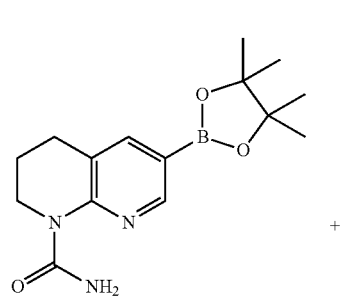
Intermediate H

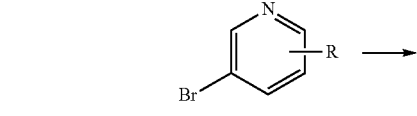
2

To the crude solution of 6-(4,4,5,5-Tetramethyl-[1,3,2]dioxaborolan-2-yl)-3,4-dihydro-2H-[1,8]naphthyridine-1-carboxylic acid amide (942 mg, 3.11 mmol, generated from the reaction to make Intermediate H) are added bromide 2 (0.85 eq.) and aqueous 2.0 M $Na_2CO_3$ solution (2.63 mL, 5.26 mmol). Argon gas is bubbled through the solution for 10 min and $Pd(dppf)Cl_2$ (192 mg, 0.263 mmol) is added. Then the reaction mixture is heated at 100° C. for 3.5 hrs. After the reaction mixture is cooled down to room temperature, it is filtered and the filtrate is concentrated to give the crude product. Purification by column chromatography affords the desired product.

Urea Formation Method I:

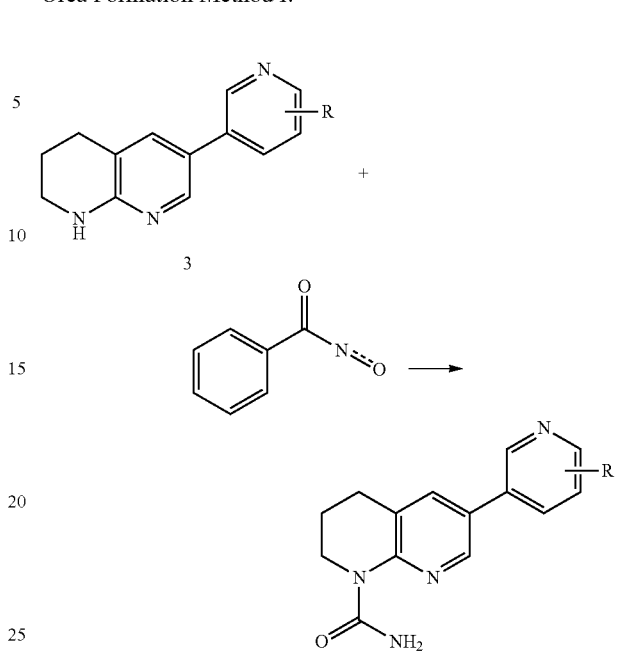

To a solution of amine 3 (1.1 mmol) in anhydrous DCM (11 mL) is added benzoyl isocyanate (250 mg, 1.7 mmol) and the mixture is heated to reflux for 3 hrs. The solvent is removed and EtOH (11 mL) is added to the residue. Then $K_2CO_3$ (260 mg, 1.9 mmol) is added and the mixture is heated to reflux. The progress of the reaction is monitored and after the reaction is completed, the solid is filtered and the filtrate is concentrated. The residue is partitioned between DCM and water. The organic layer is separated and washed with water and brine, dried over $Na_2SO_4$ and concentrated to give the crude product. Purification by column chromatography affords the desired product.

Urea Formation Method II:

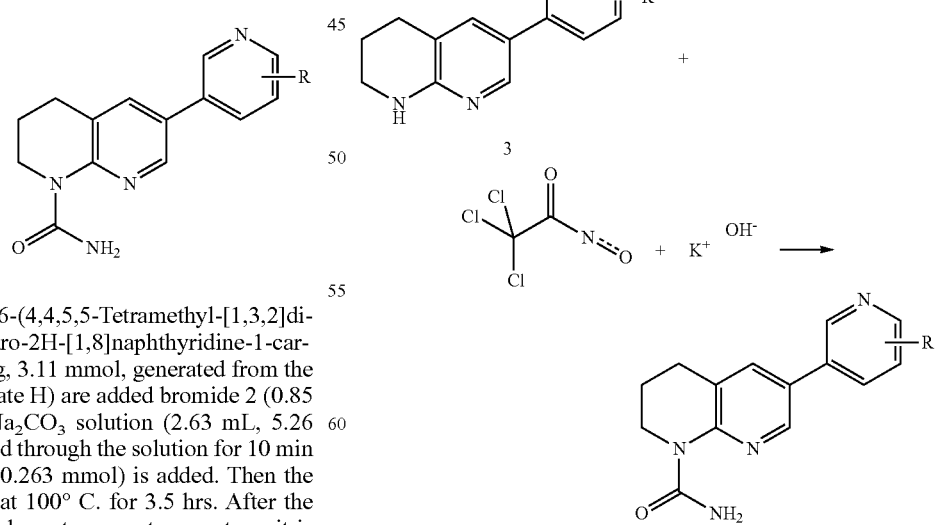

Amine 3 (13.6 mmol) is dissolved in anhydrous DCM (150 mL) and the solution is cooled down to 0° C. Trichloro-acetyl isocyanate (2.53 mL, 20.4 mmol) is added and the mixture is stirred for 1 hr at room temperature. Then 1.0 M KOH in MeOH solution (136 mL, 136 mmol) is added and the mixture is stirred for 16 hs. Water (500 mL) and DCM (200 mL) are added. The mixture is stirred for 15 min and the aqueous layer is separated, extracted with DCM (2×100 mL) and EtOAc (2×100 mL). All the organic layers are combined and concentrated to give the crude product. Purification by column chromatography affords the desired product.

SYNTHETIC EXAMPLES

Final compounds are designated by compound numbers corresponding to the compound numbers in Table 1.

Example 1

Synthesis of 5-pyridin-3-yl-2,3-dihydro-pyrrolo[2,3-b]pyridine-1-carboxylic acid amide (Cpd 1, Table 1)

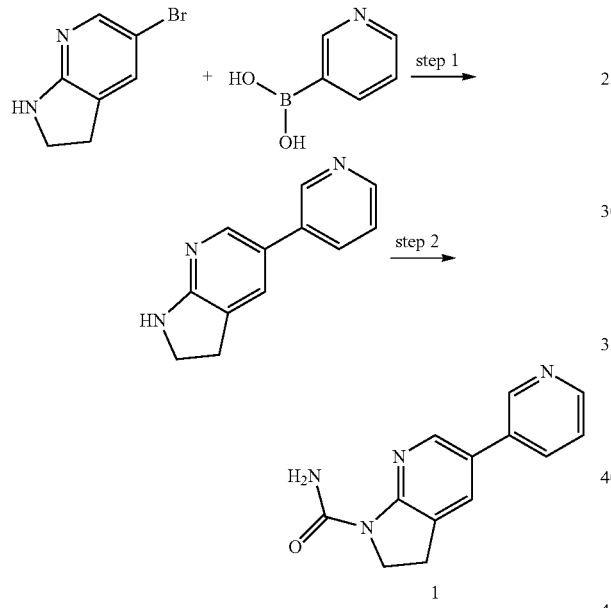

5-Bromo-2,3-dihydro-1H-pyrrolo[2,3-b]pyridine (500 mg, 2.5 mmol), 3-pyridinyl-boronic acid (370 mg, 3.0 mmol) and K$_2$CO$_3$ (694 mg, 5.0 mmol) are mixed in 6.5 mL of 1,4-dioxane and 0.65 mL of water. Argon gas is bubbled through the mixture for 10 min and bis(di-tert-butyl(4-dimethylaminophenyl)phosphine)dichloropalladium (II) (178 mg, 0.25 mmol) is added. The mixture is heated at 100° C. for 16 hrs. Then the solvents are removed and EtOAc (50 mL) is added along with 30 mL of water. The mixture is filtered to remove any solid and the organic layer is separated. The aqueous layer is extracted with EtOAc (2×25 mL) and the organic layers are combined and concentrated to give the crude product. Purification by flash column chromatography affords 300 mg of 5-pyridin-3-yl-2,3-dihydro-1H-pyrrolo[2,3-b]pyridine.

5-Pyridin-3-yl-2,3-dihydro-1H-pyrrolo[2,3-b]pyridine (50 mg, 0.25 mmol) and benzoyl isocyanate (62 mg, 0.38 mmol) are dissolved in 1.5 mL of DCM. The mixture is heated at 50° C. for 16 hrs. Then the solvent is removed in vacuum and the residue is dissolved in 1.5 mL of EtOH. K$_2$CO$_3$ (60 mg, 0.43 mmol) is added and the mixture is heated at 80° C. for 55 min. The solvent is removed and the residue is partitioned between water (35 mL) and EtOAc (55 mL). The aqueous layer is separated and extracted with EtOAc (2×30 mL). The organic layers are combined and concentrated to give the crude product. To the crude product is added DMSO: EtOAc (1:3 mL) mixture and the white solid formed is filtered, rinsed with more EtOAc and dried to give 38 mg of the titled product.

Compound 8 in Table 1 is synthesized according to the procedure for Example 1, substituting either commercially available reagents or the appropriate intermediates described above.

Example 2

Synthesis of 6-Pyridin-3-yl-3,4-dihydro-2H-[1,8]naphthyridine-1-carboxylic acid amide (Cpd 2, Table 1)

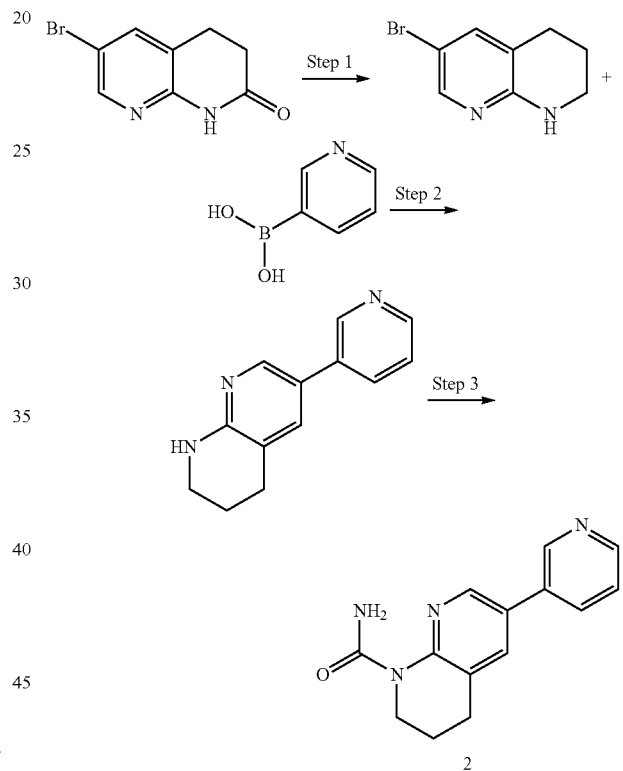

6-Bromo-1,2,3,4-tetrahydro-[1,8]naphthyridine is prepared as described above for Intermediate A.

6-Bromo-1,2,3,4-tetrahydro-[1,8]naphthyridine (243 mg, 1.1 mmol), 3-pyridinyl-boronic acid (168 mg, 1.4 mmol) and K$_2$CO$_3$ (315 mg, 2.3 mmol) are mixed in 3.0 mL of 1,4-dioxane and 0.30 mL of water. Argon gas is bubbled through the mixture for 10 min and bis(di-tert-butyl(4-dimethylaminophenyl)phosphine)dichloropalladium (II) (81 mg, 0.11 mmol) is added. The mixture is heated at 100° C. for 16 hrs. Then solvents are removed and EtOAc (50 mL) is added along with 30 mL of water. The mixture is filtered to remove any solid and the organic layer is separated. The aqueous layer is extracted with EtOAc (2×25 mL) and the organic layers are combined and concentrated to give the crude product. Purification by flash column chromatography affords 143 mg of 6-Pyridin-3-yl-1,2,3,4-tetrahydro-[1,8]naphthyridine 6-Pyridin-3-yl-1,2,3,4-tetrahydro-[1,8]naphthyridine (50 mg, 0.24 mmol) and benzoyl isocyanate (58 mg, 0.36 mmol) are dissolved in 1.5 mL of DCM. The mixture is heated at 50°

C. for 5 hrs. Then the solvent is removed in vacuum and the residue is dissolved in 1.5 mL of EtOH. K$_2$CO$_3$ (56 mg, 0.40 mmol) is added and the mixture is heated at 80° C. for 55 min. Then the solvent is removed and the residue is partitioned between water (35 mL) and EtOAc (55 mL). The aqueous layer is separated and extracted with EtOAc (2×30 mL). The organic layers are combined and concentrated to give the crude product. To the crude product is added EtOAc (1 mL) and the white solid formed is filtered, rinsed with EtOAc/heptane (1:1) mixture and dried to give 34 mg of the titled product.

Compound 10 in Table 1 is synthesized according to the procedure for Example 2, substituting either commercially available reagents or the appropriate intermediates described above.

Example 3

Synthesis of 1-(6-Pyridin-3-yl-3,4-dihydro-2H-[1,8] naphthyridin-1-yl)-ethanone (Cpd 3, Table 1)

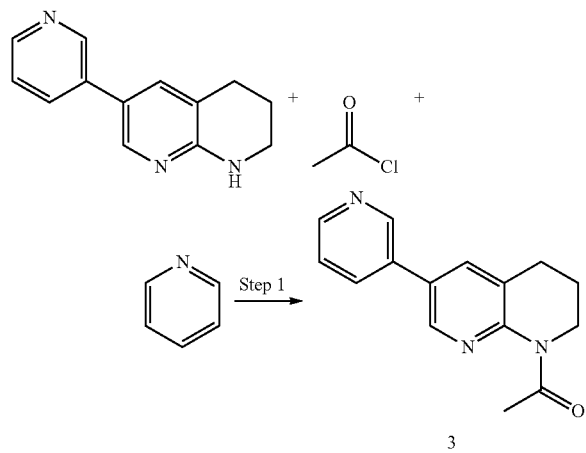

6-Pyridin-3-yl-1,2,3,4-tetrahydro-[1,8]naphthyridine (41 mg, 0.19 mmol) is dissolved in 2 mL of DCM and pyridine (0.19 mL, 2.3 mmol) is added into the solution. Then acetyl chloride (0.08 mL, 1.2 mmol) is added. The mixture is stirred for 0.5 hrs and saturated aqueous NaHCO$_3$ (2 mL) is added along with water (3 mL). The mixture is extracted with EtOAc (3×10 mL) and the organic layers are combined and concentrated to give the crude product. Purification by flash column chromatography affords 37 mg of the titled product.

Compounds 4, 7 and 17 in Table 1 are synthesized according to the procedure for Example 3, substituting either commercially available reagents or the appropriate intermediates described above.

Example 4

Synthesis of 6-(4-Methyl-pyridin-3-yl)-3,4-dihydro-2H-[1,8]naphthyridine-1-carboxylic acid amide (Cpd 5, Table 1)

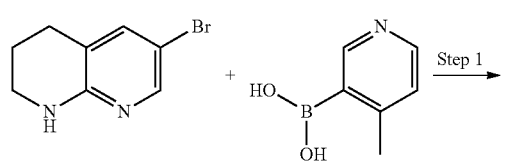

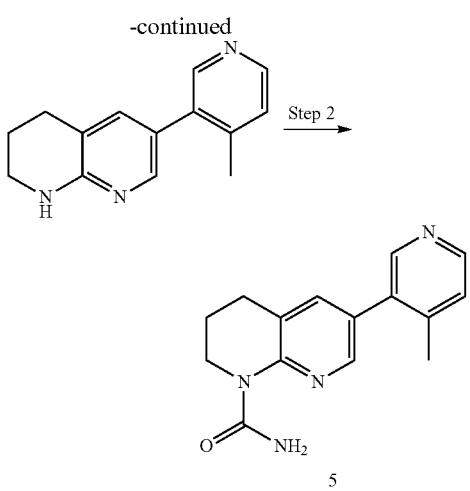

6-(4-Methyl-pyridin-3-yl)-1,2,3,4-tetrahydro-[1,8]naphthyridine is synthesized according to the procedure of Suzuki Coupling Method I, using the intermediates illustrated above.

To the solution of 6-(4-Methyl-pyridin-3-yl)-1,2,3,4-tetrahydro-[1,8]naphthyridine (50 mg, 0.22 mmol) in 5.0 mL of anhydrous DCM is added benzoyl isocyanate (39 mg, 0.24 mmol) and the solution is heated to reflux for 3 hrs. Then the solvent is removed in vacuo and to the residue is added 5.0 mL of EtOH. Then K$_2$CO$_3$ (61 mg, 44 mmol) is added and the mixture is heated to reflux for 5 hrs. After cooling down to room temperature, the solid is filtered off. The filtrate is evaporated to dryness. The residue is dissolved in DCM, washed with water and brine. The organic layer is separated, dried over Na$_2$SO$_4$, filtered and concentrated. The crude product is purified by preparative HPLC to give 14 mg of the titled product.

Compounds 6, 12-16, 20, 22, 26, 84 and 155 in Table 1 are synthesized according to the procedure for Example 4, substituting either commercially available reagents or the appropriate intermediates described above.

Example 5

Synthesis of 6-(5-Methoxy-pyridin-3-yl)-3,4-dihydro-2H-[1,8]naphthyridine-1-carboxylic acid amide (Cpd 9, Table 1)

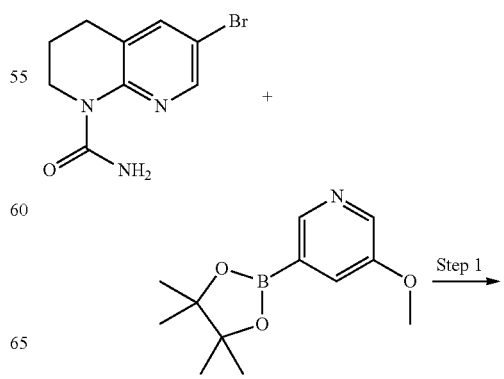

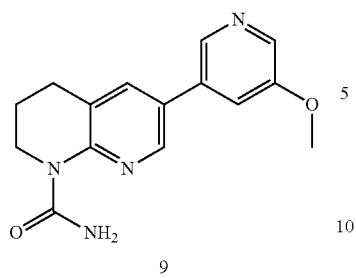

9

6-Bromo-3,4-dihydro-2H-[1,8]naphthyridine-1-carboxylic acid amide (30 mg, 0.12 mmol), 3-methoxy-5-(4,4,5,5-tetramethyl-[1,3,2]dioxaborolan-2-yl)-pyridine (43 mg, 0.18 mmol) and K₂CO₃ (32 mg, 0.23 mmol) are mixed in 1.0 mL of 1,4-dioxane and 0.10 mL of water. Argon gas is bubbled through the mixture for 10 min and bis(di-tert-butyl(4-dimethylaminophenyl)phosphine)dichloropalladium (II) (8.3 mg, 0.01 mmol) is added. The mixture is heated at 100° C. for 2 hrs. Then solvents are removed and EtOAc (20 mL) is added. The mixture is filtered to remove any solid and the filtrate is concentrated to give the crude product. Purification by flash column chromatography affords 12.3 mg of the title product.

Example 6

Synthesis of 6-(5-Acetyl-pyridin-3-yl)-3,4-dihydro-2H-[1,8]naphthyridine-1-carboxylic acid amide (Cpd 18, Table 1)

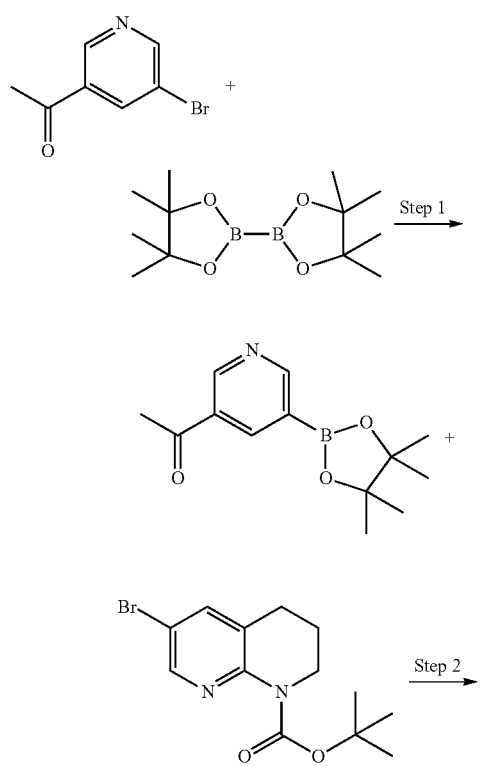

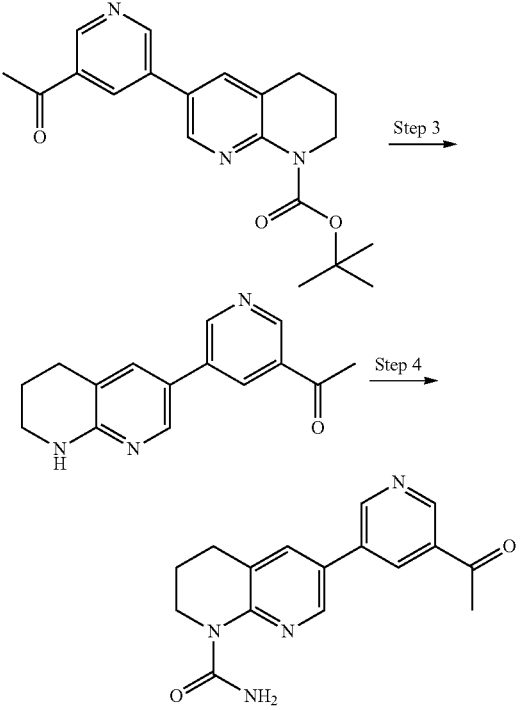

18

To a solution of 1-(5-Bromo-pyridin-3-yl)-ethanone (1.6 g, 8.0 mmol) in 50 mL of 1,4-dioxane is added diboron pinacol ester (2.5 g, 10.0 mmol) and KOAc (2.0 g, 20 mmol). The mixture is evacuated and backfilled with Ar 3 times. PdCl₂dppf DCM complex (728 mg, 0.89 mmol) is added and the mixture is heated at 70° C. for 19 hrs. Then the mixture is cooled down to room temperature and the crude 1-[5-(4,4,5,5-tetramethyl-[1,3,2]dioxaborolan-2-yl)-pyridin-3-yl]-ethanone is used in the next step without purification.

6-Bromo-3,4-dihydro-2H-[1,8]naphthyridine-1-carboxylic acid tert-butyl ester (2.1 g, 6.6 mmol) and 2.0 M Na₂CO₃ aqueous solution (10 mL, 20 mmol) are added into the above reaction crude. The mixture is evacuated and backfilled with Ar 3 times. PdCl₂dppf DCM complex (242 mg, 0.20 mmol) is added and the mixture is stirred at 100° C. for 2 hrs. After the reaction mixture is cooled down to room temperature, it is partitioned between EtOAc/H₂O. The layers are separated and the aqueous layer is further extracted with EtOAc. The combined organic layers are washed with brine, filtered through diatomaceous earth and concentrated. The crude mixture is purified by flash column chromatography to give 1.9 g of 6-(5-Acetyl-pyridin-3-yl)-3,4-dihydro-2H-[1,8]naphthyridine-1-carboxylic acid tert-butyl ester 6-(5-Acetyl-pyridin-3-yl)-3,4-dihydro-2H-[1,8]naphthyridine-1-carboxylic acid tert-butyl ester (500 mg, 1.4 mmol) is dissolved in 20 mL of 20% TFA in DCM. The mixture is stirred at room temperature for 16 hrs. Then the solvent and the extra reagent are removed and the residue is purified by reversed phase chromatography to give 135 mg of 1-[5-(5,6,7,8-tetrahydro-[1,8]naphthyridin-3-yl)-pyridin-3-yl]-ethanone 1-[5-(5,6,7,8-Tetrahydro-[1,8]naphthyridin-3-yl)-pyridin-3-yl]-ethanone (50 mg, 0.20 mmol) and benzoyl isocyanate (48 mg, 0.30 mmol) are dissolved in 2.0 mL of DCM. The mixture is heated at 50° C. for 16 hrs. Then the solvent is removed in vacuum and the residue is dissolved in 2.0 mL of EtOH. K₂CO₃ (46 mg, 0.34 mmol) is added and the mixture is heated at 80° C. for 45 min. The solvent is removed and the residue is partitioned between water (35 mL) and EtOAc (75 mL). The aqueous layer is separated and extracted with DCM (2×30 mL). The organic layers are combined and concentrated to give the crude product. EtOAc (2 mL) is added to the crude and the white solid formed is filtered, rinsed with more EtOAc (2×3 mL) and dried to give 30 mg of the titled product.

Example 7

Synthesis of 6-[5-(1-Hydroxy-ethyl)-pyridin-3-yl]-3,4-dihydro-2H-[1,8]naphthyridine-1-carboxylic acid amide (Cpd 19, Table 1)

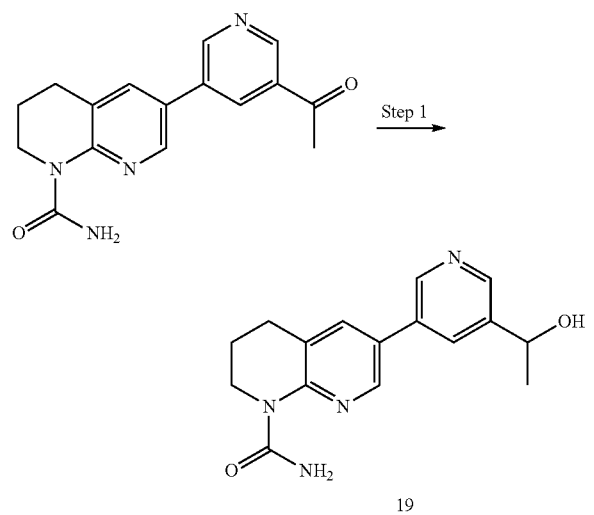

6-(5-Acetyl-pyridin-3-yl)-3,4-dihydro-2H-[1,8]naphthyridine-1-carboxylic acid amide (20 mg, 0.067 mmol) is dissolved in 2.0 mL of MeOH and NaBH₄ (7.7 mg, 0.20 mmol) is added. The mixture is stirred for 30 min and then MeOH is removed at room temperature and saturated aqueous NH₄Cl (2 mL) is added along with water (2 mL) and EtOAc (5 mL). The mixture is stirred for 5 min and the aqueous layer is separated and extracted with EtOAc (2×3 ml). The organic layers are combined and concentrated to give the crude product. Purification by reversed phase chromatography affords 15 mg of the titled product.

Enantiomers are separated using chiral CO₂ Supercritical Fluid Chromatography (Regis RegisPack 4.6×250 mm chiral column, 5-35% 1 MeOH:1 isopropylamine:1 EtOH (1% diethylamine) over 15 min at 3 mL/min, 200 Bar, 40° C., UV 254 nm detection) to give Compound 157 (retention time: 7.51 min) and Compound 158 (retention time: 9.67 min) in Table 1.

Example 8

Synthesis of 5-(8-Carbamoyl-5,6,7,8-tetrahydro-[1,8]naphthyridin-3-yl)-nicotinic acid (Cpd 21, Table 1)

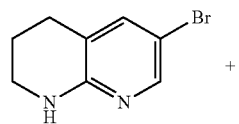

+

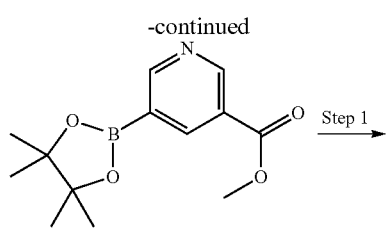

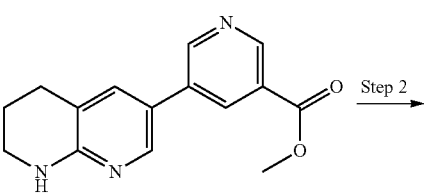

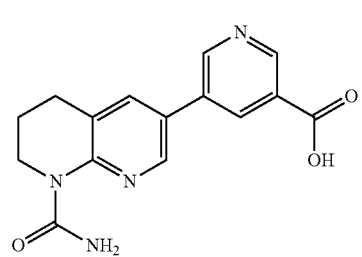

5-(5,6,7,8-Tetrahydro-[1,8]naphthyridin-3-yl)-nicotinic acid methyl ester is synthesized according to the procedure of Suzuki Coupling Method I, as illustrated above.

To the solution of 5-(5,6,7,8-tetrahydro-[1,8]naphthyridin-3-yl)-nicotinic acid methyl ester (205 mg, 0.76 mmol) in 60 mL of anhydrous DCM is added benzoyl isocyanate (170 mg, 1.1 mmol) and the solution is heated to reflux for 3 hrs. Then the solvent is removed in vacuo and to the residue is added 60 mL of MeOH. Then K₂CO₃ (180 mg, 1.3 mmol) is added and the mixture is heated to reflux for 0.5 hr. After cooling down, the organic solvent is evaporated. The residue is taken up in water and washed with DCM. The aqueous layer is separated and purified by neutral preparative HPLC to give 120 mg of the titled product.

Example 9

Synthesis of 5-(8-Carbamoyl-5,6,7,8-tetrahydro-[1,8]naphthyridin-3-yl)-nicotinic acid methyl ester (Cpd 23, Table 1)

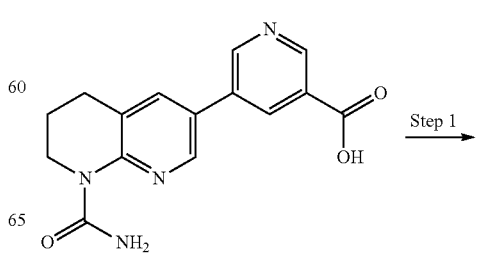

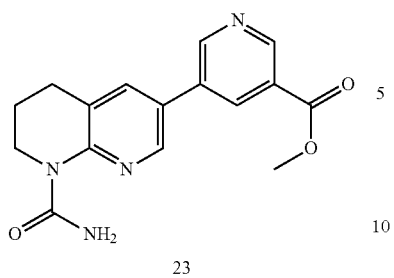

23

To the solution of 5-(8-Carbamoyl-5,6,7,8-tetrahydro-[1,8]naphthyridin-3-yl)-nicotinic acid (100 mg, 0.33 mmol) in 12 mL of toluene/MeOH 3:1 mixture is added 2.0 M trimethylsilyl-diazomethane (0.20 mL, 0.40 mmol) under $N_2$ atmosphere. The reaction solution is stirred at room temperature for 16 hrs. The solvents are removed in vacuo and the residue is purified by preparative HPLC to give 33 mg of the titled product.

Example 10

Synthesis of 6-[5-(1-Methyl-1H-indol-2-yl)-pyridin-3-yl]-3,4-dihydro-2H-[1,8]naphthyridine-1-carboxylic acid amide (Cpd 24, Table 1)

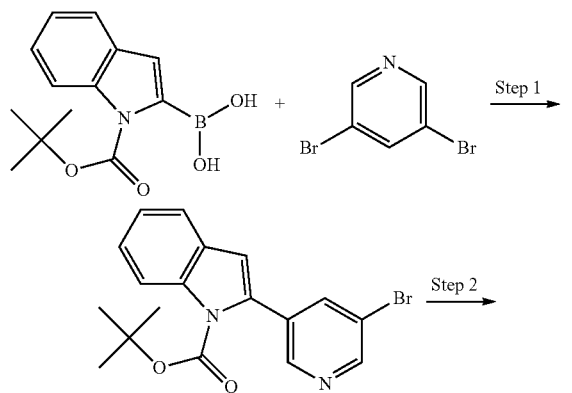

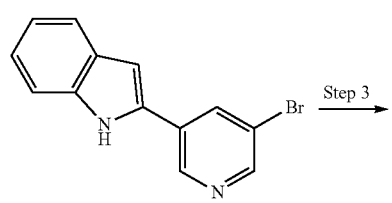

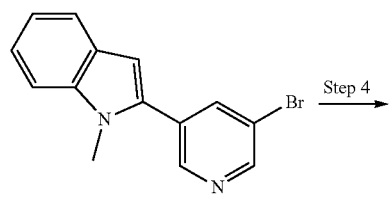

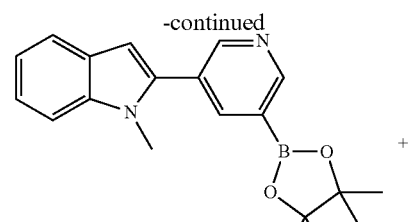

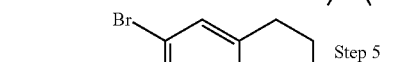

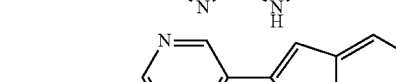

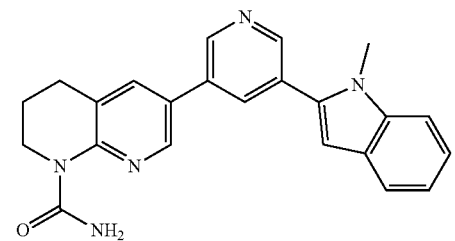

24

1-(tert-Butoxycarbonyl)indole-2-boronic acid (900 mg, 3.5 mmol), 3,5-dibromo-pyridine (810 mg, 3.5 mmol), KOAc (1.01 g, 10.4 mmol) and Pd(dppf)Cl$_2$ (252 mg, 0.35 mmol) are mixed in 1,4-dioxane (70 mL) and heated to 80° C. for 2 hours. The mixture is filtered and the filtrate is concentrated. The residue is dissolved in DCM and washed with water. The organic layer is separated, dried over Na$_2$SO$_4$, filtered and concentrated to afford the crude product which is purified by column chromatography to give 320 mg of 2-(5-bromo-pyridin-3-yl)-indole-1-carboxylic acid tert-butyl ester.

2-(5-Bromo-pyridin-3-yl)-indole-1-carboxylic acid tert-butyl ester (320 mg, 0.86 mmol) is added into 4.0 M HCl in EtOAc (10 mL) and the solution is stirred at room temperature for 16 hrs. The solvent is evaporated and the residue is dissolved in water and saturated aqueous NaHCO$_3$ solution is used to adjusted the pH to 9-10. Then the mixture is extracted with DCM for three times. The organic layers are combined, dried over Na$_2$SO$_4$, filtered and concentrated to give 192 mg of the crude 2-(5-bromo-pyridin-3-yl)-1H-indole which is used in the next step directly.

60% NaH (84 mg, 2.1 mmol) is added to a solution of 2-(5-bromo-pyridin-3-yl)-1H-indole (192 mg, 0.70 mmol) in THF (20 mL) and the temperature is kept below 0° C. After the addition, the mixture is stirred at room temperature for 30 min. MeI (125 mg, 0.88 mmol) is added to the mixture at 0° C. and the mixture is stirred at room temperature for 3 hrs. Then the solvent is removed and the residue is dissolved in EtOAc and washed with water. The organic layer is separated, dried and concentrated. The crude product is purified by flash column chromatography to give 173 mg of 2-(5-bromo-pyridin-3-yl)-1-methyl-1H-indole.

2-(5-Bromo-pyridin-3-yl)-1-methyl-1H-indole (368 mg, 1.28 mmol), bis(pinacolato)diboron (390 mg, 1.54 mmol), KOAc (377 mg, 3.85 mmol) and Pd(dppf)Cl₂ (94 mg, 0.13 mmol) are mixed in 1,4-dioxane (10 mL) and heated to reflux for 1 h. The mixture is filtered and the filtrate is concentrated to give 1-methyl-2-[5-(4,4,5,5-tetramethyl-[1,3,2]diox-aborolan-2-yl)-pyridin-3-yl]-1H-indole which is used in the next step directly to prepare 6-[5-(1-methyl-1H-indol-2-yl)-pyridin-3-yl]-1,2,3,4-tetrahydro-[1,8]naphthyridine is synthesized according to the procedure of Suzuki Coupling Method I.

To a solution of 6-[5-(1-methyl-1H-indol-2-yl)-pyridin-3-yl]-1,2,3,4-tetrahydro-[1,8]naphthyridine (110 mg; 0.32 mmol) in anhydrous DCM (5.0 mL) is added benzoyl isocyanate (71 mg; 0.48 mmol). The mixture is heated to reflux for 3 hrs. The solvent is removed and the residue is dissolved in EtOH (5.0 ml). K₂CO₃ (76 mg; 0.55 mmol) is added and the mixture is heated to reflux for 1 hr. Then the solvent is removed and the residue is purified by preparative HPLC to give 74 mg of the titled product.

Example 11

Synthesis of 6-(4-Fluoro-pyridin-3-yl)-3,4-dihydro-2H-[1,8]naphthyridine-1-carboxylic acid amide (Cpd 25, Table 1)

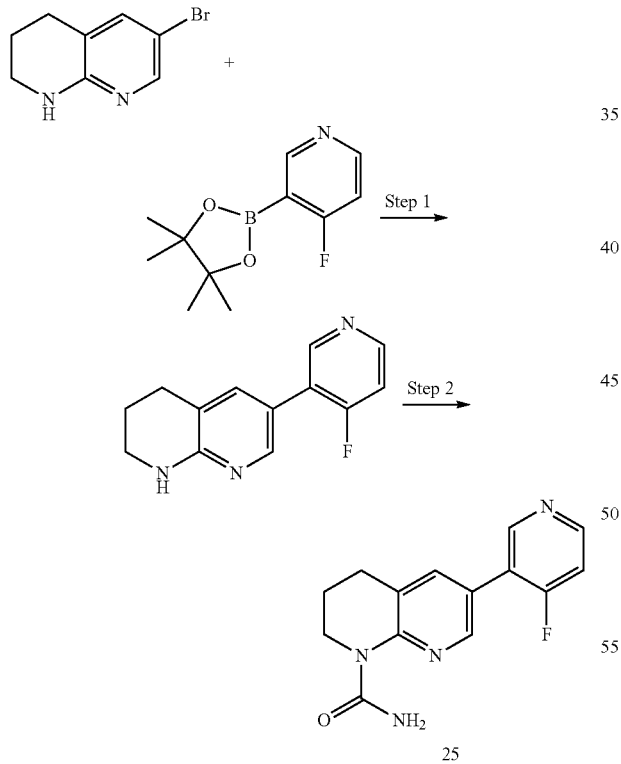

6-(4-Fluoro-pyridin-3-yl)-1,2,3,4-tetrahydro-[1,8]naphthyridine is synthesized according to the procedure of Suzuki Coupling Method II, as illustrated above. It is then used to prepare 6-(4-fluoro-pyridin-3-yl)-1,2,3,4-tetrahydro-[1,8]naphthyridine (200 mg, 0.87 mmol) according to the procedure of Urea Formation Method I.

Compound 29 in Table 1 is synthesized according to the procedure for Example 11, substituting either commercially available reagents or the appropriate intermediates described above.

Example 12

Synthesis of 7-(5-Fluoro-pyridin-3-yl)-2,3-dihydro-pyrido[3,2-b][1,4]oxazine-4-carboxylic acid amide (Cpd 27, Table 1)

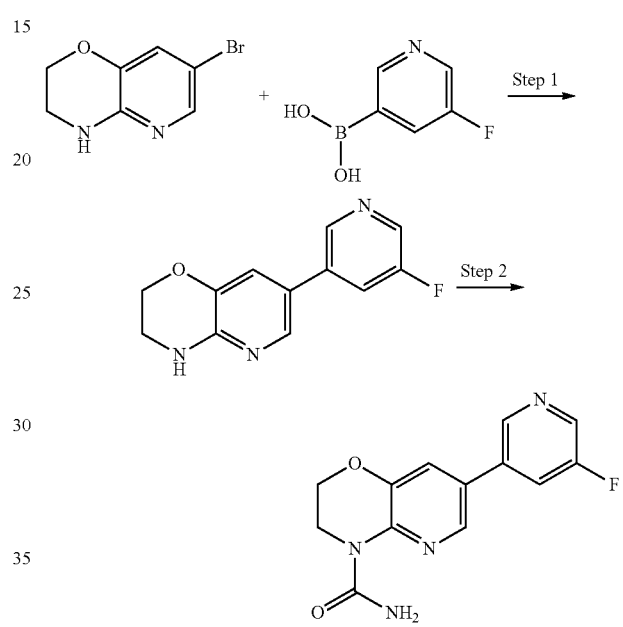

7-(5-Fluoro-pyridin-3-yl)-3,4-dihydro-2H-pyrido[3,2-b][1,4]oxazine is synthesized according to the procedure of Suzuki Coupling Method I, as illustrated above.

7-(5-Fluoro-pyridin-3-yl)-3,4-dihydro-2H-pyrido[3,2-b][1,4]oxazine (500 mg, 2.2 mmol) is converted to 65 mg of the titled product according to the procedure of Urea Formation Method I.

Example 13

Synthesis of 1-[7-(5-Fluoro-pyridin-3-yl)-2,3-dihydro-pyrido[3,2-b][1,4]oxazin-4-yl]-ethanone (Cpd 28, Table 1)

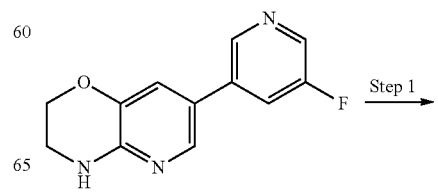

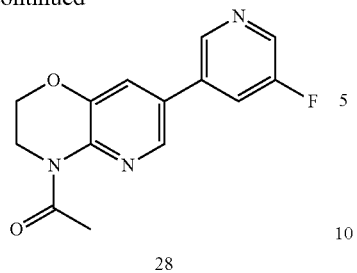

28

To a solution of 7-(5-fluoro-pyridin-3-yl)-3,4-dihydro-2H-pyrido[3,2-b][1,4]oxazine (350 mg, 1.5 mmol) (which is synthesized according to the procedure for Step 1 of Example 12) in DCM (100 mL) is added pyridine (1.7 g 18 mmol), then acetyl chloride (710 mg 9.1 mmol) is added dropwise. The solution is stirred at room temperature for 16 hrs and the solvent is removed. The residue is purified by preparative HPLC to give 54 mg of the titled product.

Example 14

Synthesis of 6-Pyrazin-2-yl-3,4-dihydro-2H-[1,8]naphthyridine-1-carboxylic acid amide (Cpd 30, Table 1)

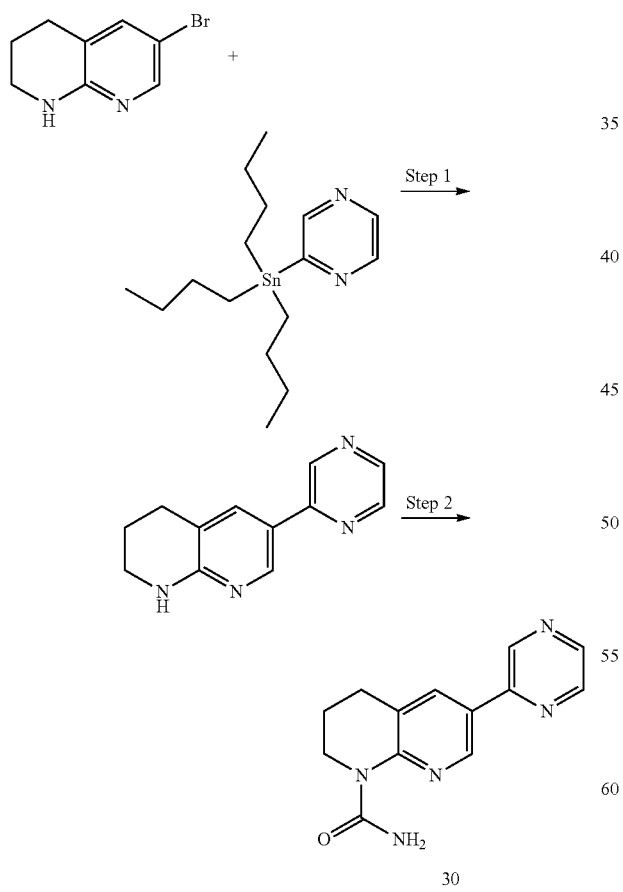

30

To a solution of 6-bromo-1,2,3,4-tetrahydro-[1,8]naphthyridine (350 mg, 1.6 mmol) in 14 mL of toluene/DMF 1:1 mixed solvents are added 2-tributylstannanyl-pyrazine (670 mg 1.8 mmol) and $Cs_2CO_3$ (1.6 g, 4.9 mmol). Then Pd(dppf)$Cl_2$ (120 mg, 0.16 mmol) is added under $N_2$ atmosphere. The mixture is heated at 110° C. for 16 hrs and the solvent is removed under vacuum. The residue is purified by flash column chromatography to give 190 mg of 6-pyrazin-2-yl-1,2,3,4-tetrahydro-[1,8]naphthyridine 6-Pyrazin-2-yl-1,2,3,4-tetrahydro-[1,8]naphthyridine (190 mg, 0.90 mmol) is converted to 92 mg of the titled product according to the procedure of Urea Formation Method I.

Example 15

Synthesis of 6-[5-(4-fluoro-phenyl)-pyridin-3-yl]-3,4-dihydro-2H-[1,8]naphthyridine-1-carboxylic acid amide (Cpd 31, Table 1)

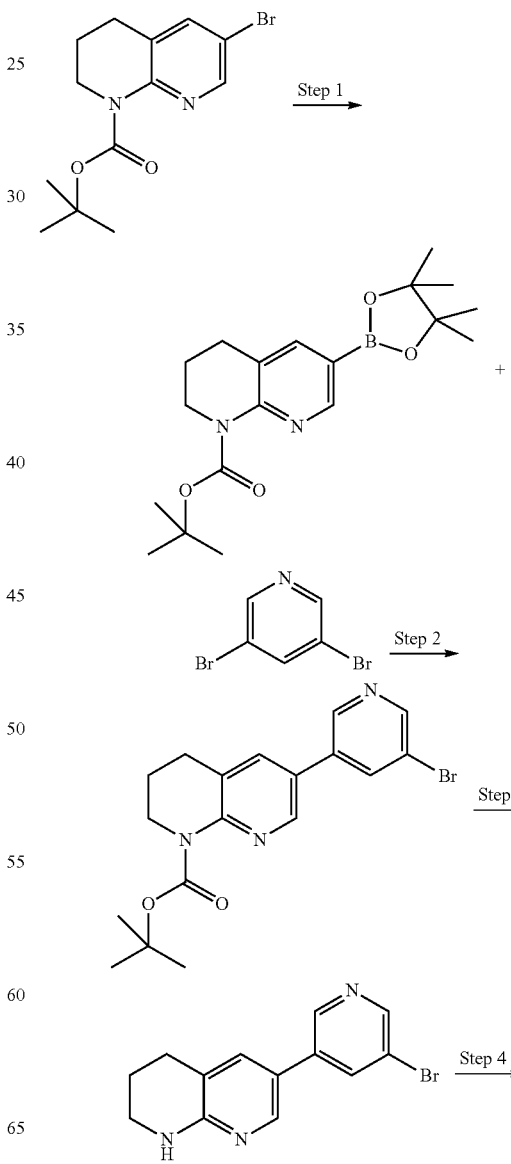

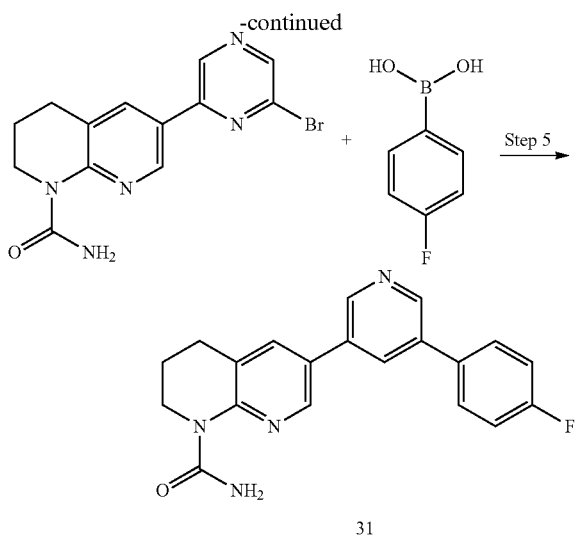

6-Bromo-3,4-dihydro-2H-[1,8]naphthyridine-1-carboxylic acid tert-butyl ester (540 mg, 1.7 mmol), bis(pinacolato) diboron (720 mg, 2.8 mmol) and KOAc (760 mg, 7.8 mmol) and 1,1'-bis(diphenylphosphino)ferrocene (dppf) (48 mg, 0.086 mmol) are added into 15 mL of 1,4-dioxane and the Argon gas is bubbled through the mixture for 5 min. Then PdCl$_2$dppf (63 mg, 0.086 mmol) is added. The mixture is heated at 110° C. for 4.5 hrs and then the mixture is cooled down to room temperature. The crude 6-(4,4,5,5-tetramethyl-[1,3,2]dioxaborolan-2-yl)-3,4-dihydro-2H-[1,8]naphthyridine-1-carboxylic acid tert-butyl ester is used in the next step without purification.

3,5-Dibromo-pyridine (1.2 g, 5.2 mmol) and 2.0 M Na$_2$CO$_3$ aqueous solution (1.7 mL, 3.4 mmol) are added into the above reaction solution. Argon gas is bubbled through the mixture for 5 min. Then PdCl$_2$dppf (63 mg, 0.086 mmol) is added. The mixture is heated at 110° C. for 4 hrs and the mixture is cooled down to room temperature. Then 30 mL of EtOAc and 20 mL of water are added and the organic layer is separated. The aqueous layer is extracted with EtOAc (2×10 mL) and the organic layers are combined, dried and concentrated to give the crude product. Purification by the flash column chromatography affords 534 mg of 6-(5-bromo-pyridin-3-yl)-3,4-dihydro-2H-[1,8]naphthyridine-1-carboxylic acid tert-butyl ester 6-(5-Bromo-pyridin-3-yl)-3,4-dihydro-2H-[1,8]naphthyridine-1-carboxylic acid tert-butyl ester (260 mg, 0.67 mmol) is dissolved in 3.0 mL of DCM and trifluoroacetic acid (1.0 mL, 12 mmol) is added. The mixture is stirred for 21 hrs. Then saturated aqueous NaHCO$_3$ is used to adjust the pH to about 8 and EtOAc (25 mL) along with 15 mL of water are added. The mixture is stirred for 10 min and the aqueous layer is separated and extracted with EtOAc (2×15 ml). The organic layers are combined and concentrated to give 6-(5-bromo-pyridin-3-yl)-1,2,3,4-tetrahydro-[1,8]naphthyridine which is used in the next step without puification.

6-(5-Bromo-pyridin-3-yl)-1,2,3,4-tetrahydro-[1,8]naphthyridine (190 mg, 0.67 mmol) and benzoyl isocyanate (220 mg, 1.3 mmol) are mixed in 3.0 mL of DCM and the mixture is stirred at 50° C. for 2 hrs and room temperature for 16 hrs. Then the solvent is removed and the residue is suspended in 3.0 mL of EtOH. K$_2$CO$_3$ (160 mg, 1.1 mmol) is added and the mixture is heated at 70° C. for 30 min. Then the solvent is removed and the residue is partitioned between water (20 mL) and EtOAc (50 mL). The aqueous layer is separated and extracted with DCM (2×50 mL). The organic layers are combined and concentrated to give the crude product. To the crude product is added EtOAc (10 mL) and the solid formed is filtered, washed again with EtOAc (2×10 mL) and dried to give 158 mg of 6-(5-bromo-pyridin-3-yl)-3,4-dihydro-2H-[1,8]naphthyridine-1-carboxylic acid amide.

6-(5-Bromo-pyridin-3-yl)-3,4-dihydro-2H-[1,8]naphthyridine-1-carboxylic acid amide (50 mg, 0.15 mmol), 4-fluorophenylboronic acid (42 mg, 0.30 mmol) and 2.0 M Na$_2$CO$_3$ aqueous solution (0.15 mL, 0.30 mmol) are dissolved in 2.0 mL of 1,4-dioxane. The Argon gas is bubbled through the solution for 5 min. Then PdCl$_2$dppf (7.7 mg, 0.011 mmol) is added. The mixture is heated at 100° C. for 2 hrs before it is cooled down to room temperature. Then 30 mL of DCM and 20 mL of water are added. The organic layer is separated and the aqueous layer is extracted with DCM (2×20 mL). All the organic layers are combined, dried and concentrated to give crude product. Purification by flash column chromatography followed by washing with EtOAc (2×1 mL) affords 35 mg of the titled product.

Compounds 32 and 38 in Table 1 are synthesized according to the procedure for Example 15, substituting either commercially available reagents or the appropriate intermediates described above.

Example 16

Synthesis of 6-[5-Fluoro-4-((R)-1-hydroxy-ethyl)-pyridin-3-yl]-3,4-dihydro-2H-[1,8]naphthyridine-1-carboxylic acid amide (Cpd 33, Table 1)

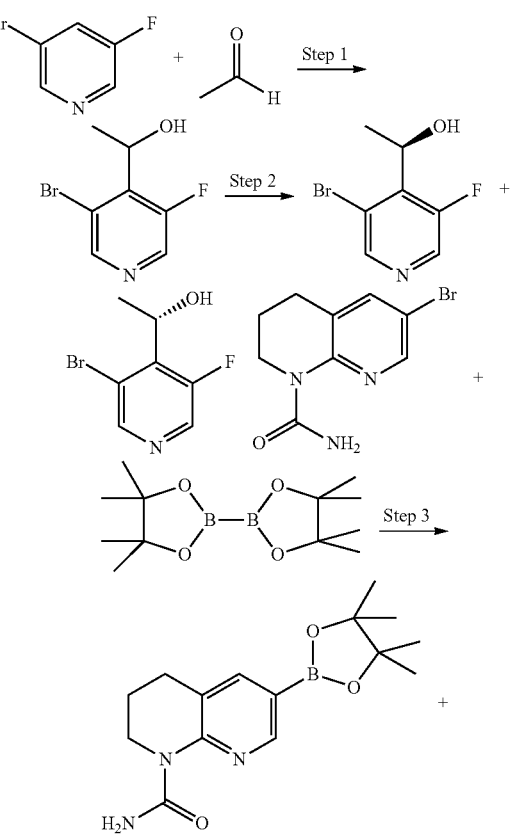

-continued

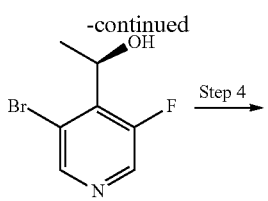

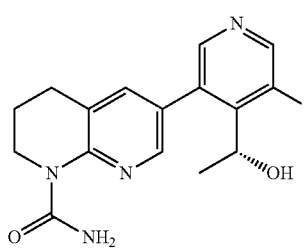
33

3-Bromo-5-fluoro-pyridine (13 g, 74 mmol) is dissolved in 140 mL of dry THF and cooled down to −78° C. LDA solution (44 mL, 2.0 M in THF, 88 mmol) is added and the mixture is stirred for 2 hrs at −78° C. Then acetaldehyde solution (30 mL, 5.0 M in THF, 150 mmol) is added at −78° C. and the reaction is continued for another 30 min. Then saturated aqueous NH$_4$Cl solution (200 mL) is added and the mixture is warmed up to room temperature. EtOAc (100 mL) is added along with 75 mL of water. The aqueous layer is separated and extracted with EtOAc (2×75 mL). The organic layers are combined and concentrated to give the crude product. Purification by flash column chromatography affords 14 g of the racemic product. Chiral separation of the racemic product using supercritical fluid chromatography affords 6.5 g of (R)-1-(3-bromo-5-fluoro-pyridin-4-yl)-ethanol and 6.4 g of (S)-1-(3-bromo-5-fluoro-pyridin-4-yl)-ethanol.

6-Bromo-3,4-dihydro-2H-[1,8]naphthyridine-1-carboxylic acid amide (4.0 g, 16 mmol), bis(pinacolato)diboron (6.6 g, 26 mmol), KOAc (7.0 g, 71 mmol) and 1,1'-bis(diphenylphosphino)ferrocene (dppf) (700 mg, 1.3 mmol) are added into 140 mL of 1,4-dioxane. The Argon gas is bubbled through the solution for 5 min. Then PdCl$_2$dppf (920 mg, 1.3 mmol) is added. The mixture is heated at 100° C. for 3.5 hrs and 85° C. for 16 hrs. After the mixture is cooled down to room temperature, 6-(4,4,5,5-tetramethyl-[1,3,2]dioxaborolan-2-yl)-3,4-dihydro-2H-[1,8]naphthyridine-1-carboxylic acid amide is used in the next step without purification.

(R)-1-(3-Bromo-5-fluoro-pyridin-4-yl)-ethanol (5.2 g, 24 mmol) and 2.0 M Na$_2$CO$_3$ aqueous solution (16 mL, 32 mmol) are added into the reaction mixture from previous step. The Argon gas is bubbled through the solution for 5 min. Then PdCl$_2$dppf (920 mg, 1.3 mmol) is added. The mixture is heated at 95° C. for 3.5 hrs and then EtOAc (250 mL) and water (100 mL) are added. The mixture is filtered off the solid. The aqueous layer is separated and extracted with EtOAc (2×75 mL). The organic layers are combined and concentrated to give the crude product. Purification by flash column chromatography affords 1.5 g of 6-[5-fluoro-4-((R)-1-hydroxy-ethyl)-pyridin-3-yl]-3,4-dihydro-2H-[1,8]naphthyridine-1-carboxylic acid amide.

Compound 34 in Table 1 is synthesized according to the procedure described above using the (S)-1-(3-bromo-5-fluoro-pyridin-4-yl)-ethanol described above.

Example 17

Synthesis of 6-[4-(4-fluoro-phenyl)-pyridin-3-yl]-3,4-dihydro-2H-[1,8]naphthyridine-1-carboxylic acid amide (Cpd 35, Table 1)

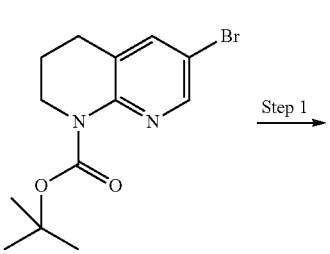

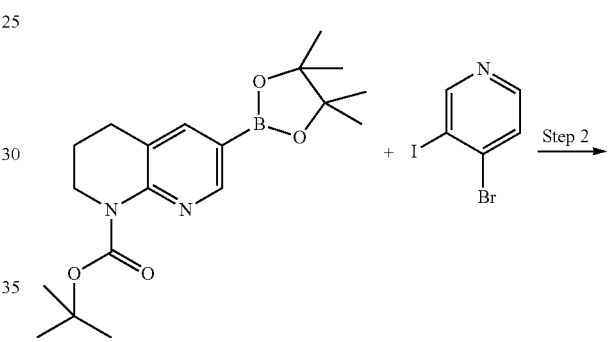

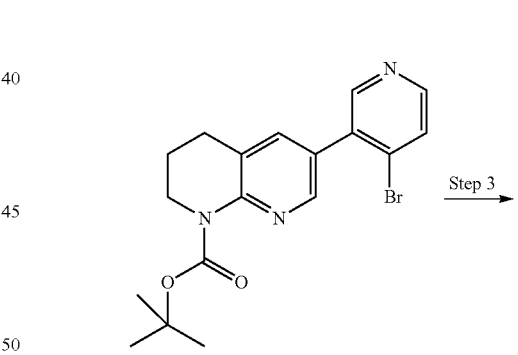

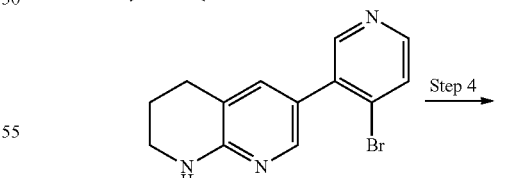

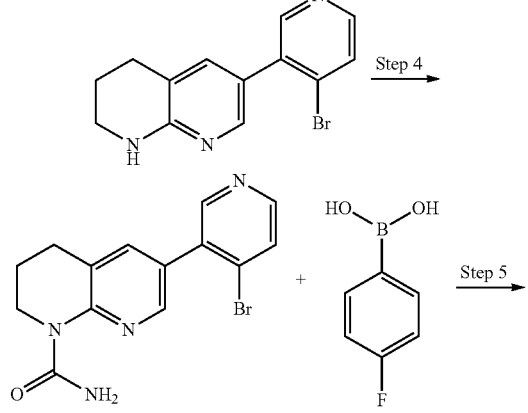

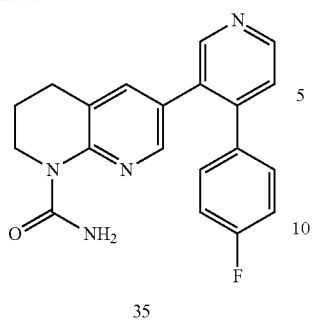

35

6-(4-Bromo-pyridin-3-yl)-3,4-dihydro-2H-[1,8]naphthyridine-1-carboxylic acid amide is synthesized using the same procedures for preparing 6-(5-bromo-pyridin-3-yl)-3,4-dihydro-2H-[1,8]naphthyridine-1-carboxylic acid amide in Example 15, replacing 3,5-dibromo-pyridine with 4-bromo-3-iodo-pyridine.

6-(4-Bromo-pyridin-3-yl)-3,4-dihydro-2H-[1,8]naphthyridine-1-carboxylic acid amide (50 mg, 0.15 mmol), 4-fluorophenylboronic acid (42 mg, 0.30 mmol) and 2.0 M $Na_2CO_3$ aqueous solution (0.15 mL, 0.30 mmol) are dissolved in 1.0 mL of 1,4-dioxane. The Argon gas is bubbled through the solution for 5 min. Then $PdCl_2dppf$ (7.7 mg, 0.011 mmol) is added. The mixture is heated at 100° C. for 3.5 hrs and then it is cooled down to room temperature. 30 mL of DCM and 20 mL of water are added and the organic layer is separated. The aqueous layer is extracted with DCM (2×20 mL) and all the organic layers are combined, dried and concentrated to give crude product. Purification by flash column chromatography affords 39 mg of the titled compound.

Compounds 36 and 37 in Table 1 are synthesized according to the procedure for Example 17, substituting either commercially available reagents or the appropriate intermediates described above.

Example 18

Synthesis of 6-(5-Carbamoyl-pyridin-3-yl)-3,4-dihydro-2H-[1,8]naphthyridine-1-carboxylic acid amide (Cpd 39, Table 1)

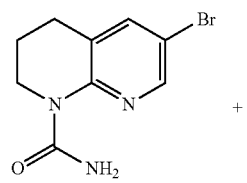

+

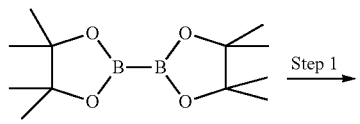

Step 1

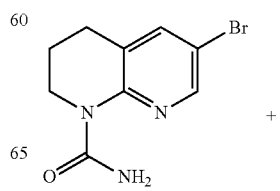

+

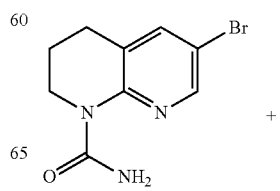

Step 2

39

6-Bromo-3,4-dihydro-2H-[1,8]naphthyridine-1-carboxylic acid amide (50 mg, 0.20 mmol) is converted to 6-(4,4,5,5-tetramethyl-[1,3,2]dioxaborolan-2-yl)-3,4-dihydro-2H-[1,8]naphthyridine-1-carboxylic acid amide using the same procedure for step 3 in Example 16. The reaction crude is used in the next step without purification.

5-Bromo-nicotinamide (81 mg, 0.39 mmol) and 2.0 M $Na_2CO_3$ aqueous solution (0.20 mL, 0.40 mmol) are added into the reaction solution from the previous step. The Argon gas is bubbled through the solution for 5 min. Then $PdCl_2dppf$ (7.2 mg, 0.010 mmol) is added. The mixture is heated at 100° C. for 3.5 hrs and all the solvents are removed. To the residue are added DCM (30 mL) and MeOH (10 mL). The mixture is stirred for 10 min and the solid is filtered. The filtrate is concentrated to give the crude product. Purification by flash column chromatography affords 11 mg of the titled product.

Compound 11 in Table 1 is synthesized according to the procedure for Example 18, substituting either commercially available reagents or the appropriate intermediates described above.

Example 19

Synthesis of 6-[5-(Acetylamino-methyl)-pyridin-3-yl]-3,4-dihydro-2H-[1,8]naphthyridine-1-carboxylic acid amide (Cpd 40, Table 1)

149

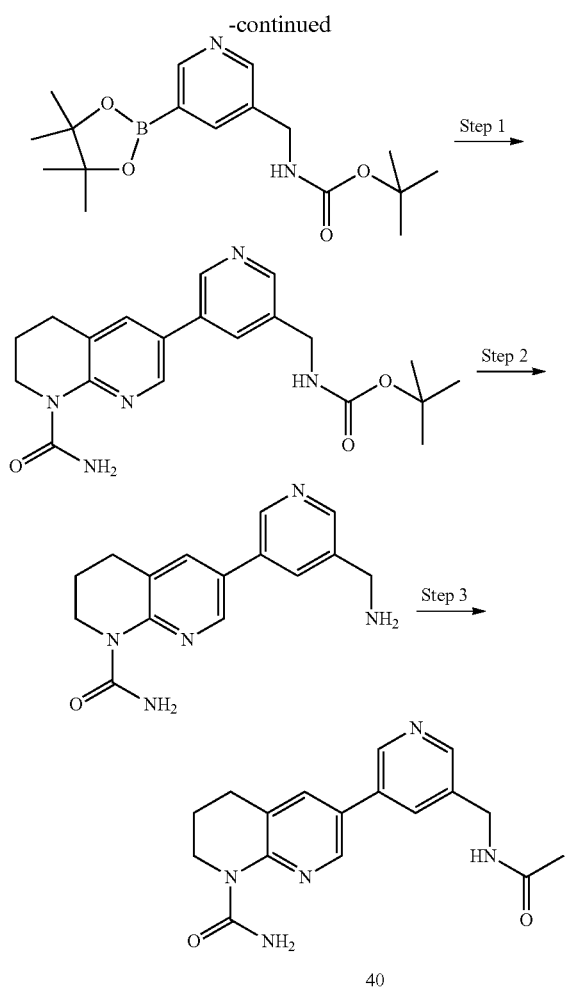

6-Bromo-3,4-dihydro-2H-[1,8]naphthyridine-1-carboxylic acid amide (79 mg, 0.31 mmol), [5-(4,4,5,5-tetramethyl-[1,3,2]dioxaborolan-2-yl)-pyridin-3-ylmethyl]-carbamic acid tert-butyl ester (205 mg, 0.61 mmol) and 2.0 M $Na_2CO_3$ aqueous solution (0.31 mL, 0.61 mmol) are dissolved in 2.0 mL of 1,4-dioxane. Argon gas is bubbled through the solution for 5 min. Then $PdCl_2dppf$ (16 mg, 0.021 mmol) is added. The mixture is heated at 100° C. for 2 hrs and the mixture is cooled down to room temperature. Then 30 mL of EtOAc and 20 mL of water are added and the organic layer is separated. The aqueous layer is extracted with EtOAc (2×20 mL). The organic layers are combined, dried and concentrated to give the crude product. Purification by flash column chromatography affords 112 mg of [5-(8-carbamoyl-5,6,7,8-tetrahydro-[1,8]naphthyridin-3-yl)-pyridin-3-ylmethyl]-carbamic acid tert-butyl ester

[5-(8-Carbamoyl-5,6,7,8-tetrahydro-[1,8]naphthyridin-3-yl)-pyridin-3-ylmethyl]-carbamic acid tert-butyl ester (100 mg, 0.26 mmol) is dissolved in 5.0 mL of DCM and trifluoroacetic acid (0.5 mL) is added. The mixture is stirred for 1 hr and the solvent is removed in vacuo. The residue is dissolved in MeOH and filtered through a StratoSpheres SPE cartridge (PL-HCO$_3$ MP SPE) to remove the acid. The filtrate is then concentrated to give 75 mg of 6-(5-aminomethyl-pyridin-3-yl)-3,4-dihydro-2H-[1,8]naphthyridine-1-carboxylic acid amide which is used in the next step without purification.

6-(5-Aminomethyl-pyridin-3-yl)-3,4-dihydro-2H-[1,8] naphthyridine-1-carboxylic acid amide (38 mg, 0.13 mmol),

150 acetic acid (0.015 mL, 0.27 mmol) and triethyl amine (0.056 mL, 0.40 mmol) are mixed in 2.5 mL of acetonitrile. Then TBTU (52 mg, 0.16 mmol) is added and the mixture is stirred for 1 hrs. All the solvents are removed and the residue is first purified by flash column chromatography and then filtered through a StratoSpheres SPE cartridge (PL-HCO$_3$ MP SPE) to remove the HOBt. The filtrate is concentrated and dried to give 38 mg of the titled product.

Compounds 208 and 216 in Table 1 are synthesized according to the procedure for Example 19, substituting either commercially available reagents or the appropriate intermediates described above.

Example 20

Synthesis of 6-[5-(Ethanesulfonylamino-methyl)-pyridin-3-yl]-3,4-dihydro-2H-[1,8]naphthyridine-1-carboxylic acid amide (Cpd 41, Table 1)

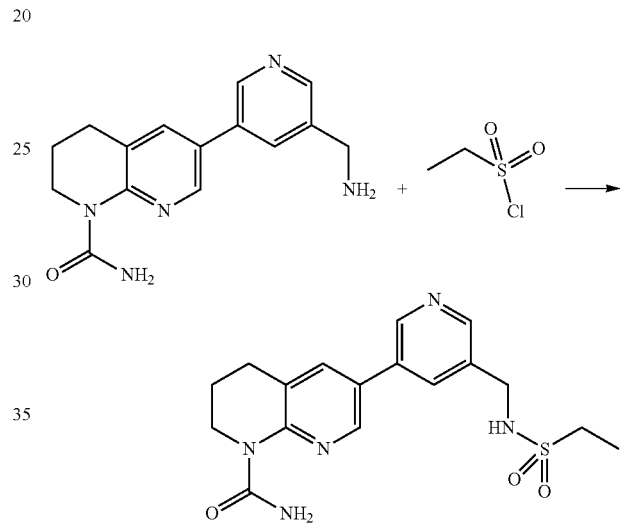

6-(5-Aminomethyl-pyridin-3-yl)-3,4-dihydro-2H-[1,8] naphthyridine-1-carboxylic acid amide (38 mg, 0.13 mmol), which is prepared according to the procedures for Step 1 and Step 2 of Example 19, is dissolved in 2.0 mL of DCM. Ethanesulfonyl chloride (0.013 mL, 0.14 mmol) is added followed by the addition of triethyl amine (0.035 mL, 0.25 mmol). The mixture is stirred for 1 hr and the solvent is removed. The residue is purified by flash column chromatography to give 33 mg of the titled product.

Example 21

Synthesis of 6-(5-Hydroxymethyl-pyridin-3-yl)-3,4-dihydro-2H-[1,8]naphthyridine-1-carboxylic acid amide (Cpd 42, Table 1)

-continued

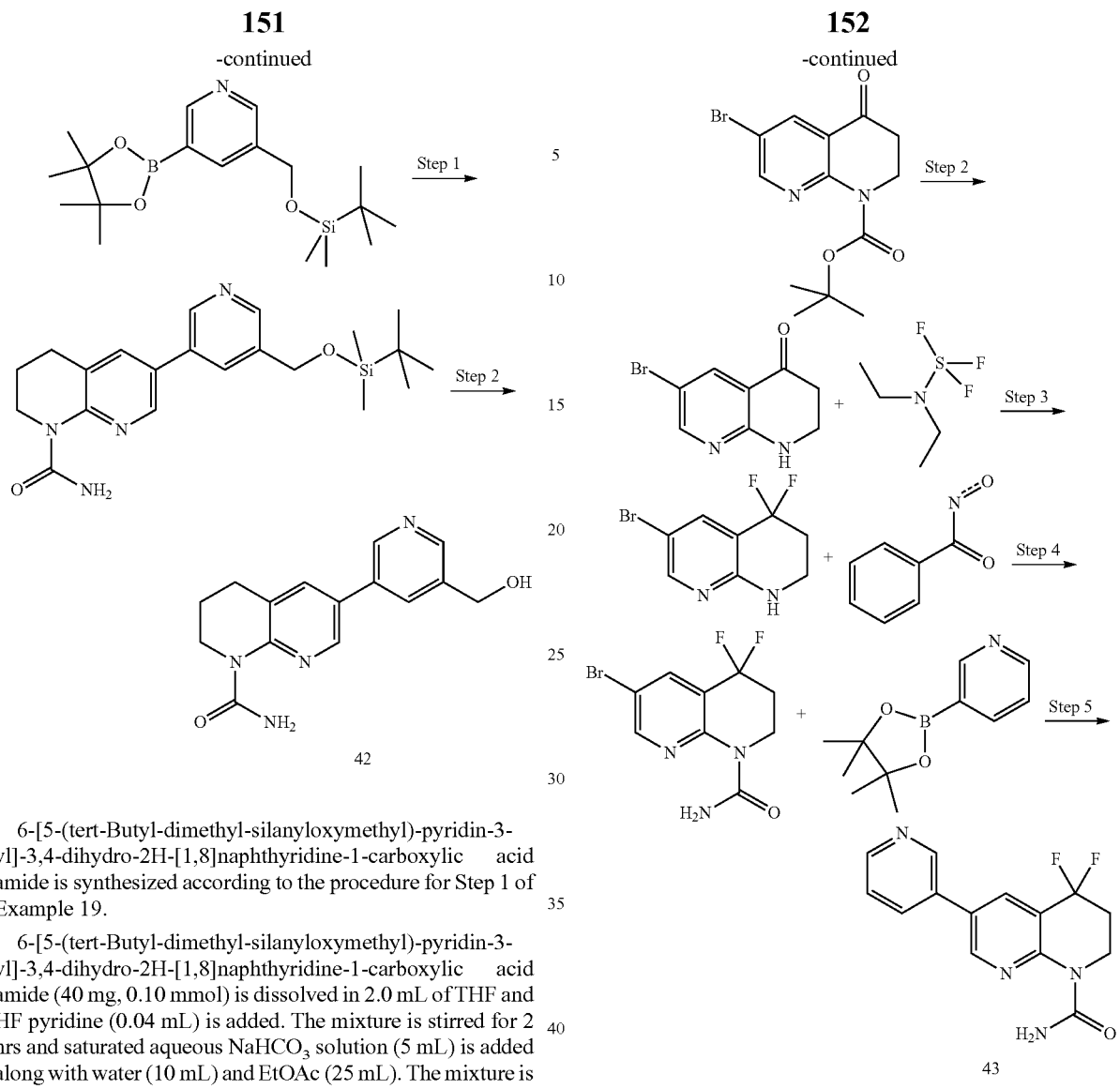

6-[5-(tert-Butyl-dimethyl-silanyloxymethyl)-pyridin-3-yl]-3,4-dihydro-2H-[1,8]naphthyridine-1-carboxylic acid amide is synthesized according to the procedure for Step 1 of Example 19.

6-[5-(tert-Butyl-dimethyl-silanyloxymethyl)-pyridin-3-yl]-3,4-dihydro-2H-[1,8]naphthyridine-1-carboxylic acid amide (40 mg, 0.10 mmol) is dissolved in 2.0 mL of THF and HF pyridine (0.04 mL) is added. The mixture is stirred for 2 hrs and saturated aqueous NaHCO₃ solution (5 mL) is added along with water (10 mL) and EtOAc (25 mL). The mixture is stirred for 10 min and the aqueous layer is separated, extracted with EtOAc (2×10 mL). The organic layers are combined and concentrated to give the crude product. Purification by flash column chromatography affords 26 mg of the titled product.

Example 22

Synthesis of 4,4-Difluoro-6-pyridin-3-yl-3,4-dihydro-2H-[1,8]naphthyridine-1-carboxylic acid amide (Cpd 43, Table 1)

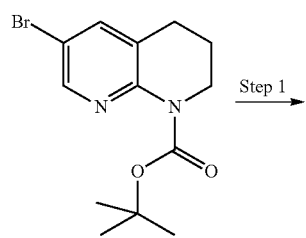

A mixture of 6-bromo-3,4-dihydro-2H-[1,8]naphthyridine-1-carboxylic acid tert-butyl ester (2.16 g, 6.90 mmol) and NaH₂PO₄ (2.38 g, 17.2 mmol) in t-butanol and water (1:1 mixture, 300 mL) is heated to 50° C. and NaMnO₄ (11.4 g, 32.2 mmol) solution (aq.) is added. The mixture is heated for 2 hrs. The reaction mixture is cooled and solid Na₂SO₃ is added until the purple color disappears. 50 mL of EtOAc and 50 mL of water are added and the mixture is filtered through diatomaceous earth to remove the black solid. The aqueous layer of the filtrate is separated and extracted with 2×100 mL of EtOAc. The organic layers are combined dried with MgSO₄ and concentrated to give the crude product. The product is dissolved into CH₂Cl₂ and purified via silica chromatography to give 1.09 g 6-bromo-4-oxo-3,4-dihydro-2H-[1,8]naphthyridine-1-carboxylic acid tert-butyl ester.

6-Bromo-4-oxo-3,4-dihydro-2H-[1,8]naphthyridine-1-carboxylic acid tert-butyl ester (628 mg, 1.92 mmol) is dissolved into 3 mL of MeOH and 3 mL of 4 M HCl/1,4-dioxane is added. The mixture is stirred for 16 h and concentrated to dryness. The residue is dissolved into 10 mL CH₂Cl₂ and 10 mL of H₂O and neutralized with saturated aqueous Na₂CO₃ solution. The aqueous layer is extracted with 2×20 mL of CH₂Cl₂. The organic phase is dried with MgSO₄, filtered and concentrated to give 386 mg of 6-bromo-2,3-dihydro-1H-[1,8]naphthyridin-4-one The 6-bromo-2,3-dihydro-1H-[1,8]naphthyridin-4-one (82.8 mg, 0.36 mmol) is dissolved into 1 mL of CH$_2$Cl$_2$ and 5 mL of diethylamino sulfur trifluoride. The mixture is stirred for 4.5 days. The mixture is quenched by slow addition of the mixture to ice. The solution is neutralized with the slow addition of saturated aqueous NaHCO$_3$. This is diluted with 50 mL EtOAc, washed with 2×20 mL of H$_2$O and 1×20 mL of brine. The organic phase is dried with MgSO$_4$, filtered and concentrated. The crude material is applied to a silica preparative TLC plate and eluted with 70% EtOAc/hexanes to give 86.2 mg of 6-bromo-4,4-difluoro-1,2,3,4-tetrahydro-[1,8]naphthyridine A mixture of 6-bromo-4,4-difluoro-1,2,3,4-tetrahydro-[1,8]naphthyridine (86.2 mg, 0.35 mmol) and benzoyl isocyanate (85.9 mg, 0.51 mmol, 90%) in 5 mL CH$_2$Cl$_2$ is heated at 50° C. for 2 hrs. The mixture is concentrated the dryness. The residue is dissolved into 5 mL of EtOH, K$_2$CO$_3$ (81.2 mg, 0.59 mmol) is added and the mixture is heated at 50° C. for 2 h. The mixture is concentrated to dryness. The residue is dissolved into 20 ml of H$_2$O and neutralized by the addition of AcOH. This is extracted with 60 mL EtOAc, washed with 2×20 mL of H$_2$O and 1×20 mL of brine. The organic phase is dried with MgSO$_4$, filtered and concentrated. The residue is applied to a silica preparative TLC plate and eluted (75% EtOAc/hexanes) to give 89.6 mg of 6-bromo-4,4-difluoro-3,4-dihydro-2H-[1,8]naphthyridine-1-carboxylic acid amide A mixture of 6-bromo-4,4-difluoro-3,4-dihydro-2H [1,8] naphthyridine-1-carboxylic acid amide (89.6 mg, 0.31 mmol), 3-(4,4,5,5-tetramethyl-[1,3,2]dioxaborolan-2-yl)-pyridine (92.3 mg, 0.46 mmol), K$_2$CO$_3$ (105 mg, 0.77 mmol) and bis(di-tert-butyl(4-dimethylaminophenyl)phosphine) dichloropalladium (II) (21.8 mg, 0.03 mmol) in 1 mL dioxane/water (9:1) is heated at 100° C. for 2 hrs. 30 mL of EtOAc is added. The mixture is washed with 2×10 mL of NaHCO$_3$ and 1×10 mL brine. The organic phase is dried with MgSO$_4$, filtered and concentrated. The residue is applied to a silica preparative TLC plate and purified (10% MeOH/CH$_2$Cl$_2$) to give 39.9 mg of the titled product.

Example 23

Synthesis of 4-Hydroxy-6-pyridin-3-yl-3,4-dihydro-2H-[1,8]naphthyridine-1-carboxylic acid amide (Cpd 44, Table 1)

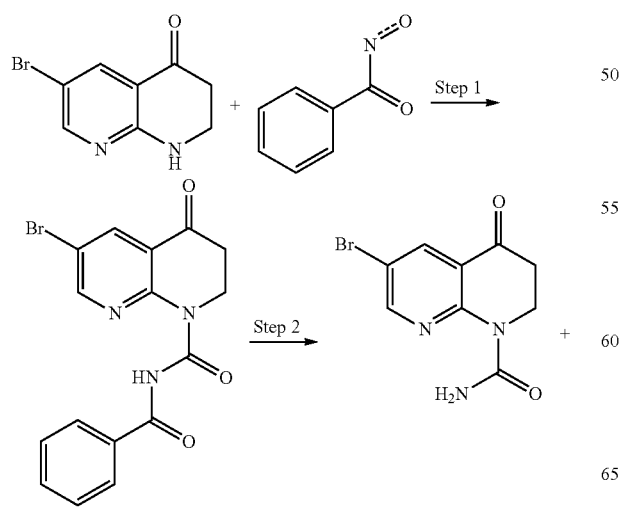

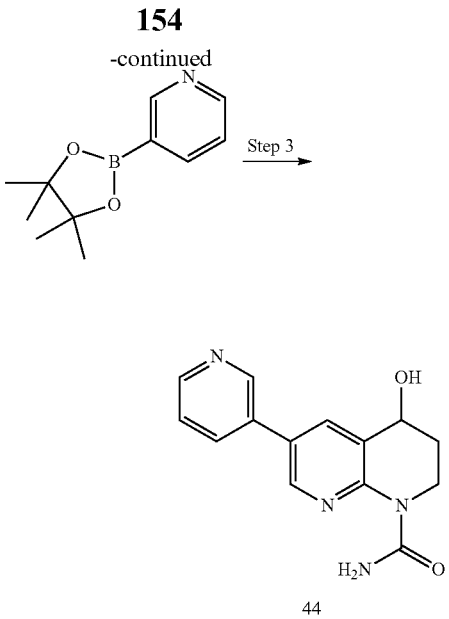

A mixture of 6-bromo-4-oxo-3,4-dihydro-2H-[1,8]naphthyridine-1-carboxylic acid tert-butyl ester (228 mg, 1.00 mmol) and benzoyl isocyanate (207 mg, 1.41 mmol, 90%) in 5 mL CH$_2$Cl$_2$ is heated at 50° C. for 2 hrs. The mixture is concentrated to give 375 mg of N-(6-bromo-4-oxo-3,4-dihydro-2H-[1,8]naphthyridine-1-carbonyl)-benzamide which is carried on without purification.

To the N-(6-bromo-4-oxo-3,4-dihydro-2H-[1,8]naphthyridine-1-carbonyl)-benzamide (188 mg, 0.50 mmol) in 2 mL of MeOH is added NaBH$_4$ (38.0 mg, 1.00 mmol) in one portion. The mixture is stirred for 30 min. and concentrated to dryness. The residue is dissolved in 40 mL EtOAc/H$_2$O, diluted with 10 mL EtOAc and quenched with 20 mL of saturated aqueous NH$_4$Cl. The organic phase is washed with 2×20 mL of H$_2$O and 1×20 mL of brine, dried with MgSO$_4$, filtered and concentrated. The crude material is applied to a silica preparative TLC plate and eluted with 100% EtOAc to give 81.5 mg of 6-bromo-4-hydroxy-3,4-dihydro-2H-[1,8] naphthyridine-1-carboxylic acid amide. This is converted to the titled product using the procedure of Step 5 of Example 22.

Example 24

Synthesis of 6-[5-(3,6-Dihydro-2H-pyran-4-yl)-pyridin-3-yl]-3,4-dihydro-2H-[1,8]naphthyridine-1-carboxylic acid amide (Cpd 45, Table 1)

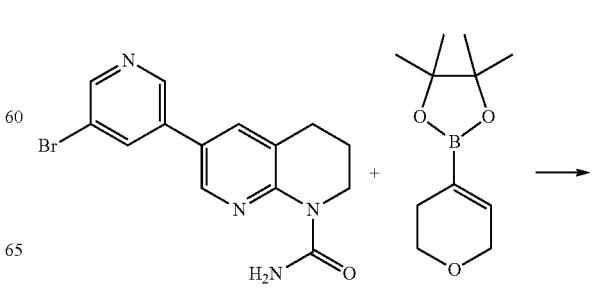

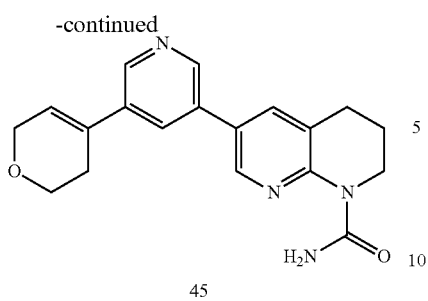
45

6-(5-Bromo-pyridin-3-yl)-3,4-dihydro-2H-[1,8]naphthyridine-1-carboxylic acid amide (100 mg, 0.30 mmol, which is prepared according to the procedure for Step 1 to Step 4 of Example 15) is dissolved into 2 mL of dioxane/water (9:1). 4-(4,4,5,5-Tetramethyl-[1,3,2]dioxaborolan-2-yl)-3,6-dihydro-2H-pyran (94.6 mg, 0.45 mmol), K$_3$PO$_4$ (318 mg, 1.50 mmol) and PdCl$_2$(DPPF)CH$_2$Cl$_2$ (24.5 mg, 0.03 mmol) are added. The mixture is heated at 100° C. for 48 hrs. The mixture is diluted with 100 mL EtOAc and quenched with 100 mL of saturated aqueous NH$_4$Cl. The organic phase is washed with 2×20 mL of H$_2$O and 1×20 mL of brine. The organic phase is dried with MgSO$_4$, filtered and concentrated. The crude material is applied to a silica preparative TLC plate and purified twice to give 52.1 mg of the titled product.

Compounds 46 and 47 in Table 1 are synthesized according to the procedure for Example 24, substituting either commercially available reagents or the appropriate intermediates described above.

Example 25

Synthesis of 6-[5-(Tetrahydro-pyran-4-yl)-pyridin-3-yl]-3,4-dihydro-2H-[1,8]naphthyridine-1-carboxylic acid amide (Cpd 48, Table 1)

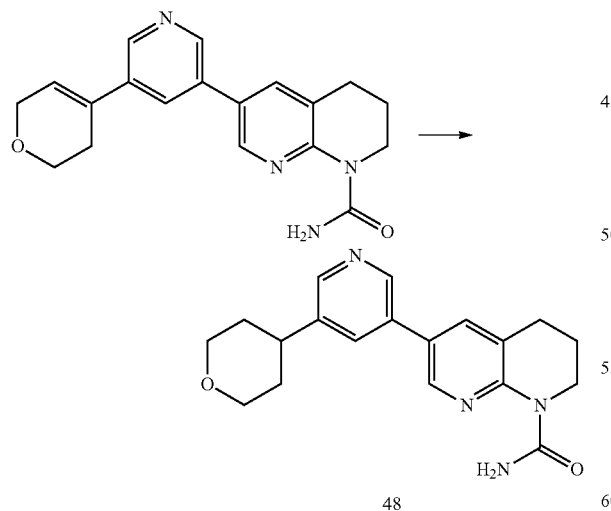

To a mixture of 6-[5-(3,6-dihydro-2H-pyran-4-yl)-pyridin-3-yl]-3,4-dihydro-2H-[1,8]naphthyridine-1-carboxylic acid amide (42.0 mg, 0.13 mmol) and 10% Pd/C (42 mg) under Argon is added 2 mL of MeOH. Then ammonium formate (10 eq) is as added and the mixture stirred for 26 hrs at 80° C. The mixture is filtered, concentrated and purified by Preparative HPLC system (10%-80% CH$_3$CN/H2O) to give 31.1 mg of the titled product.

Example 26

Synthesis of 3-(5-Trifluoromethyl-pyridin-3-yl)-7,8-dihydro-5H-6-oxa-1,9-diaza-benzocycloheptene-9-carboxylic acid amide (Cpd 49, Table 1)

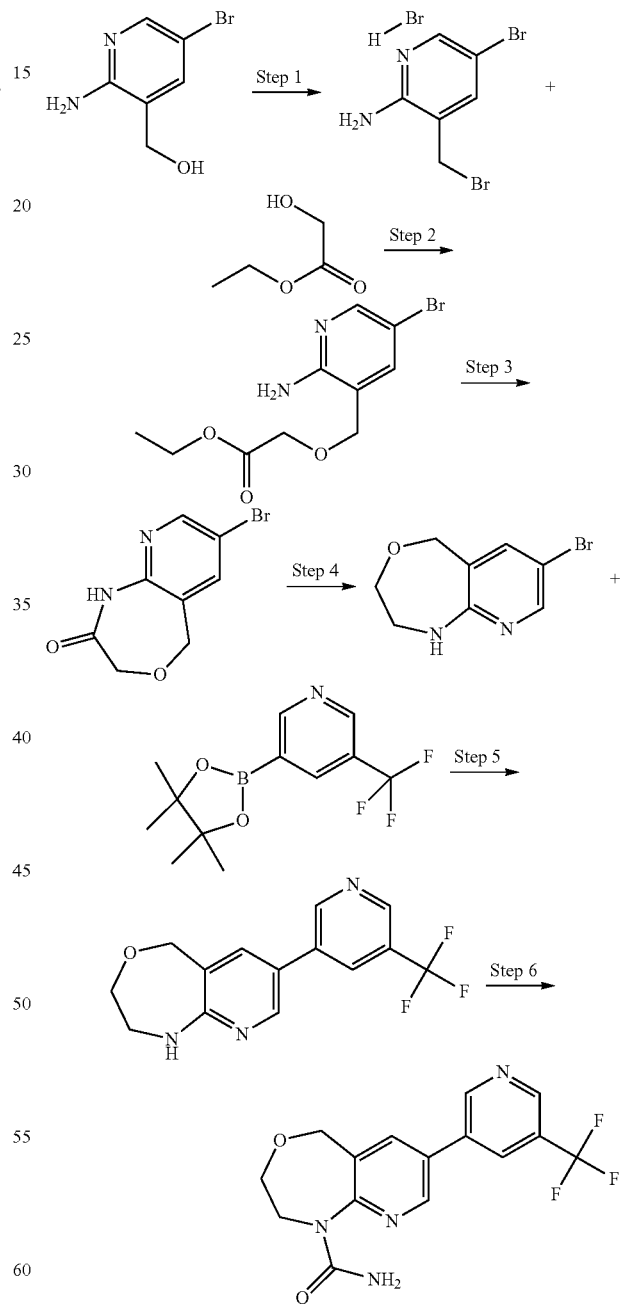

(2-Amino-5-bromo-pyridin-3-yl)-methanol (360 mg, 1.8 mmol) is dissolved in 1.0 mL of 48% HBr aqueous solution. The mixture is heated at 100° C. for 16 hrs. Then the majority of the water is removed in vacuo and toluene is added to remove the water left. The residue is concentrated to give the crude 5-bromo-3-bromomethyl-pyridin-2-ylamine hydrobromide which is used directly in the next step.

Hydroxy acetic acid ethyl ester (294 mg, 2.8 mmol) is dissolved in 5.0 mL of DMF and 60% sodium hydride (113 mg, 2.8 mmol) is added at 0° C. The mixture is stirred for 15 min and 5-bromo-3-bromomethyl-pyridin-2-ylamine hydrobromide (392 mg, 1.1 mmol) is added. The mixture is warmed up to room temperature for 2.5 hr. Then water (15 mL) is added along with EtOAc (30 mL). The mixture is stirred for 10 min and the aqueous layer is separated and extracted with EtOAc (2×20 mL). The organic layers are combined and concentrated to give (2-amino-5-bromo-pyridin-3-yl-methoxy)-acetic acid ethyl ester.

(2-Amino-5-bromo-pyridin-3-ylmethoxy)-acetic acid ethyl ester (381 mg, 1.3 mmol) is dissolved in 15 mL of DMSO and 60% sodium hydride (53 mg, 1.3 mmol) is added. The mixture is stirred for 4 hrs and then ice-cold water (100 mL) is added into reaction. The solid formed is filtered and rinsed with more water (2×50 mL) and 50% EtOAc in heptane (30 mL). Then it is dried to give 205 mg of 3-bromo-5,9-dihydro-6-oxa-1,9-diaza-benzocyclohepten-8-one which is used without purification.

3-Bromo-5,9-dihydro-6-oxa-1,9-diaza-benzocyclohepten-8-one (205 mg, 0.84 mmol) and sodium borohydride (160 mg, 4.2 mmol) are dissolved in 1.0 mL of THF and the mixture is cooled down to 0° C. Neat $BF_3$ $Et_2O$ (0.74 mL, 5.9 mmol) is added dropwise and the mixture is stirred for 3 hr at room temperature. Then saturated aqueous $NH_4Cl$ solution (15 mL) is added carefully and the mixture is further basified by adding solid $NaHCO_3$. The mixture is then extracted with EtOAc (3×35 mL). The organic layers are combined and concentrated to give the crude product. Purification by flash column chromatography affords 78 mg of 3-bromo-5,7,8,9-tetrahydro-6-oxa-1,9-diaza-benzocycloheptene 3-Bromo-5,7,8,9-tetrahydro-6-oxa-1,9-diaza-benzocycloheptene (78 mg, 0.34 mmol), 3-(4,4,5,5-tetramethyl-[1,3,2]dioxaborolan-2-yl)-5-trifluoromethyl-pyridine (190 mg, 0.68 mmol) and $K_2CO_3$ (94 mg, 0.68 mmol) are mixed in 5.0 mL of 1,4-dioxane and 0.50 mL of water. Argon gas is bubbled through the mixture for 10 min and bis(di-tert-butyl(4-dimethylaminophenyl)phosphine)dichloropalladium (II) (24 mg, 0.034 mmol) is added. The mixture is heated at 100° C. for 5 hrs. Then EtOAc (25 mL) is added along with 20 mL of water. The mixture is stirred for 10 min and the organic layer is separated. The aqueous layer is extracted with EtOAc (2×25 mL) and the organic layers are combined and concentrated to give the crude product. Purification by flash column chromatography affords 96 mg of 3-(5-trifluoromethyl-pyridin-3-yl)-5,7,8,9-tetrahydro-6-oxa-1,9-diaza-benzocycloheptene 3-(5-Trifluoromethyl-pyridin-3-yl)-5,7,8,9-tetrahydro-6-oxa-1,9-diaza-benzocycloheptene (96 mg, 0.33 mmol) and benzoyl isocyanate (80 mg, 0.49 mmol) are mixed in 2.0 mL of DCM and the mixture is heated at 50° C. for 16 hrs. Then the solvent is removed and the residue is dissolved in 2.0 mL of EtOH. $K_2CO_3$ (76 mg, 0.55 mmol) is added and the mixture is heated at 80° C. for 2 hrs. Then the solvent is removed and the residue is partitioned between water (25 mL) and EtOAc (35 mL). The aqueous layer is separated and extracted with EtOAc (2×30 mL). The organic layers are combined and concentrated to give the crude product. Purification by flash column chromatography followed by washing with 2.0 mL of EtOAc affords 47 mg of the titled product.

Example 27

Synthesis of 6-(4-Methoxy-pyridin-3-yl)-3,4-dihydro-2H-[1,8]naphthyridine-1-carboxylic acid amide (Cpd 50, Table 1)

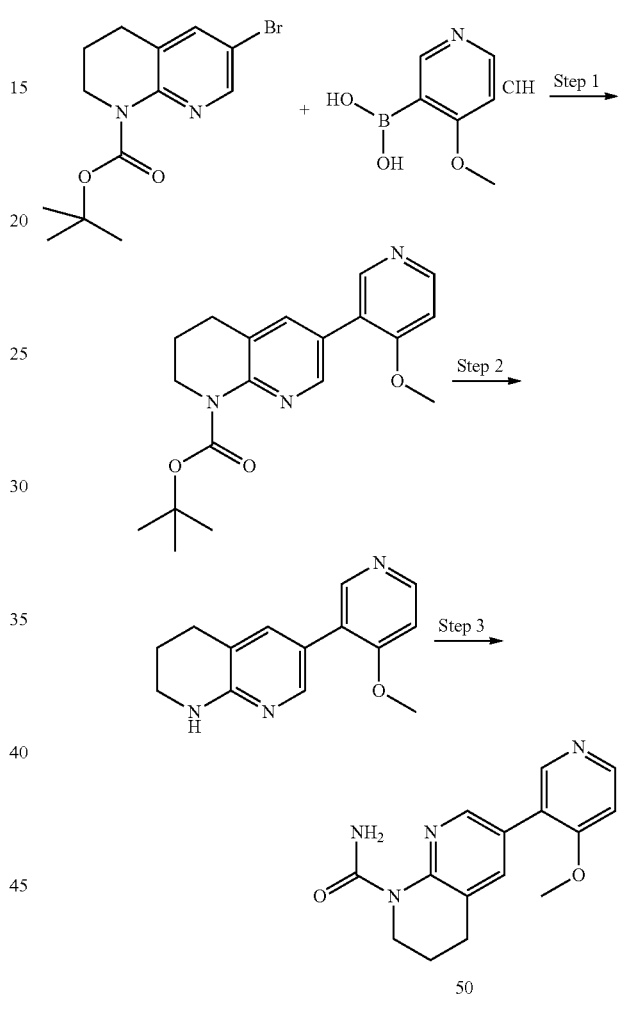

6-(4-Methoxy-pyridin-3-yl)-3,4-dihydro-2H-[1,8]naphthyridine-1-carboxylic acid tert-butyl ester is synthesized according to the procedure of Suzuki Coupling Method III, as illustrated above.

6-(4-Methoxy-pyridin-3-yl)-3,4-dihydro-2H-[1,8]naphthyridine-1-carboxylic acid tert-butyl ester (420 mg, 1.2 mmol) is dissolved in 20% trifluoroacetic acid in DCM (20 mL). The solution is stirred at room temperature for 16 hrs and then the solvent is removed. The residue is dissolved in DCM and saturated aqueous $NaHCO_3$ solution is used to adjust the pH to 9~10. The organic layer is separated, dried over $Na_2SO_4$, filtered and concentrated to give 290 mg of 6-(4-methoxy-pyridin-3-yl)-1,2,3,4-tetrahydro-[1,8]naphthyridine (290 mg crude) which is converted to 38 mg of the titled product according to the procedure of Urea Formation Method I.

Example 28

Synthesis of 3-(8-Carbamoyl-5,6,7,8-tetrahydro-[1,8]naphthyridin-3-yl)-isonicotinic acid methyl ester (Cpd 51, Table 1)

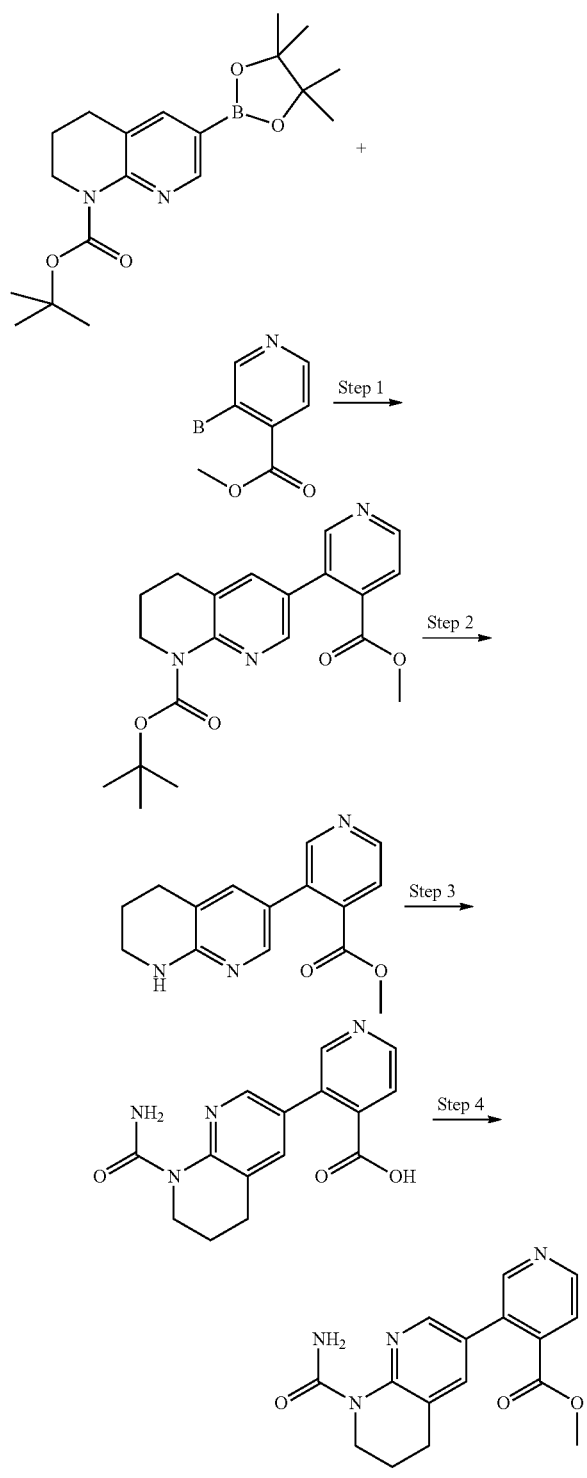

6-(4-Methoxycarbonyl-pyridin-3-yl)-3,4-dihydro-2H-[1,8]naphthyridine-1-carboxylic acid tert-butyl ester is synthesized according to the procedure of Suzuki Coupling Method IV, as illustrated above.

6-(4-Methoxycarbonyl-pyridin-3-yl)-3,4-dihydro-2H-[1,8]naphthyridine-1-carboxylic acid tert-butyl ester (400 mg, 1.1 mmol) is dissolved in 1.25 M HCl in MeOH (200 mL). The mixture is stirred at 30° C. for 16 hrs. The solvent is removed and the pH of the residue is adjusted to 9~10 using saturated aqueous $NaHCO_3$ solution. The mixture is then extracted with DCM and the organic layer is dried over $Na_2SO_4$, filtered and concentrated to give 214 mg of 3-(5,6,7,8-tetrahydro-[1,8]naphthyridin-3-yl)-isonicotinic acid methyl ester which is used in the next step without further purification.

To a solution of 3-(5,6,7,8-tetrahydro-[1,8]naphthyridin-3-yl)-isonicotinic acid methyl ester (131 mg, 0.49 mmol) in DCM (30 mL) is added benzoyl isocyanate (107 mg, 0.73 mmol). The mixture is heated to reflux for 3 hrs. The solvent is then removed and the residue is dissolved in anhydrous MeOH (10 mL). Then $K_2CO_3$ (180 mg, 1.3 mmol) is added and the mixture is heated to reflux for 0.5 h. After cooling down, the organic solvent is evaporated. The residue is dissolved in water and washed with DCM. The water layer is separated and purified by neutral preparative HPLC to give 80 mg of 3-(8-carbamoyl-5,6,7,8-tetrahydro-[1,8]naphthyridin-3-yl)-isonicotinic acid.

To a solution of 3-(8-carbamoyl-5,6,7,8-tetrahydro-[1,8]naphthyridin-3-yl)-isonicotinic acid (80 mg, 0.27 mmol) in 8.0 mL of toluene/MeOH 1:1 mixture is added 2.0 M trimethylsilyl-diazomethane (0.20 mL, 0.40 mmol) under $N_2$ atmosphere. The reaction solution is stirred at room temperature for 16 hrs. The solvent is removed and the residue is purified by preparative HPLC to give 33 mg of the titled product.

Example 29

Synthesis of 6-[4-Cyano-5-(1-methyl-1H-indol-2-yl)-pyridin-3-yl]-3,4-dihydro-2H-[1,8]naphthyridine-1-carboxylic acid amide (Cpd 52, Table 1)

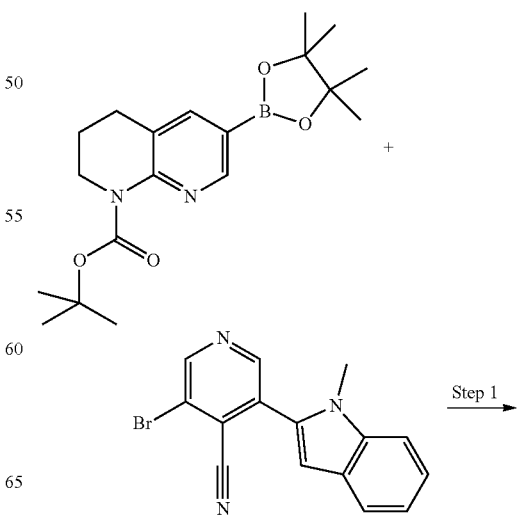

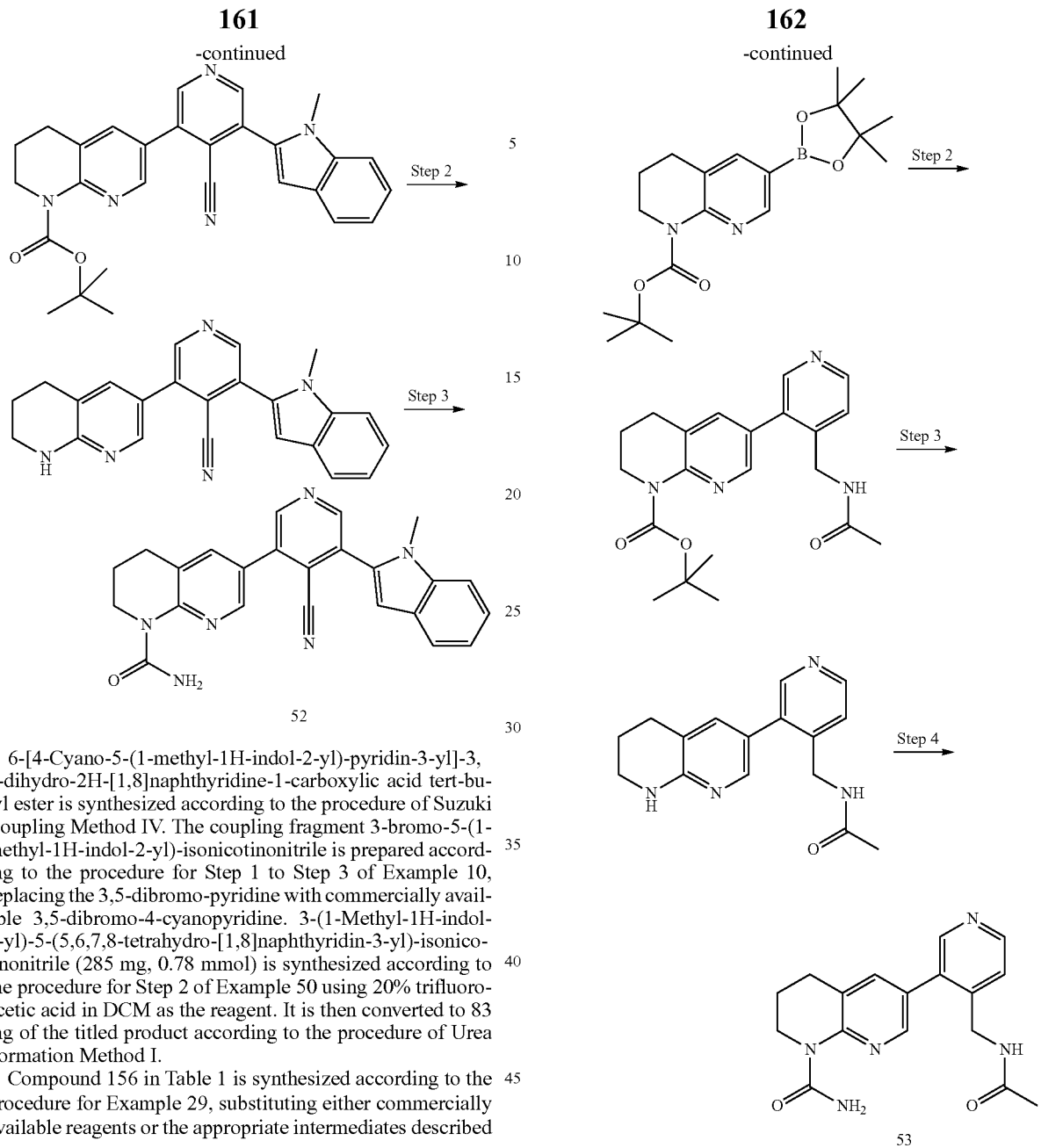

6-[4-Cyano-5-(1-methyl-1H-indol-2-yl)-pyridin-3-yl]-3,4-dihydro-2H-[1,8]naphthyridine-1-carboxylic acid tert-butyl ester is synthesized according to the procedure of Suzuki Coupling Method IV. The coupling fragment 3-bromo-5-(1-methyl-1H-indol-2-yl)-isonicotinonitrile is prepared according to the procedure for Step 1 to Step 3 of Example 10, replacing the 3,5-dibromo-pyridine with commercially available 3,5-dibromo-4-cyanopyridine. 3-(1-Methyl-1H-indol-2-yl)-5-(5,6,7,8-tetrahydro-[1,8]naphthyridin-3-yl)-isonicotinonitrile (285 mg, 0.78 mmol) is synthesized according to the procedure for Step 2 of Example 50 using 20% trifluoroacetic acid in DCM as the reagent. It is then converted to 83 mg of the titled product according to the procedure of Urea Formation Method I.

Compound 156 in Table 1 is synthesized according to the procedure for Example 29, substituting either commercially available reagents or the appropriate intermediates described above.

Example 30

Synthesis of 6-[4-(Acetylamino-methyl)-pyridin-3-yl]-3,4-dihydro-2H-[1,8]naphthyridine-1-carboxylic acid amide (Cpd 53, Table 1)

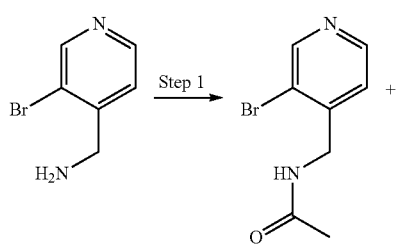

To a solution of (3-bromopyridin-4-yl) methanamine (3.5 g, 19 mmol) in DCM (880 mL) is added $Na_2CO_3$ (3.0 g, 28 mmol), then acetyl chloride (1.6 g, 21 mmol) is added at 0° C. under $N_2$ atmosphere. The mixture is stirred at room temperature for 3 hrs and then it is diluted with DCM. The mixture is washed with water and brine, dried over $Na_2SO_4$, filtered and concentrated to give the crude product. Purification by flash column chromatography affords 2.1 g of N-(3-Bromo-pyridin-4-ylmethyl)-acetamide.

6-[4-(Acetylamino-methyl)-pyridin-3-yl]-3,4-dihydro-2H-[1,8]naphthyridine-1-carboxylic acid tert-butyl ester is synthesized according to the procedure of Suzuki Coupling Method III, as illustrated above.

N-[3-(5,6,7,8-Tetrahydro-[1,8]naphthyridin-3-yl)-pyridin-4-ylmethyl]-acetamide is then prepared according to the procedure of Step 2 of Example 27 using 20% trifluoroacetic acid in DCM as the reagent. It is then converted to 64 mg of the titled product according to the procedure of Urea Formation Method I.

Example 31

Synthesis of 6-(4-Methoxymethyl-pyridin-3-yl)-3,4-dihydro-2H-[1,8]naphthyridine-1-carboxylic acid amide (Cpd 54, Table 1)

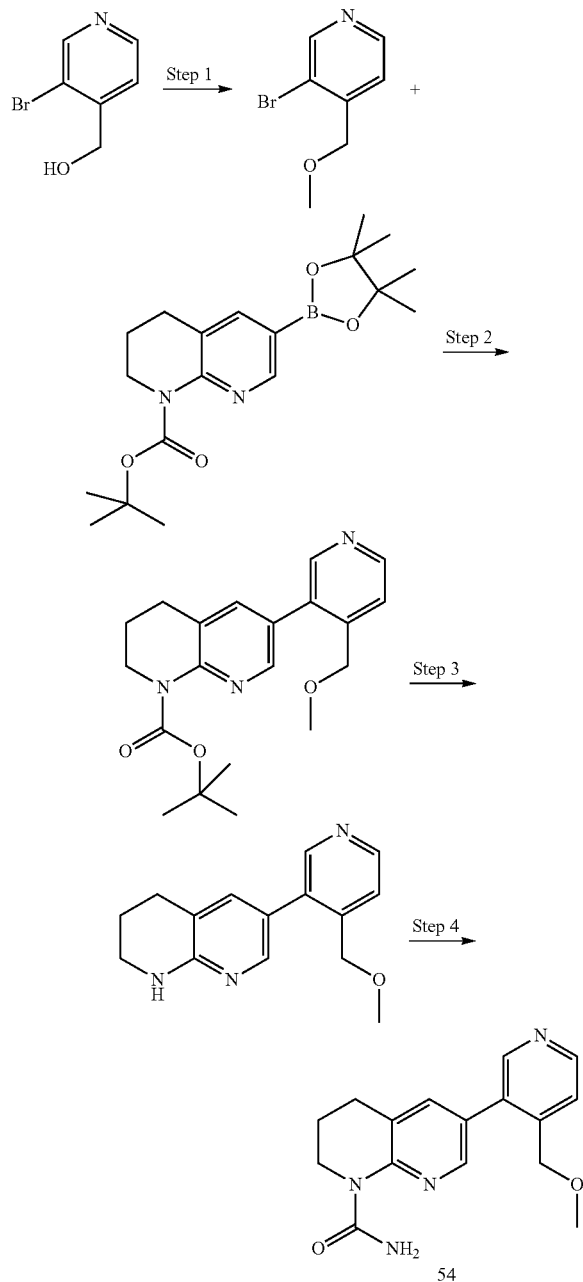

To a solution of (3-bromo-pyridin-4-yl)-methanol (300 mg, 1.6 mmol) in THF (50 mL) at 0° C. is added 60% NaH (96 mg, 2.4 mmol). Then the mixture is stirred at room temperature for 30 min. MeI (270 mg, 1.9 mmol) is added to the mixture at 0° C. and again the mixture is stirred at room temperature for 4 hrs. Then the reaction is quenched with saturated NH₄Cl aqueous solution and the mixture is extracted with EtOAc. The organic layer is separated, dried and concentrated to give the crude product. Purification by prep-TLC affords 274 mg of 3-bromo-4-methoxymethyl-pyridine.

6-(4-Methoxymethyl-pyridin-3-yl)-3,4-dihydro-2H-[1,8]naphthyridine-1-carboxylic acid tert-butyl ester is synthesized according to the procedure of Suzuki Coupling Method IV, as illustrated above.

6-(4-Methoxymethyl-pyridin-3-yl)-1,2,3,4-tetrahydro-[1,8]naphthyridine is prepared according to the procedure of Step 2 of Example 27 using 20% trifluoroacetic acid in DCM as the reagent and is then converted to 47 mg of the titled product according to the procedure of Urea Formation Method I.

Example 32

Synthesis of 6-{5-[4-(Morpholine-4-carbonyl)-phenyl]-pyridin-3-yl}-3,4-dihydro-2H-[1,8]naphthyridine-1-carboxylic acid amide (Cpd 55, Table 1)

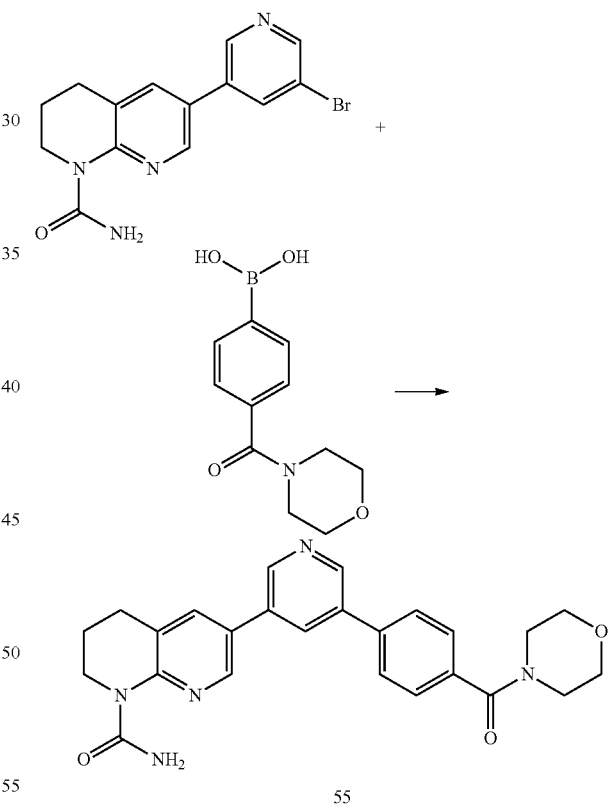

6-(5-Bromo-pyridin-3-yl)-3,4-dihydro-2H-[1,8]naphthyridine-1-carboxylic acid amide (50 mg, 0.15 mmol), which is synthesized according to the procedure for Step 1 to Step 4 of Example 15, 4-(morpholine-4-carbonyl)phenylboronic acid (71 mg, 0.30 mmol) and 2.0 M Na₂CO₃ aqueous solution (0.15 mL, 0.30 mmol) are dissolved in 2.0 mL of 1,4-dioxane. The Argon gas is bubbled through the solution for 5 min. Then PdCl₂dppf (7.7 mg, 0.011 mmol) is added. The mixture is heated at 100° C. for 2.5 hrs and it is cooled down to room temperature. 30 mL of DCM and 20 mL of water are added and the organic layer is separated. The aqueous layer is extracted with DCM (2×20 mL) and EtOAc (2×10 mL). The organic layers are combined, dried and concentrated to give the crude product which is purified by flash column chromatography to give 20 mg of the titled product.

Compounds 57, 63, 65, 71 and 72 in Table 1 are synthesized according to the procedure for Example 32, substituting either commercially available reagents or the appropriate intermediates described above.

Example 33

Synthesis of 6-[5-(4-Fluoro-phenoxymethyl)-pyridin-3-yl]-3,4-dihydro-2H-[1,8]naphthyridine-1-carboxylic acid amide (Cpd 56, Table 1)

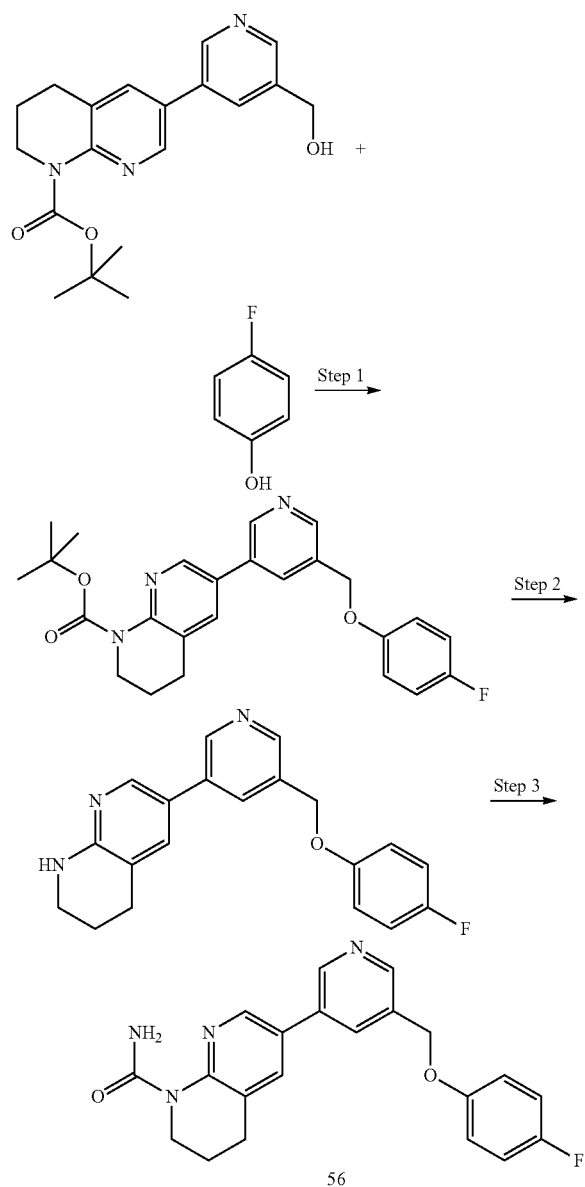

6-(5-Hydroxymethyl-pyridin-3-yl)-3,4-dihydro-2H-[1,8]naphthyridine-1-carboxylic acid tert-butyl ester (33 mg, 0.096 mmol), which is synthesized according to the procedure for Example 21, 4-fluoro-phenol (13 mg, 0.12 mmol) and triphenylphosphine (30 mg, 0.12 mmol) are mixed in 1.0 mL of DCM and diisopropyl azodicarboxylate (0.021, 0.11 mmol) is added. The mixture is stirred for 16 hrs and the reaction mixture is purified by flash column chromatography to give 42 mg of 6-[5-(4-fluoro-phenoxymethyl)-pyridin-3-yl]-3,4-dihydro-2H-[1,8]naphthyridine-1-carboxylic acid tert-butyl ester 6-[5-(4-Fluoro-phenoxymethyl)-pyridin-3-yl]-3,4-dihydro-2H-[1,8]naphthyridine-1-carboxylic acid tert-butyl ester (42 mg, 0.096 mmol) is dissolved in 1.0 mL of DCM and trifluoroacetic acid (0.3 mL) is added. The mixture is stirred for 16 hrs and then the solvent is removed. The residue is dissolved in MeOH and filtered through Varian PL-HCO$_3$ MP resin catridge to give 33 mg of 6-[5-(4-Fluoro-phenoxymethyl)-pyridin-3-yl]-1,2,3,4-tetrahydro-[1,8]naphthyridine which is used in the next step without purification.

6-[5-(4-Fluoro-phenoxymethyl)-pyridin-3-yl]-1,2,3,4-tetrahydro-[1,8]naphthyridine (32 mg, 0.096 mmol) and benzoyl isocyanate (24 mg, 0.14 mmol) are mixed in 1.0 mL of DCM and the mixture is heated at 50° C. for 16 hrs. Then the solvent is removed and the residue is dissolved in 1.0 mL of EtOH. K$_2$CO$_3$ (23 mg, 0.16 mmol) is added and the mixture is heated at 80° C. for 45 min. Then the solvent is removed and the residue is partitioned between water (35 mL) and EtOAc (75 mL). The aqueous layer is separated and extracted with EtOAc (2×30 mL). The organic layers are combined and concentrated to give the crude product. Purification by flash column chromatography affords 26 mg of the titled product.

Example 34

Synthesis of 6-(1',2',3',4',5',6'-Hexahydro-[3,4']bipyridinyl-5-yl)-3,4-dihydro-2H-[1,8]naphthyridine-1-carboxylic acid amide (Cpd 58, Table 1)

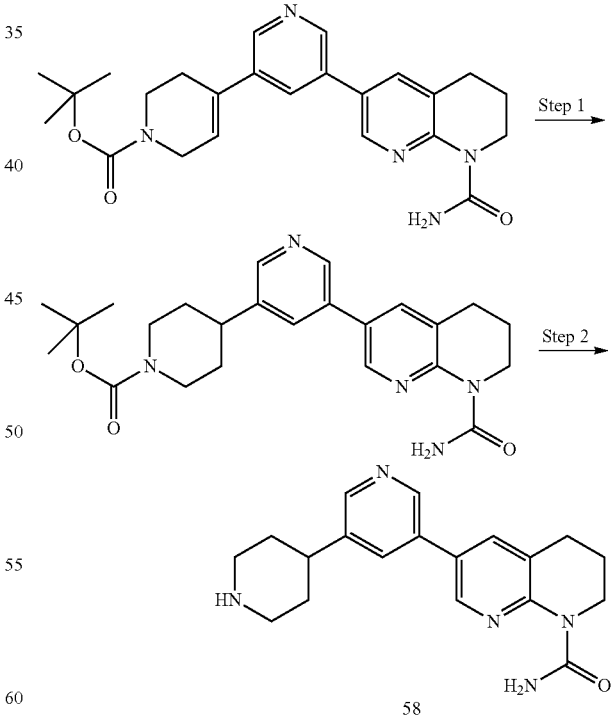

5-(8-Carbamoyl-5,6,7,8-tetrahydro-[1,8]naphthyridin-3-yl)-3',6'-dihydro-2'H-[3,4]bipyridinyl-1'-carboxylic acid tert-butyl ester is prepared using the procedure for Example 24, is converted to the titled product according to the procedure for Example 25.

To the 5-(8-carbamoyl-5,6,7,8-tetrahydro-[1,8]naphthyridin-3-yl)-3',4',5',6'-tetrahydro-2'H-[3,4']bipyridinyl-1'-carboxylic acid tert-butyl ester (19.3 mg, 0.04 mmol) in 1 mL of CH₂Cl₂ is added 1 mL of 4 M HCl in dioxane. The mixture is stirred for 16 h. The mixture is concentrated to give 16.5 mg of 6-(1',2',3',4',5',6'-hexahydro-[3,4']bipyridinyl-5-yl)-3,4-dihydro-2H-[1,8]naphthyridine-1-carboxylic acid amide Example 35

Synthesis of 6-[5-(1,1-Dioxo-1,2,3,6-tetrahydro-1lambda6-thiopyran-4-yl)-pyridin-3-yl]-3,4-dihydro-2H-[1,8]naphthyridine-1-carboxylic acid amide (Cpd 59, Table 1)

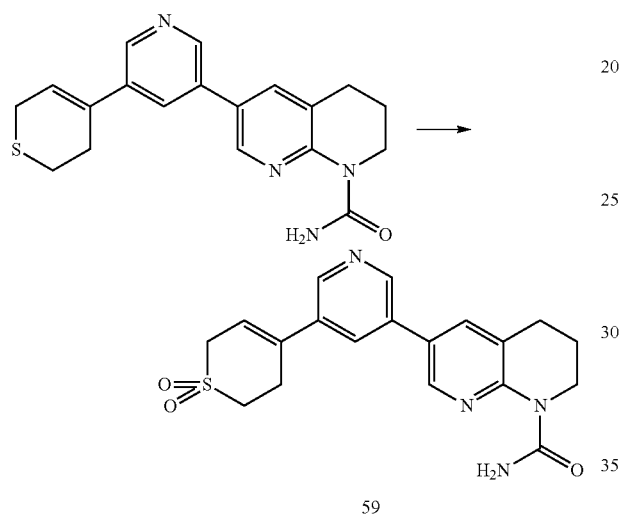

To 6-[5-(3,6-dihydro-2H-thiopyran-4-yl)-pyridin-3-yl]-3,4-dihydro-2H-[1,8]naphthyridine-1-carboxylic acid amide (57 mg, 0.16 mmol) in 2 mL of 1:1 dioxane/H₂O is added oxone (266 mg, 0.32 mmol). The mixture is stirred for 2 h. The mixture is quenched by addition of sodium sulfite and concentrated. The residue is suspended into MeOH and filtered. The filtrate is concentrated and purified via the Preparative HPLC (5%-70% CH₃CN/H₂O) to give 62.6 mg of the titled product.

Example 36

Synthesis of 6-[5-(1,1-Dioxo-hexahydro-1lambda6-thiopyran-4-yl)-pyridin-3-yl]-3,4-dihydro-2H-[1,8]naphthyridine-1-carboxylic acid amide (Cpd 60, Table 1)

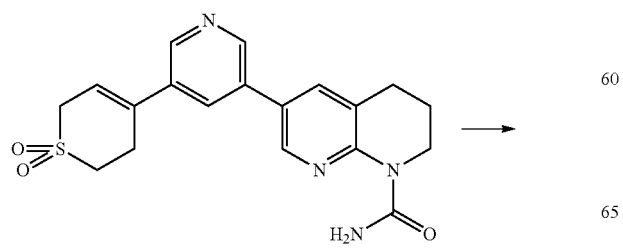

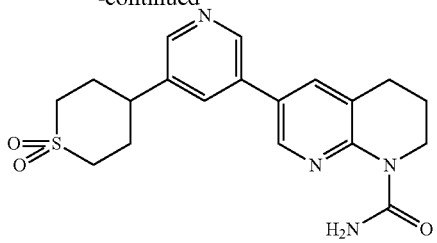

To the mixture of 6-[5-(1,1-dioxo-1,2,3,6-tetrahydro-1lambda6-thiopyran-4-yl)-pyridin-3-yl]-3,4-dihydro-2H-[1,8]naphthyridine-1-carboxylic acid amide (56 mg, 0.15 mmol) and 10% Pd/C (17 mg) is added 2 mL of MeOH under Ar. Then ammonium formate (140 mg, 2.20 mmol) is added and the mixture is stirred for 1 hr at 80° C. The mixture is filtered, concentrated and purified via Preparative HPLC (10%-80% CH₃CN/H₂O) to give 30.2 mg of the titled product.

Example 37

Synthesis of 6-[4-(Ethanesulfonylamino-methyl)-pyridin-3-yl]-3,4-dihydro-2H-[1,8]naphthyridine-1-carboxylic acid amide (Cpd 61, Table 1)

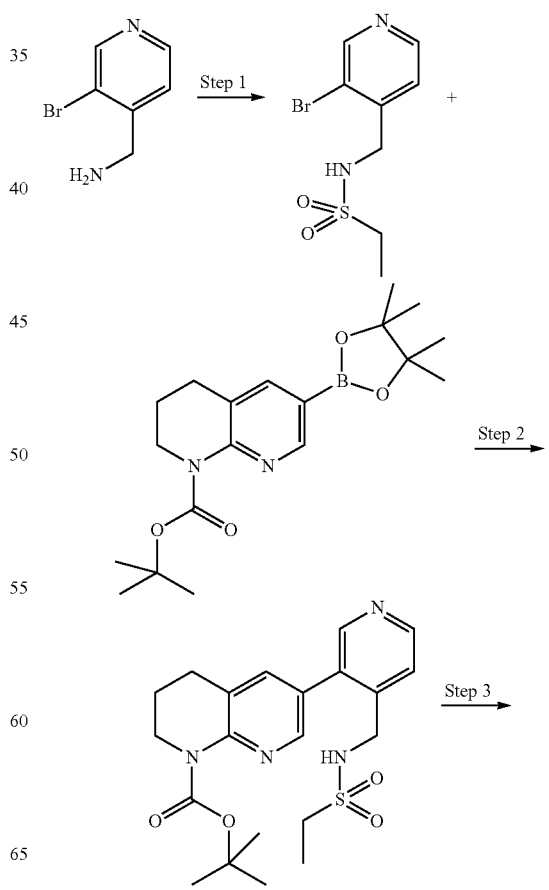

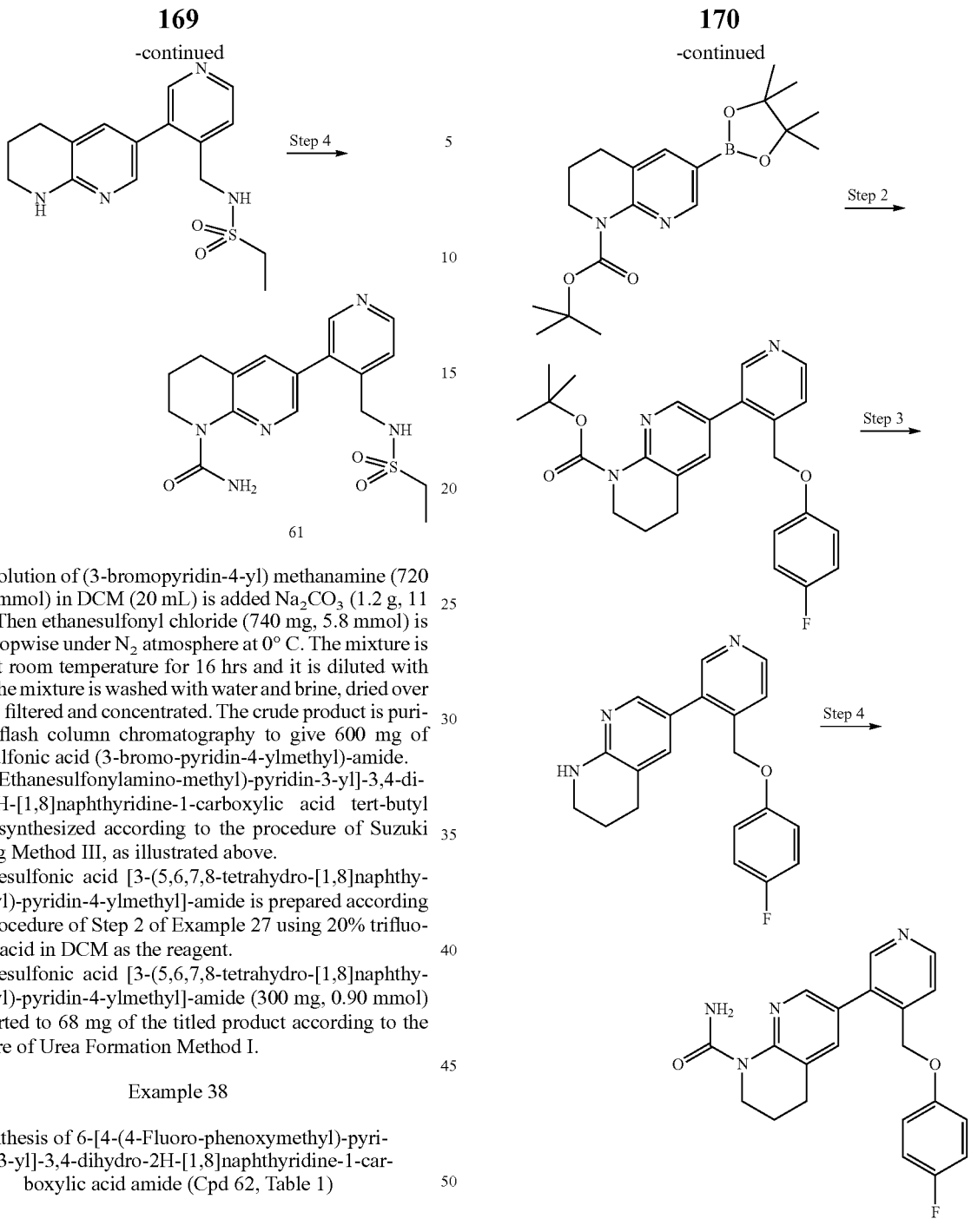

To a solution of (3-bromopyridin-4-yl) methanamine (720 mg, 3.9 mmol) in DCM (20 mL) is added $Na_2CO_3$ (1.2 g, 11 mmol). Then ethanesulfonyl chloride (740 mg, 5.8 mmol) is added dropwise under $N_2$ atmosphere at 0° C. The mixture is stirred at room temperature for 16 hrs and it is diluted with DCM. The mixture is washed with water and brine, dried over $Na_2SO_4$, filtered and concentrated. The crude product is purified by flash column chromatography to give 600 mg of ethanesulfonic acid (3-bromo-pyridin-4-ylmethyl)-amide.

6-[4-(Ethanesulfonylamino-methyl)-pyridin-3-yl]-3,4-dihydro-2H-[1,8]naphthyridine-1-carboxylic acid tert-butyl ester is synthesized according to the procedure of Suzuki Coupling Method III, as illustrated above.

Ethanesulfonic acid [3-(5,6,7,8-tetrahydro-[1,8]naphthyridin-3-yl)-pyridin-4-ylmethyl]-amide is prepared according to the procedure of Step 2 of Example 27 using 20% trifluoroacetic acid in DCM as the reagent.

Ethanesulfonic acid [3-(5,6,7,8-tetrahydro-[1,8]naphthyridin-3-yl)-pyridin-4-ylmethyl]-amide (300 mg, 0.90 mmol) is converted to 68 mg of the titled product according to the procedure of Urea Formation Method I.

Example 38

Synthesis of 6-[4-(4-Fluoro-phenoxymethyl)-pyridin-3-yl]-3,4-dihydro-2H-[1,8]naphthyridine-1-carboxylic acid amide (Cpd 62, Table 1)

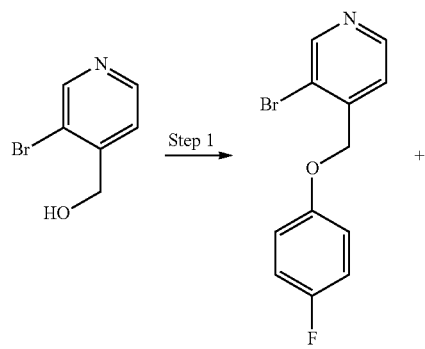

To a solution of (3-bromo-pyridin-4-yl)-methanol (650 mg, 3.5 mmol), 4-fluoro-phenol (260 mg, 2.3 mmol) and $PPh_3$ (1.7 g, 6.4 mmol) in THF (50 mL) is added a solution of di-tert-butyl azodicarboxylate (1.2 g, 5 mmol) in THF at 0° C. After addition, the mixture is stirred at room temperature for 16 hrs. The solvent is removed and the residue is purified by flash column chromatography to give 600 mg of 3-bromo-4-(4-fluoro-phenoxymethyl)-pyridine.

6-[4-(4-Fluoro-phenoxymethyl)-pyridin-3-yl]-3,4-dihydro-2H-[1,8]naphthyridine-1-carboxylic acid tert-butyl ester is synthesized according to the procedure of Suzuki Coupling Method IV, as illustrated above.

6-[4-(4-Fluoro-phenoxymethyl)-pyridin-3-yl]-1,2,3,4-tetrahydro-[1,8]naphthyridine is prepared according to the procedure of Step 2 of Example 27 using 20% trifluoroacetic acid in DCM as the reagent.

6-[4-(4-Fluoro-phenoxymethyl)-pyridin-3-yl]-1,2,3,4-tetrahydro-[1,8]naphthyridine (200 mg, 0.60 mmol) is converted to 80 mg of the titled product according to the procedure of Urea Formation Method I.

Example 39

Synthesis of 6-[5-(1-Hydroxy-1-methyl-ethyl)-pyridin-3-yl]-3,4-dihydro-2H-[1,8]naphthyridine-1-carboxylic acid amide (Cpd 64, Table 1)

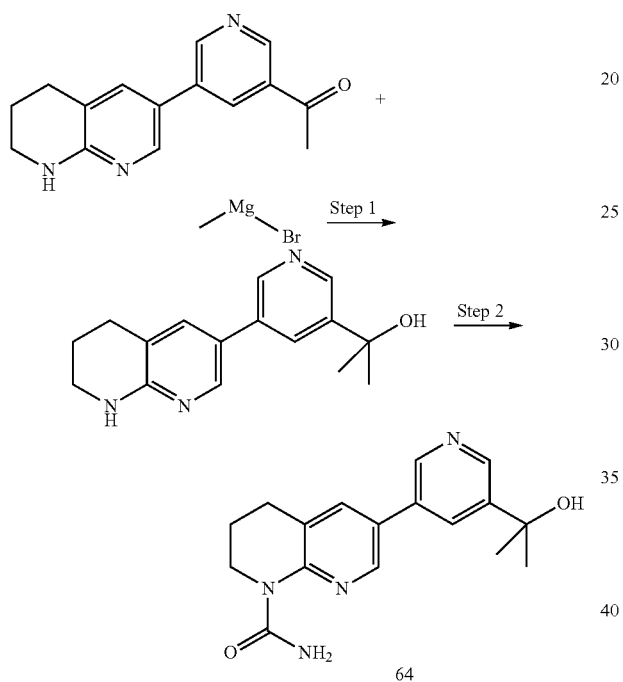

1-[5-(5,6,7,8-Tetrahydro-[1,8]naphthyridin-3-yl)-pyridin-3-yl]-ethanone (40 mg, 0.16 mmol), which is synthesized according to the procedure for Step 1 to Step 3 of Example 6, is dissolved in 1.5 mL of THF and added into 0.5 mL of THF containing 3.0 M methylmagnesium bromide (0.21 mL, 0.63 mmol). The mixture is stirred for 30 min and saturated aqueous $NH_4Cl$ solution (2 mL) is added along with EtOAc (10 mL) and water (10 mL). The aqueous layer is separated and extracted with EtOAc (3×10 ml). The organic layers are combined and concentrated to give the crude product. Purification by flash column chromatography affords 33 mg of 2-[5-(5,6,7,8-tetrahydro-[1,8]naphthyridin-3-yl)-pyridin-3-yl]-propan-2-ol.

2-[5-(5,6,7,8-Tetrahydro-[1,8]naphthyridin-3-yl)-pyridin-3-yl]-propan-2-ol (33 mg, 0.12 mmol) and benzoyl isocyanate (40 mg, 0.25 mmol) are mixed in 1.0 mL of DCM and the mixture is heated at 50° C. for 16 hrs. Then the solvent is removed and the residue is dissolved in 1.0 mL of EtOH. $K_2CO_3$ (29 mg, 0.21 mmol) is added and the mixture is heated at 80° C. for 2 hrs, cooled down to room temperature for 16 hrs and heated at 80° C. again for another 3 hrs. Then the solvent is removed and the residue is partitioned between water (15 mL) and EtOAc (25 mL). The aqueous layer is separated and extracted with EtOAc (2×30 mL). The organic layers are combined and concentrated to give the crude product. The crude is purified by flash column chromatography to give 12 mg of the titled product.

Example 40

Synthesis of 6-[5-(3-Methanesulfonyl-propoxymethyl)-pyridin-3-yl]-3,4-dihydro-2H-[1,8]naphthyridine-1-carboxylic acid amide (Cpd 66, Table 1)

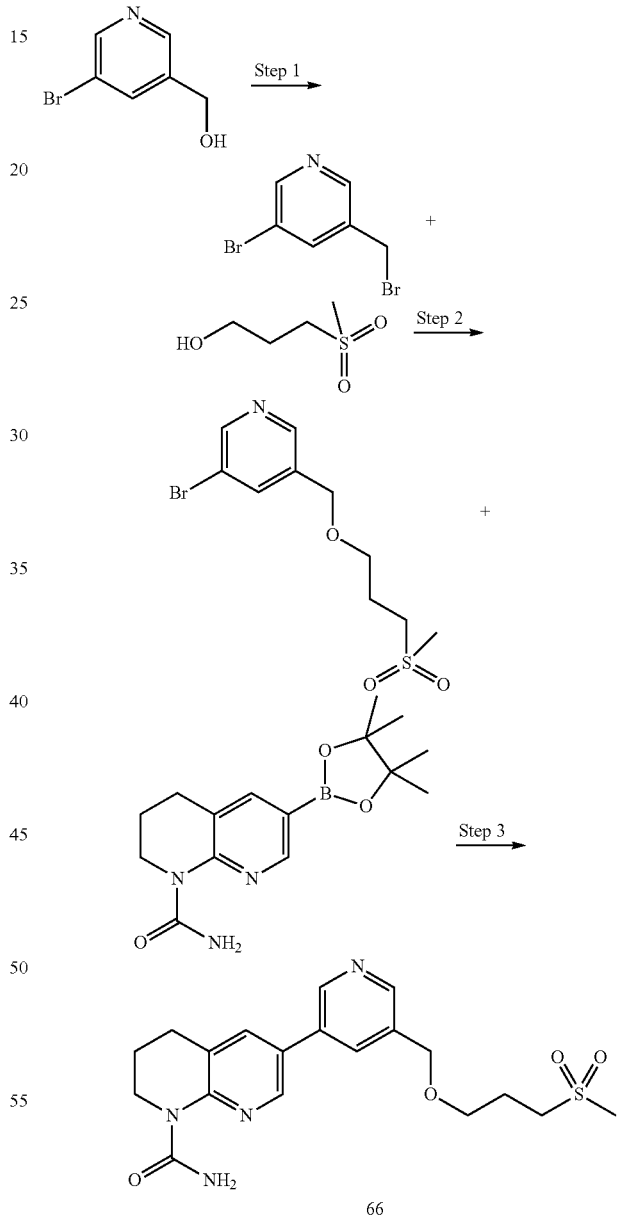

(5-Bromo-pyridin-3-yl)-methanol (500 mg, 2.7 mmol) and triphenylphosphine (840 mg, 3.2 mmol) are dissolved in 12 mL of DCM and NBS (570 mg, 3.2 mmol) is added. The mixture is stirred for 4 hrs and then the reaction mixture is directly purified by flash column chromatography give 455 mg of 3-bromo-5-bromomethyl-pyridine.

3-Methanesulfonyl-propan-1-ol (69 mg, 0.50 mmol) is dissolved in 2.0 mL of DMF and 60% sodium hydride (20 mg, 0.50 mmol) is added at 0° C. The mixture is stirred for 15 min and 3-bromo-5-bromomethyl-pyridine (50 mg, 0.20 mmol) is added. The mixture is stirred for 2 hrs and saturated aqueous NH$_4$Cl solution (3 mL) is added along with water (10 mL) and EtOAc (10 mL). The mixture is stirred for 10 min and the aqueous layer is separated and extracted with EtOAc (2×15 ml). The organic layers are combined and concentrated to give the crude product. Purification by flash column chromatography affords 61 mg of 3-bromo-5-(3-methanesulfonyl-propoxymethyl)-pyridine.

3-Bromo-5-(3-methanesulfonyl-propoxymethyl)-pyridine (61 mg, 0.20 mmol) and 2.0 M Na$_2$CO$_3$ aqueous solution (0.20 mL, 0.40 mmol) are added into the crude 6-(4,4,5,5-tetramethyl-[1,3,2]dioxaborolan-2-yl)-3,4-dihydro-2H-[1,8]naphthyridine-1-carboxylic acid amide 1,4-dioxane solution (2.0 mL, 0.24 mmol) which is synthesized according to the procedure for Step 3 of Example 16. Argon gas is bubbled through the solution for 5 min. Then PdCl$_2$dppf (7.3 mg, 0.010 mmol) is added. The mixture is heated at 100° C. for 3.5 hrs before EtOAc (15 mL) and water (15 mL) are added. The aqueous layer is separated and extracted with EtOAc (2×10 mL). The organic layers are combined and concentrated to give the crude product. Purification by flash column chromatography affords 42 mg of the titled product.

Compounds 73, 253 and 254 in Table 1 are synthesized according to the procedure for Example 40, substituting either commercially available reagents or the appropriate intermediates described above.

Chiral separation of the racemic Compound 253 (150 mg, 0.37 mmol) using Supercritical Fluid Chromatography (Column Chiralpak IA 4.6×250 mm analytical, Mobile phase: 40% 1:1:1 MeOH:EtOH:IPA (0.1% DEA):CO2 @ 2 ml/min, 200 bar, 40° C.) affords 45 mg of Compound 169 (Retention time 3.9 min) and 57 mg of Compound 170 (Retention time 5.7 min) in Table 1.

Example 41

Synthesis of 6-(4-Trifluoromethyl-pyridin-3-yl)-3,4-dihydro-2H-[1,8]naphthyridine-1-carboxylic acid amide (Cpd 67, Table 1)

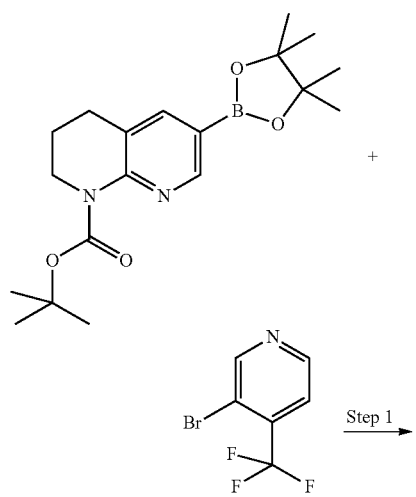

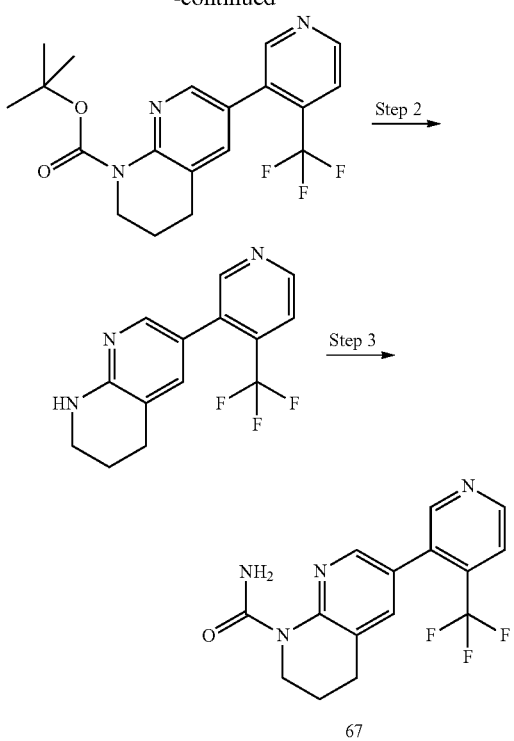

6-(4-Trifluoromethyl-pyridin-3-yl)-3,4-dihydro-2H-[1,8]naphthyridine-1-carboxylic acid tert-butyl ester is synthesized according to the procedure of Suzuki Coupling Method V, as illustrated above. It is then used in the synthesis of 6-(4-trifluoromethyl-pyridin-3-yl)-1,2,3,4-tetrahydro-[1,8]naphthyridine according to the procedure for Step 2 of Example 27 using 20% trifluoroacetic acid in DCM as the reagent.

6-(4-Trifluoromethyl-pyridin-3-yl)-1,2,3,4-tetrahydro-[1,8]naphthyridine (350 mg, 1.3 mmol) is converted to 43 mg of the titled product according to the procedure of Urea Formation Method I.

Example 42

Synthesis of 6-(4-Carbamoyl-pyridin-3-yl)-3,4-dihydro-2H-[1,8]naphthyridine-1-carboxylic acid amide (Cpd 69, Table 1)

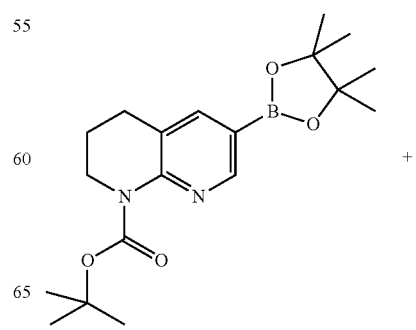

175

-continued

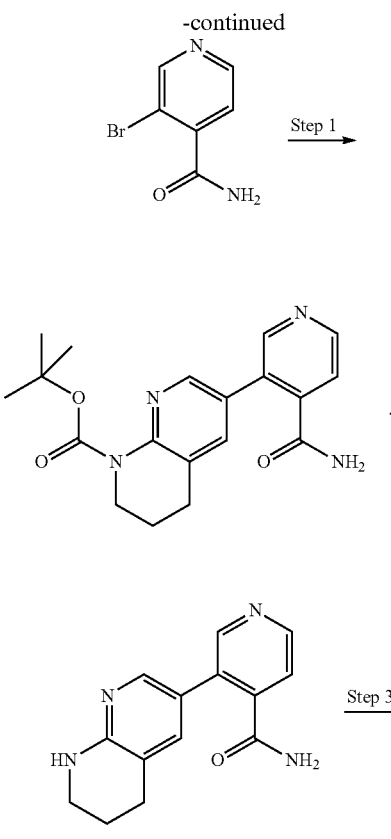

69

6-(4,4,5,5-Tetramethyl-[1,3,2]dioxaborolan-2-yl)-3,4-dihydro-2H-[1,8]naphthyridine-1-carboxylic acid tert-butyl ester (100 mg, 0.36 mmol), 3-bromo-isonicotinamide (80 mg, 0.40 mmol), saturated $Na_2CO_3$ aqueous solution (1.0 mL) and $Pd(PPh_3)_2Cl_2$ (24 mg, 0.034 mmol) are mixed in DME (5.0 mL) and EtOH (5.0 mL). The reaction mixture is microwaved at 140° C. for 45 mins. Then mixture is diluted with DCM and water. The organic layer is separated and concentrated to give the crude product. Purification by flash column chromatography affords 30 mg 6-(4-carbamoyl-pyridin-3-yl)-3,4-dihydro-2H-[1,8]naphthyridine-1-carboxylic acid tert-butyl ester. It is then used to prepare 3-(5,6,7,8-tetrahydro-[1,8]naphthyridin-3-yl)-isonicotinamide according to the procedure for Step 2 of Example 27 using 20% trifluoroacetic acid in DCM as the reagent.

3-(5,6,7,8-Tetrahydro-[1,8]naphthyridin-3-yl)-isonicotinamide (200 mg, 0.79 mmol) is converted to 38 mg of the titled product according to the procedure of Urea Formation Method I.

176

Example 43

Synthesis of 6-(5-Benzyloxy-pyridin-3-yl)-3,4-dihydro-2H-[1,8]naphthyridine-1-carboxylic acid amide (Cpd 70, Table 1)

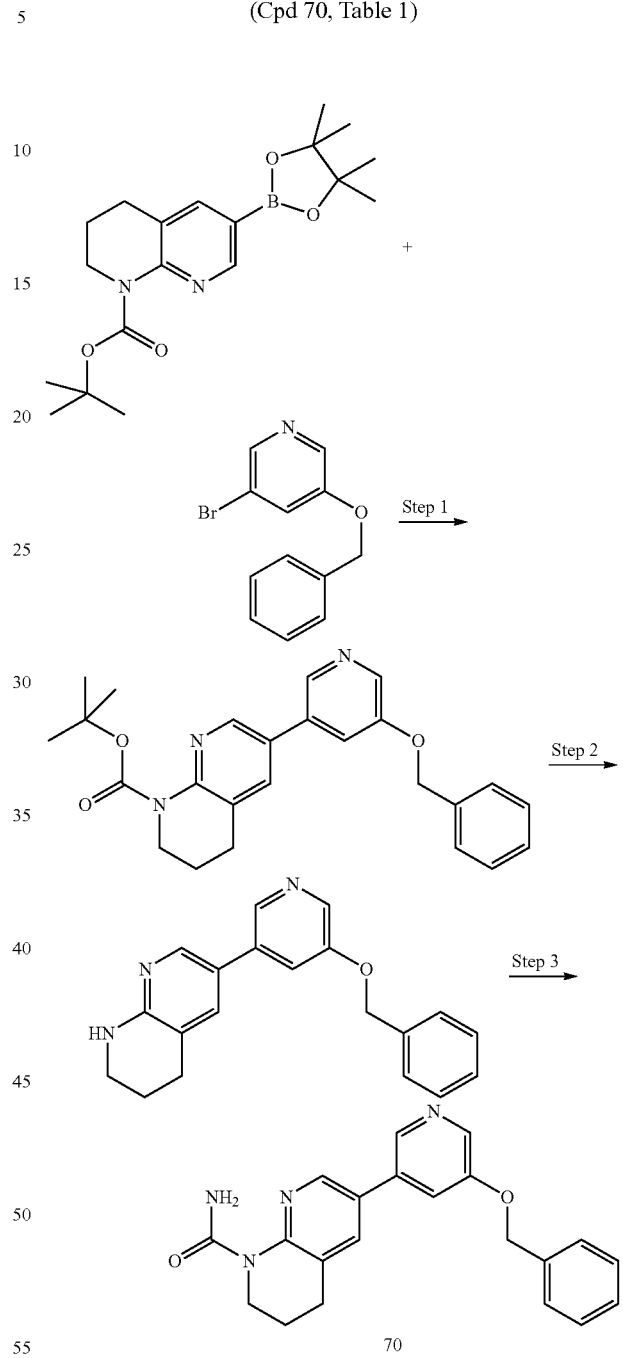

70

6-(5-Benzyloxy-pyridin-3-yl)-3,4-dihydro-2H-[1,8]naphthyridine-1-carboxylic acid tert-butyl ester is synthesized according to the procedure of Suzuki Coupling Method IV, as illustrated above. It is then used to synthesize 6-(5-benzyloxy-pyridin-3-yl)-1,2,3,4-tetrahydro-[1,8]naphthyridine according to the procedure for Step 2 of Example 27 using 20% trifluoroacetic acid in DCM as the reagent.

6-(5-Benzyloxy-pyridin-3-yl)-1,2,3,4-tetrahydro-[1,8]naphthyridine (530 mg, 1.7 mmol) is converted to 188 mg of the titled product according to the procedure of Urea Formation Method I.

Compound 68 in Table 1 is synthesized according to the procedure for Example 43, substituting either commercially available reagents or the appropriate intermediates described above.

Example 44

Synthesis of 6-(5-Dimethylcarbamoylmethyl-pyridin-3-yl)-3,4-dihydro-2H-[1,8]naphthyridine-1-carboxylic acid amide (Cpd 74, Table 1)

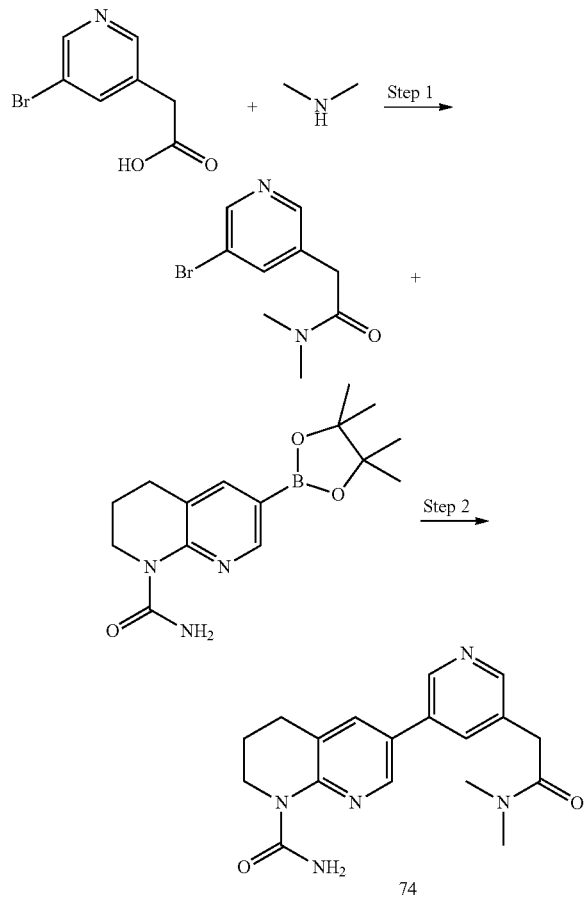

(5-Bromo-pyridin-3-yl)-acetic acid (200 mg, 0.93 mmol), 2.0 M dimethylamine solution (0.93 mL, 1.9 mmol), HOBt (25 mg, 0.19 mmol) and triethylamine (0.38 mL, 2.8 mmol) are dissolved in 5.0 mL of DMF. Then 1-ethyl-3-(3-dimethylaminopropyl)carbodiimide (290 mg, 1.9 mmol) is added. The reaction mixture is stirred for 16 hrs before 30 mL of water and 30 mL of DCM are added. The aqueous layer is separated and extracted with DCM (4×10 mL). The organic layers are combined, dried and concentrated to give the crude product which is purified by flash chromatography to give 180 mg of 2-(5-bromo-pyridin-3-yl)-N,N-dimethyl-acetamide.

2-(5-Bromo-pyridin-3-yl)-N,N-dimethyl-acetamide (73 mg, 0.30 mmol) and 2.0 M Na$_2$CO$_3$ aqueous solution (0.30 mL, 0.60 mmol) are added into the crude 6-(4,4,5,5-tetramethyl-[1,3,2]dioxaborolan-2-yl)-3,4-dihydro-2H-[1,8]naphthyridine-1-carboxylic acid amide 1,4-dioxane solution (3.0 mL, 0.36 mmol) which is synthesized according to the procedure for Step 3 of Example 16. The Argon gas is bubbled through the solution for 5 min. Then PdCl$_2$dppf (11 mg, 0.015 mmol) is added. The mixture is heated at 100° C. for 3.5 hrs before EtOAc (15 mL) and water (15 mL) are added. The aqueous layer is separated and extracted with EtOAc (2×10 mL). The organic layers are combined and concentrated to give the crude product. Purification by flash column chromatography affords 8.0 mg of the titled product.

Compounds 174, 177, 178 and 193 in Table 1 are synthesized according to the procedure for Example 44, substituting either commercially available reagents or the appropriate intermediates described above.

Example 45

Synthesis of 1-[6-(5-Trifluoromethyl-pyridin-3-yl)-3,4-dihydro-2H-[1,8]naphthyridin-1-yl]-ethanone (Cpd 75, Table 1)

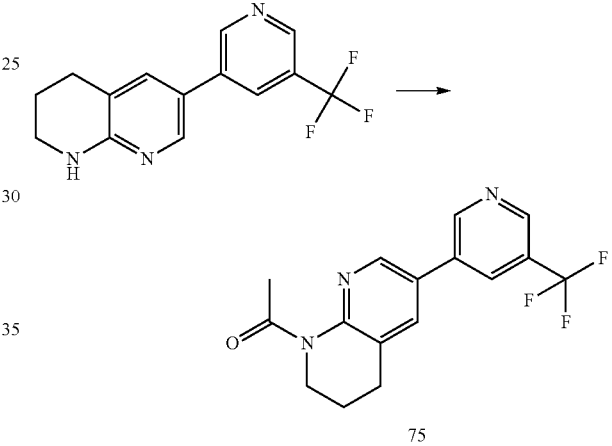

6-(5-Trifluoromethyl-pyridin-3-yl)-1,2,3,4-tetrahydro-[1,8]naphthyridine (200 mg, 0.72 mmol), whose synthesis is described in Step 1 of Example 4, is dissolved in DCM (25 mL). Triethylamine (220 mg, 2.1 mmol) is added followed by the addition of acetyl chloride (67 mg, 0.86 mmol) under N$_2$ atmosphere at 0° C. The mixture is stirred at room temperature for 3 hrs. The solvent is removed and the residue is purified by preparative TLC to give 43 mg of the titled product.

Example 46

Synthesis of 6-[5-(Tetrahydro-pyran-4-yloxymethyl)-pyridin-3-yl]-3,4-dihydro-2H-[1,8]naphthyridine-1-carboxylic acid amide (Cpd 76, Table 1)

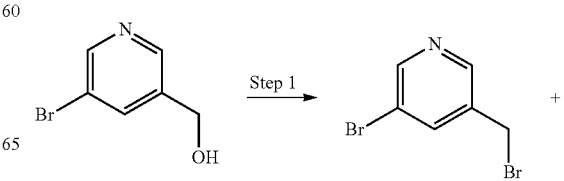

-continued

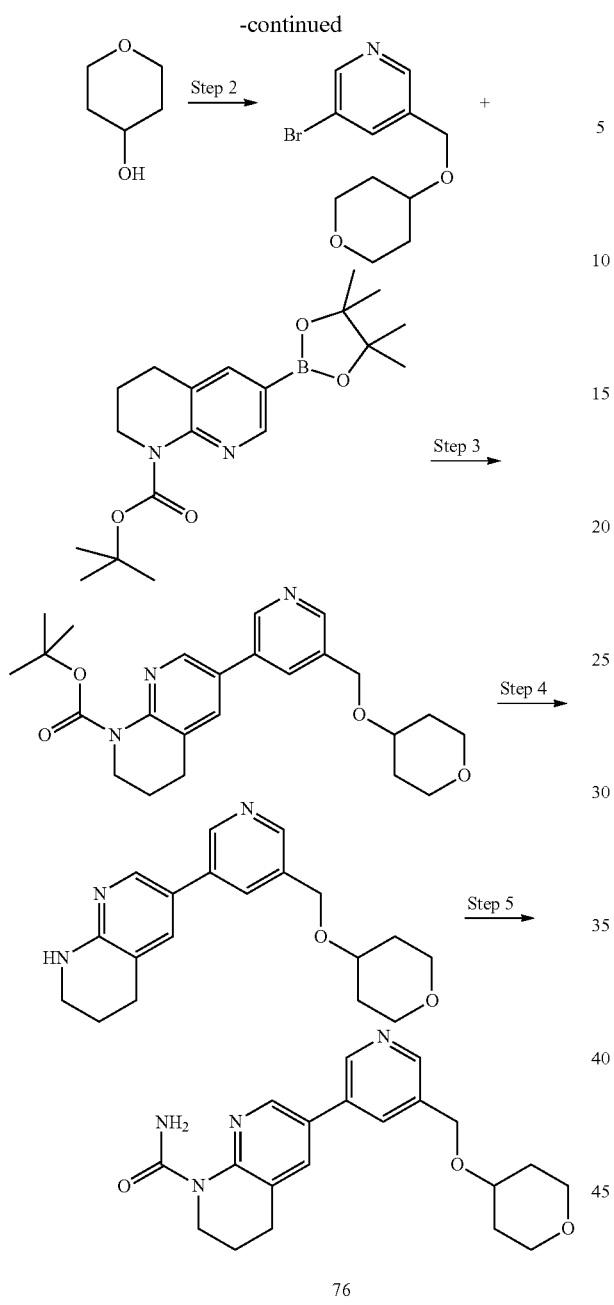

76

(5-Bromo-pyridin-3-yl)-methanol (500 mg, 2.7 mmol) and triphenylphosphine (840 mg, 3.2 mmol) are dissolved in 12 mL of DCM and NBS (570 mg, 3.2 mmol) is added. The mixture is stirred for 4 hrs and the solvent is removed. The residue is purified by flash column chromatography to give 455 mg of 3-bromo-5-bromomethyl-pyridine.

To a suspension of 60% NaH (640 mg, 16 mmol) in DMF (80 mL) is added tetrahydro-pyran-4-ol (1.6 g, 16 mmol) at 0° C. After the mixture is stirred at room temperature for 0.5 h, 3-bromo-5-bromomethyl-pyridine (1.6 g, 6.4 mmol) is added at 0° C. under $N_2$ atmosphere. The mixture is stirred at room temperature for 16 hrs. Then saturated $NH_4Cl$ aqueous solution is used to quench the reaction and the mixture is extracted with DCM. The organic layers are combined, dried over $Na_2SO_4$, filtered and concentrated. The crude product is purified by flash column chromatography to give 700 mg of 3-bromo-5-(tetrahydro-pyran-4-yloxymethyl)-pyridine.

6-[5-(Tetrahydro-pyran-4-yloxymethyl)-pyridin-3-yl]-3,4-dihydro-2H-[1,8]naphthyridine-1-carboxylic acid tert-butyl ester is synthesized according to the procedure of Suzuki Coupling Method IV, as illustrated above. It is then used to prepare 6-[5-(tetrahydro-pyran-4-yloxymethyl)-pyridin-3-yl]-1,2,3,4-tetrahydro-[1,8]naphthyridine according to the procedure for Step 2 of Example 27 using 20% trifluoroacetic acid in DCM as the reagent.

6-[5-(Tetrahydro-pyran-4-yloxymethyl)-pyridin-3-yl]-1,2,3,4-tetrahydro-[1,8]naphthyridine (370 mg, 1.1 mmol) is converted to 54 mg of the titled product according to the procedure of Urea Formation Method I.

Example 47

Synthesis of 6-(5-Dimethylcarbamoylmethoxymethyl-pyridin-3-yl)-3,4-dihydro-2H-[1,8]naphthyridine-1-carboxylic acid amide (Cpd 77, Table 1)

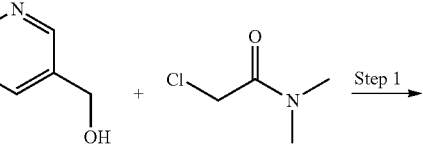

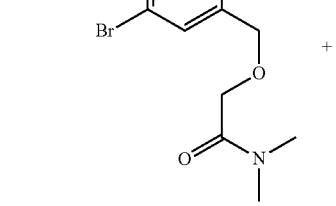

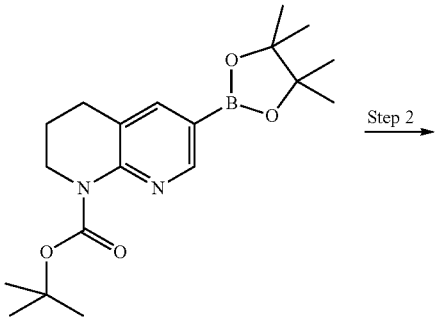

-continued

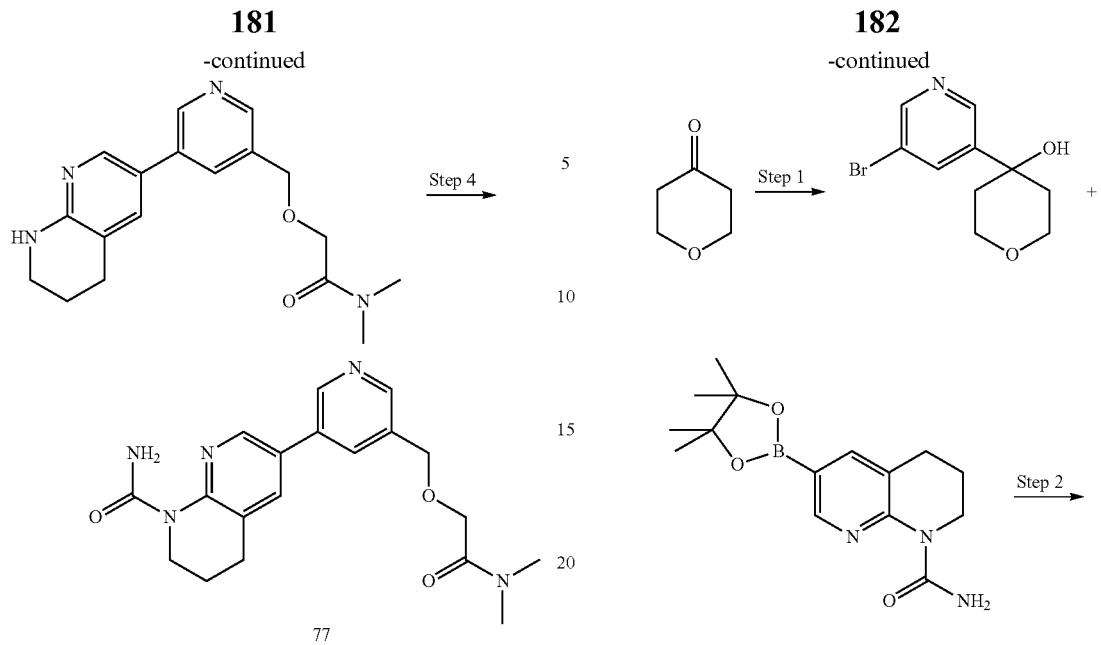

To a solution of (5-Bromo-pyridin-3-yl)-methanol (600 mg, 3.2 mmol) in THF (50 mL) is added 60% NaH (160 mg, 3.9 mmol) at 0° C. under $N_2$ atmosphere. The mixture is stirred at room temperature for 1 hour. Then 2-chloro-N,N-dimethyl-acetamide (420 mg, 3.5 mmol) is added into the mixture at 0° C. After addition, the mixture is stirred at room temperature for 16 hrs. After quenching with saturated $NH_4Cl$ aqueous solution, the mixture is extracted with EtOAc for three times. The organic layers are combined, dried over $Na_2SO_4$, filtered and concentrated. The crude product is purified by preparative TLC to give 700 mg of 2-(5-bromo-pyridin-3-ylmethoxy)-N,N-dimethyl-acetamide.

6-(5-Dimethylcarbamoylmethoxymethyl-pyridin-3-yl)-3,4-dihydro-2H-[1,8]naphthyridine-1-carboxylic acid tert-butyl ester is synthesized according to the procedure of Suzuki Coupling Method III, as illustrated above. It is then used to prepare N,N-dimethyl-2-[5-(5,6,7,8-tetrahydro-[1,8]naphthyridin-3-yl)-pyridin-3-ylmethoxy]-acetamide according to the procedure for Step 2 of Example 27 using 20% trifluoroacetic acid in DCM as the reagent.

N,N-Dimethyl-2-[5-(5,6,7,8-tetrahydro-[1,8]naphthyridin-3-yl)-pyridin-3-ylmethoxy]-acetamide (150 mg, 0.46 mmol) is converted to 58 mg of the titled product according to the procedure of Urea Formation Method I.

Example 48

Synthesis of 6-[5-(4-Hydroxy-tetrahydro-pyran-4-yl)-pyridin-3-yl]-3,4-dihydro-2H-[1,8]naphthyridine-1-carboxylic acid amide (Cpd 78, Table 1)

To 3,5-dibromopyridine (592 mg, 2.50 mmol) in 2 mL of THF at –20° C. is added 1.3M i-PrMgCl_LiCl solution (1.83 mL, 2.4 mmol) in one portion. The mixture is allowed to stir for 30 min., warming to –10° C. The mixture is cooled to –20° C. and tetrahydro-pyran-4-one (0.23 mL, 3.00 mmol) is added. The reaction is quenched with 50 mL of saturated aqueous $NH_4Cl$ and diluted with 200 mL EtOAc. The organic phase is washed with 2×100 mL of $H_2O$, 1×100 mL of brine. The organic phase is dried with $MgSO_4$, filtered and concentrated. The crude material is applied to a silica column and purified (0-10% $MeOH/CH_2Cl_2$) to give 168 mg of 4-(5-bromo-pyridin-3-yl)-tetrahydro-pyran-4-ol.

To the crude 6-(4,4,5,5-tetramethyl-[1,3,2]dioxaborolan-2-yl)-3,4-dihydro-2H-[1,8]naphthyridine-1-carboxylic acid amide (0.21 mmol, which is prepared according to the procedure for Step 3 of Example 16) is added 4-(5-bromo-pyridin-3-yl)-tetrahydro-pyran-4-ol (65.9 mg, 0.26 mmol), $PdCl_2$(DPPF) (7.8 mg, 0.01 mmol) and $Na_2CO_3$ (45.1 mg, 0.43 mmol). 0.1 mL of $H_2O$ is added and the mixture is heated for 2 hrs at 80° C. The mixture is diluted with 50 mL EtOAc, quenched with 20 mL of saturated aqueous $NH_4Cl$, washed with 2×20 mL of $H_2O$ and 1×20 mL of brine. The organic phase is dried with $MgSO_4$, filtered and concentrated. The crude material is applied to a silica preparative TLC plate, and eluted (5% $MeOH/CH_2Cl_2$) to give 73 mg of 6-[5-(4-Hydroxy-tetrahydro-pyran-4-yl)-pyridin-3-yl]-3,4-dihydro-2H-[1,8]naphthyridine-1-carboxylic acid amide.

Example 49

Synthesis of 6-(1'-Acetyl-1',2',3',4',5',6'-hexahydro-[3,4']bipyridinyl-5-yl)-3,4-dihydro-2H-[1,8]naphthyridine-1-carboxylic acid amide (Cpd 79, Table 1)

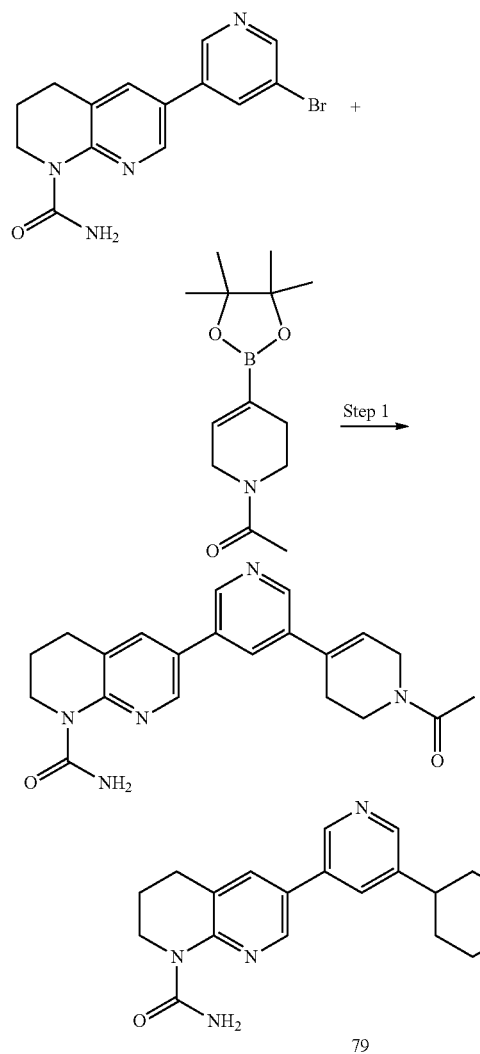

6-(5-Bromo-pyridin-3-yl)-3,4-dihydro-2H-[1,8]naphthyridine-1-carboxylic acid amide (100 mg, 0.30 mmol), which is synthesized according to the procedure for Step 1 to Step 4 of Example 15, 1-[4-(4,4,5,5-tetramethyl-[1,3,2]dioxaborolan-2-yl)-3,6-dihydro-2H-pyridin-1-yl]-ethanone (150 mg, 0.60 mmol) and 2.0 M $Na_2CO_3$ aqueous solution (0.30 mL, 0.60 mmol) are dissolved in 4.0 mL of 1,4-dioxane. The Argon gas is bubbled through the solution for 5 min. Then $PdCl_2dppf$ (15 mg, 0.021 mmol) is added. The mixture is heated at 100° C. for 5 hrs and it is cooled down to room temperature. 30 mL of DCM and 20 mL of water are added and the organic layer is separated. The aqueous layer is extracted with DCM (2×20 mL) and EtOAc (2×10 mL). The organic layers are combined and concentrated to give the crude product. Purification by flash column chromatography affords 91 mg of 6-(1'-acetyl-1',2',3',6'-tetrahydro-[3,4]bipyridinyl-5-yl)-3,4-dihydro-2H-[1,8]naphthyridine-1-carboxylic acid amide.

To a solution of 6-(1'-acetyl-1',2',3',6'-tetrahydro-[3,4]bipyridinyl-5-yl)-3,4-dihydro-2H-[1,8]naphthyridine-1-carboxylic acid amide (91 mg, 0.24 mmol) in 2.0 mL of MeOH is added 10% Pd/C (38 mg, 0.036 mmol). Then ammonium formate (60 mg, 0.96 mmol) is added and the mixture is stirred for 2 hrs at 80° C. The solid of the reaction mixture is filtered and the filtrate is concentrated to give the crude product. Purification by flash column chromatography affords 38 mg of 6-(1'-acetyl-1',2',3',4',5',6'-hexahydro-[3,4]bipyridinyl-5-yl)-3,4-dihydro-2H-[1,8]naphthyridine-1-carboxylic acid amide.

Example 50

Synthesis of 6-(5-Hydroxy-pyridin-3-yl)-3,4-dihydro-2H-[1,8]naphthyridine-1-carboxylic acid amide (Cpd 80, Table 1)

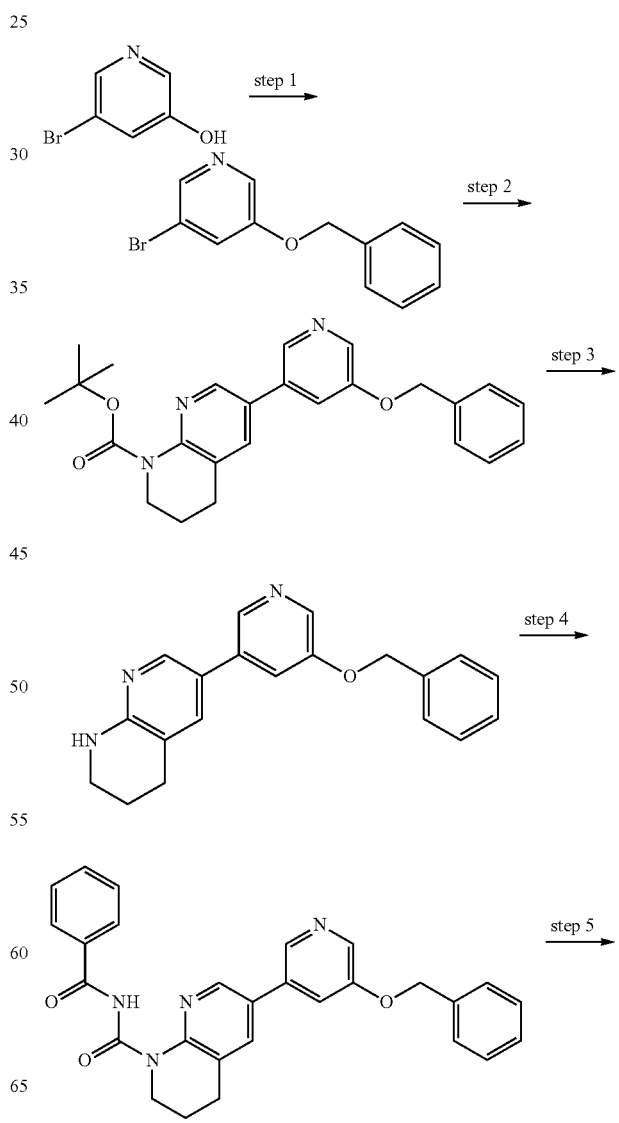

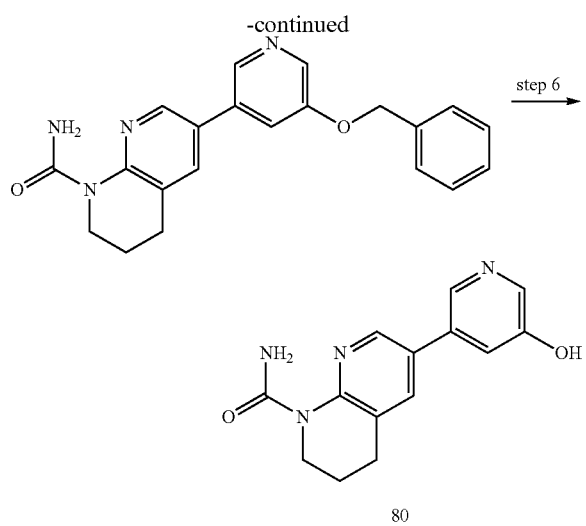

To a suspension of 5-bromo-pyridin-3-ol (1.9 g, 10.9 mmol) in acetonitrile (152 mL) is added bromomethyl-benzene (2.1 g, 12.0 mmol) and potassium carbonate (4.5 g, 32.8 mmol). The resultant mixture is stirred at room temperature for 16 h. The crude product is purified by silica gel column to afford 3-benzyloxy-5-bromo-pyridine (1.0 g).

To a solution of 6-bromo-3,4-dihydro-2H-[1,8]naphthyridine-1-carboxylic acid tert-butyl ester (800 mg, 2.6 mmol) in 1,4-dioxane (64 mL) is added bis(pinacolato)diboron (714 mg, 2.8 mmol), 1,1'-bis(diphenylphosphino)ferrocenedichloropalladium (II) (187 mg, 0.26 mmol) and potassium acetate (751 mg, 7.7 mmol) under nitrogen. The resultant mixture is heated to reflux for 2 h. After cooling to rt, 3-benzyloxy-5-bromo-pyridine (677 mg, 2.6 mmol), sodium carbonate (815 mg, 7.7 mmol) and additional 1,1'-bis(diphenylphosphino) ferrocenedichloropalladium (II) (94 mg, 0.13 mmol) are added under nitrogen. The reaction is heated to reflux for 16 h. The crude product is purified by silica gel column to obtain 6-(5-benzyloxy-pyridin-3-yl)-3,4-dihydro-2H-[1,8]naphthyridine-1-carboxylic acid tert-butyl ester (790 mg).

A solution of 6-(5-benzyloxy-pyridin-3-yl)-3,4-dihydro-2H-[1,8]naphthyridine-1-carboxylic acid tert-butyl ester (790 mg, 1.9 mmol) in 20% TFA in DCM (21 mL) is stirred at room temperature for 16 h. The solvent is removed under vacuum to afford 6-(5-benzyloxy-pyridin-3-yl)-1,2,3,4-tetrahydro-[1,8]naphthyridine (530 mg).

To a solution of 6-(5-benzyloxy-pyridin-3-yl)-1,2,3,4-tetrahydro-[1,8]naphthyridine (530 mg, 1.7 mmol) in DCM (18 mL) is added benzoyl isocyanate (368 mg, 2.5 mmol). The resultant mixture is heated at reflux for 2 h. The solvent is removed under vacuum to obtain N-[6-(5-benzyloxy-pyridin-3-yl)-3,4-dihydro-2H-[1,8]naphthyridine-1-carbonyl]-benzamide (620 mg).

To a mixture of N-[6-(5-benzyloxy-pyridin-3-yl)-3,4-dihydro-2H-[1,8]naphthyridine-1-carbonyl]-benzamide (620 mg, 1.3 mmol) in EtOH (23 ml) is added potassium carbonate (276 mg, 2.0 mmol). The resultant mixture is heated at reflux for 15 min. After cooling to rt, the solid is removed by filtration and the filtrate is concentrated under vacuum. The residue is dissolved in DCM, washed with water and brine, and is dried (Na$_2$SO$_4$). The solvent is evaporated and the crude product is purified by silica gel column to afford 6-(5-benzyloxy-pyridin-3-yl)-3,4-dihydro-2H-[1,8]naphthyridine-1-carboxylic acid amide (188 mg).

A stirred suspension of 6-(5-benzyloxy-pyridin-3-yl)-3,4-dihydro-2H-[1,8]naphthyridine-1-carboxylic acid amide (167 mg, 0.46 mmol) in EtOH (10 mL) is hydrogenated over 10% palladium on carbon (17 mg) under balloon pressure for 16 h. The catalyst is removed by filtration through diatomaceous earth, washing well with DCM. The solvent is evaporated to afford the title compound (125 mg).

Example 51

Synthesis of 6-[5-(Tetrahydro-pyran-4-ylmethoxy)-pyridin-3-yl]-3,4-dihydro-2H-[1,8]naphthyridine-1-carboxylic acid amide (Cpd 81, Table 1)

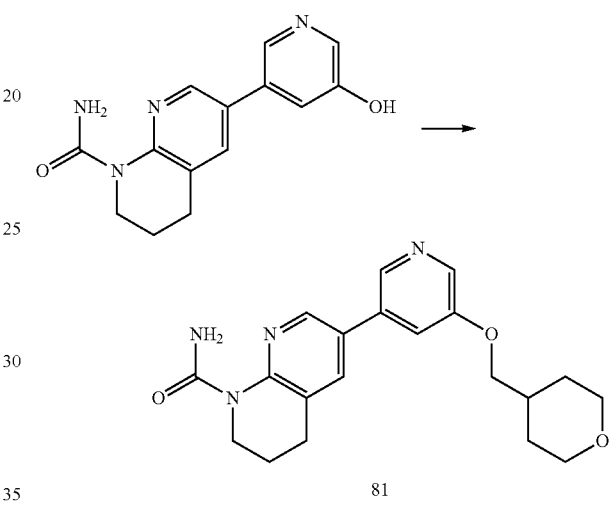

To a solution of 6-(5-hydroxy-pyridin-3-yl)-3,4-dihydro-2H-[1,8]naphthyridine-1-carboxylic acid amide (25 mg, 0.092 mmol) in DMA (1 mL) is added 4-(bromomethyl) tetrahydropyran (20 mg, 0.11 mmol) and cesium carbonate (36 mg, 0.11 mmol). The resultant mixture is stirred at 70° C. for 16 h. Water is added and the mixture is extracted with EtOAc. The organic layers are combined, washed with brine and dried (Na$_2$SO$_4$). The solvent is evaporated and the crude product is purified by silica gel column eluting (0-10% MeOH in DCM) to afford the title compound (17 mg).

Example 52

Synthesis of 6-[5-(3-Methanesulfonyl-propoxy)-pyridin-3-yl]-3,4-dihydro-2H-[1,8]naphthyridine-1-carboxylic acid amide (Cpd 82, Table 1)

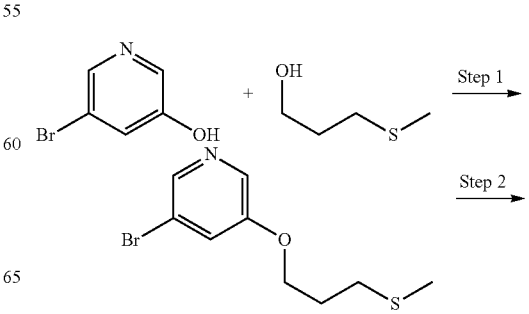

-continued

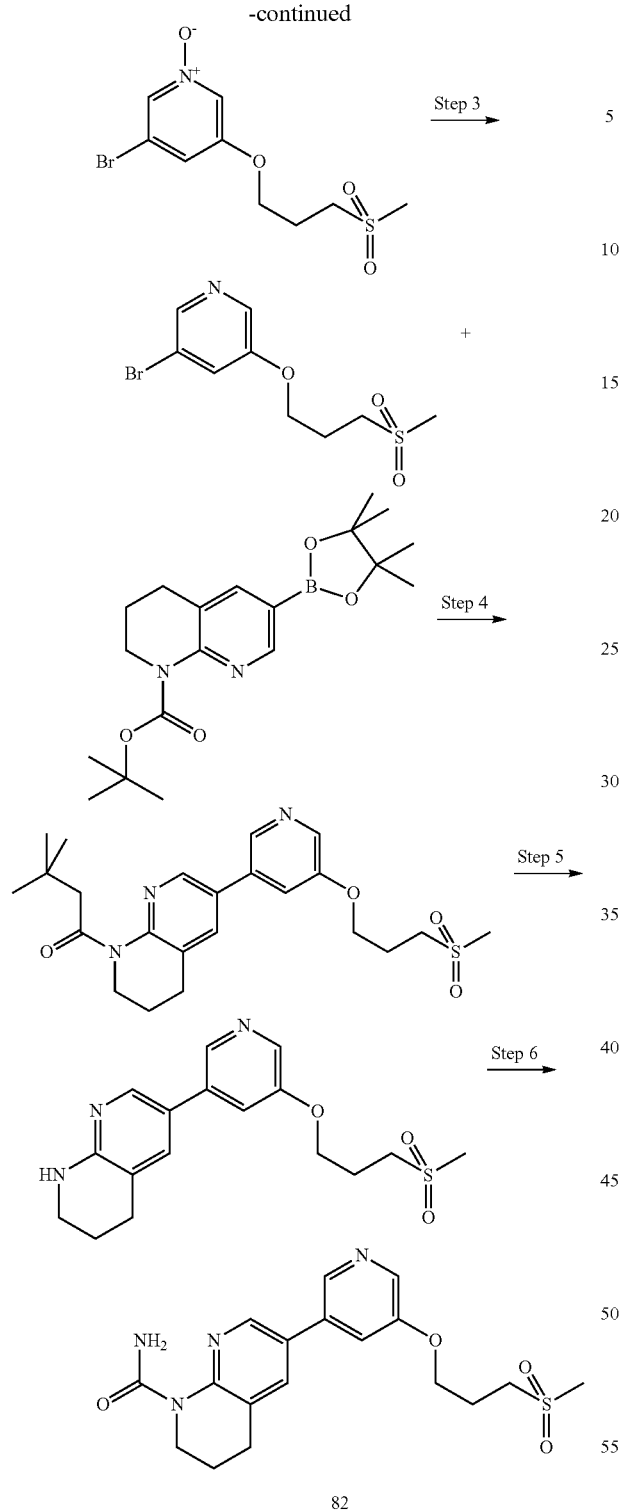

82

To a solution of PPh₃ (20 g, 76 mmol) in THF (20 mL) is added a solution of 5-bromo-pyridin-3-ol (5.0 g, 29 mmol) in THF (10 mL). Then a solution of di-tert-butyl azodicarboxylate (16 g, 69 mmol) in THF (10 ml) is added. The mixture is stirred at room temperature for 30 min and 3-methylsulfanyl-propan-1-ol (3.3 g, 31 mmol) is added. The mixture is stirred at room temperature for 16 hrs. Then the solid is filtered and the filterate is concentrated. The residue is purified by flash column chromatography to give 4.5 g of 3-bromo-5-(3-methylsulfanyl-propoxy)-pyridine.

To a solution of Oxone (12 g, 19 mmol) in H₂O (60 mL) is added a solution of 3-bromo-5-(3-methylsulfanyl-propoxy)-pyridine (2.0 g, 8.0 mmol) in acetone (60 mL). The mixture is stirred at room temperature for 16 hrs and the reaction is quenched by saturated aqueous Na₂S₂O₃ solution. The mixture is extracted with DCM and the organic layer is separated and concentrated. The residue is purified by flash column chromatography to give 2.0 g of 3-bromo-5-(3-methanesulfonyl-propoxy)-pyridine 1-oxide.

To a mixture of 3-bromo-5-(3-methanesulfonyl-propoxy)-pyridine 1-oxide (800 mg, 2.6 mmol) and saturated NH₄Cl aqueous solution (3.0 mL) in EtOH (100 mL) is added Fe (0.73 g, 13 mmol). The reaction mixture is heated at 50° C. for 16 hrs. Then the solid is filtered and the filtrate is concentrated. To the residue is added DCM and the mixture is filtered again and the filtrate is concentrated to give 0.25 g of 3-bromo-5-(3-methanesulfonyl-propoxy)-pyridine.

6-[5-(3-Methanesulfonyl-propoxy)-pyridin-3-yl]-3,4-dihydro-2H-[1,8]naphthyridine-1-carboxylic acid tert-butyl ester is synthesized according to the procedure of Suzuki Coupling Method IV, as illustrated above.

6-[5-(3-Methanesulfonyl-propoxy)-pyridin-3-yl]-1,2,3,4-tetrahydro-[1,8]naphthyridine (250 mg, 0.72 mmol) is synthesized according to the procedure for Step 2 of Example 27 using 20% trifluoroacetic acid in DCM as the reagent. It is then is converted to 25 mg of the titled product according to the procedure of Urea Formation Method I.

Example 53

Synthesis of 6-[5-(1-Acetyl-piperidin-4-yloxy)-pyridin-3-yl]-3,4-dihydro-2H-[1,8]naphthyridine-1-carboxylic acid amide (Cpd 83, Table 1)

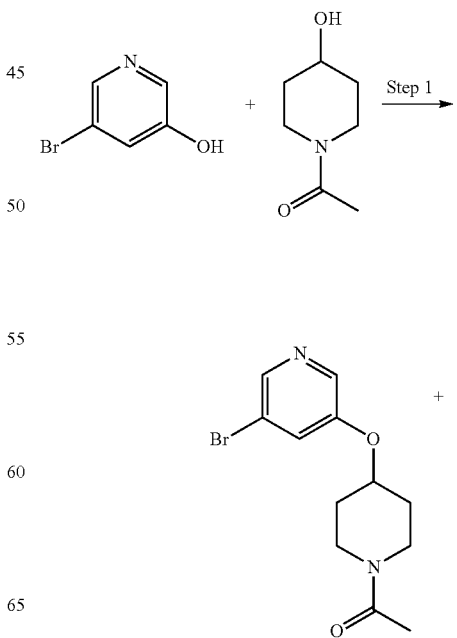

189

-continued

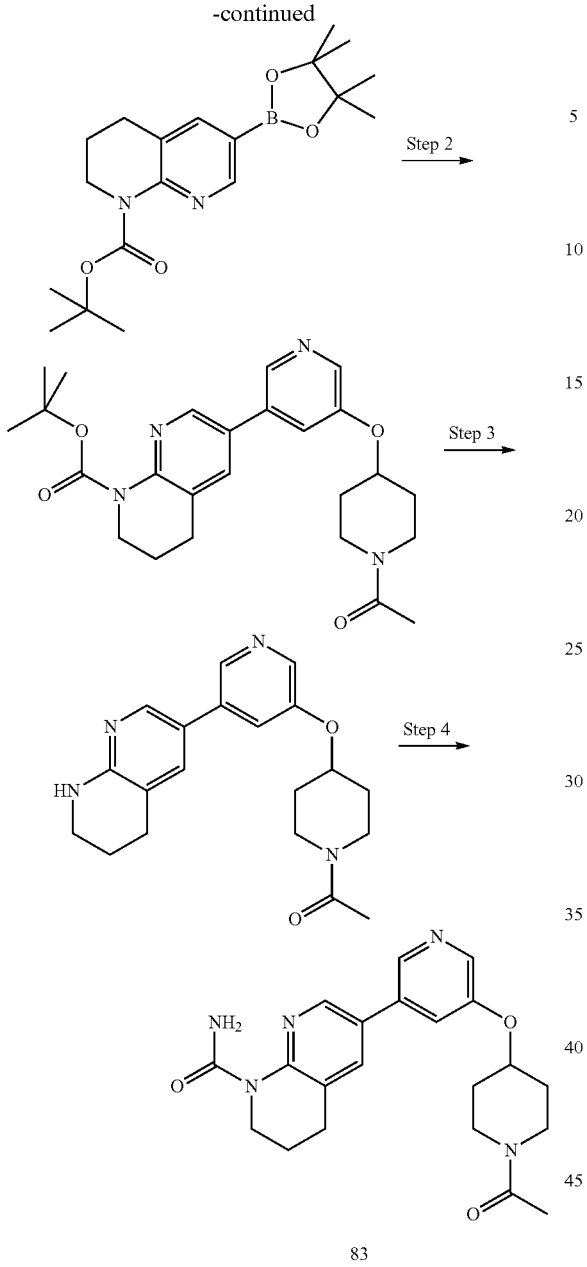

83

1-(4-Hydroxy-piperidin-1-yl)-ethanone (200 mg, 1.4 mmol) and 5-bromo-pyridin-3-ol (248 mg, 1.4 mmol) are added to a solution of PPh$_3$ (606 mg, 2.3 mmol) in THF (30 mL). Then diisopropyl azodicarboxylate (462 mg, 2.3 mmol) is added and the mixture is stirred at room temperature for 16 hrs. The mixture is then diluted with DCM, washed with water, dried over Na$_2$SO$_4$, filtered and concentrated. The residue is purified by flash column chromatography to give 250 mg of 1-[4-(5-bromo-pyridin-3-yloxy)-piperidin-1-yl]-ethanone.

6-[5-(1-Acetyl-piperidin-4-yloxy)-pyridin-3-yl]-3,4-dihydro-2H-[1,8]naphthyridine-1-carboxylic acid tert-butyl ester is synthesized according to the procedure of Suzuki Coupling Method III, as illustrated above.

1-{4-[5-(5,6,7,8-Tetrahydro-[1,8]naphthyridin-3-yl)-pyridin-3-yloxy]-piperidin-1-yl}-ethanone is synthesized according to the procedure for Step 2 of Example 27 using

190

20% trifluoroacetic acid in DCM as the reagent. 1-{4-[5-(5,6,7,8-Tetrahydro-[1,8]naphthyridin-3-yl)-pyridin-3-yloxy]-piperidin-1-yl}-ethanone (200 mg, 0.57 mmol) is converted to 34 mg of the titled product according to the procedure of Urea Formation Method I.

Example 54

Synthesis of 6-[5-(2-Hydroxy-2-methyl-propoxymethyl)-pyridin-3-yl]-3,4-dihydro-2H-[1,8]naphthyridine-1-carboxylic acid amide (Cpd 85, Table 1)

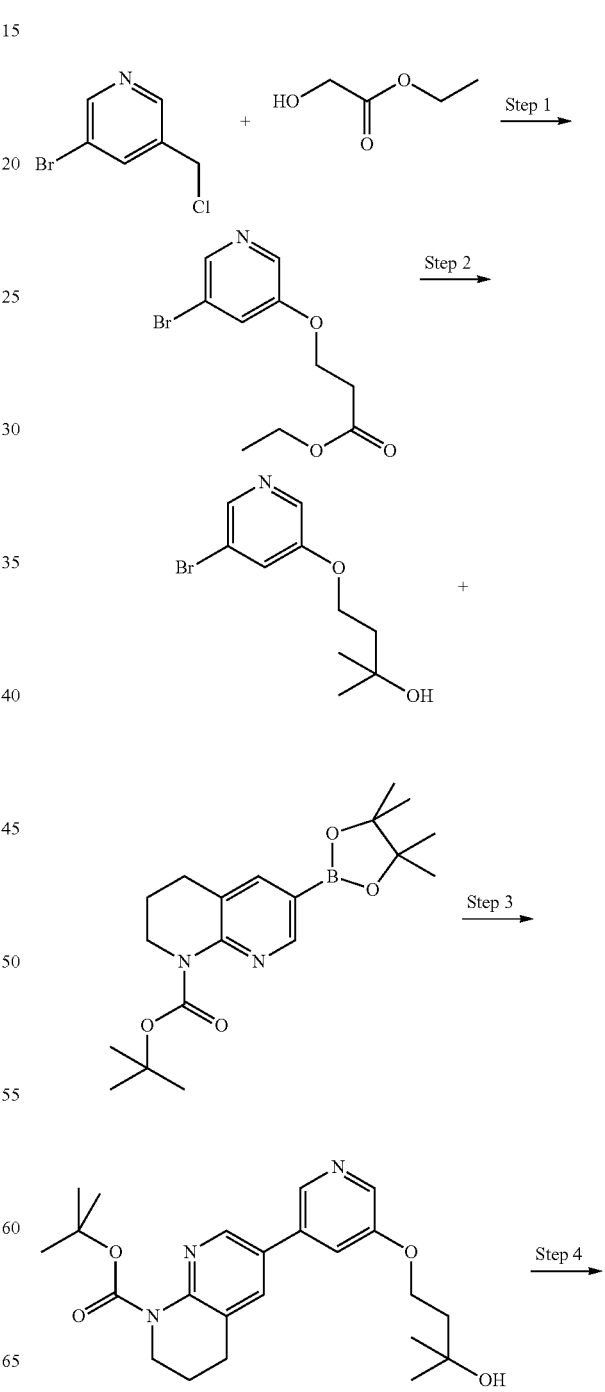

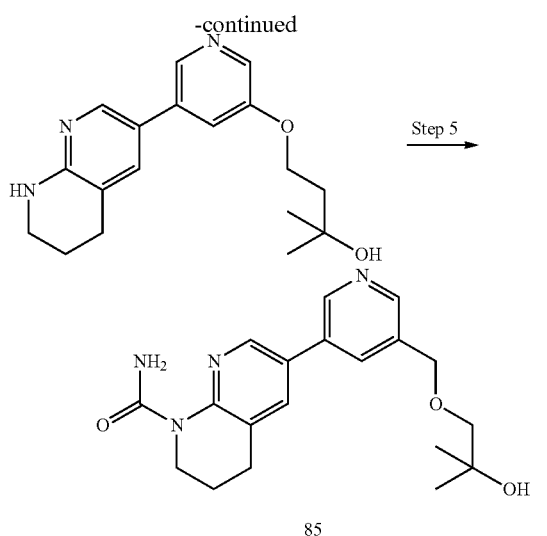

85

Hydroxy-acetic acid ethyl ester (3.7 g, 36 mmol) is added to a suspension of 60% NaH (1.5 g, 37 mmol) in DMF (70 ml) at 0° C. and the mixture is stirred at room temperature for 15 min. Then 3-bromo-5-chloromethyl-pyridine (3.0 g, 15 mmol) is added to the mixture at 0° C. and the mixture is stirred at room temperature for 16 hrs. The reaction is quenched with saturated. NH$_4$Cl aqueous solution, extracted with EtOAc three times. The organic layers are combined, washed with water and brine, dried over Na$_2$SO$_4$ and concentrated. The residue is purified by flash column chromatography to give 1.6 g of (5-bromo-pyridin-3-ylmethoxy)-acetic acid ethyl ester. 1.0 M MeMgBr (7.5 mL, 7.5 mmol) is added dropwise to a solution of (5-bromo-pyridin-3-ylmethoxy)-acetic acid ethyl ester (1.6 g, 5.9 mmol) in THF (54 mL) at 0° C. The mixture is stirred at room temperature for 16 hrs. Then the mixture is diluted with EtOAc and washed with water and brine. The organic layer is separated, dried over Na$_2$SO$_4$ and concentrated. The residue is purified by flash column chromatography to give 600 mg of 1-(5-bromo-pyridin-3-ylmethoxy)-2-methyl-propan-2-ol. It is then converted to 6-[5-(2-hydroxy-2-methyl-propoxymethyl)-pyridin-3-yl]-3,4-dihydro-2H-[1,8]naphthyridine-1-carboxylic acid tert-butyl ester according to the procedure of Suzuki Coupling Method IV.

2-Methyl-1-[5-(5,6,7,8-tetrahydro-[1,8]naphthyridin-3-yl)-pyridin-3-ylmethoxy]-propan-2-ol (300 mg, 0.96 mmol) is then synthesized according to the procedure for Step 2 of Example 27 using 20% trifluoroacetic acid in DCM as the reagent. It is then used to prepare the titled product (34 mg) according to the procedure of Urea Formation Method I.

Example 55

Synthesis of 6-[5-(3-Methanesulfonyl-propyl)-pyridin-3-yl]-3,4-dihydro-2H-[1,8]naphthyridine-1-carboxylic acid amide (Cpd 86, Table 1)

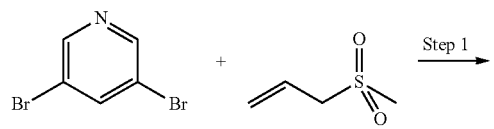

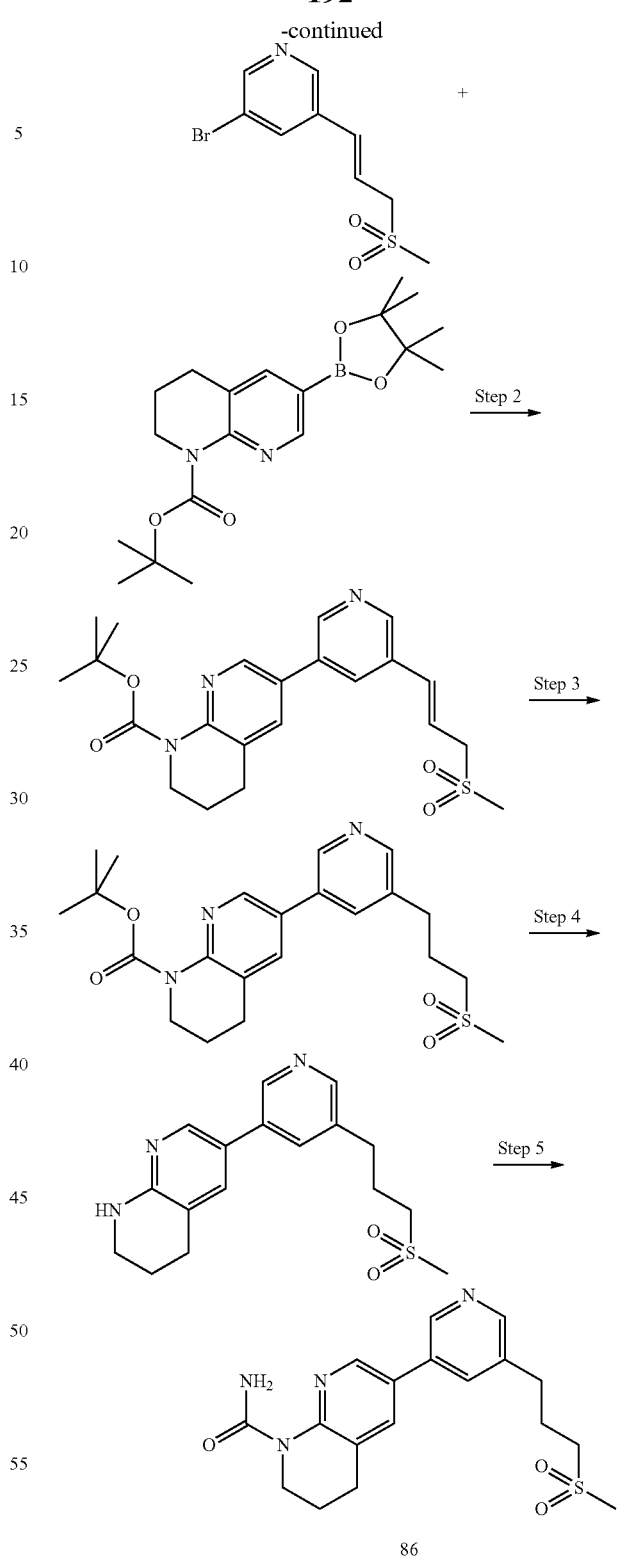

86

3-Methanesulfonyl-propene (2.4 g, 20 mmol), 3,5-dibromo-pyridine (4.7 g, 20 mmol), NaOAc (1.9 g, 60 mmol), PPh$_3$ (1.6 g, 6.0 mmol) and Pd(OAc)$_2$ (450 mg, 2.0 mmol) are mixed in 1,4-dioxane (350 ml) and heated to reflux for 16 hrs. The reaction mixture is filtered and the filtrate is concentrated. The residue is taken up in DCM and washed with water. The organic layer is dried over Na$_2$SO$_4$ and concentrated. The crude product is purified by flash column chromatography to give 2.0 g of 3-bromo-5-(-3-methanesulfonyl-propenyl)-pyridine with some PPh₃O.

The above intermediate is then used to prepare 6-[5-(-3-methanesulfonyl-propenyl)-pyridin-3-yl]-3,4-dihydro-2H-[1,8]naphthyridine-1-carboxylic acid tert-butyl ester according to the procedure of Suzuki Coupling Method V.

5% Pd on carbon (150 mg, 0.07 mmol) is added to a solution of 6-[5-(-3-methanesulfonyl-propenyl)-pyridin-3-yl]-3,4-dihydro-2H-[1,8]naphthyridine-1-carboxylic acid tert-butyl ester (340 mg, 0.79 mmol) in MeOH (30 mL). The mixture is stirred at room temperature under H₂ atmosphere of 40 PSI for 16 hrs. After filtration, the filtrate is concentrated to give 240 mg of 6-[5-(3-methanesulfonyl-propyl)-pyridin-3-yl]-3,4-dihydro-2H-[1,8]naphthyridine-1-carboxylic acid tert-butyl ester. This is then used to prepare 6-[5-(3-methanesulfonyl-propyl)-pyridin-3-yl]-1,2,3,4-tetrahydro-[1,8] naphthyridine according to the procedure for Step 2 of Example 27 using 20% trifluoroacetic acid in DCM as the reagent.

6-[5-(3-Methanesulfonyl-propyl)-pyridin-3-yl]-1,2,3,4-tetrahydro-[1,8]naphthyridine (400 mg, 1.2 mmol) is converted to 38 mg of the titled product according to the procedure of Urea Formation Method I.

Example 56

Synthesis of 6-(5-Morpholin-4-ylmethyl-pyridin-3-yl)-3,4-dihydro-2H-[1,8]naphthyridine-1-carboxylic acid amide (Cpd 87, Table 1)

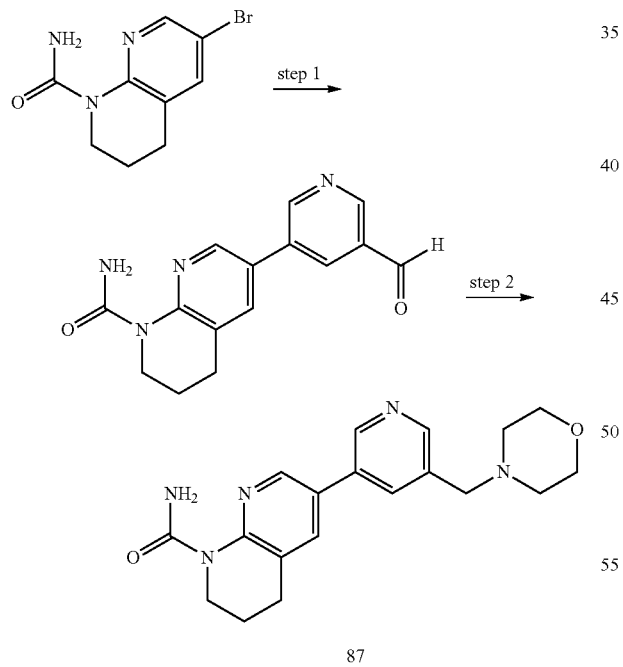

87

To a solution of 6-bromo-3,4-dihydro-2H-[1,8]naphthyridine-1-carboxylic acid amide (500 mg, 2.0 mmol) in a mixture of 1,4-dioxane (9 mL) and water (1 mL) is added 5-formylpyridine-3-boronic acid pinacol ester (501 mg, 2.1 mmol), sodium carbonate (290 mg; 2.7 mmol), and 1,1'-bis (diphenylphosphino)ferrocenedichloropalladium (II) (159 mg, 0.20 mmol). The resultant mixture is stirred at 100° C. for 2 h. EtOAc is added and the mixture is washed with saturated aqueous sodium bicarbonate solution, brine and is dried (MgSO₄). The solvent is evaporated and the crude product is purified by silica gel column (0-10% MeOH in DCM) to afford 6-(5-formyl-pyridin-3-yl)-3,4-dihydro-2H-[1,8]naphthyridine-1-carboxylic acid amide (342 mg).

To a suspension of 6-(5-formyl-pyridin-3-yl)-3,4-dihydro-2H-[1,8]naphthyridine-1-carboxylic acid amide (75 mg, 0.27 mmol) in 1,2-dicholoroethane (2 mL) is added morpholine (47 µL, 0.53 mmol) and acetic acid (3 drops). The resultant mixture is stirred at room temperature for 20 min after which sodium triacetoxyborohydride (113 mg, 0.53 mmol) is added. The mixture continues to stir at room temperature for 18 h. The reaction mixture is concentrated and purified by HPLC (C18 column, 5-50% acetonitrile/water, both 0.1% v/v TFA) and silica gel column (0-10% MeOH in DCM) to afford the title compound (75 mg).

Compounds 88 and 89 in Table 1 are synthesized according to the procedure for Example 56, substituting either commercially available reagents or the appropriate intermediates described above.

Example 57

Synthesis of 6-(5-morpholino-3-pyridyl)-3,4-dihydro-2H-1,8-naphthyridine-1-carboxamide (Compound 90, Table 1)

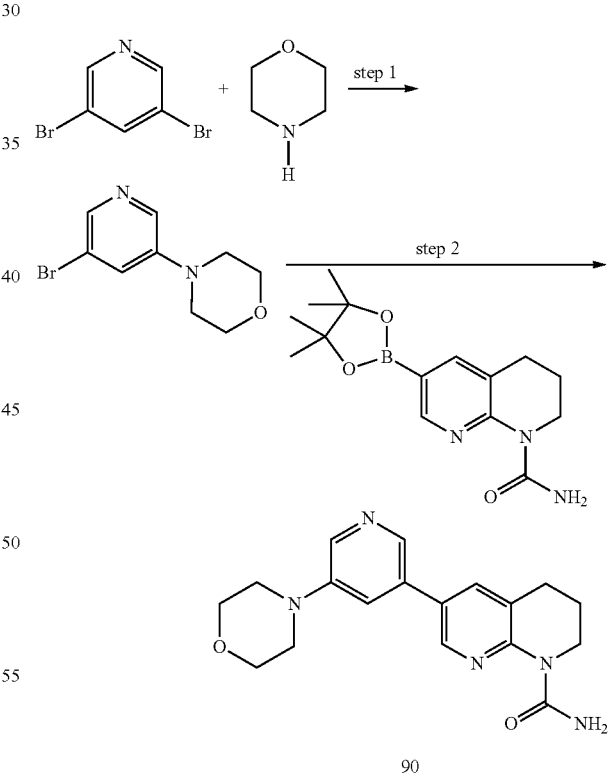

90

In a sealable tube, to a mixture of 3,5-dibromo-pyridine (3.3 g, 13.8 mmol) and NaOtBu (0.051 g, 23 mmol) in toluene (70 mL), is added morpholine (1.0 g, 11.5 mmol). The mixture is bubbled with Argon for 5 min, and then BINAP (428.9 mg, 0.69 mmol) and Pd₂(dba)₃ (210.2 mg, 0.23 mmol) are added. The reaction mixture is bubbled with Argon for another 5 min. Then the cap is sealed and the reaction mixture is heated at 120° C. overnight and then is cooled to room temperature. The reaction mixture is filtered through diatomaceous earth and washed with DCM. The filtrate is partitioned between water and DCM. The aqueous phase is further extracted with DCM (2×). The combined DCM phases are concentrated. The crude is purified by flash chromatography on a silica gel column (EtOAc/heptane 0 to 50% gradient, then 50%) to provide 1.42 g of 4-(5-bromo-3-pyridyl)morpholine.

In a sealed tube which contains the crude 6-(4,4,5,5-tetramethyl-[1,3,2]dioxaborolan-2-yl)-3,4-dihydro-2H-[1,8] naphthyridine-1-carboxylic acid amide (generated according to the procedure for Step 3 of Example 16 in 5 ml 1,4-dioxane, 0.78 mmol) is added 4-(5-bromo-pyridin-3-yl)-morpholine (228 mg, 0.94 mmol), Na$_2$CO$_3$ (166 mg, 1.56 mmol) and water (1.0 ml). The mixture is bubbled with Argon for 5 min. Then PdCl$_2$(DPPF) DCM complex (64 mg, 0.078 mmol) is added. The mixture is then bubbled with Argon for 5 min. The cap is sealed and the mixture is heated at 90° C. in oil bath for 1 h. The reaction mixture is cooled to room temperature. The reaction mixture is filtered through diatomaceous earth and washed with DCM. The filtrate is partitioned between water and DCM. The aqueous phase is extracted with DCM. The combined DCM phases are concentrated. The crude is purified by flash silica gel column (MeOH/DCM 0 to 4% gradient, then 4%). The fractions which contain the desired product are combined, concentrated and further purified by C-18 prep HPLC (MeCN with 0.1% TFA/Water with 0.1% TFA, 20 ml/min, 0 to 45% gradient over 10 min run). The desired fractions are combined and basified by 1N Na$_2$CO$_3$ to pH=10, and are extracted by DCM. The DCM phases are combined and concentrated under vacuum to obtain 60 mg of the title compound.

Compounds 92 and 93 in Table 1 are synthesized according to the procedure for Example 57, substituting either commercially available reagents or the appropriate intermediates described above.

Example 58

Synthesis of 6-[5-(2,2,2-Trifluoro-1-hydroxy-1-methyl-ethyl)-3-pyridyl]-3,4-dihydro-2H-1,8-naphthyridine-1-carboxamide (Cpd 91, Table 1)

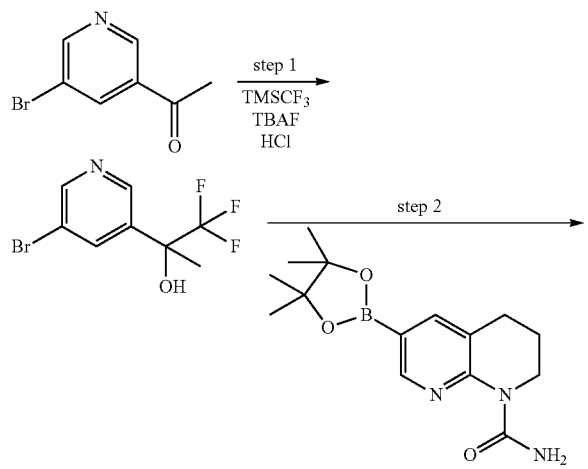

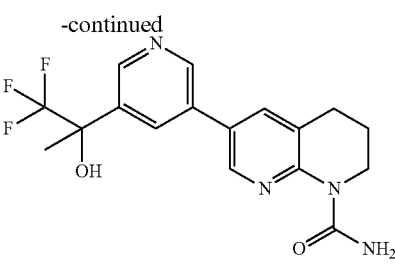

91

To a solution of 1-(5-bromo-pyridin-3-yl)-ethanone (1.0 g, 5.0 mmol) in THF (dry, 25 ml) at room temperature is added tetrabutyl-ammonium fluoride (0.35 ml, 1M in THF, 0.35 mmol). Then trimethyl-trifluoromethyl-silane (3.25 ml, 2.0M in THF, 6.5 mmol) is added to the reaction mixture dropwise. The reaction mixture is stirred for 3 h. Then HCl (4N, 6.6 ml, 26.5 mmol) is added to the mixture. The reaction mixture is stirred for 4 h at room temperature and then is neutralized by adding Na$_2$CO$_3$ powder slowly. The resulting mixture is partitioned between water and EtOAc, and the aqueous phase is extracted with EtOAc. The combined organic phases are concentrated in vacuo. The crude mixture is separated by flash silica gel column (EtOAc/Heptane 0 to 30% gradient, then 30%) to obtain 1.12 g 2-(5-bromo-3-pyridyl)-1,1,1-trifluoropropan-2-ol.

In a sealed tube which contains the crude 6-(4,4,5,5-tetramethyl-[1,3,2]dioxaborolan-2-yl)-3,4-dihydro-2H-[1,8] naphthyridine-1-carboxylic acid amide (generated according to the procedure for Step 3 of Example 16 in 5 ml 1,4-dioxane, 0.78 mmol) is added 2-(5-bromo-pyridin-3-yl)-1,1,1-trifluoro-propan-2-ol (253 mg, 0.94 mmol.), Na$_2$CO$_3$ (166 mg, 1.56 mmol) and water (1.0 ml). The mixture is bubbled with Ar for 5 min. Then PdCl$_2$(DPPF) DCM complex (64 mg, 0.078 mmol) is added. The mixture is then bubbled with Ar for 5 min. The cap is sealed and the mixture is heated at 90° C. in oil bath for 1 h and then is cooled to room temperature. The reaction mixture is filtered through diatomaceous earth and washed with DCM. The filtrate is partitioned between water and DCM. The aqueous phase is extracted with DCM. The combined DCM phases are concentrated. The crude is separated by flash silica gel column (EtOAc/heptane 0 to 100% gradient, then 100%). The fractions which contain the desired product are combined, concentrated and further purified by C-18 prep HPLC (MeCN with 0.1% TFA/Water with 0.1% TFA, 20 ml/min, 0 to 65% gradient over 10 min run). The desired fractions are combined and basified by 1N Na$_2$CO$_3$ to pH=10, and is extracted by DCM. The DCM phases are combined and concentrated under vacuum to obtain 69 mg of the title compound.

Example 59

6-[5-(1-Hydroxy-cyclobutyl)-pyridin-3-yl]-3,4-dihydro-2H-[1,8]naphthyridine-1-carboxylic acid amide (Cpd 94, Table 1)

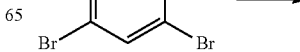

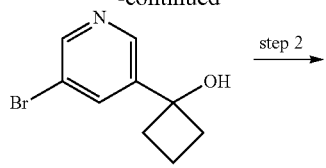

step 2

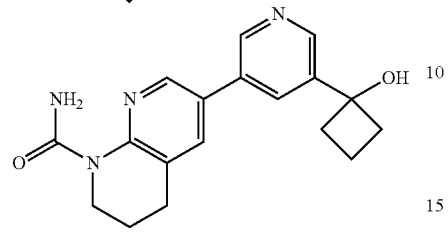

94

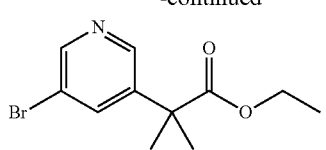

step 2

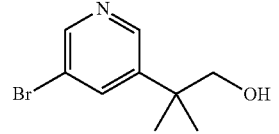

step 3

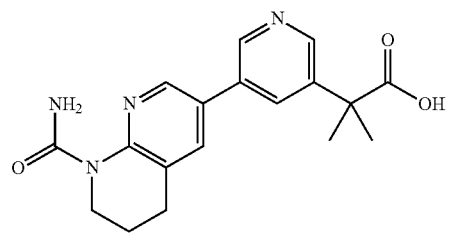

95

To a cooled (−20° C.) solution of 3,5-dibromopyridine (592 mg, 2.5 mmol) in THF (2 mL) is added a solution of isopropylmagnesium chloride-lithium chloride complex in THF (1.7 M, 1.4 mL, 2.4 mmol). The resultant mixture is stirred warming to −10° C. for 30 min. The mixture is recooled to −20° C. and cyclobutanone (230 μL, 3.0 mmol) is added. After stirring for 1 h, the reaction is quenched with saturated aqueous ammonium chloride solution and is extracted with EtOAc. The combined organic extracts are washed with water and brine, dried (MgSO$_4$) and concentrated under reduced pressure. Purification by silica gel column chromatography (0-10% MeOH in DCM) provided 1-(5-bromo-pyridin-3-yl)-cyclobutanol (322 mg).

A vial containing 6-bromo-3,4-dihydro-2H-[1,8]naphthyridine-1-carboxylic acid amide (150 mg, 0.59 mmol), bis(pinacolato)diboron (245 mg, 0.97 mmol), 1,1'-bis(diphenylphosphino)ferrocenedichloropalladium (II) (21 mg, 0.029 mmol) and potassium acetate (259 mg, 2.6 mmol) in 1,4-dioxane (14 mL) is flushed with Ar, sealed tightly and heated to 80° C. for 2 h. The reaction mixture is cooled to room temperature and 1-(5-bromo-pyridin-3-yl)-cyclobutanol (114 mg, 0.50 mmol), aqueous sodium carbonate solution (2M, 590 μL, 1.2 mmol) and additional 1,1'-bis(diphenylphosphino)ferrocenedichloropalladium (II) (21 mg, 0.029 mmol) are added. The mixture is flushed with Ar, sealed tightly and heated to 100° C. for 2 h. After cooling to room temperature the mixture is filtered through diatomaceous earth, rinsing thoroughly with EtOAc. The filtrate is concentrated and purified by HPLC (C18 column, 5-50% acetonitrile/water, both 0.1% v/v TFA) to provide the title compound (107 mg).

Example 60

Synthesis of 6-[5-(2-Hydroxy-1,1-dimethyl-ethyl)-pyridin-3-yl]-3,4-dihydro-2H-[1,8]naphthyridine-1-carboxylic acid amide (Cpd 95, Table 1)

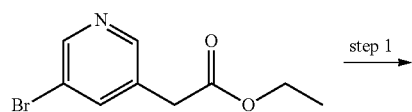

step 1

To a cooled (0° C.) solution of NaH (60% dispersion in mineral oil, 822 mg, 0.034 mol) in DMF (40 mL) is added (5-bromo-pyridin-3-yl)-acetic acid ethyl ester (3.8 g, 0.016 mol). After 2 h, iodomethane (6.4 g, 0.045 mol) is added. The resulting mixture is stirred at room temperature for 5 h. The reaction is quenched with the addition of water and is extracted with EtOAc. The combined organic layers are dried (Na$_2$SO$_4$) and concentrated. The crude product is purified by silica gel column to afford 2-(5-bromo-pyridin-3-yl)-2-methyl-propionic acid ethyl ester (2.4 g).

To a solution of 2-(5-bromo-pyridin-3-yl)-2-methyl-propionic acid ethyl ester (2.4 g, 0.009 mol) in MeOH (30 mL) is added sodium borohydride (1.7 g, 0.044 mol). The resulting mixture is heated to reflux for 5 h. The reaction is cooled to room temperature and concentrated then is washed with water and extracted with DCM. The combined organic layers are dried (Na$_2$SO$_4$), concentrated and purified by silica gel column to obtain 2-(5-bromo-pyridin-3-yl)-2-methyl-propan-1-ol (661 mg).

A vial containing 6-bromo-3,4-dihydro-2H-[1,8]naphthyridine-1-carboxylic acid amide (150 mg, 0.59 mmol), bis(pinacolato)diboron (245 mg, 0.97 mmol), 1,1'-bis(diphenylphosphino)ferrocenedichloropalladium (II) (21 mg, 0.029 mmol) and potassium acetate (259 mg, 2.6 mmol) in 1,4-dioxane (2 mL) is flushed with Ar, sealed tightly and heated to 80° C. for 2 h. The reaction mixture is cooled to room temperature and 2-(5-bromo-pyridin-3-yl)-2-methyl-propan-1-ol (114 mg, 0.50 mmol), aqueous sodium carbonate solution (2M, 590 μL, 1.2 mmol) and additional 1,1'-bis(diphenylphosphino)ferrocenedichloropalladium (II) (21 mg, 0.029 mmol) are added. The mixture is flushed with Ar, sealed tightly and heated to 100° C. for 2 h. After cooling to room temperature the mixture is filtered through diatomaceous earth, rinsing thoroughly with EtOAc. The filtrate is concentrated and purified by HPLC (C18 column, 5-50% acetonitrile/water, both 0.1% v/v TFA) to provide the title compound (110 mg).

Example 61

Synthesis of 5-[5-(1-Acetyl-piperidin-4-yloxymethyl)-pyridin-3-yl]-2,3-dihydro-pyrrolo[2,3-b]pyridine-1-carboxylic acid amide (Cpd 96, Table 1)

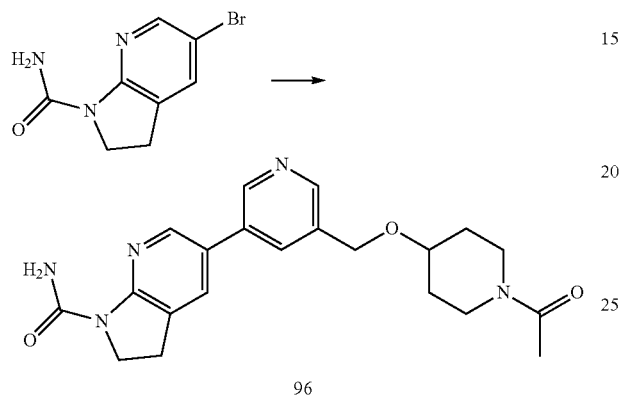

A vial containing 5-bromo-2,3-dihydro-pyrrolo[2,3-b]pyridine-1-carboxylic acid amide (150 mg, 0.62 mmol), bis(pinacolato)diboron (260 mg, 1.02 mmol), 1,1'-bis(diphenylphosphino)ferrocenedichloropalladium (II) (23 mg, 0.031 mmol) and potassium acetate (274 mg, 2.79 mmol) in 1,4-dioxane (2 mL) is flushed with Ar, sealed tightly and heated to 80° C. for 2 h. The reaction mixture is cooled to room temperature and 1-[4-(5-bromo-pyridin-3-ylmethoxy)-piperidin-1-yl]-ethanone (165 mg, 0.53 mmol), aqueous sodium carbonate solution (2M, 620 µL, 1.2 mmol) and additional 1,1'-bis(diphenylphosphino)ferrocenedichloropalladium (II) (23 mg, 0.031 mmol) are added. The mixture is flushed with Ar, sealed tightly and heated to 100° C. for 2 h. After cooling to room temperature the mixture is filtered through diatomaceous earth, rinsing thoroughly with EtOAc. The filtrate is concentrated and purified by HPLC (C18 column, 5-50% acetonitrile/water, both 0.1% v/v TFA) to provide the title compound (124 mg).

Example 62

Synthesis of 6-[5-(1-Hydroxy-2-methyl-propyl)-pyridin-3-yl]-3,4-dihydro-2H-[1,8]naphthyridine-1-carboxylic acid amide (Cpd 97, Table 1)

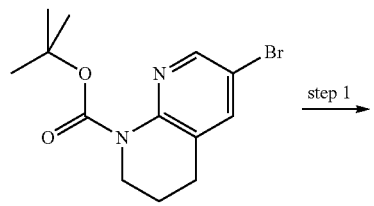

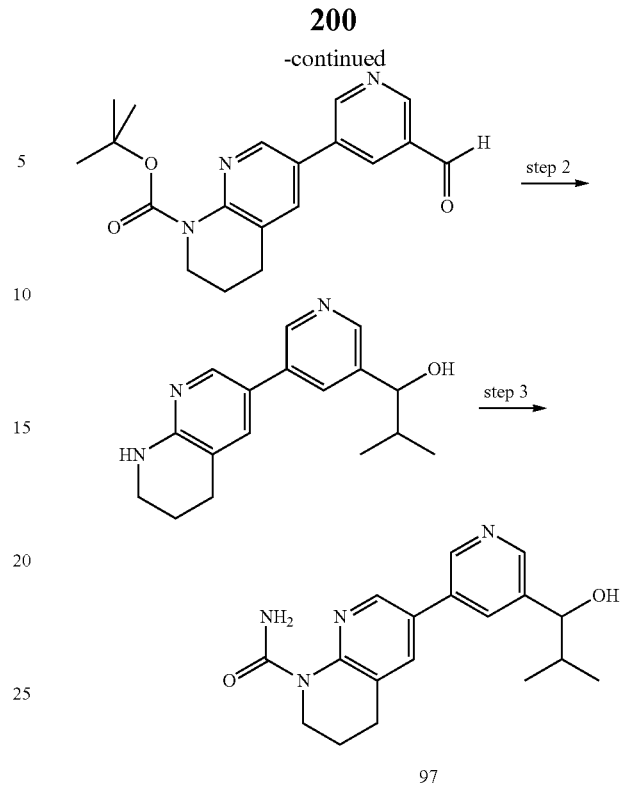

A vial containing 6-bromo-3,4-dihydro-2H-[1,8]naphthyridine-1-carboxylic acid tert-butyl ester (3.35 g, 10.7 mmol), 5-formylpyridine-3-boronic acid pinacol ester (2.74 g, 11.8 mmol), 1,1'-bis(diphenylphosphino)ferrocenedichloropalladium (II) (870 mg, 1.1 mmol), and aqueous sodium carbonate solution (2M, 7.5 mL, 15.0 mmol) in 1,4-dioxane (75 mL) is flushed with Ar, sealed tightly and heated to 100° C. for 1 h. The reaction mixture is cooled to room temperature and partitioned between water and EtOAc. The layers are separated and the aqueous is further extracted with EtOAc. The combined organic layers are washed with brine and filtered through diatomaceous earth, rinsing well with EtOAc. The filtrate is dried (Na$_2$SO$_4$) and concentrated. The crude product is purified on silica gel column (25-100% EtOAc in heptane) to afford 6-(5-formyl-pyridin-3-yl)-3,4-dihydro-2H-[1,8]naphthyridine-1-carboxylic acid tert-butyl ester (2.9 g).

To a cooled (0° C.) suspension of 6-(5-formyl-pyridin-3-yl)-3,4-dihydro-2H-[1,8]naphthyridine-1-carboxylic acid tert-butyl ester (125 mg, 0.37 mmol) in THF (1 mL) is added a solution of isopropylmagnesium chloride in THF (1.3M, 850 µL, 1.1 mmol). The resultant mixture is stirred warming to room temperature for 3 h. The reaction is quenched with saturated aqueous ammonium chloride solution and is extracted with EtOAc. The combined organic extracts are washed with water and brine, dried (Na$_2$SO$_4$) and concentrated under reduced pressure. The residue is taken up in MeOH (1 mL) and 4N HCl in 1,4-dioxane (1 mL) is added. The reaction is stirred at room temperature for 16 h then is concentrated to provide 2-methyl-1-[5-(5,6,7,8-tetrahydro-[1,8]naphthyridin-3-yl)-pyridin-3-yl]-propan-1-ol (124 mg) as the dihydrochloride salt.

To a cooled (0° C.) solution of 2-methyl-1-[5-(5,6,7,8-tetrahydro-[1,8]naphthyridin-3-yl)-pyridin-3-yl]-propan-1-ol (122 mg, 0.34 mmol) in DCM (1.5 mL) is added trichloroacetyl isocyanate (43 uL, 0.36 mmol). After stirring at 0° C. for 1 h, a solution of methanolic KOH (1.0 M, 1 mL) is added. The resulting mixture is allowed to warm and stir at room temperature for 1 h. Additional methanolic KOH (1M, 1 mL) is added and the reaction continues to stir at room temperature for 16 h. The reaction is concentrated and purified by HPLC (C18 column, 5-50% acetonitrile/water, both 0.1% v/v TFA) to provide the title compound (28 mg).

Example 63

Synthesis of 6-[5-(2-morpholinoethoxymethyl)-3-pyridyl]-3,4-dihydro-2H-1,8-naphthyridine-1-carboxamide (Cpd 98, Table 1)

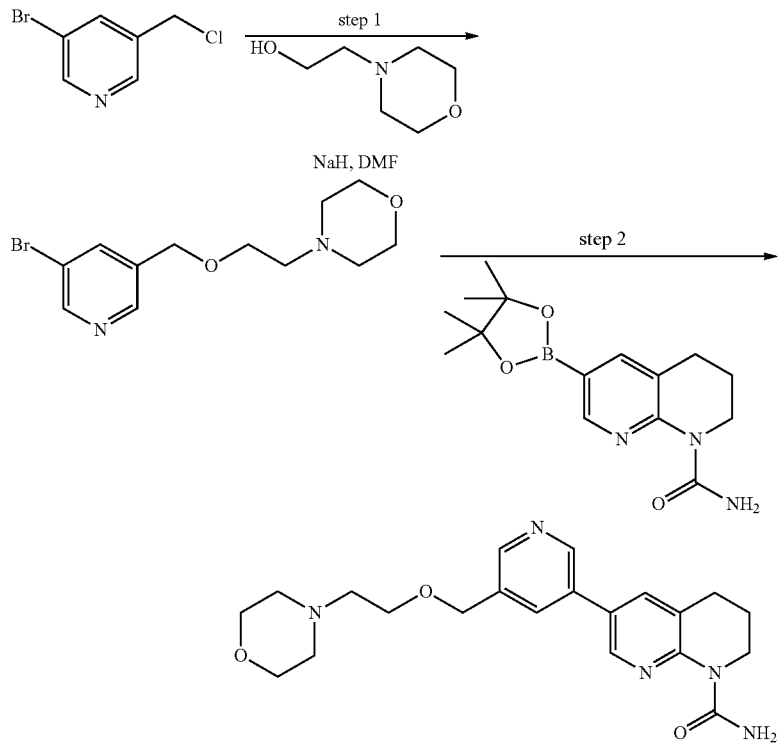

98

To the NaH (484 mg, 60% in mineral oil, 12.1 mmol) in DMF (dry, 1 mL) at 0° C., is slowly added 2-morpholin-4-yl-ethanol (1.47 ml, 12.1 mmol). Then the mixture is stirred at 0° C. for 30 min. 3-bromo-5-chloromethyl-pyridine (500 mg, 2.42 mmol) is added at 0° C. The mixture is then stirred at room temperature overnight and is quenched by adding water dropwise. The mixture is partitioned between DCM and water. The DCM phase is separated and then washed with water twice. The DCM phase is evaporated under high vacuum. The residue is separated by silica gel flash column (MeOH/DCM 0 to 5% gradient, then 5%) to obtain 370 mg of 4-[2-[(5-bromo-3-pyridyl)methoxy]ethyl]morpholine.

To a sealed tube which contained the crude 6-(4,4,5,5-tetramethyl-[1,3,2]dioxaborolan-2-yl)-3,4-dihydro-2H-[1,8] naphthyridine-1-carboxylic acid amide (generated according to the procedure for Step 3 of Example 16 in 5 ml 1,4-dioxane, 0.78 mmol) is added 4-[2-(5-bromo-pyridin-3-ylmethoxy)-ethyl]-morpholine (282 mg, 0.937 mmol), Na$_2$CO$_3$ (166 mg, 1.56 mmol) and Water (0.5 ml). The mixture is bubbled with Ar for 5 min. Then PdCl$_2$(DPPF) (57.1 mg, 0.078 mmol) is added. The mixture is then bubbled with Ar for 5 min. The cap is sealed and the mixture is heated at 90° C. for 1 h, and then is cooled to room temperature. The reaction mixture is filtered through diatomaceous earth and washed with DCM. The filtrate is partitioned between water and DCM. The aqueous phase is extracted with DCM. The combined DCM phases are concentrated. The crude is separated by flash silica gel column (MeOH/DCM 0 to 10% gradient, then 10%). The fractions which contained the desired product are combined, concentrated and then further purified by C-18 prep HPLC (MeCN with 0.1% TFA/Water with 0.1% TFA, 20 ml/min, 0 to 45% gradient over 10 min run). The desired fractions are combined and basified by 1N Na$_2$CO$_3$ to pH=11, and is extracted by DCM. The DCM phases are combined and concentrated under vacuum to obtain 89 mg of the title compound.

Example 64

Synthesis of 6-[5-(1-methoxy-1-methyl-ethyl)-3-pyridyl]-3,4-dihydro-2H-1,8-naphthyridine-1-carboxamide (Cpd 99, Table 1)

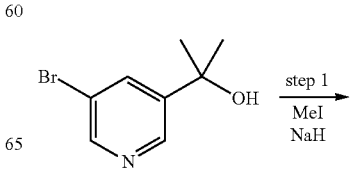

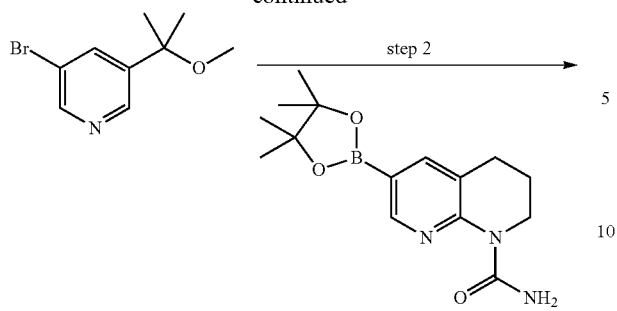

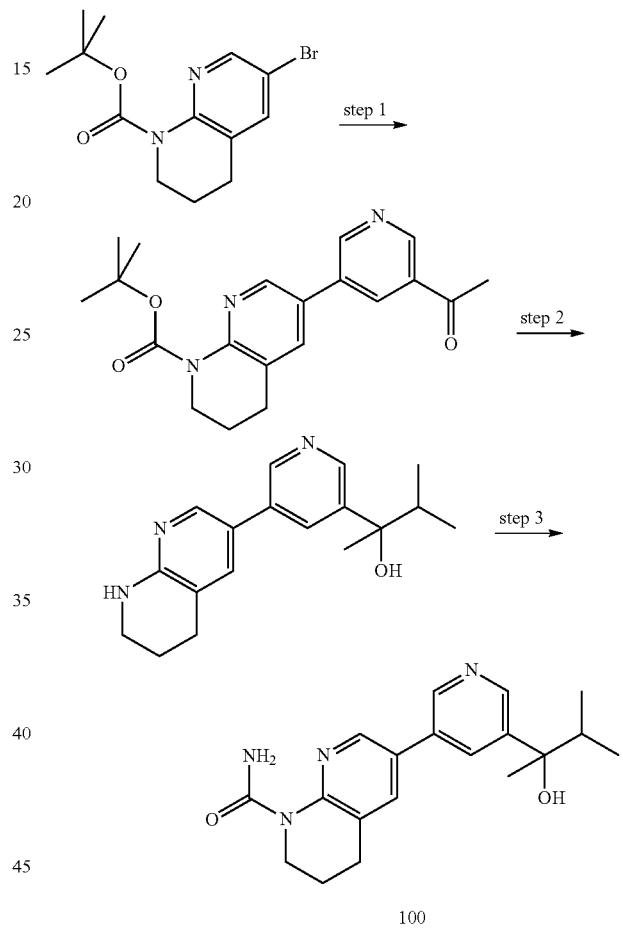

To a mixture of NaH (240 mg, 6.02 mmol) in DMF (dry, 4 mL) at 0° C. is added the solution of 2-(5-bromo-pyridin-3-yl)-propan-2-ol (500 mg, 2.31 mmol) in DMF (dry, 4 mL). The mixture is stirred at 0° C. for 15 min then raised to room temperature and stirred for 1 h. The mixture is then cooled back to 0° C. and iodomethane (397 mg, 2.80 mmol) iss added. The reaction mixture is stirred at room temperature overnight and is quenched by adding water dropwise. The mixture is partitioned between DCM and water. The DCM phase is separated and then washed with water twice. The DCM phase is evaporated under high vacuum. The residue is separated by silica gel flash column (EtOAc/Hepane 0 to 40% gradient, then 40%) to obtain 371 mg 3-bromo-5-(1-methoxy-1-methyl-ethyl)pyridine.

To a sealed tube which contained the crude 6-(4,4,5,5-tetramethyl-[1,3,2]dioxaborolan-2-yl)-3,4-dihydro-2H-[1,8] naphthyridine-1-carboxylic acid amide (generated according to the procedure for Step 3 of Example 16 in 5 mL 1,4-dioxane, 0.78 mmol) is added 3-bromo-5-(1-methoxy-1-methyl-ethyl)-pyridine (216 mg, 0.937 mmol), $Na_2CO_3$ (166 mg, 1.56 mmol) and water (0.5 mL). The mixture is bubbled with Ar for 5 min. Then $PdCl_2(DPPF)$ (57 mg, 0.078 mmol) is added. The mixture is then bubbled with Ar for 5 min. The cap is sealed and the mixture is heated at 90° C. for 1 h and then is cooled to room temperature. The reaction mixture is filtered through diatomaceous earth and washed with DCM. The filtration is partitioned between water and DCM. The aqueous phase is extracted with DCM. The combined DCM phases are concentrated. The crude is separated by flash silica gel column (MeOH/DCM 0 to 5% gradient, then 5%) and then separated by C-18 prep HPLC ((MeCN with 0.1% TFA/ Water with 0.1% TFA, 20 ml/min, 0 to 65% gradient over 10 min run). The resulting material is further purified by C-18 HPLC (31% $CH_3CN$ in 2.5 mM $NH_4HCO_3$ aqueous solution, isocratic for 15 min plus 5 min wash at 17 ml/min) to obtain 66 mg of the title compound.

Example 65

Synthesis of 6-[5-(1-Hydroxy-1,2-dimethyl-propyl)-pyridin-3-yl]-3,4-dihydro-2H-[1,8]naphthyridine-1-carboxylic acid amide (Cpd 100, Table 1)

A vial containing 1-(5-bromo-pyridin-3-yl)-ethanone (1.59 g, 8.0 mmol), bis(pinacolato)diboron (2.53 g, 9.9 mmol), 1,1'-bis(diphenylphosphino)ferrocenedichloropalladium(II) DCM complex (486 mg, 0.66 mmol) and potassium acetate (1.96 g, 19.9 mmol) in 1,4-dioxane (100 mL) is flushed with Ar, sealed tightly and heated to 70° C. for 16 h. The reaction mixture is cooled to room temperature and 6-bromo-3,4-dihydro-2H-[1,8]naphthyridine-1-carboxylic acid tert-butyl ester (2.08 g, 6.6 mmol), aqueous sodium carbonate solution (2M, 9.9 mL, 19.9 mmol) and additional 1,1'-bis(diphenylphosphino)ferrocenedichloropalladium (II) (486 mg, 0.66 mmol) are added. The mixture is flushed with Ar, sealed tightly and heated to 100° C. for 2 h. The reaction mixture is cooled to room temperature and partitioned between water and EtOAc. The layers are separated and the aqueous is further extracted with EtOAc. The combined organic layers are washed with brine and filtered through diatomaceous earth, rinsing well with EtOAc. The filtrate is dried (Na$_2$SO$_4$) and concentrated. The crude product is purified by silica gel column (25-100% EtOAc in heptane) to afford 6-(5-acetyl-pyridin-3-yl)-3,4-dihydro-2H-[1,8]naphthyridine-1-carboxylic acid tert-butyl ester (1.85 g).

To a cooled (0° C.) suspension of 6-(5-acetyl-pyridin-3-yl)-3,4-dihydro-2H-[1,8]naphthyridine-1-carboxylic acid tert-butyl ester (125 mg, 0.35 mmol) in THF (2 mL) is added a solution of isopropylmagnesium chloride in THF (1.3M, 816 μL, 1.1 mmol). The resultant mixture is stirred warming to room temperature for 1 h. The reaction is quenched with saturated aqueous ammonium chloride solution and is extracted with EtOAc. The combined organic extracts are washed with water and brine, dried (Na$_2$SO$_4$) and concentrated under reduced pressure. The residue is taken up in MeOH (3 mL) and 4N HCl in 1,4-dioxane (3 mL) is added. The reaction is stirred at room temperature for 16 h and is concentrated to provide 3-methyl-2-[5-(5,6,7,8-tetrahydro-[1,8]naphthyridin-3-yl)-pyridin-3-yl]-butan-2-ol (131 mg) as the dihydrochloride salt.

To a cooled (0° C.) solution of 3-methyl-2-[5-(5,6,7,8-tetrahydro-[1,8]naphthyridin-3-yl)-pyridin-3-yl]-butan-2-ol (131 mg, 0.35 mmol) in DCM (1.5 mL) is added a trichloroacetyl isocyanate (44 μL, 0.36 mmol). After stirring at 0° C. for 1 h, a solution of methanolic KOH (1M, 1 mL) is added. The resulting mixture is allowed to warm and stir at room temperature for 16 h. The reaction is concentrated and purified by HPLC (C18 column, 5-50% acetonitrile/water, both 0.1% v/v TFA) to provide the title compound (26 mg).

Example 66

Synthesis of 1-{4-[5-(8-Acetyl-5,6,7,8-tetrahydro-[1,8]naphthyridin-3-yl)-pyridin-3-ylmethoxy]-piperidin-1-yl}-ethanone (Cpd 101, Table 1)

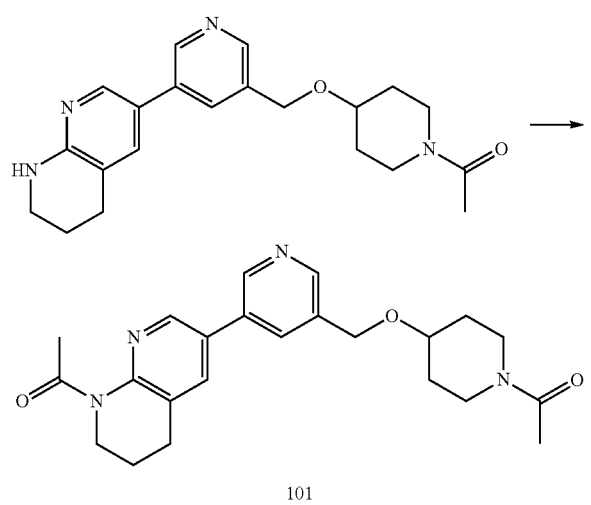

To a solution of 1-{4-[5-(5,6,7,8-tetrahydro-[1,8]naphthyridin-3-yl)-pyridin-3-ylmethoxy]-piperidin-1-yl}-ethanone (36 mg, 0.098 mmol) in DCM (1 mL) is added acetyl chloride (21 μL, 0.30 mmol) and pyridine (47 μL, 0.59 mmol). The resultant mixture is stirred at room temperature for 16 h. The reaction mixture is concentrated and purified by HPLC (C18 column, 5-60% acetonitrile/water, both 0.1% v/v TFA) to provide the title compound (28 mg).

Example 67

Synthesis of 6-[5-(3-Hydroxy-oxetan-3-yl)-pyridin-3-yl]-3,4-dihydro-2H-[1,8]naphthyridine-1-carboxylic acid amide (Cpd 102, Table 1)

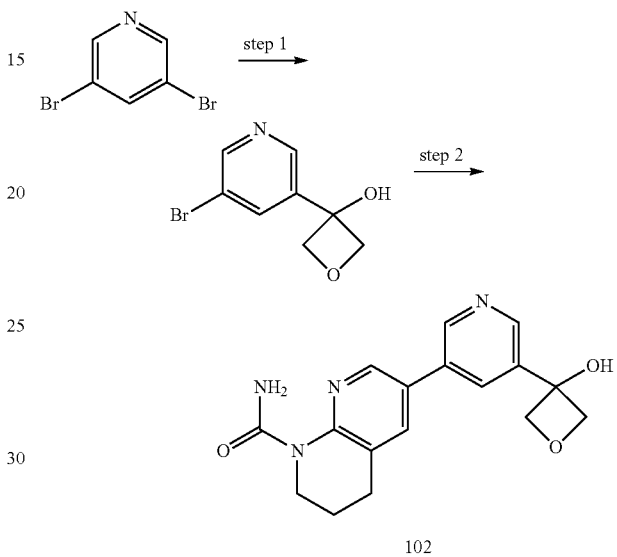

To a cooled (−20° C.) solution of 3,5-dibromopyridine (1.2 g, 5.0 mmol) in THF (2 mL) is added a solution of isopropylmagnesium chloride-lithium chloride complex in THF (1.7 M, 2.9 mL, 4.9 mmol). The resultant mixture is stirred warming to −10° C. for 30 min. The mixture is recooled to −20° C. and 3-oxetanone (432 mg, 6.0 mmol) is added. After stirring for 1 h, the reaction is quenched with saturated aqueous ammonium chloride solution and is extracted with EtOAc. The combined organic extracts are washed with water and brine, dried (MgSO$_4$) and concentrated under reduced pressure. Purification by silica gel column (0-10% MeOH in DCM) provided 3-(5-bromo-pyridin-3-yl)-oxetan-3-ol (320 mg).

A vial containing 6-bromo-3,4-dihydro-2H-[1,8]naphthyridine-1-carboxylic acid amide (350 mg, 1.4 mmol), bis(pinacolato)diboron (573 mg, 2.3 mmol), 1,1'-bis(diphenylphosphino)ferrocenedichloropalladium (II) (50 mg, 0.068 mmol) and potassium acetate (604 mg, 6.2 mmol) in 1,4-dioxane (10 mL) is flushed with Ar, sealed tightly and heated to 80° C. for 2 h. The reaction mixture is cooled to room temperature and a solution of 3-(5-bromo-pyridin-3-yl)-oxetan-3-ol (314 mg, 1.37 mmol) in 1,4-dioxane (4 mL), aqueous sodium carbonate solution (2M, 1.4 mL, 2.7 mmol) and additional 1,1'-bis(diphenylphosphino)ferrocenedichloropalladium (II) (50 mg, 0.068 mmol) are added. The mixture is flushed with Ar, sealed tightly and heated to 100° C. for 90 min. After cooling to room temperature the mixture is partitioned between water and EtOAc. The layers are separated and the aqueous is further extracted with EtOAc. The combined organic layers are washed with brine, dried (Na$_2$SO$_4$) and concentrated. To the residue is added MeOH to form a precipitate which is collected by filtration to afford the title compound (28 mg).

Example 68

Synthesis of 6-Pyridin-3-yl-3,4-dihydro-2H-[1,8]naphthyridine-1-carboxylic acid methylamide (Cpd 103, Table 1)

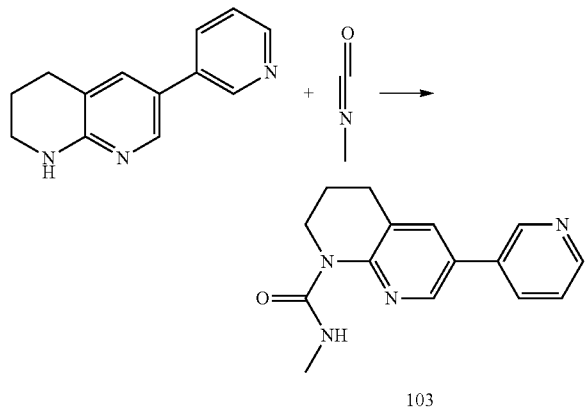

A solution of 6-pyridin-3-yl-1,2,3,4-tetrahydro-[1,8]naphthyridine (40 mg, 0.19 mmol) in 2 mL of THF is added to methyl isocyanate (16 mg, 0.28 mmol) followed by the addition of Et$_3$N (61 mg, 0.60 mmol). The mixture is stirred at ambient temperature for 16 hrs. To the mixture is added 0.5 mL of water, stirred for 5 minutes and concentrated in vacuo. The residue is dissolved in 1 mL of DMF, filtered and purified by reverse phase HPLC to give 23 mg of the titled product.

Example 69

Synthesis of 6-[5-(Pyrrolidine-1-carbonyl)-pyridin-3-yl]-3,4-dihydro-2H-[1,8]naphthyridine-1-carboxylic acid amide (Cpd 104, Table 1)

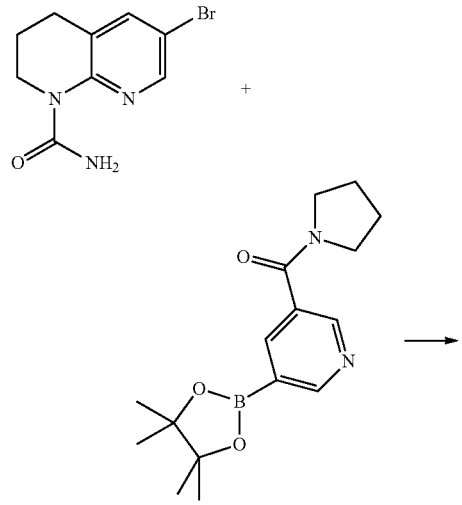

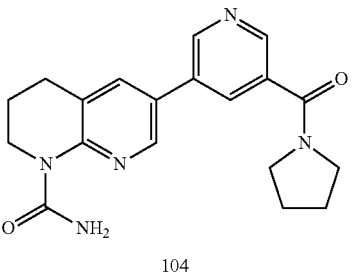

To a mixture of 6-bromo-3,4-dihydro-2H-[1,8]naphthyridine-1-carboxylic acid amide (55 mg, 0.22 mmol) and pyrrolidin-1-yl-[5-(4,4,5,5-tetramethyl-[1,3,2]dioxaborolan-2-yl)-pyridin-3-yl]-methanone (78 mg, 0.26 mmol) in 1,4-dioxane (2 mL) is added 2.0 N aqueous sodium carbonate solution (0.23 mL, 0.46 mmol). Argon gas is bubbled through the solution for 5 min. To the mixture is added PdCl$_2$(dppf) catalyst (12 mg, 0.02 mmmol) in one portion. The mixture is heated at 90° C. for 2 hrs. The mixture is filtered through short pad of diatomaceous earth, rinsing with EtOAC (3×1 mL). The filtrate is dried under reduced pressure. The reaction mixture is purified by Mass-triggered reverse phase HPLC to give 36 mg of the titled product.

Compounds 105 to 117 in Table 1 are synthesized according to the procedure for Example 69, substituting either commercially available reagents or the appropriate intermediates described above.

Example 70

Synthesis of 6-[5-(4-Cyano-phenyl)-pyridin-3-yl]-3,4-dihydro-2H-[1,8]naphthyridine-1-carboxylic acid amide (Cpd 118, Table 1)

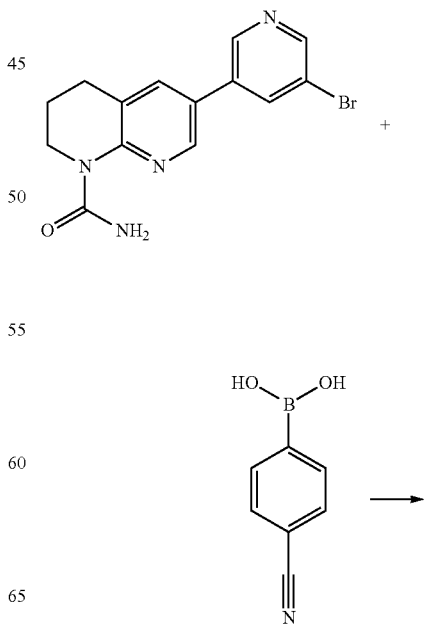

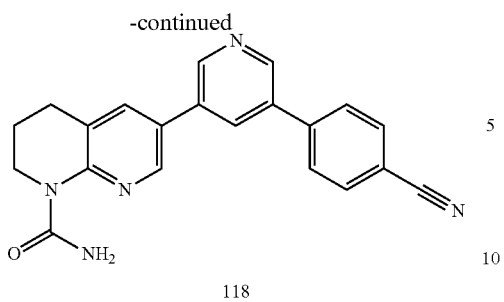

118

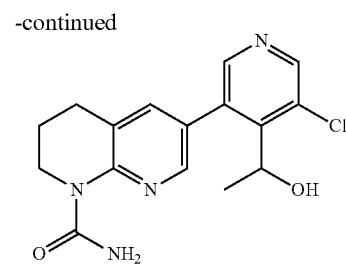

159

A solution of 6-(5-bromo-pyridin-3-yl)-3,4-dihydro-2H-[1,8]naphthyridine-1-carboxylic acid amide (50 mg, 0.15 mmol), which is synthesized according to the procedure for Step 1 to Step 4 of Example 15) in 2 mL of degassed 1,4-dioxane and 2.0 M Na$_2$CO$_3$ solution (0.15 mL, 0.30 mmol) are added to 4-cyanophenyl boronic acid (44 mg, 0.30 mmol) with silicycle catalyst DPP-Pd (60 mg, 0.015 mmol). The mixture is heated to 100° C. for 2 hrs, filtered and rinsed with 5 mL of MeOH. The solvent is removed in vacuo. The residue is dissolved in 1 mL of DMF, filtered and purified by reverse phase HPLC. The appropriate fractions are concentrated to give 1.0 mg of the titled product.

Compounds 119-154 in Table 1 are synthesized according to the procedure for the synthesis of Compound 118, substituting commercially available boronic acids/esters for the appropriate reagents described above.

Example 71

Synthesis of 6-[5-Chloro-4-(1-hydroxy-ethyl)-pyridin-3-yl]-3,4-dihydro-2H-[1,8]naphthyridine-1-carboxylic acid amide (Cpd 159, Table 1)

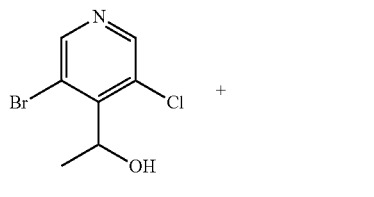

Step 1

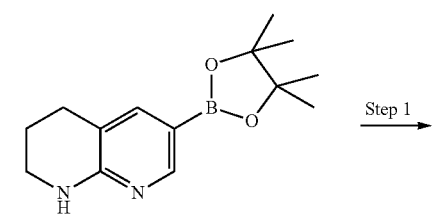

Step 2

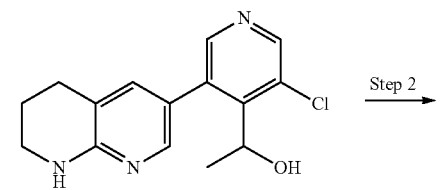

1-[3-Chloro-5-(5,6,7,8-tetrahydro-[1,8]naphthyridin-3-yl)-pyridin-4-yl]-ethanol is synthesized according to the procedure of Suzuki Coupling Method VI using 1-(3-bromo-5-chloro-pyridin-4-yl)-ethanol (which is prepared according to Step 1 of Example 78) and crude 6-(4,4,5,5-tetramethyl-[1,3,2]dioxaborolan-2-yl)-1,2,3,4-tetrahydro-[1,8]naphthyridine (that is prepared according to Step 4 of Example 105).

6-[5-Chloro-4-(1-hydroxy-ethyl)-pyridin-3-yl]-3,4-dihydro-2H-[1,8]naphthyridine-1-carboxylic acid amide is synthesized according to the procedure of Urea Formation Method II using 1-[3-chloro-5-(5,6,7,8-tetrahydro-[1,8]naphthyridin-3-yl)-pyridin-4-yl]-ethanol.

Example 72

Synthesis of 6-[5-(3-Hydroxy-tetrahydro-furan-3-yl)-pyridin-3-yl]-3,4-dihydro-2H-[1,8]naphthyridine-1-carboxylic acid amide (Cpd 160, Table 1)

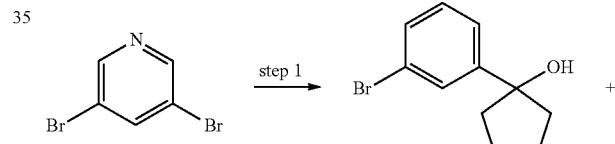

step 1

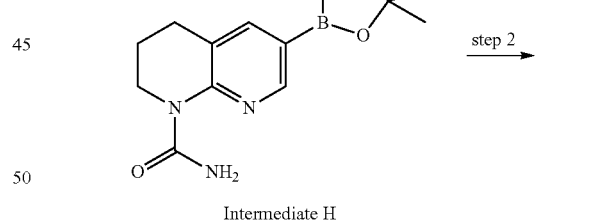

step 2

Intermediate H

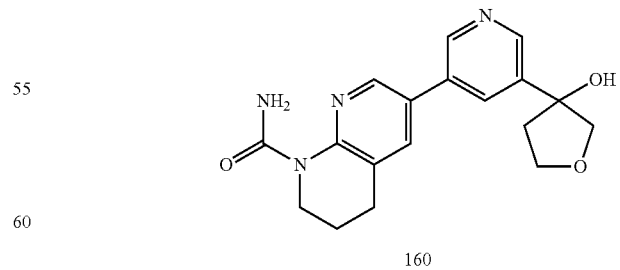

160

To a cooled (−15° C.) solution of 3,5-dibromopyridine (1.2 g, 5.0 mmol) in THF (12 mL) is added a solution of isopropylmagnesium chloride-lithium chloride complex in THF (1.7 M; 2.9 mL, 4.9 mmol). The resultant mixture is stirred at −15° C. for 30 min and dihydro-furan-3-one (517 mg, 6.0 mmol) is added. After stirring for 16 h, the reaction is quenched with saturated aqueous NH₄Cl solution and is extracted with EtOAc. The combined organic extracts are washed with water and brine, dried and concentrated under reduced pressure. Purification by flash column chromatography provides 125 mg of 3-(5-bromo-pyridin-3-yl)-tetrahydro-furan-3-ol.

The titled product is synthesized according to the procedure of Suzuki Coupling Method VI using 3-(5-bromo-pyridin-3-yl)-tetrahydro-furan-3-ol and crude Intermediate H.

Chiral separation of the racemic titled product (67 mg, 0.20 mmol) using Supercritical Fluid Chromatography (Column: LUX 5µ Cellulose 1 Analytical, Mobile phase: 30% 1:1:1 MeOH:EtOH:IPA (0.1% DEA):CO2 @ 3 ml/min, 200 bar, 40° C.) affords 29 mg of Compound 168 (Retention time 7.8 min) and 24 mg of Compound 167 (Retention time 9.5 min) in Table 1.

Compounds 180 and 224 in Table 1 are synthesized according to the procedure for Example 72, substituting either commercially available reagents or the appropriate intermediates described above.

Chiral separation of the racemic Compound 180 (169 mg, 0.48 mmol) using Supercritical Fluid Chromatography (Column: LUX 5µ Cellulose 3 Analytical, Mobile phase: 20% 1:1:1 MeOH:EtOH:iPA (0.1% DEA):CO2 @ 3 ml/min, 200 bar, 40° C.) affords 52 mg of Compound 181 (Retention time 3.4 min) and 53 mg of Compound 182 (Retention time 4.9 min) in Table 1.

Example 73

Synthesis of 6-(5-Oxetan-3-yl-pyridin-3-yl)-3,4-dihydro-2H-[1,8]naphthyridine-1-carboxylic acid amide (Cpd 161, Table 1)

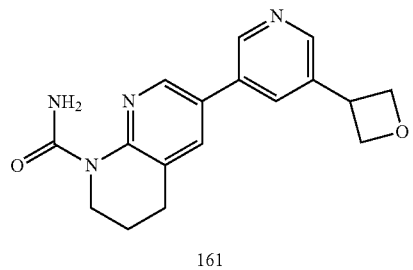

161

A mixture of (5-bromopyridin-3-yl)boronic acid (330 mg, 1.6 mmol), nickel(II) iodide (15 mg, 0.049 mmol), trans-2-amino-cyclohexanol hydrochloride (7 mg, 0.049 mmol) and sodium bis(trimethylsilyl)amide solution in THF (1M; 1.6 mL, 1.6 mmol) in 2-propanol (2 mL) is stirred under Ar for 10 min. 3-Iodo-oxetane (150 mg, 0.82 mmol) is added and the mixture is heated at 80° C. for 90 min. After cooling to room temperature, the mixture is filtered through diatomaceous earth, rinsing thoroughly with EtOH. The filtrate is concentrated to give crude product. Purification by flash column chromatography affords 50 mg of 3-bromo-5-oxetan-3-yl-pyridine.

6-(5-Oxetan-3-yl-pyridin-3-yl)-3,4-dihydro-2H-[1,8] naphthyridine-1-carboxylic acid amide is synthesized according to the procedure of Suzuki Coupling Method VI using 3-bromo-5-oxetan-3-yl-pyridine and Intermediate H (crude).

Example 74

Synthesis of 6-[5-(2-Methanesulfonyl-ethyl)-pyridin-3-yl]-3,4-dihydro-2H-[1,8]naphthyridine-1-carboxylic acid amide (Cpd 162, Table 1)

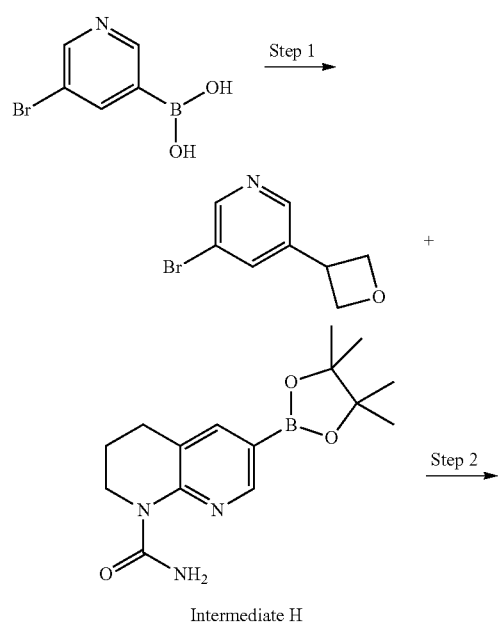

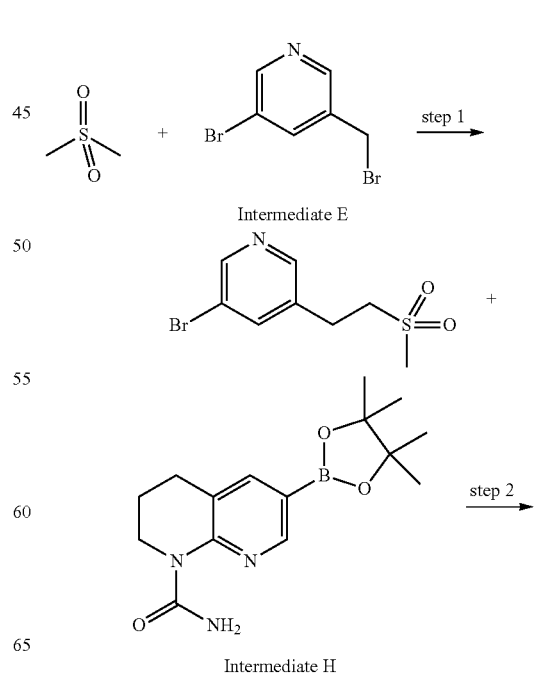

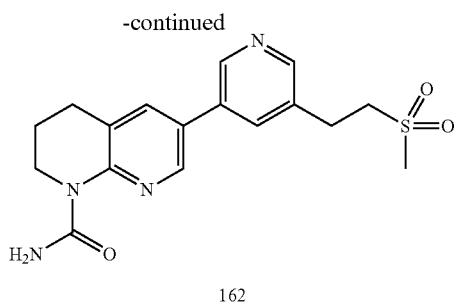

162

Dimethyl sulfone (93.8 mg, 0.996 mmol) is dissolved in THF (2 mL) and cooled to −78° C. Butyllithium (1.6M in hexane, 0.623 mL, 0.996 mmol) is added dropwise. The mixture is stirred at −78° C. for 15 min then at −25° C. for 5 min. The temperature is lowered to −78° C. again. Intermediate E (50 mg, 0.199 mmol) dissolved in THF (2.5 mL) is added dropwise. The temperature slowly rises to −55° C. in a period of 50 min and the reaction is continued to stir at −50° C. to −60° C. for 1 h. At −50° C., the reaction is quenched by slow addition of water (2 mL). The mixture is warmed to room temperature, then filtered through diatomaceous earth and washed with MeOH. The filtrate is concentrated. The resulting crude product is purified by normal phase chromatography using 0-6% MeOH in DCM as the gradient to afford 3-bromo-5-(2-methanesulfonyl-ethyl)-pyridine.

Suzuki Coupling Method VI is applied using the crude solution of Intermediate H for step 2 to afford the title compound.

Example 75

Synthesis of 6-(5-Ureido-pyridin-3-yl)-3,4-dihydro-2H-[1,8]naphthyridine-1-carboxylic acid amide (Cpd 163, Table 1)

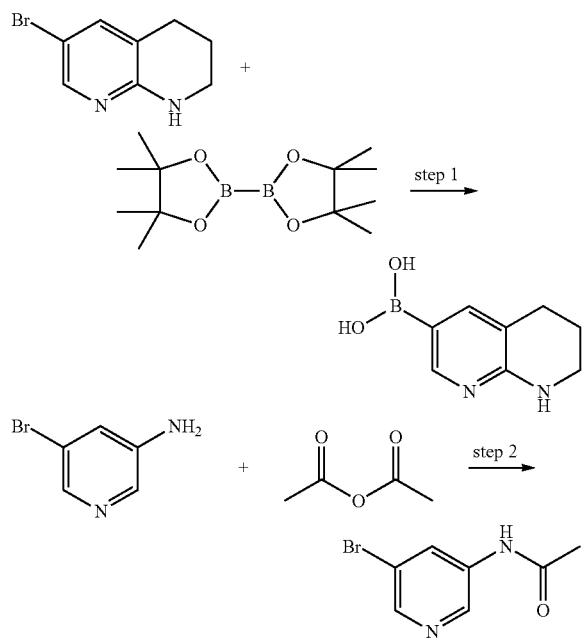

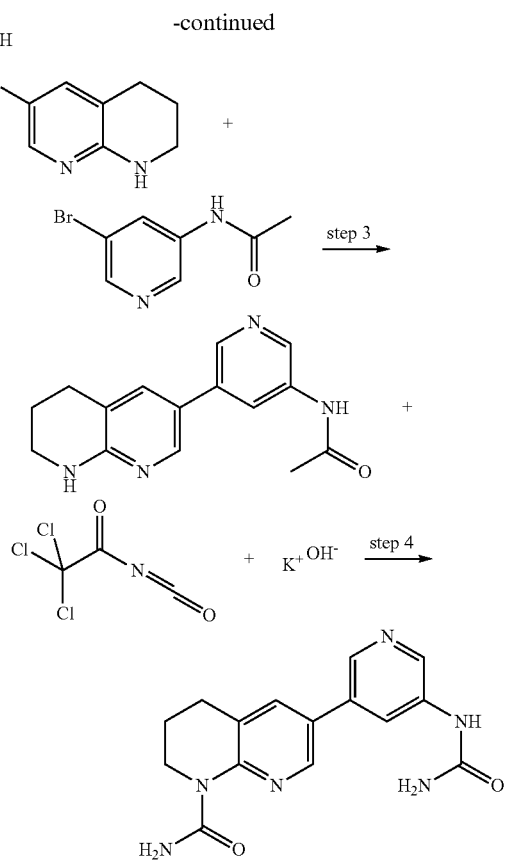

163

To a reaction vial are added 6-bromo-1,2,3,4-tetrahydro-[1,8]naphthyridine (160 mg, 0.75 mmol), bis(pinacolato)diboron (238 mg, 0.938 mmol), KOAc (294 mg, 3.0 mmol) followed by 1,4-dioxane (5.8 mL). Argon is bubbled through the reaction solution for 5 min. $PdCl_2(dppf)$ (54.9 mg, 0.075 mmol) is added. The vial is sealed and the mixture is heated at 120° C. for 50 min. The mixture is cooled to room temperature. No work up or purification is performed as the crude reaction solution is carried to the next step directly.

To a solution of 3-amino-5-bromopyridine (1.0 g, 5.78 mmol) and pyridine (1.3 mL, 12.9 mmol) in DCM (5 mL) is added acetic anhydride (0.6 mL, 6.358 mmol) dropwise. The mixture is stirred at room temperature for 17 h. The mixture is concentrated and the resulting crude product is purified by normal phase using 0-75% EtOAc in heptane as the gradient to afford N-(5-bromo-pyridin-3-yl)-acetamide (1.18 g, 95% yield).

At room temperature under argon, N-(5-bromo-pyridin-3-yl)-acetamide (303 mg, 1.409 mmol), sodium carbonate (249 mg, 2.348 mmol), and water (HPLC grade, 0.6 mL) are added to the crude reaction solution of step 1. Argon is bubbled through the solution for 5 min. $PdCl_2(dppf)$ (43 mg, 0.059 mmol) is then added. The vial is sealed and the mixture is heated at 120° C. for 2 h. The reaction mixture is filtered through diatomaceous earth and rinsed with MeOH (50 mL). The filtrate is concentrated. The resulting crude product is purified by normal phase chromatography using 0-10% MeOH in DCM as the gradient to afford N-[5-(5,6,7,8-tetrahydro-[1,8]naphthyridin-3-yl)-pyridin-3-yl]-acetamide (167 mg, 53% yield).

N-[5-(5,6,7,8-tetrahydro-[1,8]naphthyridin-3-yl)-pyridin-3-yl]-acetamide (165 mg, 0.615 mmol) is partially dissolved in DCM (7 mL) and cooled to 0° C. Trichloroacetyl isocyanate (0.11 mL, 0.922 mmol) is added dropwise. The mixture is stirred at 0° C. for 5 min. The ice/water bath is removed and the mixture is stirred at room temperature for 1 h. KOH (1.0M in MeOH, 6.2 mL, 6.2 mmol) is added slowly and the mixture is stirred at room temperature for 16 h. The pH of the mixture is adjusted to ~8 by addition of 1N HCl aq solution (~5 mL). The mixture is then filtered through diatomaceous earth. The filtrate is concentrated. The resulting crude product is purified by flash column using 0-10% MeOH in DCM as the gradient to afford the title compound (134 mg, 70% yield).

Example 76

Synthesis of 6-[5-(5-Oxo-pyrrolidin-2-yl)-pyridin-3-yl]-3,4-dihydro-2H-[1,8]naphthyridine-1-carboxylic acid amide (Cpd 165, Table 1)

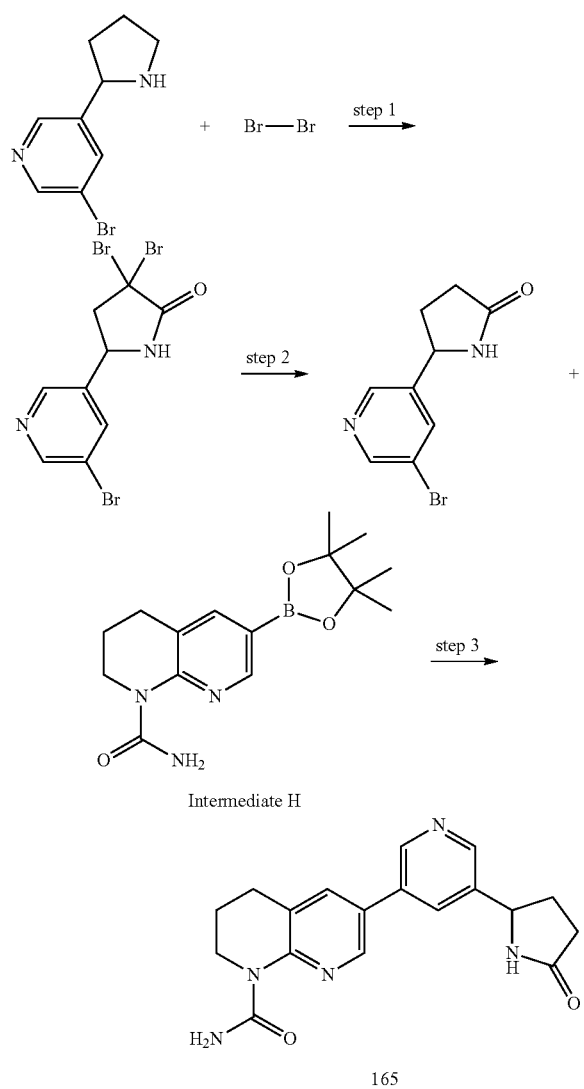

To a reaction vial (20 mL) is added 3-bromo-5-(pyrrolidin-2-yl)pyridine (400 mg, 1.76 mmol), acetic acid (glacial, 4.0 mL), and water (1 mL). Bromine (0.8 mL) is added dropwise. The vial is sealed and the reaction is heated to 90° C. in an oil bath and continued to stir at that temperature for 3 h. The mixture is cooled to room temperature. Water (15 mL) is added to the cooled reaction mixture and the mixture is saturated with solid potassium carbonate. The mixture is extracted with EtOAc (3×30 mL). The combined organics are dried over sodium sulfate, filtered, and concentrated. The crude product is dry-loaded and purified by normal phase chromatography using 0-6% MeOH in DCM as the gradient to afford 3,3-dibromo-5-(5-bromo-pyridin-3-yl)-pyrrolidin-2-one (0.65 g, 75% yield).

Sodium borohydride (0.74 g, 19.6 mmol) is suspended in ethanol (17 mL) and tellurium metal powder (1.25 g, 9.78 mmol) is added in portions. The mixture is heated under reflux (external temperature 80° C.) for 15 min and the mixture becomes a light purple color. The mixture is cooled to room temperature. 3,3-Dibromo-5-(5-bromo-pyridin-3-yl)-pyrrolidin-2-one (0.65 g, 1.63 mmol) dissolved in EOH (5 mL) is added slowly. The mixture is stirred at room temperature over the weekend (72 h). The mixture is filtered through diatomaceous earth and washed with MeOH. The filtrate is concentrated. The resulting crude product is purified by normal phase chromatography using 0-6% MeOH in DCM as the gradient to afford 5-(5-bromo-pyridin-3-yl)-pyrrolidin-2-one (291 mg, 74% yield).

Suzuki Coupling Method VI is applied using the crude solution of Intermediate H for step 3 to afford the titled product.

Enantiomers of the titled compound are separated using chiral $CO_2$ Supercritical Fluid Chromatography to give Compounds 262 and 263 (Analytical conditions: Chiralpak IA-SFC, 4.6×100 m column; 45% 1:1:1 MeOH:IPA:EtOH (+1% DEA):$CO_2$ @ 3 mL/min; 40° C.; 200 bars; Retention time, Compound 262: 2.84 min, Compound 263: 5.96 min) in Table 1.

Example 77

Synthesis of 6-[4-(1-Hydroxy-ethyl)-pyridin-3-yl]-3,4-dihydro-2H-[1,8]naphthyridine-1-carboxylic acid amide (Cpd 171, Table 1)

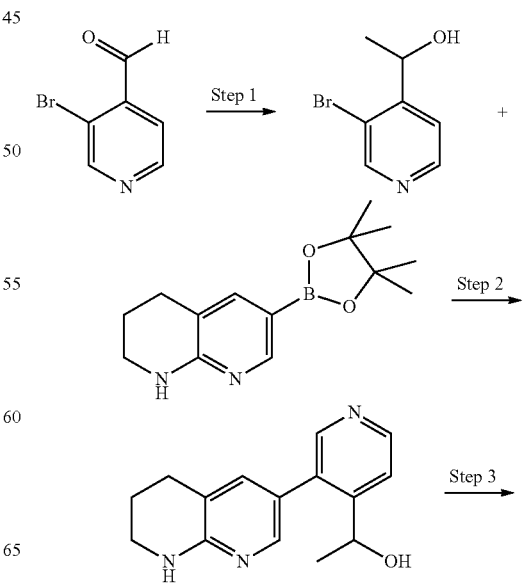

-continued

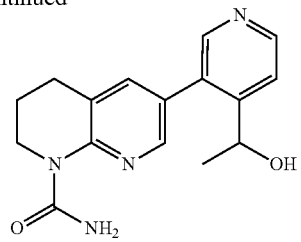

171

To a cooled (0° C.) solution of 3-bromo-pyridine-4-carbaldehyde (2.0 g, 10.8 mmol) in dry THF (45 mL) is added methyl magnesium bromide solution in $Et_2O$ (3M; 3.9 mL, 11.8 mmol). The mixture is stirred at 0° C. for 1 h then warmed and stirred at room temperature for 1 h. Saturated aqueous $NH_4Cl$ solution is added and the mixture is extracted with EtOAc. The organic layers are combined and concentrated to afford 2.1 g of 1-(3-bromo-pyridin-4-yl)-ethanol.

1-[3-(5,6,7,8-Tetrahydro-[1,8]naphthyridin-3-yl)-pyridin-4-yl]-ethanol is synthesized according to the procedure of Suzuki Coupling Method VI using 1-(3-bromo-pyridin-4-yl)-ethanol and crude 6-(4,4,5,5-Tetramethyl-[1,3,2]dioxaborolan-2-yl)-1,2,3,4-tetrahydro-[1,8]naphthyridine (which is prepared according to Step 4 of Example 105).

The titled product is synthesized according to the procedure of Urea Formation Method II using 1-[3-(5,6,7,8-tetrahydro-[1,8]naphthyridin-3-yl)-pyridin-4-yl]-ethanol.

Chiral separation of the racemic titled product (330 mg, 1.1 mmol) using Supercritical Fluid Chromatography (Column: LUX 5µ Cellulose 1 analytical, Mobile phase: 25% 1:1:1 MeOH:EtOH:iPA (0.1% DEA):CO2 @ 3 ml/min, 200 bar, 40° C.) affords 129 mg of Compound 173 (Retention time 5.5 min) and 116 mg of Compound 172 (Retention time 4.0 min) in Table 1.

Example 78

Syntheses of Enantiomers of 6-[5-Chloro-4-(1-hydroxy-ethyl)-pyridin-3-yl]-3,4-dihydro-2H-[1,8]naphthyridine-1-carboxylic acid amide (Cpd 175 and 176, Table 1)

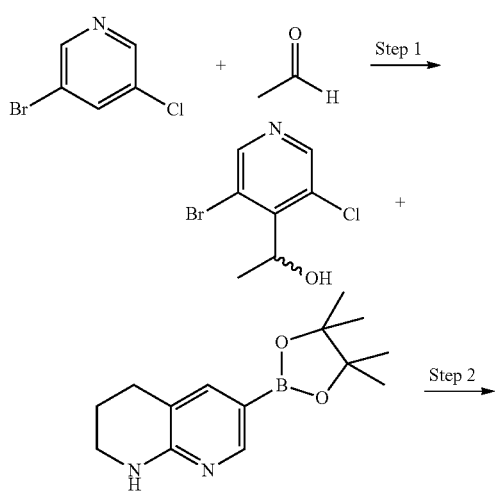

-continued

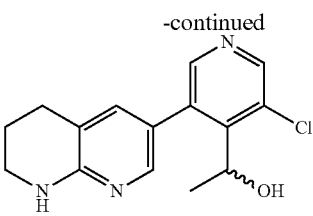

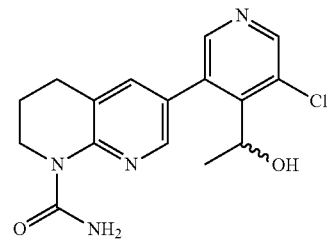

175 and 176

To a cooled (−78° C.) solution of 3-bromo-5-chloro-pyridine (2.0 g, 10.4 mmol) in dry THF (80 mL) is added LDA in THF solution (2M; 6.2 mL, 12.5 mmol) and the mixture is stirred at −78° C. for 2 h. Acetaldehyde in THF solution (5M; 4.2 mL, 20.8 mmol) is added and stifling continues at −78° C. for 30 min, then at room temperature for 16 hr. Saturated aqueous $NH_4Cl$ solution is added and the mixture is extracted with EtOAc. The organic layers are combined and concentrated to give the crude product. Purification by flash column chromatography affords 638 mg of the racemic product. Chiral separation of the racemic product using Chiral Chromatography (Column: Chiralpak AD-H analytical, 2.1×150 mm, Mobile phase: 20% EtOH:Heptane:0.7 ml/min, 40° C.) affords 270 mg of Enantiomer A (Retention time 9.0 min) and 264 of Enantiomer B (Retention time 11.8 min).

Enantiomer A and B are each coupled with crude 6-(4,4,5,5-tetramethyl-[1,3,2]dioxaborolan-2-yl)-1,2,3,4-tetrahydro-[1,8]naphthyridine (which is prepared according to Step 4 of Example 105) to give corresponding two enantiomers of 1-[3-Chloro-5-(5,6,7,8-tetrahydro-[1,8]naphthyridin-3-yl)-pyridin-4-yl]-ethanol according to the procedure of Suzuki Coupling Method VI.

Two enantiomers of 1-[3-chloro-5-(5,6,7,8-tetrahydro-[1,8]naphthyridin-3-yl)-pyridin-4-yl]-ethanol are each converted to Compounds 175 and 176 in Table 1 according to the procedure of Urea Formation Method II (Analytical conditions: LUX 5µ Cellulose 4 Analytical column; 30% 1:1:1 MeOH:EtOH:IPA (1% DEA):$CO_2$ @ 3 mL/min; 40° C.; 200 bars; Retention time, Compound 176: 5.2 min, Compound 175: 6.0 min).

Example 79

Synthesis of 6-[4-(1-Benzyloxy-ethyl)-5-cyano-pyridin-3-yl]-3,4-dihydro-2H-[1,8]naphthyridine-1-carboxylic acid amide (Cpd 179, Table 1)

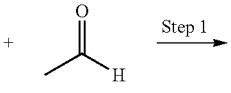

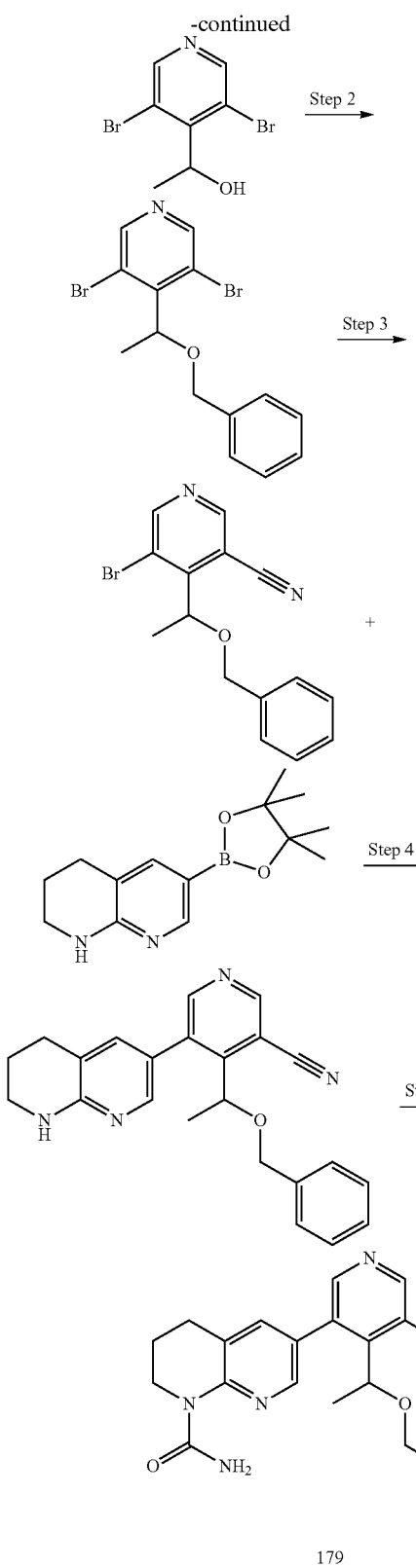

30 min, then at room temperature for 16 h. Saturated aqueous NH₄Cl solution is added and the mixture is extracted with EtOAc. The organic layers are combined and concentrated to give the crude product. Purification by flash column chromatography affords 2.9 g (67% purity) of 1-(3,5-dibromo-pyridin-4-yl)-ethanol.

To a cooled (0° C.) solution of 1-(3,5-dibromo-pyridin-4-yl)-ethanol (600 mg, 1.4 mmol) in DMF (12 mL) is added sodium hydride (60% dispersion in mineral oil, 60 mg, 1.5 mmol). After stirring at 0° C. for 30 min, benzyl bromide (281 mg, 1.6 mmol) is added. The reaction is warmed and stirred at room temperature for 16 h. The reaction is quenched with the addition of saturated aqueous NH₄Cl and H₂O and is extracted with EtOAc. The combined organic layers are dried and concentrated. The crude product is purified by flash column chromatography to provide 306 mg of 4-(1-benzyloxy-ethyl)-3,5-dibromo-pyridine.

To a solution of 4-(1-benzyloxy-ethyl)-3,5-dibromo-pyridine (400 mg, 1.1 mmol) in DMF (5 mL) is added copper cyanide (116 mg, 1.3 mmol). The mixture is heated and stirred at 150° C. for 3 h, then stirred at room temperature for 16 h. H₂O is added and the mixture is extracted with EtOAc. The organic layers are combined and concentrated to give the crude product. Purification by flash column chromatography provides 225 mg of 4-(1-benzyloxy-ethyl)-5-bromo-nicotinonitrile.

4-(1-Benzyloxy-ethyl)-5-(5,6,7,8-tetrahydro-[1,8]naphthyridin-3-yl)-nicotinonitrile is synthesized according to the procedure of Suzuki Coupling Method VI using 4-(1-benzyloxy-ethyl)-5-bromo-nicotinonitrile and crude 6-(4,4,5,5-Tetramethyl-[1,3,2]dioxaborolan-2-yl)-1,2,3,4-tetrahydro-[1,8]naphthyridine (which is prepared according to Step 4 of Example 105).

The titled product is synthesized according to the procedure of Urea Formation Method II using 4-(1-benzyloxy-ethyl)-5-(5,6,7,8-tetrahydro-[1,8]naphthyridin-3-yl)-nicotinonitrile.

Example 80

Synthesis of [5-(8-Carbamoyl-5,6,7,8-tetrahydro-[1,8]naphthyridin-3-yl)-pyridin-3-yl]-acetic acid (Cpd 183, Table 1)

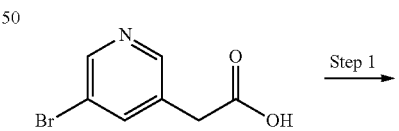

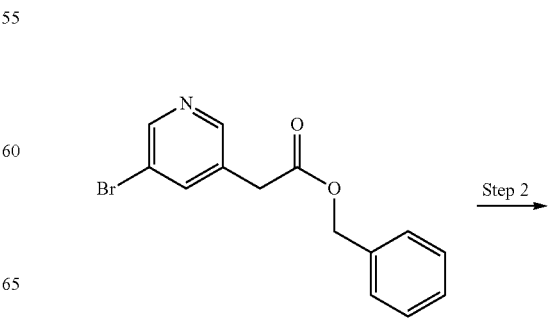

To a cooled (−78° C.) solution of 3,5-dibromo-pyridine (2.0 g, 8.4 mmol) in dry THF (80 mL) is added LDA in THF solution (2M; 5.1 mL, 10.1 mmol) and the mixture is stirred at −78° C. for 2 h. Acetaldehyde in THF solution (5M; 3.4 mL, 16.9 mmol) is added and the mixture is stirred at −78° C. for

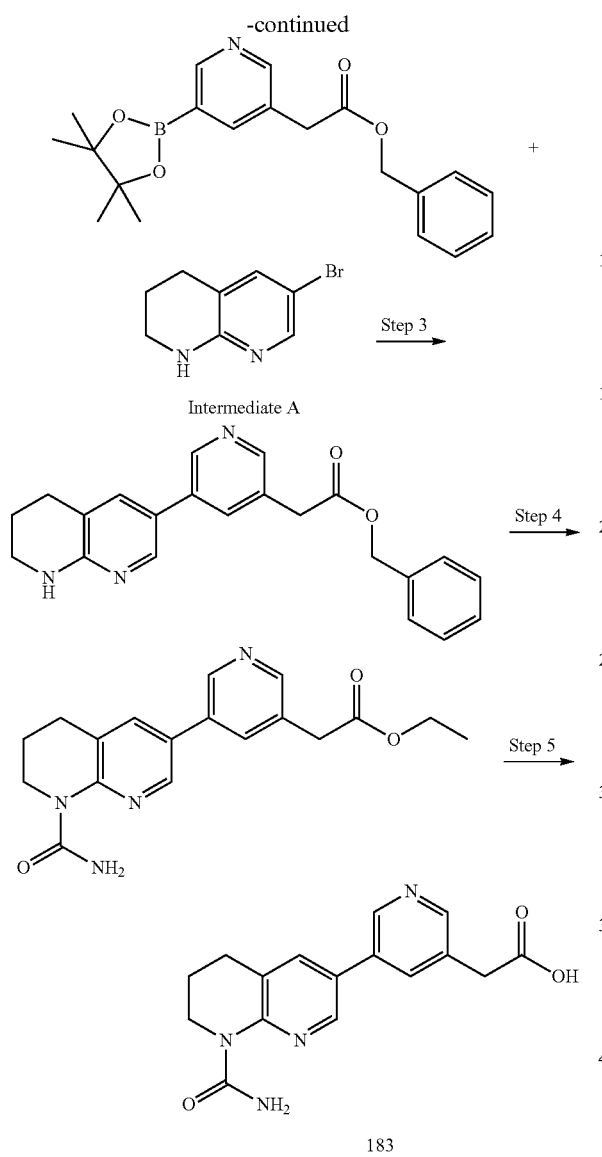

183

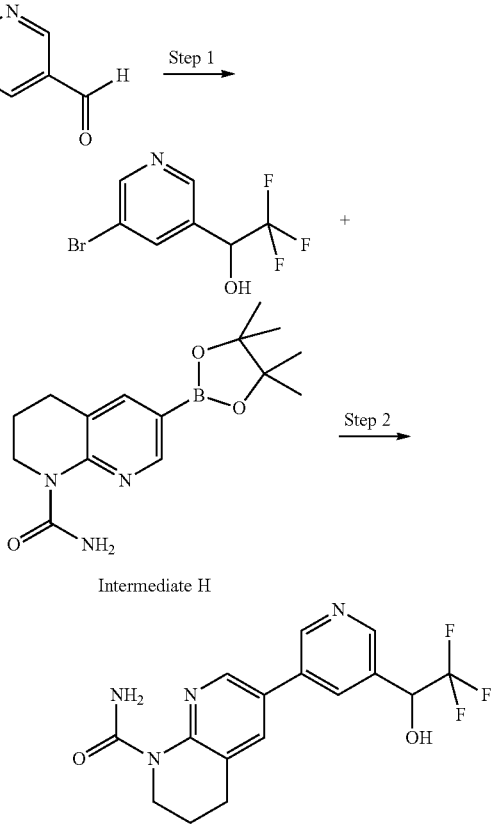

A mixture of (5-bromo-pyridin-3-yl)-acetic acid (2.0 g, 9.3 mmol), benzyl alcohol (1.0 g, 9.2 mmol), DCC (1.9 g, mmol), and DMAP (1.0 g, mmol) in DCM (30 mL) is stirred at room temperature for 16 h. The mixture is filtered and the filtrate is concentrated to give the crude product. Purification by flash column chromatography affords 1.2 g of (5-bromo-pyridin-3-yl)-acetic acid benzyl ester.

A mixture of (5-bromo-pyridin-3-yl)-acetic acid benzyl ester (1.0 g, 3.3 mmol), bis(pinacolato)diboron (800 mg, 3.2 mmol), 1,1'-bis(diphenylphosphino)ferrocenedichloropalladium(II) (200 mg, 0.27 mmol) and potassium acetate (960 mg, 9.8 mmol) in 1,4-dioxane (10 mL) is flushed with $N_2$ and heated to 110° C. for 1 h. After cooling to room temperature, the [5-(4,4,5,5-tetramethyl-[1,3,2]dioxaborolan-2-yl)-pyridin-3-yl]-acetic acid benzyl ester solution is used in the next step without purification.

6-Bromo-1,2,3,4-tetrahydro-[1,8]naphthyridine (280 mg, 1.3 mmol), cesium carbonate (350 mg, 3.3 mmol) and 1,1'-bis(diphenylphosphino)ferrocenedichloropalladium(II) (80 mg, 0.11 mmol) are added to the reaction solution from the previous step. The mixture is flushed with $N_2$ and heated to 110° C. for 16 h. After cooling to room temperature the mixture is partitioned between $H_2O$ and EtOAc. The layers are separated and the aqueous is further extracted with EtOAc. The combined organic layers are washed with brine and concentrated to afford crude product. Purification by flash column chromatography affords 150 mg of [5-(5,6,7,8-tetrahydro-[1,8]naphthyridin-3-yl)-pyridin-3-yl]-acetic acid benzyl ester.

[5-(8-Carbamoyl-5,6,7,8-tetrahydro-[1,8]naphthyridin-3-yl)-pyridin-3-yl]-acetic acid ethyl ester is synthesized according to the procedure of Urea Formation Method I using [5-(5,6,7,8-tetrahydro-[1,8]naphthyridin-3-yl)-pyridin-3-yl]-acetic acid benzyl ester.

A mixture of [5-(8-carbamoyl-5,6,7,8-tetrahydro-[1,8]naphthyridin-3-yl)-pyridin-3-yl]-acetic acid ethyl ester (1.0 g, 2.9 mmol) and lithium hydroxide (123 mg, 5.1 mmol) in EtOH (10 mL) and $H_2O$ (10 mL) are stirred at room temperature for 16 h. The reaction is concentrated to remove the EtOH and the remaining aqueous mixture is treated with 1N HCl and diluted with EtOAc. The solid formed is filtered, rinsed and dried to give 500 mg of the titled product.

Example 81

Synthesis of 6-[5-(2,2,2-Trifluoro-1-hydroxy-ethyl)-pyridin-3-yl]-3,4-dihydro-2H-[1,8]naphthyridine-1-carboxylic acid amide (Cpd 184, Table 1)

To a cooled (0° C.) solution of 5-bromo-pyridine-3-carbaldehyde (2.0 g, 10.8 mmol) in THF (25 mL) are added trimethyl-trifluoromethyl-silane (2.8 mL, 18.8 mmol) and TBAF in THF solution (1.0 M; 10.8 mL, 10.8 mmol). The mixture is warmed to room temperature for 3 hrs. The solvent is evaporated to give the crude product. Purification by flash column chromatography affords 1.9 g of 1-(5-bromo-pyridin-3-yl)-2,2,2-trifluoro-ethanol.

6-[5-(2,2,2-Trifluoro-1-hydroxy-ethyl)-pyridin-3-yl]-3,4-dihydro-2H-[1,8]naphthyridine-1-carboxylic acid amide is synthesized according to the procedure of Suzuki Coupling Method VI using 1-(5-bromo-pyridin-3-yl)-2,2,2-trifluoro-ethanol and Intermediate H.

Chiral separation of the racemic 6-[5-(2,2,2-Trifluoro-1-hydroxy-ethyl)-pyridin-3-yl]-3,4-dihydro-2H-[1,8]naphthyridine-1-carboxylic acid amide using chiral $CO_2$ Supercritical Fluid Chromatography (Column: ChiralPak IA 4.6×250 mm analytical, Mobile phase: 15% (1:1:1 MeOH:EtOH:IPA (1% DEA):$CO_2$ 3 mL/min, 200 bar, 40° C.) affords 141 mg of Compound 196 (Retention time 8.9 min) and 140 mg of Compound 195 (Retention time 6.7 min) in Table 1.

Example 82

Synthesis of 6-{5-[2-(4,4-Difluoro-piperidin-1-yl)-2-oxo-ethyl]-pyridin-3-yl}-3,4-dihydro-2H-[1,8]naphthyridine-1-carboxylic acid amide (Cpd 186, Table 1)

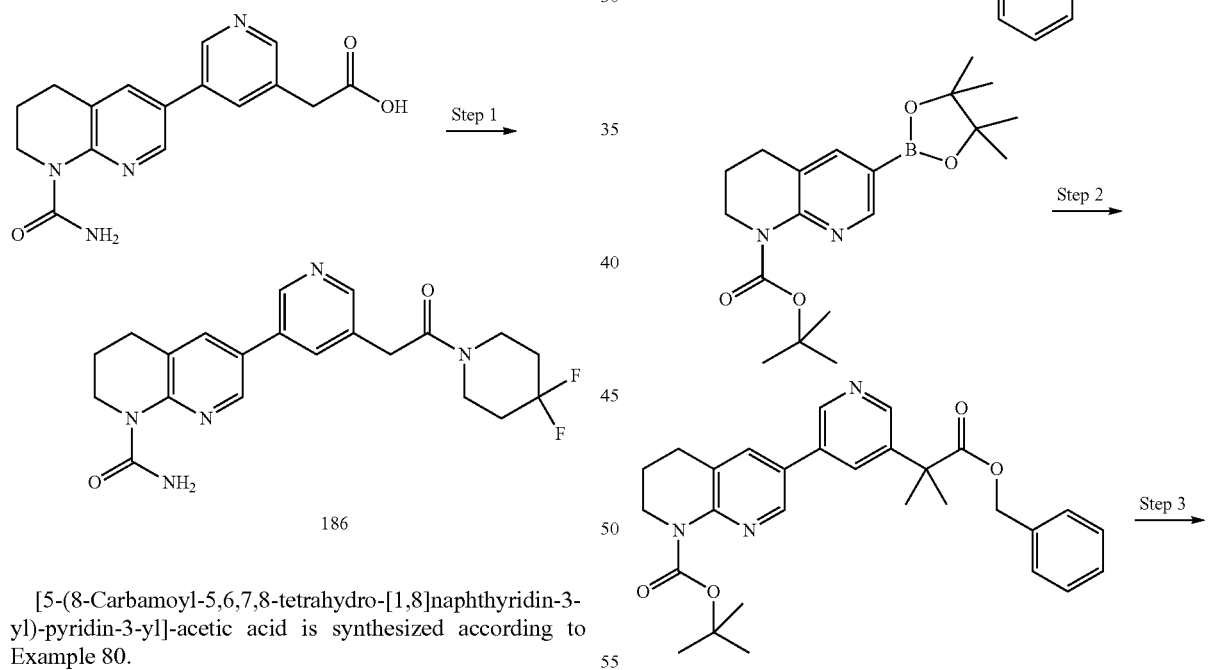

186

[5-(8-Carbamoyl-5,6,7,8-tetrahydro-[1,8]naphthyridin-3-yl)-pyridin-3-yl]-acetic acid is synthesized according to Example 80.

To a suspension of [5-(8-carbamoyl-5,6,7,8-tetrahydro-[1,8]naphthyridin-3-yl)-pyridin-3-yl]-acetic acid (25 mg, 0.080 mmol) in DMF (1.5 mL) is added 1,1'-carbonyldiimidazole (14 mg, 0.088 mmol) and the mixture is stirred at room temperature for 16 h. 4,4-Difluoro-piperidine hydrochloride salt (15 mg, 0.096 mmol) and N,N-diisopropylethylamine (0.042 mL, 0.24 mmol) are added and stifling continues for an additional 16 h. $H_2O$ is added and the resulting precipitate is collected by filtration to afford 21 mg of the titled product.

Compounds 187, 188 and 189 in Table 1 are synthesized according to the procedure for Example 82, substituting either commercially available reagents or the appropriate intermediates described above.

Example 83

Synthesis of 6-[5-(1,1-Dimethyl-2-morpholin-4-yl-2-oxo-ethyl)-pyridin-3-yl]-3,4-dihydro-2H-[1,8]naphthyridine-1-carboxylic acid amide (Cpd 194, Table 1)

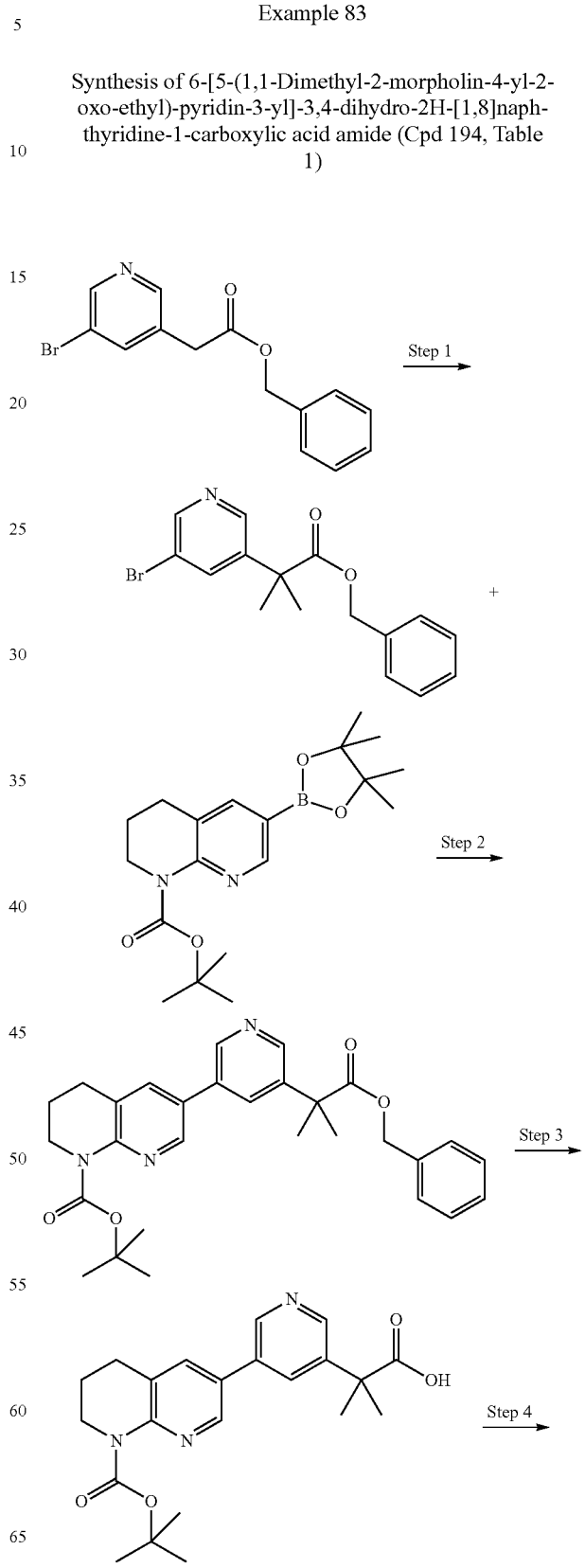

-continued

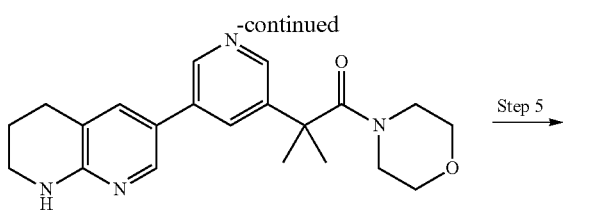

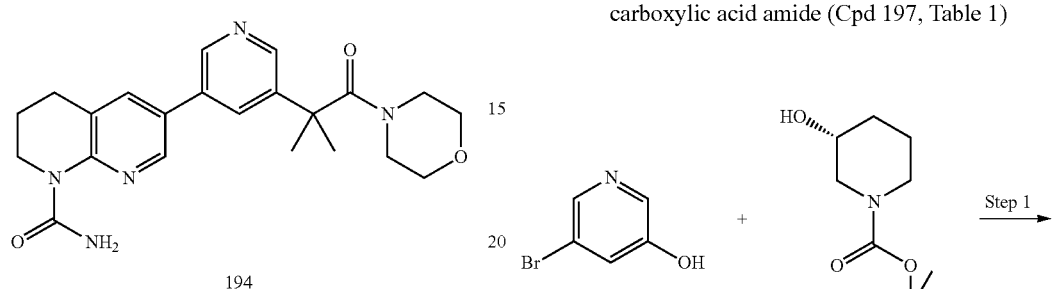

194

To a cooled (0° C.) suspension of sodium hydride (60% dispersion in mineral oil, 1.0 g, 43.3 mmol) in DMF (50 mL) is added (5-bromo-pyridin-3-yl)-acetic acid benzyl ester (5.3 g, 17.3 mmol). After stirring at 0° C. for 1 h, iodomethane (5.4 g, 38.1 mmol) is added. The reaction is warmed and stirred at room temperature for 2 h. The reaction is quenched with saturated aqueous $NH_4Cl$ and $H_2O$ and is extracted with EtOAc. The combined organic layers are dried and concentrated. The crude product is purified by flash column chromatography to provide 3.5 g of 2-(5-bromo-pyridin-3-yl)-2-methyl-propionic acid benzyl ester.

6-[5-(1-Benzyloxycarbonyl-1-methyl-ethyl)-pyridin-3-yl]-3,4-dihydro-2H-[1,8]naphthyridine-1-carboxylic acid tert-butyl ester is synthesized according to the procedure of Suzuki Coupling Method VI using 2-(5-bromo-pyridin-3-yl)-2-methyl-propionic acid benzyl ester and crude 6-(4,4,5,5-Tetramethyl-[1,3,2]dioxaborolan-2-yl)-3,4-dihydro-2H-[1, 8]naphthyridine-1-carboxylic acid tert-butyl ester (Intermediate G).

To a stirred solution of 6-[5-(1-benzyloxycarbonyl-1-methyl-ethyl)-pyridin-3-yl]-3,4-dihydro-2H-[1,8]naphthyridine-1-carboxylic acid tert-butyl ester (500 mg, 1.0 mmol) in MeOH (25 mL) is added 10% Pd/C (250 mg). The reaction mixture is stirred under 40 psi $H_2$ for 16 h. The catalyst is removed by filtration through diatomaceous earth and the solvent is evaporated to afford 160 mg of 6-[5-(1-carboxy-1-methyl-ethyl)-pyridin-3-yl]-3,4-dihydro-2H-[1,8]naphthyridine-1-carboxylic acid tert-butyl ester To a suspension 6-[5-(1-carboxy-1-methyl-ethyl)-pyridin-3-yl]-3,4-dihydro-2H-[1,8]naphthyridine-1-carboxylic acid tert-butyl ester (50 mg, 0.13 mmol) in DMF (1 mL) is added HATU (57 mg, 0.15 mmol), morpholine (11 mg, 0.13 mmol) and N,N-diisopropylethylamine (0.14 mL, 0.81 mmol). The mixture is stirred at room temperature for 16 h. The reaction mixture is purified by reverse phase HPLC (mobile phase contains 1% TFA) to afford 53 mg of 2-methyl-1-morpholin-4-yl-2-[5-(5,6,7,8-tetrahydro-[1,8]naphthyridin-3-yl)-pyridin-3-yl]-propan-1-one.

The titled product is synthesized according to the procedure of Urea Formation Method II using 2-methyl-1-morpholin-4-yl-2-[5-(5,6,7,8-tetrahydro-[1,8]naphthyridin-3-yl)-pyridin-3-yl]-propan-1-one.

Example 84

Synthesis of 6-[5-((R)-1-acetyl-piperidin-3-yloxy)-pyridin-3-yl]-3,4-dihydro-2H-[1,8]naphthyridine-1-carboxylic acid amide (Cpd 197, Table 1)

Intermediate H

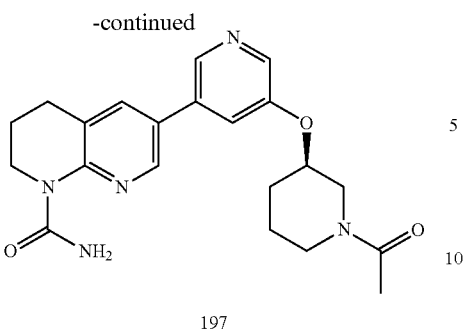

197

To a cooled (0° C.) solution of PPh₃ (1.2 g, 4.5 mmol) in THF (50 mL) is added DIAD (0.81 mL, 4.1 mmol), dropwise. After stirring at 0° C. for 15 min, 5-bromo-pyridin-3-ol (441 mg, 2.5 mmol) and (S)-3-hydroxy-piperidine-1-carboxylic acid tert-butyl ester (500 mg, 2.5 mmol) are added and the mixture is warmed and stirred at room temperature for 16 h. The mixture is concentrated and purified by flash column chromatography to give 596 mg of (R)-3-(5-bromo-pyridin-3-yloxy)-piperidine-1-carboxylic acid tert-butyl ester.

A solution of (R)-3-(5-bromo-pyridin-3-yloxy)-piperidine-1-carboxylic acid tert-butyl ester (596 mg, 1.7 mmol) in MeOH (5 mL) and HCl solution in 1,4-dioxane (4N; 1.5 mL) is stirred at room temperature for 16 h. The mixture is concentrated to provide 525 mg 3-bromo-5-((R)-piperidin-3-yloxy)-pyridine as the hydrochloride salt.

To a solution of 3-bromo-5-((R)-piperidin-3-yloxy)-pyridine hydrochloride salt (525 mg, 1.8 mmol) in DMF (10 mL) is added acetyl chloride (0.19 mL, 2.7 mmol) and N,N-diisopropylethylamine (1.4 mL, 8.0 mmol). The mixture is stirred at room temperature for 16 h. The reaction is partitioned between H₂O and EtOAc and the layers are separated. The aqueous is extracted with EtOAc and the combined organic layers are dried and concentrated. The crude product is purified by flash column chromatography to provide 271 mg of 1-[(R)-3-(5-bromo-pyridin-3-yloxy)-piperidin-1-yl]-ethanone.

The titled product is synthesized according to the procedure of Suzuki Coupling Method VI using 1-[(R)-3-(5-bromo-pyridin-3-yloxy)-piperidin-1-yl]-ethanone and crude Intermediate H.

Compound 252 in Table 1 is synthesized according to the procedure for Example 84, substituting either commercially available reagents or the appropriate intermediates described above.

Example 85

Synthesis of 1-{4-[5-(8-Acetyl-5,6,7,8-tetrahydro-[1,8]naphthyridin-3-yl)-4-chloro-pyridin-3-ylmethoxy]-piperidin-1-yl}-ethanone (Cpd 198, Table 1)

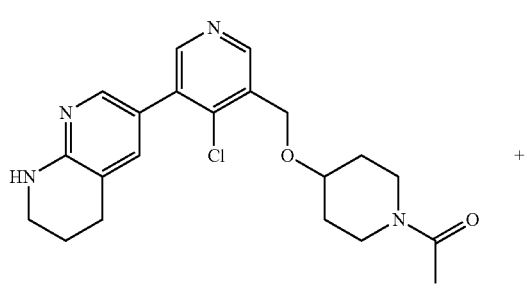

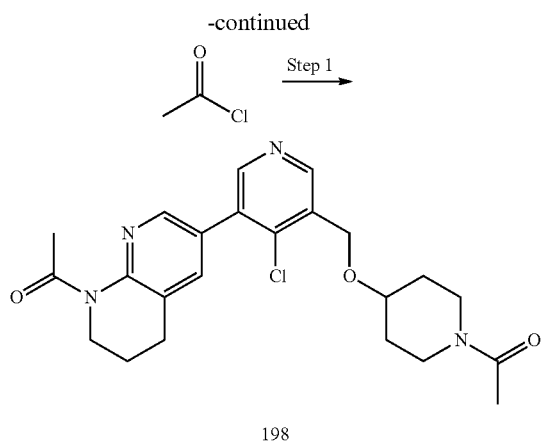

198

1-{4-[4-Chloro-5-(5,6,7,8-tetrahydro-[1,8]naphthyridin-3-yl)-pyridin-3-ylmethoxy]-piperidin-1-yl}-ethanone is synthesized using procedures described in Example 105.

1-{4-[4-Chloro-5-(5,6,7,8-tetrahydro-[1,8]naphthyridin-3-yl)-pyridin-3-ylmethoxy]-piperidin-1-yl}-ethanone (26 mg, 0.065 mmol) and pyridine (0.016 mL, 0.195 mmol) are dissolved in DCM (1.0 mL) and the mixture is cooled down to 0° C. Acetyl chloride (0.007 mL, 0.097 mmol) is added and the mixture is warmed up to room temperature and stirred for 1 hr. Then saturated NaHCO₃ aqueous solution (10 mL) is added along with DCM (30 mL) and water (15 mL). The mixture is stirred for 15 min and the aqueous layer is separated, extracted with DCM (2×10 mL) and EtOAc (2×10 mL). All the organic layers are combined and concentrated to give the crude product. Purification by flash column chromatography affords 17 mg of the titled product.

Example 86

Synthesis of 6-[5-fluoro-4-(1-hydroxy-1-methyl-ethyl)-pyridin-3-yl]-3,4-dihydro-2H-[1,8]naphthyridine-1-carboxylic acid amide (Cpd 199, Table 1)

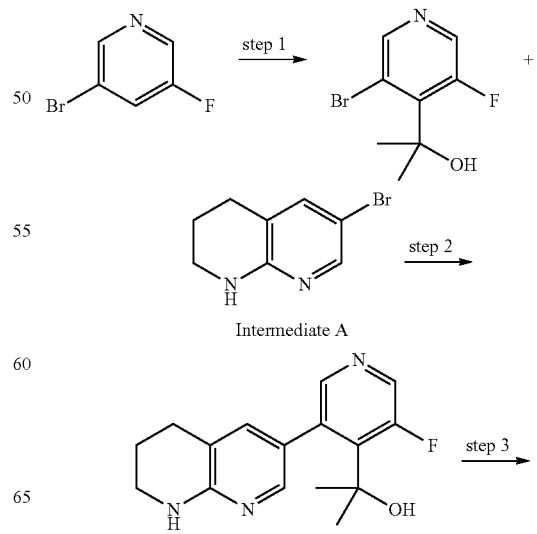

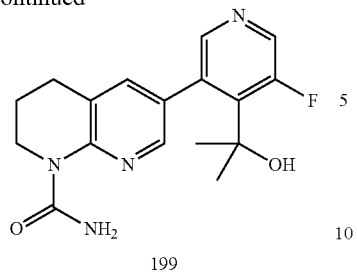

199

To a round bottom flask is added 3-bromo-5-fluoropyridine (475 mg, 2.7 mmol) in 4 ml of dry THF at −78° C., followed by the addition of lithium diisopropylamine (1.6 ml, 3.2 mmol). The reaction mixture is stirred at −78° C. for 1 hour, followed by the addition of acetone (0.6 ml). The reaction mixture is warmed up and stirred at room temperature for 30 minutes. The reaction mixture is diluted with EtOAc, washed with water, brine, dried over anhydrous $Na_2SO_4$, filtered and concentrated to give the crude product. Purification by the flash column chromatography affords 190 mg of 2-(3-bromo-5-fluoro-pyridin-4-yl)-propan-2-ol.

To a vial is added 6-bromo-1,2,3,4-tetrahydro-[1,8]naphthyridine, Intermediate A (144 mg, 0.68 mmol), bis(pinacolato)diboron (223 mg, 0.88 mmol), potassium acetate (200 mg, 2 mmol) and [1,1'-bis(diphenylphosphino)ferrocene)dichloropalladium(II) (50 mg, 0.07 mmol) in 5 ml of 1,4-dioxane. The reaction mixture is stirred at 120° C. under Ar for 2 hours. The reaction mixture is cooled down to room temperature, followed by the addition of 2-(3-bromo-5-fluoro-pyridin-4-yl)-propan-2-ol (190 mg, 0.81 mmol), 2M $Na_2CO_3$ (0.67 ml, 1.35 mmol) and [1,1'-bis(diphenylphosphino)ferrocene)dichloropalladium(II) (25 mg, 0.034 mmol). The reaction mixture is stirred under Ar at 120° C. for 3 hours. The reaction mixture is concentrated. The residue is diluted with EtOAc, washed with water, brine, dried over anhydrous $Na_2SO_4$, filtered and concentrated to give the crude product. Purification by the flash column chromatography affords 72 mg of 2-[3-fluoro-5-(5,6,7,8-tetrahydro-[1,8]naphthyridin-3-yl)-pyridin-4-yl]-propan-2-ol.

2-[3-fluoro-5-(5,6,7,8-tetrahydro-[1,8]naphthyridin-3-yl)-pyridin-4-yl]-propan-2-ol (72 mg, 0.25 mmol) is converted to 54 mg of the titled product using Urea Formation Method II.

Compounds 200, 201, 202 and 203 in Table 1 are synthesized according to the procedure for Example 86, substituting either commercially available reagents or the appropriate intermediates described above.

Enantiomers of Compound 202 are separated using chiral $CO_2$ Supercritical Fluid Chromatography to give Compound 212 and Compound 213 (Analytical conditions: LUX 5 u Cellulose 3 Analytical, 4.6×100 m column; 30% 1:1:1 MeOH:IPA:EtOH (+1% DEA):$CO_2$ @ 3 mL/min; 40° C.; 200 bars; Retention time, Compound 212: 10.05 min, Compound 213: 15.99 min).

Enantiomers of Compound 203 are separated using chiral $CO_2$ Supercritical Fluid Chromatography to give Compound 215 and Compound 214 (Analytical conditions: LUX 5 u Cellulose 3 Analytical, 4.6×100 m column; 30% 1:1:1 MeOH:IPA:EtOH (+1% DEA):$CO_2$ @ 3 mL/min; 40° C.; 200 bars; Retention time, Compound 215: 9.54 min, Compound 214: 12.75 min).

Example 87

Synthesis of 6-(5-methanesulfonylmethyl-pyridin-3-yl)-3,4-dihydro-2H-[1,8]naphthyridine-1-carboxylic acid amide (Cpd 205, Table 1)

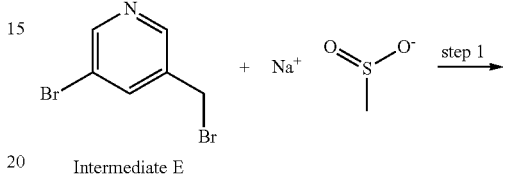

Intermediate E

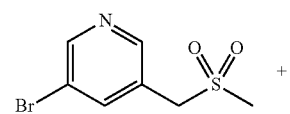

+

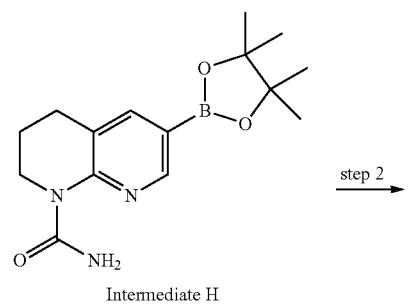

Intermediate H

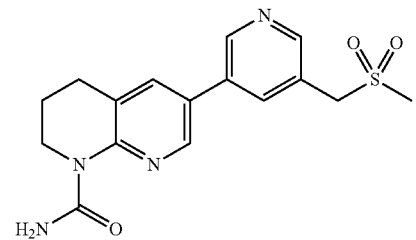

205

To a reaction vial are added Intermediate E (100 mg, 0.399 mmol), sodium methanesulphinate (122 mg, 1.20 mmol), and DMF (1 mL). The vial is sealed and the reaction is stirred at 65° C. in a heating block for 1 h. The mixture is cooled to room temperature, diluted with EtOAc (30 mL), washed with water (3×15 mL), and brine, dried over sodium sulfate, filtered, and concentrated. The crude product is purified by normal phase using 0-100% EtOAc in heptane as the gradient to afford 3-bromo-5-methanesulfonylmethyl-pyridine (70 mg, 70% yield).

Suzuki Coupling Method VI is applied using the crude solution of Intermediate H for step 2 to afford the title compound.

Example 88

Synthesis of 6-[4-((R)-1-Amino-ethyl)-5-fluoro-pyridin-3-yl]-3,4-dihydro-2H-[1,8]naphthyridine-1-carboxylic acid amide (Cpd 206, Table 1)

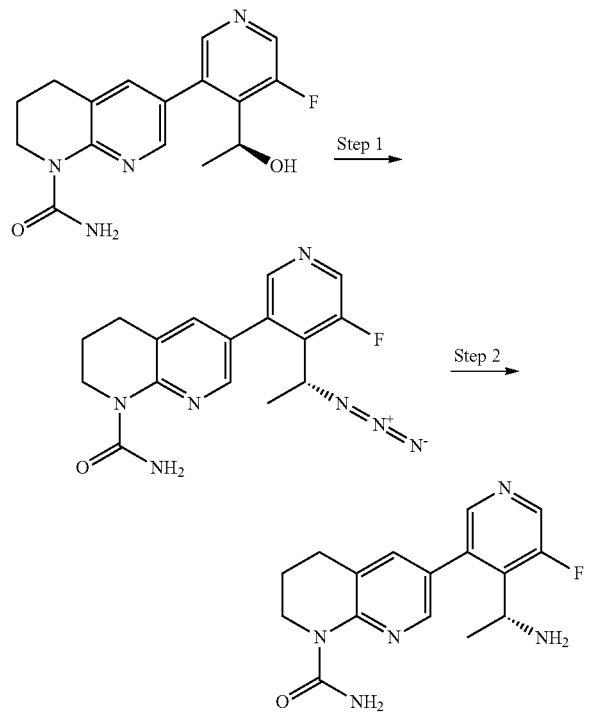

206

6-[5-Fluoro-4-((S)-1-hydroxy-ethyl)-pyridin-3-yl]-3,4-dihydro-2H-[1,8]naphthyridine-1-carboxylic acid amide is synthesized according to the procedure of Example 16.

6-[5-Fluoro-4-((S)-1-hydroxy-ethyl)-pyridin-3-yl]-3,4-dihydro-2H-[1,8]naphthyridine-1-carboxylic acid amide (100 mg, 0.32 mmol), THF (1.4 mL) and phosphorazidic acid diphenyl ester (0.088 mL, 0.41 mmol) are combined and cooled to 0° C. DBU (0.061 mL, 0.41 mmol) is added dropwise. After 10 minutes, the reaction is warmed to room temperature for 18 hrs. The reaction mixture is diluted with EtOAc and water. The layers are separated. The aqueous layer is extracted with EtOAc. The combined organic layers are washed with water and brine, dried over MgSO4, filtered and concentrated in vacuo to the crude product. Purification by flash column chromatography affords 90 mg of 6-[4-((R)-1-azido-ethyl)-5-fluoro-pyridin-3-yl]-3,4-dihydro-2H-[1,8]naphthyridine-1-carboxylic acid amide.

6-[4-((R)-1-azido-ethyl)-5-fluoro-pyridin-3-yl]-3,4-dihydro-2H-[1,8]naphthyridine-1-carboxylic acid amide (90 mg, 0.24 mmol) is dissolved in a mixture of EtOAc (2 mL) and MeOH (3 mL). The flask is flushed with Argon. Pd/C (26 mg, 0.024 mmol, 10%) is added and the flask is flushed with H$_2$. After stirring for 18 hrs, the reaction is diluted with EtOAc and MeOH (10 mL of a 1:1 mixture), filtered and concentrated. The residue is dissolve in 1 mL of MeOH and 2 drops of water is added. The solution is filtered and purified by reverse phase HPLC to give 26 mg of the titled product.

Example 89

Synthesis of 6-[5-(1-ethanesulfonylamino-ethyl)-pyridin-3-yl]-3,4-dihydro-2H-[1,8]naphthyridine-1-carboxylic acid amide (Cpd 209, Table 1)

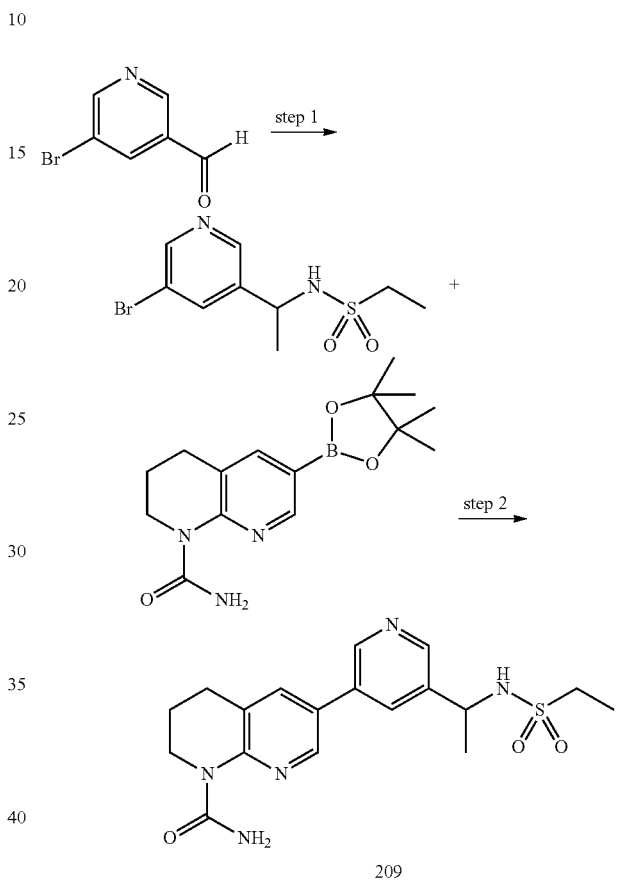

209

To a vial is added 5-bromonicotinaldehyde (300 mg, 1.61 mmol) and ethanesulfonamide (220 mg, 2.02 mmol) in 6 ml of toluene, followed by the addition of titanium(IV) isopropoxide (1 ml, 3.23 mmol). The reaction mixture is stirred at 120° C. for 6 hours. The reaction mixture is concentrated. The residue is dissolved in 5 ml of THF and is cooled to −40° C., methylmagnesium bromide, 3M in ether (1.6 ml, 4.84 mmol) is added dropwise. The reaction mixture is warm up and stirred at room temperature for 18 hours. The reaction mixture is diluted with EtOAc, washed with saturated NH$_4$Cl, (aq.) brine, dried over anhydrous Na$_2$SO$_4$, filtered and concentrated to give the crude product. Purification by the flash column chromatography affords 130 mg of ethanesulfonic acid [1-(5-bromo-pyridin-3-yl)-ethyl]-amide.

Ethanesulfonic acid [1-(5-bromo-pyridin-3-yl)-ethyl]-amide (130 mg, 0.45 mmol) is converted to 40 mg of the titled product using Suzuki Coupling Method VI.

Compound 204 in Table 1 is synthesized according to the procedure for Example 89, substituting either commercially available reagents or the appropriate intermediates described above.

Enantiomers of Compound 204 are separated using chiral CO$_2$ Supercritical Fluid Chromatography to give Compound 217 and Compound 218 (Analytical conditions: LUX 5 u Cellulose 3 Analytical, 4.6×100 m column; 10% 1:1:1 MeOH:IPA:EtOH (+1% DEA):CO$_2$ @ 3 mL/min; 40° C.; 200 bars; Retention time, Compound 217: 11.37 min, Compound 218: 12.79 min) in Table 1.

Example 90

Synthesis of 6-[5-(1-Acetylamino-1-methyl-ethyl)-pyridin-3-yl]-3,4-dihydro-2H-[1,8]naphthyridine-1-carboxylic acid amide (Cpd 210, Table 1)

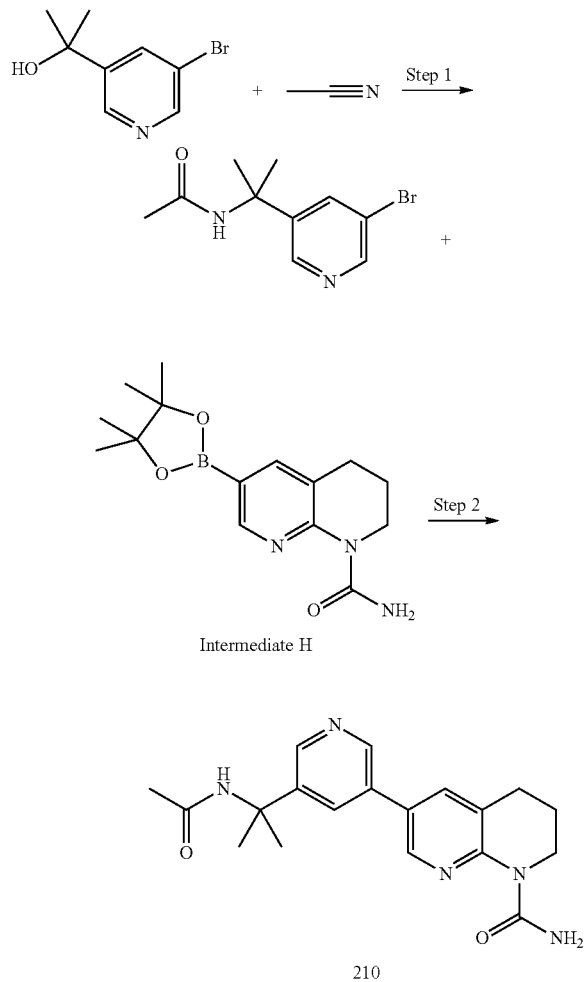

To the mixture of 2-(5-bromo-pyridin-3-yl)-propan-2-ol (700 mg, 3.24 mmol) in acetonitrile (14 mL) is added dropwise boron trifluoride diethyl ether complex (1.1 mL, 8.7 mmol) at room temperature. Then trifluoroacetic acid (1.8 ml, 23 mmol) is added dropwise and the reaction mixture is heated to reflux for 16 hrs. All the solvent is removed in vacuo and DCM is added. 1.0 M Na$_2$CO$_3$ solution is used to adjust the pH of aqueous phase to 8. The aqueous layer is separated and extracted with DCM twice. All the organic layers are combined and concentrated to give the crude product. Purification by flash column chromatography affords 252 mg of N-[1(5-bromo-pyridin-3-yl)-1-methyl-ethyl]-acetamide.

N-[1(5-bromo-pyridin-3-yl)-1-methyl-ethyl]-acetamide (120 mg, 0.47 mmol) is coupled with Intermediate H (0.39 mmol, using crude) to give 75 mg of the titled product using Suzuki Coupling Method VI.

Example 91

Synthesis of 3-(8-carbamoyl-5,6,7,8-tetrahydro-[1,8]naphthyridin-3-yl)-5-fluoro-isonicotinic acid methyl ester (Cpd 211, Table 1)

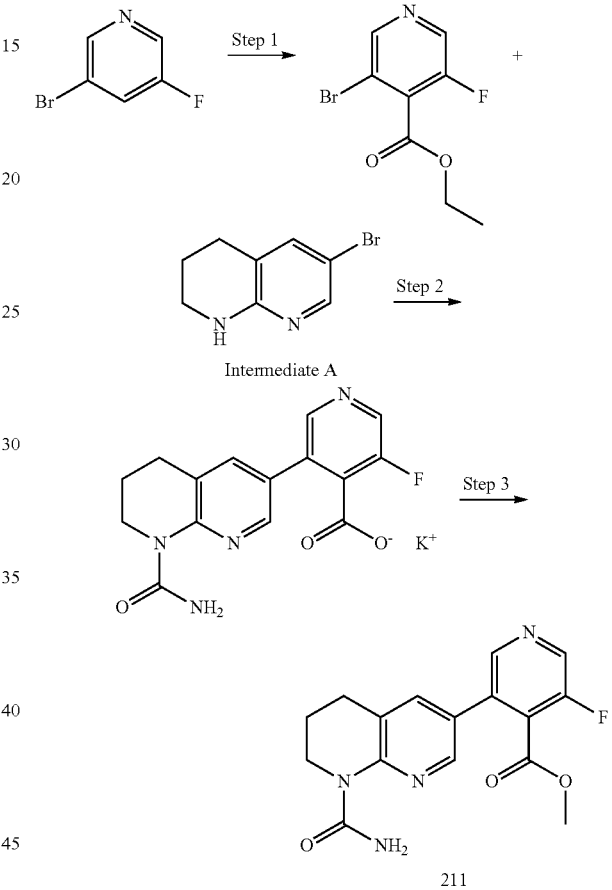

To a round bottom flask is added 3-bromo-5-fluoropyridine (475 mg, 2.7 mmol) in 4 ml of dry THF at −78° C., followed by the addition of lithium diisopropylamine (1.62 ml, 3.24 mmol). The reaction mixture is stirred at −78° C. for 1 hour, followed by the addition of ethyl chloroformate (586 mg, 5.4 mmol). The reaction mixture is warmed up to room temperature and stirred for 1 hour. The reaction mixture is diluted with EtOAc, washed with saturated NH$_4$Cl/water, brine, dried over anhydrous Na$_2$SO$_4$, filtered and concentrated to give the crude product. Purification by the flash column chromatography affords 670 mg of 3-bromo-5-fluoro-isonicotinic acid ethyl ester.

3-Bromo-5-fluoro-isonicotinic acid ethyl ester (586 mg, 2.25 mmol) is converted to 133 mg of 3-(8-carbamoyl-5,6,7,8-tetrahydro-[1,8]naphthyridin-3-yl)-5-fluoro-isonicotinic acid potassium salt using the procedures described in Example 86.

To a vial is added 3-(8-carbamoyl-5,6,7,8-tetrahydro-[1,8]naphthyridin-3-yl)-5-fluoro-isonicotinic acid potassium salt (100 mg, 0.28 mmol) in 2 ml of DMF, followed by the addition of iodomethane (48 mg, 0.34 mmol) and potassium carbonate (47 mg, 0.34 mmol). The reaction mixture is stirred at room temperature for 18 hours. The reaction mixture is concentrated in vacuo. The residue is diluted with EtOAc, washed with water, brine, dried over anhydrous Na$_2$SO$_4$, filtered and concentrated to give the crude product. Purification by the flash column chromatography affords 28 mg of the titled product.

Example 92

Synthesis of 6-(5-Aminomethyl-pyridin-3-yl)-3,4-dihydro-2H-[1,8]naphthyridine-1-carboxylic acid amide (Cpd 219, Table 1)

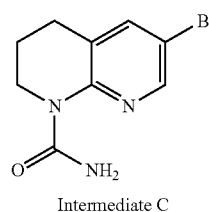
Intermediate C

+

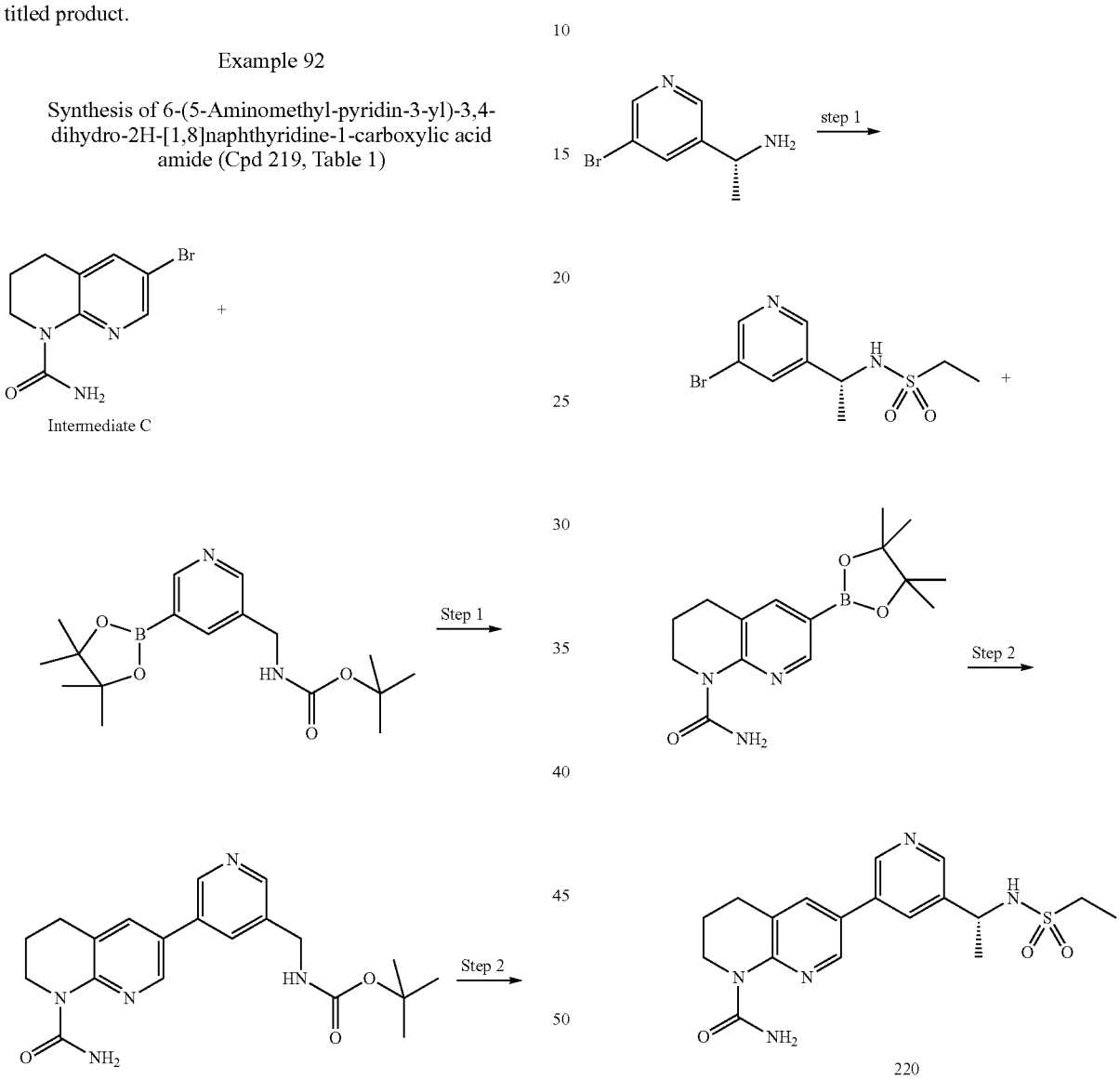

The titled product is synthesized according to the Step 1 and Step 2 of Example 19.

Example 93

Synthesis of 6-[5-((R)-1-Ethanesulfonylaminoethyl)-pyridin-3-yl]-3,4-dihydro-2H-[1,8]naphthyridine-1-carboxylic acid amide (Cpd 220, Table 1)

To a vial is added (1R)-1-(5-bromo(3-pyridyl))ethylamine (300 mg, 1.26 mmol) in 3 ml of CH$_2$Cl$_2$, followed by the addition of N,N-diisopropylethylamine (490 mg, 3.79 mmol). Then ethanesulfonyl chloride (195 mg, 1.52 mmol) is added. The reaction mixture is stirred at room temperature for 2 hours. The reaction mixture is diluted with DCM, washed with water, brine, dried over anhydrous Na$_2$SO$_4$, filtered and concentrated to give the crude product. Purification by the flash column chromatography affords 278 mg of ethanesulfonic acid [(R)-1-(5-bromo-pyridin-3-yl)-ethyl]-amide.

Ethanesulfonic acid [(R)-1-(5-bromo-pyridin-3-yl)-ethyl]-amide (83 mg, 0.27 mmol) is converted to 29 mg of the titled product using Suzuki Coupling Method VI.

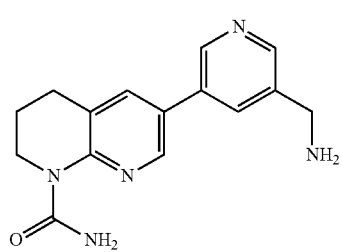
219

237

Compound 221 in Table 1 is synthesized according to the procedure for Example 93, substituting either commercially available reagents or the appropriate intermediates described above.

Example 94

Synthesis of 6-{5-[(R)-1-(Ethanesulfonyl-methyl-amino)-ethyl]-pyridin-3-yl}-3,4-dihydro-2H-[1,8]naphthyridine-1-carboxylic acid amide (Cpd 222, Table 1)

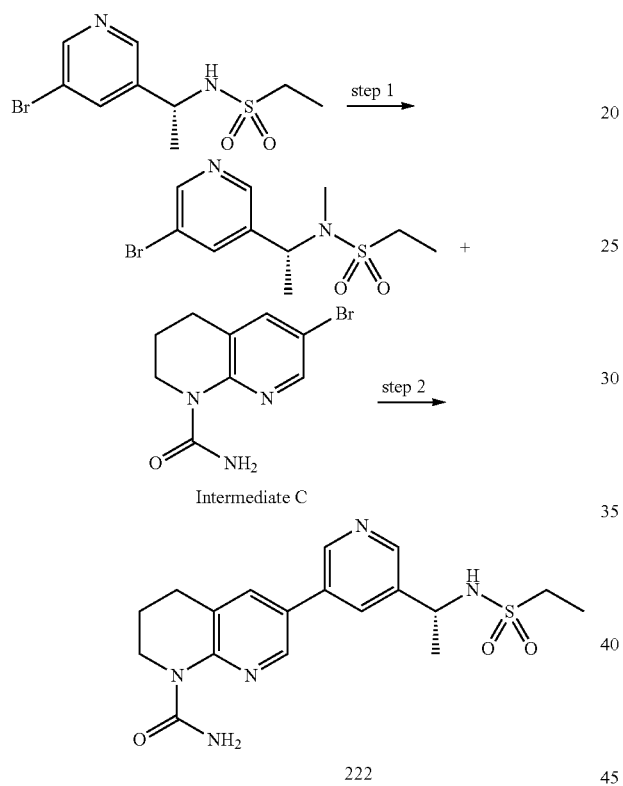

[(R)-1-(5-bromo-pyridin-3-yl)-ethyl]-amide is synthesized according to the procedures described in Example 93.

To a vial is added ethanesulfonic acid [(R)-1-(5-bromo-pyridin-3-yl)-ethyl]-amide (180 mg, 0.61 mmol) in 3 ml of THF, followed by the addition of NaH (35 mg, 0.92 mmol). Then iodomethane (131 mg, 0.92 mmol) is added. The reaction mixture is stirred at room temperature for 18 hours. The reaction mixture is diluted with DCM, washed with water, brine, dried over anhydrous $Na_2SO_4$, filtered and concentrated to give the crude product. Purification by the flash column chromatography affords 116 mg of ethanesulfonic acid [(R)-1-(5-bromo-pyridin-3-yl)-ethyl]-methyl-amide.

Ethanesulfonic acid [(R)-1-(5-bromo-pyridin-3-yl)-ethyl]-methyl-amide (116 mg, 0.38 mmol) is converted to 133 mg of the titled product using procedures described in Example 101.

238

Compound 223 in Table 1 is synthesized according to the procedure for Example 94, substituting either commercially available reagents or the appropriate intermediates described above.

Example 95

Synthesis of 6-(5-{[Methyl-(tetrahydro-pyran-4-carbonyl)-amino]-methyl}-pyridin-3-yl)-3,4-dihydro-2H-[1,8]naphthyridine-1-carboxylic acid amide (Cpd 225, Table 1)

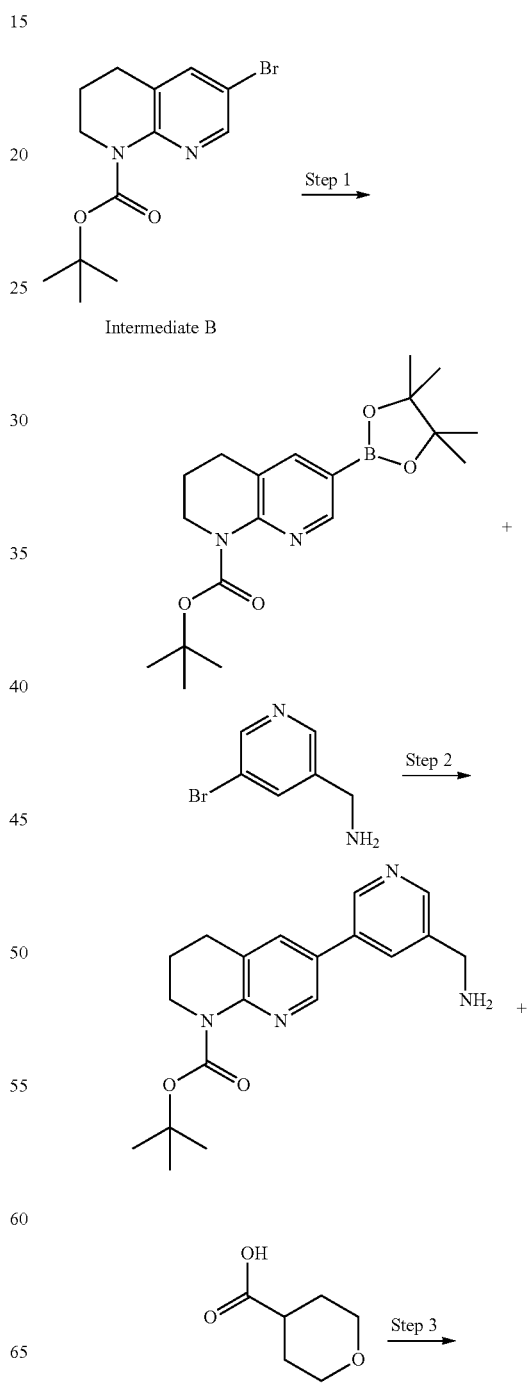

-continued

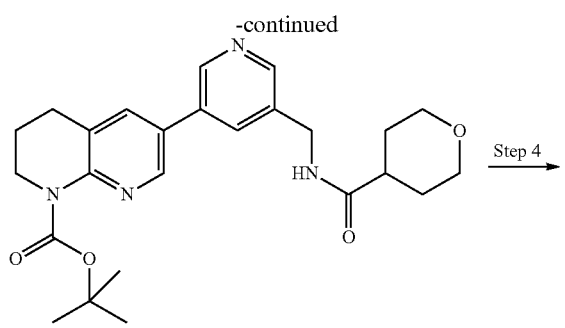
Step 4

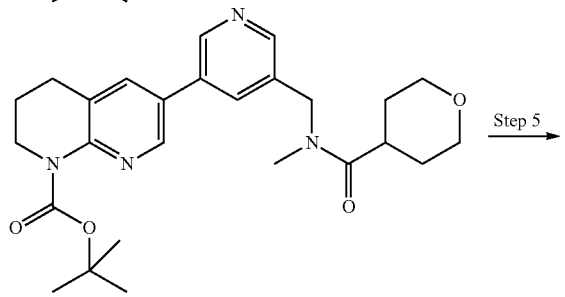
Step 5

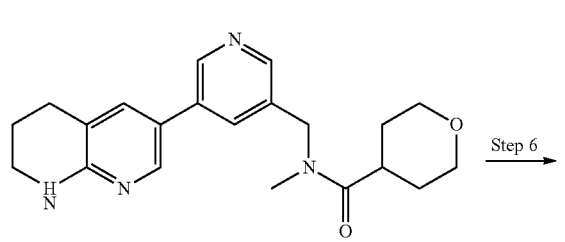
Step 6

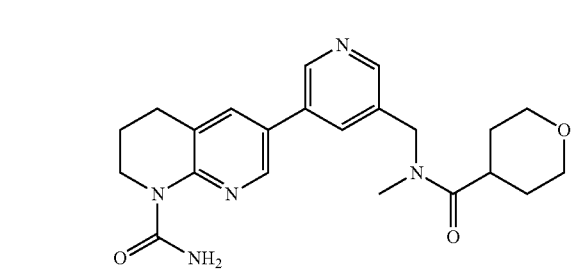
225

To a solution of Intermediate B (800 mg, 2.55 mmol) in 1,4-dioxane (26 mL) are added bis(pinacolato)diboron (714 mg, 2.81 mmol) and KOAc (751 mg, 7.66 mmol). Then Pd(dppf)Cl$_2$ (187 mg, 0.255 mmol) is added under N$_2$. The reaction mixture is heated to reflux for 2 hrs. After cooling down to room temperature, the crude reaction mixture containing 6-(4,4,5,5-Tetramethyl-[1,3,2]dioxaborolan-2-yl)-3,4-dihydro-2H-[1,8]naphthyridine-1-carboxylic acid tert-butyl ester is used in the next step without purification.

(5-Bromo-pyridin-3-yl)-methylamine (2.0 g, 11 mmol), Cs$_2$CO$_3$ (10 g, 31 mmol) and Pd(dppf)Cl$_2$ (470 mg, 0.64 mmol) are added into 6-(4,4,5,5-tetramethyl-[1,3,2]dioxaborolan-2-yl)-3,4-dihydro-2H-[1,8]naphthyridine-1-carboxylic acid tert-butyl ester (7.8 mmol, crude) 1,4-dioxane solution. The reaction mixture is heated to reflux for 16 hrs. The solvent is removed in vacuo and the residue is purified by flash column chromatography to give 1.3 g of 6-(5-aminomethyl-pyridin-3-yl)-3,4-dihydro-2H-[1,8]naphthyridine-1-carboxylic acid tert-butyl ester.

6-(5-aminomethyl-pyridin-3-yl)-3,4-dihydro-2H-[1,8]naphthyridine-1-carboxylic acid tert-butyl ester (100 mg, 0.29 mmol), tetrahydro-pyran-4-carboxylic acid (57 mg, 0.44 mmol) and triethyl amine (0.12 mL, 0.88 mmol) are mixed in acetonitrile (3.0 mL). Then TBTU (113 mg, 0.35 mmol) is added and the mixture is stirred for 16 hrs. All the solvent is removed in vacuo and to the residue are added saturated NaHCO$_3$ aqueous solution (5 mL), water (15 mL) and EtOAc (20 mL). The mixture is stirred for 10 min and the aqueous layer is separated and extracted with EtOAc (2×15 mL). The organic layers are combined and concentrated to give the crude 6-(5-{[(Tetrahydro-pyran-4-carbonyl)-amino]-methyl}-pyridin-3-yl)-3,4-dihydro-2H-[1,8]naphthyridine-1-carboxylic acid tert-butyl ester which is used in the next step directly.

6-(5-{[(Tetrahydro-pyran-4-carbonyl)-amino]-methyl}-pyridin-3-yl)-3,4-dihydro-2H-[1,8]naphthyridine-1-carboxylic acid tert-butyl ester (132 mg, 0.29 mmol) is dissolved in DMF (4.0 mL) and cooled down to 0° C. Sodium hydride 60% in mineral oil (14 mg, 0.35 mmol) is added and the mixture is stirred for 10 min. Then iodomethane (0.036 mL, 0.58 mmol) is added and the reaction mixture is warmed up to room temperature for 2 hrs. Saturated NH$_4$Cl aqueous solution (2.0 mL) is added along with water (10 mL) and EtOAc (15 mL). The mixture is stirred for 10 min, the aqueous layer is separated and extracted with EtOAc (2×10 mL). The organic layers are combined and concentrated to give the crude product. Purification by flash column chromatography affords 70 mg of 6-(5-{[methyl-(tetrahydro-pyran-4-carbonyl)-amino]-methyl}-pyridin-3-yl)-3,4-dihydro-2H-[1,8]naphthyridine-1-carboxylic acid tert-butyl ester.

6-(5-{[Methyl-(tetrahydro-pyran-4-carbonyl)-amino]-methyl}-pyridin-3-yl)-3,4-dihydro-2H-[1,8]naphthyridine-1-carboxylic acid tert-butyl ester (70 mg, 0.15 mmol) is dissolved in DCM (2.0 mL) and trifluoroacetic acid (0.5 mL) is added. The mixture is stirred for 16 hrs and the solvent is removed in vacuo. The residue is dissolved in MeOH and filtered through StratoSphere PL-HCO$_3$ MP SPE cartridge, concentrated and dried to give 50 mg of crude tetrahydro-pyran-4-carboxylic acid methyl-[5-(5,6,7,8-tetrahydro-[1,8]naphthyridin-3-yl)-pyridin-3-ylmethyl]-amide which is used without purification.

Tetrahydro-pyran-4-carboxylic acid methyl-[5-(5,6,7,8-tetrahydro-[1,8]naphthyridin-3-yl)-pyridin-3-ylmethyl]-amide (50 mg, 0.14 mmol) is converted to 32 mg of the titled product using Urea Formation Method II.

Example 96

Synthesis of 6-[5-(2-Oxo-2-piperidin-1-yl-ethoxymethyl)-pyridin-3-yl]-3,4-dihydro-2H-[1,8]naphthyridine-1-carboxylic acid amide (Cpd 228, Table 1)

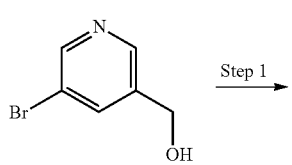
Step 1

241
-continued

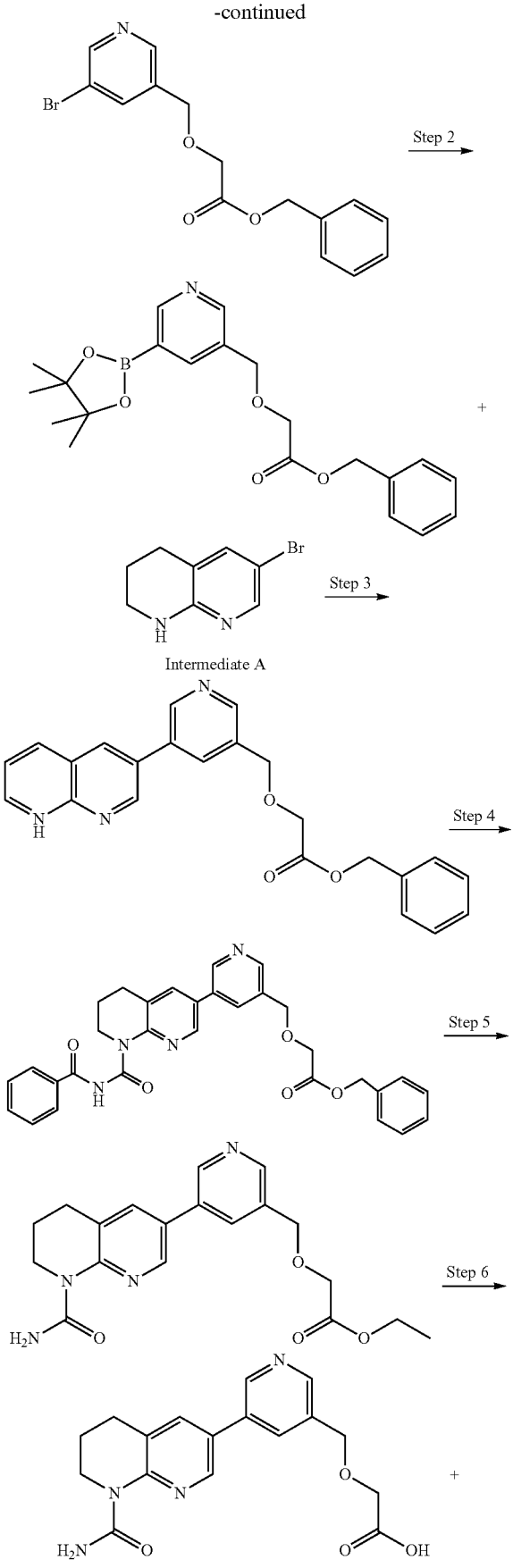

Intermediate A

242
-continued

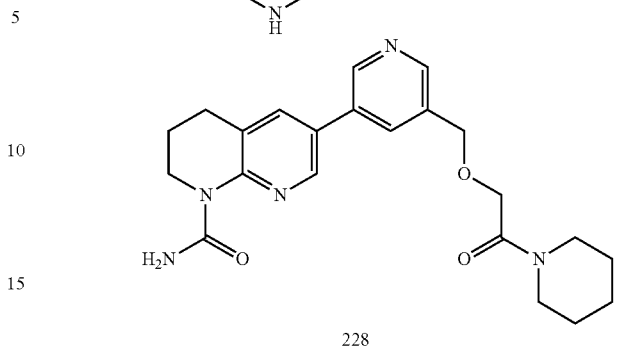

228

(5-Bromo-pyridin-3-yl)-methanol (25.0 g, 0.13 mol) is added to a solution of NaH (6.45 g, 0.27 mol) in THF (500 ml) at 0° C. and stirred at room temperature for 30 min. Benzyl bromoacetate (34.4 g, 0.15 mol) is added to this solution at 0° C. and stirred at room temperature overnight. The mixture is quenched with water and diluted with DCM. The organic layer is dried over $Na_2SO_4$ and concentrated in vacuo. The product is chromatographed on silica gel to give (5-bromo-pyridin-3-ylmethoxy)-acetic acid benzyl ester (10 g).

(5-Bromo-pyridin-3-ylmethoxy)-acetic acid benzyl ester (10.0 g, 30.0 mmol), bis(pinacolato)diboron (8.35 g, 32.9 mmol) and KOAc (8.65 g, 88.2 mmol) and $PdCl_2dppf$ (2.00 g, 2.7 mmol) are added into 700 mL of 1,4-dioxane and heated at reflux for 2 hrs. The mixture is cooled down to room temperature and the crude boronic acid is used in the next step without purification.

The crude boronic ester (3.0 g, 10.0 mmol), Intermediate A (3.0 g, 14.1 mmol), $PdCl_2dppf$ (0.60 g, 0.82 mmol) and $Cs_2CO_3$ (12.0 g, 36.8 mmol) are mixed in 210 mL of 1,4-dioxane and heated at reflux overnight. The mixture is cooled to room temperature and [5-(5,6,7,8-tetrahydro-[1,8]naphthyridin-3-yl)-pyridin-3-ylmethoxy]-acetic acid benzyl ester (1.0 g) is obtained by chromatography.

[5-(5,6,7,8-Tetrahydro-[1,8]naphthyridin-3-yl)-pyridin-3-ylmethoxy]-acetic acid benzyl ester (6.0 g, 15.4 mmol) and benzoyl isocyanate (3.8 g, 25.8 mmol) are mixed in 100 mL DCM and heated to reflux for 3 h. [5-(8-Benzoylaminocarbonyl-5,6,7,8-tetrahydro-[1,8]naphthyridin-3-yl)-pyridin-3-ylmethoxy]-acetic acid benzyl ester (8.3 g,) is obtained by concentrating the reaction mixture in vacuo.

[5-(8-Benzoylaminocarbonyl-5,6,7,8-tetrahydro-[1,8] naphthyridin-3-yl)-pyridin-3-ylmethoxy]-acetic acid benzyl ester (6.0 g, 11.2 mmol) and $K_2CO_3$ (3.6 g, 26.0 mmol) are mixed in 100 mL EtOH and heated to reflux for 1 hr. Upon cooling to room temperature [5-(8-Carbamoyl-5,6,7,8-tetrahydro-[1,8]naphthyridin-3-yl)-pyridin-3-ylmethoxy]-acetic acid ethyl ester (3.0 g) is obtained.

[5-(8-Carbamoyl-5,6,7,8-tetrahydro-[1,8]naphthyridin-3-yl)-pyridin-3-ylmethoxy]-acetic acid ethyl ester (1.0 g, 2.7 mmol) and LiOH (0.10 g, 4.2 mmol) are mixed in $H_2O$ (10 mL) and EtOH (10 mL) and stirred at room temperature overnight. The reaction mixture is concentrated under vacuum and treated with 1 N HCl, and ethyl acetate. The organic layer is concentrated to give [5-(8-carbamoyl-5,6,7,8-tetrahydro-[1,8]naphthyridin-3-yl)-pyridin-3-ylmethoxy]-acetic acid (0.80 g).

243

To a stirred solution of [5-(8-carbamoyl-5,6,7,8-tetrahydro-[1,8]naphthyridin-3-yl)-pyridin-3-ylmethoxy]-acetic acid (80 mg, 0.23 mmol) in DMF (3 mL) is added HATU (107 mg, 0.28 mmol) followed by piperidine (20 mg, 0.23 mmol) and DIEA (0.26 ml, 1.50 mmol). The resulting mixture is stirred at room temperature for 2 hrs. The reaction is concentrated and the remaining residue is purified via flash column chromatography to give the titled product (29 mg).

Compounds 226, 227, 229, 230, 231, 232, 248 and 249 in Table 1 are synthesized according to the procedure for Example 96, substituting either commercially available reagents or the appropriate intermediates described above.

Example 97

Synthesis of 6-[5-((R)-1-acetylamino-ethyl)-pyridin-3-yl]-3,4-dihydro-2H-[1,8]naphthyridine-1-carboxylic acid amide (Cpd 233, Table 1)

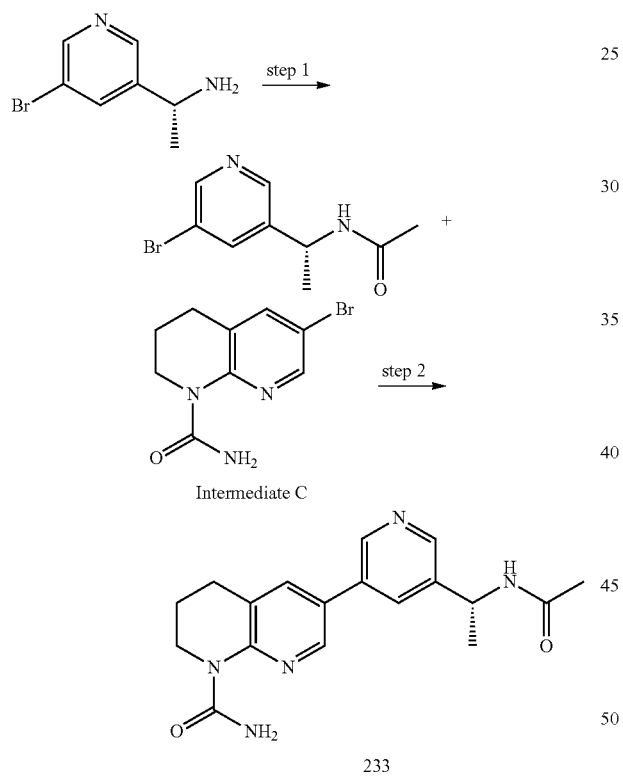

To a vial is added (1R)-1-(5-bromo(3-pyridyl))ethylamine HCl (500 mg, 2.1 mmol) in 2.5 ml of DCM, followed by the addition of N,N-diisopropylethylamine (816 mg, 2.52 mmol). Then acetyl chloride 1M in DCM solution (2.5 ml, 2.5 mmol) is added at 0° C. The reaction mixture is stirred at room temperature for 2 hours. The reaction mixture is diluted with DCM, washed with water, brine, dried over anhydrous Na$_2$SO$_4$, filtered and concentrated to give the crude product. Purification by the flash column chromatography affords 273 mg of N-[(R)-1-(5-bromo-pyridin-3-yl)-ethyl]-acetamide.

N-[(R)-1-(5-bromo-pyridin-3-yl)-ethyl]-acetamide (112 mg, 0.46 mmol) is converted to 54 mg of the titled product using procedures described in Example 101.

244

Compound 234 in Table 1 is synthesized according to the procedure for Example 97, substituting either commercially available reagents or the appropriate intermediates described above.

Example 98

Synthesis of 6-[5-(2-Methyl-3-oxo-morpholin-4-ylmethyl)-pyridin-3-yl]-3,4-dihydro-2H-[1,8]naphthyridine-1-carboxylic acid amide (Cpd 235, Table 1)

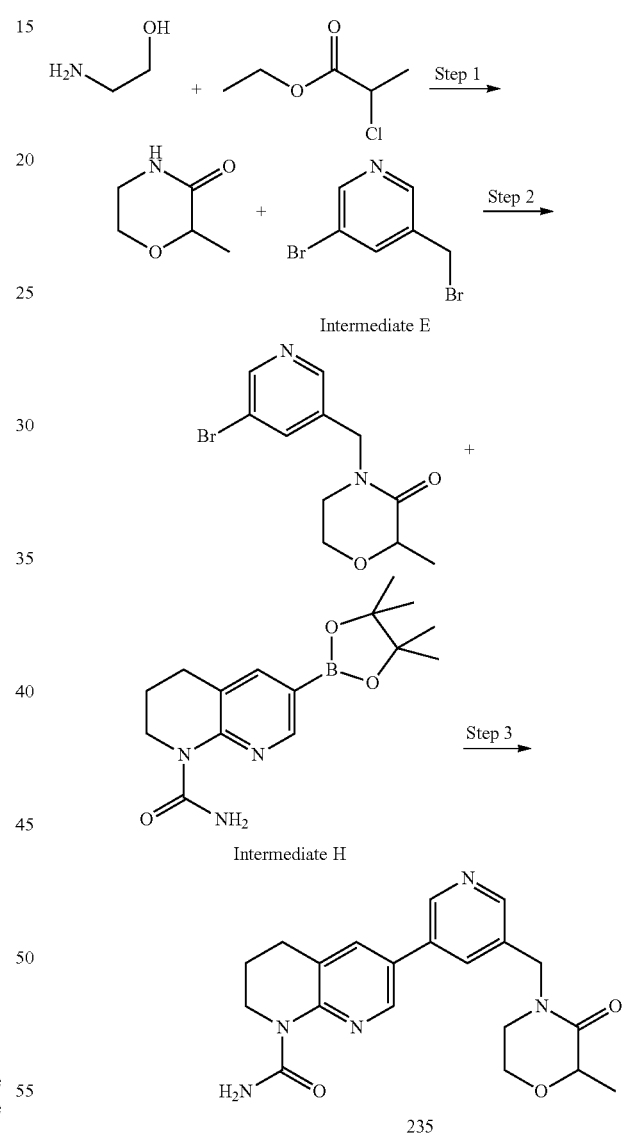

2-Amino-ethanol (4.58 g, 75 mmol) is dissolved in 1,4-dioxane (40 mL) and 60% sodium hydride in mineral oil (3.2 g, 80 mmol) is added at 0° C. The mixture is heated at 110° C. for 10 min and cooled down to 0° C. Then 2-chloro-propionic acid ethyl ester (10.2 g, 75 mmol) in 15 mL of 1,4-dioxane is added at 0° C. and the mixture is heated at 110° C. for another 1 hr. The reaction mixture is filtered and the filtrate is concentrated to give the crude product. Purification by the flash column chromatography affords 6.5 g of 2-methyl-morpholin-3-one. 2-Methyl-morpholin-3-one (298 mg, 2.59 mmol) is dissolved in DMF (10 mL) and 60% sodium hydride in mineral oil (96 mg, 2.39 mmol) is added at 0° C. The mixture is stirred for 15 min and Intermediate E (500 mg, 1.99 mmol) is added at 0° C. The mixture is warmed up to room temperature and stirred for another 2 hrs. Then saturated NH₄Cl aqueous solution (5.0 mL) is added along with EtOAc (25 mL) and water (15 mL). The mixture is stirred for 10 min and the aqueous layer is separated and extracted with EtOAc (2×15 mL). The organic layers are combined and concentrated to give the crude product. Purification by flash column chromatography affords 550 mg of 4-(5-bromo-pyridin-3-ylmethyl)-2-methyl-morpholin-3-one.

4-(5-Bromo-pyridin-3-ylmethyl)-2-methyl-morpholin-3-one (550 mg, 1.93 mmol) is coupled with Intermediate H (2.34 mmol, using crude) to give 523 mg of the titled product using Suzuki Coupling Method VI.

Enantiomers of the titled compound are separated using chiral CO₂ Supercritical Fluid Chromatography to give Compound 240 and Compound 241 (Analytical conditions: Chiralpak IA-SFC 4.6×100 mm column; 50% MeOH:CO₂ @ 2.5 mL/min; 40° C.; 200 bars; Retention time, Compound 240: 4.86 min, Compound 241: 18.57 min) in Table 1.

Example 99

Synthesis of 6-(5-Cyclopropyl-pyridin-3-yl)-3,4-dihydro-2H-[1,8]naphthyridine-1-carboxylic acid amide (Cpd 237, Table 1)

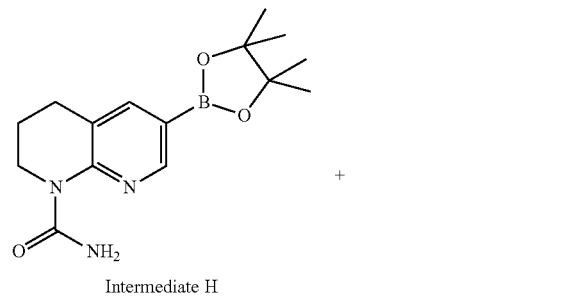

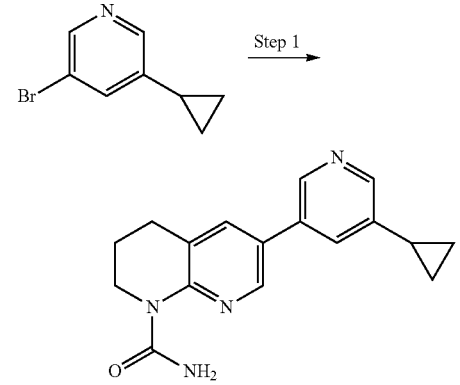

3-Bromo-5-cyclopropyl-pyridine (77 mg, 0.39 mmol) is coupled with Intermediate H (0.39 mmol, using crude) to give 70 mg of the titled product using Suzuki Coupling Method VI.

Example 100

Synthesis of 6-[5-[(R)-1-(Acetyl-methyl-amino)-ethyl]-pyridin-3-yl]-3,4-dihydro-2H-[1,8]naphthyridine-1-carboxylic acid amide (Cpd 238, Table 1)

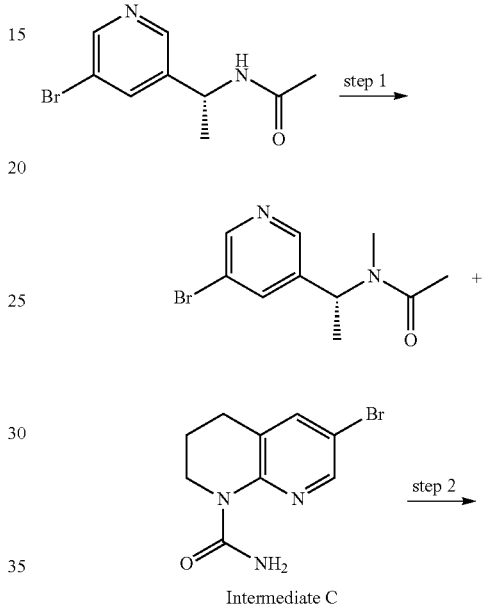

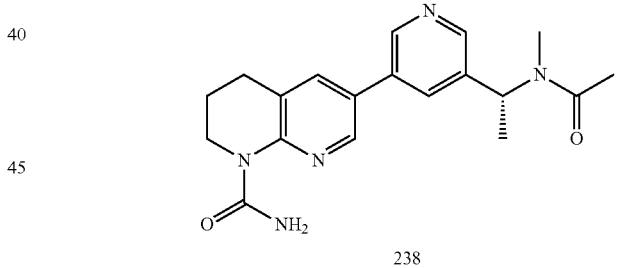

N-[(R)-1-(5-Bromo-pyridin-3-yl)-ethyl]-acetamide is synthesized according to the procedures described in Example 97.

To a vial is added N-[(R)-1-(5-bromo-pyridin-3-yl)-ethyl]-acetamide (111 mg, 0.46 mmol) in 3 ml of THF, followed by the addition of 60% NaH (35 mg, 0.92 mmol). Then iodomethane (130 mg, 0.91 mmol) is added. The reaction mixture is stirred at room temperature for 18 hours. The reaction mixture is diluted with DCM, washed with water, brine, dried over anhydrous Na₂SO₄, filtered and concentrated to give the crude product. Purification by the flash column chromatography affords 103 mg of N-[(R)-1-(5-bromo-pyridin-3-yl)-ethyl]-N-methyl-acetamide.

N-[(R)-1-(5-bromo-pyridin-3-yl)-ethyl]-N-methyl-acetamide (103 mg, 0.4 mmol) is converted to 50 mg of the titled product using procedures described in Example 101.

Compound 239 in Table 1 is synthesized according to the procedure for Example 100, substituting either commercially available reagents or the appropriate intermediates described above.

Example 101

Synthesis of 6-[5-(1,1-dioxo-1lambda6-[1,2]thiazinan-2-ylmethyl)-pyridin-3-yl]-3,4-dihydro-2H-[1,8]naphthyridine-1-carboxylic acid amide (Cpd 243. Table 1)

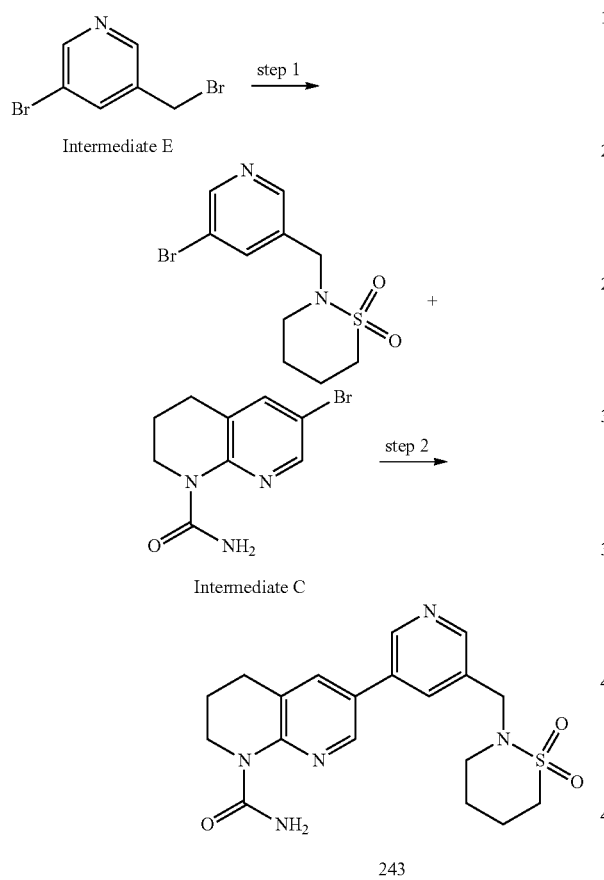

To a vial is added 1,4-butanesultam (81 mg, 0.60 mmol) in 2 ml of DMF, followed by the addition of 60% NaH (24 mg, 0.6 mmol) at 0° C. The reaction mixture is stirred for 15 minutes, followed by the addition of To a vial is added 3-bromo-5-bromomethyl-pyridine, Intermediate E (100 mg, 0.40 mmol). The reaction mixture is stirred at room temperature for 2 hours. The reaction mixture is diluted with EtOAc, washed with water, brine, dried over anhydrous $Na_2SO_4$, filtered and concentrated to give the crude product. Purification by the flash column chromatography affords 86 mg of 2-(5-bromo-pyridin-3-ylmethyl)-[1,2]thiazinane 1,1-dioxide.

To a vial is added 2-(5-bromo-pyridin-3-ylmethyl)-[1,2]thiazinane 1,1-dioxide (75 mg, 0.26 mmol), bis(pinacolato)diboron (98 mg, 0.39 mmol), potassium acetate (101 mg, 1.03 mmol) and [1,1'-bis(diphenylphosphino)ferrocene)dichloropalladium(II) (19 mg, 0.026 mmol) in 3 ml of 1,4-dioxane. The reaction mixture is stirred at 120° C. under Ar for 1 hour. The reaction mixture is cooled down to room temperature, followed by the addition of—Intermediate C, 2M $Na_2CO_3$ (0.22 ml, 0.43 mmol) and [1,1'-bis(diphenylphosphino)ferrocene)dichloropalladium(II) (8 mg, 0.011 mmol). The reaction mixture is stirred under Ar at 90° C. for 4 hours. The reaction mixture is concentrated. The residue is diluted with EtOAc, washed with water, brine, dried over anhydrous $Na_2SO_4$, filtered and concentrated to give the crude product. Purification by the flash column chromatography affords 62 mg of the titled product.

Compound 242 in Table 1 is synthesized according to the procedure for Example 101, substituting either commercially available reagents or the appropriate intermediates described above.

Example 102

Synthesis of 6-(1'-Acetyl-4-cyano-1',2',3',4',5',6'-hexahydro-[3,4']bipyridinyl-5-yl)-3,4-dihydro-2H-[1,8]naphthyridine-1-carboxylic acid amide (Cpd 244, Table 1)

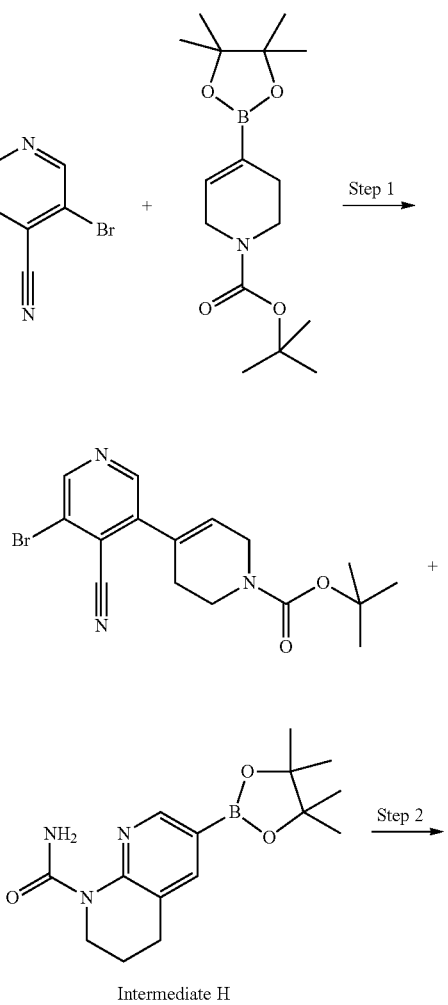

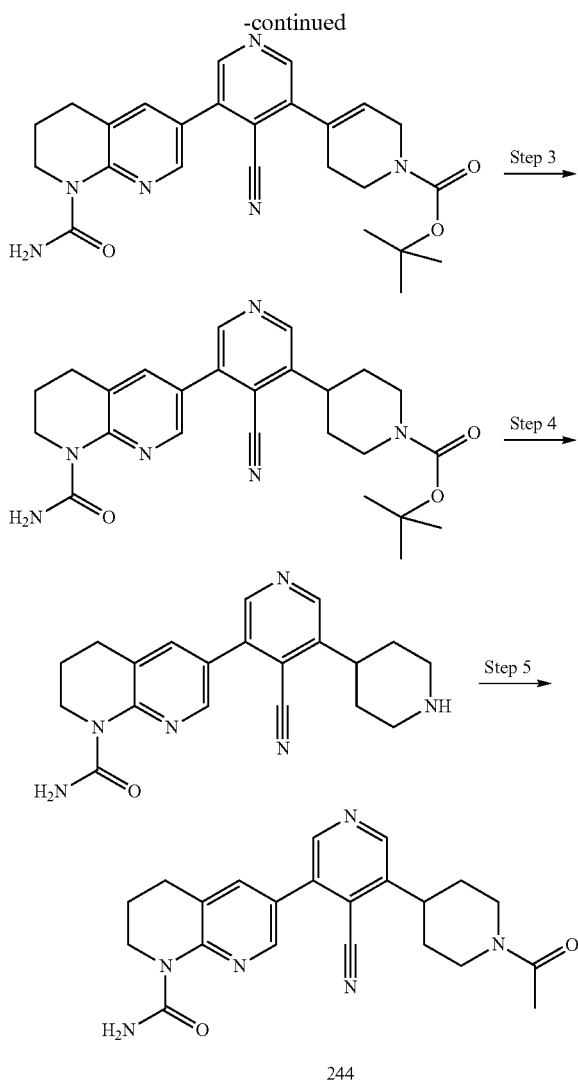

244

3,5-Dibromo-isonicotinonitrile (500 mg, 1.9 mmol), 4-(4,4,5,5-tetramethyl-[1,3,2]dioxaborolan-2-yl)-3,6-dihydro-2H-pyridine-1-carboxylic acid tert-butyl ester (710 mg, 2.3 mmol) and 2.0 M $Na_2CO_3$ aqueous solution (1.9 mL, 3.8 mmol) are added into the 1,4-dioxane (20 mL). Argon gas is bubbled through the solution for 5 min. Then $PdCl_2dppf$ (140 mg, 0.19 mmol) is added and the mixture is heated at 100° C. for 3.5 hrs. The reaction mixture is filtered and the filtrate is concentrated to give the crude product. Purification by flash column chromatography affords 295 mg of 5-bromo-4-cyano-3',6'-dihydro-2'H-[3,4']bipyridinyl-1'-carboxylic acid tert-butyl ester.

5-Bromo-4-cyano-3',6'-dihydro-2'H-[3,4']bipyridinyl-1'-carboxylic acid tert-butyl ester (295 mg, 0.81 mmol) is coupled with Intermediate H (1.0 mmol, using crude) to give 179 mg of 5-(8-carbamoyl-5,6,7,8-tetrahydro-[1,8]naphthyridin-3-yl)-4-cyano-3',6'-dihydro-2'H-[3,4']bipyridinyl-1'-carboxylic acid tert-butyl ester using Suzuki Coupling Method VI.

5-(8-carbamoyl-5,6,7,8-tetrahydro-[1,8]naphthyridin-3-yl)-4-cyano-3',6'-dihydro-2'H-[3,4']bipyridinyl-1'-carboxylic acid tert-butyl ester (100 mg, 0.22 mmol), 10% Pd on carbon (88 mg, 0.083 mmol) and ammonium formate (210 mg, 3.3 mmol) are mixed in MeOH (2.0 mL). The reaction mixture is heated at 60° C. for 24 hrs. Then the solid is filtered and the filtrate is concentrated to give the crude 5-(8-carbamoyl-5,6,7,8-tetrahydro-[1,8]naphthyridin-3-yl)-4-cyano-3',4',5',6'-tetrahydro-2'H-[3,4']bipyridinyl-1'-carboxylic acid tert-butyl ester which is used in the next step without purification.

The crude 5-(8-carbamoyl-5,6,7,8-tetrahydro-[1,8]naphthyridin-3-yl)-4-cyano-3',4',5',6'-tetrahydro-2'H-[3,4']bipyridinyl-1'-carboxylic acid tert-butyl ester (0.22 mmol) is dissolved in DCM (2.0 mL) and trifluoroacetic acid (0.5 mL) is added. The mixture is stirred for 16 hrs and all the solvent is removed in vacuo. The residue is dissolved in MeOH and is passed through StratoSpheres SPE $PL-HCO_3$ cartridge. The solution is concentrated to give the crude 6-(4-cyano-1',2',3',4',5',6'-hexahydro-[3,4]bipyridinyl-5-yl)-3,4-dihydro-2H-[1,8]naphthyridine-1-carboxylic acid amide which is used without purification.

The crude 6-(4-cyano-1',2',3',4',5',6'-hexahydro-[3,4]bipyridinyl-5-yl)-3,4-dihydro-2H-[1,8]naphthyridine-1-carboxylic acid amide (0.22 mmol), acetic acid (0.025 mL, 0.43 mmol) and triethyl amine (0.091 mL, 0.65 mmol) are mixed in acetonitrile (2.5 mL). Then TBTU (104 mg, 0.33 mmol) is added and the mixture is stirred for 16 hrs. All the solvent is removed and the residue is purified by flash column chromatography to give 38 mg of the titled product.

Example 103

Synthesis of 6-[4-Chloro-5-(1-hydroxy-ethyl)-pyridin-3-yl]-3,4-dihydro-2H-[1,8]naphthyridine-1-carboxylic acid amide (Cpd 245, Table 1)

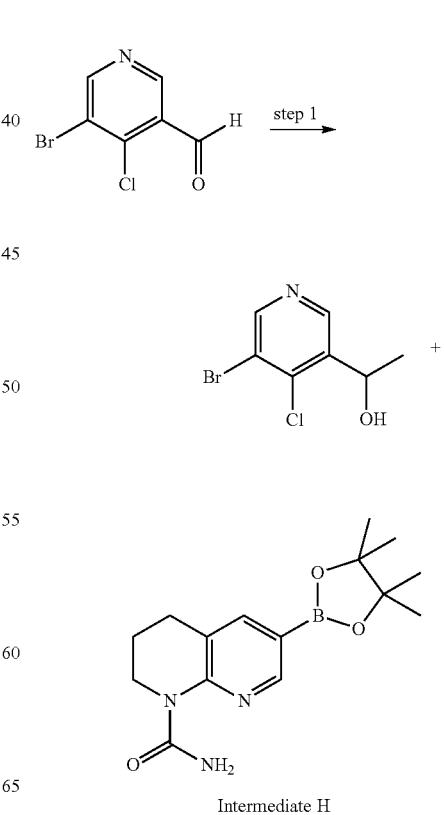

Intermediate H

251

-continued

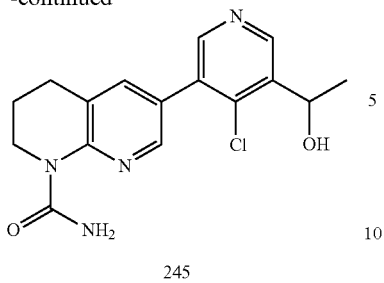

245

To a round bottom flask is added 5-bromo-4-chloro-pyridine-3-carbaldehyde (490 mg, 2.22 mmol) in 10 ml of THF at 0° C., followed by the addition of methylmagnesium bromide, 3M in ether (0.89 ml, 2.67 mmol). The reaction mixture is stirred at room temperature for 1 hour. The reaction mixture is concentrated. The residue is diluted with EtOAc/saturated NH₄Cl. The organic layer is separated, washed with water, brine, dried over anhydrous Na₂SO₄, filtered and concentrated to give the crude product. Purification by the flash column chromatography affords 287 mg of 1-(5-bromo-4-chloro-pyridin-3-yl)-ethanol.

1-(5-Bromo-4-chloro-pyridin-3-yl)-ethanol (287 mg, 1.22 mmol) is converted to 28 mg of the titled product using Suzuki Coupling Method VI.

Example 104

Syntheses of enantiomers of 6-{5-[1-(3-Oxo-morpholin-4-yl)-ethyl]-pyridin-3-yl}-3,4-dihydro-2H-[1, 8]naphthyridine-1-carboxylic acid amide (Cpd 246 and 247, Table 1)

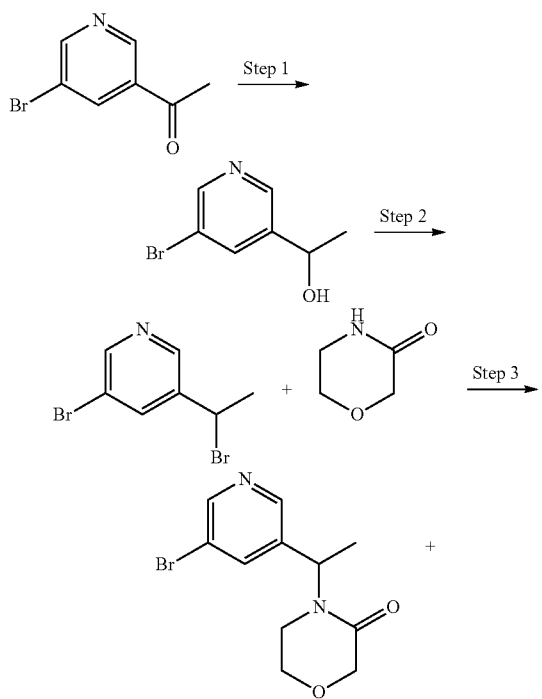

252

-continued

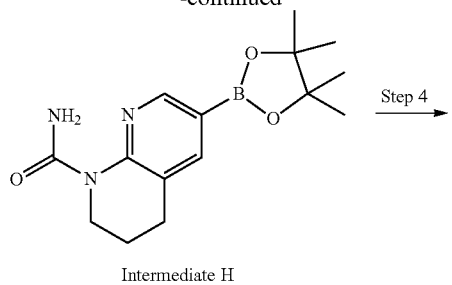

Intermediate H 246 and 247

1-(5-Bromo-pyridin-3-yl)-ethanone (3.0 g, 15 mmol) is dissolved in MeOH (20 mL) and sodium borohydride (1.1 g, 30 mmol) is added in 5 small portions every 15 min. The mixture is stirred for 16 hrs and the solvent is then removed in vacuo. Saturated aqueous NH₄Cl solution (10 mL) is added along with 30 mL of water. The mixture is extracted with EtOAc (3×50 mL) and the organic layers are combined and concentrated to give the crude product. Purification by flash column chromatography affords 2.9 g of 1-(5-bromo-pyridin-3-yl)-ethanol.

1-(5-Bromo-pyridin-3-yl)-ethanol (1.5 g, 7.4 mmol) is dissolved in DCM (70 mL) and phosphorus tribromide (0.73 mL, 7.4 mmol) is added. The mixture is stirred for 4 hrs and saturated NaHCO₃ aqueous solution is used to adjust the pH to about 7. The mixture is then extracted with DCM (3×50 mL). The organic layers are combined and concentrated to give the crude product. Purification by flash column chromatography affords 850 mg of 3-bromo-5-(1-bromo-ethyl)-pyridine.

Morpholin-3-one (650 mg, 6.4 mmol) is dissolved in DMF (20 mL) and 60% sodium hydride in mineral oil (190 mg, 4.8 mmol) is added at 0° C. The mixture is stirred for 15 min and 3-bromo-5-(1-bromo-ethyl)-pyridine (850 mg, 3.2 mmol) is added at 0° C. The mixture is warmed up to room temperature for 2 hrs. Then saturated NH₄Cl aqueous solution (25 mL) is added along with EtOAc (50 mL) and water (50 mL). The mixture is stirred for 10 min and the aqueous layer is separated and extracted with EtOAc (2×50 mL). The organic layers are combined, washed with water (3×30 mL) and concentrated to give the crude product. Purification by flash column chromatography affords 750 mg of 4-[1-(5-bromo-pyridin-3-yl)-ethyl]-morpholin-3-one. 4-[1-(5-Bromo-pyridin-3-yl)-ethyl]-morpholin-3-one (750 mg, 2.6 mmol) is coupled with Intermediate H (3.1 mmol, using crude) to give 850 mg of the titled product using Suzuki Coupling Method VI.

Enantiomers of the titled compound are separated using chiral CO₂ Supercritical Fluid Chromatography to give Compound 247 and Compound 246 (Analytical conditions: LUX 5 u Cellulose 1 analytical column; 30% (1:1:1 MeOH:EtOH:isopropylamine)+1% diethylamine:CO₂ @ 2.5 mL/min; 40°

Example 105

Synthesis of 6-[5-(1-Acetyl-piperidin-4-yloxymethyl)-4-chloro-pyridin-3-yl]-3,4-dihydro-2H-[1,8]naphthyridine-1-carboxylic acid amide (Cpd 255, Table 1)

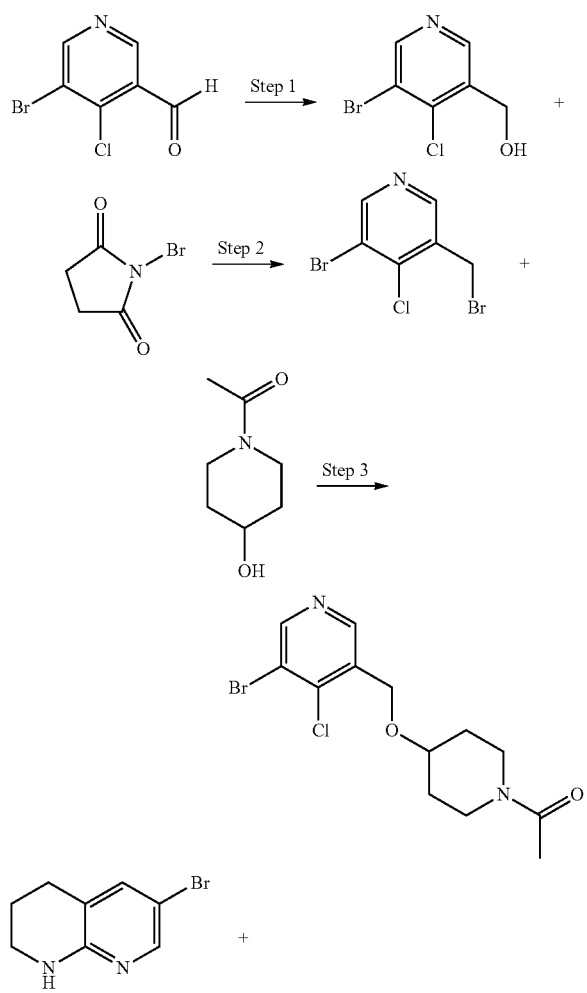

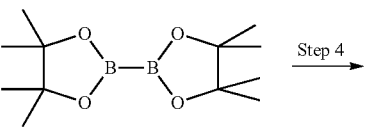

Intermediate A

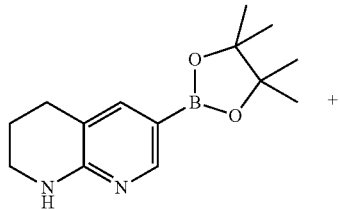

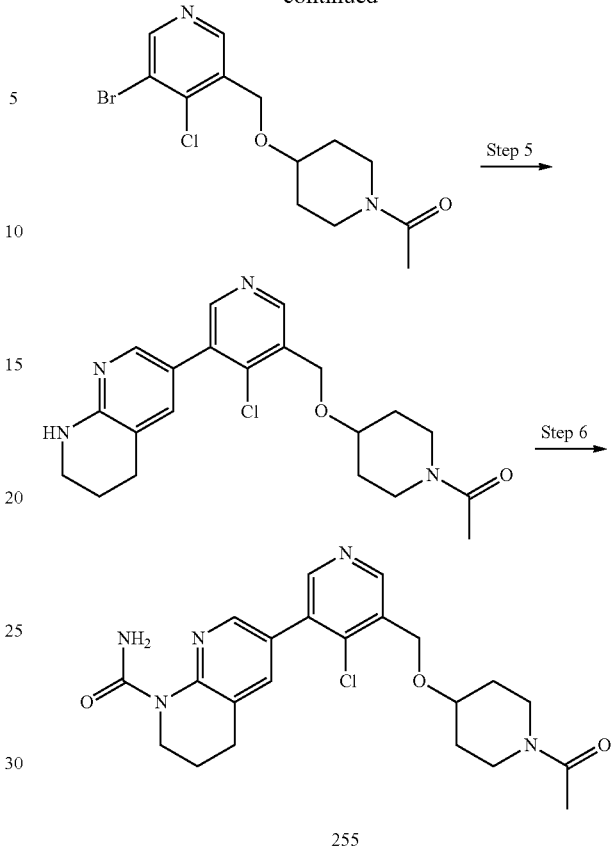

255

5-Bromo-4-chloro-pyridine-3-carbaldehyde (500 mg, 2.27 mmol) is dissolved in MeOH (20 mL) and sodium borohydride (257 mg, 6.80 mmol) is added. The mixture is stirred for 1 hr at room temperature and the solvent is removed in vacuo. Then saturated NH$_4$Cl aqueous solution (20 mL), water (50 mL) and EtOAc (50 mL) are added and the mixture is stirred for 10 min. The aqueous layer is separated and extracted with EtOAc (2×50 mL). The organic layers are combined and concentrated to give the crude product. Purification by flash column chromatography affords 400 mg of (5-bromo-4-chloro-pyridin-3-yl)-methanol.

(5-Bromo-4-chloro-pyridin-3-yl)-methanol (400 mg, 1.80 mmol) and triphenylphosphine (566 mg, 2.16 mmol) are dissolved in DCM (20 mL) and N-bromosuccinimide (384 mg, 2.16 mmol) is added. The mixture is stirred for 4 hrs at room temperature. Then the reaction mixture is purified by flash column chromatography directly (without work-up) to give 300 mg of 3-bromo-5-bromomethyl-4-chloro-pyridine.

1-(4-Hydroxy-piperidin-1-yl)-ethanone (301 mg, 2.10 mmol) is dissolved in DMF (10 mL) and 60% sodium hydride in mineral oil (84 mg, 2.10 mmol) is added at 0° C. The mixture is stirred for 15 min at 0° C. and 3-bromo-5-bromomethyl-4-chloro-pyridine (300 mg, 1.05 mmol) is added at that temperature. Then the mixture is warmed up to room temperature and stirred for 1 hr. Saturated NH$_4$Cl aqueous solution (15 mL) is added, along with water (50 mL) and EtOAc (50 mL). The mixture is stirred for 10 min and the aqueous layer is separated and extracted with EtOAc (2×50 ml). The organic layers are combined and concentrated to give the crude product. Purification by flash column chromatography affords 112 mg of 1-[4-(5-bromo-4-chloro-pyridin-3-ylmethoxy)-piperidin-1-yl]-ethanone.

Intermediate A (92 mg, 0.43 mmol), bis(pinacolato)diboron (142 mg, 0.56 mmol) and KOAc (127 mg, 1.29 mmol) are added into 1,4-dioxane (7.0 mL) and Argon gas is bubbled through the solution for 5 min. Then PdCl$_2$dppf (31 mg, 0.043 mmol) is added and the mixture is heated at 120° C. for 1 hr. After cooling down to room temperature, the crude reaction mixture containing 6-(4,4,5,5-tetramethyl-[1,3,2]dioxaborolan-2-yl)-1,2,3,4-tetrahydro-[1,8]naphthyridine is used in the next step without purification.

1-[4-(5-Bromo-4-chloro-pyridin-3-ylmethoxy)-piperidin-1-yl]-ethanone (100 mg, 0.29 mmol) and 2.0 M Na$_2$CO$_3$ aqueous solution (0.29 mL, 0.58 mmol) are added into the crude reaction mixture from the previous step. Argon gas is bubbled through the solution for 5 min. Then PdCl$_2$dppf (22 mg, 0.030 mmol) is added. The mixture is heated at 110° C. for 2.5 hrs and DCM (50 mL) and water (50 mL) are added. The mixture is filtered and the aqueous layer of the filtrate is separated, extracted with EtOAc (2×100 mL) and DCM (2×100 mL). The organic layers are combined and concentrated to give the crude product. Purification by flash column chromatography affords 52 mg of 1-{4-[4-chloro-5-(5,6,7,8-tetrahydro-[1,8]naphthyridin-3-yl)-pyridin-3-ylmethoxy]-piperidin-1-yl}-ethanone.

1-{4-[4-chloro-5-(5,6,7,8-tetrahydro-[1,8]naphthyridin-3-yl)-pyridin-3-ylmethoxy]-piperidin-1-yl}-ethanone (26 mg, 0.065 mmol) is converted to 15 mg of the titled product using Urea Formation Method II.

Compound 236 in Table 1 is synthesized according to the procedure for Example 105, substituting 1-(4-Hydroxy-piperidin-1-yl)-ethanone with morpholin-3-one in Step 3.

Example 106

Synthesis of 6-[5-(1-Methanesulfonyl-pyrrolidin-2-yl)-pyridin-3-yl]-3,4-dihydro-2H-[1,8]naphthyridine-1-carboxylic acid amide (Cpd 257, Table 1)

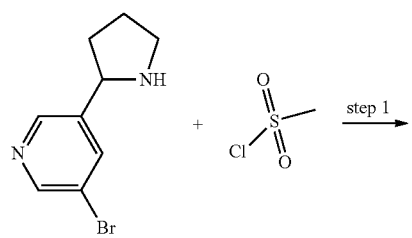

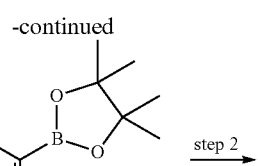

Intermediate H

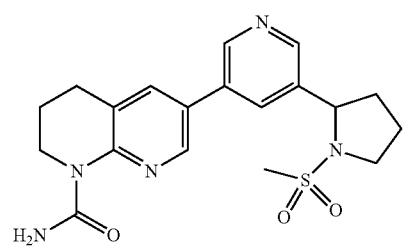

257

To a stirred solution of 3-bromo-5-(2-pyrrolidinyl)pyridine (0.2 g, 0.881 mmol) and pyridine (0.157 mL, 1.937 mmol) in DCM (1 mL) is added methanesulfonyl chloride in DCM (1 mL) dropwise. The mixture is stirred at room temperature for 2 h. The mixture is concentrated. The resulting crude product is purified by normal phase chromatography using 0-3% MeOH in DCM as the gradient to afford 3-bromo-5-(1-methanesulfonyl-pyrrolidin-2-yl)-pyridine (211.2 mg, 79% yield).

Suzuki Coupling Method VI is applied using the crude solution of Intermediate H for step 2 to afford the titled product.

Enantiomers of the titled compound are separated using chiral CO$_2$ Supercritical Fluid Chromatography to give Compound 268 and Compound 269 (Analytical conditions: LUX 5 u Cellulose 3 Analytical column; 25% 1:1:1 MeOH:IPA:EtOH (+1% DEA):CO$_2$ @ 3 mL/min; 40° C.; 200 bars; Retention time, Compound 268: 3.08 min, Compound 269: 3.63 min) in Table 1.

Compound 256 in Table 1 is synthesized according to the procedure for Example 106, substituting the sulfonamide obtained in the first step with the acetamide obtained as follows:

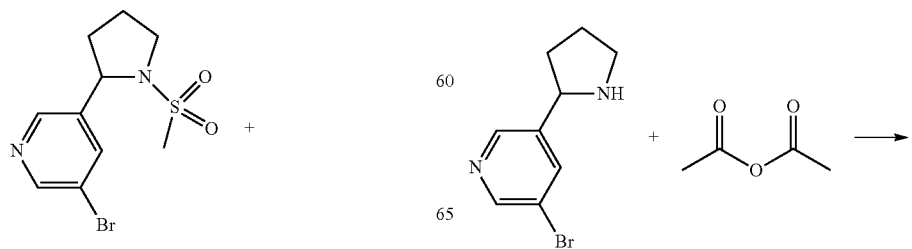

257
-continued

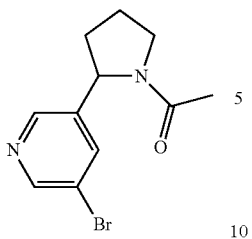

To a solution of 3-bromo-5-(2-pyrrolidinyl)pyridine (200 mg, 0.881 mmol) and pyridine (0.2 mL, 1.96 mmol) in DCM (1 mL) in a 8-mL vial is added acetic anhydride (0.093 mL, 0.969 mmol) dropwise. The mixture is stirred at room temperature for 2.5 h. The mixture is concentrated. The resulting crude product is purified by normal phase chromatography using 0-4.5% MeOH in DCM as the gradient to afford 1-[2-(5-bromo-pyridin-3-yl)-pyrrolidin-1-yl]-ethanone (313 mg, 83% yield).

Enantiomers of Compound 256 are separated using chiral $CO_2$ Supercritical Fluid Chromatography to give Compound 272 and Compound 273 (Analytical conditions: Chiralpak IA-SFC, 4.6×100 mm column; 30% 1:1:1 MeOH:IPA:EtOH (+1% DEA):$CO_2$ @ 3 mL/min; 40° C.; 200 bars; Retention time, Compound 272: 6.02 min, Compound 273: 13.10 min) in Table 1.

Example 107

Synthesis of 6-[5-(1-methyl-5-oxo-pyrrolidin-2-yl)-pyridin-3-yl]-3,4-dihydro-2H-[1,8]naphthyridine-1-carboxylic acid amide (Cpd 258, Table 1)

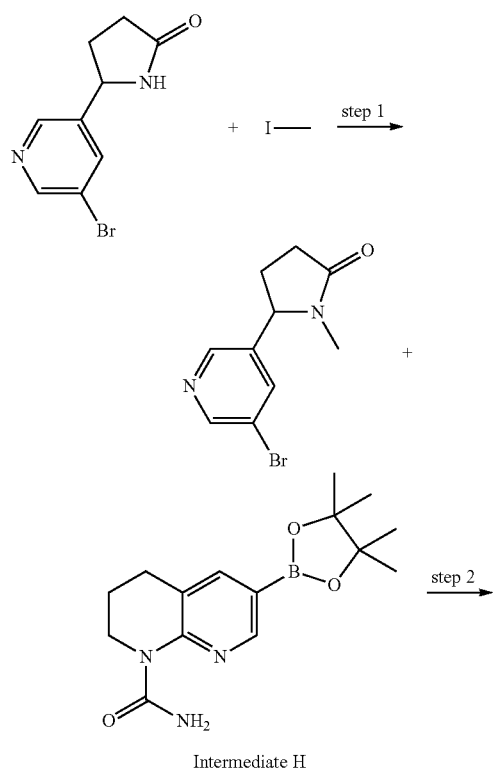

Intermediate H

258
-continued

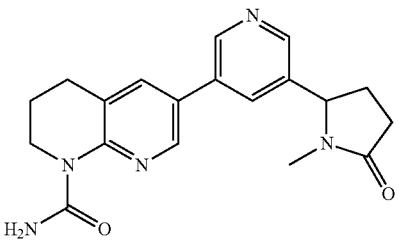

258

5-(5-Bromo-pyridin-3-yl)-pyrrolidin-2-one is prepared as described in Example 76. To a solution of 5-(5-bromo-pyridin-3-yl)-pyrrolidin-2-one (202 mg, 0.84 mmol) in THF (5.0 mL) is added 60% NaH (50 mg, 1.3 mmol). The mixture is stirred at room temperature for 5 min and methyl iodide (0.078 mL, 1.3 mmol) is then added dropwise. The mixture is stirred at room temperature for 16 h. The mixture is then concentrated and purified by normal phase chromatography to give 157 mg of 5-(5-bromo-pyridin-3-yl)-1-methyl-pyrrolidin-2-one.

Suzuki Coupling Method VI is applied using the crude solution of Intermediate H for step 4 to afford the titled product.

Enantiomers of the titled compound are separated using chiral $CO_2$ Supercritical Fluid Chromatography to give Compound 270 and Compound 271 (Analytical conditions: Chiralpak IA-SFC, 4.6×100 m column; 30% 1:1:1 MeOH:IPA:EtOH (+1% DEA):$CO_2$ @ 3 mL/min; 40° C.; 200 bars; Retention time, Compound 270: 6.25 min, Compound 271: 11.32 min) in Table 1.

Example 108

Synthesis of 6-[5-(Cyano-methyl-methyl)-pyridin-3-yl]-3,4-dihydro-2H-[1,8]naphthyridine-1-carboxylic acid amide (Cpd 259, Table 1)

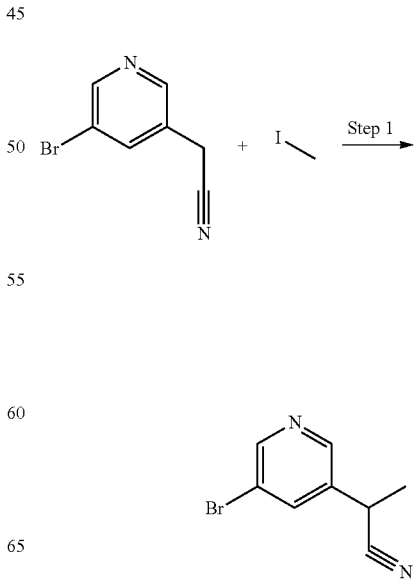

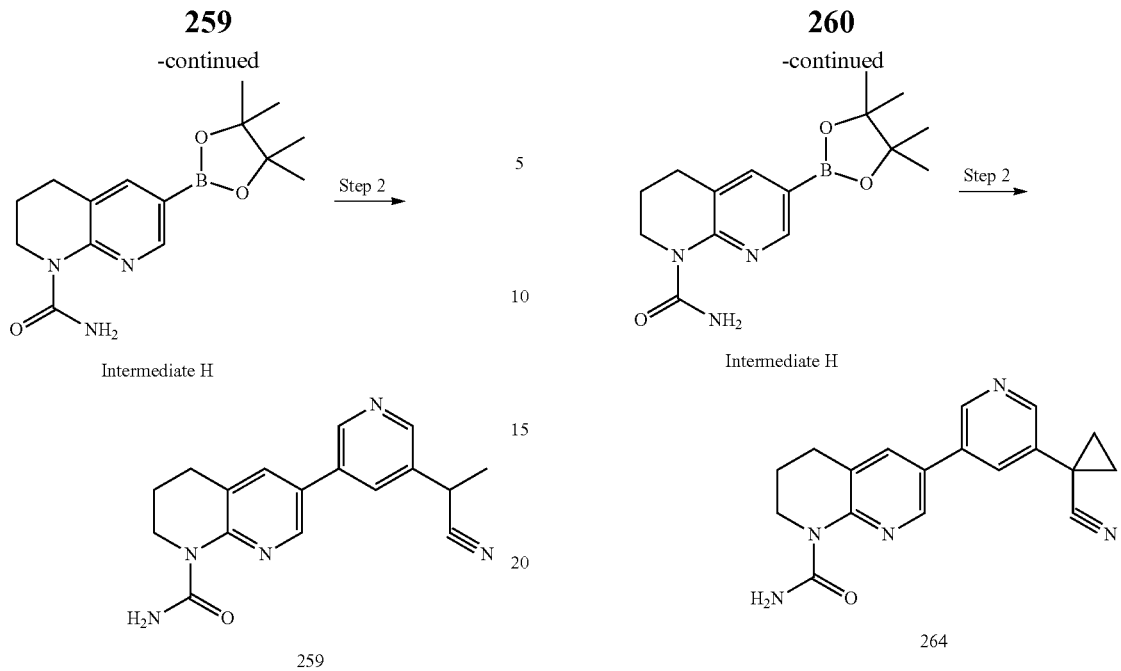

(5-Bromo-pyridin-3-yl)-acetonitrile (1.0 g, 0.005 mol) and 60% NaH (0.780 g) are mixed in DMF (25 mL) at 0° C. and stirred at room temperature for 1 h. MeI (1.2 ml) is added to this mixture at 0° C. and stirred at room temperature overnight. 2-(5-bromo-pyridin-3-yl)-propionitrile is obtained by prep-HPLC (0.3 g, 28% yield).

Suzuki Coupling Method VI is applied using the crude solution of Intermediate H for step 2 to afford the title compound.

Compound 261 in Table 1 is synthesized according to the procedure for Example 108, substituting either commercially available reagents or the appropriate intermediates described above.

To a suspension of (5-bromo-pyridin-3-yl)-acetonitrile (1.0 g, 5.1 mmol) in 50% NaOH (20.000 ml) is added 1-bromo-2-chloro-ethane (764 mg, 5.33 mmol) and benzyl triethylammonium chloride (15 mg, 0.11 mmol). The resultant mixture is heated to 60° C. for 2 h. After cooling down to room temperature, EtOAc is added and extracted. The organic layer is combined and washed with brine, dried over Na$_2$SO$_4$, filtered and concentrated. The product is purified by column to afford 626 mg of 1-(5-bromo-pyridin-3-yl)-cyclopropanecarbonitrile (55% yield).

Suzuki Coupling Method VI is applied using the crude solution of Intermediate H for step 2 to afford the title compound.

Compounds 164 and 166 in Table 1 are synthesized according to the procedure of Step 2 of Example 109 substituting the commercially available reagent (the bromide).

Example 109

Synthesis of 6-[5-(1-Cyano-cyclopropyl)-pyridin-3-yl]-3,4-dihydro-2H-[1,8]naphthyridine-1-carboxylic acid amide (Cpd 264, Table 1)

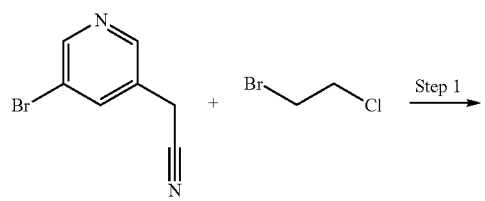

Example 110

Synthesis of 6-[5-(1-carbamoyl-cyclopropyl)-pyridin-3-yl]-3,4-dihydro-2H-[1,8]naphthyridine-1-carboxylic acid amide (Cpd 265, Table 1)

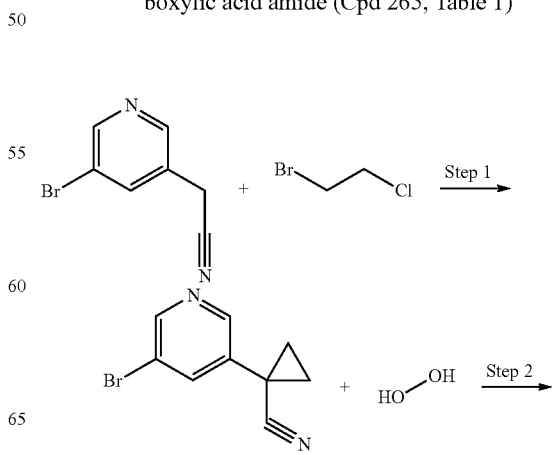

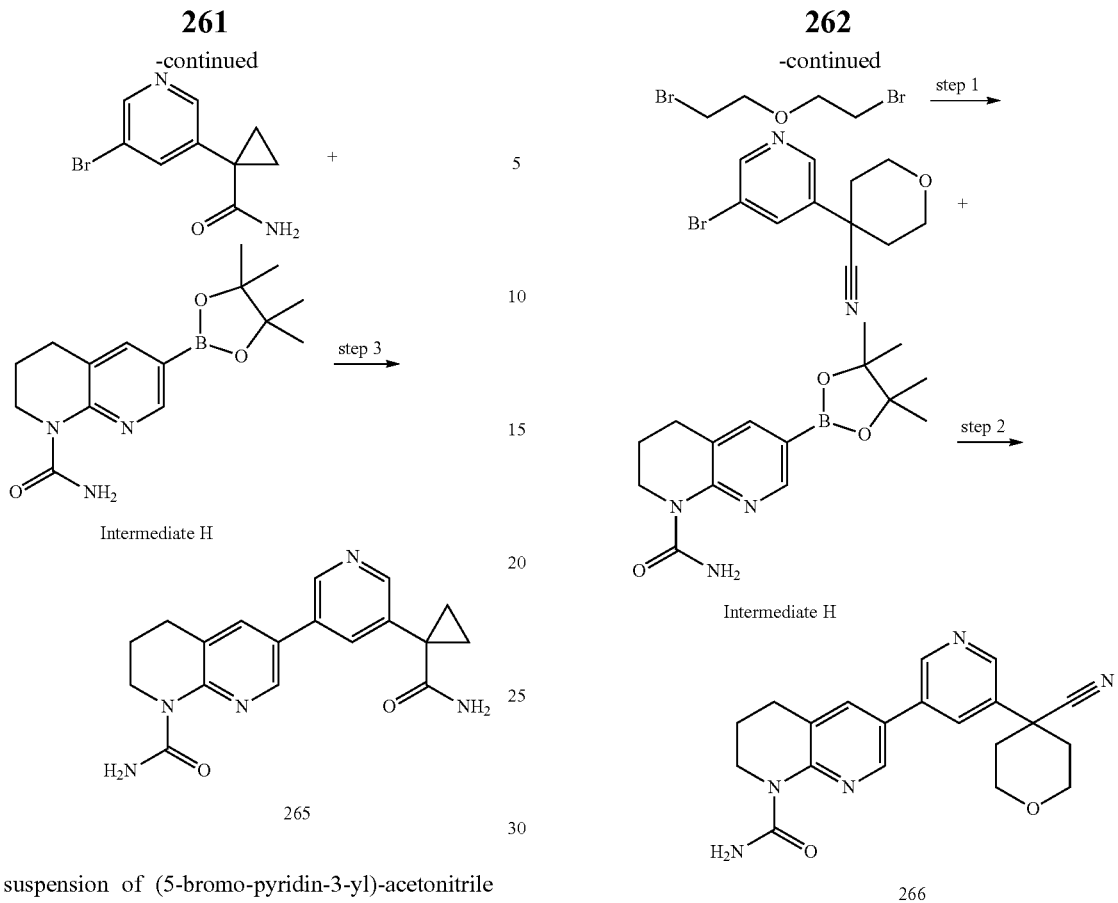

To a suspension of (5-bromo-pyridin-3-yl)-acetonitrile (1.0 g, 5.1 mmol) in 50% NaOH (20 mL) is added 1-bromo-2-chloro-ethane (764 mg, 5.33 mmol) and benzyl triethylammonium chloride (15 mg, 0.11 mmol). The resultant mixture is heated to 60° C. for 2 h. After cooling down to room temperature, EtOAc is added and extracted. The organic layers are combined and washed with brine, dried over Na$_2$SO$_4$, filtered and concentrated. The product is purified by column to afford 626 mg 1-(5-bromo-pyridin-3-yl)-cyclopropanecarbonitrile (55% yield).

1-(5-Bromo-pyridin-3-yl)-cyclopropanecarbonitrile (150 mg, 0.672 mmol) is dissolved in THF (1.5 mL) in a reaction vial. Ammonium hydroxide (1 mL) is then added. Hydrogen peroxide (30% aq solution, 0.5 mL) is added slowly. The mixture is stirred at room temperature for 4 h. The volatiles is evaporated to afford 1-(5-bromo-pyridin-3-yl)-cyclopropanecarboxylic acid amide (157.5 mg, 97% crude yield).

Suzuki Coupling Method VI is applied using the crude solution of Intermediate H for step 3 to afford the title compound.

Under argon, NaH (60% in mineral oil, 0.497 g, 12.4 mmol) is added into THF (10 mL). The reaction mixture is cooled on a bath of dry ice/CH$_3$OH. A solution of (5-bromo-pyridin-3-yl)-acetonitrile (1.0 g, 5.0 mmol) and 2-bromoethyl ether (0.719 mL, 5.15 mmol) in THF (4.5 mL) is added dropwise. The reaction is stirred for 30 min. The dry ice/MeOH bath is removed and the mixture is stirred at room temperature for 14 hrs. The reaction is quenched by slow addition of MeOH (5 mL). The mixture is then concentrated. The resulting crude product is purified by normal phase chromatography using 0-3% MeOH in DCM as the gradient to afford 4-(5-bromo-pyridin-3-yl)-tetrahydro-pyran-4-carbonitrile (1.07 g, 79% yield).

Suzuki Coupling Method VI is applied using the crude solution of Intermediate H for step 2 to afford the title compound.

Example 111

Synthesis of 6-[5-(4-Cyano-tetrahydro-pyran-4-yl)-pyridin-3-yl]-3,4-dihydro-2H-[1,8]naphthyridine-1-carboxylic acid amide (Cpd 266, Table 1)

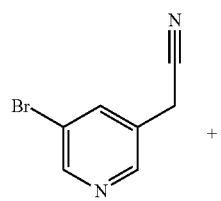

Example 112

Synthesis of 6-[5-(2-Oxo-oxazolidin-3-yl)-pyridin-3-yl]-3,4-dihydro-2H-[1,8]naphthyridine-1-carboxylic acid amide (Cpd 267, Table 1)

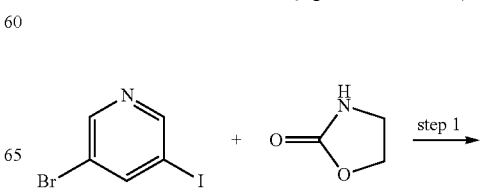

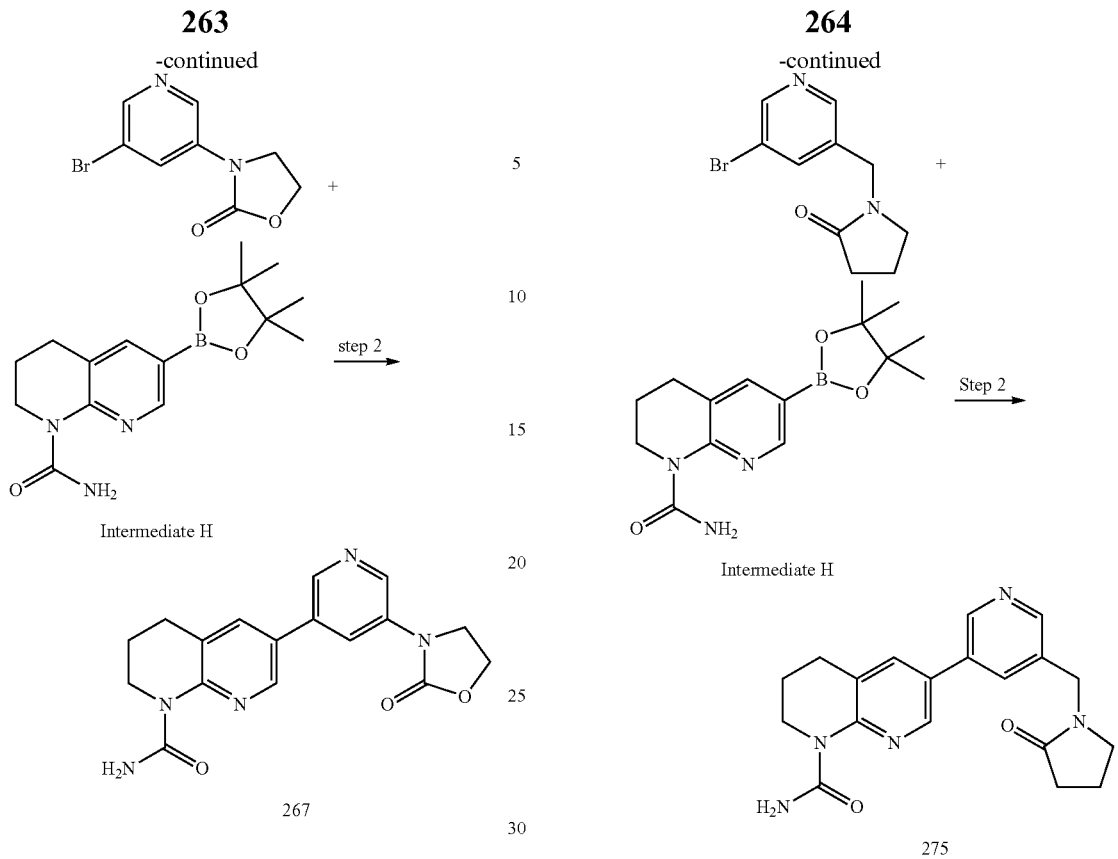

An argon purged flask (100 mL) is charged with reagent 3-bromo-5-iodopyridine (200 mg, 0.704 mmol), 2-oxazolidone (61.3 mg, 0.704 mmol), tris(dibenzylideneacetone)dipalladium(0) (64.5 mg, 0.07 mmol), 4,5-bis(diphenylphosphino)-9,9-dimethylxanthene (61.1 mg, 0.106 mmol), and cesium carbonate (459 mg, 1.409 mmol). Toluene (bubbled with argon before use, 14 mL) is then added. The resulting mixture is heated at 90° C. under argon for 16 h. The mixture is filtered through diatomaceous earth and washed with MeOH (30 mL). The filtrate is concentrated. The resulting crude product is purified by normal phase chromatography using 0-4.5% MeOH in DCM as the gradient to afford 3-(5-bromo-pyridin-3-yl)-oxazolidin-2-one (60 mg, 35% yield).

Suzuki Coupling Method VI is applied using the crude solution of Intermediate H for step 2 to afford the title compound.

Compounds 260, 274 and 276 in Table 1 are synthesized according to the procedure for Example 112, substituting either commercially available reagents or the appropriate intermediates described above.

2-Pyrrolidinone (0.061 mL, 0.797 mmol) is dissolved in DMF (1.5 mL) and NaH (60% in mineral oil, 23.9 mg, 0.598 mmol) is added. The mixture is stirred for 5 min. The mixture is cooled to 0° C. Intermediate E (dissolved in 1 mL of DMF) is added dropwise. The mixture is allowed to warm to room temperature for 90 hrs. The reaction is quenched with water (1 mL). The mixture is filtered through diatomaceous earth. The filtrate is concentrated. The resulting crude oil is purified by normal phase chromatography using 0-5% MeOH in DCM as the gradient to afford 1-(5-bromo-pyridin-3-ylmethyl)-pyrrolidin-2-one (80 mg, 79% yield).

Suzuki Coupling Method VI is applied using the crude solution of Intermediate H for step 2 to afford the title compound.

Compounds 207, 277 and 278 in Table 1 are synthesized according to the procedure for Example 113, substituting commercially available reagents or the appropriate intermediates described above.

Example 113

Synthesis of 6-[5-(2-Oxo-pyrrolidin-1-ylmethyl)-pyridin-3-yl]-3,4-dihydro-2H-[1,8]naphthyridine-1-carboxylic acid amide (Cpd 275, Table 1)

Example 114

Synthesis of 2-[5-(8-Acetyl-5,6,7,8-tetrahydro-[1,8]naphthyridin-3-yl)-pyridin-3-yl]-1-morpholin-4-yl-ethanone(Cpd 281, Table 1)

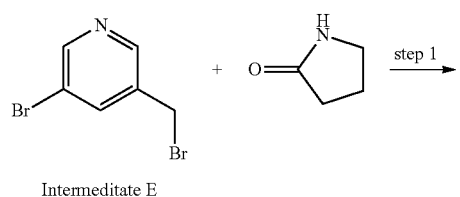

Intermeditate E

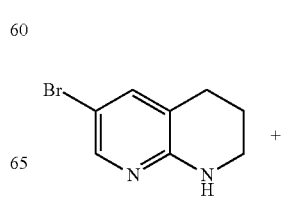

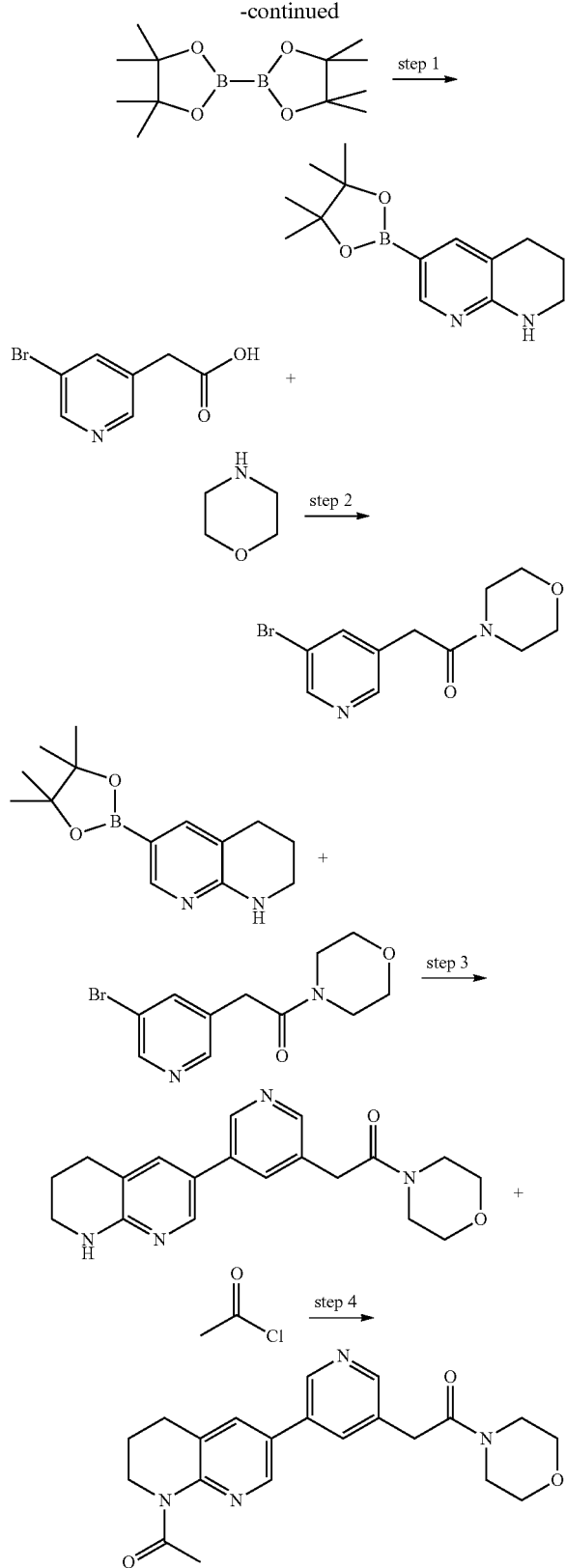

boron (238 mg, 0.938 mmol), KOAc (294 mg, 3.0 mmol) followed by 1,4-dioxane (5.8 mL). Argon is bubbled through the reaction solution for 5 min. Reactant $PdCl_2$(dppf) (54.9 mg, 0.075 mmol) id added. The vial is sealed and the mixture is heated at 120° C. for 50 min. The mixture is cooled to room temperature. No work up or purification is performed as the crude reaction solution is carried to the next step directly.

To the solution of 5-bromo-3-pyridineacetic acid (500 mg, 2.314 mmol) in DMF (3 mL) is added TBTU (1.11 g, 3.472 mmol). Morpholine (0.61 mL, 6.94 mmol) is added dropwise and the mixture is stirred at room temperature for 18 h. The mixture is diluted with EtOAc (50 mL), washed with water (3×5 mL), and brine, dried over sodium sulfate, filtered, and concentrated. The resulting crude product is purified by normal phase chromatography using 0-4.5% MeOH in DCM as the gradient to afford 2-(5-bromo-pyridin-3-yl)-1-morpholin-4-yl-ethanone.

At room temperature under argon, 2-(5-bromo-pyridin-3-yl)-1-morpholin-4-yl-ethanone (0.264 g, 0.626 mmol, dissolved in 3-mL of 1,4-dioxane), $PdCl_2$(dppf) (0.027 g, 0.038 mmol), 2M $Na_2CO_3$ aqueous solution (0.79 mL 1.58 mmol) are added to the crude reaction solution of step 1. Argon is bubbled through the solution for 5 min. The vial is sealed and the mixture is heated at 120° C. for 1 h. The mixture is cooled down to room temperature. The mixture is filtered through diatomaceous earth and rinsed with EtOAc (50 mL). The filtrate is concentrated. The resulting crude product is purified by normal phase chromatography using 0-6% MeOH in DCM as the gradient to afford 1-morpholin-4-yl-2-[5-(5,6,7,8-tetrahydro-[1,8]naphthyridin-3-yl)-pyridin-3-yl]-ethanone.

1-Morpholin-4-yl-2-[5-(5,6,7,8-tetrahydro-[1,8]naphthyridin-3-yl)-pyridin-3-yl]-ethanone (62.4 mg, 0.184 mmol) is dissolved in DCM (2 mL). Pyridine (0.089 mL, 1.11 mmol) is added. Acetyl chloride (1.0M in DCM, 0.55 mL, 0.55 mmol) is added dropwise and the mixture is stirred for 16 h. The mixture is diluted with EtOAc (50 mL), washed with water (3×5 mL), and brine, dried over sodium sulfate, filtered, and concentrated. The resulting crude product is purified by normal phase chromatography using 0-6% MeOH in DCM as the gradient to afford the title compound.

Compound 279 in Table 1 is synthesized according to the procedure for Example 114, substituting the bromide obtained in the second step with the bromide obtained as follows:

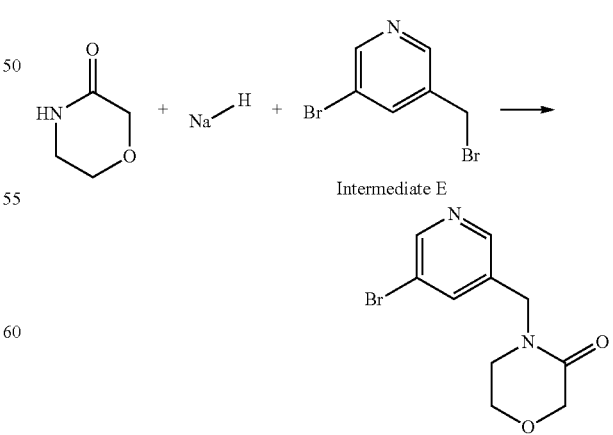

Intermediate E

Morpholin-3-one (161 mg; 1.59 mmol) is dissolved in DMF (5 mL). NaH (60% in mineral oil, 47.8 mg; 1.196 mmol) is added at 0° C. The mixture is stirred for 15 min and Intermediate E (200 mg, 0.797 mmol) is added at 0° C. The mixture is stirred for another 2 h. Saturated NH₄Cl aq solution (2 mL) is added along with EtOAc (25 mL) and water (15 mL). The mixture is stirred for 10 min and the aqueous layer is separated and extracted with EtOAc (2×15 mL). The organic layers are combined and concentrated to give the crude product. Purification by flash column chromatography using MeOH in DCM affords 190 mg of 4-(5-bromo-pyridin-3-ylmethyl)-morpholin-3-one.

Compound 280 in Table 1 is synthesized according to the procedure for Example 114, substituting the bromide obtained in the second step with the bromide obtained as follows:

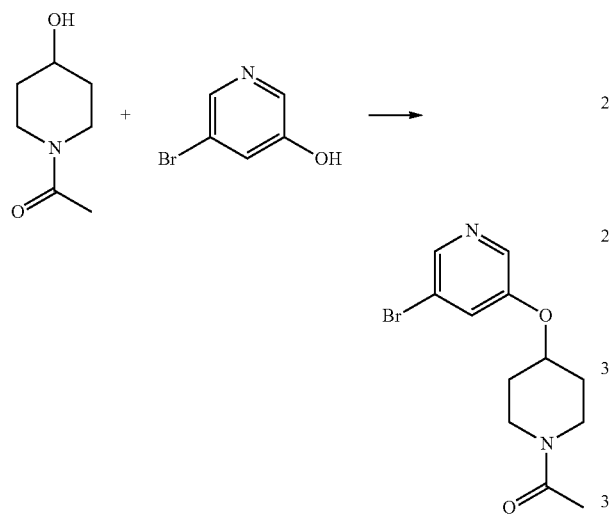

1-(4-Hydroxy-piperidin-1-yl)-ethanone (200 mg 1.40 mmol) and 5-bromo-pyridin-3-ol (248 mg; 1.425 mmol) are added dropwise to a solution of PPh₃ (606 mg) in THF (30 ml). DIAD (462 mg) is added to the solution. The mixture is stirred at room temperature overnight. The mixture is washed with water, diluted with DCM and dried over Na₂SO₄, filtered and concentrated to give 1-[4-(5-bromo-pyridin-3-yloxy)-piperidin-1-yl]-ethanone.

Compound 282 in Table 1 is synthesized according to the procedure for Example 114, substituting the bromide obtained in the second step with the bromide obtained as follows:

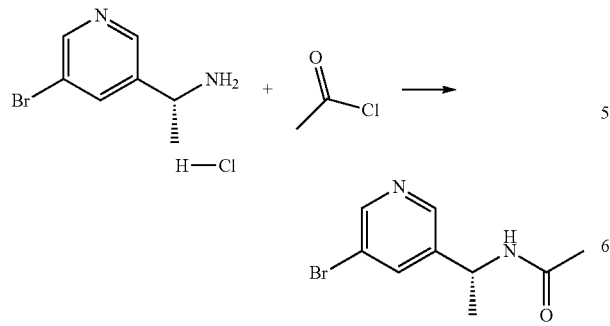

To a 100-mL rbf are added (1R)-1-(5-bromo(3-pyridyl)) ethylamine HCl salt (500 mg, 2.105 mmol), DCM (5 mL), and triethylamine (1.2 mL, 8.42 mmol). The mixture is cooled to 0° C. 1M acetyl chloride DCM solution (dissolved with 3-mL of DCM) is added dropwise. The reaction is stirred in the ice/water bath for 20 min. The ice/water bath is removed and the mixture is stirred at room temperature for 35 min. The mixture is diluted with EtOAc (50 mL), washed with water (3×5 mL), and brine, dried over sodium sulfate, filtered, and concentrated. The resulting crude product is purified by normal phase chromatography using 0-5% MeOH in DCM as the gradient to afford N-[(R)-1-(5-bromo-pyridin-3-yl)-ethyl]-acetamide (357.7 mg, 70% yield).

Compound 283 in Table 1 is synthesized according to the procedure for Example 114, substituting the bromide obtained in the second step with the bromide obtained as follows:

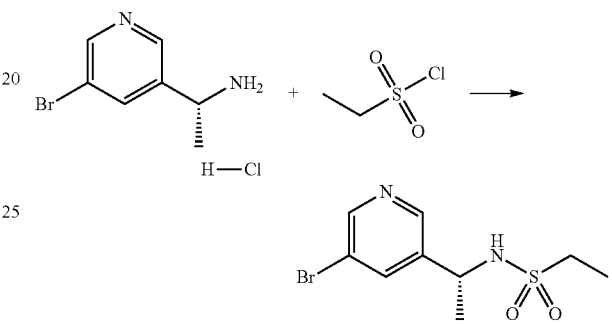

To a 100-mL flask are added (1R)-1-(5-bromo(3-pyridyl)) ethylamine HCl salt (0.5 g, 2.105 mmol), DCM (5 mL), and triethylamine (1.2 mL, 8.52 mmol). The mixture is cooled to 0° C. Ethanesulfonyl chloride (0.24 mL, 2.526 mmol, dissolved in 3 mL of DCM) is added dropwise. The mixture is stirred at 0° C. for 15 min. The ice/water bath is removed and the mixture is stirred at room temperature for 25 min. The mixture is diluted with EtOAc (50 mL), washed with water (3×5 mL), and brine, dried over sodium sulfate, filtered, and concentrated. The resulting crude product is purified by normal phase chromatography using 0-5% MeOH in DCM as the gradient to afford ethanesulfonic acid [(R)-1-(5-bromo-pyridin-3-yl)-ethyl]-amide (482.5 mg, 78% yield).

Example 115

Synthesis of 6-{5-[2-(2-Oxo-oxazolidin-3-yl)-ethoxy]-pyridin-3-yl}-3,4-dihydro-2H-[1,8]naphthyridine-1-carboxylic acid amide (Cpd 284, Table 1)

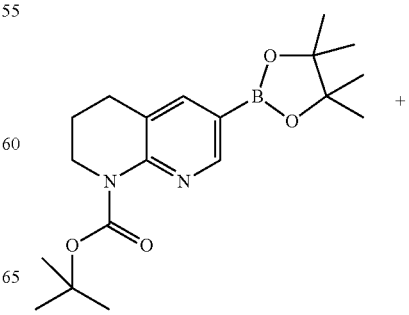

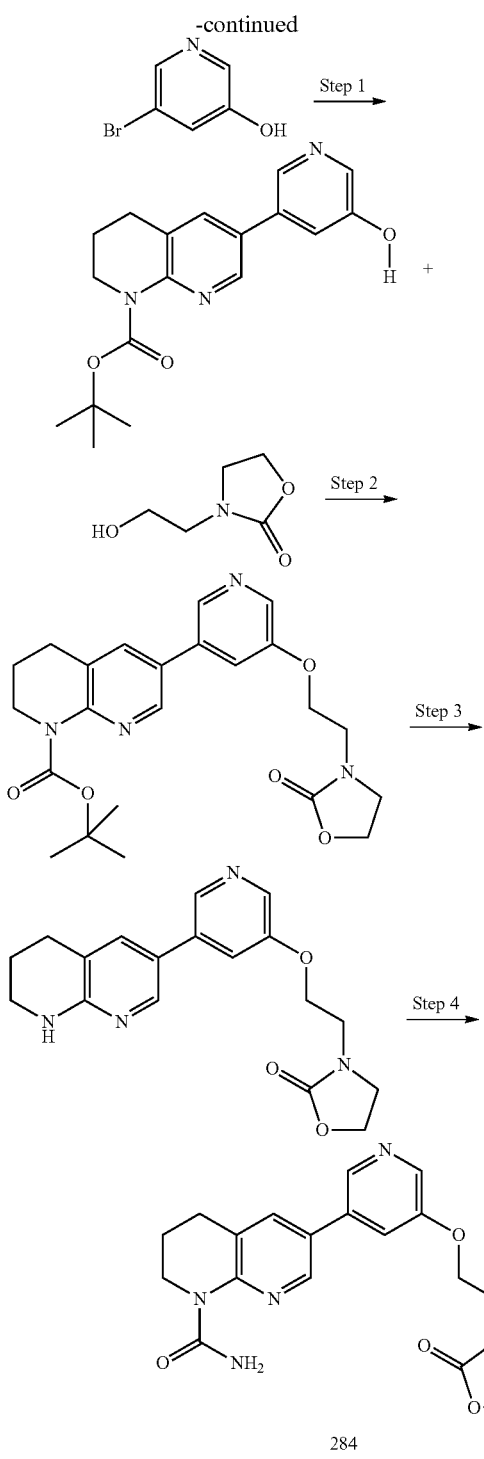

mmol) is dissolved in 2 mL DMF and added to 3-(2-hydroxy-ethyl)-oxazolidin-2-one (48 mg, 0.37 mmol). Triphenylphosphine (192 mg, 0.733 mmol) in 1 mL DMF is added followed by di-t-butyl azodicarboxylate (168 mg, 0.733 mmol) in 1 mL DMF. The solution is shaken at room temperature for 16 hrs. The reaction mixture is evaporated to dryness to afford the crude product. Purification by HPLC chromatography affords 6-{5-[2-(2-oxo-oxazolidin-3-yl)-ethoxy]-pyridin-3-yl}-3,4-dihydro-2H-[1,8]naphthyridine-1-carboxylic acid tert-butyl ester.

6-{5-[2-(2-Oxo-oxazolidin-3-yl)-ethoxy]-pyridin-3-yl}-3,4-dihydro-2H-[1,8]naphthyridine-1-carboxylic acid tert-butyl ester (0.305 mmol) is dissolved in 2 mL of a 20% TFA solution in $CH_2Cl_2$ and the solution is shaken overnight at room temperature. The reaction is evaporated to dryness to give crude 3-{2-[5-(5,6,7,8-tetrahydro-[1,8]naphthyridin-3-yl)-pyridin-3-yloxy]-ethyl}-oxazolidin-2-one and used as is in the next step.

The crude 3-{2-[5-(5,6,7,8-tetrahydro-[1,8]naphthyridin-3-yl)-pyridin-3-yloxy]-ethyl}-oxazolidin-2-one is converted to the titled product using Urea Formation Method II.

Compounds 285-288 in Table 1 are synthesized according to the procedure for Example 115, substituting either commercially available reagents or the appropriate intermediates described above.

Example 116

Synthesis of 5-(4-Methyl-pyridin-3-yl)-2,3-dihydro-pyrrolo[2,3-b]pyridine-1-carboxylic acid amide (Cpd 289, Table 1)

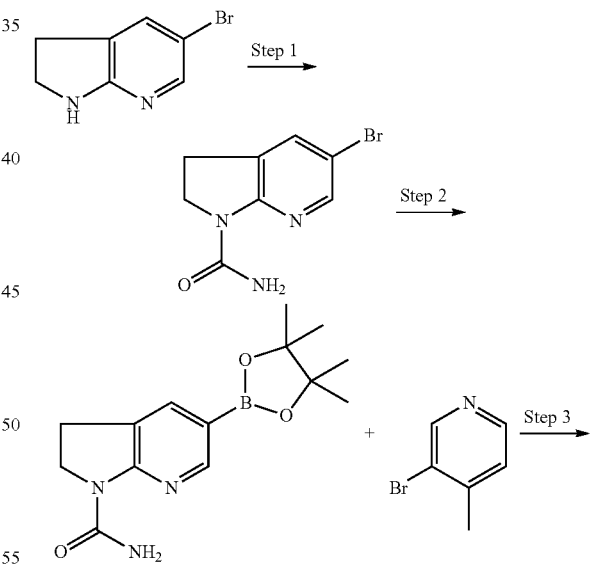

6-(4,4,5,5-Tetramethyl-[1,3,2]dioxaborolan-2-yl)-3,4-dihydro-2H-[1,8]naphthyridine-1-carboxylic acid tert-butyl ester is synthesized according to Step 1 of Example 95.

6-(4,4,5,5-Tetramethyl-[1,3,2]dioxaborolan-2-yl)-3,4-dihydro-2H-[1,8]naphthyridine-1-carboxylic acid tert-butyl ester is coupled with 5-bromo-pyridin-3-ol to give 6-(5-hydroxy-pyridin-3-yl)-3,4-dihydro-2H-[1,8]naphthyridine-1-carboxylic acid tert-butyl ester using Suzuki Coupling Method VI.

6-(5-Hydroxy-pyridin-3-yl)-3,4-dihydro-2H-[1,8]naphthyridine-1-carboxylic acid tert-butyl ester (100 mg, 0.305

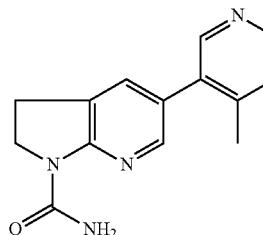

5-Bromo-2,3-dihydro-1H-pyrrolo[2,3-b]pyridine is converted to 5-bromo-2,3-dihydro-pyrrolo[2,3-b]pyridine-1-carboxylic acid amide using Urea Formation Method II.

5-Bromo-2,3-dihydro-pyrrolo[2,3-b]pyridine-1-carboxylic acid amide is converted to 5-(4,4,5,5-tetramethyl-[1,3,2]dioxaborolan-2-yl)-2,3-dihydro-pyrrolo[2,3-b]pyridine-1-carboxylic acid amide according to the procedure used to prepare Intermediate H and used as crude.

A crude solution of 5-(4,4,5,5-tetramethyl-[1,3,2]dioxaborolan-2-yl)-2,3-dihydro-pyrrolo[2,3-b]pyridine-1-carboxylic acid amide (0.41 mmol) is added to 3-bromo-4-methyl-pyridine (64 mg, 0.37 mmol) followed by the addition of aqueous 2.0 M $Na_2CO_3$ solution (0.41 mL, 0.82 mmol) and 1,1'-bis(diphenylphosphino)ferrocene palladium (II) chloride (420 mg, 0.52 mmol). The vial is sealed and the mixture is sparged with Ar (10 seconds). The reaction is stirred for 3 hours at 100° C. The reaction mixture is concentrated to dryness and dissolved in 2 mL of DMF, filtered and purified by reverse phase HPLC to afford the titled product.

Compounds 185, 190, 191, 192, 250, 251 and 290-293 in Table 1 are synthesized according to the procedure for Example 116, substituting either commercially available reagents or the appropriate intermediates described above.

Example 117

Synthesis of 6-{5-[(Cyclopropanecarbonyl-amino)-methyl]-pyridin-3-yl}-3,4-dihydro-2H-[1,8]naphthyridine-1-carboxylic acid amide (Cpd 294, Table 1)

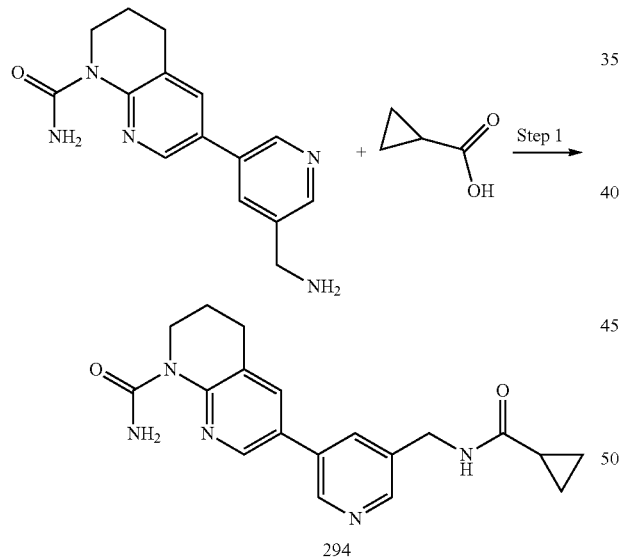

6-(5-Aminomethyl-pyridin-3-yl)-3,4-dihydro-2H-[1,8]naphthyridine-1-carboxylic acid amide is synthesized using the procedure described in Example 92.

To the cyclopropanecarboxylic acid (16 mg, 0.18 mmol) is added a solution of 6-(5-aminomethyl-pyridin-3-yl)-3,4-dihydro-2H-[1,8]naphthyridine-1-carboxylic acid amide (40 mg, 0.14 mmol) in DMF (1 mL) followed by HATU (100 mg, 0.26 mmol) in DMF (1 mL) followed by triethylamine (51 mg, 0.50 mmol). The mixture is stirred overnight. The mixture is concentrated in vacuo, dissolved in 2 mL of DMF, filtered and purified by reverse phase HPLC to afford the titled product.

Compounds 295-298 in Table 1 are synthesized according to the procedure for Example 117, substituting either commercially available reagents or the appropriate intermediates described above.

Example 118

Synthesis of 6-[5-(1-Thiazol-2-yl-ethylcarbamoyl)-pyridin-3-yl]-3,4-dihydro-2H-[1,8]naphthyridine-1-carboxylic acid amide (Cpd 299, Table 1)

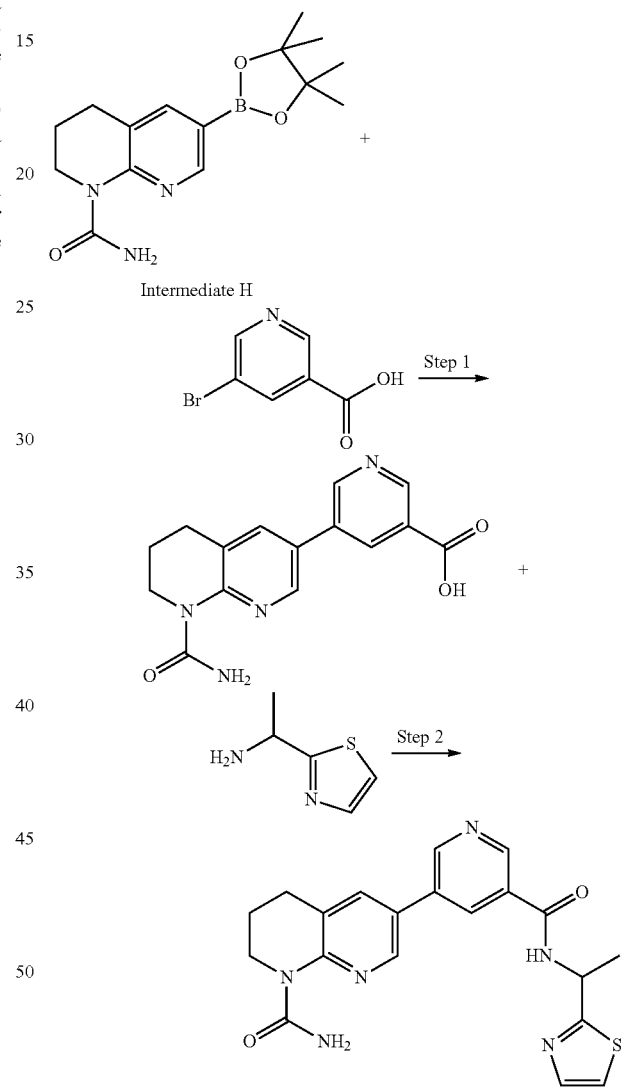

Intermediate H (crude) is coupled with 5-bromo-nicotinic acid to give 5-(8-carbamoyl-5,6,7,8-tetrahydro-[1,8]naphthyridin-3-yl)-nicotinic acid using Suzuki Coupling Method VI.

To a solution of methyl-(tetrahydro-pyran-4-yl)-amine (32 mg, 0.25 mmol) in 1 mL of DMF is added a slurry of 5-(8-carbamoyl-5,6,7,8-tetrahydro-[1,8]naphthyridin-3-yl)-nicotinic acid (50 mg, 0.17 mmol) in DMF. To this mixture is added HATU (120 mg, 0.31 mmol) in 1 mL of DMF followed by triethyl amine (0.10 mL, 0.72 mmol). The mixture is stirred overnight. The mixture is concentrated in vacuo, dissolved in 2 mL of DMF, filtered and purified by reverse phase HPLC to afford the titled product.

Compounds 300-304 in Table 1 are synthesized according to the procedure for Example 118, substituting either commercially available reagents or the appropriate intermediates described above.

Example 119

Synthesis of 5-Chloro-6-[5-(4-hydroxy-tetrahydro-pyran-4-yl)-pyridin-3-yl]-3,4-dihydro-2H-[1,8]naphthyridine-1-carboxylic acid amide (Cpd 305, Table 1)

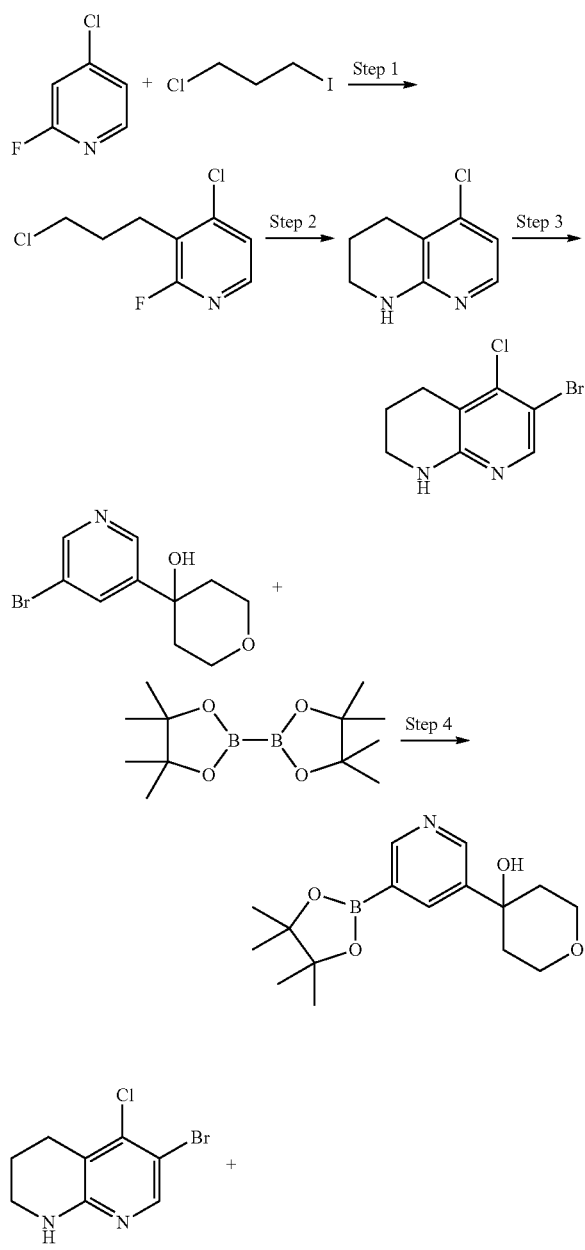

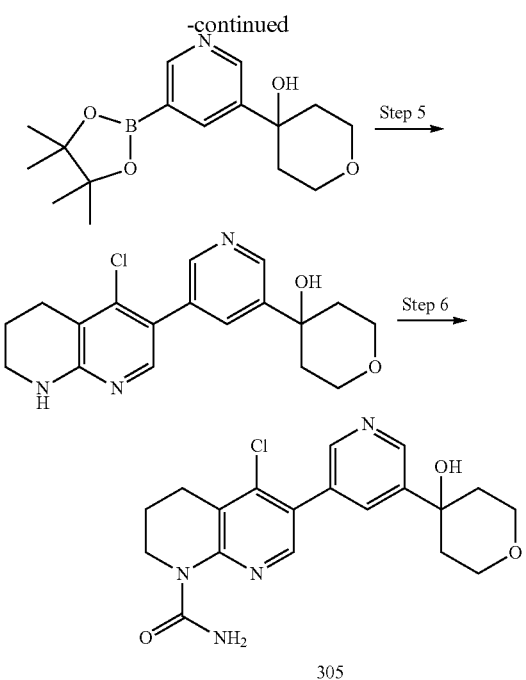

To a cooled (−78° C.) solution of 4-chloro-2-fluoro-pyridine (2.0 g, 15 mmol) in THF (15 mL) is added LDA solution (9.1 mL, 18 mmol, 2.0 M in THF). After the mixture is allowed to stir at −78° C. for 90 min, 1-chloro-3-iodo-propane (4.9 mL, 46 mmol) is added and the mixture is allowed to slowly warm to room temperature for 16 hrs. Then reaction is quenched with saturated NH$_4$Cl and the mixture is extracted with DCM (3×). The combined organic layers are washed with brine, dried over Na$_2$SO$_4$ and concentrated to give the crude product. Purification by flash column chromatography affords 2.4 g of 4-chloro-3-(3-chloro-propyl)-2-fluoro-pyridine.

In 350 mL screw top flask is added 3-(3-chloro-propyl)-2-fluoro-4-iodo-pyridine (2.4 g, 12 mmol), DMF (22.00 mL), ammonium hydroxide (580 mmol), NH$_4$OAc (12 g, 160 mmol), KI (4.0 g, 24 mmol) and K$_2$CO$_3$ (8.0 g, 58 mmol). The flask is sealed and resultant mixture is heated to 60° C. for 90 hrs. The mixture is cooled to room temperature and is partitioned between EtOAc/H$_2$O. The layers are separated and the aqueous layer is further extracted with EtOAc (2×). The combined organic layers are washed with brine, dried (Na$_2$SO$_4$), filtered and concentrated to the crude product. Purification by flash column chromatography affords 1.9 g of 5-chloro-1,2,3,4-tetrahydro-[1,8]naphthyridine.

To a solution of 5-chloro-1,2,3,4-tetrahydro-[1,8]naphthyridine (500 mg, 3.0 mmol) in DCM (40 mL) is added N-bromosuccinimide (530 mg, 3.0 mmol). The reaction mixture is stirred at room temperature for 2 hrs. The reaction mixture is concentrated to give the crude product. Purification by flash column chromatography affords 680 mg of 6-bromo-5-chloro-1,2,3,4-tetrahydro-[1,8]naphthyridine.

4-(5-Bromo-pyridin-3-yl)-tetrahydro-pyran-4-ol (which is synthesized according to Example 48) is converted to 4-[5-(4,4,5,5-tetramethyl-[1,3,2]dioxaborolan-2-yl)-pyridin-3-yl]-tetrahydro-pyran-4-ol using procedure described in Intermediate H.

4-[5-(4,4,5,5-tetramethyl-[1,3,2]dioxaborolan-2-yl)-pyridin-3-yl]-tetrahydro-pyran-4-ol is coupled with 6-bromo-5-chloro-1,2,3,4-tetrahydro-[1,8]naphthyridine to give 4-[5-(4- chloro-5,6,7,8-tetrahydro-[1,8]naphthyridin-3-yl)-pyridin-3-yl]-tetrahydro-pyran-4-ol using Suzuki Coupling Method VI.

4-[5-(4-Chloro-5,6,7,8-tetrahydro-[1,8]naphthyridin-3-yl)-pyridin-3-yl]-tetrahydro-pyran-4-ol is converted to the titled product using Urea Formation Method II.

Compounds 314 and 315 in Table 1 are synthesized according to the procedure for Example 119, substituting either commercially available reagents or the appropriate intermediates described above.

Compound 306 in Table is also synthesized according to the Step 4 to Step 6 of Example 119, substituting 6-bromo-5-chloro-1,2,3,4-tetrahydro-[1,8]naphthyridine with commercially available 6-bromo-5-methyl-1,2,3,4-tetrahydro-[1,8]naphthyridine.

Example 120

Synthesis of 6-[5-(4-Hydroxy-tetrahydro-pyran-4-yl)-pyridin-3-yl]-7-methyl-3,4-dihydro-2H-[1,8]naphthyridine-1-carboxylic acid amide (Cpd 307, Table 1)

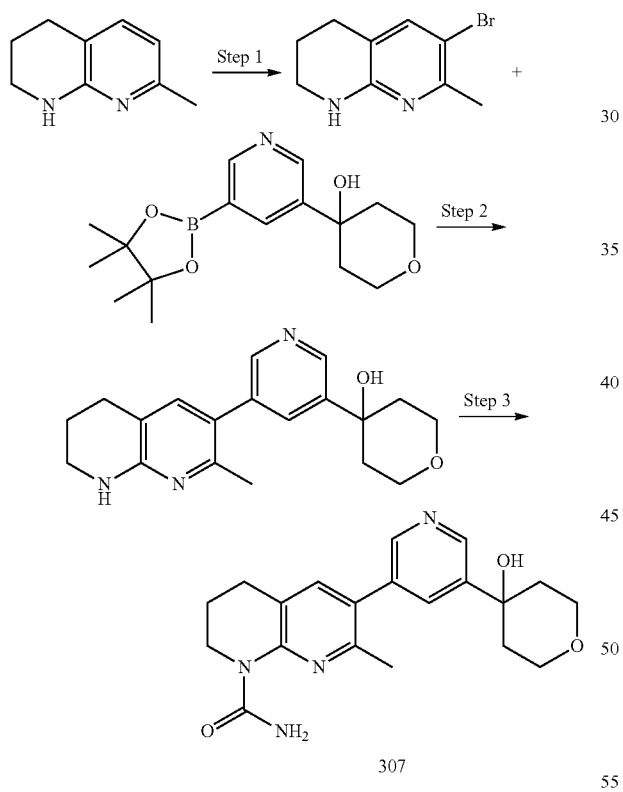

307

To a vial is added 7-methyl-1,2,3,4-tetrahydro-[1,8]naphthyridine (390 mg, 2.63 mmol) and N-bromosuccinimide (468 mg, 2.63 mmol) in 20 mL of $CH_2Cl_2$. The reaction mixture is stirred at room temperature for 1 hour. The reaction mixture is concentrated. The residue is purified by flash column chromatography to give 575 mg of 6-bromo-7-methyl-1,2,3,4-tetrahydro-[1,8]naphthyridine.

6-Bromo-7-methyl-1,2,3,4-tetrahydro-[1,8]naphthyridine is converted to 4-[5-(2-methyl-5,6,7,8-tetrahydro-[1,8]naphthyridin-3-yl)-pyridin-3-yl]-tetrahydro-pyran-4-ol according to Step 4 and Step 5 of Example 119.

4-[5-(2-Methyl-5,6,7,8-tetrahydro-[1,8]naphthyridin-3-yl)-pyridin-3-yl]-tetrahydro-pyran-4-ol is converted to the titled product using Urea Formation Method II.

Compounds 312 and 313 in Table 1 are synthesized according to the procedure for Example 120, substituting the corresponding boronic ester prepared from appropriate bromide described above in Step 2.

Example 121

Synthesis of 7-Cyano-6-[5-(4-hydroxy-tetrahydro-pyran-4-yl)-pyridin-3-yl]-3,4-dihydro-2H-[1,8]naphthyridine-1-carboxylic acid amide (Cpd 308, Table 1)

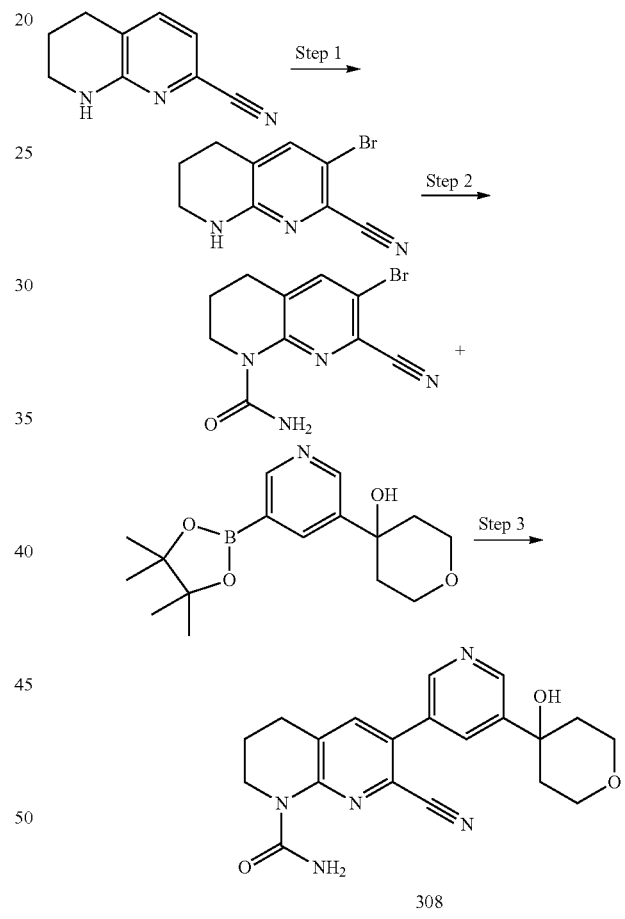

308

To a vial is added 5,6,7,8-tetrahydro-1,8-naphthyridine-2-carbonitrile (370 mg, 2.32 mmol) and N-bromosuccinimide (413 mg, 2.32 mmol) in 20 mL of $CH_2Cl_2$. The reaction mixture is stirred at room temperature for 18 hours. The reaction mixture is concentrated. The residue is purified by flash column chromatography to give 550 mg of 3-bromo-5,6,7,8-tetrahydro-[1,8]naphthyridine-2-carbonitrile.

3-Bromo-5,6,7,8-tetrahydro-[1,8]naphthyridine-2-carbonitrile is converted to 6-bromo-7-cyano-3,4-dihydro-2H-[1,8]naphthyridine-1-carboxylic acid amide using Urea Formation Method II.

6-Bromo-7-cyano-3,4-dihydro-2H-[1,8]naphthyridine-1-carboxylic acid amide is coupled with 4-[5-(4,4,5,5-tetramethyl-[1,3,2]dioxaborolan-2-yl)-pyridin-3-yl]-tetrahydropyran-4-ol (which is prepared according to Step 4 of Example 119) to give the titled product using Suzuki Coupling Method VI.

Example 122

Synthesis of 5-Fluoro-6-[5-(4-hydroxy-tetrahydropyran-4-yl)-pyridin-3-yl]-3,4-dihydro-2H-[1,8]naphthyridine-1-carboxylic acid amide (Cpd 309, Table 1)

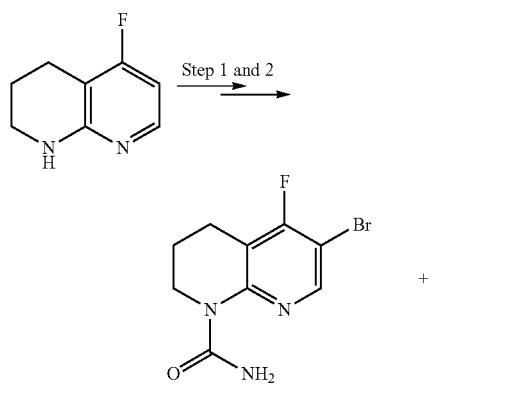

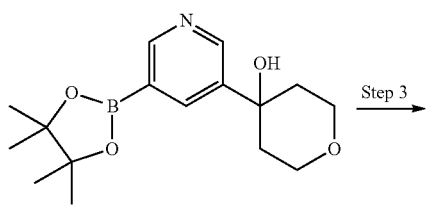

309

5-Fluoro-1,2,3,4-tetrahydro-[1,8]naphthyridine is converted to 6-bromo-5-fluoro-3,4-dihydro-2H-[1,8]naphthyridine-1-carboxylic acid amide according to Step 1 and Step 2 of Example 121. 6-Bromo-5-fluoro-3,4-dihydro-2H-[1,8]naphthyridine-1-carboxylic acid amide is coupled with 4-[5-(4,4,5,5-tetramethyl-[1,3,2]dioxaborolan-2-yl)-pyridin-3-yl]-tetrahydro-pyran-4-ol (which is prepared according to Step 4 of Example 119) to give the titled product using Suzuki Coupling Method VI.

Compounds 310 and 311 in Table 1 are synthesized according to the procedure for Example 122, substituting the corresponding boronic ester prepared from appropriate bromide described above in Step 3.

Example 123

Synthesis of 6-(4-Acetyl-5-fluoro-pyridin-3-yl)-3,4-dihydro-2H-[1,8]naphthyridine-1-carboxylic acid amide (Cpd 316, Table 1)

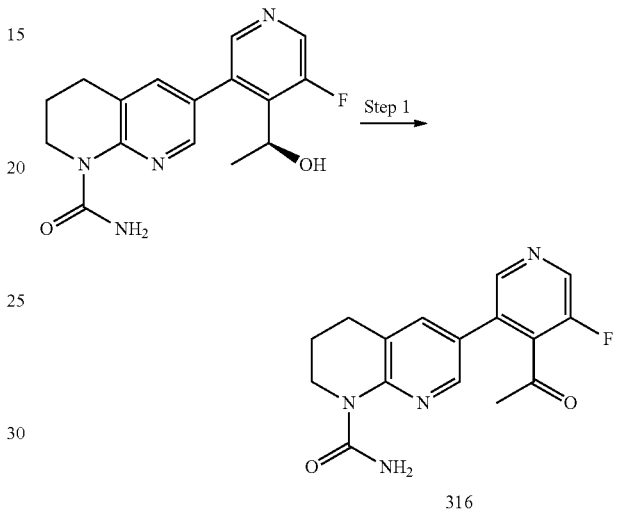

316

To a solution of 6-[5-fluoro-4-((S)-1-hydroxy-ethyl)-pyridin-3-yl]-3,4-dihydro-2H-[1,8]naphthyridine-1-carboxylic acid amide (100 mg, 0.3 mmol, Compound 34, Example 16) in 5 mL of dichloromethane is added Dess-Martin periodinane (135 mg, 0.3 mmol, 1 eq.). The reaction is stirred at room temperature until the reaction is complete. The reaction mixture is filtered through diatomaceous earth and the filtrate is concentrated. The crude reaction product is purified by flash column chromatography to give 75 mg of the titled product.

Example 124

Synthesis of 6-(5-{[Imino(methyl)oxo-$\lambda^6$-sulfanyl]methyl}pyridin-3-yl)-1,2,3,4-tetrahydro-1,8-naphthyridine-1-carboxamide (Cpd 317, Table 1)

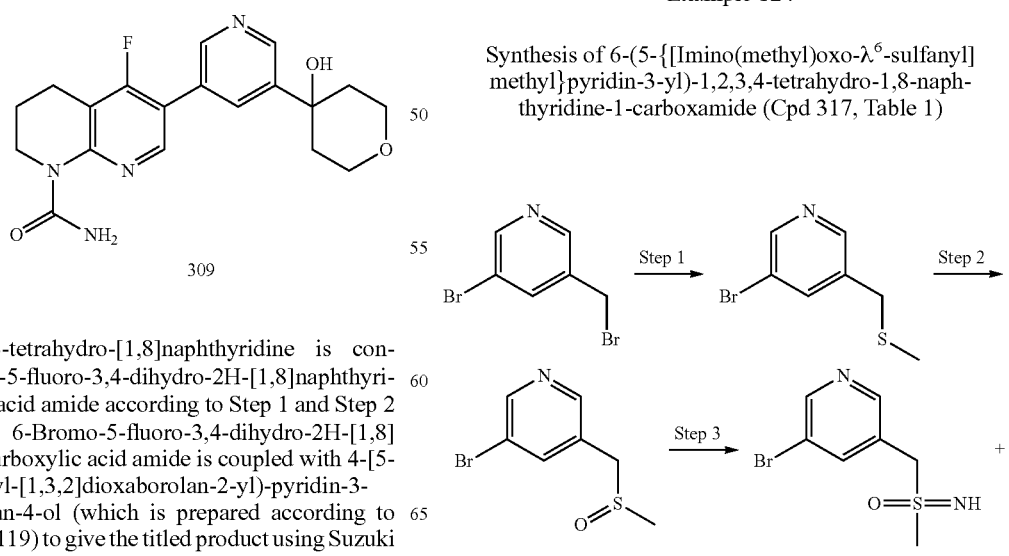

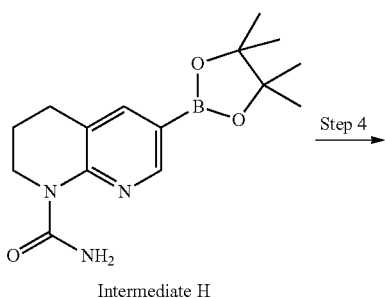

Intermediate H

3-Bromo-5-bromomethyl-pyridine (7.5 g, 30 mmol) is dissolved in EtOH (200 mL). The solution is cooled down to 0° C. Sodium thiomethoxide (3.1 g, 45 mmol) is added slowly and the reaction mixture is stirred for 16 hrs. Then the solvent is removed, water and EtOAc are added. The aqueous layer is separated and extracted with EtOAc. Organic layers are combined and concentrated to give 6.0 g of the 3-bromo-5-methylsulfanylmethyl-pyridine.

3-Bromo-5-methylsulfanylmethyl-pyridine (6.0 g, 28 mmol) is dissolved in chloroform (200 mL) and the solution is cooled to 0° C. Meta-chloroperoxybenzoic acid (7.2 g, 30 mmol, 72%) is added slowly at 0° C. and the reaction mixture is stirred at 0° C. for 1 hr. Then the solvent is removed and the residue is purified by flash column chromatography to give 3.5 g of 3-bromo-5-methanesulfinylmethyl-pyridine.

3-Bromo-5-methanesulfinylmethyl-pyridine (3.0 g, 13 mmol) is dissolved in chloroform (100 mL) and the solution is cooled to 0° C. Sodium azide (1.3 g, 21 mmol) is added and the reaction mixture is stirred for 5 minutes. Then concentrated $H_2SO_4$ (10 mL) is slowly added at 0° C. and then the mixture is heated up to 50° C. for 16 hrs. After cooling down to room temperature, ice cold water is added and the mixture is extracted with $CH_2Cl_2$. The aqueous layer is separated, basified with saturated $Na_2CO_3$ solution and extracted with more $CH_2Cl_2$. Organic layers are combined, dried over anhydrous $Na_2SO_4$ and concentrated to give the crude product. Purification by flash column chromatography affords 1.6 g of 3-bromo-5-[imino(methyl)oxo-$\lambda^6$-sulfanyl]methyl-pyridine.

3-Bromo-5-[imino(methyl)oxo-$\lambda^6$-sulfanyl]methyl-pyridine (250 mg, 1.0 mol) is coupled with Intermediate H (1.2 mmol, using crude) to give 193 mg of the titled product using Suzuki Coupling Method VI.

Example 125

Synthesis of 6-[5-({[Methyl(oxo)phenyl-$\lambda^6$-sulfanylidene]amino}methyl)pyridine-3-yl]-1,2,3,4-tetrahydro-1,8-naphthyridine-1-carboxamide (Cpd 318, Table 1)

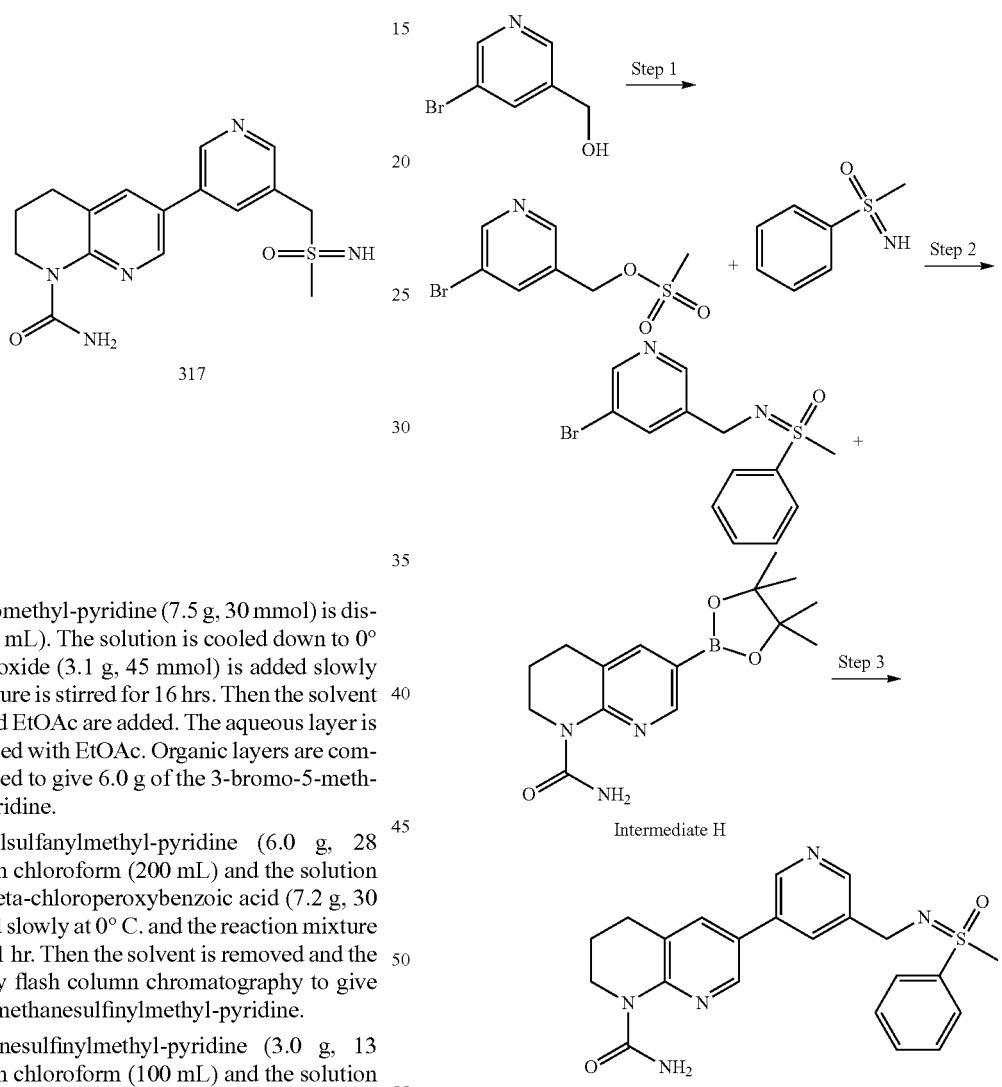

To the stirred solution (5-bromo-pyridin-3-yl)-methanol (3.0 g, 16 mmol) in $CH_2Cl_2$ (30 mL) is added triethylamine (2.4 g, 24 mmol). The reaction mixture is cooled to 0° C., methanesulfonyl chloride (2.2 g, 19 mmol) is added slowly at 0° C. Then the reaction mixture is warmed up to room temperature for 3 hrs. Ice cold water is added and the mixture is extracted with $CH_2Cl_2$. Organic layers are combined, dried over $Na_2SO_4$ and concentrated to give 3.0 g of the crude methanesulfonic acid 5-bromo-pyridin-3-ylmethyl ester which is used without purification.

To the stirred solution of methanesulfonic acid 5-bromo-pyridin-3-ylmethyl ester (3.0 g, 11 mmol) and s-methyl-s-phenylsulphoximine (2.1 g, 14 mmol) in DMF (30 mL) is added potassium carbonate (2.3 g, 17 mmol). The reaction mixture is heated to 80° C. for 4 hrs. The reaction is cooled down to room temperature and ice cold water is added. The mixture is extracted with EtOAc and the organic layers are combined, dried over anhydrous $Na_2SO_4$ and concentrated to give the crude product. Purification by flash column chromatography affords 500 mg of 3-bromo-5-{[methyl(oxo)phenyl-$\lambda^6$-sulfanylidene]amino}methyl-pyridine.

3-Bromo-5-{[methyl(oxo)phenyl-$\lambda^6$-sulfanylidene]amino}methyl-pyridine (325 mg, 1.0 mol) is coupled with Intermediate H (1.2 mmol, using crude) to give 245 mg of the titled product using Suzuki Coupling Method VI.

LCMS Data for Compounds in Table 1 are shown in Table 2, which are measured using the methods set forth in the following Table.

LCMS Methods

| Method | Mobile Phase A | Mobile Phase B | Gradient Time (min) | % A | % B | Flow (mL/min.) | Column |
|---|---|---|---|---|---|---|---|
| A | 0.1% Formic Acid in Water | 0.1% Formic Acid in Acetonitrile | 0<br>0.5<br>1.5<br>2.5<br>3.3<br>4.0 | 90.0<br>90.0<br>1.0<br>1.0<br>90.0<br>90.0 | 10.0<br>10.0<br>99.0<br>99.0<br>10.0<br>10.0 | 0.5 | Thermo Scientific, Aquasil C18, 50 × 2.1 mm, 5μ |
| B | 2.5 mM Aqueous Ammonium Bicarbonate | 100% Acetonitrile | 0<br>0.5<br>1.5<br>2.5<br>3.30<br>4.50 | 90.0<br>90.0<br>1.0<br>1.0<br>90.0<br>90.0 | 10.0<br>10.0<br>99.0<br>99.0<br>10.0<br>10.0 | 0.5 | Phenomex Luna, 3μ C18(2) 100A, 50 × 2.00 mm |
| C | 95% Water 5% Acetonitrile + 0.05% Formic Acid | Acetonitrile + 0.05% Formic Acid | 90% A to 100% B in 4.45 minutes, hold at 100% B to 4.58 minutes | | | 0.8 | BEH 2.1 × 50 mm C18, 1.7 μm particle diameter |
| D | 95% Water 5% Acetonitrile + 0.05% Formic Acid | Acetonitrile + 0.05% Formic Acid | 100% A hold for 1.00 minute, 100% A to 95% B in 4.50 minutes, hold at 100% B to 4.91 minutes | | | 0.6 | HSS T3 2.1 × 100 mm, 1.8 μm particle diameter |
| E | 95% Water 5% Acetonitrile + 0.05% Formic Acid | Acetonitrile + 0.05% Formic Acid | 90% A to 100% B in 1.19 minutes, hold at 100% B to 1.70 minutes | | | 0.8 | BEH 2.1 × 50 mm C18, 1.7 μm particle diameter |
| F | 2.5 mM Aqueous Ammonium Bicarbonate | 100% Acetonitrile | 0<br>1.19<br>1.77<br>1.78 | 90.0<br>5.0<br>5.0<br>90.0 | 10.0<br>95.0<br>95.0<br>10.0 | 0.8 | BEH 2.1 × 50 mm C18, 1.7 μm particle diameter |
| G | 95% Water 5% Acetonitrile + 0.05% Formic Acid | Acetonitrile + 0.05% Formic Acid | 95% A to 100% B in 3.65 minutes, hold at 100% B to 4.95 minutes | | | 0.6 | HSS T3 2.1 × 100 mm, 1.8 um particle diameter |

TABLE 2

| Cpd No. | Mass Found | Retention Time (min) | LCMS Method |
|---|---|---|---|
| 1 | 240.9 | 0.32 | E |
| 2 | 255.3 | 2.44 | A |
| 3 | 254.4 | 2.43 | A |
| 4 | 240.3 | 2.54 | B |
| 5 | 269.4 | 0.33 | E |
| 6 | 289.2 | 2.91 | A |
| 7 | 256.3 | 2.57 | B |
| 8 | 257.1 | 2.52 | B |
| 9 | 285.3 | 2.72 | A |
| 10 | 273.3 | 2.91 | A |
| 11 | 294.1 | 0.48 | E |
| 12 | 333.1 | 2.53 | A |
| 13 | 256.3 | 2.45 | A |
| 14 | 331.4 | 3.05 | A |
| 15 | 323.3 | 2.9 | A |
| 16 | 299.3 | 2.495 | A |
| 17 | 271.5 | 0.63 | E |
| 18 | 297.2 | 2.78 | A |
| 19 | 299.2 | 2.6 | B |
| 20 | 269.3 | 2.52 | A |
| 21 | 299.3 | 2.58 | A |
| 22 | 280.2 | 2.58 | A |
| 23 | 313.3 | 0.61 | E |
| 24 | 384.3 | 3.23 | A |
| 25 | 273.3 | 2.63 | A |

TABLE 2-continued

| Cpd No. | Mass Found | Retention Time (min) | LCMS Method |
|---|---|---|---|
| 26 | 280.3 | 2.66 | A |
| 27 | 275.2 | 2.69 | A |
| 28 | 274.2 | 2.78 | A |
| 29 | 289.2 | 2.94 | A |
| 30 | 256.3 | 2.78 | A |
| 31 | 349.4 | 3.12 | A |
| 32 | 335.4 | 2.54 | A |
| 33 | 317.2 | 2.43 | A |
| 34 | 317.2 | 2.41 | A |
| 35 | 349.2 | 2.7 | A |
| 36 | 335.2 | 2.17 | A |
| 37 | 409.3 | 2.51 | A |
| 38 | 409.3 | 2.87 | A |
| 39 | 298.2 | 2.57 | A |
| 40 | 326.3 | 1.07 | A |
| 41 | 376.2 | 2.36 | A |
| 42 | 285.3 | 2.46 | B |
| 43 | 291.2 | 2.52 | A |
| 44 | 271.2 | 0.34 | A |
| 45 | 337.4 | 2.62 | A |
| 46 | 353.3 | 3.01 | A |
| 47 | 436.3 | 3.32 | A |
| 48 | 339.4 | 2.65 | A |
| 49 | 339.4 | 2.69 | A |
| 50 | 285.3 | 0.3 | A |
| 51 | 313.3 | 2.63 | A |
| 52 | 409.3 | 3 | A |
| 53 | 326.4 | 0.36 | A |
| 54 | 299.3 | 2.41 | A |
| 55 | 444.3 | 2.83 | A |
| 56 | 379.3 | 3.12 | A |
| 57 | 388.3 | 2.63 | A |
| 58 | 338.4 | 0.34 | A |
| 59 | 385.4 | 2.64 | A |
| 60 | 387.3 | 2.59 | A |
| 61 | 376.3 | 2.47 | B |
| 62 | 379.4 | 2.78 | A |
| 63 | 402.4 | 2.71 | A |
| 64 | 313.3 | 2.46 | B |
| 65 | 374.4 | 2.7 | A |
| 66 | 405.4 | 2.59 | A |
| 67 | 323.2 | 2.93 | A |
| 68 | 285.3 | 0.34 | A |
| 69 | 298.1 | 0.29 | E |
| 70 | 361.3 | 3.17 | A |
| 71 | 418.3 | 2.66 | A |
| 72 | 459.3 | 2.6 | A |
| 73 | 410.4 | 2.62 | A |
| 74 | 340.3 | 2.48 | A |
| 75 | 322.3 | 2.92 | A |
| 76 | 369.4 | 2.63 | A |
| 77 | 370.3 | 2.49 | A |
| 78 | 355.3 | 2.41 | A |
| 79 | 380.3 | 2.53 | A |
| 80 | 271.1 | 0.45 | C |
| 81 | 369.3 | 2.76 | B |
| 82 | 391.3 | 2.56 | A |
| 83 | 396.3 | 2.66 | A |
| 84 | 309.2 | 2.73 | A |
| 85 | 357.4 | 2.46 | A |
| 86 | 375.4 | 2.37 | A |
| 87 | 354.3 | 2.56 | B |
| 88 | 367.3 | 2.48 | B |
| 89 | 354.3 | 2.49 | B |
| 90 | 340.3 | 2.47 | A |
| 91 | 367.2 | 2.66 | A |
| 92 | 353.3 | 0.36 | A |
| 93 | 396.3 | 2.56 | A |
| 94 | 325.3 | 2.56 | A |
| 95 | 327.3 | 2.52 | A |
| 96 | 396.2 | 2.61 | A |
| 97 | 327.3 | 2.6 | A |
| 98 | 398.4 | 0.37 | A |
| 99 | 326.7 | 2.68 | A |
| 100 | 341.3 | 2.63 | A |
| 101 | 409.4 | 2.7 | A |
| 102 | 327.2 | 2.14 | D |
| 103 | 269.2 | 2.38 | A |
| 104 | 352.3 | 2.63 | A |
| 105 | 348.3 | 2.685 | A |
| 106 | 347.3 | 2.97 | A |
| 107 | 374.3 | 2.63 | A |
| 108 | 297.4 | 0.74 | E |
| 109 | 311.3 | 0.54 | E |
| 110 | 311.3 | 0.55 | E |
| 111 | 368.3 | 2.53 | A |
| 112 | 299.3 | 2.39 | A |
| 113 | 269.3 | 0.28 | E |
| 114 | 289.1 | 2.98 | A |
| 115 | 324.0 | 0.48 | E |
| 116 | 360.3 | 2.72 | A |
| 117 | 283.2 | 2.64 | A |
| 118 | 356.2 | 0.84 | F |
| 119 | 332.2 | 0.68 | F |
| 120 | 375.2 | 0.99 | F |
| 121 | 356.3 | 2.98 | A |
| 122 | 374.3 | 2.65 | A |
| 123 | 362.2 | 0.82 | F |
| 124 | 356.2 | 0.83 | F |
| 125 | 348.2 | 0.54 | F |
| 126 | 374.3 | 2.72 | A |
| 127 | 375.3 | 3.14 | A |
| 128 | 375.3 | 3.1 | A |
| 129 | 349.3 | 2.76 | A |
| 130 | 388.3 | 2.81 | A |
| 131 | 410.3 | 2.73 | A |
| 132 | 362.2 | 0.60 | F |
| 133 | 434.3 | 2.51 | A |
| 134 | 424.3 | 2.85 | A |
| 135 | 346.3 | 2.65 | A |
| 136 | 370.4 | 2.96 | A |
| 137 | 346.3 | 2.59 | A |
| 138 | 333.2 | 1.51 | F |
| 139 | 375.2 | 0.98 | F |
| 140 | 361.2 | 0.70 | F |
| 141 | 361.3 | 2.77 | A |
| 142 | 370.4 | 2.96 | A |
| 143 | 409.3 | 2.82 | A |
| 144 | 361.3 | 2.78 | A |
| 145 | 349.2 | 0.68 | F |
| 146 | 349.2 | 0.63 | F |
| 147 | 335.3 | 2.85 | A |
| 148 | 321.3 | 2.58 | A |
| 149 | 424.2 | 2.7 | A |
| 150 | 417.4 | 2.77 | A |
| 151 | 332.3 | 2.62 | A |
| 152 | 454.3 | 2.62 | A |
| 153 | 454.3 | 2.62 | A |
| 154 | 321.2 | 0.59 | F |
| 155 | 314.1 | 2.78 | A |
| 156 | 374.4 | 2.89 | A |
| 157 | 299.3 | 2.55 | A |
| 158 | 299.3 | 2.55 | A |
| 159 | 333.1 | 0.6 | E |
| 160 | 340.7 | 2.61 | A |
| 161 | 311.3 | 2.65 | A |
| 162 | 361.3 | 2.62 | A |
| 163 | 312.7 | 0.43 | A |
| 164 | 270.1 | 1.94 | D |
| 165 | 338.2 | 2.18 | D |
| 166 | 324.2 | 1.99 | D |
| 167 | 341.1 | 1.2 | G |
| 168 | 341.2 | 1.2 | G |
| 169 | 410.2 | 1.59 | G |
| 170 | 410.1 | 1.58 | G |
| 171 | 299.2 | 2.04 | D |
| 172 | 299.9 | 1.01 | G |
| 173 | 299 | 1.01 | G |
| 174 | 311.7 | 0.38 | A |
| 175 | 333.1 | 2.21 | D |
| 176 | 333.2 | 2.2 | D |
| 177 | 326.2 | 0.46 | E |
| 178 | 382.2 | 0.51 | E |
| 179 | 414.2 | 1.01 | E |

TABLE 2-continued

| Cpd No. | Mass Found | Retention Time (min) | LCMS Method |
|---|---|---|---|
| 180 | 355.2 | 0.41 | E |
| 181 | 355.3 | 0.53 | E |
| 182 | 355.3 | 0.53 | E |
| 183 | 312.7 | 1.64 | A |
| 184 | 353 | 1.79 | D |
| 185 | 396.3 | 2.3 | D |
| 186 | 416.3 | 1.68 | D |
| 187 | 410.3 | 0.46 | E |
| 188 | 382.3 | 0.35 | E |
| 189 | 382.3 | 0.35 | E |
| 190 | 319.2 | 0.58 | E |
| 191 | 319.2 | 0.58 | E |
| 192 | 368.2 | 0.35 | E |
| 193 | 396.3 | 0.41 | E |
| 194 | 410.3 | 0.57 | E |
| 195 | 353.2 | 1.84 | A |
| 196 | 353.2 | 1.84 | A |
| 197 | 396.4 | 0.56 | E |
| 198 | 443.2 | 0.67 | E |
| 199 | 330.9 | 2.73 | A |
| 200 | 343.1 | 2.8 | A |
| 201 | 345.3 | 2.66 | A |
| 202 | 331.1 | 2.75 | A |
| 203 | 345.2 | 2.82 | A |
| 204 | 415.7 | 2.74 | A |
| 205 | 347.3 | 2.64 | A |
| 206 | 316.3 | 0.42 | A |
| 207 | 367.7 | 2.65 | A |
| 208 | 396.2 | 0.39 | E |
| 209 | 390.1 | 0.51 | E |
| 210 | 353.6 | 2.65 | A |
| 211 | 331.1 | 0.73 | E |
| 212 | 331.1 | 0.63 | E |
| 213 | 331.2 | 0.63 | E |
| 214 | 345.2 | 0.7 | E |
| 215 | 345.2 | 0.7 | E |
| 216 | 370.2 | 0.38 | E |
| 217 | 415.7 | 1.8 | A |
| 218 | 415.7 | 1.81 | A |
| 219 | 283.7 | 0.38 | A |
| 220 | 390.1 | 0.51 | E |
| 221 | 390.1 | 0.51 | E |
| 222 | 403.7 | 1.85 | A |
| 223 | 403.7 | 1.85 | A |
| 224 | 383.2 | 0.55 | E |
| 225 | 410.2 | 0.48 | E |
| 226 | 396.4 | 1.79 | A |
| 227 | 356.3 | 1.69 | A |
| 228 | 410.4 | 1.88 | A |
| 229 | 440.4 | 1.7 | A |
| 230 | 436.3 | 1.99 | A |
| 231 | 446.4 | 1.85 | A |
| 232 | 412.4 | 1.71 | A |
| 233 | 340.2 | 0.5 | E |
| 234 | 340.2 | 0.5 | E |
| 235 | 382.2 | 0.45 | E |
| 236 | 402.2 | 0.67 | E |
| 237 | 295.3 | 0.67 | E |
| 238 | 354.3 | 0.48 | E |
| 239 | 354.3 | 0.48 | E |
| 240 | 382.1 | 0.45 | E |
| 241 | 382 | 0.45 | E |
| 242 | 387.7 | 1.75 | A |
| 243 | 402.2 | 0.54 | E |
| 244 | 405.4 | 1.93 | A |
| 245 | 333.2 | 0.58 | E |
| 246 | 381.7 | 0.43 | E |
| 247 | 381.7 | 0.43 | E |
| 248 | 398.9 | 0.7 | E |
| 249 | 425 | 0.77 | E |
| 250 | 354.3 | 1.66 | A |
| 251 | 369.2 | 0.55 | E |
| 252 | 396.2 | 0.56 | E |
| 253 | 410 | 0.54 | E |
| 254 | 396.3 | 0.47 | E |
| 255 | 444.2 | 0.6 | E |
| 256 | 366 | 2.31 | D |
| 257 | 401.8 | 2.38 | D |
| 258 | 351.9 | 2.51 | D |
| 259 | 308.2 | 2.6 | D |
| 260 | 337.5 | 2.64 | D |
| 261 | 321.5 | 3.06 | C |
| 262 | 338.2 | 0.42 | E |
| 263 | 338.2 | 0.43 | E |
| 264 | 320.2 | 2.93 | D |
| 265 | 338 | 2.23 | D |
| 266 | 363.6 | 2.9 | D |
| 267 | 340.2 | 2.35 | D |
| 268 | 402.2 | 2.37 | D |
| 269 | 401.9 | 2.36 | D |
| 270 | 352.2 | 2.48 | D |
| 271 | 352.4 | 2.49 | D |
| 272 | 366.3 | 2.3 | D |
| 273 | 366.3 | 2.3 | D |
| 274 | 353.3 | 2.3 | D |
| 275 | 352.3 | 2.28 | D |
| 276 | 354.3 | 1.75 | A |
| 277 | 354.3 | 1.72 | A |
| 278 | 367.3 | 2.28 | D |
| 279 | 367.3 | 2.28 | D |
| 280 | 395.3 | 2.51 | D |
| 281 | 381.3 | 1.71 | A |
| 282 | 339.4 | 1.67 | A |
| 283 | 389.3 | 1.73 | A |
| 284 | 384.3 | 2.68 | A |
| 285 | 356.3 | 0.46 | A |
| 286 | 371.3 | 2.78 | A |
| 287 | 365.2 | 2.87 | A |
| 288 | 363.4 | 2.78 | A |
| 289 | 255.1 | 0.56 | F |
| 290 | 266.1 | 0.54 | F |
| 291 | 270.7 | 0.46 | A |
| 292 | 309.1 | 0.67 | F |
| 293 | 303.1 | 0.47 | F |
| 294 | 352.3 | 0.53 | F |
| 295 | 423.3 | 0.6 | F |
| 296 | 388.3 | 0.57 | F |
| 297 | 340.3 | 0.5 | F |
| 298 | 392.3 | 0.44 | F |
| 299 | 409.3 | 0.6 | F |
| 300 | 410.4 | 0.58 | F |
| 301 | 403.4 | 0.61 | F |
| 302 | 366.3 | 0.68 | F |
| 303 | 370.3 | 0.54 | F |
| 304 | 445.4 | 0.52 | F |
| 305 | 389.2 | 0.54 | E |
| 306 | 369.2 | 0.52 | E |
| 307 | 369.2 | 0.54 | E |
| 308 | 380.2 | 0.6 | E |
| 309 | 373.2 | 0.69 | E |
| 310 | 386.2 | 0.51 | E |
| 311 | 414.2 | 0.62 | E |
| 312 | 382.3 | 1.72 | A |
| 313 | 410.4 | 1.87 | A |
| 314 | 402.3 | 0.56 | E |
| 315 | 430 | 0.62 | E |
| 316 | 314.8 | 0.65 | E |
| 317 | 345.9 | 0.35 | E |
| 318 | 421.8 | 0.51 | E |

ASSESSMENT OF BIOLOGICAL ACTIVITY

Inhibition of Aldosterone Synthase

The compounds of the invention may be evaluated for aldosterone synthase inhibition by the following assay:

The aldosterone synthase inhibition assay employs cynomolgus adrenal gland mitochondria as the source of aldosterone synthase (CYP11B2). Mitochondria are prepared from frozen cynomolgus monkey adrenal glands according to Method A described in by J. D. McGarry et al. (Biochem. J., 1983, 214, 21-28), with a final resuspension in the AT buffer described in R. Yamaguchi et al. (Cell Death and Differentiation, 2007, 14, 616-624), frozen as aliquots in liquid nitrogen and stored at −80° C. until use.

Assays are performed in 96-well format in a final volume of 60 μL/well, containing 100 mM potassium phosphate, pH 7.4, 1% (v/v) DMSO, and additionally, 2 μM of corticosterone and 6 mg of mitochondrial protein. Reactions are started by the addition of NADPH to 1 mM and allowed to proceed for 60-90 minutes at 37° C. Reactions are terminated by the addition of 60 μL of acetonitrile. One hundred microliters are then transferred to a glass filter plate and centrifuged at 570×g for 5 minutes and the filtrate is collected. Reaction product aldosterone is quantified by mass spectrometry. To determine the assay blank value (0% activity), NADPH is omitted from some reactions.

Dose dependent inhibition is quantified by the inclusion of compound at various concentrations. Maximum activity (100%) is defined by reactions containing NADPH, but without compound. Activities at each concentration are expressed as a percentage of the maximum activity (y-axis) and plotted against concentration of compound (x-axis) and the concentration corresponding to 50% activity (IC50) determined using the XLFit curve-fitting program using a 4-parameter logistic model.

Representative compounds of the present invention were tested for activity in the above assay. Preferred compounds have an $IC_{50}<1,000$ nM and more preferred compounds have an $IC_{50}<100$ nM in this assay. As examples, data for representative compounds from Table 1 are shown in Table 3.

TABLE 3

| Cpd No. | $IC_{50}$ (nM) |
|---|---|
| 1 | 28 |
| 2 | 15.5 |
| 3 | 21.0 |
| 4 | 120 |
| 5 | 2 |
| 6 | 6.3 |
| 7 | 16 |
| 8 | 9.1 |
| 9 | 3.6 |
| 10 | 11.5 |
| 11 | 7.3 |
| 12 | 140 |
| 13 | 130 |
| 14 | 5.3 |
| 15 | 12 |
| 16 | 7.1 |
| 17 | 10 |
| 18 | 11 |
| 19 | 10 |
| 20 | 2 |
| 21 | >1000 |
| 22 | 7.3 |
| 23 | 5 |
| 24 | 31 |
| 25 | 3.1 |
| 26 | 164.6 |
| 27 | 18 |
| 28 | 37 |
| 29 | 5.1 |
| 30 | 110 |
| 31 | 5.2 |
| 32 | 13 |
| 33 | 22.8 |
| 34 | 47.6 |
| 35 | 90 |
| 36 | >1000 |
| 37 | >1000 |
| 38 | 4 |
| 39 | 120 |
| 40 | 23.5 |
| 41 | 22.6 |
| 42 | 9.2 |
| 43 | 79 |
| 44 | 370 |
| 45 | 36 |
| 46 | 22 |
| 47 | 110 |
| 48 | 22.1 |
| 49 | 250 |
| 50 | 21 |
| 51 | 37 |
| 52 | 5.7 |
| 53 | 95.6 |
| 54 | 6.8 |
| 55 | 14.9 |
| 56 | 5.4 |
| 57 | 5.2 |
| 58 | 490 |
| 59 | 72.1 |
| 60 | 35.4 |
| 61 | 650 |
| 62 | 27 |
| 63 | 5.9 |
| 64 | 16.2 |
| 65 | 6.9 |
| 66 | 17 |
| 67 | 5.8 |
| 68 | 12 |
| 69 | 310 |
| 70 | 6.8 |
| 71 | 6.1 |
| 72 | 20 |
| 73 | 15.4 |
| 74 | 19 |
| 75 | 17.3 |
| 76 | 6.1 |
| 77 | 26.3 |
| 78 | 66.1 |
| 79 | 83.2 |
| 80 | 5.2 |
| 81 | 4.6 |
| 82 | 15.4 |
| 83 | 12 |
| 84 | 57.4 |
| 85 | 15.5 |
| 86 | 15.4 |
| 87 | 39.8 |
| 88 | 74.5 |
| 89 | 102.8 |
| 90 | 22.2 |
| 91 | 12.2 |
| 92 | 41.7 |
| 93 | 12.2 |
| 94 | 5.2 |
| 95 | 11 |
| 96 | 17 |
| 97 | 8.6 |
| 98 | 19.8 |
| 99 | 21.4 |
| 100 | 11.6 |
| 101 | 21 |
| 102 | 27 |
| 103 | 120 |
| 104 | 250 |
| 105 | 20 |
| 106 | 10.1 |
| 107 | 15.1 |
| 108 | |
| 109 | 44 |
| 110 | 85.0 |
| 111 | 620 |
| 112 | 11.6 |
| 113 | |
| 114 | >1000 |
| 115 | |
| 116 | 3.5 |
| 117 | 5.9 |
| 118 | |

TABLE 3-continued

| Cpd No. | IC$_{50}$ (nM) |
|---|---|
| 119 | |
| 120 | |
| 121 | 45 |
| 122 | 151 |
| 123 | |
| 124 | |
| 125 | |
| 126 | 11.5 |
| 127 | 25.1 |
| 128 | 10.9 |
| 129 | 7.5 |
| 130 | 8.4 |
| 131 | 2.7 |
| 132 | |
| 133 | 24 |
| 134 | 7.5 |
| 135 | 6.3 |
| 136 | 3.6 |
| 137 | 10.7 |
| 138 | |
| 139 | |
| 140 | |
| 141 | 6 |
| 142 | 3.3 |
| 143 | 64.7 |
| 144 | 4.6 |
| 145 | |
| 146 | |
| 147 | 17 |
| 148 | 15.7 |
| 149 | 92 |
| 150 | 5.4 |
| 151 | 8.0 |
| 152 | 13.8 |
| 153 | 7.7 |
| 154 | |
| 155 | 3.1 |
| 156 | 7.3 |
| 157 | 6.6 |
| 158 | 6.9 |
| 159 | 21.9 |
| 160 | 27.7 |
| 161 | 14.3 |
| 162 | 17.1 |
| 163 | 257.9 |
| 164 | 16.3 |
| 165 | 47 |
| 166 | 295.6 |
| 167 | 21.2 |
| 168 | 18.5 |
| 169 | 25.8 |
| 170 | 24.5 |
| 171 | 28.5 |
| 172 | 28.5 |
| 173 | 16.9 |
| 174 | 65.5 |
| 175 | 16.1 |
| 176 | 11.5 |
| 177 | 15.5 |
| 178 | 30 |
| 179 | 83.2 |
| 180 | 23.4 |
| 181 | 23.5 |
| 182 | 24.3 |
| 183 | 249 |
| 184 | 5.2 |
| 185 | 48.5 |
| 186 | 13.7 |
| 187 | 19.5 |
| 188 | 40 |
| 189 | 35 |
| 190 | 27.8 |
| 191 | 19.9 |
| 192 | 63.9 |
| 193 | 40 |
| 194 | 147.6 |
| 195 | 4.3 |
| 196 | 2.6 |
| 197 | 42.5 |
| 198 | 34.9 |
| 199 | 37 |
| 200 | 154.3 |
| 201 | 209 |
| 202 | 61.2 |
| 203 | 403.5 |
| 204 | 54.9 |
| 205 | 20.6 |
| 206 | 424.7 |
| 207 | 18.3 |
| 208 | 50.1 |
| 209 | 22.5 |
| 210 | 58.6 |
| 211 | 37.3 |
| 212 | 48.1 |
| 213 | 69.6 |
| 214 | 404.7 |
| 215 | 326.2 |
| 216 | 35 |
| 217 | 33.2 |
| 218 | 73.5 |
| 219 | 374.7 |
| 220 | 19.4 |
| 221 | 26.8 |
| 222 | 9.1 |
| 223 | 9.6 |
| 224 | 89.7 |
| 225 | 47.5 |
| 226 | 10.1 |
| 227 | 18.7 |
| 228 | 4.3 |
| 229 | 41 |
| 230 | 7.2 |
| 231 | 8.6 |
| 232 | 22 |
| 233 | 42.9 |
| 234 | 50.9 |
| 235 | 19.8 |
| 236 | 32 |
| 237 | 4.1 |
| 238 | 36.3 |
| 239 | 42.1 |
| 240 | 25.2 |
| 241 | 32.9 |
| 242 | 14.6 |
| 243 | 10.8 |
| 244 | 147 |
| 245 | 11.4 |
| 246 | 57.3 |
| 247 | 50.3 |
| 248 | 9 |
| 249 | 6.3 |
| 250 | 36.1 |
| 251 | 169.7 |
| 252 | 60.2 |
| 253 | 20.9 |
| 254 | 31 |
| 255 | 10 |
| 256 | 140.7 |
| 257 | 34.6 |
| 258 | 52.7 |
| 259 | 4.4 |
| 260 | 53.5 |
| 261 | 14.8 |
| 262 | 12.4 |
| 263 | 159.1 |
| 264 | 3.7 |
| 265 | 31.1 |
| 266 | 15.5 |
| 267 | 16.9 |
| 268 | 16.5 |
| 269 | 18.4 |
| 270 | 16.6 |
| 271 | 104.9 |
| 272 | 37.7 |
| 273 | 116.8 |
| 274 | 50.8 |

TABLE 3-continued

| Cpd No. | IC$_{50}$ (nM) |
|---|---|
| 275 | 6.7 |
| 276 | 79.6 |
| 277 | 14.8 |
| 278 | 16.5 |
| 279 | 33 |
| 280 | 28.3 |
| 281 | 33.2 |
| 282 | 67.5 |
| 283 | 19.6 |
| 284 | 39.7 |
| 285 | 62.5 |
| 286 | 27.4 |
| 287 | 11.3 |
| 288 | 9.6 |
| 289 | 3.2 |
| 290 | 9.1 |
| 291 | 17.5 |
| 292 | 3.2 |
| 293 | 43.6 |
| 294 | 12 |
| 295 | 11 |
| 296 | 42 |
| 297 | 18 |
| 298 | 42 |
| 299 | 340 |
| 300 | 37 |
| 301 | 490 |
| 302 | 47 |
| 303 | 270 |
| 304 | 59 |
| 305 | 8.7 |
| 306 | 34.4 |
| 307 | 48.5 |
| 308 | >1000 |
| 309 | 17.3 |
| 310 | 20.7 |
| 311 | 22.8 |
| 312 | 43.4 |
| 313 | 20.8 |
| 314 | 5.8 |
| 315 | 23.4 |
| 316 | 9.7 |

METHODS OF THERAPEUTIC USE

In accordance with the invention, there are provided novel methods of using the compounds of formula (I). The compounds disclosed herein effectively inhibit aldosterone synthase. The inhibition of aldosterone synthase is an attractive means for preventing and treating a variety of diseases or conditions that can be alleviated by lowering levels of aldosterone. Thus, the compounds are useful for the treatment of diseases and conditions as described in the Background section, including the following conditions and diseases:

Diabetic Kidney Disease Including Diabetic Nephropathy;

Non-diabetic kidney disease including glomerulosclerosis, glomerulonephritis, IGA nephropathy, nephritic syndrome and focal segmental glomerulosclerosis (FSGS);

Cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism;

Adrenal Hyperplasia and Primary and Secondary Hyperaldosteronism.

These disorders have been well characterized in man, but also exist with a similar etiology in other mammals, and can be treated by pharmaceutical compositions of the present invention.

Accordingly, a compound of formula I according to any of the embodiments described herein or a pharmaceutically acceptable salt thereof may be used for the preparation of a medicament for treating a disease or disorder mediated by aldosterone synthase, including diabetic nephropathy, glomerulosclerosis, glomerulonephritis, IGA nephropathy, nephritic syndrome focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism, adrenal hyperplasia and primary and secondary hyperaldosteronism.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of the formula I

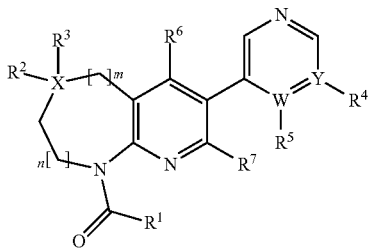

wherein:
$R^1$ is selected from —$NH_2$, —$NHCH_3$ and —$CH_3$;
m is 0;
n is 1; and
X is selected from C and O; or
m is 0;
n is 0; and
X is C; or
m is 1;
n is 1; and
X is O;
Y and W are selected from C and N, wherein if Y is N, then W is C and $R^4$ is an electron pair and if W is N, then Y is C and $R^5$ is an electron pair;
$R^2$ and $R^3$ are independently selected from —H, —F, —OH and $C_{1-4}$ alkyl, when X is C;
$R^2$ and $R^3$ is an electron pair when X is O;
$R^4$ is the group of —$(CR^aR^b)_p(A)_{0-1}(CR^aR^b)_qB$, wherein:
p and q are independently selected from integers between 0 and 5, but p+q is always equal or less than 6;
A is selected from O, S and $NR^e$;
B is selected from:
—H;
—OH;
—CN;
halogen;
—$SO_2R^c$;
—$C(O)R^c$;
—$CO_2R^c$;
—$NR^cSO_2R^d$;
—$SO_2NR^cR^d$;
—$CONR^cR^d$;
—$NR^cCOR^d$;

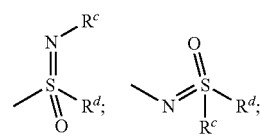

—$NR^cR^d$;
-Phenyl, optionally substituted with 1 to 3 groups selected from halogen, —CN, —$CH_2CN$, —$NR^cC$(O)$R^d$, —$SO_2C_{1-3}$alkyl, —$C(O)NR^cR^d$, $C_{1-4}$alkoxy, —$SO_2NR^cR^d$, —$CO_2R^c$, —$NR^cSO_2R^d$ —$(CH_2)_{0-3}SO_2C_{1-3}$alkyl and $C_{1-3}$alkyl, wherein said $C_{1-3}$alkyl is optionally substituted with —OH, halogen or —$OCH_3$;
-heteroaryl optionally substituted with 1 to 2 groups independently selected from, —OH, $C_{1-3}$alkoxy, —$(CH_2)_{0-2}$morpholin-4-yl and $C_{1-6}$alkyl wherein said $C_{1-6}$alkyl is optionally substituted with —OH, —CN, $C_{1-3}$alkoxy-$N(R^e)_2$, —$CON(R^e)_2$, —$SO_2C_{1-3}$alkyl, —$SO_2N(R^e)_2$ or halogen; and
—$C_{3-7}$ cycloalkyl, optionally partially unsaturated, wherein up to 3 ring constituting carbons of the cycloalkyl can be optionally replaced with a group selected from O, S, N, $NR^e$, SO, $SO_2$ and CO; and wherein the resulting cycloalkyl or heterocyclyl is optionally substituted with 1 to 3 groups selected from —OH, oxo, —CN, $C_{1-3}$alkoxy, —$N(R^e)_2$, —$CON(R^e)_2$, —$CO_2C_{1-4}$alkyl, —$C(O)C_{1-3}$alkyl, —$SO_2C_{1-3}$alkyl, —$SO_2N(R^e)_2$, halogen and $C_{1-6}$alkyl, wherein the $C_{1-6}$alkyl is optionally substituted with —OH;
$R^5$ is selected from
—H;
—$C_{1-6}$alkyl optionally substituted with —OH, oxo, —$OC_{1-6}$alkyl or —$OCH_2$phenyl;
—$C_{3-6}$ cycloalkyl, wherein up to 3 ring constituting carbons can be optionally replaced with a group selected from O, S, N, $NR^e$, SO, $SO_2$ or CO and wherein the resulting cycloalkyl or heterocyclyl is optionally substituted with —OH, —CN, halogen or $C_{1-3}$alkyl, wherein the $C_{1-3}$alkyl is optionally substituted with —OH;
—$CO_2R^c$;
—CN;
—$CF_3$;
-halogen;
—$(CR^aR^b)_{0-2}OC_{1-3}$alkyl;
—$C(O)NR^cR^d$;
—$CH_2O$phenyl, wherein the phenyl is optionally substituted with halogen;
-Phenyl, optionally substituted with halogen or $SO_2C_{1-3}$alkyl;
—$CR^aR^bNHR^e$; and
-heteroaryl, optionally substituted with $C_{1-3}$alkyl;
$R^6$ and $R^7$ are independently selected from H, —Cl, —F, —CN and —$CH_3$;
wherein at least one of $R^6$ or $R^7$ is H;
$R^a$ and $R^b$ are independently selected from
—H;
—$C_{1-6}$alkyl;
—$C_{3-7}$cycloalkyl wherein up to 3 ring constituting carbons can be optionally replaced with a group selected from O, S, $NR^e$, SO, $SO_2$ and CO;
—OH;
—CN;
-halogen; and
—$OC_{1-3}$alkyl; or
$R^a$ and $R^b$, attached to the same or different atom, along with the atoms that they are attached to can form a $C_{3-7}$cycloalkyl ring in which up to 3 ring constituting carbon atoms can be optionally replaced with a group selected from O, S, $NR^e$, SO, $SO_2$ and CO;

$R^c$ and $R^d$ are independently selected from:
- —H;
- —$C_{1-6}$alkyl optionally substituted with —OH, oxo, —CN, $C_{1-3}$alkoxyl, —N($R^e$)$_2$, —CON($R^e$)$_2$, —SO$_2$C$_{1-3}$alkyl, —SO$_2$N($R^e$)$_2$, halogen, heterocyclyl or heteroaryl;
- —$C_{3-7}$cycloalkyl optionally substituted with —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ or halogen; wherein up to 3 ring constituting carbon atoms of the ring can be optionally replaced with a group selected from O, S, NR$^e$, SO, SO$_2$ and CO;
- —(CH$_2$)$_{0-1}$phenyl, optionally substituted with 1 to 3 groups selected from —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ and halogen;
- -heteroaryl optionally substituted with 1 to 2 groups independently selected from —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ and halogen;
- —SO$_2$C$_{1-3}$ alkyl; and
- —CO$_2$C$_{1-3}$ alkyl; or $R^c$ and $R^d$ along with the atoms that they are attached to can form a $C_{3-7}$cycloalkyl ring in which up to 3 ring constituting carbon atoms can be optionally replaced by O, S, N, NR$^e$, SO, SO$_2$ or CO, wherein the cycloalkyl or heterocyclyl ring formed can be optionally substituted with one to three groups selected from —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ and halogen, wherein if the ring is substituted with two groups on the same carbon, the groups may join to form a spiro ring;

each $R^e$ is independently selected from:
- —H;
- —$C_{1-6}$alkyl optionally substituted with —OH, —CN or halogen;
- —COC$_{1-3}$alkyl;
- —CO$_2$C$_{1-4}$alkyl; and
- —SO$_2$C$_{1-3}$alkyl;

or a salt thereof.

2. The compound according to claim 1, wherein $R^5$ is selected from
- —H;
- —$C_{1-6}$alkyl optionally substituted with —OH;
- —$C_{3-6}$ cycloalkyl, wherein up to 3 ring constituting carbons can be optionally replaced with a group selected from O, S, NR$^e$, SO, SO$_2$ and CO and wherein the resulting cycloalkyl or heterocyclyl is optionally substituted with —OH, —CN, halogen or $C_{1-3}$alkyl, wherein the $C_{1-3}$alkyl is optionally substituted with —OH;
- —CO$_2$R$^c$;
- —CN;
- —CF$_3$;
- -halogen;
- —(CR$^a$R$^b$)$_{0-2}$OC$_{1-3}$alkyl;
- —C(O)NR$^c$R$^d$;
- —CH$_2$Ophenyl, wherein the phenyl is optionally substituted with halogen;
- -Phenyl, optionally substituted with halogen or SO$_2$C$_{1-3}$alkyl;
- —CR$^a$R$^b$NHR$^e$; and
- -heteroaryl, optionally substituted with $C_{1-3}$alkyl;

$R^6$ is H;
$R^7$ is H;

$R^c$ and $R^d$ are independently selected from:
- —H;
- —$C_{1-6}$alkyl optionally substituted with —OH, oxo, —CN, $C_{1-3}$alkoxyl, —N($R^e$)$_2$, —CON($R^e$)$_2$, —SO$_2$C$_{1-3}$alkyl, —SO$_2$N($R^e$)$_2$ or halogen;
- —$C_{3-7}$cycloalkyl optionally substituted with —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ or halogen; wherein up to 3 ring constituting carbon atoms of the ring can be optionally replaced with a group selected from O, S, NR$^e$, SO, SO$_2$ and CO;
- —(CH$_2$)$_{0-1}$phenyl, optionally substituted with 1 to 3 groups selected from —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ and halogen;
- -heteroaryl optionally substituted with 1 to 2 groups independently selected from —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ and halogen;
- —SO$_2$C$_{1-3}$ alkyl; and
- —CO$_2$C$_{1-3}$ alkyl; or $R^c$ and $R^d$ along with the atoms that they are attached to can form a $C_{3-7}$cycloalkyl ring in which up to 3 ring constituting carbon atoms can be optionally replaced by O, S, NR$^e$, SO, SO$_2$ or CO, wherein the cycloalkyl or heterocyclyl ring formed can be optionally substituted with —OH, —CN, $C_{1-6}$alkyl, $C_{1-3}$alkoxyl, —N($R^e$)$_2$, —CON($R^e$)$_2$, —SO$_2$C$_{1-3}$alkyl, —SO$_2$N($R^e$)$_2$ or halogen;

or a salt thereof.

3. The compound according to claim 1, wherein:
$R^1$ is selected from —NH$_2$ and —CH$_3$;
$R^2$ and $R^3$ are independently selected from —H, —F and —OH, when X is C; $R^2$ and $R^3$ is an electron pair when X is O;
$R^4$ is selected from
- —H;
- —OH;
- —(CH$_2$)$_{0-1}$CN;
- —$C_{1-6}$alkyl, optionally substituted with one to seven groups independently selected from halogen, —OH or —OCH$_3$;
- —OC$_{1-4}$alkyl, optionally substituted with —OH;
- -halogen;
- —CF$_3$;
- —(CH$_2$)$_{0-1}$(O)$_{0-1}$(CH$_2$)$_{0-3}$SO$_2$C$_{1-3}$alkyl;
- —C(O)C$_{1-3}$alkyl;
- —CO$_2$R$^c$;
- —C$_{0-2}$alkyl-NHSO$_2$C$_{1-3}$alkyl;
- —C$_{0-2}$alkyl-NHC(O)NHC$_{1-3}$alkyl;
- —(O)$_{0-1}$(CH$_2$)$_{0-1}$(O)$_{0-1}$C(O)NR$^c$R$^d$;
- —(CH$_2$)$_{0-1}$NR$^c$R$^d$;
- —(O)$_{0-1}$(CH$_2$)$_{0-1}$(O)$_{0-1}$phenyl, optionally substituted with 1 to 3 groups selected from halogen, —CN, —CH$_2$CN, —NHC(O)C$_{1-3}$alkyl, —SO$_2$C$_{1-3}$alkyl, —C(O)NR$^c$R$^d$, hydroxyC$_{2-4}$alkoxy, C$_{1-3}$alkoxy, C(O)morphilin-4-yl, —SO$_2$NH(CH$_2$)$_{2-3}$OH, —SO$_2$NR$^c$R$^d$ and C$_{1-3}$alkyl optionally substituted with —OH or —OCH$_3$;
- —(O)$_{0-1}$(CH$_2$)$_{0-2}$heteroaryl selected from indolyl, pyridinyl, pyrazolyl, pyrazinyl, and pyrimidinyl, wherein said heteroaryl is optionally substituted with one to two groups independently selected from C$_{1-3}$alkyl, —OH, C$_{1-3}$alkoxy, hydroxymethyl, —CO$_2$C$_{1-4}$alkyl, —C(O)C$_{1-3}$alkyl and —(CH$_2$)$_{0-2}$morpholin-4-yl;
- —O$_{0-1}$(CH$_2$)$_{0-2}$(O)$_{0-1}$heterocyclyl, wherein the heterocyclyl is selected from 3,6-dihydro-2H-thiopyranyl, 3,6-dihydro-2H-pyranyl, oxetanyl, tetrahydrofuranyl, tetrahydropyranyl, 1,2,3,6-tetrahydropyridinyl, 3,6-dihydro-2H-thiopyranyl-1,1-dioxide, tetrahydrothiopyranyl-1,1-dioxide, piperidinyl, morpholinyl, piperazinyl and pyrrolidinyl;
wherein said heterocyclyl is optionally substituted with a group selected from —C(O)$C_{1-3}$alkyl, —OH, oxo, —$(CH_2)_{1-2}$morpholin-4-yl, —$CO_2C_{1-4}$alkyl and $C_{1-3}$alkyl optionally substituted with —OH or —$OCH_3$;
—C(O)heterocyclyl, wherein the heterocyclyl is selected from morpholin-4-yl, pyrrolidinyl and piperidin-1-yl; and
—$(CH_2)_{0-1}O(CH_2)_{1-2}$heterocyclyl, wherein the heterocyclyl is selected from morpholin-4-yl, pyrrolidinyl and piperidin-1-yl; and
—$C_{3-6}$cycloalkyl, optionally substituted 1 to 3 groups selected from OH—CN, $C_{1-6}$alkyl, $C_{1-3}$alkoxyl, and halogen;
$R^5$ is selected from
—H;
—$C_{1-3}$alkyl;
—$CO_2C_{1-3}$alkyl;
—CN;
—$CF_3$;
-halogen;
—$OC_{1-3}$alkyl;
—$CH_2OC_{1-3}$alkyl;
—$C(O)NH_2$;
—$C_{1-2}$alkyl-OH;
—$CH(OH)C_{1-3}$alkyl;
—$CH_2O$phenyl, wherein the phenyl is optionally substituted with halogen;
-Phenyl, optionally substituted with halogen or $SO_2C_{1-3}$alkyl;
—$CH_2NHR^c$; and
-pyrazolyl, optionally substituted with $C_{1-3}$alkyl;
$R^6$ is H;
$R^7$ is H; and
$R^c$ and $R^d$ are independently selected from
H, $C_{1-6}$alkyl, —$C(O)C_{1-3}$alkyl, —$(CH_2)_{1-3}$OH, —$(CH_2)_{2-3}NHC(O)C_{1-3}$alkyl, —$CH_2$phenyl, and —$SO_2C_{1-2}$alkyl;
or a salt thereof.

4. The compound according to claim 1, wherein:
$R^1$ is —$NH_2$;
X is C;
Y and W are C;
$R^2$ and $R^3$ are H;
$R^4$ is selected from
—H;
—OH;
—$(CH_2)_{0-1}$CN;
—$C_{1-6}$alkyl, optionally substituted with one to four groups independently selected from —F, —OH or —$OCH_3$;
-halogen selected from —F and —Cl;
—$CF_3$;
—$C(O)C_{1-3}$alkyl;
—$C_{0-2}$alkyl-$NHSO_2C_{1-3}$alkyl;
—$(O)_{0-1}(CH_2)_{0-1}(O)_{0-1}C(O)NR^cR^d$;
—$O_{0-1}(CH_2)_{0-2}(O)_{0-1}$heterocyclyl, wherein the heterocyclyl is selected from 3,6-dihydro-2H-thiopyranyl, 3,6-dihydro-2H-pyranyl, oxetanyl, tetrahydrofuranyl, tetrahydropyranyl, 1,2,3,6-tetrahydropyridinyl, 3,6-dihydro-2H-thiopyranyl-1,1-dioxide, tetrahydrothiopyranyl-1,1-dioxide, piperidinyl, morpholinyl, piperazinyl and pyrrolidinyl;
wherein said heterocyclyl is optionally substituted with a group selected from —$C(O)C_{1-3}$alkyl, —OH, oxo, —$(CH_2)_{1-2}$morpholin-4-yl, —$CO_2C_{1-4}$alkyl and $C_{1-3}$alkyl optionally substituted with —OH or —$OCH_3$; and
—$(CH_2)_{0-1}C(O)$heterocyclyl, wherein the heterocyclyl is selected from morpholin-4-yl, pyrrolidinyl and piperidin-1-yl; and
$R^5$ is selected from
—H;
—$C_{1-3}$ alkyl;
—CN;
—$CF_3$;
-halogen;
—$CH(OH)C_{1-3}$alkyl;
-Phenyl, optionally substituted with halogen or $SO_2C_{1-3}$alkyl; and
—$CH_2NHR^c$;
$R^6$ is H;
$R^7$ is selected from —H and —$CH_3$; and
$R^c$ and $R^d$ are independently selected from
H, $C_{1-6}$alkyl, —$C(O)C_{1-3}$alkyl, —$(CH_2)_{1-3}$OH, —$(CH_2)_{2-3}NHC(O)C_{1-3}$alkyl, —$CH_2$phenyl, and —$SO_2C_{1-2}$alkyl;
m is 0; and
n is 1;
or a salt thereof.

5. The compound according to claim 1, wherein:
$R^4$ is H;
$R^6$ is H; and
$R^7$ is H;
or a salt thereof.

6. The compound according to claim 1, wherein:
$R^5$ is H;
$R^6$ is H; and
$R^7$ is H;
or a salt thereof.

7. The compound according to claim 1, wherein:
n is 1;
$R^6$ is H; and
$R^7$ is H;
or a salt thereof.

8. The compound according to claim 1, wherein:
m=0;
$R^6$ is H; and
$R^7$ is H;
or a salt thereof.

9. The compound according to claim 1, wherein:
W and Y are C;
$R^6$ is H; and
$R^7$ is H;
or a salt thereof.

10. The compound according to claim 1, wherein:
X is C;
$R^6$ is H; and
$R^7$ is H;
or a salt thereof.

11. The compound according to claim 1, wherein:
$R^1$ is —$NH_2$;
$R^6$ is H; and
$R^7$ is H;
or a salt thereof.

12. The compound according to claim 1, wherein:
$R^6$ is selected from H, —Cl, —F, and —$CH_3$; and
$R^7$ is selected from H, —$CH_3$ and —CN,
wherein at least one of $R^6$ or $R^7$ is H;
or a salt thereof.

13. The compound according to claim 1, wherein
R$^1$ is —NH$_2$;
X is C;
Y and W are C;
R$^2$ and R$^3$ are H;
R$^6$ is selected from H, —Cl, —F, and —CH$_3$;
R$^7$ is selected from H, —CH$_3$ and —CN,
wherein at least one of R$^6$ or R$^7$ is H;
m is 0; and
n is 1;
or a salt thereof.
14. The compound according to claim 1 selected from the group consisting of
| Cpd No | STRUCTURE |
|---|---|
| 1 | |
| 2 | |
| 3 | |
| 4 | |
| 5 | |
| 6 | 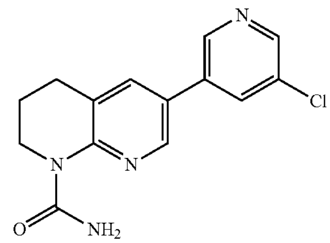 [SMILES: NC(=O)N1CCCc2cc(-c3cncc(Cl)c3)cnc21] |
| 7 | 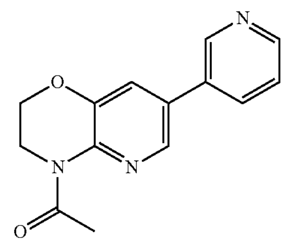 [SMILES: CC(=O)N1CCOc2cc(-c3cccnc3)cnc21] |
| 8 | 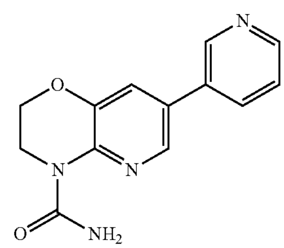 [SMILES: NC(=O)N1CCOc2cc(-c3cccnc3)cnc21] |
| 9 | 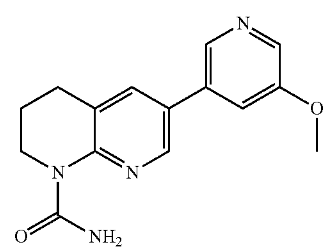 [SMILES: COc1cncc(-c2cnc3c(c2)CCCN3C(N)=O)c1] |
| 10 | 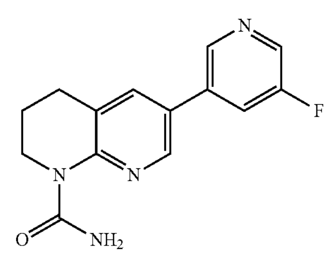 [SMILES: NC(=O)N1CCCc2cc(-c3cncc(F)c3)cnc21] |
| 11 | 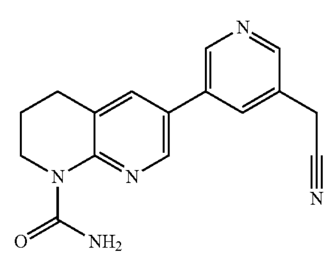 [SMILES: N#CCc1cncc(-c2cnc3c(c2)CCCN3C(N)=O)c1] |
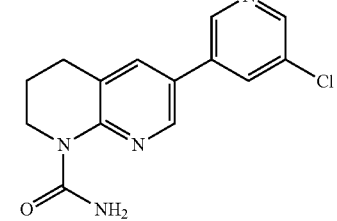
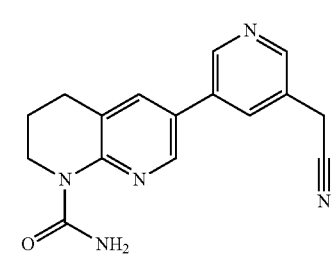

-continued

| Cpd No | STRUCTURE |
|---|---|
| 12 | (5,6,7,8-tetrahydro-1,8-naphthyridin-3-yl linked to 5-(methylsulfonyl)pyridin-3-yl; N8-carboxamide) |
| 13 | (5,6,7,8-tetrahydro-1,8-naphthyridin-3-yl linked to pyrimidin-5-yl; N8-carboxamide) |
| 14 | (5,6,7,8-tetrahydro-1,8-naphthyridin-3-yl linked to 5-phenylpyridin-3-yl; N8-carboxamide) |
| 15 | (5,6,7,8-tetrahydro-1,8-naphthyridin-3-yl linked to 5-(trifluoromethyl)pyridin-3-yl; N8-carboxamide) |
| 16 | (5,6,7,8-tetrahydro-1,8-naphthyridin-3-yl linked to 5-(methoxymethyl)pyridin-3-yl; N8-carboxamide) |
| 17 | (5,6,7,8-tetrahydro-1,8-naphthyridin-3-yl linked to 5-fluoropyridin-3-yl; N8-acetyl) |

-continued

| Cpd No | STRUCTURE |
|---|---|
| 18 | (5,6,7,8-tetrahydro-1,8-naphthyridin-3-yl linked to 5-acetylpyridin-3-yl; N8-carboxamide) |
| 19 | (5,6,7,8-tetrahydro-1,8-naphthyridin-3-yl linked to 5-(1-hydroxyethyl)pyridin-3-yl; N8-carboxamide) |
| 20 | (5,6,7,8-tetrahydro-1,8-naphthyridin-3-yl linked to 5-methylpyridin-3-yl; N8-carboxamide) |
| 21 | (5,6,7,8-tetrahydro-1,8-naphthyridin-3-yl linked to 5-carboxypyridin-3-yl; N8-carboxamide) |
| 22 | (5,6,7,8-tetrahydro-1,8-naphthyridin-3-yl linked to 4-cyanopyridin-3-yl; N8-carboxamide) |
| 23 | (5,6,7,8-tetrahydro-1,8-naphthyridin-3-yl linked to 5-(methoxycarbonyl)pyridin-3-yl; N8-carboxamide) |

303
-continued
| Cpd No | STRUCTURE |
|---|---|
| 24 | 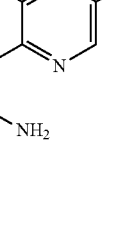 |
| 25 | 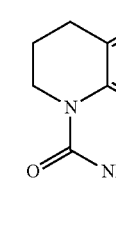 |
| 26 | 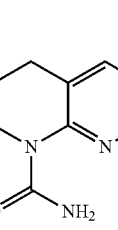 |
| 27 | 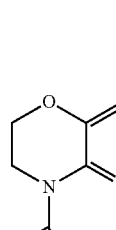 |
| 28 | 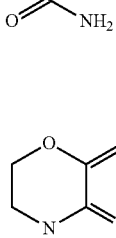 |
| 29 | 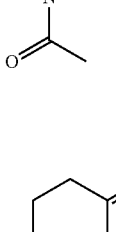 |
304
-continued
| Cpd No | STRUCTURE |
|---|---|
| 30 | |
| 31 | |
| 32 | |
| 33 | |
| 34 | |
| 35 | |

-continued
| Cpd No | STRUCTURE |
|---|---|
| 36 | 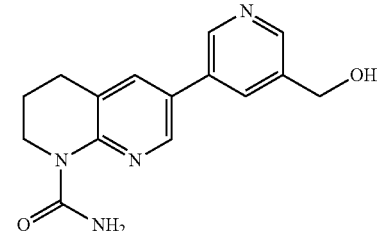 |
| 37 | 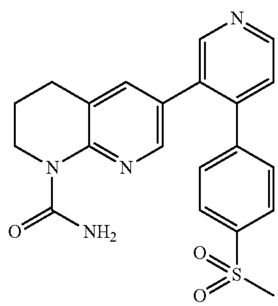 [SMILES: CS(=O)(=O)c1ccc(-c2ccncc2-c2cnc3c(c2)CCCN3C(N)=O)cc1] |
| 38 | 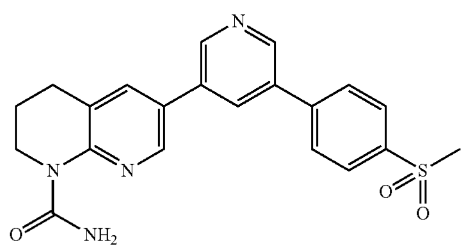 [SMILES: CS(=O)(=O)c1ccc(-c2cncc(-c3cnc4c(c3)CCCN4C(N)=O)c2)cc1] |
| 39 | 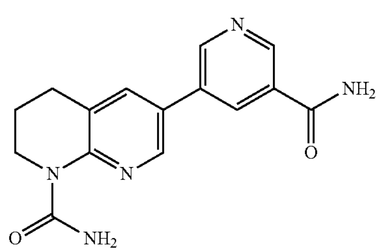 [SMILES: NC(=O)c1cncc(-c2cnc3c(c2)CCCN3C(N)=O)c1] |
| 40 | 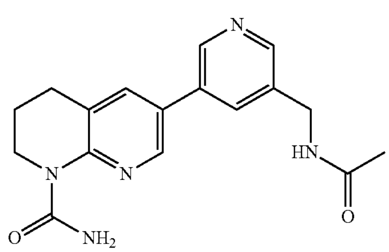 [SMILES: CC(=O)NCc1cncc(-c2cnc3c(c2)CCCN3C(N)=O)c1] |
| 41 | 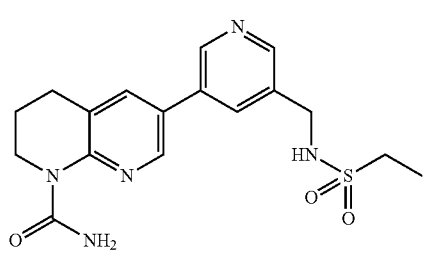 [SMILES: CCS(=O)(=O)NCc1cncc(-c2cnc3c(c2)CCCN3C(N)=O)c1] |
-continued
| Cpd No | STRUCTURE |
|---|---|
| 42 | 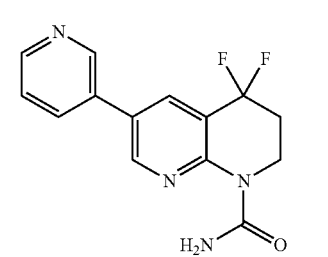 |
| 43 | 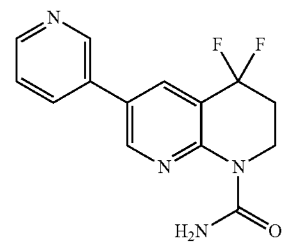 [SMILES: NC(=O)N1CCC(F)(F)c2cc(-c3cccnc3)cnc21] |
| 44 | 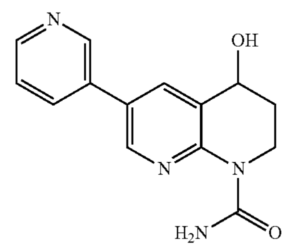 [SMILES: NC(=O)N1CCC(O)c2cc(-c3cccnc3)cnc21] |
| 45 | 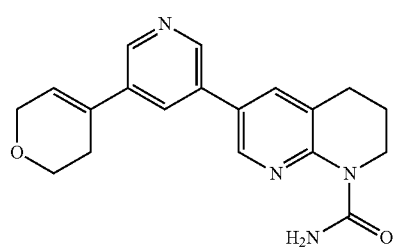 |
| 46 | 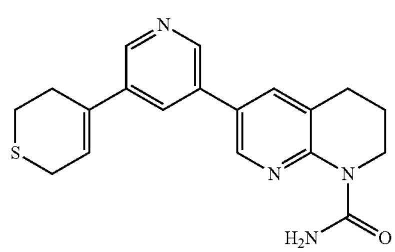 [SMILES: NC(=O)N1CCCc2cc(-c3cncc(C4=CCSCC4)c3)cnc21] |
| 47 | 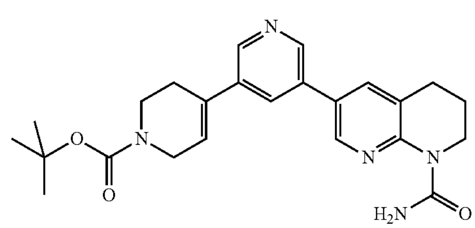 [SMILES: CC(C)(C)OC(=O)N1CC=C(c2cncc(-c3cnc4c(c3)CCCN4C(N)=O)c2)CC1] |

| Cpd No | STRUCTURE |
|---|---|
| 48 | 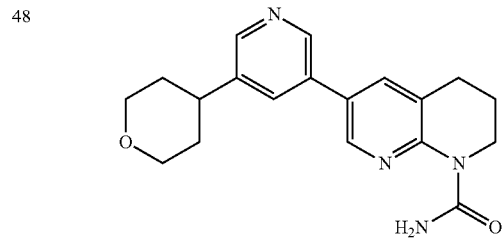 |
| 49 | 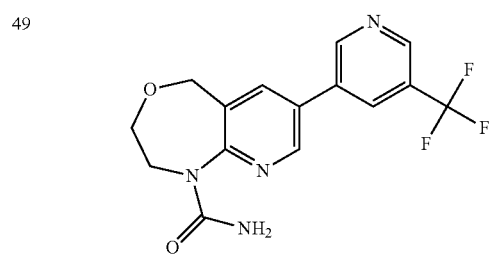 |
| 50 | 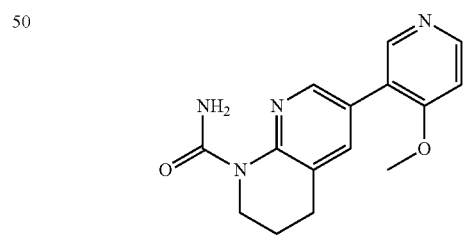 |
| 51 | 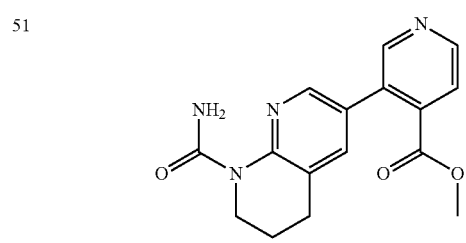 |
| 52 | 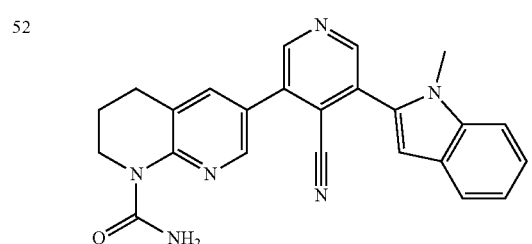 |
| 53 | 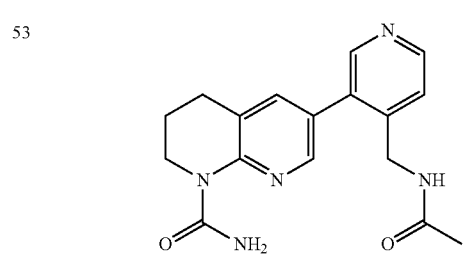 |
| Cpd No | STRUCTURE |
|---|---|
| 54 | 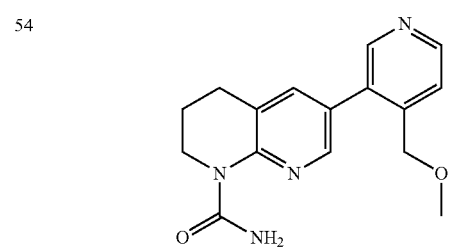 |
| 55 | 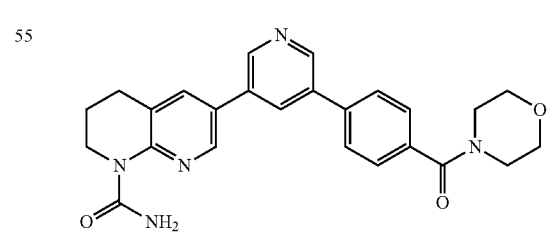 |
| 56 | 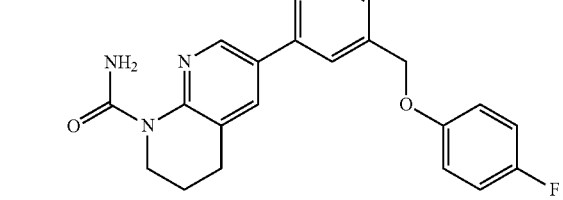 |
| 57 | 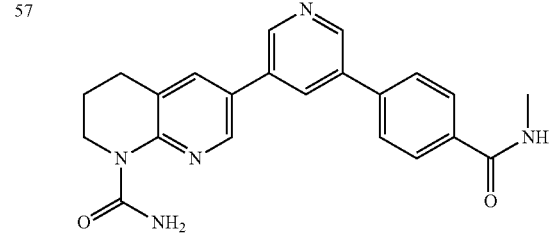 |
| 58 | 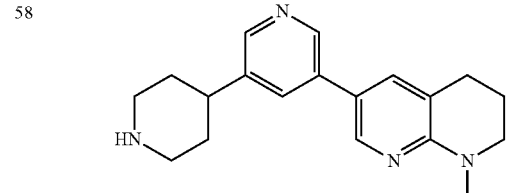 |
| 59 | 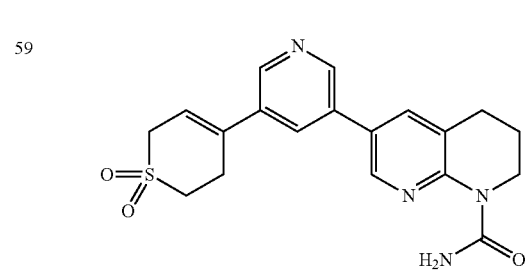 |

309
-continued
| Cpd No | STRUCTURE |
|---|---|
| 60 | 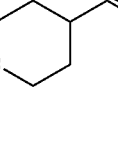 |
| 61 | 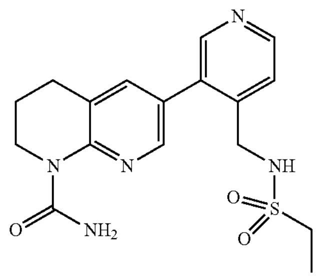 [SMILES: CCS(=O)(=O)NCc1ccncc1-c1cnc2c(c1)CCCN2C(N)=O] |
| 62 | 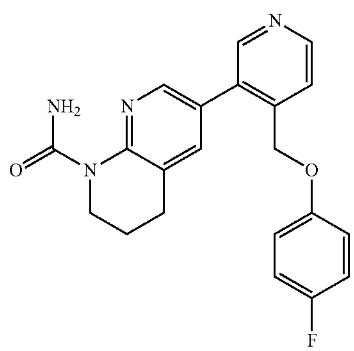 [SMILES: NC(=O)N1CCCc2cc(-c3cnccc3COc3ccc(F)cc3)cnc21] |
| 63 | 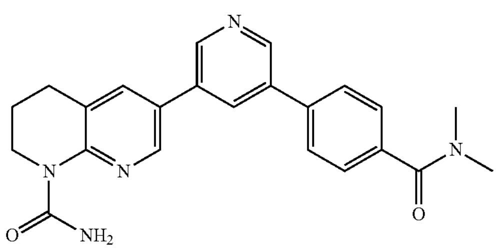 [SMILES: CN(C)C(=O)c1ccc(-c2cncc(-c3cnc4c(c3)CCCN4C(N)=O)c2)cc1] |
| 64 | 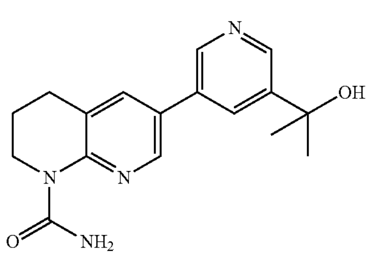 |
310
-continued
| Cpd No | STRUCTURE |
|---|---|
| 65 | 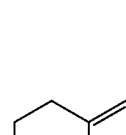 |
| 66 | 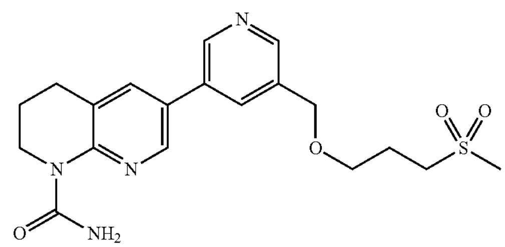 [SMILES: CS(=O)(=O)CCCOCc1cncc(-c2cnc3c(c2)CCCN3C(N)=O)c1] |
| 67 | 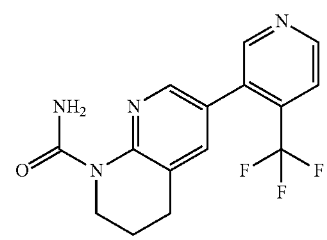 [SMILES: NC(=O)N1CCCc2cc(-c3cnccc3C(F)(F)F)cnc21] |
| 68 | 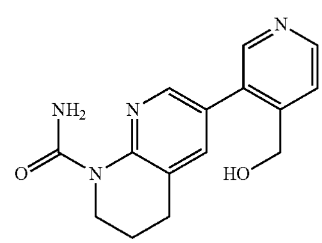 [SMILES: NC(=O)N1CCCc2cc(-c3cnccc3CO)cnc21] |
| 69 | 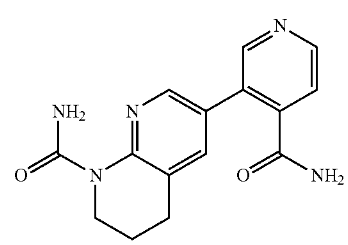 [SMILES: NC(=O)c1ccncc1-c1cnc2c(c1)CCCN2C(N)=O] |
| 70 | 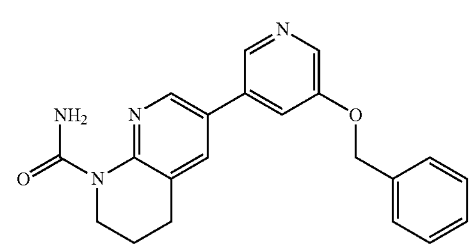 [SMILES: NC(=O)N1CCCc2cc(-c3cncc(OCc4ccccc4)c3)cnc21] |

311
-continued

| Cpd No | STRUCTURE |
|---|---|
| 71 | 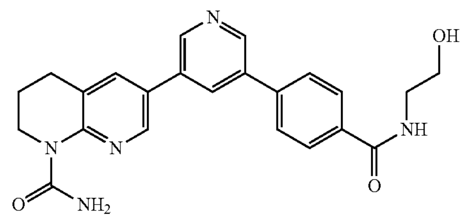 [SMILES: NC(=O)N1CCCc2cc(-c3cncc(-c4ccc(C(=O)NCCO)cc4)c3)cnc21] |
| 72 | 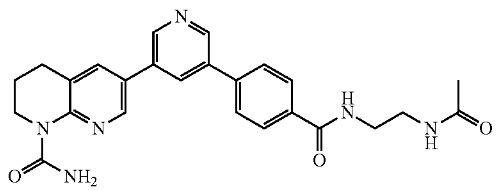 [SMILES: CC(=O)NCCNC(=O)c1ccc(-c2cncc(-c3cnc4c(c3)CCCN4C(N)=O)c2)cc1] |
| 73 | 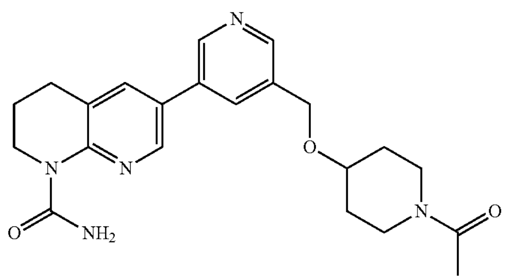 [SMILES: CC(=O)N1CCC(OCc2cncc(-c3cnc4c(c3)CCCN4C(N)=O)c2)CC1] |
| 74 | 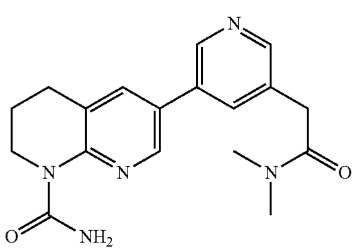 [SMILES: CN(C)C(=O)Cc1cncc(-c2cnc3c(c2)CCCN3C(N)=O)c1] |
| 75 | 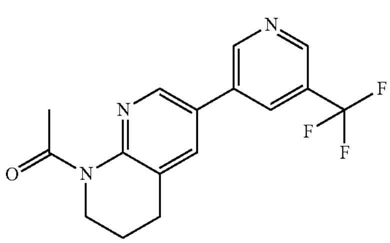 [SMILES: CC(=O)N1CCCc2cc(-c3cncc(C(F)(F)F)c3)cnc21] |
| 76 | 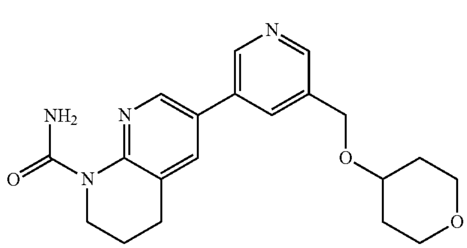 |

312
-continued

| Cpd No | STRUCTURE |
|---|---|
| 77 | 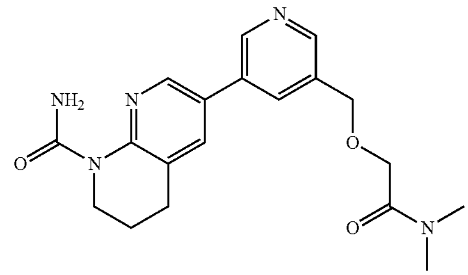 [SMILES: CN(C)C(=O)COCc1cncc(-c2cnc3c(c2)CCCN3C(N)=O)c1] |
| 78 | 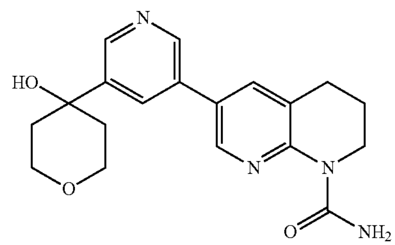 [SMILES: NC(=O)N1CCCc2cc(-c3cncc(C4(O)CCOCC4)c3)cnc21] |
| 79 | 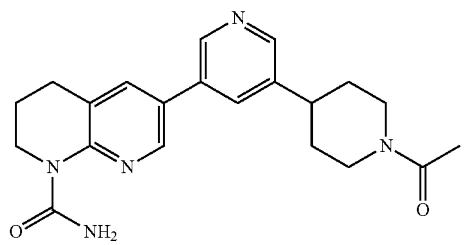 [SMILES: CC(=O)N1CCC(c2cncc(-c3cnc4c(c3)CCCN4C(N)=O)c2)CC1] |
| 80 | 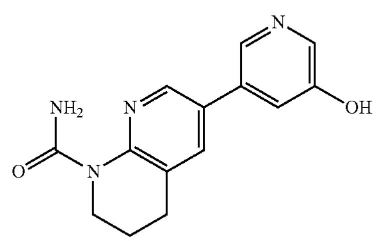 [SMILES: NC(=O)N1CCCc2cc(-c3cncc(O)c3)cnc21] |
| 81 | 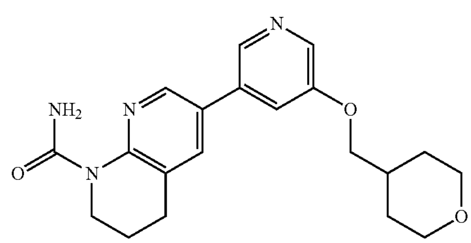 [SMILES: NC(=O)N1CCCc2cc(-c3cncc(OCC4CCOCC4)c3)cnc21] |
| 82 | 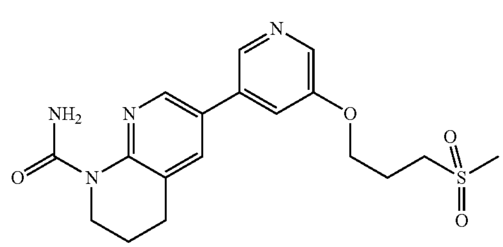 [SMILES: CS(=O)(=O)CCCOc1cncc(-c2cnc3c(c2)CCCN3C(N)=O)c1] |

-continued

| Cpd No | STRUCTURE |
|---|---|
| 83 | 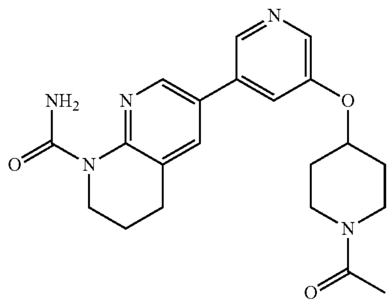 [SMILES: CC(=O)N1CCC(Oc2cncc(-c3cnc4c(c3)CCCN4C(N)=O)c2)CC1] |
| 84 | 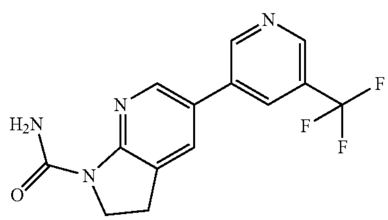 [SMILES: NC(=O)N1CCc2cc(-c3cncc(C(F)(F)F)c3)cnc21] |
| 85 | 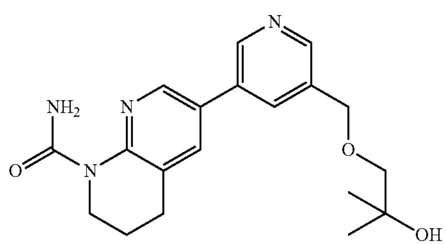 [SMILES: CC(C)(O)COCc1cncc(-c2cnc3c(c2)CCCN3C(N)=O)c1] |
| 86 | 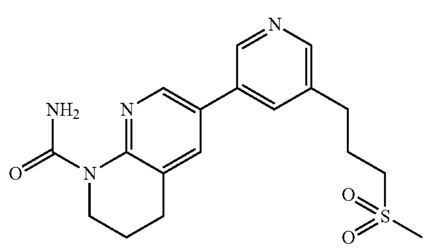 [SMILES: CS(=O)(=O)CCCc1cncc(-c2cnc3c(c2)CCCN3C(N)=O)c1] |
| 87 | 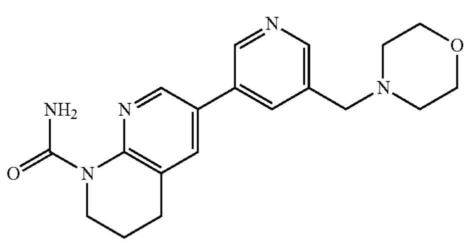 [SMILES: NC(=O)N1CCCc2cc(-c3cncc(CN4CCOCC4)c3)cnc21] |
| 88 | 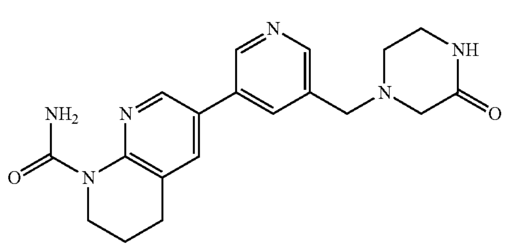 [SMILES: NC(=O)N1CCCc2cc(-c3cncc(CN4CCNC(=O)C4)c3)cnc21] |

-continued

| Cpd No | STRUCTURE |
|---|---|
| 89 | 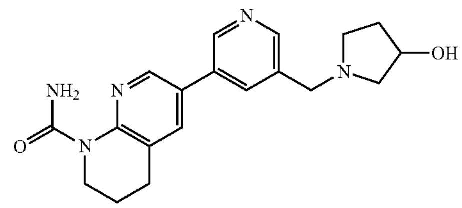 [SMILES: NC(=O)N1CCCc2cc(-c3cncc(CN4CCC(O)C4)c3)cnc21] |
| 90 | 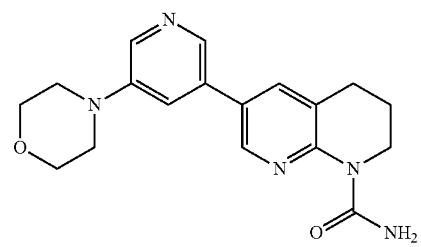 [SMILES: NC(=O)N1CCCc2cc(-c3cncc(N4CCOCC4)c3)cnc21] |
| 91 | 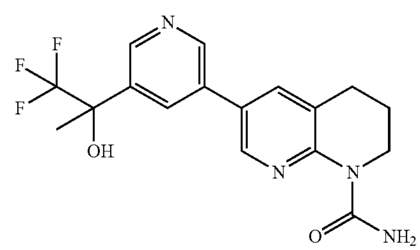 [SMILES: CC(O)(c1cncc(-c2cnc3c(c2)CCCN3C(N)=O)c1)C(F)(F)F] |
| 92 | 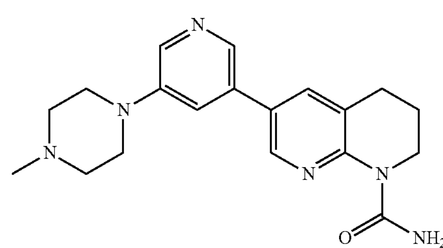 |
| 93 | 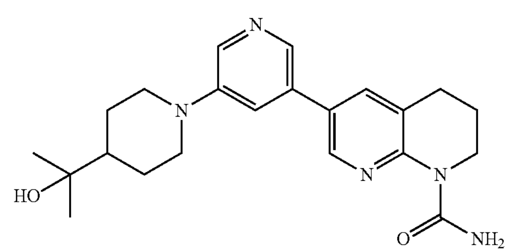 [SMILES: CC(C)(O)C1CCN(c2cncc(-c3cnc4c(c3)CCCN4C(N)=O)c2)CC1] |
| 94 | 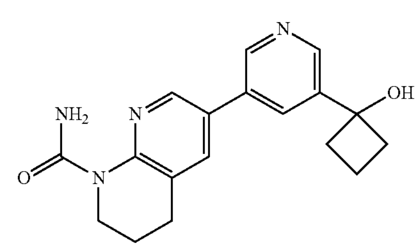 [SMILES: NC(=O)N1CCCc2cc(-c3cncc(C4(O)CCC4)c3)cnc21] |

| Cpd No | STRUCTURE |
|---|---|
| 95 | 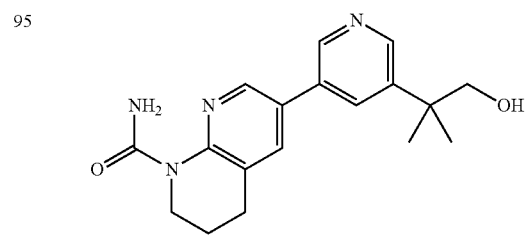 |
| 96 | 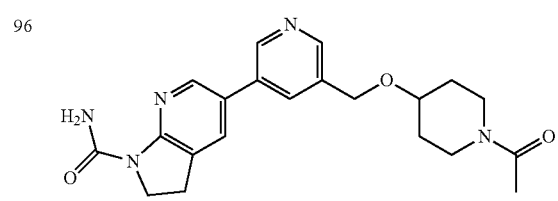 |
| 97 | 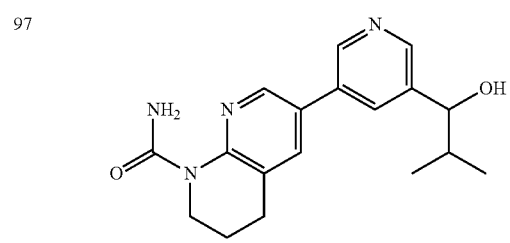 |
| 98 | 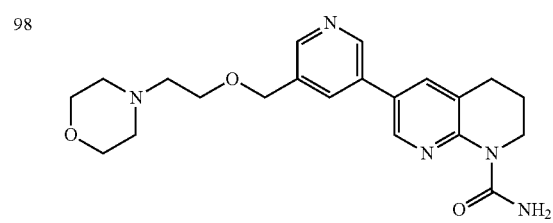 |
| 99 | 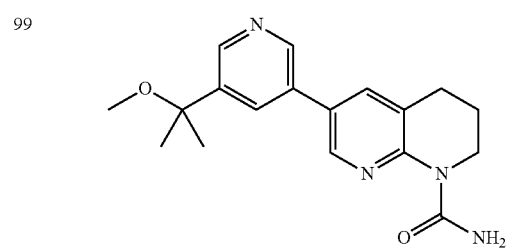 |
| 100 | 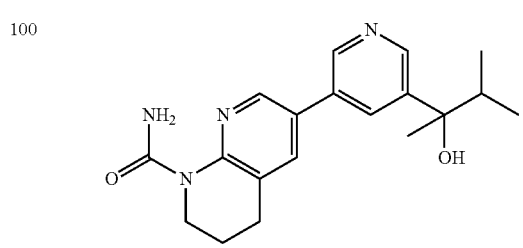 |
| Cpd No | STRUCTURE |
|---|---|
| 101 | 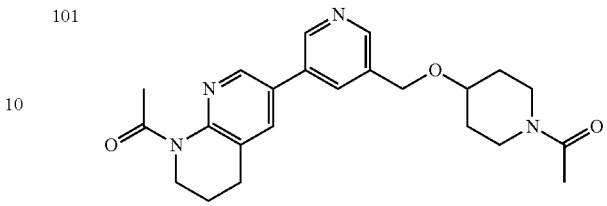 |
| 102 | 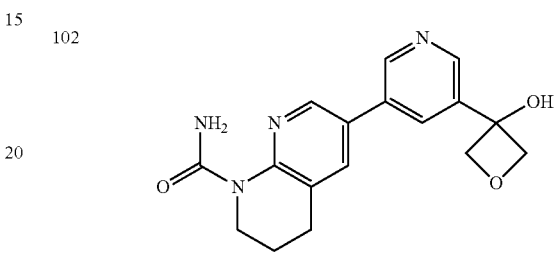 |
| 103 | 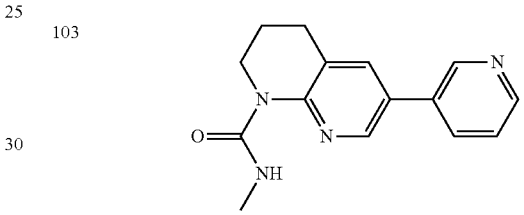 |
| 104 | 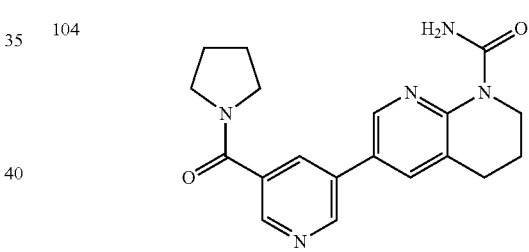 |
| 105 | 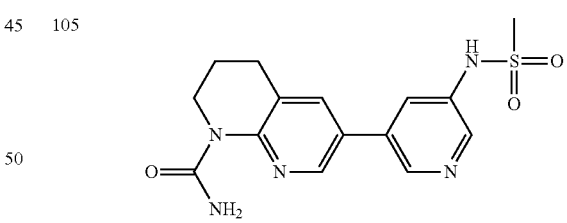 |
| 106 | 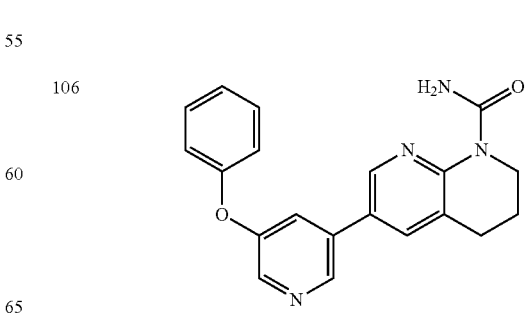 |

| Cpd No | STRUCTURE |
|---|---|
| 107 | (structure) |
| 108 | (structure) |
| 109 | (structure) |
| 110 | (structure) |
| 111 | (structure) |
| 112 | (structure) |

| Cpd No | STRUCTURE |
|---|---|
| 113 | (structure) |
| 114 | (structure) |
| 115 | (structure) |
| 116 | (structure) |
| 117 | (structure) |
| 118 | (structure) |

| Cpd No | STRUCTURE |
|---|---|
| 119 | 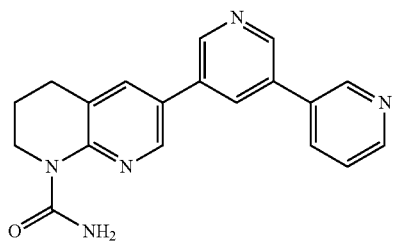 [SMILES: NC(=O)N1CCCc2cc(-c3cncc(-c4cccnc4)c3)cnc21] |
| 120 | 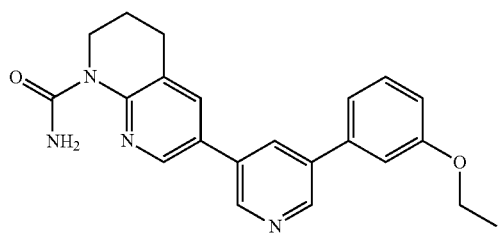 [SMILES: CCOc1cccc(-c2cncc(-c3cnc4c(c3)CCCN4C(N)=O)c2)c1] |
| 121 | 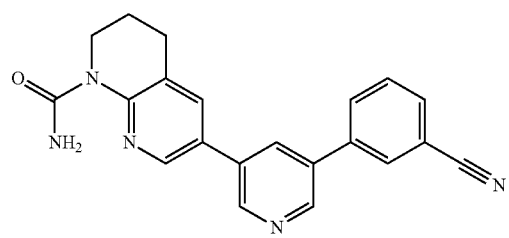 [SMILES: N#Cc1cccc(-c2cncc(-c3cnc4c(c3)CCCN4C(N)=O)c2)c1] |
| 122 | 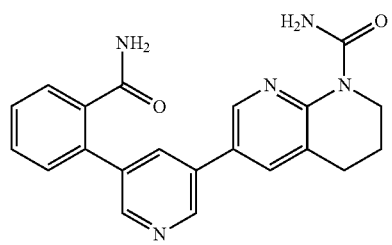 |
| 123 | 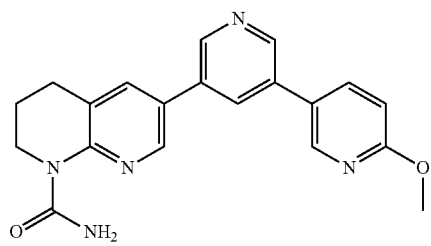 [SMILES: COc1ccc(-c2cncc(-c3cnc4c(c3)CCCN4C(N)=O)c2)cn1] |
| 124 | 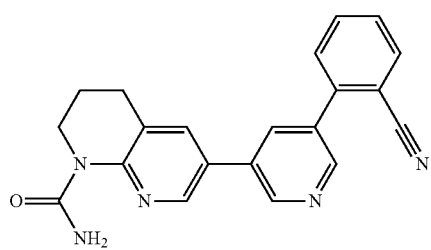 [SMILES: N#Cc1ccccc1-c1cncc(-c2cnc3c(c2)CCCN3C(N)=O)c1] |
| Cpd No | STRUCTURE |
|---|---|
| 125 | 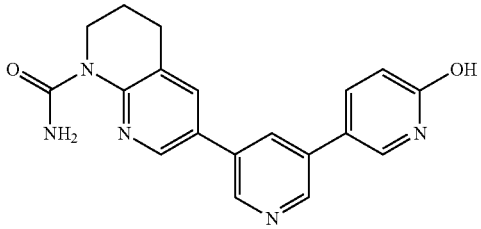 [SMILES: NC(=O)N1CCCc2cc(-c3cncc(-c4ccc(O)nc4)c3)cnc21] |
| 126 | 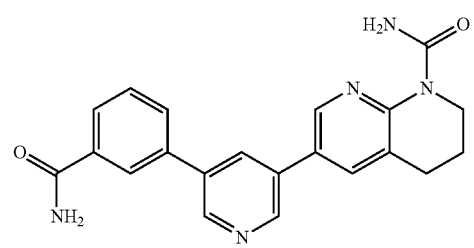 [SMILES: NC(=O)c1cccc(-c2cncc(-c3cnc4c(c3)CCCN4C(N)=O)c2)c1] |
| 127 | 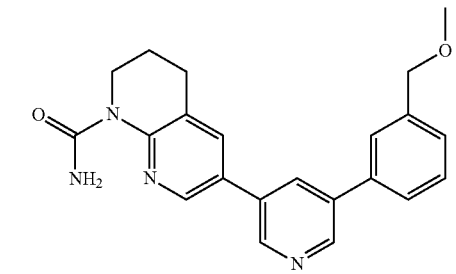 [SMILES: COCc1cccc(-c2cncc(-c3cnc4c(c3)CCCN4C(N)=O)c2)c1] |
| 128 | 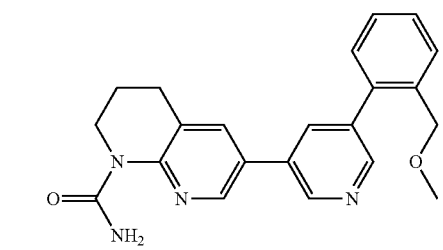 [SMILES: COCc1ccccc1-c1cncc(-c2cnc3c(c2)CCCN3C(N)=O)c1] |
| 129 | 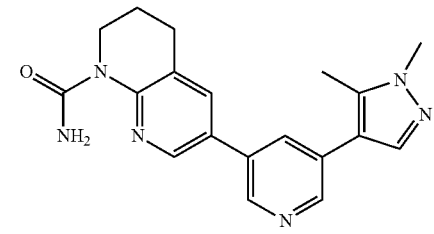 [SMILES: Cc1c(-c2cncc(-c3cnc4c(c3)CCCN4C(N)=O)c2)cnn1C] |
| 130 | 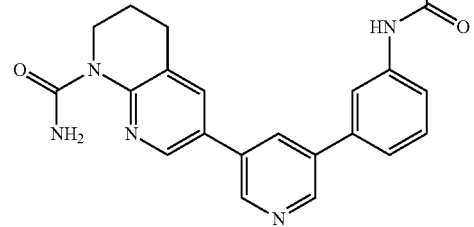 |

321
-continued

| Cpd No | STRUCTURE |
|---|---|
| 131 | 5-(5-(4-sulfamoylphenyl)pyridin-3-yl)-3,4-dihydro-1,8-naphthyridine-1(2H)-carboxamide |
| 132 | 6-(6'-(hydroxymethyl)-[3,3'-bipyridin]-5-yl)-3,4-dihydro-1,8-naphthyridine-1(2H)-carboxamide |
| 133 | 6-(5-(1-(2-morpholinoethyl)-1H-pyrazol-4-yl)pyridin-3-yl)-3,4-dihydro-1,8-naphthyridine-1(2H)-carboxamide |
| 134 | 6-(5-(3-(N-methylsulfamoyl)phenyl)pyridin-3-yl)-3,4-dihydro-1,8-naphthyridine-1(2H)-carboxamide |
| 135 | 6-(6'-methyl-[3,3'-bipyridin]-5-yl)-3,4-dihydro-1,8-naphthyridine-1(2H)-carboxamide |
| 136 | 6-(5-(3-(cyanomethyl)phenyl)pyridin-3-yl)-3,4-dihydro-1,8-naphthyridine-1(2H)-carboxamide |

322
-continued

| Cpd No | STRUCTURE |
|---|---|
| 137 | 6-(6'-methyl-[3,4'-bipyridin]-5-yl)-3,4-dihydro-1,8-naphthyridine-1(2H)-carboxamide |
| 138 | 6-(5-(pyrimidin-5-yl)pyridin-3-yl)-3,4-dihydro-1,8-naphthyridine-1(2H)-carboxamide |
| 139 | 6-(5-(4-ethoxyphenyl)pyridin-3-yl)-3,4-dihydro-1,8-naphthyridine-1(2H)-carboxamide |
| 140 | 6-(5-(4-(hydroxymethyl)phenyl)pyridin-3-yl)-3,4-dihydro-1,8-naphthyridine-1(2H)-carboxamide |
| 141 | 6-(5-(3-(hydroxymethyl)phenyl)pyridin-3-yl)-3,4-dihydro-1,8-naphthyridine-1(2H)-carboxamide |
| 142 | 6-(5-(4-(cyanomethyl)phenyl)pyridin-3-yl)-3,4-dihydro-1,8-naphthyridine-1(2H)-carboxamide |

| Cpd No | STRUCTURE |
|---|---|
| 143 | 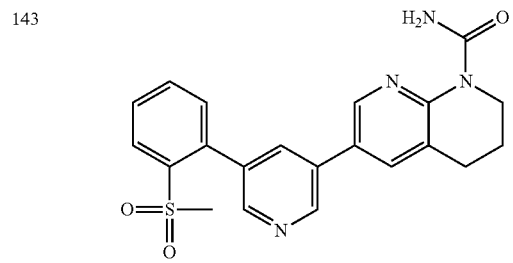 |
| 144 | 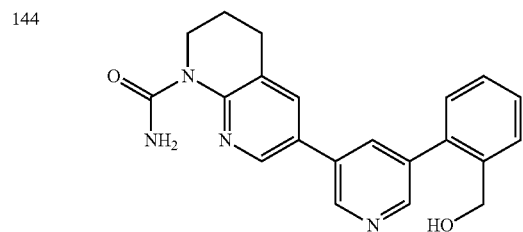 |
| 145 | 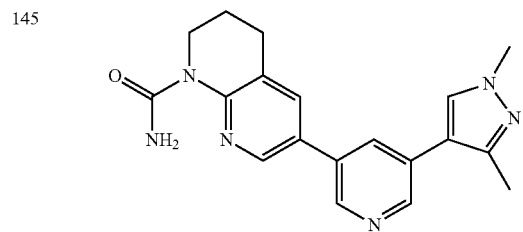 |
| 146 | 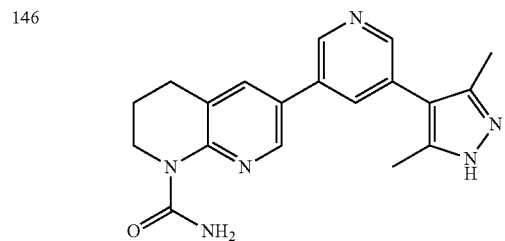 |
| 147 | 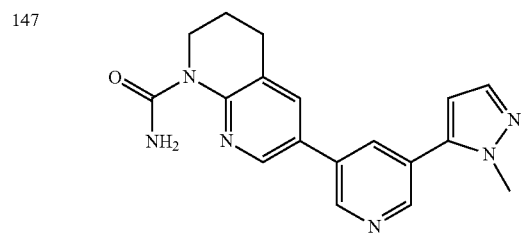 |
| 148 | 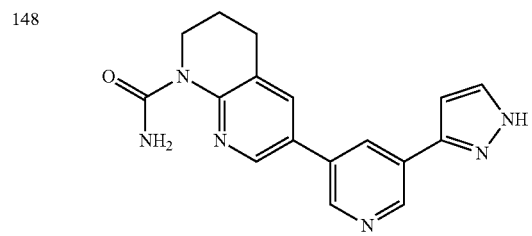 |
| Cpd No | STRUCTURE |
|---|---|
| 149 | 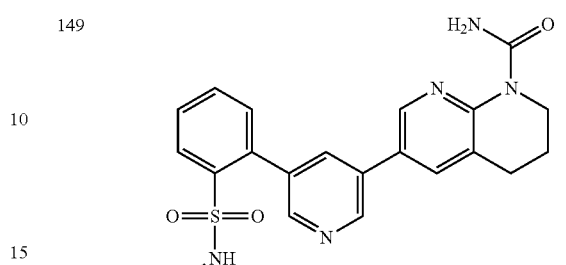 |
| 150 | 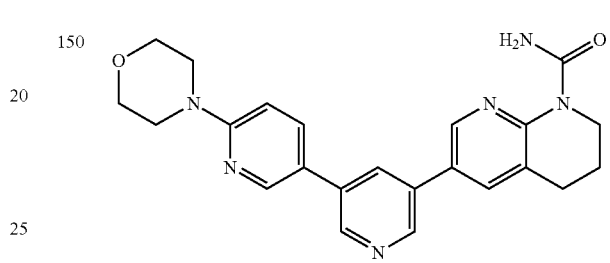 |
| 151 | 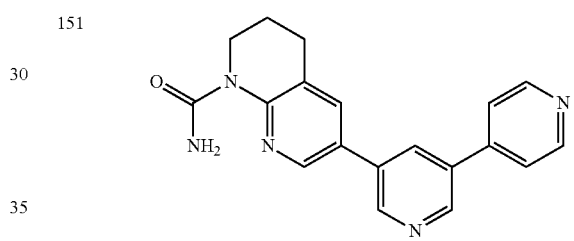 |
| 152 | 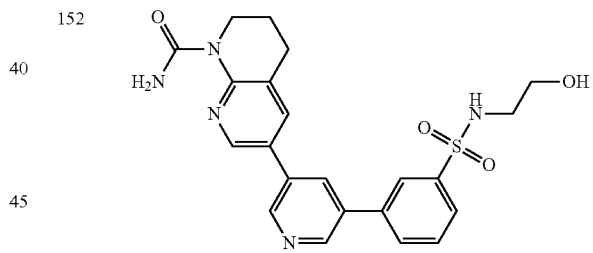 |
| 153 | 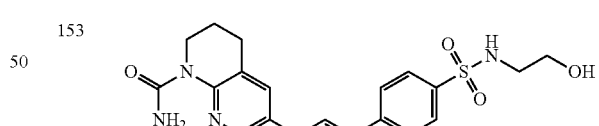 |
| 154 | 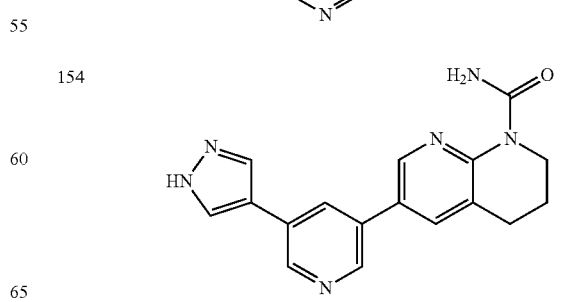 |

325
-continued
| Cpd No | STRUCTURE |
|---|---|
| 155 | 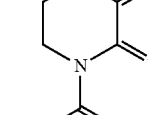 |
| 156 | 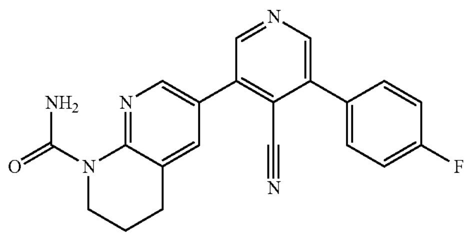 [SMILES: N#Cc1c(-c2ccc(F)cc2)cncc1-c1cnc2c(c1)CCCN2C(N)=O] |
| 157 | 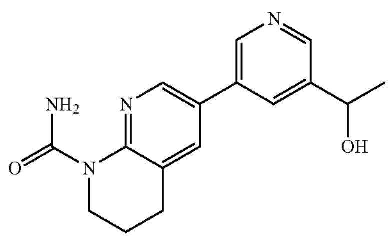 [SMILES: CC(O)c1cncc(-c2cnc3c(c2)CCCN3C(N)=O)c1] |
| 158 | 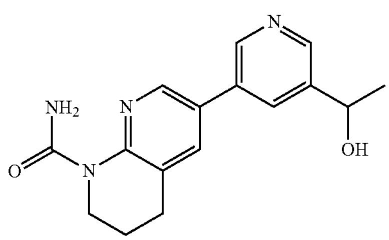 [SMILES: CC(O)c1cncc(-c2cnc3c(c2)CCCN3C(N)=O)c1] |
| 159 | 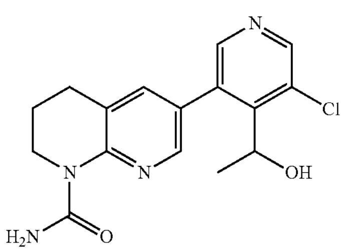 [SMILES: CC(O)c1c(Cl)cncc1-c1cnc2c(c1)CCCN2C(N)=O] |
| 160 | 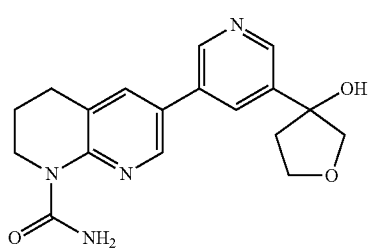 [SMILES: NC(=O)N1CCCc2cc(-c3cncc(C4(O)CCOC4)c3)cnc21] |
326
-continued
| Cpd No | STRUCTURE |
|---|---|
| 161 | 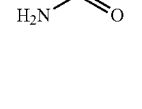 |
| 162 | 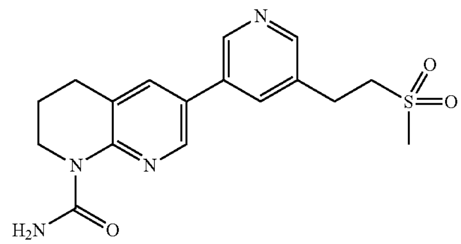 [SMILES: CS(=O)(=O)CCc1cncc(-c2cnc3c(c2)CCCN3C(N)=O)c1] |
| 163 | 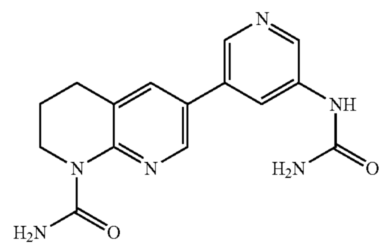 [SMILES: NC(=O)Nc1cncc(-c2cnc3c(c2)CCCN3C(N)=O)c1] |
| 164 | 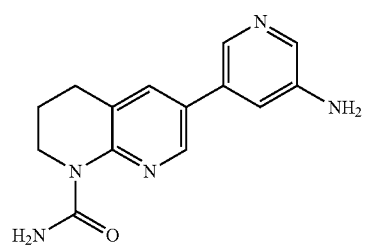 [SMILES: NC(=O)N1CCCc2cc(-c3cncc(N)c3)cnc21] |
| 165 | 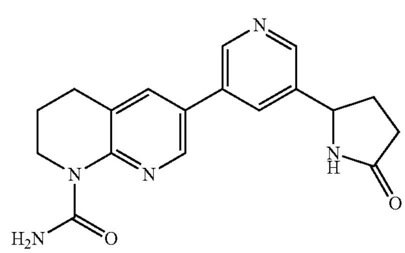 [SMILES: NC(=O)N1CCCc2cc(-c3cncc(C4CCC(=O)N4)c3)cnc21] |
| 166 | 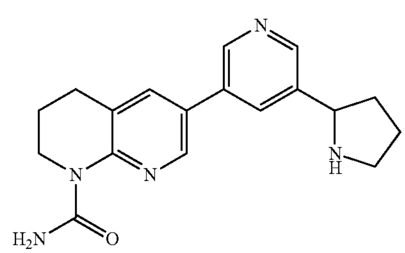 [SMILES: NC(=O)N1CCCc2cc(-c3cncc(C4CCCN4)c3)cnc21] |

| Cpd No | STRUCTURE |
|---|---|
| 167 | 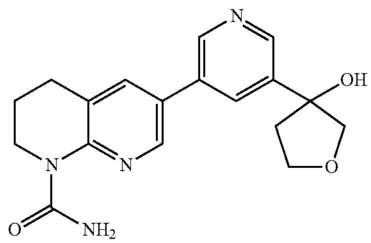 [SMILES: NC(=O)N1CCCc2cc(-c3cncc(C4(O)CCOC4)c3)cnc21] |
| 168 | 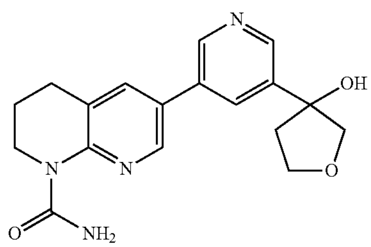 [SMILES: NC(=O)N1CCCc2cc(-c3cncc(C4(O)CCOC4)c3)cnc21] |
| 169 | 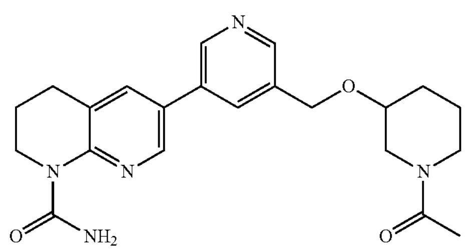 [SMILES: CC(=O)N1CCCC(OCc2cncc(-c3cnc4c(c3)CCCN4C(N)=O)c2)C1] |
| 170 | 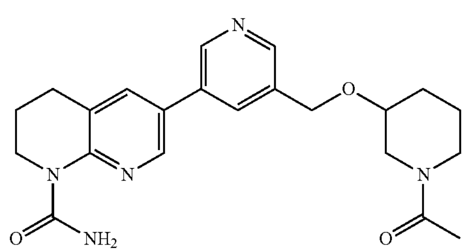 [SMILES: CC(=O)N1CCCC(OCc2cncc(-c3cnc4c(c3)CCCN4C(N)=O)c2)C1] |
| 171 | 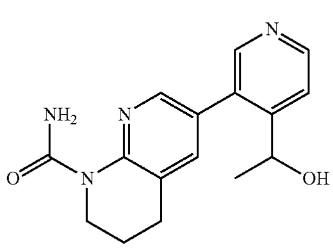 |
| 172 | 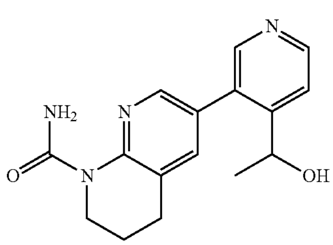 |

| Cpd No | STRUCTURE |
|---|---|
| 173 | 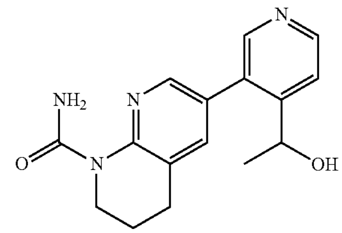 [SMILES: CC(O)c1ccncc1-c1cnc2c(c1)CCCN2C(N)=O] |
| 174 | 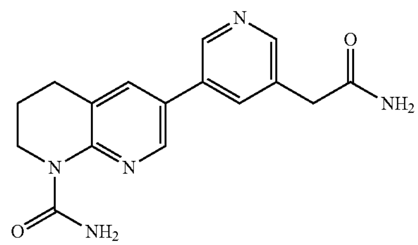 [SMILES: NC(=O)Cc1cncc(-c2cnc3c(c2)CCCN3C(N)=O)c1] |
| 175 | 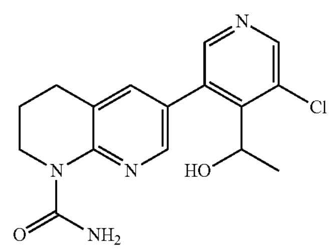 [SMILES: CC(O)c1c(Cl)cncc1-c1cnc2c(c1)CCCN2C(N)=O] |
| 176 | 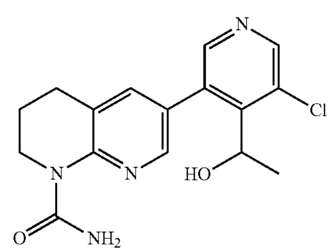 [SMILES: CC(O)c1c(Cl)cncc1-c1cnc2c(c1)CCCN2C(N)=O] |
| 177 | 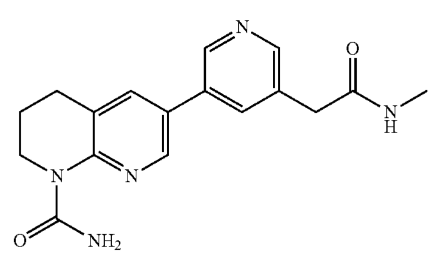 [SMILES: CNC(=O)Cc1cncc(-c2cnc3c(c2)CCCN3C(N)=O)c1] |
| 178 | 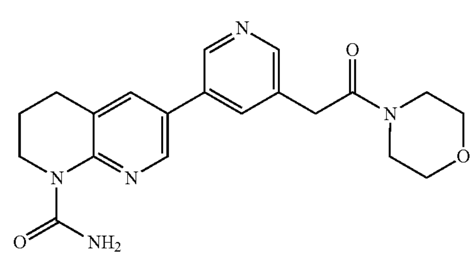 [SMILES: NC(=O)N1CCCc2cc(-c3cncc(CC(=O)N4CCOCC4)c3)cnc21] |

329
-continued
| Cpd No | STRUCTURE |
|---|---|
| 179 | 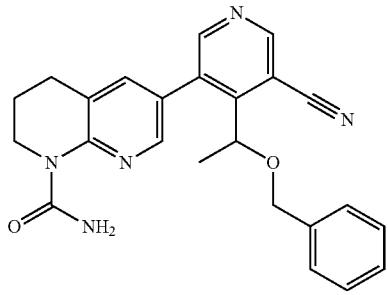 [SMILES: CC(OCc1ccccc1)c1c(C#N)cncc1-c1cnc2c(c1)CCCN2C(N)=O] |
| 180 | 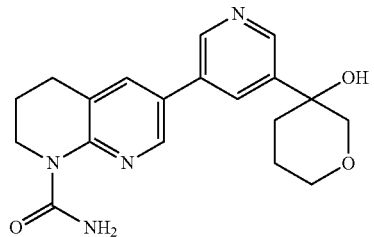 [SMILES: NC(=O)N1CCCc2cc(-c3cncc(C4(O)CCCOC4)c3)cnc21] |
| 181 | 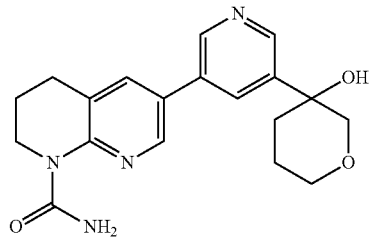 [SMILES: NC(=O)N1CCCc2cc(-c3cncc(C4(O)CCCOC4)c3)cnc21] |
| 182 | 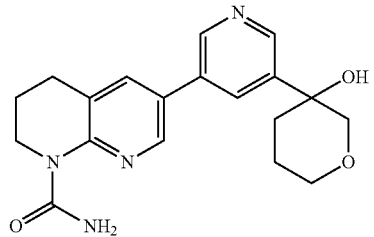 [SMILES: NC(=O)N1CCCc2cc(-c3cncc(C4(O)CCCOC4)c3)cnc21] |
| 183 | 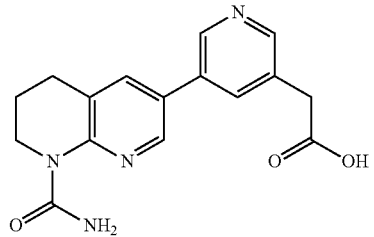 [SMILES: NC(=O)N1CCCc2cc(-c3cncc(CC(=O)O)c3)cnc21] |
| 184 | 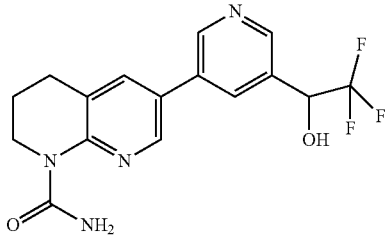 |
330
-continued
| Cpd No | STRUCTURE |
|---|---|
| 185 | 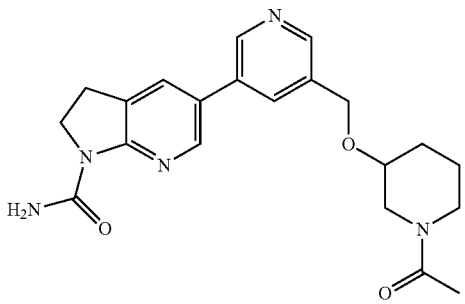 [SMILES: CC(=O)N1CCCC(OCc2cncc(-c3cnc4c(c3)CCN4C(N)=O)c2)C1] |
| 186 | 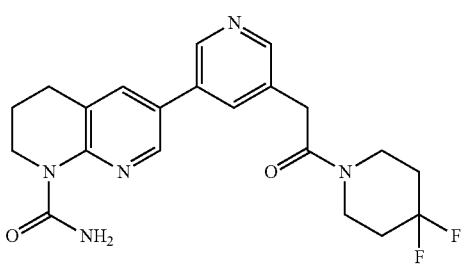 [SMILES: NC(=O)N1CCCc2cc(-c3cncc(CC(=O)N4CCC(F)(F)CC4)c3)cnc21] |
| 187 | 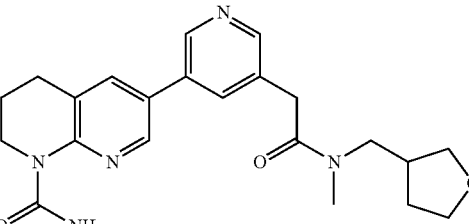 |
| 188 | 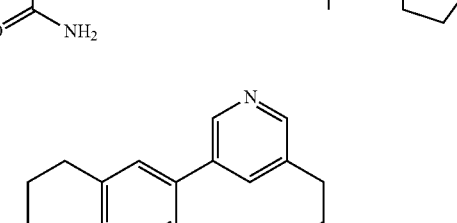 |
| 189 | 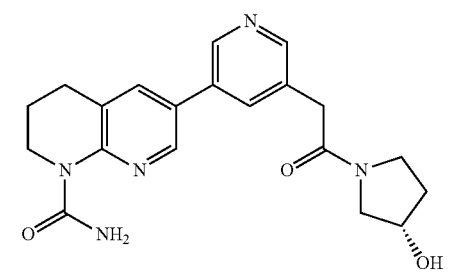 [SMILES: NC(=O)N1CCCc2cc(-c3cncc(CC(=O)N4CC[C@H](O)C4)c3)cnc21] |

| Cpd No | STRUCTURE | | Cpd No | STRUCTURE |
|---|---|---|---|---|
| 190 | 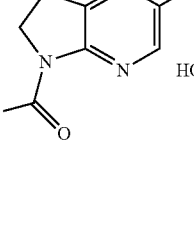 | | 196 | 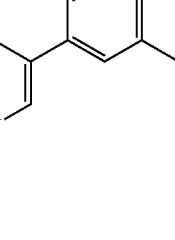 |
| 191 | | | 197 | |
| 192 | 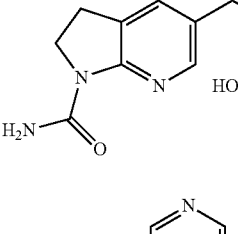 | | 198 | 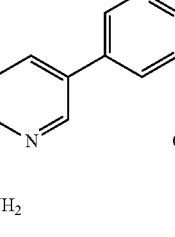 |
| 193 | | | 199 | |
| 194 | 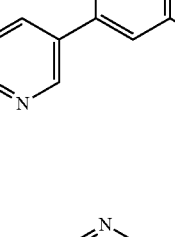 | | 200 | 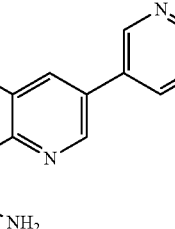 |
| 195 | | | 201 | |

US 9,181,272 B2
333
-continued
| Cpd No | STRUCTURE |
|---|---|
| 202 | 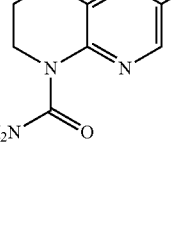 |
| 203 | 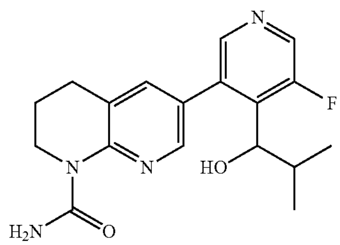 [SMILES: CC(C)C(O)c1c(F)cncc1-c1cnc2c(c1)CCCN2C(N)=O] |
| 204 | 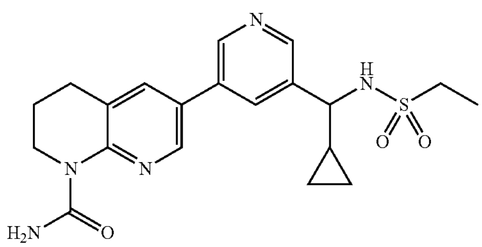 [SMILES: CCS(=O)(=O)NC(c1cncc(-c2cnc3c(c2)CCCN3C(N)=O)c1)C1CC1] |
| 205 | 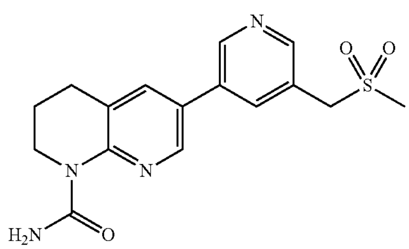 [SMILES: CS(=O)(=O)Cc1cncc(-c2cnc3c(c2)CCCN3C(N)=O)c1] |
| 206 | 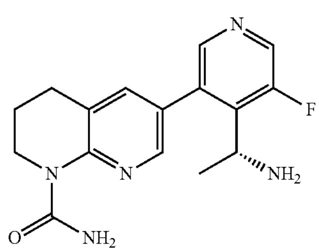 [SMILES: C[C@@H](N)c1c(F)cncc1-c1cnc2c(c1)CCCN2C(N)=O] |
| 207 | 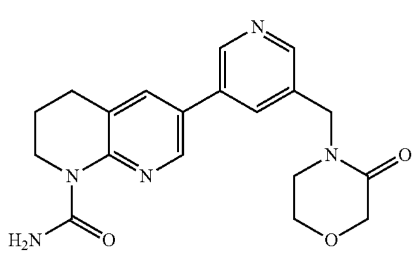 [SMILES: NC(=O)N1CCCc2cc(-c3cncc(CN4CCOCC4=O)c3)cnc21] |
334
-continued
| Cpd No | STRUCTURE |
|---|---|
| 208 | 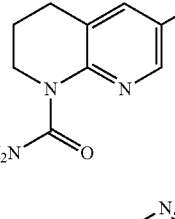 |
| 209 | 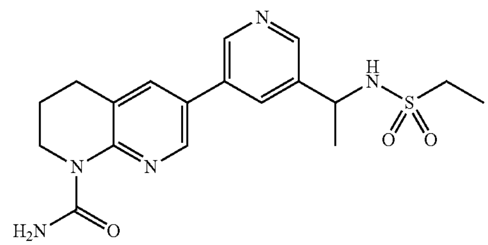 [SMILES: CCS(=O)(=O)NC(C)c1cncc(-c2cnc3c(c2)CCCN3C(N)=O)c1] |
| 210 | 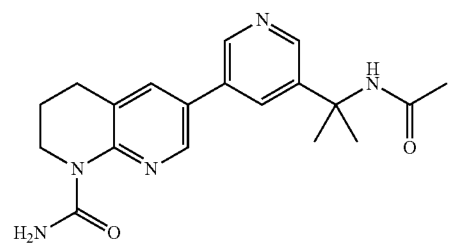 [SMILES: CC(=O)NC(C)(C)c1cncc(-c2cnc3c(c2)CCCN3C(N)=O)c1] |
| 211 | 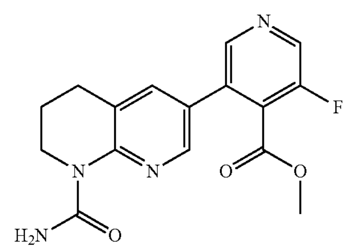 [SMILES: COC(=O)c1c(F)cncc1-c1cnc2c(c1)CCCN2C(N)=O] |
| 212 | 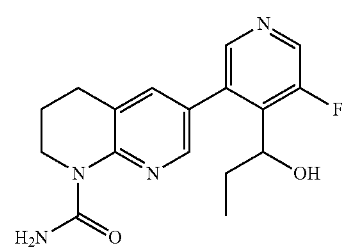 |
| 213 | 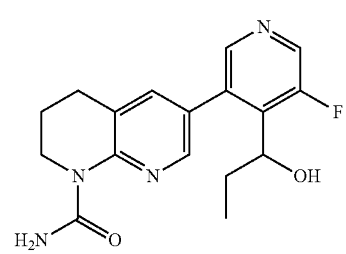 [SMILES: CCC(O)c1c(F)cncc1-c1cnc2c(c1)CCCN2C(N)=O] |

| Cpd No | STRUCTURE |
|---|---|
| 214 | 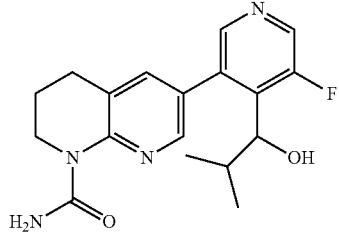 [SMILES: CC(C)C(O)c1c(F)cncc1-c1cnc2c(c1)CCCN2C(N)=O] |
| 215 | 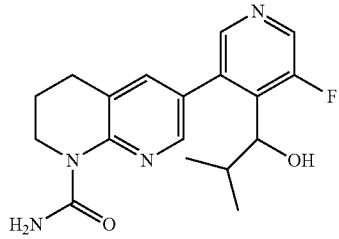 [SMILES: CC(C)C(O)c1c(F)cncc1-c1cnc2c(c1)CCCN2C(N)=O] |
| 216 | 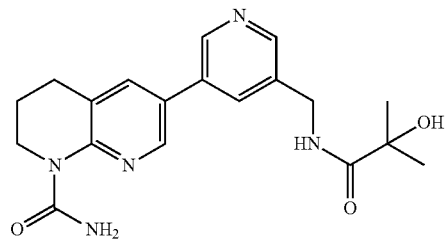 [SMILES: CC(C)(O)C(=O)NCc1cncc(-c2cnc3c(c2)CCCN3C(N)=O)c1] |
| 217 | 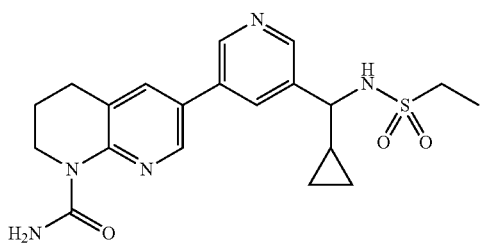 [SMILES: CCS(=O)(=O)NC(c1cncc(-c2cnc3c(c2)CCCN3C(N)=O)c1)C1CC1] |
| 218 | 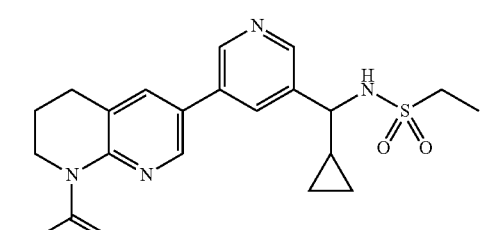 |
| 219 | 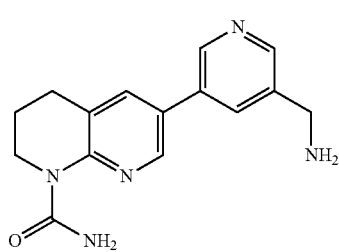 |
| Cpd No | STRUCTURE |
|---|---|
| 220 | 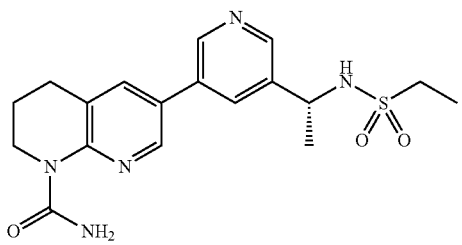 [SMILES: CCS(=O)(=O)N[C@H](C)c1cncc(-c2cnc3c(c2)CCCN3C(N)=O)c1] |
| 221 | 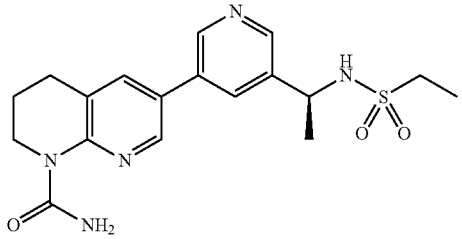 [SMILES: CCS(=O)(=O)N[C@@H](C)c1cncc(-c2cnc3c(c2)CCCN3C(N)=O)c1] |
| 222 | 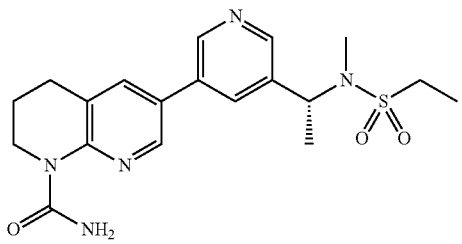 |
| 223 | 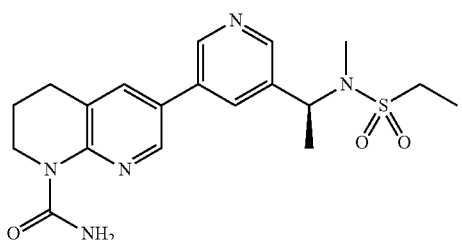 |
| 224 | 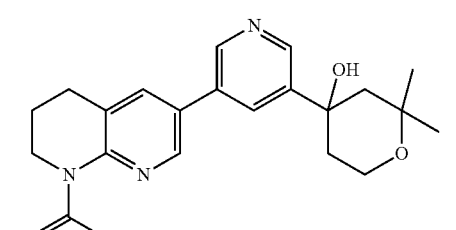 |
| 225 | 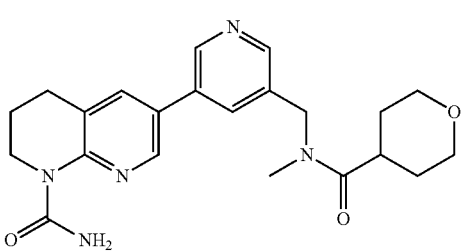 |

337
-continued
| Cpd No | STRUCTURE |
|---|---|
| 226 | 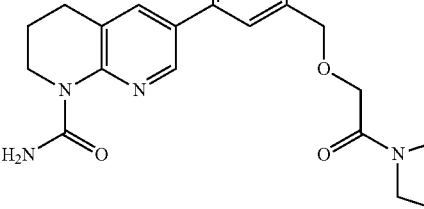 |
| 227 | 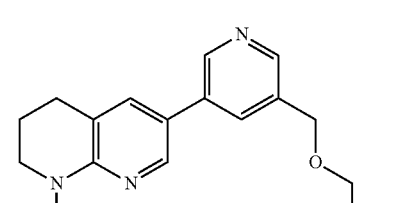 |
| 228 | 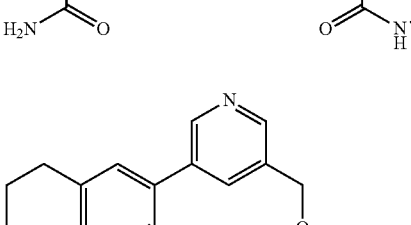 |
| 229 | 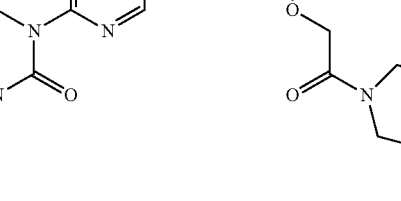 |
| 230 | 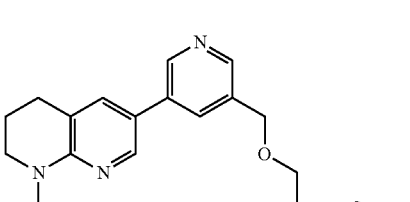 |
338
-continued
| Cpd No | STRUCTURE |
|---|---|
| 231 | 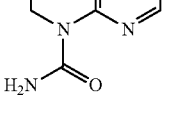 |
| 232 | 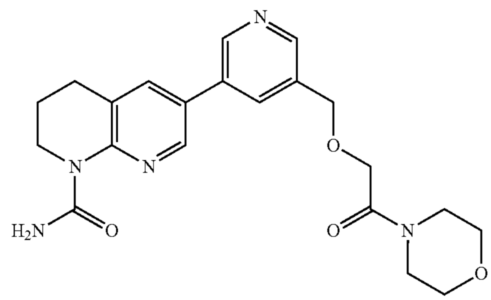 [SMILES: NC(=O)N1CCCc2cc(-c3cncc(COCC(=O)N4CCOCC4)c3)cnc21] |
| 233 | 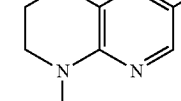 |
| 234 | 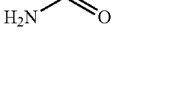 |
| 235 | 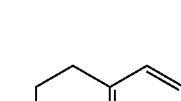 |
| 236 | 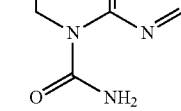 |

339
-continued
| Cpd No | STRUCTURE |
|---|---|
| 237 | 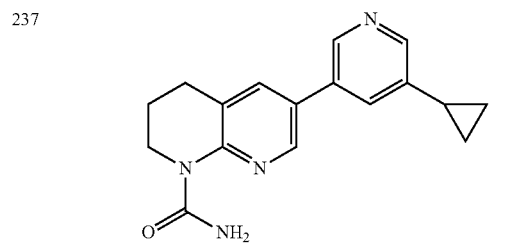 |
| 238 | 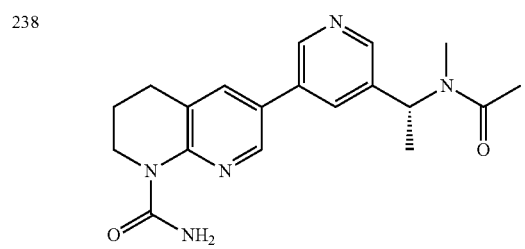 |
| 239 | 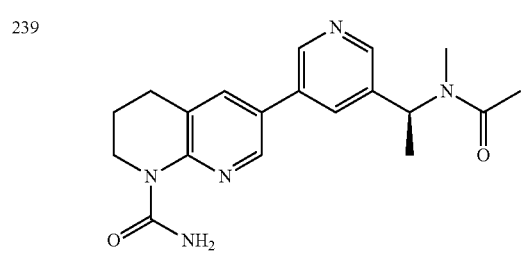 |
| 240 | 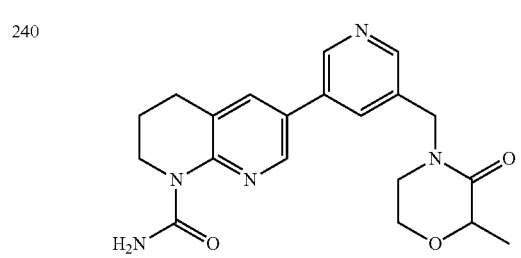 |
| 241 | 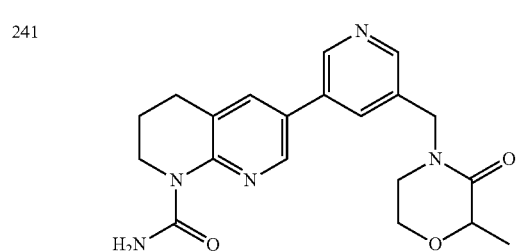 |
| 242 | 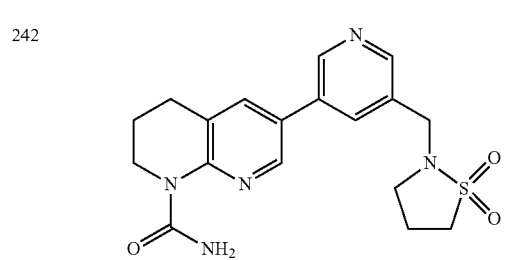 |
340
-continued
| Cpd No | STRUCTURE |
|---|---|
| 243 | 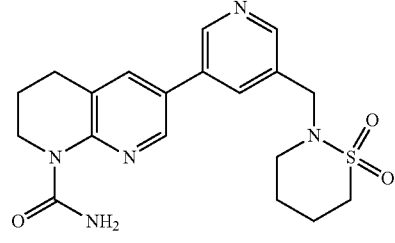 [SMILES: NC(=O)N1CCCc2cc(-c3cncc(CN4CCCCS4(=O)=O)c3)cnc21] |
| 244 | 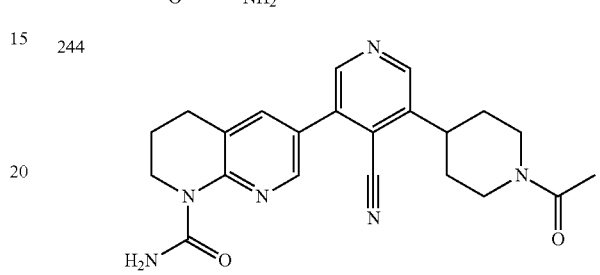 |
| 245 | 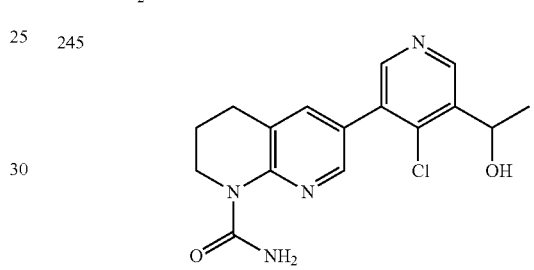 |
| 246 | 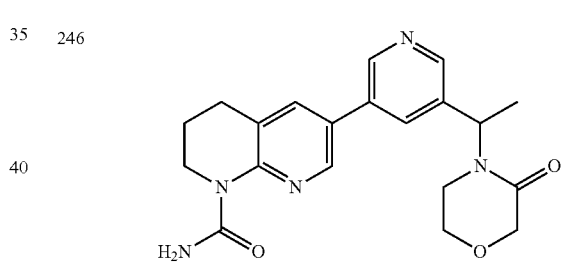 |
| 247 | 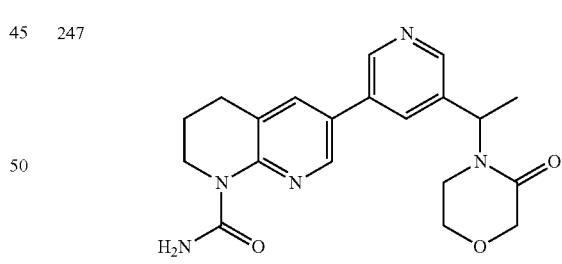 |
| 248 | 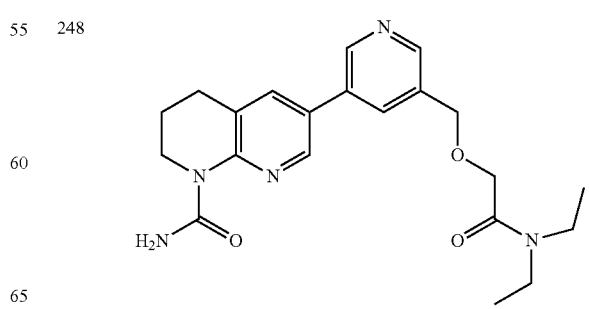 |

| Cpd No | STRUCTURE |
|---|---|
| 249 | 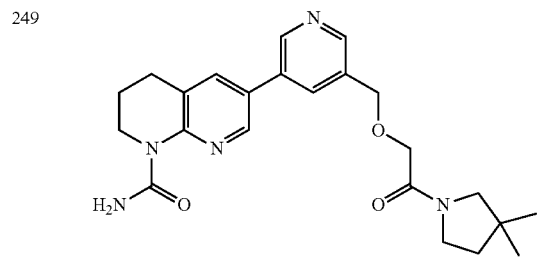 |
| 250 | 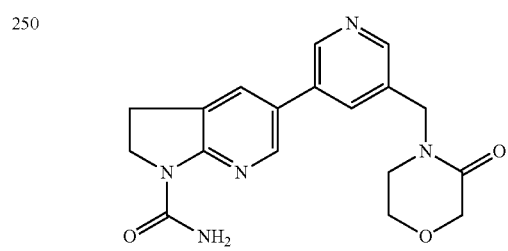 |
| 251 | 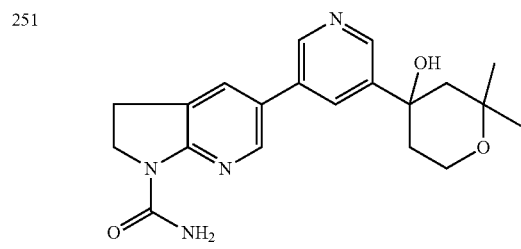 |
| 252 | 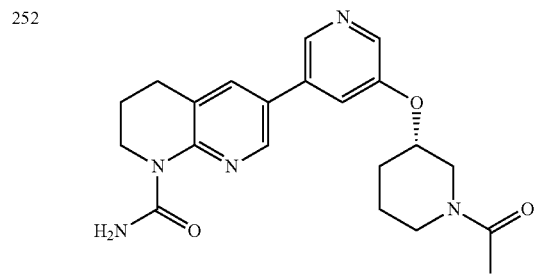 |
| 253 | 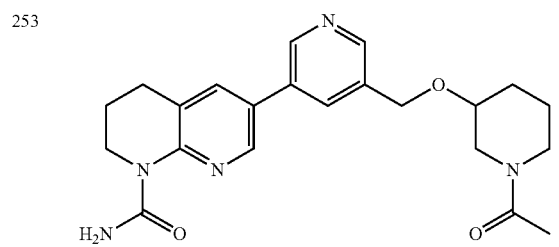 |
| 254 | 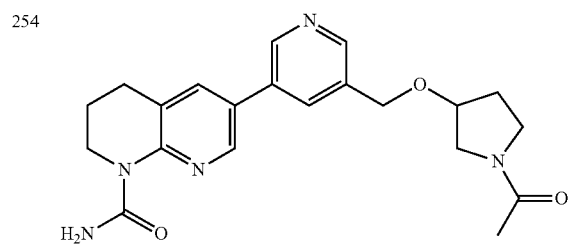 |
| Cpd No | STRUCTURE |
|---|---|
| 255 | 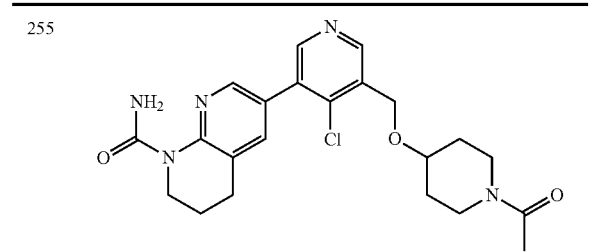 |
| 256 | 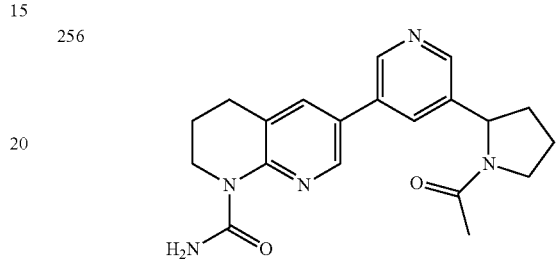 |
| 257 | 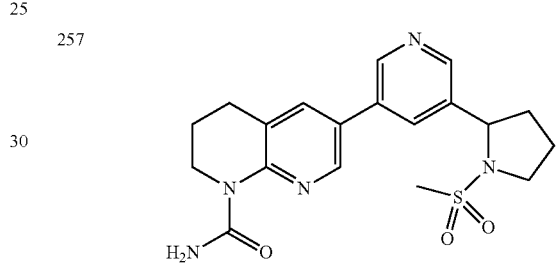 |
| 258 | 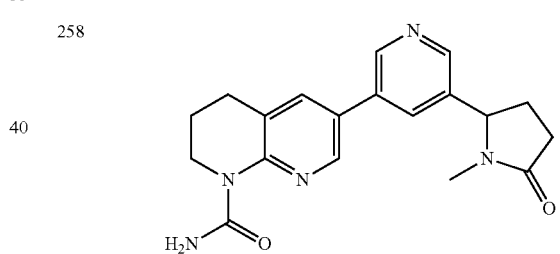 |
| 259 | 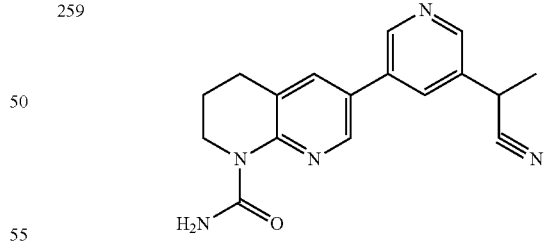 |
| 260 | 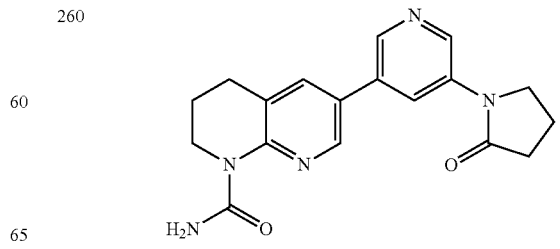 |

| Cpd No | STRUCTURE |
|---|---|
| 261 | 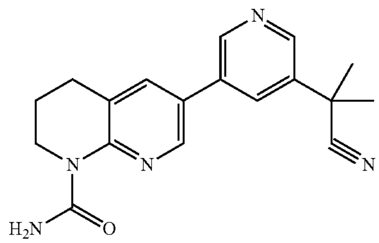 [SMILES: CC(C)(C#N)c1cncc(-c2cnc3c(c2)CCCN3C(N)=O)c1] |
| 262 | 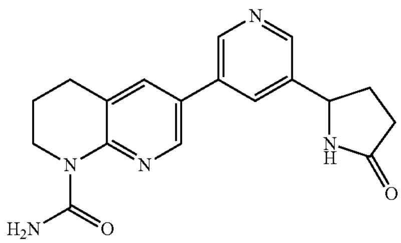 [SMILES: NC(=O)N1CCCc2cc(-c3cncc(C4CCC(=O)N4)c3)cnc21] |
| 263 | 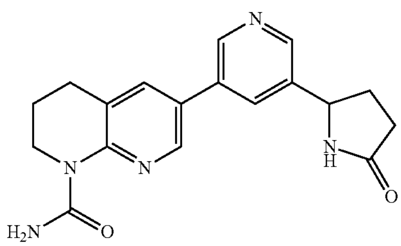 [SMILES: NC(=O)N1CCCc2cc(-c3cncc(C4CCC(=O)N4)c3)cnc21] |
| 264 | 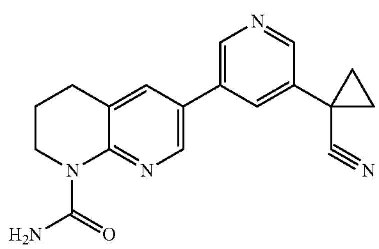 [SMILES: N#CC1(c2cncc(-c3cnc4c(c3)CCCN4C(N)=O)c2)CC1] |
| 265 | 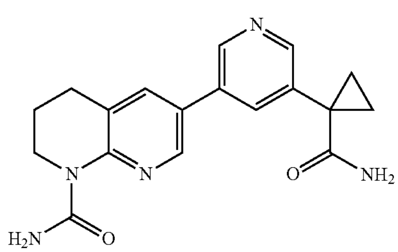 [SMILES: NC(=O)N1CCCc2cc(-c3cncc(C4(C(N)=O)CC4)c3)cnc21] |
| 266 | 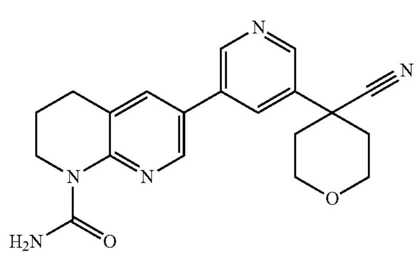 [SMILES: N#CC1(c2cncc(-c3cnc4c(c3)CCCN4C(N)=O)c2)CCOCC1] |

| Cpd No | STRUCTURE |
|---|---|
| 267 | 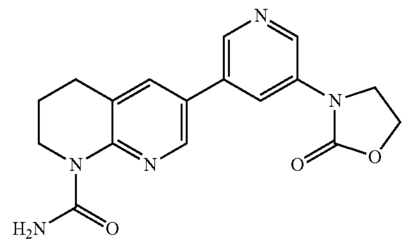 [SMILES: NC(=O)N1CCCc2cc(-c3cncc(N4CCOC4=O)c3)cnc21] |
| 268 | 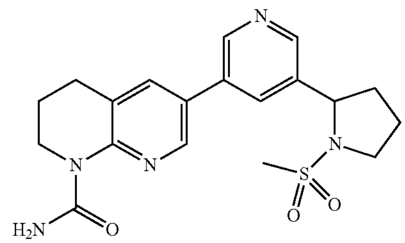 |
| 269 | 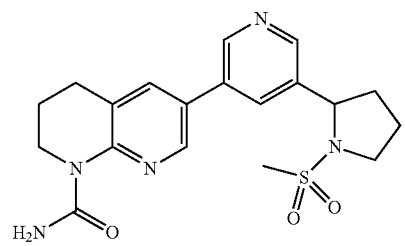 |
| 270 | 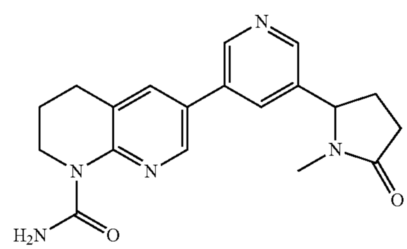 |
| 271 | 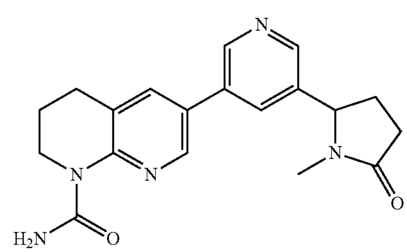 |
| 272 | 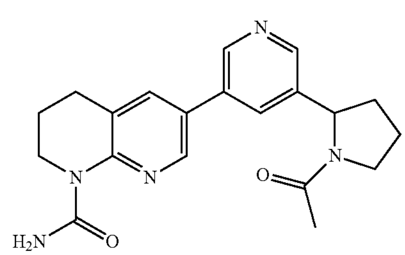 |

345
-continued
| Cpd No | STRUCTURE |
|---|---|
| 273 | 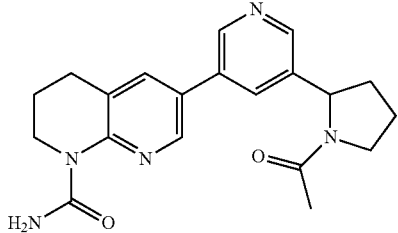 |
| 274 | 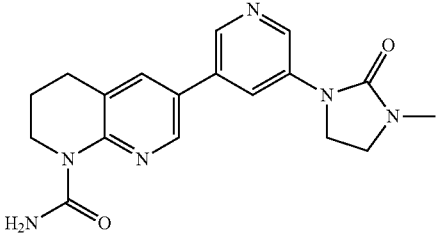 [SMILES: CN1CCN(c2cncc(-c3cnc4c(c3)CCCN4C(N)=O)c2)C1=O] |
| 275 | 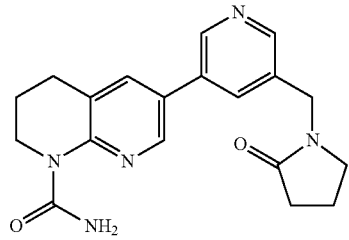 |
| 276 | 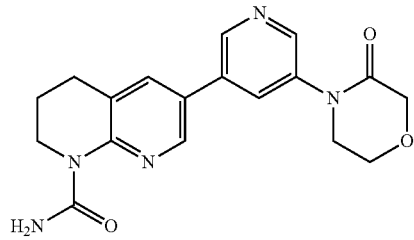 [SMILES: NC(=O)N1CCCc2cc(-c3cncc(N4CCOCC4=O)c3)cnc21] |
| 277 | 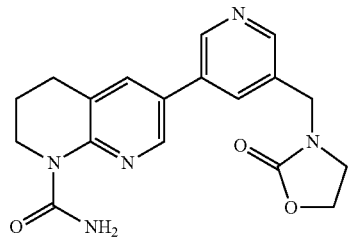 [SMILES: NC(=O)N1CCCc2cc(-c3cncc(CN4CCOC4=O)c3)cnc21] |
| 278 | 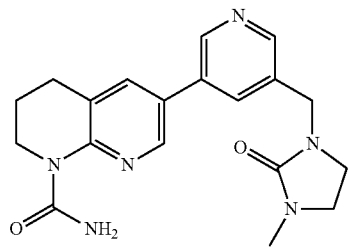 [SMILES: CN1CCN(Cc2cncc(-c3cnc4c(c3)CCCN4C(N)=O)c2)C1=O] |
346
-continued
| Cpd No | STRUCTURE |
|---|---|
| 279 | 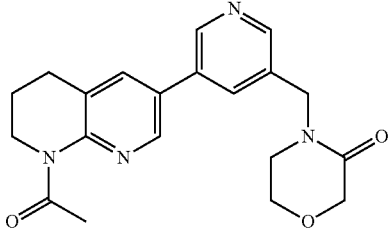 [SMILES: CC(=O)N1CCCc2cc(-c3cncc(CN4CCOCC4=O)c3)cnc21] |
| 280 | 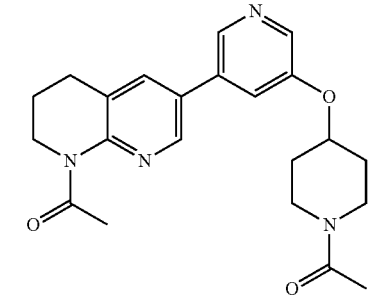 [SMILES: CC(=O)N1CCC(Oc2cncc(-c3cnc4c(c3)CCCN4C(C)=O)c2)CC1] |
| 281 | 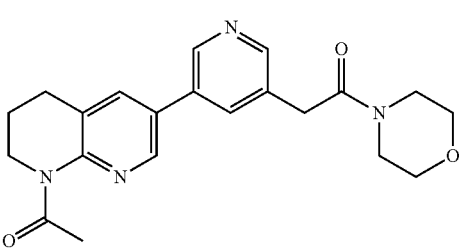 [SMILES: CC(=O)N1CCCc2cc(-c3cncc(CC(=O)N4CCOCC4)c3)cnc21] |
| 282 | 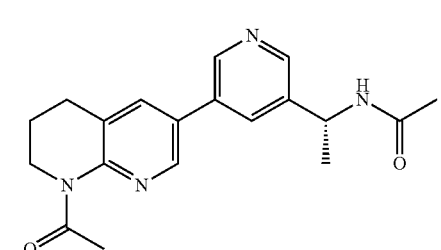 |
| 283 | 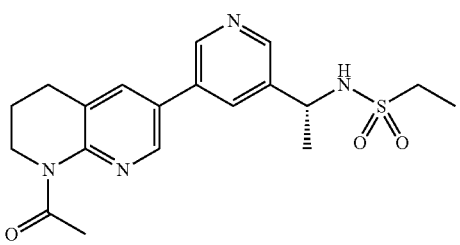 [SMILES: CCS(=O)(=O)N[C@H](C)c1cncc(-c2cnc3c(c2)CCCN3C(C)=O)c1] |
| 284 | 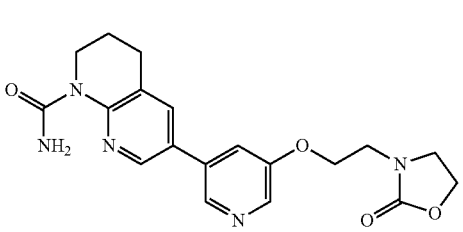 [SMILES: NC(=O)N1CCCc2cc(-c3cncc(OCCN4CCOC4=O)c3)cnc21] |

| Cpd No | STRUCTURE | | Cpd No | STRUCTURE |
|---|---|---|---|---|
| 285 | 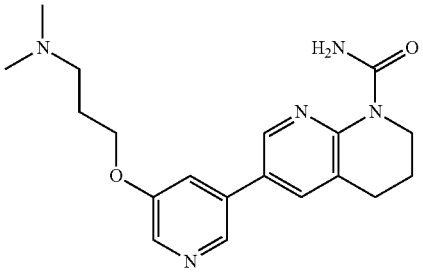 [SMILES: CN(C)CCCOc1cncc(-c2cnc3c(c2)CCCN3C(N)=O)c1] | | 292 | 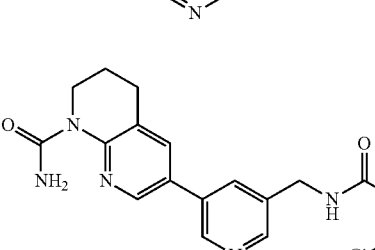 |
| 286 | 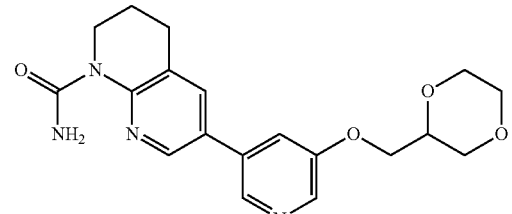 | | 293 | 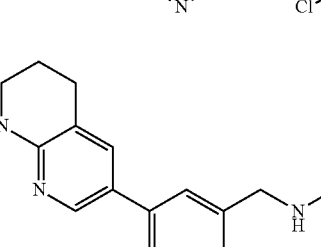 |
| 287 | 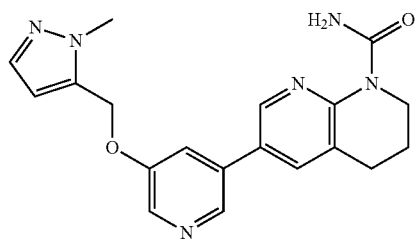 [SMILES: Cn1nccc1COc1cncc(-c2cnc3c(c2)CCCN3C(N)=O)c1] | | 294 | 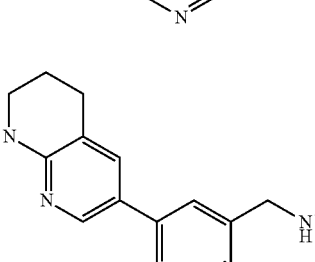 |
| 288 | 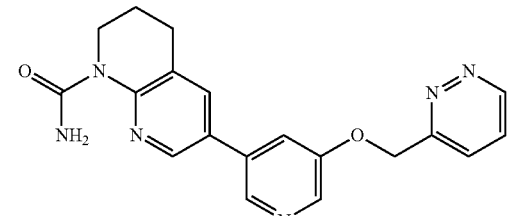 | | 295 | 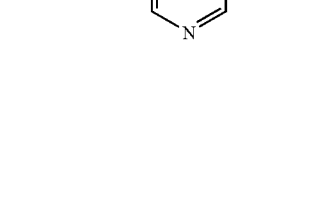 |
| 289 | 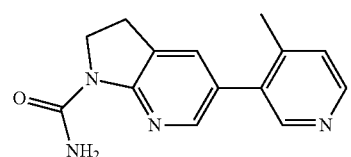 | | 296 | 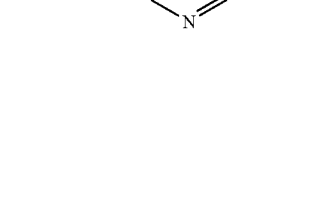 |
| 290 | 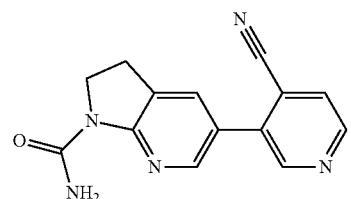 | | 297 | 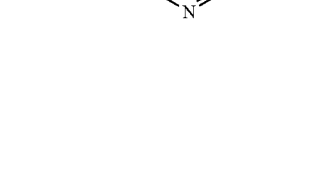 |
| 291 | 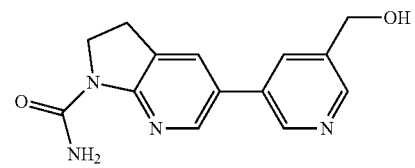 | | | |

TABLE 349-continued
| Cpd No | STRUCTURE |
|---|---|
| 298 | 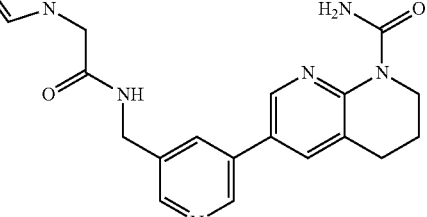 |
| 299 | 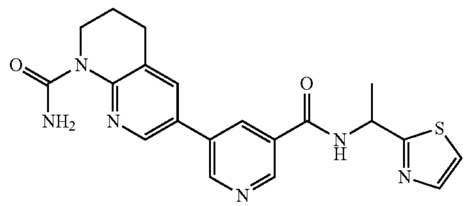 [SMILES: CC(NC(=O)c1cncc(-c2cnc3c(c2)CCCN3C(N)=O)c1)c1nccs1] |
| 300 | 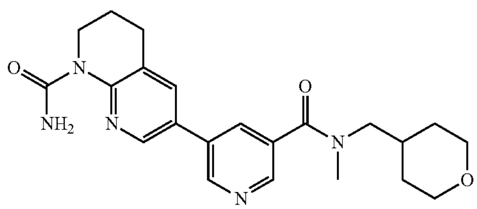 [SMILES: CN(CC1CCOCC1)C(=O)c1cncc(-c2cnc3c(c2)CCCN3C(N)=O)c1] |
| 301 | 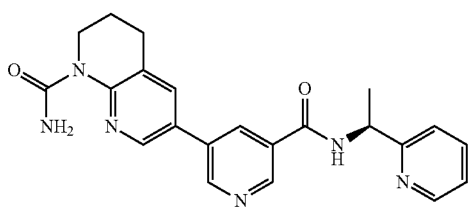 [SMILES: C[C@H](NC(=O)c1cncc(-c2cnc3c(c2)CCCN3C(N)=O)c1)c1ccccn1] |
| 302 | 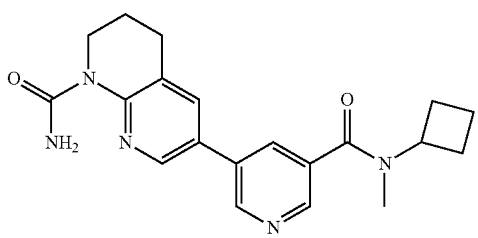 [SMILES: CN(C(=O)c1cncc(-c2cnc3c(c2)CCCN3C(N)=O)c1)C1CCC1] |
| 303 | 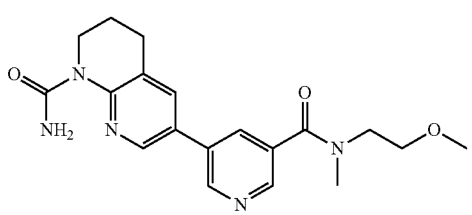 [SMILES: COCCN(C)C(=O)c1cncc(-c2cnc3c(c2)CCCN3C(N)=O)c1] |
TABLE 350-continued
| Cpd No | STRUCTURE |
|---|---|
| 304 | 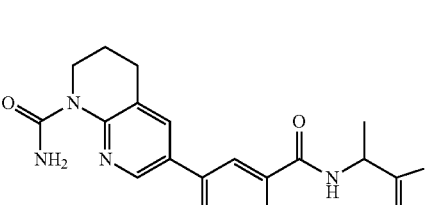 |
| 305 | 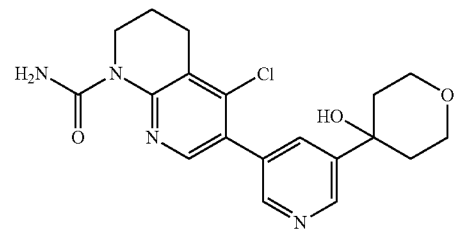 [SMILES: NC(=O)N1CCCc2c1ncc(-c1cncc(C3(O)CCOCC3)c1)c2Cl] |
| 306 | 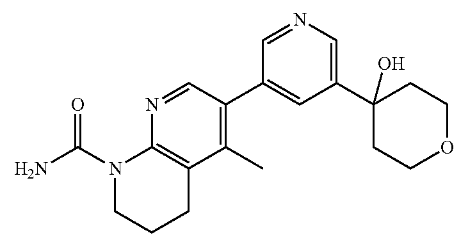 [SMILES: Cc1c(-c2cncc(C3(O)CCOCC3)c2)cnc2c1CCCN2C(N)=O] |
| 307 | 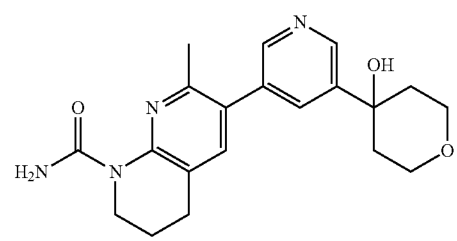 [SMILES: Cc1nc2c(cc1-c1cncc(C3(O)CCOCC3)c1)CCCN2C(N)=O] |
| 308 | 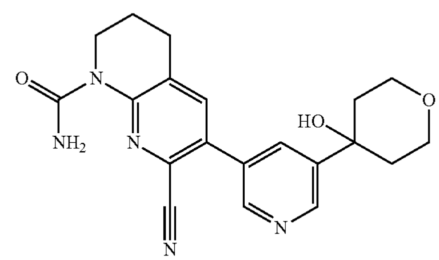 [SMILES: N#Cc1nc2c(cc1-c1cncc(C3(O)CCOCC3)c1)CCCN2C(N)=O] |
| 309 | 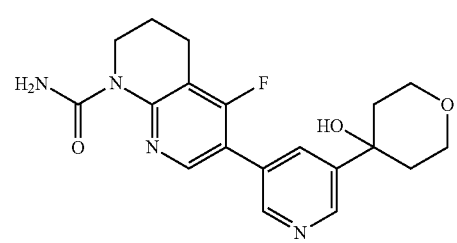 [SMILES: NC(=O)N1CCCc2c1ncc(-c1cncc(C3(O)CCOCC3)c1)c2F] |

| Cpd No | STRUCTURE |
|---|---|
| 310 | |
| 311 | |
| 312 | |
| 313 | |
| 314 | |
| 315 | |
| 316 | |
| 317 | |
| 318 | | and the pharmaceutically acceptable salts thereof.

15. The compound according to claim 14 selected from the group consisting of compound numbers 1-3, 5-11, 14-20, 22-25, 27-29, 31-35, 38, 40-43, 45, 46, 48, 50-57, 59, 60, 62-68, 70-88, 90-102, 105-107, 109, 110, 112, 116, 117, 121, 126-131, 133-137, 141-144, 147-153, 155-162, 164, 165, 167-182, 184-193, 195-199, 202, 204, 205, 207-213, 216-218, 220-243, 245-250, 252-255, 257-262, 264-270, 272, 274-298, 300, 302, 304-307 and 309-316 and the pharmaceutically acceptable salts thereof.

16. A pharmaceutical composition comprising a compound according to claim 1 and a pharmaceutically acceptable excipient or carrier.

\* \* \* \* \*